US007807385B2

(12) United States Patent
Goddard et al.

(10) Patent No.: US 7,807,385 B2

(45) Date of Patent: Oct. 5, 2010

(54) METHOD OF DETECTING PRO9917

(75) Inventors: Audrey Goddard, San Francisco, CA (US); Paul J. Godowski, Hillsborough, CA (US); Austin L. Gurney, Belmont, CA (US); Victoria Smith, Burlingame, CA (US); William I. Wood, Hillsborough, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 12/270,133

(22) Filed: Nov. 13, 2008

(65) Prior Publication Data

US 2009/0226953 A1 Sep. 10, 2009

Related U.S. Application Data

(60) Division of application No. 11/552,437, filed on Oct. 24, 2006, now Pat. No. 7,476,723, which is a continuation of application No. 10/216,168, filed on Aug. 9, 2002, now Pat. No. 7,157,558, which is a continuation of application No. 10/119,480, filed on Apr. 9, 2002, now abandoned, which is a continuation of application No. PCT/US01/21066, filed on Jun. 29, 2001, which is a continuation-in-part of application No. PCT/US01/17800, filed on Jun. 1, 2001.

(51) Int. Cl.

*G01N 33/53* (2006.01)
*C07K 16/18* (2006.01)
*C07K 16/30* (2006.01)
*C07K 14/435* (2006.01)

(52) U.S. Cl. .................. 435/7.1; 530/387.9; 530/389.7; 530/350

(58) Field of Classification Search ....................... None
See application file for complete search history.

(56) References Cited

U.S. PATENT DOCUMENTS

| | | | | |
|---|---|---|---|---|
| 6,613,515 | B1 | 9/2003 | Xu et al. | |
| 6,617,109 | B1 | 9/2003 | Xu et al. | |
| 6,710,170 | B2 | 3/2004 | Xu et al. | |
| 6,720,146 | B2 | 4/2004 | Stolk et al. | |
| 7,144,990 | B2 | 12/2006 | Goddard et al. | |
| 7,157,558 | B2 | 1/2007 | Goddard et al. | |
| 7,208,316 | B2 | 4/2007 | Goddard et al. | |
| 7,598,051 | B2 * | 10/2009 | Fanger et al. | 435/7.23 |
| 2003/0129192 | A1 | 7/2003 | Chenault et al. | |
| 2003/0148408 | A1 | 8/2003 | Frantz et al. | |
| 2003/0206918 | A1 | 11/2003 | Fanger et al. | |
| 2003/0232056 | A1 | 12/2003 | Fanger et al. | |
| 2004/0229277 | A1 | 11/2004 | Frantz et al. | |
| 2004/0242860 | A1 | 12/2004 | Frantz et al. | |
| 2006/0057141 | A1 | 3/2006 | Fanger et al. | |

FOREIGN PATENT DOCUMENTS

| | | |
|---|---|---|
| EP | 1 067 182 A2 | 1/2001 |
| WO | WO 00/61629 | 10/2000 |
| WO | 00/77026 | 12/2000 |
| WO | 01/18046 | 3/2001 |
| WO | 01/81634 | 11/2001 |
| WO | 01/92581 | 12/2001 |
| WO | WO 02/39885 A2 | 5/2002 |
| WO | 2007/109567 A1 | 9/2007 |

OTHER PUBLICATIONS

Takaba et al. (2000). Carcinogenesis. 21(4):691-700.*
U.S. Appl. No. 11/687,309, filed Mar. 16, 2007, Liang et al.
U.S. Appl. No. 12/012,201, filed Jan. 31, 2008, Goddard et al.
Ballow et al., "Immunopharmacology, Immunomodulation and Immunotherapy" *Journal of the American Medical Assn.* 278:2008-2017 (1997).
Bork, et al., "Go hunting in sequence databases but watch out for the traps" *Trends in Genetics* 12(10):425-427 (Oct. 1996).
Bork, P., "Powers and Pitfalls in Sequence Analysis: The 70% Hurdle" *Genome Research* 10(4):398-400 (Apr. 2000).
Brenner, S.E., "Errors in genome annotation" *Trends in Genetics* 15(4):132-133 (Apr. 1999).
Buchsbaum et al., "Experimental radioimmunotherapy" *Med. Phys.* 20(2):551-567 (1993).
Chen et al., "Discordant Protein and mRNA Expression in Lung Adenocarcinomas" *Molecular & Cellular Proteomics* 1:304-313 (2002).
Database Search, DNA sequence alignments, (BLASTN 2.2.6 Apr. 9, 2003 NCBI) pp. 1-118.
Database Search, protein sequence alignments, (BLASTP 2.2.6 Apr. 9, 2003 NCBI) pp. 1-18.
Dillman, R.O., "Monoclonal antibodies in the treatment of malignancy: basic concepts and recent developments" *Cancer Invest* 19(8):833-841 (2001).
Doerks, et al., "Protein annotation: detective work for function prediction" *Trends in Genetics* 14(6):248-250 (Jun. 1998).
EMBL Sequence Database *Accession No. AA613995* (Oct. 13, 1997).
Ex parte Baker et al., USPTO Board of Patent Appeals and Interferences, Appeal No. 2007-2230 in U.S. Appl. No. 10/187,744, decided Sep. 17, 2007.
Explanation of blast hits—DNA sequence alignments: GenBank (Rel 153 Apr. 2006) pp. 119-166.
Explanation of blast hits—protein sequence alignments: Dayhoff Protein Database (Rel 48 Oct. 2005) pp. 19-53.
Haynes et al., "Proteome analysis: Biological assay or data archive?" *Electrophoresis* 19:1862-1871 (1998).
Hegde et al., "A Concise Guide to cDNA Microarray Analysis" *BioTechniques* 29(3):548-562 (Sep. 2000).
Hu et al., "Analysis of genomic and proteomic data using advanced literature mining" *J. Proteome Res* 2:405-412 (2003).

(Continued)

*Primary Examiner*—Christine J Saoud
*Assistant Examiner*—Jon M Lockard
(74) *Attorney, Agent, or Firm*—Danielle M. Pasqualone

(57) ABSTRACT

The present invention is directed to novel polypeptides and to nucleic acid molecules encoding those polypeptides. Also provided herein are vectors and host cells comprising those nucleic acid sequences, chimeric polypeptide molecules comprising the polypeptides of the present invention fused to heterologous polypeptide sequences, antibodies which bind to the polypeptides of the present invention and to methods for producing the polypeptides of the present invention.

2 Claims, 246 Drawing Sheets

OTHER PUBLICATIONS

Moore, G.P., "Genetically Engineered Antibodies" *Clinical Chemistry* 35(9):1849-1853 (1989).

NCBI Database, *Accession No. AB041649* (Jun. 30, 2000).

NCBI Database, Accession No. AX136281 (May 30, 2001).

NCBI Database, Accession No. Q9JJ96 (Oct. 1, 2000).

Ngo et al., "Computational Complexity, Protein Structure Prediction, and the Levinthal Paradox" *The Protein Folding Problem and Tertiary Structure Prediction*, Merz & Le Grand, Boston:Birkhauser pp. 491-495 (1994).

Orntoft, Torben F., et al., "Genome-wide Study of Gene Copy Numbers, Transcripts, and Protein Levels in Pairs of Non-Invasive and Invasive Human Transitional Cell Carcinomas" *Molecular & Cellular Proteomics* 1:37-45 (2002).

Osband et al., "Problems in the investigational study and clinical use of cancer immunotherapy" *Immunology Today* 11(6):193-195 (1990).

Pennica D, et al., "WISP genes are members of the connective tissue growth factor family that are up-regulated in wnt-l-transformed cells and aberrantly expressed in human colon tumors" *Proc. Natl. Acad. Sci. USA* 95(25):14717-14722 (Dec. 8, 1998).

Preliminary Amendment filed with Reissue Application No. 12/012,201 (for U.S. Patent No. 7,208,316 B2) (Filed Jan. 31, 2008).

Qi et al., "Identification of genes responsible for osteoblast differentiation from human mesodermal progenitor cells" *Proc. Natl. Acad. Sci USA* 100:3305-3310 (2003).

Reissue Application Declaration by the Assignee filed in Reissue Application 12/012,201 (for U.S. Patent No. 7,208,316 B2) (Filed Jan. 31, 2008).

Saito-Hisaminato et al., "Genome-wide profiling of gene expression in 29 normal human tissues with a cDNA microarray" *DNA Res* 9:35-45 (2002).

Schlom, J., "Monoclonal Antibodies: They're More and Less Than You Think" *Molecular Foundations of Oncology*, Broder, S. ed., Baltimore, MD:Williams & Wilkins, Chapter 6, pp. 95-134 (1991).

Seaver, "Monoclonal Antibodies in Industry: More Difficult Than Originally Thought" *Genetic Engineering News* pp. 10 and 21 (Aug. 1994).

Sen et al., "Aneuploidy and cancer" *Curr. Opin. Oncol.* 12:82-88 (2000).

Skolnick et al., "From Genes to protein structure and function: novel applications of computational approaches in the genomic era" *TIBTECH* 18:34-39 (Jan. 2000).

Smith, et al., "The challenges of genome sequence annotation or "The devil is in the details"" *Nature Biotechnology* 15(12):1222-1223 (Nov. 1997).

Trail et al., "Monoclonal antibody drug conjugates in the treatment of cancer" *Current Opinion in Immunology* 11:584-588 (1999).

Wawrzynczak et al., "Strategies in antibody therpay of cancer" *Clin. exp. Immunol.* 82:189-193 (1990).

Wells, "Additivity of Mutational Effects in Proteins" *Biochemistry* 29:8509-8517 (1990).

* cited by examiner

FIGURE 1A

GCAGCCCTAGCAGGGATGGACATGATGCTGTTGGTGCAGGGTGCTTGTTGCTCGAACCAGTG
GCTGGCGGCGGTGCTCCTCAGCCTGTGCTGCCTGCTACCCTCCTGCCTCCCGGCTGGACAGA
GTGTGGACTTCCCCTGGGCGGCCGTGGACAACATGATGGTCAGAAAAGGGGACACGGCGGTG
CTTAGGTGTTATTTGGAAGATGGAGCTTCAAAGGGTGCCTGGCTGAACCGGTCAAGTATTAT
TTTTGCGGGAGGTGATAAGTGGTCAGTGGATCCTCGAGTTTCAATTTCAACATTGAATAAAA
GGGACTACAGCCTCCAGATACAGAATGTAGATGTGACAGATGATGGCCCATACACGTGTTCT
GTTCAGACTCAACATACACCCAGAACAATGCAGGTGCATCTAACTGTGCAAGTTCCTCCTAA
GATATATGACATCTCAAATGATATGACCGTCAATGAAGGAACCAACGTCACTCTTACTTGTT
TGGCCACTGGGAAACCAGAGCCTTCCATTTCTTGGCGACACATCTCCCCATCAGCAAAACCA
TTTGAAAATGGACAATATTTGGACATTTATGGAATTACAAGGGACCAGGCTGGGGAATATGA
ATGCAGTGCGGAAAATGATGTGTCATTCCCAGATGTGAGGAAAGTAAAAGTTGTTGTCAACT
TTGCTCCTACTATTCAGGAAATTAAATCTGGCACCGTGACCCCCGGACGCAGTGGCCTGATA
AGATGTGAAGGTGCAGGTGTGCCGCCTCCAGCCTTTGAATGGTACAAAGGAGAGAAGAAGCT
CTTCAATGGCCAACAAGGAATTATTATTCAAAATTTTAGCACAAGATCCATTCTCACTGTTA
CCAACGTGACACAGGAGCACTTCGGCAATTATACTTGTGTGGCTGCCAACAAGCTAGGCACA
ACCAATGCGAGCCTGCCTCTTAACCCTCCAAGTACAGCCCAGTATGGAATTACCGGGAGCGC
TGATGTTCTTTTCTCCTGCTGGTACCTTGTGTTGACACTGTCCTCTTTCACCAGCATATTCT
ACCTGAAGAATGCCATTCTACAATAAATTCAAAGACCCATAAAAGGCTTTTAAGGATTCTCT
GAAAGTGCTGATGGCTGGATCCAATCTGGTACAGTTTGTTAAAAGCAGCGTGGGATATAATC
AGCAGTGCTTACATGGGGATGATCGCCTTCTGTAGAATTGCTCATTATGTAAATACTTTAAT
TCTACTCTTTTTTGATTAGCTACATTACCTTGTGAAGCAGTACACATTGTCCTTTTTTTAAG
ACGTGAAAGCTCTGAAATTACTTTTAGAGGATATTAATTGTGATTTCATGTTTGTAATCTAC
AACTTTTCAAAAGCATTCAGTCATGGTCTGCTAGGTTGCAGGCTGTAGTTTACAAAAACGAA
TATTGCAGTGAATATGTGATTCTTTAAGGCTGCAATACAAGCATTCAGTTCCCTGTTTCAAT
AAGAGTCAATCCACATTTACAAAGATGCATTTTTTTCTTTTTTGATAAAAAAGCAAATAATA
TTGCCTTCAGATTATTTCTTCAAAATATAACACATATCTAGATTTTTCTGCTCGCATGATAT
TCAGGTTTCAGGAATGAGCCTTGTAATATAACTGGCTGTGCAGCTCTGCTTCTCTTTCCTGT
AAGTTCAGCATGGGTGTGCCTTCATACAATAATATTTTTCTCTTTGTCTCCAACTAATATAA
AATGTTTTGCTAAATCTTACAATTTGAAAGTAAAAATAAACCAGAGTGATCAAGTTAAACCA
TACACTATCTCTAAGTAACGAAGGAGCTATTGGACTGTAAAAATCTCTTCCTGCACTGACAA
TGGGGTTTGAGAATTTTGCCCCACACTAACTCAGTTCTTGTGATGAGAGACAATTTAATAAC
AGTATAGTAAATATACCATATGATTTCTTTAGTTGTAGCTAAATGTTAGATCCACCGTGGGA
AATCATTCCCTTTAAAATGACAGCACAGTCCACTCAAAGGATTGCCTAGCAATACAGCATCT
TTTCCTTTCACTAGTCCAAGCCAAAAATTTTAAGATGATTTGTCAGAAAGGGCACAAAGTCC
TATCACCTAATATTACAAGAGTTGGTAAGCGCTCATCATTAATTTTATTTTGTGGCAGCTAA
GTTAGTATGACAGAGGCAGTGCTCCTGTGGACAGGAGCATTTTGCATATTTTCCATCTGAAA
GTATCACTCAGTTGATAGTCTGGAATGCATGTTATATATTTTAAAACTTCCAAAATATATTA
TAACAAACATTCTATATCGGTATGTAGCAGACCAATCTCTAAAATAGCTAATTCTTCAATAA
AATCTTTCTATATAGCCATTTCAGTGCAAACAAGTAAAATCAAAAAAGACCATCCTTTATTT
TTCCTTACATGATATATGTAAGATGCGATCAAATAAAGACAAAACACCAGTGATGAGAATAT
CTTAAGATAAGTAATTATCAAATTATTGTGAATGTTAAATTATTTCTACTATAAAGAAGCAA
AACTACATTTTTGAAGGAAAATGCTGTTACTCTAACATTAATTTACAGGAATAGTTTGATGG
TTTCACTCTTTACTAAAGAAAGGCCATCACCTTGAAAGCCATTTTACAGGTTTGATGAAGTT
ACCAATTTCAGTACACCTAAATTTCTACAAATAGTCCCCTTTTACAAGTTGTAACAACAAAG
ACCCTATAATAAAATTAGATACAAGAAATTTTGCAGTGGTTATACATATTTGAGATATCTAG
TATGTTGCCCTAGCAGGGATGGCTTAAAAACTGTGATTTTTTTTCTTCAAGTAAAACTTAGT
CCCAAAGTACATCATAAATCAATTTTAATTAGAAAAATGAATCTTAAATGAGGGGACATAAG
TATACTCTTTCCACAAAATGGCAATAATAAGGCATAAAGCTAGTAAATCTACTAACTGTAAT
AAATGTATGACATTATTTTGATTGATACATTAAAAAAGAGTTTTTAGAACAAATATGGCATT
TAACTTTATTATTTATTTGCTTTTAAGAAATATTCTTTGTGGAATTGTTGAATAAACTATAA
AATATTATTTTGTATTGCAGCTTTAAAGTGGCACACTCCATAATAATCTACTTACTAGAAAT

FIGURE 1B

AGTGGTGCTACCACAAAAAATGTTAACCATCAGTACCATTGTTTGGGAGAAAGAAACAGATC
AAGAATGCATATTATTCAGTGACCGCTTTCCTAGAGTTAAAATACCTCCTCTTTGTAAGGTT
TGTAGGTAAATTGAGGTATAAACTATGGATGAACCAAATAATTAGTTCAAAGTGTTGTCATG
ATTCCAAATTTGTGGAGTCTGGTGTTTTTACCATAGAATGTGACAGAAGTACAGTCATAGCT
CAGTAGCTATATGTATTTGCCTTTATGTTAGAAGAGACTTTCTTGAGTGACATTTTTAAATA
GAGGAGGTATTCACTATGTTTTTCTGTATCACAGCAGCATTCCTAGTCCTTAGGCCCTCGGA
CAGAGTGAAATCATGAGTATTTATGAGTTCAATATTGTCAAATAAGGCTACAGTATTTGCTT
TTTTGTGTGAATGTATTGCATATAATGTTCAAGTAGATGATTTTACATTTATGGACATATAA
AATGTCTGATTACCCCATTTTATCAGTCCTGACTGTACAAGATTGTTGCAATTTCAGAATAG
CAGTTTTATAAATTGATTTATCTTTTAATCTATAACAATTTGTGTTAGCTGTTCATTTCAGG
ANTATATTTTCTACAAGTTCCACTTGTGGGACTCCTTTTGTTGCCCCTATTTTTTTTTAAAG
AAGGAAGAAAGAAAAATAAGTAGCAGTTTAAAAATGAGAATGGAGAGAAAAGAAAAAGAATG
AAAAGGAAAGGCAGTAAAGAGGGAAAAAAAAGGAAGGATGGAAGGAATGAAGGAAGGAAGGG
AGGAAGGGGAGAAGGTAGGAAGAAAGAAAGGATGAGAGGGAAGGAAGAATCAGAGTATTAGG
GTAGTTAACTTACACATTTGCATTCTTAGTTTAACTGCAAGTGGTGTAACTATGTTTTTCAA
TGATCGCATTTGAAACATAAGTCCTATTATACCATTAAGTTCCTATTATGCAGCAATTATAT
AATAAAAAGTACTGCCCAAGTTATAGTAATGTGGGTGTTTTTGAGACACTAAAAGATTTGAG
AGGGAGAATTTCAAACTTAAAGCCACTTTTGGGGGGTTTATAACTTAACTGAAAAATTAATG
CTTCATCATAACATTTAAGCTATATCTAGAAAGTAGACTGGAGAACTGAGAAAATTACCCAG
GTAATTCAGGGAAAAAAAAAAATATATATATATATAAATACCCCTACATTTGAAGTCAGAAA
ACTCTGAAAAACTGAATTATCAAAGTCAATCATCTATAATGATCAAATTTACTGAACAATTG
TTAATTTATCCATTGTGCTTAGCTTTGTGACACAGCCAAAAGTTACCTATTTAATCTTTTCA
ATAAAAATTGTTTTTTGAAATCCAGAAATGATTTAAAAAGAGGTCAGGTTTTTAACTATTTA
TTGAAGTATGTGGATGTACAGTATTTCAATAGATATGAATATGAATAAATGGTATGCCTTAA
GATTCTTTGAATATGTATTTACTTTAAAGACTGGAAAAAGCTCTTCCTGTCTTTTAGTAAAA
CATCCATATTTCATAACCTGATGTAAAATATGTTGTACTGTTTCCAATAGGTGAATATAAAC
TCAGTTTATCAATTAAAAAAAAAAAAAAAAAAAAAAAAAAAAAAAAAAAAAAAAAAAAAAAAAA

FIGURE 2

></usr/seqdb2/sst/DNA/Dnaseqs.full/ss.DNA92259
><subunit 1 of 1, 354 aa, 1 stop
><MW: 38719, pI: 6.12, NX(S/T): 6
MDMMLLVQGACCSNQWLAAVLLSLCCLLPSCLPAGQSVDFPWAAVDNMMVRKGDTAVLRCYL
EDGASKGAWLNRSSIIFAGGDKWSVDPRVSISTLNKRDYSLQIQNVDVTDDGPYTCSVQTQH
TPRTMQVHLTVQVPPKIYDISNDMTVNEGTNVTLTCLATGKPEPSISWRHISPSAKPFENGQ
YLDIYGITRDQAGEYECSAENDVSFPDVRKVKVVVNFAPTIQEIKSGTVTPGRSGLIRCEGA
GVPPPAFEWYKGEKKLFNGQQGIIIQNFSTRSILTVTNVTQEHFGNYTCVAANKLGTTNASL
PLNPPSTAQYGITGSADVLFSCWYLVLTLSSFTSIFYLKNAILQ

Important features of the protein:
Signal peptide:
amino acids 1-33

Transmembrane domain:
amino acids 322-343

N-glycosylation sites.
amino acids 73-77, 155-159, 275-279, 286-290, 294-298, 307-311

Tyrosine kinase phosphorylation site.
amino acids 180-188

N-myristoylation sites.
amino acids 9-15, 65-71, 69-75, 153-159, 241-247, 293-299, 304-310, 321-327

Myelin P0 protein.
amino acids 94-123

FIGURE 3

CACTGCCCGTCCGCTCTTCAGCAGCCGGTCGCGGGCGGTGGAAAAGCGAGTGAAGAGAGCGC
GACGGCGGCGGCGGCGGCGGCGCAGCTATTGCTGGACGGCCAGTGGGAGAGCGAGGCCTGAG
CCTCTGCGTCTAGGATCAAAATGGTTTCAATCCCAGAATACTATGAAGGCAAGAACGTCCTC
CTCACAGGAGCTACCGGTTTTCTAGGGAAGGTGCTTCTGGAAAAGTTGCTGAGGTCTTGTCC
TAAGGTGAATTCAGTATATGTTTTGGTGAGGCAGAAAGCTGGACAGACACCACAAGAGCGAG
TGGAAGAAGTCCTTAGTGGCAAGCTTTTTGACAGATTGAGAGATGAAAATCCAGATTTTAGA
GAGAAAATTATAGCAATCAACAGCGAACTCACCCAACCTAAACTGGCTCTCAGTGAAGAAGA
TAAAGAGGTGATCATAGATTCTACCAATATTATATTCCACTGTGCAGCTACAGTAAGGTTTA
ATGAAAATTTAAGAGATGCTGTTCAGTTAAATGTGATTGCAACGCGACAGCTTATTCTCCTT
GCACAACAAATGAAGAATCTGGAAGTGTTCATGCATGTATCAACAGCATATGCCTACTGTAA
TCGCAAGCATATTGATGAAGTAGTCTATCCACCACCTGTGGATCCCAAGAAGCTGATTGATTCT
TTAGAGTGGATGGATGATGGCCTAGTAAATGATATCACGCCAAAATTGATAGGAGACAGACC
TAATACATACATATACACAAAAGCATTGGCAGAATATGTTGTACAACAAGAAGGAGCAAAAC
TAAATGTGGCAATTGTAAGGCCATCGATTGTTGGTGCCAGTTGGAAAGAACCTTTTCCAGGA
TGGATTGATAACTTTAATGGACCAAGTGGTCTCTTTATTGCGGCAGGGAAAGGAATTCTTCG
AACAATACGTGCCTCCAACAATGCCCTTGCAGATCTTGTTCCTGTAGATGTAGTTGTCAACA
TGAGTCTTGCGGCAGCCTGGTATTCCGGAGTTAATAGACCAAGAAACATCATGGTGTATAAT
TGTACAACAGGCAGCACTAATCCTTTCCACTGGGGTGAAGTTGAGTACCATGTAATTTCCAC
TTTCAAGAGGAATCCTCTCGAACAGGCCTTCAGACGGCCCAATGTAAATCTAACCTCCAATC
ATCTTTTATATCATTACTGGATTGCTGTAAGCCATAAGGCCCCAGCATTCCTGTATGATATC
TACCTCAGGATGACTGGAAGAAGCCCAAGGATGATGAAAACAATAACTCGTCTTCACAAAGC
TATGGTGTTTCTTGAATATTTCACAAGTAATTCTTGGGTTTGGAATACTGAGAATGTCAATA
TGTTAATGAATCAACTAAACCCTGAAGATAAAAAGACCTTCAATATTGATGTACGGCAGTTA
CATTGGGCAGAATATATAGAGAACTACTGCTTGGGAACTAAGAAGTACGTATTGAATGAAGA
AATGTCTGGCCTCCCTGCAGCCAGAAAACATCTGAACAAGTTGCGGAATATACGTTATGGTT
TTAATACTATCCTTGTGATCCTCATCTGGCGCATTTTTATTGCAAGATCACAAATGGCAAGA
AATATCTGGTACTTTGTGGTTAGTCTGTGTTACAAGTTTTTGTCATACTTCCGAGCATCCAG
CACTATGAGATACTGAAGACCAAGGATTCAGCATTAGAACATCTATACATATGGTGATCTAA
ATGTACAAAATGTAAAATGTATAAGTCATCTCACTTTTTGTCAAGACATTAAACCATCTTAG
ATCGGAGTGTGAAGTAAATTATGGTATATTTTATGTAACATTTTAATGTTTATGCTCATAAA
ACTTAGTGAACACACTGTGTTATGCCAGCTCAAATCTACAGTAGCCACCAAAACCATGACTT
AATATTTTGAGCCCTAGAAGAAAGGGGTGTGCTGAGGACAAGAGTGGGGAAATAGGAACACT
GACCAGTATAACTGTGCAATTCTGGAACATATTAATTAAAATAATATGCCTTAACATATAGT
GAATTTCTAATTCTAATGTTCAGTGCAATGGAAGACATTTATTTGGACAGTATACTAGCAAA
GTTGGTAGATATTTGATTCTTCATTTTTTGTTTTTTTCATTAGTTGAAGTGGGTTTTAGTTT
TGTTTAAAATTATAACCAGCGTATTTTCACATCATTCTGTAAGTTAAATGATATCAAACATG
AAAGAGATGTTCTCATTTTTCTTTTTCTGATTAAACGTCTGATGCATATCATTTTTCTATAA
GTAATCAGTTGCTTTTAAAATCAGAAGGCTATATTATTCTAATGACCCTATTCGATCTAAAT
GGGTTTGAGAATCCATATCAGCAACATACGTGTTTTTTGACAGAAAGTGAAAACAAATTCCG
TAAAACTGTTAGTATCAAAAAGAATAGGAATACAGTTTTCTTTTCCACATTATGATCAAATAAA
AATCTTGTGAGATTGTTAAAAA

FIGURE 4

```
></usr/seqdb2/sst/DNA/Dnaseqs.min/ss.DNA94849
><subunit 1 of 1, 515 aa, 1 stop
><MW: 59357, pI: 9.40, NX(S/T): 3
MVSIPEYYEGKNVLLTGATGFLGKVLLEKLLRSCPKVNSVYVLVRQKAGQTPQERVEEVL
SGKLFDRLRDENPDFREKIIAINSELTQPKLALSEEDKEVIIDSTNIIFHCAATVRFNEN
LRDAVQLNVIATRQLILLAQQMKNLEVFMHVSTAYAYCNRKHIDEVVYPPPVDPKKLIDS
LEWMDDGLVNDITPKLIGDRPNTYIYTKALAEYVVQQEGAKLNVAIVRPSIVGASWKEPF
PGWIDNFNGPSGLFIAAGKGILRTIRASNNALADLVPVDVVVNMSLAAAWYSGVNRPRNI
MVYNCTTGSTNPFHWGEVEYHVISTFKRNPLEQAFRRPNVNLTSNHLLYHYWIAVSHKAP
AFLYDIYLRMTGRSPRMMKTITRLHKAMVFLEYFTSNSWVWNTENVNMLMNQLNPEDKKT
FNIDVRQLHWAEYIENYCLGTKKYVLNEEMSGLPAARKHLNKLRNIRYGFNTILVILIWR
IFIARSQMARNIWYFVVSLCYKFLSYFRASSTMRY
```

Important features of the protein:
Transmembrane domain:
Amino acids 469-488

N-glycosylation sites:
Amino acids 283-287;304-308;341-345

Tyrosine kinase phosphorylation site:
Amino acids 160-169

N-myristoylation sites:
Amino acids 219-225;252-258;260-266;452-458

Leucine zipper pattern:
Amino acids 439-461

FIGURE 5

CGATGCCGGCGGTCAGTGGTCCAGGTCCCTTATTCTGCCTTCTCCTCCTGCTCCTGGACCCC
CACAGCCCTGAGACGGGGTGTCCTCCTCTACGCAGGTTTGAGTACAAGCTCAGCTTCAAAGG
CCCAAGGCTGGCATTGCCTGGGGCTGGAATACCCTTCTGGAGCCATCATGGAGACGCCATCC
TGGGCCTGGAGGAAGTGCGGCTGACGCCATCCATGAGGAACCGGAGTGGCGCCGTGTGGAGC
AGGGCCTCTGTCCCCTTCTCTGCCTGGGAAGTAGAGGTGCAGATGAGGGTGACGGGACTGGG
GCGCCGGGGAGCCCAGGGCATGGCCGTGTGGTACACCCGGGGCAGGGGCCATGTAGGCTCTG
TCCTTGGGGGGCTGGCTTCGTGGGACGGCATCGGGATCTTCTTTGACTCTCCGGCAGAGGAT
ACTCAGGACAGTCCTGCCATCCGTGTGCTGGCCAGCGACGGGCACATCCCCTCTGAGCAGCC
TGGGGATGGAGCTAGCCAAGGGCTGGGCTCCTGTCATTGGGACTTCCGGAACCGGCCACACT
CCTTCAGAGCACGGATCACCTACTGGGGGCAGAGGCTGCGCATGTCCTTGAACAGTGGCCTC
ACTCCCAGTGATCCAGGTGAGTTCTGTGTGGATGTGGGGCCCCTGCTTTTGGTCCCTGGAGG
TTTCTTTGGGGTCTCAGCAGCCACCGGCACCCTGGCAGGTGAGGATCCCACTGGACAGGTTC
CCCCTCAGCCCTTCCTGGAGATGCAGCAGCTCCGCCTGGCGAGGCAGCTGGAAGGGCTGTGG
GCAAGGCTGGGCTTGGGCACCAGGGAGGATGTAACTCCAAAATCAGACTCTGAAGCTCAAGG
AGAAGGGGAAAGGCTCTTTGACCTGGAGGAGACGCTGGGCAGACACCGCCGGATCCTGCAGG
CTCTGCGGGGTCTCTCCAAGCAGCTGGCCCAGGCTGAGAGACAATGGAAGAAGCAGCTGGGG
CCCCCAGGCCAAGCCAGGCCTGACGGAGGCTGGGCCCTGGATGCTTCCTGCCAGATTCCATC
CACCCCAGGGAGGGGTGGCCACCTCTCCATGTCACTCAATAAGGACTCTGCCAAGGTCGGTG
CCCTGCTCCATGGACAGTGGACTCTGCTCCAGGCCCTGCAAGAGATGAGGGATGCAGCTGTC
CGCATGGCTGCAGAAGCCCAGGTCTCCTACCTGCCTGTGGGCATTGAGCATCATTTCTTAGA
GCTGGACCACATCCTGGGCCTCCTGCAGGAGGAGCTTCGGGGCCCGGCGAAGGCAGCAGCCA
AGGCCCCCCGCCCACCTGGCCAGCCCCCAAGGGCCTCCTCGTGCCTGCAGCCTGGCATCTTC
CTGTTCTACCTCCTCATTCAGACTGTAGGCTTCTTCGGCTACGTGCACTTCAGGCAGGAGCT
GAACAAGAGCCTTCAGGAGTGTCTGTCCACAGGCAGCCTTCCTCTGGGTCCTGCACCACACA
CCCCCAGGGCCCTGGGGATTCTGAGGAGGCAGCCTCTCCCTGCCAGCATGCCTGCCTGACCC
ACCTCAGAGCCTGCTTTGCATCACTGGGAAGCAGGCAGTGTCTTGGGTGGGGGCTTGGTCAG
TATCCTCTCCGTCTGGGTGCCCAGCTCCCACGCACACCTGAGCTTTCGGCATGCTCCCACCT
CGTTAAAGGTGATTTCCCTCTCCCCAAAAAAAAAAAAAAAAAAAAAAAAAAAAAAAAAAA
AAAAAAAAAAAAAAAAAAAAAA

FIGURE 6

></usr/seqdb2/sst/DNA/Dnaseqs.min/ss.DNA96883
><subunit 1 of 1, 514 aa, 1 stop
><MW: 55687, pI: 8.78, NX(S/T): 2
MPAVSGPGPLFCLLLLLLDPHSPETGCPPLRRFEYKLSFKGPRLALPGAGIPFWSHHGDA
ILGLEEVRLTPSMRNRSGAVWSRASVPFSAWEVEVQMRVTGLGRRGAQGMAVWYTRGRGH
VGSVLGGLASWDGIGIFFDSPAEDTQDSPAIRVLASDGHIPSEQPGDGASQGLGSCHWDF
RNRPHSFRARITYWGQRLRMSLNSGLTPSDPGEFCVDVGPLLLVPGGFFGVSAATGTLAG
EDPTGQVPPQPFLEMQQLRLARQLEGLWARLGLGTREDVTPKSDSEAQGEGERLFDLEET
LGRHRRILQALRGLSKQLAQAERQWKKQLGPPGQARPDGGWALDASCQIPSTPGRGGHLS
MSLNKDSAKVGALLHGQWTLLQALQEMRDAAVRMAAEAQVSYLPVGIEHHFLELDHILGL
LQEELRGPAKAAAKAPRPPGQPPRASSCLQPGIFLFYLLIQTVGFFGYVHFRQELNKSLQ
ECLSTGSLPLGPAPHTPRALGILRRQPLPASMPA

Important features of the protein:
Signal peptide:
Amino acids 1-23

Transmembrane domain:
Amino acids 215-232;450-465

N-glycosylation sites:
Amino acids 75-79;476-480

Glycosaminoglycan attachment site:
Amino acids 5-9

N-myristoylation sites:
Amino acids 78-84;122-128;126-132;168-174;172-178;
205-211;226-232;230-236;236-242;356-362

Amidation site:
Amino acids 102-106

FIGURE 7

GCCCCCAGCATGGCTTGGCAGGGCTGGCCCGCGGCGTGGCAGTGGGTCGCCGGCTGCTGGCT
CCTCCTCGTCCTTGTCCTCGTCCTACTTGTGAGCCCCCGCGGCTGCCGAGCGCGGCGGGGCC
TCCGCGGTCTGCTCATGGCGCACAGCCAGCGGCTGCTCTTCCGAATCGGGTACAGCCTGTAC
ACCCGCACCTGGCTCGGGTACCTCTTCTACCGACAGCAGCTGCGCAGGGCTCGGAATCGCTAC
CCTAAAGGCCACTCGAAAACCCAGCCCCGCCTCTTCAATGGAGTGAAGGTGCTTCCCATCCC
TGTCCTCTCGGACAACTACAGCTACCTCATCATCGACACCCAGGCCCAGCTGGCTGTGGCTG
TGGACCCTTCAGACCCTCGGGCTGTGCAGGCTTCCATTGAAAAGGAAGGGGTCACCTTGGTC
GCCATTCTGTGTACTCACAAGCACTGGGACCACAGTGGAGGGAACCGTGACCTCAGCCGGCG
GCACCGGGACTGTCGGGTGTACGGGAGCCCTCAGGACGGCATCCCCTACCTCACCCATCCCC
TGTGTCATCAAGATGTGGTCAGCGTGGGACGGCTTCAGATCCGGGCCCTGGCTACACCTGGC
CACACACAAGGCCATCTGGTCTACCTACTGGATGGGGAGCCCTACAAGGGTCCCTCCTGCCT
CTTCTCAGGGGACCTGCTCTTCCTCTCTGGCTGTGGGCGGACCTTTGAGGGCAATGCAGAGA
CCATGCTGAGCTCACTGGACACTGTGCTGGGGCTAGGGGATGACACCCTTCTGTGGCCTGGT
CATGAGTATGCAGAGGAGAACCTGGGCTTTGCAGGTGTGGTGGAGCCCGAGAACCTGGCCCG
GGAGAGGAAGATGCAGTGGGTGCAGCGGCAGCGGCTGGAGCGCAAGGGCACGTGCCCATCTA
CCCTGGGAGAGGAGCGCTCCTACAACCCGTTCCTGAGAACCCACTGCCTGGCGCTACAGGAG
GCTCTGGGGCCGGGGCCGGGCCCCACTGGGGATGATGACTACTCCCGGGCCCAGCTCCTGGA
AGAGCTCCGCCGGCTGAAGGATATGCACAAGAGCAAGTGATGCCCCCAGCGCCCCCAGCCCA
GCCCACTCCCCGCATGGGGAGGCCGCCACCACCAACACCTCATCATCCTTCTCATCGCTAAC
ACCACCACCTCCATCGGCACCCAAGCGGGCATCATCCCCCCACACTGCTCAGGGGAGGGGAG
GGATCAGGCGATGAGACTGTGAGGCCAAAAGAAGGGGGCCTGTTGGAGGCTGGGAACCCCGC
AGCGCGAGGCTGCCTCATCAACGGCAAGAGGAAAGGAGGGGTCTCGGGACATCTCCAGACCC
TACCAACTGGGAGGGTCCCCTCCTCCTTCCCTACTCCTGGGACGGCAGCAAGGACATGGGGG
CTGCTGTTAGCTTCTCCGTCAGGAGGCCTCATCTCACTGTAGCCCTGGAACCCAGGGTCCAT
CTTGCCCTTCCCCCATCCATGGTTGGGAAAGAAGCTCAGCCCCTCACAGTGGCCTCAAGTGT
GATGCCTTACAAAAGCACCACTCAGATGGGCAGCTGGACTCTGGTGTCCTGAGACTCTGCCC
TCTTCCCACAGCCTCCCTGCCCCACCCATCCCTGCAAAGCCATTTTTCAGACAGAGCCATTC
CTAAGAACACTGAAGGGCTGGAATGCTGGCTGGCCACTCTCTGCCTCAGTGGCCTCCCTACA
GCCTGGAAGAAGGAGGGTCCTGATTGCCAAGGAAACCTCCTCATTGGGCTAAGGAGACACTG
GAGTCTGGAGTGTGGAGCCCCACAGTCTTGCAGGTCACATGCTCTCCTTGCACATCTGGCCT
GGTTGTACCCACTGGCCTCTGCCTCTGCCCTGGGCCAAAAGGGCCCCTCCTTGCCAGGGGAG
AGACAGCCACGGTCCTCTTTGGCCGATGCTGTATTCTCATTTTGGCCCTTGTTCTTAGGCCC
GTCTGCCCGCCCTCCTCCATCTAACCTTTCCTGTTTTATCCGCAGCCCTTTTCTTCTTTGAG
TTAGTAAAGATTTATTCTGTAACCTGACACTCATCTGGCCCTTTGCAGTTTGCCAGCCATATTC
CCATGTGATTTCCCACTGGATCCAGGCCCCCATCCGGCTGGCAGGAGGGGGCTCTGACGTAC
AGGTTGGAAATCAGAAGTCTGTGAGAGCGCGGGAGTGCATGGCAGCTCTGGGTCCCAGACCT
GGCCCGACCCCTCTGCTTCACCTCCAGCTCTGCTGCTCCTCTACTCTTGGGTCGAGATCCCT
TTGGAGCCACAGCGAGGAACCCTGTGGTCCTCAGGCAGGTGTACCTTGAGTCAGCCAGGAGC
CCTCTTTTCCTGTGTCAAAGCCTGCCCTCGGGCTCTGCTCACCTCTGGTGACCCTCCAAGAT
GCCCCTGCCCTCAGTTTCCCCTCATGATCTGGCCTCTGCCCCCTTCTCTAGCCACAGCCTCT
AGTACACTTTAGCAATACCACCAGACTAGTTAGAGTTCCCCACTCACCAAGCAAGACATGCA
GTTTCATGCCTCTGTGCCTTCGCTCATGCTGTTTCTTCCGACTGGAATGCCTTCCCCTGCTC
CTCCTGCCTTGTCTGCCTGGCAAGTTCATCTCTCACGATCCCCTCAAAGGCCCCCTCCTCCA
GGAAGGCAACCCCTGTGCCCCTCCCCTCCAGGCTACCTCTGCACTTTGTCAATGCTTCTCTT
GTGGCACTTATCACACTGTATTTTACTTGTTTACATGTTTGTCTCCCCTTCTAGACTGTGAA
TCCTTAAGGGCATGGACTGTATCTTATGCATCTCTGTATTTCTGCGCCTAGCACGGTGCCTA
GCACACAGTAGGCGCTCAATAAATGTTGAATGAATGAAAAAAAAAAAAAAAAAAAAAAAAAA
AAAAAAAAAAAAAAAAAAAAAAAAAAAAAAAAAAAAAAAAAAAAAAAAAAAAAAAAAAAAAA
AAAAAAAAAAAAAAAAAAAAAAAAAAAAAA

FIGURE 8

></usr/seqdb2/sst/DNA/Dnaseqs.min/ss.DNA96894
><subunit 1 of 1, 361 aa, 1 stop
><MW: 40747, pI: 9.20, NX(S/T): 1
MAWQGWPAAWQWVAGCWLLLVLVLVLLVSPRGCRARRGLRGLLMAHSQRLLFRIGYSLYT
RTWLGYLFYRQQLRRARNRYPKGHSKTQPRLFNGVKVLPIPVLSDNYSYLIIDTQAQLAV
AVDPSDPRAVQASIEKEGVTLVAILCTHKHWDHSGGNRDLSRRHRDCRVYGSPQDGIPYL
THPLCHQDVVSVGRLQIRALATPGHTQGHLVYLLDGEPYKGPSCLFSGDLLFLSGCGRTF
EGNAETMLSSLDTVLGLGDDTLLWPGHEYAEENLGFAGVVEPENLARERKMQWVQRQRLE
RKGTCPSTLGEERSYNPFLRTHCLALQEALGPGPGPTGDDDYSRAQLLEELRRLKDMHKS
K

Important features of the protein:
Signal peptide:
Amino acids 1-35

N-glycosylation site:
Amino acids 106-110

Glycosaminoglycan attachment site:
Amino acids 234-238 cAMP- and cGMP-dependent protein kinase phosphorylation site:
Amino acids 301-305

Tyrosine kinase phosphorylation site:
Amino acids 162-171

N-myristoylation sites:
Amino acids 41-47;235-241;242-248;303-309

Prokaryotic membrane lipoprotein lipid attachment site:
Amino acids 6-17 cAMP phosphodiesterases class-II proteins:
Amino acids 144-161

FIGURE 9

GCTGACAATCCCCTTGACGTTCTATCCCGGAAGCTCCACCTGGGGCCCAATGTTGGGCGTGA
TGTTCCTCGCCTGTCTCTGCCTGGAAAACTGGTCTTCCCAAGCTCCACTGGCAGCCACTTCT
CCATGTTGGGCATCGGAGACATCGTTATGCCTGGTCTCCTACTATGCTTTGTCCTTCGCTAT
GACAACTACAAAAAGCAAGCCAGTGGGGACTCCTGTGGGGCCCCTGGACCTGCCAACATCTC
CGGGCGCATGCAGAAGGTCTCCTACTCTCACTGCACCCTCATCGGATACTTTGTAGGCCTGC
TCACTGCTACTGTGGCGTCTCGCATTCACCGGGCCGCCCAGCCCGCCCTTCTCTATTTGGTG
CCATTTACTTTATTGCCACTCCTCACGATGGCCTATTTAAAGGGCGACCTCCGGCGGATGTG
GTCTGAGCCTTTCCACTCCAAGTCCAGCAGCTCCCGATTCCTGGAAGTATGATGGATCACGT
GGAAAGTGACCAGATGGCCGTCATAGTCCTTTTCTCTCAACTCATGGTTTGTTTCCTCTTAG
AGCTGGCCTGGTACTCAGAAATGTACCTGTGTTTAAGGAACTGCCGTGTGACTGGATTTGGC
ATTGAAAGGGAGCTCGTTTGCAGGAGAGAGGTGCTGGAGCCCTGTTTGGTTCCTTCTCTTCC
TGCGGATGTAGAGGTGGGGCCCCTTCCAAGAGGGACAGGCCTCTCCCCAGCGCGCCTTCCTC
CCACGTTTTTATGGATCTGCACCAGACTGTTACCTTCTGGGGGAGATGGAGATTTGACTGTT
TAAAAACTGAAAACAGCGAGGAGTCTTTCTAGAACTTTTGAACACTAAAAGGATGAAAAAAT
TAGC

FIGURE 10

></usr/seqdb2/sst/DNA/Dnaseqs.min/ss.DNA100272
><subunit 1 of 1, 108 aa, 1 stop
><MW: 12055, pI: 4.69, NX(S/T): 0
MMDHVESDQMAVIVLFSQLMVCFLLELAWYSEMYLCLRNCRVTGFGIERELVCRREVLEP
CLVPSLPADVEVGPLPRGTGLSPARLPPTFLWICTRLLPSGGDGDLTV

Important features of the protein:
Signal peptide:
Amino acids 1-30

N-myristoylation site:
Amino acids 80-86

FIGURE 11

TCGCACACTGGTGGCTTCAGAAGAAATTCTCAACACCTAGCTCGCCAGAGAGTCTATGTATG
GGATTGAACAATCTGTAAACTAAAGGATCCTAATCATGAAAATAAGTATGATAAATTATAAG
TCACTATTGGCACTGTTGTTTATATTAGCCTCCTGGATCATTTTTACAGTTTTCCAGAACTC
CACAAAGGTTTGGTCTGCTCTAAACTTATCCATCTCCCTCCATTACTGGAACAACTCCACAA
AGTCCTTATTCCCTAAAACACCACTGATATCATTAAAGCCACTAACAGAGACTGAACTCAGA
ATAAAGGAAATCATAGAGAAACTAGATCAGCAGATCCCACCCAGACCTTTCACCCACGTGAA
CACCACCACCAGCGCCACACATAGCACAGCCACCATCCTCAACCCTCGAGATACGTACTGCA
GGGGAGACCAGCTGCACATCCTGCTGGAGGTGAGGGACCACTTGGGACGCAGGAAGCAATAT
GGCGGGGATTTCCTGAGGGCCAGGATGTCTTCCCCAGCGCTGATGGCAGGTGCTTCAGGAAA
GGTGACTGACTTCAACAACGGCACCTACCTGGTCAGCTTCACTCTGTTCTGGGAGGGCCAGG
TCTCTCTGTCTCTGCTGCTCATCCACCCCAGTGAAGGGGTGTCAGCTCTCTGGAGTGCAAGG
AACCAAGGCTATGACAGGGTGATCTTCACTGGCCAGTTTGTCAATGGCACTTCCCAAGTCCA
CTCTGAATGTGGCCTGATCCTAAACACAAATGCTGAATTGTGCCAGTACCTGGACAACAGAG
ACCAAGAAGGCTTCTACTGTGTGAGGCCTCAACACATGCCCTGTGCTGCACTCACTCACATG
TATTCTAAGAACAAGAAAGTTTCTTATCTTAGCAAACAAGAAAAGAGCCTCTTTGAAAGGTC
AAATGTGGGTGTAGAGATTATGGAAAAATTCAATACAATTAGTGTCTCCAAATGCAACAAAG
AAACAGTTGCAATGAAAGAGAAATGCAAGTTTGGAATGACATCCACAATCCCCAGTGGGCAT
GTCTGGAGAAACACATGGAATCCTGTCTCCTGTAGTTTGGCTACAGTCAAAATGAAGGAATGC
CTGAGAGGAAAACTCATATACCTAATGGGAGATTCCACGATCCGCCAGTGGATGGAATACTT
CAAAGCCAGTATCAACACACTGAAGTCAGTGGATCTGCATGAATCTGGAAAATTGCAACACC
AGCTTGCTGTGGATTTGGATAGGAACATCAACATCCAGTGGCAAAAATATTGTTATCCCTTG
ATAGGATCAATGACCTATTCAGTCAAAGAGATGGAGTACCTCACCCGGGCCATTGACAGAAC
TGGAGGAGAAAAAAATACTGTCATTGTTATTTCCCTGGGCCAGCATTTCAGACCCTTTCCCA
TTGATGTTTTTATCCGAAGGGCCCTCAATGTCCACAAAGCCATTCAGCATCTTCTTCTGAGA
AGCCCAGACACTATGGTTATCATCAAAACAGAAAACATCAGGGAGATGTACAATGATGCAGA
AAGATTTAGTGACTTTCATGGTTACATTCAATATCTCATCATAAAGGACATTTTCCAGGATC
TCAGTGTGAGTATCATTGATGCCTGGGATATAACAATTGCATATGGCACAAATAATGTACAC
CCACCTCAACATGTAGTCGGAAATCAGATTAATATATTATTAAACTATATTTGTTAAATAACAA

FIGURE 12

></usr/seqdb2/sst/DNA/Dnaseqs.min/ss.DNA108696
><subunit 1 of 1, 544 aa, 1 stop
><MW: 62263, pI: 9.17, NX(S/T): 7
MKISMINYKSLLALLFILASWIIFTVFQNSTKVWSALNLSISLHYWNNSTKSLFPKTPLI
SLKPLTETELRIKEIIEKLDQQIPPRPFTHVNTTTSATHSTATILNPRDTYCRGDQLHIL
LEVRDHLGRRKQYGGDFLRARMSSPALMAGASGKVTDFNNGTYLVSFTLFWEGQVSLSLL
LIHPSEGVSALWSARNQGYDRVIFTGQFVNGTSQVHSECGLILNTNAELCQYLDNRDQEG
FYCVRPQHMPCAALTHMYSKNKKVSYLSKQEKSLFERSNVGVEIMEKFNTISVSKCNKET
VAMKEKCKFGMTSTIPSGHVWRNTWNPVSCSLATVKMKECLRGKLIYLMGDSTIRQWMEY
FKASINTLKSVDLHESGKLQHQLAVDLDRNINIQWQKYCYPLIGSMTYSVKEMEYLTRAI
DRTGGEKNTVIVISLGQHFRPFPIDVFIRRALNVHKAIQHLLLRSPDTMVIIKTENIREM
YNDAERFSDFHGYIQYLIIKDIFQDLSVSIIDAWDITIAYGTNNVHPPQHVVGNQINILL
NYIC

Important features of the protein:

Signal peptide:
Amino acids 1-22

N-glycosylation sites:
Amino acids 29-33;38-42;47-51;48-52;92-96;160-164;210-214 cAMP- and cGMP-dependent protein kinase phosphorylation site:
Amino acids 262-266

Tyrosine kinase phosphorylation site:
Amino acids 236-243;486-494

N-myristoylation sites:
Amino acids 206-212;220-226;310-316;424-430;533-539

Amidation site:
Amino acids 127-131

Cell attachment sequence:
Amino acids 113-116

FIGURE 13

GCAAAGAGAAGACTGAAAGACAAACCTGGGTGCAGCCAGAGAGGTCCAGATAGATGAGCTTG
TGGCATCCATTCCCCAAGTTCAGCCTAGGGACTCCACGTACCCCAGCTGGGTCTCATTGTTC
CAGAACTGCATTAGTTAAGATTACCCAGACTTGGATTTCAAAGGAATACTTTCATTGTTCCG
TCTGTAACACGAAGTAATTGGGGCCAGCTGGATGTCAGG<u>ATG</u>CGTGTGGTTACCATTGTAAT
CTTGCTCTGCTTTTGCAAAGCGGCTGAGCTGCGCAAAGCAAGCCCAGGCAGTGTGAGAAGCC
GAGTGAATCATGGCCGGGCGGGTGGAGGCCGGAGAGGCTCCAACCCGGTCAAACGCTACGCA
CCAGGCCTCCCGTGTGACGTGTACACATATCTCCATGAGAAATACTTAGATTGTCAAGAAAG
AAAATTAGTTTATGTGCTGCCTGGTTGGCCTCAGGATTTGCTGCACATGCTGCTAGCAAGAA
ACAAGATCCGCACATTGAAGAACAACATGTTTTCCAAGTTTAAAAAGCTGAAAAGCCTGGAT
CTGCAGCAGAATGAGATCTCTAAAATTGAGAGTGAGGCGTTCTTTGGTTTAAACAAACTCAC
CACCCTCTTACTGCAGCACAACCAGATCAAAGTCTTGACGGAGGAAGTGTTCATTTACACAC
CTCTCTTGAGCTACCTGCGTCTTTATGACAACCCCTGGCACTGTACTTGTGAGATAGAAACG
CTTATTTCAATGTTGCAGATTCCCAGGAACCGGAATTTGGGGAACTACGCCAAGTGTGAAAG
TCCACAAGAACAAAAAAATAAAAAACTGCGGCAGATAAAATCTGAACAGTTGTGTAATGAAG
AAAAGGAACAATTGGACCCGAAACCCCAAGTGTCAGGGAGACCCCCAGTCATCAAGCCTGAG
GTGGACTCAACTTTTTGCCACAATTATGTGTTTCCCATACAAACACTGGACTGCAAAAGGAA
AGAGTTGAAAAAAGTGCCAAACAACATCCCTCCAGATATTGTTAAACTTGACTTGTCATACA
ATAAAATCAACCAACTTCGACCCAAGGAATTTGAAGATGTTCATGAGCTGAAGAAATTAAAC
CTCAGCAGCAATGGCATTGAATTCATCGATCCTGCCGCTTTTTTAGGGCTCACACATTTAGA
AGAATTAGATTTATCAAACAACAGTCTGCAAAACTTTGACTATGGCGTATTAGAAGACTTGT
ATTTTTTGAAACTCTTGTGGCTCAGAGATAACCCTTGGAGATGTGACTACAACATTCACTAC
CTCTACTACTGGTTAAAGCACCACTACAATGTCCATTTTAATGGCCTGGAATGCAAAACGCCT
GAAGAATACAAAGGATGGTCTGTGGGAAAATATATTAGAAGTTACTATGAAGAATGCCCCAA
AGACAAGTTACCAGCATATCCTGAGTCATTTGACCAAGACACAGAAGATGATGAATGGGAAA
AAAAACATAGAGATCACACCGCAAAGAAGCAAAGCGTAATAATTACTATAGTAGGA<u>TAA</u>GGT
AGAAATTGTTCTGATTGTAATTAGTTTTGTATTTTCTATACTGGTGTTAGAAAACATATGTT
TACATTTGATTAACTGTGTTGCCTATTTATGCAGGGTAATCCAGCTAAAGGAAGCTTTCTTT
AATTATAAGTATTATTGTGACTATTATAGTAATCAAGAGAATGCTATCATCCTGCTTGCCTG
TCCATTTGTGGAACAGCATCTGGTGATATGCAATTCCACACTGGTAACCTGCAGCAGTTGGG
TCCTAATGATGGCATTAGACTTTCATAATGTCCTGTATAAATGTTTTTACTGCTTTTAGAAA
ATAAAGAAAAAAAACTTGGTTCATGTTTAAAA

FIGURE 14

></usr/seqdb2/sst/DNA/Dnaseqs.min/ss.DNA117935
><subunit 1 of 1, 440 aa, 1 stop
><MW: 51670, pI: 8.70, NX(S/T): 2
MRVVTIVILLCFCKAAELRKASPGSVRSRVNHGRAGGGRRGSNPVKRYAPGLPCDVYTYL
HEKYLDCQERKLVYVLPGWPQDLLHMLLARNKIRTLKNNMFSKFKKLKSLDLQQNEISKI
ESEAFFGLNKLTTLLLQHNQIKVLTEEVFIYTPLLSYLRLYDNPWHCTCEIETLISMLQI
PRNRNLGNYAKCESPQEQKNKKLRQIKSEQLCNEEKEQLDPKPQVSGRPPVIKPEVDSTF
CHNYVFPIQTLDCKRKELKKVPNNIPPDIVKLDLSYNKINQLRPKEFEDVHELKKLNLSS
NGIEFIDPAAFLGLTHLEELDLSNNSLQNFDYGVLEDLYFLKLLWLRDNPWRCDYNIHYL
YYWLKHHYNVHFNGLECKTPEEYKGWSVGKYIRSYYEECPKDKLPAYPESFDQDTEDDEW
EKKHRDHTAKKQSVIITIVG

Important features of the protein:

Signal peptide:
Amino acids 1-15

N-glycosylation sites:
Amino acids 297-301;324-328 cAMP- and cGMP-dependent protein kinase phosphorylation sites:
Amino acids 19-23;39-43;430-434

N-myristoylation sites:
Amino acids 24-30;37-43

Amidation site:
Amino acids 37-41

FIGURE 15

GCGGCAGCAGCGCGGGCCCCAGCAGCCTCGGCAGCCACAGCCGCTGCAGCCGGGGCAGCCTC
CGCTGCTGTCGCCTCCTCTGATGCGCTTGCCCTCTCCCGGCCCCGGGACTCCGGGAGAATGT
GGGTCCTAGGCATCGCGGCAACTTTTTGCGGATTGTTCTTGCTTCCAGGCTTTGCGCTGCAA
ATCCAGTGCTACCAGTGTGAAGAATTCCAGCTGAACAACGACTGCTCCTCCCCCGAGTTCAT
TGTGAATTGCACGGTGAACGTTCAAGACATGTGTCAGAAAGAAGTGATGGAGCAAAGTGCCG
GGATCATGTACCGCAAGTCCTGTGCATCATCAGCGGCCTGTCTCATCGCCTCTGCCGGGTAC
CAGTCCTTCTGCTCCCCAGGGAAACTGAACTCAGTTTGCATCAGCTGCTGCAACACCCCTCT
TTGTAACGGGCCAAGGCCCAAGAAAAGGGGAAGTTCTGCCTCGGCCCTCAGGCCAGGGCTCC
GCACCACCATCCTGTTCCTCAAATTAGCCCTCTTCTCGGCACACTGCTGAAGCTGAAGGAGA
TGCCACCCCCTCCTGCATTGTTCTTCCAGCCCTCGCCCCCAACCCCCCACCTCCCTGAGTGA
GTTTCTTCTGGGTGTCCTTTTATTCTGGGTAGGGAGCGGGAGTCCGTGTTCTCTTTTGTTCC
TGTGCAAATAATGAAAGAGCTCGGTAAAGCATTCTGAATAAATTCAGCCTGACTGAATTTTC
AGTATGTACTTGAAGGAAGGAGGTGGAGTGAAAGTTCACCCCCATGTCTGTGTAACCGGAGT
CAAGGCCAGGCTGGCAGAGTCAGTCCTTAGAAGTCACTGAGGTGGGCATCTGCCTTTTGTAA
AGCCTCCAGTGTCCATTCCATCCCTGATGGGGGCATAGTTTGAGACTGCAGAGTGAGAGTGA
CGTTTTCTTAGGGCTGGAGGGCCAGTTCCCACTCAAGGCTCCCTCGCTTGACATTCAAACTT
CATGCTCCTGAAAACCATTCTCTGCAGCAGAATTGGCTGGTTTCGCGCCTGAGTTGGGCTCT
AGTGACTCGAGACTCAATGACTGGGACTTAGACTGGGGCTCGGCCTCGCTCTGAAAAGTGCT
TAAGAAAATCTTCTCAGTTCTCCTTGCAGAGGACTGGCGCCGGGACGCGAAGAGCAACGGGC
GCTGCACAAAGCGGGCGCTGTCGGTGGTGGAGTGCGCATGTACGCGCAGGCGCTTCTCGTGG
TTGGCGTGCTGCAGCGACAGGCGGCAGCACAGCACCTGCACGAACACCCGCCGAAACTGCTG
CGAGGACACCGTGTACAGGAGCGGGTTGATGACCGAGCTGAGGTAGAAAAACGTCTCCGAGA
AGGGGAGGAGGATCATGTACGCCCGGAAGTAGGACCTCGTCCAGTCGTGCTTGGGTTTGGCC
GCAGCCATGATCCTCCGAATCTGGTTGGGCATCCAGCATACGGCCAATGTCACAACAATCAG
CCCTGGGCAGACACGAGCAGGAGGGAGAGACAGAGA

FIGURE 16

></usr/seqdb2/sst/DNA/Dnaseqs.min/ss.DNA119474
><subunit 1 of 2, 141 aa, 1 stop
><MW: 15240, pI: 8.47, NX(S/T): 1
MWVLGIAATFCGLFLLPGFALQIQCYQCEEFQLNNDCSSPEFIVNCTVNVQDMCQKEVME
QSAGIMYRKSCASSAACLIASAGYQSFCSPGKLNSVCISCCNTPLCNGPRPKKRGSSASA
LRPGLRTTILFLKLALFSAHC

Important features of the protein:
Signal peptide:
Amino acids 1-22

N-glycosylation site:
Amino acids 45-49 cAMP- and cGMP-dependent protein kinase phosphorylation site:
Amino acids 113-117

N-myristoylation sites:
Amino acids 5-11;115-121;124-130

Ly-6 / u-PAR domain proteins:
Amino acids 94-107

FIGURE 17

CGCAAAGCCGCCCTCGGGGCGCTCATGGCGGGACGCCTCCTGGGAAAGGCTTTAGCCGCGGT
GTCTCTCTCTCTGGCCTTGGCCTCTGTGACTATCAGGTCCTCGCGCTGCCGCGGCATCCAGG
CGTTCAGAAACTCGTTTTCATCTTCTTGGTTTCATCTTAATACCAACGTCATGTCTGGTTCT
AATGGTTCCAAAGAAAATTCTCACAATAAGGCTCGGACGTCTCCTTACCCAGGTTCAAAAGT
TGAACGAAGCCAGGTTCCTAATGAGAAAGTGGGCTGGCTTGTTGAGTGGCAAGACTATAAGC
CTGTGGAATACACTGCAGTCTCTGTCTTGGCTGGACCCAGGTGGGCAGATCCTCAGATCAGT
GAAAGTAATTTTTCTCCCAAGTTTAACGAAAAGGATGGGCATGTTGAGAGAAAGAGCAAGAA
TGGCCTGTATGAGATTGAAAATGGAAGACCGAGAAATCCTGCAGGACGGACTGGACTGGTGG
GCCGGGGGCTTTTGGGGCGATGGGGCCCAAATCACGCTGCAGATCCCATTATAACCAGATGG
AAAAGGGATAGCAGTGGAAATAAAATCATGCATCCTGTTTCTGGGAAGCATATCTTACAATT
TGTTGCAATAAAAAGGAAAGACTGTGGAGAATGGGCAATCCCAGGGGGGATGGTGGATCCAGGA
GAGAAGATTAGTGCCACACTGAAAAGAGAATTTGGTGAGGAAGCTCTCAACTCCTTACAGAA
AACCAGTGCTGAGAAGAGAGAAATAGAGGAAAAGTTGCACAAACTCTTCAGCCAAGACCACC
TAGTGATATATAAGGGATATGTTGATGATCCTCGAAACACTGATAATGCATGGATGGAGACA
GAAGCTGTGAACTACCATGACGAAACAGGTGAGATAATGGATAATCTTATGCTAGAAGCTGG
AGATGATGCTGGAAAAGTGAAATGGGTGGACATCAATGATAAACTGAAGCTTTATGCCAGTC
ACTCTCAATTCATCAAACTTGTGGCTGAGAAACGAGATGCACACTGGAGCGAGGACTCTGAA
GCTGACTGCCATGCGTTGTAGCTGATGGTCTCCGTGTAAGCCAAAGGCCCACAGAGGAGCAT
ATACTGAAAAGAAGGCAGTATCACAGAATTTATACTATAAAAAGGGCAGGGTAGGCCACTTG
GCCTATTTACTTTCAAAACAATTTGCATTTAGAGTGTTTCGCATCAGAATAACATGAGTAAG
ATGAACTGGAACACAAAATTTTCAGCTCTTTGGTCAAAAGGAATATAAGTAATCATATTTTG
TATGTATTCGATTTAAGCATGGCTTAAATTAAATTTAAACAACTAATGCTCTTTGAAGAATC
ATAATCAGAATAAAGATAAATTCTTGATCAGCTATA

FIGURE 18

></usr/seqdb2/sst/DNA/Dnaseqs.min/ss.DNA119498
><subunit 1 of 1, 350 aa, 1 stop
><MW: 39125, pI: 8.53, NX(S/T): 2
MAGRLLGKALAAVSLSLALASVTIRSSRCRGIQAFRNSFSSSWFHLNTNVMSGSNGSKEN
SHNKARTSPYPGSKVERSQVPNEKVGWLVEWQDYKPVEYTAVSVLAGPRWADPQISESNF
SPKFNEKDGHVERKSKNGLYEIENGRPRNPAGRTGLVGRGLLGRWGPNHAADPIITRWKR
DSSGNKIMHPVSGKHILQFVAIKRKDCGEWAIPGGMVDPGEKISATLKREFGEEALNSLQ
KTSAEKREIEEKLHKLFSQDHLVIYKGYVDDPRNTDNAWMETEAVNYHDETGEIMDNLML
EAGDDAGKVKWVDINDKLKLYASHSQFIKLVAEKRDAHWSEDSEADCHAL

Important features of the protein:
Signal peptide:
Amino acids 1-20

N-glycosylation site:
Amino acids 55-59 cAMP- and cGMP-dependent protein kinase phosphorylation site:
Amino acids 179-183

N-myristoylation sites:
Amino acids 53-59;56-62 mutT domain signature:
Amino acids 215-235

FIGURE 19

CGAGGGCTCCTGCTGGTACTGTGTTCGCTGCTGCACAGCAAGGCCCTGCCACCCACCTTCAG
GCCATGCAGCCATGTTCCGGGAGCCCTAATTGCACAGAAGCCCATGGGGAGCTCCAGACTGG
CAGCCCTGCTCCTGCCTCTCCTCCTCATAGTCATCGACCTCTCTGACTCTGCTGGGATTGGC
TTTCGCCACCTGCCCCACTGGAACACCCGCTGTCCTCTGGCCTCCCACACGGATGACAGTTT
CACTGGAAGTTCTGCCTATATCCCTTGCCGCACCTGGTGGGCCCTCTTCTCCACAAAGCCTT
GGTGTGTGCGAGTCTGGCACTGTTCCCGCTGTTTGTGCCAGCATCTGCTGTCAGGTGGCTCA
GGTCTTCAACGGGGCCTCTTCCACCTCCTGGTGCAGAAATCCAAAAAGTCTTCCACATTCAA
GTTCTATAGGAGACACAAGATGCCAGCACCTGCTCAGAGGAAGCTGCTGCCTCGTCGTCACC
TGTCTGAGAAGAGCCATCACATTTCCATCCCCTCCCCAGACATCTCCCACAAGGGACTTCGC
TCTAAAAGGACCCAACCTTCGGATCCAGAGACATGGGAAAGTCTTCCCAGATTGGACTCACA
AAGGCATGGAGGACCCGAGTTCTCCTTTGATTTGCTGCCTGAGGCCCGGGCTATTCGGGTGA
CCATATCTTCAGGCCCTGAGGTCAGCGTGCGTCTTTGTCACCAGTGGGCACTGGAGTGTGAA
GAGCTGAGCAGTCCCTATGATGTCCAGAAAATTGTGTCTGGGGGCCACACTGTAGAGCTGCC
TTATGAATTCCTTCTGCCCTGTCTGTGCATAGAGGCATCCTACCTGCAAGAGGACACTGTGA
GGCGCAAAAAATGTCCCTTCCAGAGCTGGCCAGAAGCCTATGGCTCGGACTTCTGGAAGTCA
GTGCACTTCACTGACTACAGCCAGCACACTCAGATGGTCATGGCCCTGACACTCCGCTGCCC
ACTGAAGCTGGAAGCTGCCCTCTGCCAGAGGCACGACTGGCATACCCTTTGCAAAGACCTCC
CGAATGCCACGGCTCGAGAGTCAGATGGGTGGTATGTTTTGGAGAAGGTGGACCTGCACCCC
CAGCTCTGCTTCAAGTTCTCTTTTGGAAACAGCAGCCATGTTGAATGCCCCCACCAGACTGG
GTCTCTCACATCCTGGAATGTAAGCATGGATACCCAAGCCCAGCAGCTGATTCTTCACTTCT
CCTCAAGAATGCATGCCACCTTCAGTGCTGCCTGGAGCCTCCCAGGCTTGGGGCAGGACACT
TTGGTGCCCCCCGTGTACACTGTCAGCCAGGCCCGGGGCTCAAGCCCAGTGTCACTAGACCT
CATCATTCCCTTCCTGAGGCCAGGGTGCTGTGTCCTGGTGTGGCGGTCAGATGTCCAGTTTG
CCTGGAAGCACCTCTTGTGTCCAGATGTCTCTTACAGACACCTGGGGCTCTTGATCCTGGCA
CTGCTGGCCCTCCTCACCCTACTGGGTGTTGTTCTGGCCCTCACCTGCCGGCGCCCACAGTC
AGGCCCGGGCCCAGCGCGGCCAGTGCTCCTCCTGCACGCGGCGGACTCGGAGGCGCAGCGGC
GCCTGGTGGGAGCGCTGGCTGAACTGCTACGGGCAGCGCTGGGCGGCGGGCGCGACGTGATC
GTGGACCTGTGGGAGGGGAGGCACGTGGCGCGCGTGGGCCCGCTGCCGTGGCTCTGGGCGGC
GCGGACGCGCGTAGCGCGGGAGCAGGGCACTGTGCTGCTGCTGTGGAGCGGCGCCGACCTTC
GCCCGGTCAGCGGCCCCGACCCCCGCGCCGCGCCCCTGCTCGCCCTGCTCCACGCTGCCCCG
CGCCCGCTGCTGCTGCTCGCTTACTTCAGTCGCCTCTGCGCCAAGGGCGACATCCCCCCGCC
GCTGCGCGCCCTGCCGCGCTACCGCCTGCTGCGCGACCTGCCGCGTCTGCTGCGGGCGCTGG
ACGCGCGGCCTTTCGCAGAGGCCACCAGCTGGGGCCGCCTTGGGGCGCGGCAGCGCAGGCAG
AGCCGCCTAGAGCTGTGCAGCCGGCTTGAACGAGAGGCCGCCCGACTTGCAGACCTAGGTTG
AGCAGAGCTCCACCGCAGTCCCGGGTGTCT

FIGURE 20

></usr/seqdb2/sst/DNA/Dnaseqs.min/ss.DNA119502
><subunit 1 of 1, 667 aa, 1 stop
><MW: 74810, pI: 9.55, NX(S/T): 3
MGSSRLAALLLPLLLIVIDLSDSAGIGFRHLPHWNTRCPLASHTDDSFTGSSAYIPCRTW
WALFSTKPWCVRVWHCSRCLCQHLLSGGSGLQRGLFHLLVQKSKKSSTFKFYRRHKMPAP
AQRKLLPRRHLSEKSHHISIPSPDISHKGLRSKRTQPSDPETWESLPRLDSQRHGGPEFS
FDLLPEARAIRVTISSGPEVSVRLCHQWALECEELSSPYDVQKIVSGGHTVELPYEFLLP
CLCIEASYLQEDTVRRKKCPFQSWPEAYGSDFWKSVHFTDYSQHTQMVMALTLRCPLKLE
AALCQRHDWHTLCKDLPNATARESDGWYVLEKVDLHPQLCFKFSFGNSSHVECPHQTGSL
TSWNVSMDTQAQQLILHFSSRMHATFSAAWSLPGLGQDTLVPPVYTVSQARGSSPVSLDL
IIPFLRPGCCVLVWRSDVQFAWKHLLCPDVSYRHLGLLILALLALLTLLGVVLALTCRRP
QSGPGPARPVLLLHAADSEAQRRLVGALAELLRAALGGGRDVIVDLWEGRHVARVGPLPW
LWAARTRVAREQGTVLLLWSGADLRPVSGPDPRAAPLLALLHAAPRPLLLLAYFSRLCAK
GDIPPPLRALPRYRLLRDLPRLLRALDARPFAEATSWGRLGARQRRQSRLELCSRLEREA
ARLADLG

Important features of the protein:
Signal peptide:
Amino acids 1-23

Transmembrane domain:
Amino acids 455-472

N-glycosylation sites:
Amino acids 318-322;347-351;364-368

Glycosaminoglycan attachment site:
Amino acids 482-486 cAMP- and cGMP-dependent protein kinase phosphorylation sites:
Amino acids 104-108;645-649

Tyrosine kinase phosphorylation site:
Amino acids 322-329

N-myristoylation sites:
Amino acids 90-96;358-364;470-476

Eukaryotic cobalamin-binding proteins:
Amino acids 453-462

FIGURE 21

CGGCTCGAGGCCCTTTGTGAGGGCTGTGAGCTGCGCCTGACGGTGGCACCATGAGCAGCTCA
GGTGGGGCGCCCGGGGCGTCCGCCAGCTCTGCGCCGCCCGCGCAGGAAGAGGGCATGACGTG
GTGGTACCGCTGGCTGTGTCGCCTGTCTGGGGTGCTGGGGGCAGTCTCTTGCGCGATCTCTG
GCCTCTTCAACTGCATCACCATCCACCCTCTGAACATCGCGGCCGGCGTGTGGATGATCATG
AATGCCTTCATCTTGTTGCTGTGTGAGGCGCCCTTCTGCTGCCAGTTCATCGAGTTTGCAAA
CACAGTGGCGGAGAAGGTGGACCGGCTGCGCTCCTGGCAGAAGGCTGTCTTCTACTGCGGGA
TGGCGGTCGTTCCCATCGTCATCAGCCTGACCCTGACCACGCTGCTGGGCAACGCCATCGCC
TTTGCTACGGGGGTGCTGTACGGACTCTCTGCTCTGGGCAAAAAGGGCGATGCGATCTCCTA
TGCCAGGATCCAGCAGCAGAGGCAGCAGGCGGATGAGGAGAAGCTCGCGGAGACCCTGGAGG
GGGAGCTGTGAAGGGCTGGGCGCCCCTCCCTCCCTGTCCCCTCTTCTGGCTCTGTGTGGGTC
CAAGTGAGGCCTGGACTGTCCACGCTGAGGCACAGCCTGGAGAGGGGCCTTTGCACGTGTCC
CTACACCTGGAGTCCTCTGCTCCTTTCTCCAGACTGGCTTAAGCCAGGAGCCACTGGCTGCT
GGTGTGAGGGTCTGGGCTGCTGGACTTGAGGCAGAGCCTGCAGCAGCTGTGTGGACACTACC
CAGCCCTACTCCTCTGCTGGGTGGGTCTGCAGATCTCACACCACAGACAGGGCTGCCTGTGA
CCTGCTGTGACCTGGGAGCAGCTTCCCCTGGAGATGCTGGTCCTGGCTTGAGGGGAGGGGCA
AGTGGGACCCTGCCACCTGGGCACTGAGCAGAGGGACCTCCCCCAGCTCTCTTAGCAGGTGG
AGCCCCAGGGCCTGGGACAGCCTGCCGCTGCCAGCAACCTCCCACTGCTGCCTAGGGTGCAG
CGCCCACTGTCACCCTGCCTTCTGAAGAAGCCCACAGGGCTCCTAAGGTGCACCCCGGTACC
TGGAACTGCAGCCTTGGCAGTGACTGGACAGCTGGGTGGGGGATGCTCCCTGCTGGCCCTGG
GAACCTTGGACAGGCCACCTCAAGGCCCCTCGGCTGCCCCTCCTCCCTGGGCCTGCTGGGGC
CCCTAGGTTCTACCCATCACCCCCCGCCCCTGCTGGCCTTGGTGCTAAGGAAGTGGGGAGAG
CAGGCTCTCCCTGGCACCGAGGGTGCCCACCCTCTCCCTGGTGTGGCCCCGTCAACATCAGC
CACAGCCCAGCCCCATTAGTGGGTTAGTGGGTCTGACCTCAGCCCCACTCAGGTGCTCCTGC
TGGCCTGCCCAAGCCCTGCCCTCAGGGAGCTTCTGCCTTTTAAGAACTGGGCAGAGGCCACAGT
CACCTCCCCACACAGAGCTGTCCCCACTGCCCTGGGTGCCAGGCTGTCCGGAGCCAGGCCTA
CCCAGGGAGGATGCAGAGAGCTGGTGCCCAGGATGTGCACCCCCATATTCCCTCTGCCCTGT
GGCCTCAGCCCGCTGGCCTCTCTGACCGTGAGGCTGGCTCTCAGCCATCGGGCAGGTGCCTG
GTCAGGCCTGGCTTAGCCCAGGTGGGGCTTGGCAGAAGCGGGCGGGTGTGGAAGATATTCCA
TCTGGGGCCAACCCCAGGCTGGGCCTGCGCTGAGCTTCTGGAGCGCAGGTACTGGGTCTTGC
TAAGTGAACTGTTTCCCAGGAACACCTCTCGGGCCCATCTGCGTCTGAGGCTGGGAGTGGCA
TCTGAGGCCGGGAGTGGCATCTGAGGCCAGGAGTGGCAGGCTGGTGGGCTGGGCGTGGGGTT
TTCTGGGCCCTGCCCAGTACTGCCCTGGGGACTTGGTGGGCTCCTGGGTCAGCAGCATCCCA
CCCCTGGGAGTCTGGCCAGCTGAGCCCCAGGGTGGCAGGGGCATTATAGCCTGGTGGACATG
TGCCTTCAGGGTTCCTCCGGGGCCACCTTCCTCAGGCCAGTGCTGGGTTCAAAGGGCTGTGT
GTGTGTGTGTTTGTGTGTGTATGTATATGTGTGTGGGTGCACACATCTGTCCCATGTATGCA
GTGAGACCTGTCTACCTCCCACAAGGAGCAAGGGCTCTGCCCGCCCTCTGCTCATTCCTACC
CAGGTAGTGGGACCCCGGGCCCCCTTCTGCCTGGCTTGCCTGCTTCTGCCCTTTCCAGAGGG
GTCTCACTGACAGCCAGAGACAGCAGGAGAAGGGTTGGCTGTGGATCAAGGAAGGCTGCCCC
TGTACCCTGTGGGGAAATGGTGGGTGCATGGCTGGATGCAGAGGTGGAAGGCCCTGGGCCAC
AGGCGAGAGTGGGCGTGTCACCTGTCCCAGGTTCCCAGCAAGTCTGCAGCTGTGCAGTCCTG
GGGTCCCTGACCCTGTCGCCCAGGGGGCGTGCTGTCCAGCAGGGGCCCTGCCTTGCAAGGAA
CGTCTCTCCGGCGGCTGGGCCGCTCCTGCCTGGTCTGGGCTGTGTGTGGCGCCCTTTCCTCC
TTGTTTGTTCCTCTGTGTTCTGTGTGCGTCTTAAGCAATAAAGCGTGGCCGTGGGAAAAAAA
AAAAAAAAAAAAAAAAAAAAAAAAAAAAAAAAAAAAAAAAAAAAAA

FIGURE 22

></usr/seqdb2/sst/DNA/Dnaseqs.min/ss.DNA119516
><subunit 1 of 1, 172 aa, 1 stop
><MW: 18470, pI: 5.45, NX(S/T): 0
MSSSGGAPGASASSAPPAQEEGMTWWYRWLCRLSGVLGAVSCAISGLFNCITIHPLNIAA
GVWMIMNAFILLLCEAPFCCQFIEFANTVAEKVDRLRSWQKAVFYCGMAVVPIVISLTLT
TLLGNAIAFATGVLYGLSALGKKGDAISYARIQQQRQQADEEKLAETLEGEL

Important features of the protein:
Signal peptide:
Amino acids 1-42

Transmembrane domains:
Amino acids 64-77;109-128

Tyrosine kinase phosphorylation site:
Amino acids 142-150

N-myristoylation sites:
Amino acids 5-11;6-12;9-15;35-41;38-44;46-52;124-130;132-138

Amidation site:
Amino acids 140-144

FIGURE 23

GTGAAACACCCATGGTTTTATGCTCTATTTCTCTTTTCCTCATCTTCTTCCACATCCTCTTT
CTGAATGTATCAAACTACTTCCTTGAAGTGGGGCACCAGGAGGGCCACTCCAGTCTCCAATG
CAGGGACTCAGGGGCAGGGATCTCTGAGAAAGTGGCCATCTCGTTATTAAAGCTCTGTCCTC
TGCTTCCCTCTCACCTCAGAAGCAGCCCGTTTATTCAACAGAGCTCCAGGTTGCCAGCTAGG
GGTTTTCGGGACCATAGACCAAGCAACCCCGAGAGACTGAGTACTGACCTGCAGTTGTTCCAG
AAACTCTGCTGGGAATTAGGTTGTGACCTAGAAGTGAACTGACACTAACAGTGAGAAGGCAG
GGTAAGAATGCAGTCTAGAGCGCAACCTTTCTCCACTAGACTTGTAAGTAATTTAAGTGAAT
CCTGTCCCCCTGGGGTTCTATCCTGGCTGGCTCTGCTGGTGAACTTGACTGGCCAGCATAGG
GCACTTGATGAGACCCTGGAATGCTGAGGCCAGTTGGGCAGCAAGCTTTCACCTCATCCTTC
TGCCCATCTATCCAGCCATTCAAACATTCATTCGCCTGAAGACATTTATCAAGCTCCTGCAA
TGGGTCAGGCATCTGCTAGGCACTGGGGACACAGAGCTCACAGTCTCCTGGAGGGGGTGAGA
GATGACTGACAGGTGGTCTGTGGTGCAGTGTGACCTGGGAATGCACACAGTACTGTGGAAAC
ACGGGAGAGGCATCTAGCACAACCTGAGAGGGCCAGGGGAGGCTTCCTGGCAGGTTTCCCTT
TAACCATCTTAAGGGAAAGAGGCACTAGGTAGGAAAATAAAGGGACAGTGGTGTCCCAGACA
GAGGGCACTCTACATGGAA

FIGURE 24

></usr/seqdb2/sst/DNA/Dnaseqs.min/ss.DNA119530
><subunit 1 of 1, 113 aa, 1 stop
><MW: 12799, pI: 7.53, NX(S/T): 1
MVLCSISLFLIFFHILFLNVSNYFLEVGHQEGHSSLQCRDSGAGISEKVAISLLKLCPLL
PSHLRSSPFIQQSSRLPARGFRDHRPSNPERLSTDLQLFQKLCWELGCDLEVN

Important features of the protein:
Signal peptide:
Amino acids 1-18

N-glycosylation site:
Amino acids 19-23

Glycosaminoglycan attachment site:
Amino acids 41-45

N-myristoylation site:
Amino acids 42-48

FIGURE 25

CGGGCTCCGCGCGGTCCCACTTCCCGGCTCCCTTCGCCTCCAGGATGCGCTGAGCCCTACAA
CACCCCCAGCGGCCGCCGGCTCCCCCACGAGGTGTGAATGACAGAGGTGGTGCCATCCAGCG
CGCTCAGCGAGGTCAGCCTGCGCCTCCTCTGCCACGATGACATAGACACTGTGAAGCACCTG
TGTGGCGACTGGTTCCCCATCGAGTACCCAGACTCATGGTATCGTGATATCACATCCAACAA
GAAGTTCTTTTCCCTTGCTGCAACCTACAGAGGTGCCATTGTGGGAATGATAGTAGCTGAAA
TTAAGAACAGGACCAAAATACATAAAGAGGATGGAGATATTCTAGCAACCAACTTCTCTGTT
GACACACAAGTCGCGTACATCCTAAGTCTGGGCGTCGTGAAAGAGTTCAGGAAGCACGGCAT
AGGTTCCCTCTTACTTGAAAGTTTAAAGGATCACATATCAACCACCGCCCAGGACCACTGCA
AAGCCATTTACCTGCATGTCCTCACCACCAACAACACAGCAATAAACTTCTATGAAAACAGA
GACTTCAAGCAGCACCACTATCTCCCCTATTACTACTCCATTCGAGGGGTCCTCAAAGATGG
CTTCACCTATGTCCTCTACATCAACGGCGGGCACCCTCCCTGGACGATTTTGGACTACATCC
AGCACCTGGGCTCTGCACTAGCCAGCCTGAGCCCCTGCTCCATTCCGCACAGAGTCTACCGC
CAGGCCCACAGCCTGCTCTGCAGCTTCCTGCCATGGTCGGGCATCTCTTCCAAGAGTGGCAT
CGAGTACAGCCGGACCATGTGATGTCGGCTGGGCAGCCGCCACCAGGCCCCACCCTTCAGCC
GCCCGCAGAGCCCGCCTTCCTGTCCATCTGACCCCTTCTGTTTTCTGCAAGGAGCTGCCAGC
CATCTAACTGGGCTCGTCGGCCTGCCCCAGCTGCAGGCCCGGTGCTACACGGGCTCGGGAAC
AGAACATCGTGGGCATGCGCAGAGCATGCCCATCCGTGGCAGGCTCTTCAGCTCCCCTCCCT
GCTTCTGGAAACCTCTGCCTGCTGCCCTGGCCCTGCCCCCCTGCGCATGCACCATCCCCAGG
GCTGACCCAGTGTGGCTGCATTCACTGGGAGGGGCCTGCCCTCACTGGGCCTCTCCCACTCCG
CTGCCTGTTCTTGCAGCTCCTTCCTGGAAAGCTGGAGGGGACTTTCTCCTGCAAGGGAGGAA
CGCAAGTATTATGGACACACTTGACCGTAAAGGCACAGGAGCCTCGGAACAAGGGGGCGCAA
TAAAGGGAATGGCCCGTCCCCTTCCAGAACCAGCCCAAAGAAGCCTGGGGGGTGAGGAGTGG
CCCCCACTCCTCCATGAGGGGCTGATGAGGGGTGGGCAGCCTGGGGGAGGCTTTCCTCGCAA
GCACAGAGCTCTGAGGCTCAGCCCCCTGGCACAGGCGGTCACGCATCAGGACGGTTCCTACT
CCTCAGCACCTTCCGTGCAGTTACCAGTGCCCTGGGAGGTCACACTGCCCGTCGGACCTTGG
CATGCTCCATTCAGCTGACCTGCTGAGGACAGGCATCGCCGAGACTCCTTGGGTCCTCCCCG
CCCTCCCTCATGCTGCCACAAGCTGCTGCTCCAAGGCCTGGCCACATGCAGACAGGAGGAAG
CTGAGCTCGACATTAGGCCTCAAGGCTGCCATCTGTCTTGTAGGGCCTGGCCTTGTGGGCAG
GGGGCAGTCCTGTGCCTTGTGGGCCCTCAGCCTCTGAGGGCAGAGATGCTGTCAGTGCCGCA
GGTGCATCACATACTTCTAGCATCCTCTCCACCCTGCATTCCAAATGCTGCTTGCTGCCTGC
CCTGCCCTCCGATGCAGGGGTGGGGTGGGGGGCGGAGTCCCGCCCAGCATAGCTGCAGTGTC
ACAAAGCCATGGCAGAGGGTCCTAGCGGCGCCACCCTGCCCCAGCCTGAGGAGGAGGGAGAG
GGAGGAACAACCCTGGGCAGACGGGGTCTCAGGGACCTGTGTCCTTCCGCCTCCAGAGCTGC
CCAGCCACGGGCTCTCAGGGTGCTGGGGCAGCCCCAGGTCCCCTCTTGAACTCAGCTGGGGC
CAGGGGCCCTCAGAATGAAGGCAGGCACCAGGCAGGAGCAGCATCCCCCTCCTTGACGGTGC
TGGCAGGAGGGCCGCGCCATGCTGACTGCTTGAACCTCTGCTGACCTGACAGTGCTGGCGGG
AGGGCCGCACCATGCTGACTGCCTGAATCTCTGCTGAGGCTGCCTGCCTGCCGGGCCCAGCT
CAGCGCCCTCTCCACTGCGAATCAGTGGCGATCATGTGATTTCTATTTCTGCCCCACAGGGT
AAGGGACGAGTCTTCTGGAAGGCTCTGCCATGGACATTTGTCCTCGGGCTCAGAGGCCCCAC
CCTGCCCCACACCTGCCCCTAATCACTGCAGTGTCCAGCCCAGTGTTGAACAGATTGTAGCG
TTCTGTCTCATTACGAGCAAATAAATAGACTTTCATTGGAAAAAAAAAAAAA

FIGURE 26

></usr/seqdb2/sst/DNA/Dnaseqs.min/ss.DNA121772
><subunit 1 of 1, 242 aa, 1 stop
><MW: 27465, pI: 7.72, NX(S/T): 3
MTEVVPSSALSEVSLRLLCHDDIDTVKHLCGDWFPIEYPDSWYRDITSNKKFFSLAATYR
GAIVGMIVAEIKNRTKIHKEDGDILATNFSVDTQVAYILSLGVVKEFRKHGIGSLLLESL
KDHISTTAQDHCKAIYLHVLTTNNTAINFYENRDFKQHHYLPYYYSIRGVLKDGFTYVLY
INGGHPPWTILDYIQHLGSALASLSPCSIPHRVYRQAHSLLCSFLPWSGISSKSGIEYSR
TM

N-glycosylation sites:
Amino acids 73-77;88-92;143-147

N-myristoylation sites:
Amino acids 61-67;65-71;198-204;235-241

Matrixins cysteine switch motif:
Amino acids 18-31

FIGURE 27

GTTGGGCAGCAGCCACCCGCTCACCTCCATCCCCAGGACTTAGAGGGACGCAGGGCGTTGGG
AACAGAGGACACTCCAGGCGCTGACCCTGGGAGGCCAGGACCAGGGCCAAAGTCCCGTGGGC
AAGAGGAGTCCTCAGAGGTCCTTCATTCAGCGGTTCCGGGAGGTCTGGGAAGCCCACGGCCT
GGCTGGGGCAGGGTCAACGCCGCCAGGCCGCCATGGTCCTGTGCTGGCTGCTGCTTCTGGTG
ATGGCTCTGCCCCCAGGCACGACGGGCGTCAAGGACTGCGTCTTCTGTGAGCTCACCGACTC
CATGCAGTGTCCTGGTACCTACATGCACTGTGGCGATGACGAGGACTGCTTCACAGGCCACG
GGGTCGCCCCGGGCACTGGTCCGGTCATCAACAAAGGCTGCCTGCGAGCCACCAGCTGCGGC
CTTGAGGAACCCGTCAGCTACAGGGGCGTCACCTACAGCCTCACCACCAACTGCTGCACCGG
CCGCCTGTGTAACAGAGCCCCGAGCAGCCAGACAGTGGGGGCCACCACCAGCCTGGCACTGG
GGCTGGGTATGCTGCTTCCTCCACGTTTGCTGTGACCAACAGGGAGGACAGGGCCTGGGACT
GTTCTCCCAGATCCGCCACTCCCCATGTCCCCATGTCCTTCCCCCACTAAATGGCCAGAGAG
GCCCTGGACAACCTCTTGCGGCCCTGGCTTCATCCCTTCTAAGGCTGTCCACCAGGAGCCCG
GTGCTAGGGGAAGCATCCCCAGGCCTGACTGAGCGGCAGGGGAGCACGGCCCGTGGGTTTGA
TTGTATTACTCTGTTCCACTGGTTCTAAGACGCAGAGCTTCTCACATCTCAATCAGGATGCT
TCTCTCCATTGGTAGCACTTTAGAGTCCATGAAATATGGTAAAAAATATATATATATCATAA
TAAATGACAGCTGATGTTCATGGGGGAAAAAAAAAAAAAAAAAAAAAAAAAAAAAAAAA

FIGURE 28

></usr/seqdb2/sst/DNA/Dnaseqs.min/ss.DNA125148
><subunit 1 of 1, 124 aa, 1 stop
><MW: 13004, pI: 5.70, NX(S/T): 0
MVLCWLLLLVMALPPGTTGVKDCVFCELTDSMQCPGTYMHCGDDEDCFTGHGVAPGTGPV
INKGCLRATSCGLEEPVSYRGVTYSLTTNCCTGRLCNRAPSSQTVGATTSLALGLGMLLP
PRLL

Important features of the protein:
Signal peptide:
Amino acids 1-13

N-myristoylation sites:
Amino acids 19-25;52-58;64-70;81-87;106-112

Ly-6 / u-PAR domain proteins:
Amino acids 84-97

FIGURE 29

GGCATTTTGAAAGCCCAGTGTTGCCCAGGGGGCATCTCCTTTGTGTTTATGAGAGACCTGCA
TTCTCCCTGGCTCAGTTCTCTCAGGCTCTCCAGAGCTCAGGACCTCTGAGAAGAATGGAGCC
CTCCTGGCTTCAGGAACTCATGGCTCACCCCTTCTTGCTGCTGATCCTCCTCTGCATGTCTC
TGCTGCTGTTTCAGGTAATCAGGTTGTACCAGAGGAGGAGATGGATGATCAGAGCCCTGCAC
CTGTTTCCTGCACCCCCTGCCCACTGGTTCTATGGCCACAAGGAGTTTTACCCAGTAAAGGA
GTTTGAGGTGTATCATAAGCTGATGGAAAAATACCCATGTGCTGTTCCCTTGTGGGTTGGAC
CCTTTACGATGTTCTTCAGTGTCCATGACCCAGACTATGCCAAGATTCTCCTGAAAAGACAA
GATCCCAAAAGTGCTGTTAGCCACAAAATCCTTGAATCCTGGGTTGGTCGAGGACTTGTGAC
CCTGGATGGTTCTAAATGGAAAAAGCACCGCCAGATTGTGAAACCTGGCTTCAACATCAGCA
TTCTGAAAATATTCATCACCATGATGTCTGAGAGTGTTCGGATGATGCTGAACAAATGGGAG
GAACACATTGCCCAAAACTCACGTCTGGAGCTCTTTCAACATGTCTCCCTGATGACCCTGGA
CAGCATCATGAAGTGTGCCTTCAGCCACCAGGGCAGCATCCAGTTGGACAGTACCCTGGACT
CATACCTGAAAGCAGTGTTCAACCTTAGCAAAATCTCCAACCAGCGCATGAACAATTTTCTA
CATCACAACGACCTGGTTTTCAAATTCAGCTCTCAAGGCCAAATCTTTTCTAAATTTAACCA
AGAACTTCATCAGTTCACAGAGAAAGTAATCCAGGACCGGAAGGAGTCTCTTAAGGATAAGC
TAAAACAAGATACTACTCAGAAAAGGCGCTGGGATTTTCTGGACATACTTTTGAGTGCCAAA
AGCGAAAACACCAAAGATTTCTCTGAAGCAGATCTCCAGGCTGAAGTGAAAACGTTCATGTT
TGCAGGACATGACACCACATCCAGTGCTATCTCCTGGATCCTTTACTGCTTGGCAAAGTACC
CTGAGCATCAGCAGAGATGCCGAGATGAAATCAGGGAACTCCTAGGGGATGGGTCTTCTATT
ACCTGGGAACACCTGAGCCAGATGCCTTACACCACGATGTGCATCAAGGAATGCCTCCGCCT
CTACGCACCGGTAGTAAACATATCCCGGTTACTCGACAAACCCATCACCTTTCCAGATGGAC
GCTCCTTACCTGCAGGAATAACTGTGTTTATCAATATTTGGGCTCTTCACCACAACCCCTAT
TTCTGGGAAGACCCTCAGGTCTTTAACCCCTTGAGATTCTCCAGGGAAAATTCTGAAAAAAT
ACATCCCTATGCCTTCATACCATTCTCAGCTGGATTAAGGAACTGCATTGGGCAGCATTTTG
CCATAATTGAGTGTAAAGTGGCAGTGGCATTAACTCTGCTCCGCTTCAAGCTGGCTCCAGAC
CACTCAAGGCCTCCCCAGCCTGTTCGTCAAGTTGTCCTCAAGTCCAAGAATGGAATCCATGT
GTTTGCAAAAAAAGTTTGCTAATTTTAAGTCCTTTCGTATAAGAATTAATGAGACAATTTTCCT
ACCAAAGGAAGAACAAAAGGATAAATATAATACAAAATATATGTATATGGTTGTTTGACAAA
TTATATAACTTAGGATACTTCTGACTGGTTTTGACATCCATTAACAGTAATTTTAATTTCTT
TGCTGTATCTGGTGAAACCCACAAAAACACCTGAAAAAACTCAAGCTGACTTCCACTGCGAA
GGGAAATTATTGGTTTGTGTAACTAGTGGTAGAGTGGCTTTCAAGCATAGTTTGATCAAAAC
TCCACTCAGTATCTGCATTACTTTTATCTCTGCAAATATCTGCATGATAGCTTTATTCTCAG
TTATCTTTCCCCATAATAAAAAATATCTGCCAAA

FIGURE 30

```
></usr/seqdb2/sst/DNA/Dnaseqs.min/ss.DNA125150
><subunit 1 of 1, 505 aa, 1 stop
><MW: 59086, pI: 9.50, NX(S/T): 3
MEPSWLQELMAHPFLLLILLCMSLLLFQVIRLYQRRRWMIRALHLFPAPPAHWFYGHKEF
YPVKEFEVYHKLMEKYPCAVPLWVGPFTMFFSVHDPDYAKILLKRQDPKSAVSHKILESW
VGRGLVTLDGSKWKKHRQIVKPGFNISILKIFITMMSESVRMMLNKWEEHIAQNSRLELF
QHVSLMTLDSIMKCAFSHQGSIQLDSTLDSYLKAVFNLSKISNQRMNNFLHHNDLVFKFS
SQGQIFSKFNQELHQFTEKVIQDRKESLKDKLKQDTTQKRRWDFLDILLSAKSENTKDFS
EADLQAEVKTFMFAGHDTTSSAISWILYCLAKYPEHQQRCRDEIRELLGDGSSITWEHLS
QMPYTTMCIKECLRLYAPVVNISRLLDKPITFPDGRSLPAGITVFINIWALHHNPYFWED
PQVFNPLRFSRENSEKIHPYAFIPFSAGLRNCIGQHFAIIECKVAVALTLLRFKLAPDHS
RPPQPVRQVVLKSKNGIHVFAKKVC
```

Important features of the protein:
Signal peptide:
Amino acids 1-28

Transmembrane domain:
Amino acids 451-470

N-glycosylation sites:
Amino acids 145-149;217-221;381-385 cAMP- and cGMP-dependent protein kinase phosphorylation site:
Amino acids 264-268

N-myristoylation sites:
Amino acids 243-249;351-357;448-454;454-460

Cytochrome P450 cysteine heme-iron ligand signature:
Amino acids 445-455

Cytochrome P450 cysteine heme-iron ligand proteins:
Amino acids 442-473

FAD-dependent glycerol-3-phosphate dehydrogenase proteins:
Amino acids 124-141

FIGURE 31

TCCGCTGTCGCCCAGTCCCGGCCGCTGGCGGGAACTGACCTGGAGCAAGCAGGACCTTCCCT
CCCACCTCTCCCGCCTGGCCTCCGCGGGAGTCCCCTACGATCCCGCTCAGCAGTGGGGCACT
CGCTGAGGACAGCGAGTCCTGGGAGTGAGCCCAAGGCCACCCCTGGCCAGCCCAGGAGAGAT
AGCCAGGGCAGGCCCAGCAGCCCGAGGCCAGGCTCTGGCCACGGCGGTCTCCGACATGGAGA
GACATTGTCTGCTTTTTATCCTGTTAACCTGTCTTCGGTGGTTGTGCCACGACATTCCCCAG
GGTTCAGGTGCCCGGTGGCCGAGGGTCAGTCCAGTGGTAGAGCCTTGCTCTCCTAGGCTCAT
CCTGCTGGCGGTCCTCCTGCTTCTGCTGTGTGGTGTCACAGCTGGTTGTGTCCGGTTCTGCT
GCCTCCGGAAGCAGGCACAGGCCCAGCCACATCTGCCACCAGCACGGCAGCCCTGCGACGTG
GCAGTCATCCCTATGGACAGTGACAGCCCTGTACACAGCACTGTGACCTCCTACAGCTCCGT
GCAGTACCCACTGGGCATGCGGTTGCCCCTGCCCTTTGGGGAGCTGGACCTGGACTCCACGG
CTCCTCCTGCCTACAGCCTGTACACCCCGGAGCCTCCACCCTCCTACGATGAAGCTGTCAAG
ATGGCCAAGCCCAGAGAGGAAGGACCAGCACTCTCCCAGAAACCCAGCCCTCTCCTTGGGGC
CTCGGGCCTAGAGACCACTCCAGTGCCCCAGGAGTCGGGCCCCAATACTCAACTACCACCTT
GTAGCCCTGGTGCCCCTTGAAGGAGGTAGGAGAACGGACCAGAGCTTGGAGAACTAATGCTT
GGAGCCAAGGGCCCCAGCCCACCCCACCGTCCCACACATTGCTGTGGCCCCAACCTCGGTGC
CATGTTACACCGGCCCCTGGCGTCACCCACTAGGCAGGCTGCTGCTTTCAGCCTCAGCCCCT
GGCCCAGCCCCAGCAGGCCCTCAGCCTGGAAGAGGCCCCTTGGGCCTAAGCCTCGGGTGGGA
GCTCAGGGCCACCTGTGACGTCTGCATCTTCTTGGAGAGAGAATAAAGTTTGTATTTAAGTGGT

FIGURE 32

></usr/seqdb2/sst/DNA/Dnaseqs.min/ss.DNA125151
><subunit 1 of 1, 194 aa, 1 stop
><MW: 20882, pI: 6.44, NX(S/T): 0
MERHCLLFILLTCLRWLCHDIPQGSGARWPRVSPVVEPCSPRLILLAVLLLLLCGVTAGC
VRFCCLRKQAQAQPHLPPARQPCDVAVIPMDSDSPVHSTVTSYSSVQYPLGMRLPLPFGE
LDLDSTAPPAYSLYTPEPPPSYDEAVKMAKPREEGPALSQKPSPLLGASGLETTPVPQES
GPNTQLPPCSPGAP

Important features of the protein:
Signal peptide:
Amino acids 1-20

Transmembrane domain:
Amino acids 39-58

N-myristoylation site:
Amino acids 55-61

Prokaryotic membrane lipoprotein lipid attachment site:
Amino acids 50-61

FIGURE 33

CCTTGCTTGGTGCTTGGCACACACAAATCCAGTGGGCTACACAGGTTTTCCAGAAGCCCCAC
GAGGTGGTAATGGTGCTGCTGATTCAGACCCTGGGGGCCCTCATGCCCTCGCTGCCCTCCTG
CCTCAGCAACGGCGTGGAGAGGGCAGGGCCCGAGCAGGAGCTCACCAGGCTGCTGGAGTTCT
ACGACGCCACCGCCCACTTCGCCAAGGGCTTGGAGATGGCACTGCTCCCCCACCTACATGAA
CACAATCTGGTAAAAGTCACGGAGCTGGTGGATGCTGTGTATGATCCATACAAACCCTACCAG
CTGAAGTATGGCGACATGGAAGAGAGCAACCTCCTCATCCAGATGAGTGCTGTGCCTCTGGA
GCATGGGGAAGTGATTGACTGTGTGCAGGAGCTGAGCCACTCCGTGAACAAGCTGTTTGGTC
TGGCGTCTGCAGCCGTTGACAGATGCGTCAGATTCACCAATGGCCTGGGGACCTGCGGCCTG
TTGTCAGCCCTGAAATCCCTCTTTGCCAAGTATGTGTCTGATTTCACCAGCACTCTCCAGTC
CATACGAAAGAAGTGCAAACTGGACCACATTCCTCCCAACTCCCTCTTCCAGGAAGATTGGA
CGGCTTTTCAGAACTCCATTAGGATAATAGCCACCTGTGGAGAGCTTTTGCGGCATTGTGGG
GACTTCGAGCAGCAGCTAGCCAACAGGATTTTGTCCACAGCTGGGAAGTATCTATCTGATTC
CTGCAGCCCCCGGAGCCTGGCTGGTTTTCAGGAGAGCATCTTGACAGACAAGAAGAACTCTG
CCAAGAACCCATGGCAAGAATATAATTACCTCCAGAAAGATAACCCTGCTGAATATGCCAGT
TTAATGGAAATACTTTATACCCTTAAGGAAAAAGGGTCAAGCAACCACAACCTGCTGGCTGC
ACCTCGAGCAGCGCTGACTCGGCTTAACCAGCAGGCCCACCAGCTGGCTTTCGATTCCGTGT
TCCTGCGCATCAAACAACAGCTGTTGCTTATTTCGAAGATGGACAGCTGGAATACGGCTGGC
ATCGGAGAAACCCTCACAGATGAACTGCCCGCCTTTAGTCTCACCCCTCTCGAGTACATCAG
CAACATCGGGCAGTACATCATGTCCCTCCCCCTGAATCTTGAGCCATTTGTGACTCAGGAGG
ACTCTGCCTTAGAGTTGGCATTGCACGCTGGAAAGCTGCCATTTCCTCCTGAGCAGGGGGAT
GAATTGCCCGAGCTGGACAACATGGCTGACAACTGGCTGGGCTCGATCGCCAGAGCCACAAT
GCAGACCTACTGTGATGCGATCCTACAGATCCCTGAGCTGAGCCCACACTCTGCCAAGCAGC
TGGCCACTGACATCGACTATCTGATCAACGTGATGGATGCCCTGGGCCTGCAGCCGTCCCGC
ACCCTCCAGCACATCGTGACGCTACTGAAGACCAGGCCTGAGGACTATAGACAGGTCAGCAA
AGGCCTGCCCCGTCGCCTGGCCACCACCGTGGCCACCATGCGGAGTGTGAATTACTGACCCC
ACCACACACCGGACCACCAAGAGAGCCAGGGCTGCTGTTTCGTGACTCACCAGCACAGATTT
GCTCAGAAACTCTGCCCAAGATTGGGCAGAAGTTACTTTAAAAAGACTTGGTTCAGCTGGTC
ACGGTGGCTCACGCCTGTAATCCCAGCACTTTGGGAGGCCAAGCCAGATGGATCATGAGGCC
AGGAGTTCGAGACCAGCCTGACCAACATGGTGAAACCCCATCTCTACTAAAAATACAAAAAT
TAACAGCAGAGCGAGACTCTGTCTCAAAAAAAAAAAAAAAAAAGACTTGGTTCATTTGTATAA
TCAAAAAGAGTTGTAAATTAAAGATGTATTATTTATCAGAGAAGACTTTTTAGATAATTTTT
TTAAAGGATCAGATCTTGAAAATGGAATAAATAACTACTGTGAAATGCAAAAA

FIGURE 34

></usr/seqdb2/sst/DNA/Dnaseqs.min/ss.DNA125181
><subunit 1 of 1, 491 aa, 1 stop
><MW: 54759, pI: 5.61, NX(S/T): 0
MVLLIQTLGALMPSLPSCLSNGVERAGPEQELTRLLEFYDATAHFAKGLEMALLPHLHEH
NLVKVTELVDAVYDPYKPYQLKYGDMEESNLLIQMSAVPLEHGEVIDCVQELSHSVNKLF
GLASAAVDRCVRFTNGLGTCGLLSALKSLFAKYVSDFTSTLQSIRKKCKLDHIPPNSLFQ
EDWTAFQNSIRIIATCGELLRHCGDFEQQLANRILSTAGKYLSDSCSPRSLAGFQESILT
DKKNSAKNPWQEYNYLQKDNPAEYASLMEILYTLKEKGSSNHNLLAAPRAALTRLNQQAH
QLAFDSVFLRIKQQLLLISKMDSWNTAGIGETLTDELPAFSLTPLEYISNIGQYIMSLPL
NLEPFVTQEDSALELALHAGKLPFPPEQGDELPELDNMADNWLGSIARATMQTYCDAILQ
IPELSPHSAKQLATDIDYLINVMDALGLQPSRTLQHIVTLLKTRPEDYRQVSKGLPRRLA
TTVATMRSVNY

Important features of the protein:
Signal peptide:
Amino acids 1-20 cAMP- and cGMP-dependent protein kinase phosphorylation site:
Amino acids 242-246

N-myristoylation sites:
Amino acids 22-28;48-54;121-127;136-142;141-147;328-334;
447-453

Leucine zipper pattern:
Amino acids 295-317

FIGURE 35

GCAAGTGCCACCATGCTAGTGTGATTTGGACTTCAGTAAAAGTTAGTTTGCTTCCTTCCCGT
TGTCCCATCTCACTCCTGGGCCACCCATGGGGCTGCTGGTAGCTGGTGTGTGGCTGCTGCTG
GACTGTGTGGCAGTCCATCCATCTGTCAGCAGCCACTGCGGGCCTACTTGCTGGGTGCCCAG
CACCGCACTCACCACTGCAGGCGTGGCCAGGAGCGTGAGATCCCCAGAGCCCATGGCCAGTG
AGAGGCGGCCAGGGATAGGTACCCAGGGAATGCCACAGGAGTTTGCTGGGCTCACGGAGCTC
TTTCACTGGTCAGAGAGGAGTGTGTGTAGGAGAGGACTTCTACTTGGTGTTGAAGGACAGAT
GGGGTTTGGCTGGGAGAGAGGAGGAATGTGGGCGGGCCTTATAGGCAGGCGAGAAGGTGAGA
GCCAAGGCCCTCTGTGGGCAGGGCGAGGTGGCGTGTTGAGGAGACTCGTCCAGCTGGGCAGA
GGCTCATGTTGAGGGATGAGGCAGAGCTGGGGGAGGAGGGAGCCCAGAAATGGCAGGTCCTT
GAATGCAGGTTTGGAAGCAGGGACGCCCTGTGAGGGTACAGAGTCTGGGCTGTTACCTTCTG
TGGCTTTTGCTAGAAGGTGAGATGTCAGGGAGGAAGACAGGACTCCAGGATGTCTCCTGTCTCT
CTCTGGAAAAAGGAGGTGGGCCCCTTTCTCAGCAGTCAGCTGCTGTTTTTGAGGTCTTCTCC
ATGGATAATCCACGGTGTTGGAAGTGGTTAAGGTAATGGATCCTCATGGGCTTACCATAAAA
ATATCTGGAGGCTGGACCATTTTCCTTAAAACGTTATAAAAGCTGGAATTGAATGCCATCGG
TGTCACCCCTGGGAAGTGTGCTTTCTCTTGAGCTCTTTTGGCCCCGAGATAGCAGTCACTCC
ATAGTTTCGTGAAGACCAGCCTGGTGTTGCCTGGTTTTCTGCCATTAGGGAGCAGCTAGAGG
TCTTCCAGTAGCTCCTGTGTAAAGTGATGAAAGAAAAGGGCTGGGTGCTGACTGCTCCTGGA
GAAAAGCAACACACTCCCAAAGTCTTAATTGCCTGCTTCCAGGGAGCTGTGGTGGTTTCCCT
TGGGCAGGGCACACGCCCCAGTGGTTGACTTAATAAGGATACATTTTAATCAGAGGACAAAA
ATGTGCCCTGACTTGATTTCCGCATGGGCTTCCAGCATGGTCAAAGG

FIGURE 36

></usr/seqdb2/sst/DNA/Dnaseqs.min/ss.DNA125192
><subunit 1 of 1, 139 aa, 1 stop
><MW: 14841, pI: 9.20, NX(S/T): 0
MGLLVAGVWLLLDCVAVHPSVSSHCGPTCWVPSTALTTAGVARSVRSPEPMASERRPGIG
TQGMPQEFAGLTELFHWSERSVCRRGLLLGVEGQMGFGWERGGMWAGLIGRREGESQGPL
WAGRGGVLRRLVQLGRGSC

Important features of the protein:
Signal peptide:
Amino acids 1-22

N-myristoylation sites:
Amino acids 2-8;40-46;86-92;102-108;103-109

Amidation site:
Amino acids 109-113

FIGURE 37

GGCCAGGAATGGGGTCCCCGGGCATGGTGCTGGGCCTCCTGGTGCAGATCTGGGCCCTGCAA
GAAGCCTCAAGCCTGAGCGTGCAGCAGGGGCCCAACTTGCTGCAGGTGAGGCAGGGCAGTCA
GGCGACCCTGGTCTGCCAGGTGGACCAGGCCACAGCCTGGGAACGGCTCCGTGTTAAGTGGACA
AAGGATGGGGCCATCCTGTGTCAACCGTACATCACCAACGGCAGCCTCAGCCTGGGGGTCTG
CGGGCCCCAGGGACGGCTCTCCTGGCAGGCACCCAGCCATCTCACCCTGCAGCTGGACCCTG
TGAGCCTCAACCACAGCGGGGCGTACGTGTGCTGGGCGGCCGTAGAGATTCCTGAGTTGGAG
GAGGCTGAGGGCAACATAACAAGGCTCTTTGTGGACCCAGATGACCCCACACAGAACAGAAA
CCGGATCGCAAGCTTCCCAGGATTCCTCTTCGTGCTGCTGGGGGTGGGAAGCATGGGTGTGG
CTGCGATCGTGTGGGGTGCCTGGTTCTGGGCCGCCGCAGCTGCCAGCAAAGGGACTCAGGA
AATGCATTCTACAGCAACGTCCTATACCGGCCCCGGGGGGCCCCAAAGAAGAGTGAGGACTG
CTCTGGAGAGGGGAAGGACCAGAGGGGCCAGAGCATTTATTCAACCTCCTTCCCGCAACCGG
CCCCCCGCCAGCCGCACCTGGCGTCAAGACCCTGCCCCAGCCCGAGACCCTGCCCCAGCCCC
AGGCCCGGCCACCCCGTCTCTATGGTCAGGGTCTCTCCTAGACCAAGCCCCACCCAGCAGCC
GAGGCCAAAAGGGTTCCCCAAAGTGGGAGAGGAGTGAGAGATCCCAGGAGACCTCAACAGGA
CCCCACCCATAGGTACACACAAAAAAGGGGGGATCGAGGCCAGACACGGTGGCTCACGCCTG
TAATCCCAGCAGTTTGGGAAGCCGAGGCGGGTGGAACACTTGAGGTCAGGGGTTTGAGACCA
GCCTGGCTTGAACCTGGGAGGCGGAGGTTGCAGTGAGCCGAGATTGCGCCACTGCACTCCAG
CCTGGGCGACAGAGTGAGACTCCGTCTCAAAAAAAAAACAAAAAGCAGGAGGATTGGGAGCC
TGTCAGCCCCATCCTGAGACCCCGTCCTCATTTCTGTAATGATGGATCTCGCTCCCACTTTC
CCCCAAGAACCTAATAAAGGCTTGTGAAGAAAAAAAAAAAAAAAA

FIGURE 38

></usr/seqdb2/sst/DNA/Dnaseqs.min/ss.DNA125196
><subunit 1 of 1, 278 aa, 1 stop
><MW: 30319, pI: 9.21, NX(S/T): 3
MGSPGMVLGLLVQIWALQEASSLSVQQGPNLLQVRQGSQATLVCQVDQATAWERLRVKWT
KDGAILCQPYITNGSLSLGVCGPQGRLSWQAPSHLTLQLDPVSLNHSGAYVCWAAVEIPE
LEEAEGNITRLFVDPDDPTQNRNRIASFPGFLFVLLGVGSMGVAAIVWGAWFWGRRSCQQ
RDSGNAFYSNVLYRPRGAPKKSEDCSGEGKDQRGQSIYSTSFPQPAPRQPHLASRPCPSP
RPCPSPRPGHPVSMVRVSPRPSPTQQPRPKGFPKVGEE

Important features of the protein:
Signal peptide:
Amino acids 1-22

Transmembrane domain:
Amino acids 149-166

N-glycosylation sites:
Amino acids 73-77;105-109;127-131

Glycosaminoglycan attachment site:
Amino acids 206-210

N-myristoylation sites:
Amino acids 5-11;37-43;63-69;108-114

Amidation site:
Amino acids 173-179

FIGURE 39

ACCAGCAGAAGGCTGGGAGTCTGTAGTTTGTTCCTGCTGCCAGGCTCCACTGAGGGGAACGG
GGACCTGTCTGAAGAGAAGATGCCCCTGCTGACACTCTACCTGCTCCTCTTCTGGCTCTCAG
GCTACTCCATTGCCACTCAAATCACCGGTCCAACAACAGTGAATGGCTTGGAGCGGGGCTCC
TTGACCGTGCAGTGTGTTTACAGATCAGGCTGGGAGACCTACTTGAAGTGGTGGTGTCGAGG
AGCTATTTGGCGTGACTGCAAGATCCTTGTTAAAACCAGTGGGTCAGAGCAGGAGGTGAAGA
GGGACCGGGTGTCCATCAAGGACAATCAGAAAAACCGCACGTTCACTGTGACCATGGAGGAT
CTCATGAAAACTGATGCTGACACTTACTGGTGTGGAATTGAGAAAACTGGAAATGACCTTGG
GGTCACAGTTCAAGTGACCATTGACCCAGCACCAGTCACCCAAGAAGAAACTAGCAGCTCCC
CAACTCTGACCGGCCACCACTTGGACAACAGGCACAAGCTCCTGAAGCTCAGTGTCCTCCTG
CCCCTCATCTTCACCATATTGCTGCTGCTTTTGGTGGCCGCCTCACTCTTGGCTTGGAGGATG
ATGAAGTACCAGCAGAAAGCAGCCGGGATGTCCCCAGAGCAGGTACTGCAGCCCCTGGAGGG
CGACCTCTGCTATGCAGACCTGACCCTGCAGCTGGCCGGAACCTCCCCGCGAAAGGCTACCA
CGAAGCTTTCCTCTGCCCAGGTTGACCAGGTGGAAGTGGAATATGTCACCATGGCTTCCTTG
CCGAAGGAGGACATTTCCTATGCATCTCTGACCTTGGGTGCTGAGGATCAGGAACCGACCTA
CTGCAACATGGGCCACCTCAGTAGCCACCTCCCCGGCAGGGGCCCTGAGGAGCCCACGGAAT
ACAGCACCATCAGCAGGCCTTAGCCTGCACTCCAGGCTCCTTCTTGGACCCCAGGCTGTGAG
CACACTCCTGCCTCATCGACCGTCTGCCCCCTGCTCCCCTCATCAGGACCAACCCGGGGACT
GGTGCCTCTGCCTGATCAGCCAGCATTGCCCCTAGCTCTGGGTTGGGCTTGGGGCCAAGTCT
CAGGGGGCTTCTAGGAGTTGGGGTTTTCTAAACGTCCCCTCCTCTCCTACATAGTTGAGGAG
GGGGCTAGGGATATGCTCTGGGGCTTTCATGGGAATGATGAAGATGATAATGAGAAAAATGT
TATCATTATTATCATGAAGTACCATTATCATAATACAATGAACCTTTATTTATTGCCTACCA
CATGTTATGGGCTGAATAATGGCCCCCAAAGATATCTGTGTCCTAATCCTCAGAACTTGTGA
CTGTTACCTTCTGTGGCAGAAAGGGACAGTGCAGATGTATGTAAGTTAAGGACTTTGAGATA
GAGAGGTTATTCTTGCTGATTCAGGTGGGCCCAAAATATCACCACAAGGGTCCTCATAAGAA
AGAGGCCAGAAGGTCAAAGAGGTAGAGACAAAGTGATGATGGAAGTGGACGTGGGTGTGACG
TGAGCAGGGGCCATGAATGCCGCAGCCTTCAGATGCCAGAAAGGGAAAGGAATGGATTCCCC
TGCCTGGAGCCTCCAAAAGAAACCAGCCCTGCCCACGCCTTGACTTGAGCCCATTGAAACTG
ATCTTGAGCTCCTGGCCTCCAGAATTGCAGGAGAATAAATTTGTGTTGTTTTTAATGAAAAA
AAAAAAAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAG

FIGURE 40

></usr/seqdb2/sst/DNA/Dnaseqs.min/ss.DNA125200
><subunit 1 of 1, 290 aa, 1 stop
><MW: 32335, pI: 5.82, NX(S/T): 1
MPLLTLYLLLFWLSGYSIATQITGPTTVNGLERGSLTVQCVYRSGWETYLKWWCRGAIWR
DCKILVKTSGSEQEVKRDRVSIKDNQKNRTFTVTMEDLMKTDADTYWCGIEKTGNDLGVT
VQVTIDPAPVTQEETSSSPTLTGHHLDNRHKLLKLSVLLPLIFTILLLLLVAASLLAWRM
MKYQQKAAGMSPEQVLQPLEGDLCYADLTLQLAGTSPRKATTKLSSAQVDQVEVEYVTMA
SLPKEDISYASLTLGAEDQEPTYCNMGHLSSHLPGRGPEEPTEYSTISRP

Important features of the protein:
Signal peptide:
Amino acids 1-15

Transmembrane domain:
Amino acids 155-174

N-glycosylation site:
Amino acids 88-92 cAMP- and cGMP-dependent protein kinase phosphorylation site:
Amino acids 218-222

Tyrosine kinase phosphorylation site:
Amino acids 276-285

N-myristoylation sites:
Amino acids 30-36;109-115;114-120

FIGURE 41

AAGAACACTGTTGCTCTTGGTGGACGGGCCCAGAGGAATTCAGAGTTAAACCTTGAGTGCCT
GCGTCCGTGAGAATTCAGCATGGAATGTCTCTACTATTTCCTGGGATTTCTGCTCCTGGCTG
CAAGATTGCCACTTGATGCCGCCAAACGATTTCATGATGTGCTGGGCAATGAAAGACCTTCT
GCTTACATGAGGGAGCACAATCAATTAAATGGCTGGTCTTCTGATGAAAATGACTGGAATGA
AAAACTCTACCCAGTGTGGAAGCGGGGAGACATGAGGTGGAAAAACTCCTGGAAGGGAGGCC
GTGTGCAGGCGGTCCTGACCAGTGACTCACCAGCCCTCGTGGGCTCAAATATAACATTTGCG
GTGAACCTGATATTCCCTAGATGCCAAAAGGAAGATGCCAATGGCAACATAGTCTATGAGAA
GAACTGCAGAAATGAGGCTGGTTTATCTGCTGATCCGTATGTTTACAACTGGACAGCATGGT
CAGAGGACAGTGACGGGGAAAATGGCACCGGCCAAAGCCATCATAACGTCTTCCCTGATGGG
AAACCTTTTCCTCACCACCCCGGATGGAGAAGATGGAATTTCATCTACGTCTTCCACACACTT
GGTCAGTATTTCCAGAAATTGGGACGATGTTCAGTGAGAGTTTCTGTGAACACAGCCAATGT
GACACTTGGGCCTCAACTCATGGAAGTGACTGTCTACAGAAGACATGGACGGGCATATGTTC
CCATCGCACAAGTGAAAGATGTGTACGTGGTAACAGATCAGATTCCTGTGTTTGTGACTATG
TTCCAGAAGAACGATCGAAATTCATCCGACGAAACCTTCCTCAAAGATCTCCCCATTATGTT
TGATGTCCTGATTCATGATCCTAGCCACTTCCTCAATTATTCTACCATTAACTACAAGTGGA
GCTTCGGGGATAATACTGGCCTGTTTGTTTCCACCAATCATACTGTGAATCACACGTATGTG
CTCAATGGAACCTTCAGCCTTAACCTCACTGTGAAAGCTGCAGCACCAGGACCTTGTCCGCC
ACCGCCACCACCACCCAGACCTTCAAAACCCACCCCTTCTTTAGCAACTACTCTAAAATCTT
ATGATTCAAACACCCCAGGACCTACTGGTGACAACCCCCTGGAGCTGAGTAGGATTCCTGAT
GAAAACTGCCAGATTAACAGATATGGCCACTTTCAAGCCACCATCACAATTGTAGAGGGAAT
CTTAGAGGTTAACATCATCCAGATGACAGACGTCCTGATGCCGGTGCCATGGCCTGAAAGCT
CCCTAATAGACTTTGTCGTGACCTGCCAAGGGAGCATTCCCACGGAGGTCTGTACCATCATT
TCTGACCCCACCTGCGAGATCACCCAGAACACAGTCTGCAGCCCTGTGGATGTGGATGAGAT
GTGTCTGCTGACTGTGAGACGAACCTTCAATGGGTCTGGGACGTACTGTGTGAACCTCACCC
TGGGGGATGACACAAGCCTGGCTCTCACGAGCACCCTGATTTCTGTTCCTGACAGAGACCCA
GCCTCGCCTTTAAGGATGGCAAACAGTGCCCTGATCTCCGTTGGCTGCTTGGCCATATTTGT
CACTGTGATCTCCCTCTTGGTGTACAAAAAACACAAGGAATACAACCCAATAGAAAATAGTC
CTGGGAATGTGGTCAGAAGCAAAGGCCTGAGTGTCTTTCTCAACCGTGCAAAAGCCGTGTTC
TTCCCGGGAAACCAGGAAAAGGATCCGCTACTCAAAAACCAAGAATTTAAAGGAGTTTCTTA
AATTTCGACCTTGTTTCTGAAGCTCACTTTTCAGTGCCATTGATGTGAGATGTGCTGGAGTG
GCTATTAACCTTTTTTTCCTAAAGATTATTGTTAAATAGATATTGTGGTTTGGGGAAGTTGA
ATTTTTTATAGGTTAAATGTCATTTTAGAGATGGGGAGAGGGATTATACTGCAGGCAGCTTC
AGCCATGTTGTGAAACTGATAAAAGCAACTTAGCAAGGCTTCTTTTCATTATTTTTTATGTT
TCACTTATAAAGTCTTAGGTAACTAGTAGGATAGAAACACTGTGTCCCGAGAGTAAGGAGAG
AAGCTACTATTGATTAGAGCCTAACCCAGGTTAACTGCAAGAAGAGGCGGGATACTTTCAGC
TTTCCATGTAACTGTATGCATAAAGCCAATGTAGTCCAGTTTCTAAGATCATGTTCCAAGCTA
ACTGAATCCCACTTCAATACACACTCATGAACTCCTGATGGAACAATAACAGGCCCAAGCCT
GTGGTATGATGTGCACACTTGCTAGACTCAGAAAAAATACTACTCTCATAAATGGGTGGGAG
TATTTTGGTGACAACCTACTTTGCTTGGCTGAGTGAAGGAATGATATTCATATATTCATTTA
TTCCATGGACATTTAGTTAGTGCTTTTTATATACCAGGCATGATGCTGAGTGACACTCTTGT
GTATATTTCCAAATTTTTGTACAGTCGCTGCACATATTTGAAATCATATATTAAGACTTTCC
AAAGATGAGGTCCCTGGTTTTTCATGGCAACTTGATCAGTAAGGATTTCACCTCTGTTTGTA
ACTAAAACCATCTACTATATGTTAGACATGACATTCTTTTTCTCTCCTTCCTGAAAAATAAA
GTGTGGGAAGAGACA

FIGURE 42

```
></usr/seqdb2/sst/DNA/Dnaseqs.min/ss.DNA125214
><subunit 1 of 1, 572 aa, 1 stop
><MW: 63953, pI: 6.55, NX(S/T): 12
MECLYYFLGFLLLAARLPLDAAKRFHDVLGNERPSAYMREHNQLNGWSSDENDWNEKLYP
VWKRGDMRWKNSWKGGRVQAVLTSDSPALVGSNITFAVNLIFPRCQKEDANGNIVYEKNC
RNEAGLSADPYVYNWTAWSEDSDGENGTGQSHHNVFPDGKPFPHHPGWRRWNFIYVFHTL
GQYFQKLGRCSVRVSVNTANVTLGPQLMEVTVYRRHGRAYVPIAQVKDVYVVTDQIPVFV
TMFQKNDRNSSDETFLKDLPIMFDVLIHDPSHFLNYSTINYKWSFGDNTGLFVSTNHTVN
HTYVLNGTFSLNLTVKAAAPGPCPPPPPPPRPSKPTPSLATTLKSYDSNTPGPTGDNPLE
LSRIPDENCQINRYGHFQATITIVEGILEVNIIQMTDVLMPVPWPESSLIDFVVTCQGSI
PTEVCTIISDPTCEITQNTVCSPVDVDEMCLLTVRRTFNGSGTYCVNLTLGDDTSLALTS
TLISVPDRDPASPLRMANSALISVGCLAIFVTVISLLVYKKHKEYNPIENSPGNVVRSKG
LSVFLNRAKAVFFPGNQEKDPLLKNQEFKGVS
```

Important features of the protein:

Signal peptide:
Amino acids 1-21

Transmembrane domain:
Amino acids 496-516

N-glycosylation sites:
Amino acids 93-97;134-138;146-150;200-204;249-253;275-279;
296-300;300-304;306-310;312-316;459-463;467-471

N-myristoylation sites:
Amino acids 91-97;147-153;290-296;418-424

Prokaryotic membrane lipoprotein lipid attachment site:
Amino acids 496-507

Cell attachment sequence:
Amino acids 64-67

FIGURE 43

GCATAGATGAATGTATCAGTGGATGGATAGTTGGCTAGATGGGTGGGTTGGTGGATGAATGG
CAGAGCTTGCACCTGCCAGTCCATCTGACATCAAAGCCAGTGTCTCTAATGGTGACACCACC
CTCCTCTGCAGCAGGAGGCAGAGCTGTGGGATGAATGAGGTTCGCCAGGTCTCCCTTACCTA
TCCTGGGTCCCCAGCTCCTTCTCACTCTCTTCCCTTGCAGCCTCGAAGCGGAGGATCCCTGT
GTCCCAGCCGGGCATGGCCGACCCCCACCAGCTTTTCGATGACACAAGTTCAGCCCAGAGCC
GGGGCTATGGGGCCCAGCGGGCACCTGGTGGCCTGAGTTATCCTGCAGCCTCTCCCACGCCC
CATGCAGCCTTCCTGGCTGACCCGGTGTCCAACATGGCCATGGCCTATGGGAGCAGCCTGGC
CGCGCAGGGCAAGGAGCTGGTGGATAAGAACATCGACCGCTTCATCCCCATCACCAAGCTCA
AGTATTACTTTGCTGTGGACACCATGTATGTGGGCAGAAAGCTGGGCCTGCTGTTCTTCCCC
TACCTACACCAGGACTGGGAAGTGCAGTACCAACAGGACACCCCGGTGGCCCCCCGCTTTGAC
GTCAATGCCCCGGACCTCTACATTCCAGCAATGGCTTTCATCACCTACGTTTTGGTGGCTGG
TCTTGCGCTGGGGACCCAGGATAGGTTCTCCCCAGACCTCCTGGGGCTGCAAGCGAGCTCAG
CCCTGGCCTGGCTGACCCTGGAGGTGCTGGCCATCCTGCTCAGCCTCTATCTGGTCACTGTC
AACACCGACCTCACCACCATCGACCTGGTGGCCTTCTTGGGCTACAAATATGTCGGGATGAT
TGGCGGGGTCCTCATGGGCCTGCTCTTCGGGAAGATTGGCTACTACCTGGTGCTGGGCTGGT
GCTGCGTAGCCATCTTTGTGTTCATGATCCGGACGCTGCGGCTGAAGATCTTGGCAGACGCA
GCAGCTGAGGGGGTCCCGGTGCGTGGGGCCCGGAACCAGCTGCGCATGTACCTGACCATGGC
GGTGGCGGCGGCGCAGCCTATGCTCATGTACTGGCTCACCTTCCACCTGGTGCGGTGAGCGC
GCCCGCTGAACCTCCCGCTGCTGCTGCTGCTGCTGGGGGCCACTGTGGCCGCCGAACTCATC
TCCTGCCTGCAGGCCCCAAGGTCCACCCTGTCTGGCCACAGGCACCGCCTCCATCCCATGTC
CCGCCCAGCCCCGCCCCCAACCCAAGGTGCTGAGAGATCTCCAGCTGCACAGGCCACCGCCC
CAGGGCGTGGCCGCTGTTACAGAAACAATAAACCCTGATGGGCATGGCAAAAAAAAAAAAAA
AAAAAAAAAAAAAAAAAAAAAAAAAAAAAAAAAAAAAAAAAAAAAAAAAAAAAAAAAAAAAA
AAAAAGA

FIGURE 44

></usr/seqdb2/sst/DNA/Dnaseqs.min/ss.DNA125219
><subunit 1 of 1, 283 aa, 1 stop
><MW: 31175, pI: 7.51, NX(S/T): 0
MADPHQLFDDTSSAQSRGYGAQRAPGGLSYPAASPTPHAAFLADPVSNMAMAYGSSLAAQ
GKELVDKNIDRFIPITKLKYYFAVDTMYVGRKLGLLFFPYLHQDWEVQYQQDTPVAPRFD
VNAPDLYIPAMAFITYVLVAGLALGTQDRFSPDLLGLQASSALAWLTLEVLAILLSLYLV
TVNTDLTTIDLVAFLGYKYVGMIGGVLMGLLFGKIGYYLVLGWCCVAIFVFMIRTLRLKI
LADAAAEGVPVRGARNQLRMYLTMAVAAAQPMLMYWLTFHLVR

Important features of the protein:
Transmembrane domain:
Amino acids 126-142;164-179;215-233

N-myristoylation sites:
Amino acids 54-60;141-147;156-162;201-207;205-211;209-215

Amidation site:
Amino acids 89-93

FIGURE 45

GCTGAGCACCAACAGGAACTATTCCAGTGAAGAGCAAGTGCTGCCCGACCCAGGACCCTGTG
CCAGGCTGGCAGCCCTCCAGCTCCCTCCAGAGAGGAAACCTCTGTCTGGCTGAGGGTGGGAC
TAGCTGGGATGTCTCACTCCAGTTGCTCAGGTTCACCCAGGAAGCTCCTCCGTGGAGTGGCC
AGCCTGATTCTAGCCCTGTCCTCTCTGGCAGCACATGCCACACCTGCCTGGGCCTTCTGCTC
CCTGATGCTTGATGAGCCCCTGCCTCCTCAATGTTTCTCAAAGACAGACCCCCCTGAGGCCAGC
TTGAATGTGAAGACTGCTGAAGTCAGCTGGCTTCACTTGAGCTGCAGAAAAGGTGGCTGGGA
TGGCCCAGGTGCACCCAGAGGCCCCAGCCCTTTGGCTGCCTTTGGGTTGTGACTTGGGTTGT
CTCTGAGGCCCTGCCAGAGCTGGGCCTGCGGGTGGTGGGCGGTCCGACCTCGGGCAGTCAGT
GCTCCGCAGCCTCAGCACTGCATCCCAGACCCAGTGTCCTCAGAGGGAAGAGCCAGCCTCCC
TGCCTCATGGAACCAGGAGTCCCAAAAAGTCAGGAGCCTGGAGGCTCTGAAAGGAGCAGGGA
TTCCATAGTGCGTGAAGCTGAAATAGGCGCCCTCCTGGGGAGCCCCCAGCAAAACTGTTTTT
CATACCCACTCCCAGAACTGCCCCGCTCCAGCTCCAGCGCCAGCGCCAGCTGGTTGCCAGGC
GTCATTGGAGAGGCCTGGCTGCCCCAGGGGCAGCAGGGAGTGGTGGACCTGTATGGGCTGGC
AGGAGGCCATTGGCCATGCTGACAAGTGTCACCTGCCTTCCTAGCCTGGAGCCACCCCTCAG
GTGGCCTGCTTGCACCTCCTATCCGGAGGTAGCCTGCCCCACCTGTAGGCAGAGGGGGCTCT
TGCTTGAGGCCTGCACAGGAAGCAAGTATAGCCCCGGTGCCCCAGAGTGGGTTCCACTTAGC
CCTGGCGAGATGGCCTGTCCTGAGATCTCTGCTCCCAGACCCCACCATCTGGGGAGCACAGT
CCTTAGGCTGCCTGGTCCAGGAAGGGGGTGCGGCTCTGTCAGGAAACCTGGACTCTCAAGGC
CCACCAGCCTCTCCGTGAGTGTTAGAAATCACAGATACAGTATATACTTAATTACACTACTC
ACTACTCAAAAAAAAAAAAAAAAAA

FIGURE 46

></usr/seqdb2/sst/DNA/Dnaseqs.min/ss.DNA128309
><subunit 1 of 1, 97 aa, 1 stop
><MW: 10112, pI: 8.64, NX(S/T): 0
MSHSSCSGSPRKLLRGVASLILALSSLAAHATPAWAFCSLMLDEPLPPQCFSKTDPPEAS
LNVKTAEVSWLHLSCRKGGWDGPGAPRGPSPLAAFGL

Important features of the protein:
Signal peptide:
Amino acids 1-31

FIGURE 47

TTCCGGGCCCTGGCGTCTCGTCTCCTTACCCTGGGGCTACCCTTGCCCGGTCCTACTGCCCG
CGGTTAACCCGCCGCGAGCCGCCTCTCCCCTCCCCGCCCGACTCAACCCTGCCCTCCCCCGT
GCTTTGCAGACGCCGCCCGGGGGCCCAGGCGGCTGATGCGTGTGGGCCTCGCGCTGATCTTG
GTGGGCCACGTGAACCTGCTGCTGGGGGCCGTGCTGCATGGCACCGTCCTGCGGCACGTGGC
CAATCCCCGCGGCGCTGTCACGCCGGAGTACACCGTAGCCAATGTCATCTCTGTCGGCTCGG
GGCTGCTGAGCGTTTCCGTGGGACTTGTGGCCCTCCTGGCGTCCAGGAACCTTCTTCGCCCT
CCACTGCACTGGGTCCTGCTGGCACTAGCTCTGGTGAACCTGCTCTTGTCCGTTGCCTGCTC
CCTGGGCCTCCTTCTTGCTGTGTCACTCACTGTGGCCAACGGTGGCCGCCGCCTTATTGCTG
ACTGCCACCCAGGACTGCTGGATCCTCTGGTACCACTGGATGAGGGGCCGGGACATACTGAC
TGCCCCTTTGACCCCACAAGAATCTATGATACAGCCTTGGCTCTCTGGATCCCTTCTTTGCT
CATGTCTGCAGGGGAGGCTGCTCTATCTGGTTACTGCTGTGTGGCTGCACTCACTCTACGTG
GAGTTGGGCCCTGCAGGAAGGACGGACTTCAGGGGCAGCTAGAGGAAATGACAGAGCTTGAA
TCTCCTAAATGTAAAAGGCAGGAAAATGAGCAGCTACTGGATCAAAATCAAGAAATCCGGGC
ATCACAGAGAAGTTGGGTTTAGGACAGGTGCTGTTCCGAGACTCAGTCCTAAAGGGTTTTTT
TTCCCACTAAGCAAGGGGCCCTGACCTCGGGATGAGATAACAAATTGTAATAAAGTAACTTC
TCTTTTCTTCTAAAAAAAAAAAAAAAAAAAAAAAAAAAAAAAAAAAAAAAAAAA

FIGURE 48

></usr/seqdb2/sst/DNA/Dnaseqs.min/ss.DNA129535
><subunit 1 of 1, 222 aa, 1 stop
><MW: 23566, pI: 6.70, NX(S/T): 0
MRVGLALILVGHVNLLLGAVLHGTVLRHVANPRGAVTPEYTVANVISVGSGLLSVSVGLV
ALLASRNLLRPPLHWVLLALALVNLLLSVACSLGLLLAVSLTVANGGRRLIADCHPGLLD
PLVPLDEGPGHTDCPFDPTRIYDTALALWIPSLLMSAGEAALSGYCCVAALTLRGVGPCR
KDGLQGQLEEMTELESPKCKRQENEQLLDQNQEIRASQRSWV

Important features of the protein:
Signal peptide:
Amino acids 1-18

Transmembrane domain:
Amino acids 44-60;76-96

N-myristoylation sites:
Amino acids 94-100;175-181

Amidation site:
Amino acids 106-110

Prokaryotic membrane lipoprotein lipid attachment site:
Amino acids 81-92

FIGURE 49

CGTCAGTCTAGAAGGATAAGAGAAAGAAAGTTAAGCAACTACAGGAAATGGCTTTGGGAG
TTCCAATATCAGTCTATCTTTTATTCAACGCAATGACAGCACTGACCGAAGAGGCAGCCG
TGACTGTAACACCTCCAATCACAGCCCAGCAAGCTGACAACATAGAAGGACCCATAGCCT
TGAAGTTCTCACACCTTTGCCTGGAAGATCATAACAGTTACTGCATCAACGGTGCTTGTG
CATTCCACCATGAGCTAGAGAAAGCCATCTGCAGGTGTTTTACTGGTTATACTGGAGAAA
GGTGTGAGCACTTGACTTTAACTTCATATGCTGTGGATTCTTATGAAAAATACATTGCAA
TTGGGATTGGTGTTGGATTACTATTAAGTGGTTTTCTTGTTATTTTTTACTGCTATATAA
GAAAGAGGTATGAAAAAGACAAAATATGAAGTCACTTCATATGCAATCGTTTGACAAATA
GTTATTCAGGCCCTATAATGTGTCAGGCACTGACATGTAAAATTTTTTTAATTAAAAAAG
AGCTGTAATCTGGCAAAAAGTTTCTATGTAATATTTTTCATGCCTTTTCTCATAAACCCA
GACGAGTGGTAAAAATTTGCCTTCAGTTGTAATAGGAGAGTTCAAACGTACAGTCTCCCT
TCAACCTATCTCTGTCTGCCCATATCAAAATTATAAATGAGGAGGACAGCAGGCCCCAAG
AAAGTAGGGACTAAGTATGTCTTGTTCAAAATTGTATATTCAGTGACTTACACTATGCCT
AGCACACAACACACACTGAGTAAATATTTGTTGAGTGAAATAAAATCAAGAAACAAGTAA
AAACTGA

FIGURE 50

></usr/seqdb2/sst/DNA/Dnaseqs.min/ss.DNA129549
><subunit 1 of 1, 133 aa, 1 stop
><MW: 14792, pI: 5.97, NX(S/T): 0
MALGVPISVYLLFNAMTALTEEAAVTVTPPITAQQADNIEGPIALKFSHLCLEDHNSYCI
NGACAFHHELEKAICRCFTGYTGERCEHLTLTSYAVDSYEKYIAIGIGVGLLLSGFLVIF
YCYIRKRYEKDKI

Important features of the protein:
Signal peptide:

1-20 (weak)

Transmembrane domain:

103-117

N-myristoylation site.
4-10;106-112;110-116

EGF-like domain cysteine pattern signature.
75-87

Integrins beta chain cysteine-rich domain proteins
66-88

FIGURE 51

GGCTCGAGCTTGGCTCTCAGACCATCCTGGTGGAAGAAACACTAGCAGTCTGCCCAATCTGA
ATGCAAATCCAGAATAATCTTTTCTTTTGTTGTTACACAGTTATGAGTGCAATTTTTAAATG
GCTGCTACTCTACAGCCTGCCTGCCTTATGCTTTCTCCTGGGCACGCAGGAAAGTGAGAGCT
TCCACTCCAAAGCAGAGATCCTAGTGACACTAAGTCAGGTAATAATCTCTCCAGCTGGACCT
CATGCACTCACATGGACAACACACTTCTCTCCTTCAGTGATCATCATCCTTGTACCATGTTG
GTGGCATGCTGTAATCGTGACTCAACATCCGGTTGCCAATTGCTATGTAACAAACCACCTCA
ACATTCAGTGGCTTGAATTGAAAGCAGGGTCTTGAAGAGATATTTGCACATTTCATCCTCCC
AGCAGCATTATTCACAACAGCCAATAGGCAGAAGCAACCCAATGTCCAACCATAGATGAGTG
GATAACCAAAATGTAGTCCATCCATACAATGAAATATGATTCAGCCTTAACAAGGAAGGAAG
TCCCGCCACGTGCTACAACATGGATGGACCTTGAGGACACTATGCTAAGTGAAGTAAGCCAG
GCACAAAAGGACAAATACTCTATGATTCCATTTTATAGGGTACCAAAGAGAATCAAACTCAC
AGAGATAGAAAGTAGACTGGGGTGGCCAGGGACTCGGGGAGAGAGGAAAGGGCAGTTATTGT
TTAAAAGGTACAGAGTTTCAGTTTGGGAAGATGAAAATGTTCTGGAAACGGTTAATGGTGAT
TTTACATTGTTTATGTTACCACGATTTGTAAAAGAGCAGCTGCGCTGAGAATGAGCATGCTT
GTCATTGGCAGCTCTCTGAGATTTTCAGTGCCTCTTACTGGCTTGTTAAGAAGACGGCAAAA
AAAAAAAAAAAAAAAAAAAAAAAAAAAAAAAAAAAAAAAAAAAAAAAA

FIGURE 52

></usr/seqdb2/sst/DNA/Dnaseqs.min/ss.DNA129580
><subunit 1 of 1, 114 aa, 1 stop
><MW: 12886, pI: 7.04, NX(S/T): 0
MQIQNNLFFCCYTVMSAIFKWLLLYSLPALCFLLGTQESESFHSKAEILVTLSQVIISPA
GPHALTWTTHFSPSVIIILVPCWWHAVIVTQHPVANCYVTNHLNIQWLELKAGS

Important features of the protein:
Signal peptide:
Amino acids 1-33

Transmembrane domain:
Amino acids 71-86

N-myristoylation site:
Amino acids 35-41

FIGURE 53

TTTTGAAATGGTTTATGACCTCTTCCCCACTTCCCCGCTTGCTTTGCTCATTAGTGTTCCTA
GGTGGCTGCTGGGTGACGGGCTTTTCATCATCTCTGATGTGGGCCAGTGCGAAAGAGCAGCT
GCAACATCTGTTTCTAATTGGGTCGTGCCTTTATAAATACTTCTTGCCTATTTGTCACATTG
CTTCCCTCCCACCCTGTCTTCCTTGGAGTACTGCAGAATCTGTAAGCGTCCCTGGAATGCAC
ACGTGGACCTTGTCATTCCCAAACAGACTTTCTGCTGGTCAGCACTTTGTAATGTTCGGCTG
TTACAGGCATTAGTCACTTGTGCTCAGAGAGAGACTGTGGTCTTTGGAAACTGAAGAAAATGTC
TTTTTTGTTGTTGTTAATTCTTGGCATCCAGTTAGATTTAACTTCTCAAGAGTTTACACAGA
CTTTTAGAAAAACATTCTGTCTCTAAGAAAAAAGTGCTCTAGCTTTGTACAGTTTTTGGATT
TTCACACTTGGTGGTTGTTTGCTGAAATGCTGTTTTGCTAGTGATTCCCCTCCTCCCCCTAT
CTGGGGTTGTAAGCAGCTCTGGGGCTCTGTTCACTTCGGATACCTGTTTCTGGGGACTGCTT
TTCAACAGCGTTTTTCCTAAGGGCATATGAGAAATTTAATTTCTGATGGAATGAAGGTGAAA
CTCTAGTCCCAGGTAAACCTGGGTAGGCTGTAGAGACAGAAAGGGGGCTGCAGGTCTAGGTG
GAAGAACGAGAACGAATGCAGCATGGTATTTCCAGGCCTTTTAGATTCGGCTTCATCCACAA
CCAATGTGAGTTCTTATCTGCAAAGCGGGCCTAAGTGTAATGGAGGGAAGGTGGGCCAGGCA
CCAGGGTCCTGGGTTCTCCCGCGCCTCACTCTGTCTCCACCTGGCCCATGCATAAAGAACAC
TAGTCAAGTAGCCATTGTACCTGTTTCCTTATCTGAAAATGAGAAGGTTGGAGAGTATGACT
TCTGTTGAAACAACAAGGCGCTTACAAATTTTGGTGAAGTCGAATGAGGGCAGCGTTAAGAG
AAATATCAAAGTTAGTCATTGGATTTCAGGGCTTAGGGATGGAAACCAGCTGGTAGTAGACT
GGTTGTAGTTATGTCCAAAGGGCAGAGTGGGAAAAATTTGGCCGAAAAGAGTGTGGTGGGTG
ACCAGCAAATGTTAGAGGTATACATCAGGGCACAGAGGAGAAAAGCTAACATGATACTGATG
ACTTCAAGTCTTCACTGTCCAATTCAGAGGATAGGGGAGGGTTTAAGCTGATTAAACAGTGG
GCTTTTTTTCTCCTGCAAGAGGGTGGAGGTCTATAACTGTGCAGATTTTATCAGATGCATGC
TAATACATGTTATTCTGGGGGACTCTCTTATACCTTGAAGTAGACATTGCTGCTATTTGCGT
GAAAAAAATAGGAGGACTTATTTGAATTGAGAATGGGGATAGGCTGAGTTCCACCGAGATGT
TGGCTTAGAGATGCCTGGGCCATGCTGTACAGTAGGAAGCCCAGCAGAGGAGATTGGGCTGT
GTGGGTCATGACAAAGGGAGTTGTTAGCTTATGGTTGGCTATTAAAGTCATGGGCAAGGATG
GGCAAGAAAAGTGTGTAAAATGAGCTGACAAAAGATAAATATGTTAATTA

FIGURE 54

></usr/seqdb2/sst/DNA/Dnaseqs.min/ss.DNA129794
><subunit 1 of 1, 102 aa, 1 stop
><MW: 11382, pI: 8.72, NX(S/T): 0
MTSSPLPRLLCSLVFLGGCWVTGFSSSLMWASAKEQLQHLFLIGSCLYKYFLPICHIASL
PPCLPWSTAESVSVPGMHTWTLSFPNRLSAGQHFVMFGCYRH

Important features of the protein:
Signal peptide:
Amino acids 1-21

N-myristoylation site:
Amino acids 18-24

Prokaryotic membrane lipoprotein lipid attachment sites:
Amino acids 9-20;36-47;
89-100

FIGURE 55

ACACTGGCCAAACACTCGCATCCCAGGGCGTCTCCGGCTGCTCCCATTGAGCTGTCTGCTCG
CTGTGCCCGCTGTGCCTGCTGTGCCCGCGCTGTCGCCGCTGCTACCGCGTCTGCTGGACGCG
GGAGACGCCAGCGAGCTGGTGATTGGAGCCCTGCGGAGAGCTCAAGCGCCCAGCTCTGCCCG
AGGAGCCCAGGCTGCCCCGTGAGTCCCATAGTTGCTGCAGGAGTGGAGCCATGAGCTGCGTC
CTGGGTGGTGTCATCCCCTTGGGGCTGCTGTTCCTGGTCTGCGGATCCCAAGGCTACCTCCT
GCCCAACGTCACTCTCTTAGAGGAGCTGCTCAGCAAATACCAGCACAACGAGTCTCACTCCC
GGGTCCGCAGAGCCATCCCCAGGGAGGACAAGGAGGAGATCCTCATGCTGCACAACAAGCTT
CGGGGCCAGGTGCAGCCTCAGGCCTCCAACATGGAGTACATGACCTGGGATGACGAACTGGA
GAAGTCTGCTGCAGCGTGGGCCAGTCAGTGCATCTGGGAGCACGGGCCCACCAGTCTGCTGG
TGTCCATCGGGCAGAACCTGGGCGCTCACTGGGGCAGGTATCGCTCTCCGGGGTTCCATGTG
CAGTCCTGGTATGACGAGGTGAAGGACTACACCTACCCCTACCCGAGCGAGTGCAACCCCTG
GTGTCCAGAGAGGTGCTCGGGGCCTATGTGCACGCACTACACACAGATAGTTTGGGCCACCA
CCAACAAGATCGGTTGTGCTGTGAACACCTGCCGGAAGATGACTGTCTGGGGAGAAGTTTGG
GAGAACGCGGTCTACTTTGTCTGCAATTATTCTCCAAAGGGGAACTGGATTGGAGAAGCCCC
CTACAAGAATGGCCGGCCCTGCTCTGAGTGCCCACCCAGCTATGGAGGCAGCTGCAGGAACA
ACTTGTGTTACCGAGAAGAAACCTACACTCCAAAACCTGAAACGGACGAGATGAATGAGGTG
GAAACGGCTCCCATTCCTGAAGAAAACCATGTTTGGCTCCAACCGAGGGTGATGAGACCCAC
CAAGCCCAAGAAAACCTCTGCGGTCAACTACATGACCCAAGTCGTCAGATGTGACACCAAGA
TGAAGGACAGGTGCAAAGGGTCCACGTGTAACAGGTACCAGTGCCCAGCAGGCTGCCTGAAC
CACAAGGCGAAGATCTTTGGAAGTCTGTTCTATGAAAGCTCGTCTAGCATATGCCGCGCCGC
CATCCACTACGGGATCCTGGATGACAAGGGAGGCCTGGTGGATATCACCAGGAACGGGAAGG
TCCCCTTCTTCGTGAAGTCTGAGAGACACGGCGTGCAGTCCCTCAGCAAATACAAACCTTCC
AGCTCATTCATGGTGTCAAAAGTGAAAGTGCAGGATTTGGACTGCTACACGACCGTTGCTCA
GCTGTGCCCGTTTGAAAAGCCAGCAACTCACTGCCCAAGAATCCATTGTCCGGCACACTGCA
AAGACGAACCTTCCTACTGGGCTCCGGTGTTTGGAACCAACATCTATGCAGATACCTCAAGC
ATCTGCAAGACAGCTGTGCACGCGGGAGTCATCAGCAACGAGAGTGGGGGTGACGTGGACGT
GATGCCCGTGGATAAAAAGAAGACCTACGTGGGCTCGCTCAGGAATGGAGTTCAGTCTGAAA
GCCTGGGGACTCCTCGGGATGGAAAGGCCTTCCGGATCTTTGCTGTCAGGCAGTGAATTTCC
AGCACCAGGGGAGAAGGGGCGTCTTCAGGAGGGCTTCGGGGTTTTGCTTTTATTTTTATTTT
GTCATTGCGGGGTATATGGAGAGTCA

FIGURE 56

```
></usr/seqdb2/sst/DNA/Dnaseqs.min/ss.DNA131590
><subunit 1 of 1, 497 aa, 1 stop
><MW: 55906, pI: 8.43, NX(S/T): 4
MSCVLGGVIPLGLLFLVCGSQGYLLPNVTLLEELLSKYQHNESHSRVRRAIPREDKEEIL
MLHNKLRGQVQPQASNMEYMTWDDELEKSAAAWASQCIWEHGPTSLLVSIGQNLGAHWGR
YRSPGFHVQSWYDEVKDYTYPYPSECNPWCPERCSGPMCTHYTQIVWATTNKIGCAVNTC
RKMTVWGEVWENAVYFVCNYSPKGNWIGEAPYKNGRPCSECPPSYGGSCRNNLCYREETY
TPKPETDEMNEVETAPIPEENHVWLQPRVMRPTKPKKTSAVNYMTQVVRCDTKMKDRCKG
STCNRYQCPAGCLNHKAKIFGSLFYESSSSICRAAIHYGILDDKGGLVDITRNGKVPFFV
KSERHGVQSLSKYKPSSSFMVSKVKVQDLDCYTTVAQLCPFEKPATHCPRIHCPAHCKDE
PSYWAPVFGTNIYADTSSICKTAVHAGVISNESGGDVDVMPVDKKKTYVGSLRNGVQSES
LGTPRDGKAFRIFAVRQ
```

Important features of the protein:

Signal peptide:
Amino acids 1-22

N-glycosylation sites:
Amino acids 27-31;41-45;451-455 cAMP- and cGMP-dependent protein kinase phosphorylation sites:
Amino acids 181-185;276-280;464-468

Tyrosine kinase phosphorylation site:
Amino acids 385-393

N-myristoylation sites:
Amino acids 111-117;115-121;174-180;204-210;227-233;300-306;
447-453;470-476

Extracellular proteins SCP/Tpx-1/Ag5/PR-1/Sc7 signature 2:
Amino acids 195-207

SCP-like extracellular protein:
Amino acids 56-208

FIGURE 57

GCACGAGGCCAAACACAGCAGCCTCAACATGAAGGTGGTTATGGTCCTCCTGCTTGCTGCCC
TCCCCCTTTACTGCTATGCAGGTTCTGGTTGCGTTCTTCTGGAGAGCGTCGTGGAAAAGACC
ATCGATCCATCGGTTTCTGTGGAGGAATACAAAGCAGATCTTCAGAGGTTCATCGACACTGA
GCAAACCGAAGCAGCTGTAGAGGAGTTCAAGGAGTGCTTCCTCAGCCAGAGCAATGAGACTC
TGGCCAACTTCCGAGTCATGGTGCATACGATATATGACAGCCTTTACTGTGCTGCGTATTAA
CTGTCACAAGAACTTTGGCTCAGAGGAATCCAGACGATGCTCACAACCCGACTGTGGACTGG
CAGAAATCTCAACTTTTCCTTTTGACTTTCCCCTTTGATCAGTAATATGGAAGACGTTGTTG
AAACCTGAAGTATAGTTAATTTAAATAAACCCACTGCAAGAAAAAAAAAAAA

FIGURE 58

></usr/seqdb2/sst/DNA/Dnaseqs.min/ss.DNA135173
><subunit 1 of 1, 93 aa, 1 stop
><MW: 10456, pI: 4.37, NX(S/T): 1
MKVVMVLLLAALPLYCYAGSGCVLLESVVEKTIDPSVSVEEYKADLQRFIDTEQTEAAVE
EFKECFLSQSNETLANFRVMVHTIYDSLYCAAY

Important features of the protein:
Signal peptide:
Amino acids 1-18

Prokaryotic membrane lipoprotein lipid attachment site:
Amino acids 12-23

FIGURE 59A

CAAGTCCGTTGAGGCTGCCAGGCGAGTCAGGTCTCTCTGGACCTCGCCTGACTCGGCTGGGC
TGTGCCTGAAATTGACCCAGCTCCACCATACTCCTTGATTATGAGAAAACAAGGAGTAAGCT
CAAAGCGGCTGCAATCTTCCGGCCGCAGCCAGTCTAAGGGGCGGCGCGGGGCCTCCCTCGCC
CGGGAGCCGGAGGTAGAGGAGGAGGTGGAAAAGTCGGTCCTAGGCGGCGGGAAACTGCCAAG
GGGCGCCTGGAGGTCCTCCCCGGGGAGGATCCAAAGTCTGAAAGAGCGAAAAGGCTTGGAGC
TAGAGGTGGTGGCCAAGACCTTTCTTCTCGGCCCCTTCCAGTTCGTCCGTAATTCCCTGGCG
CAGCTCCGGGAAAAGGTGCAGGAACTGCAGGCGCGGCGGTTCTCCAGCAGAACCACTCTCGG
CATCGCTGTCTTTGTGGCAATTTTACATTGGTTACATTTAGTAACACTTTTTGAAAATGATC
GTCATTTCTCTCACCTCTCATCTTTGGAACGGGAGATGACTTTTCGCACTGAAATGGGACTT
TATTATTCATACTTCAAGACCATTATTGAAGCACCTTCGTTTTTGGAAGGACTGTGGATGAT
TATGAATGACAGGCTTACTGAATATCCTCTTATAATTAATGCAATAAAACGCTTCCATCTTT
ATCCAGAGGTAATCATAGCCTCCTGGTATTGCACATTCATGGGAATAATGAATTTATTTGGA
CTAGAAACTAAGACCTGCTGGAATGTCACCAGAATAGAACCTCTTAATGAAGTTCAAAGCTG
TGAAGGATTGGGAGATCCTGCTTGCTTTTATGTTGGTGTAATCTTTATTTTAAATGGACTAA
TGATGGGATTGTTCTTCATGTATGGAGCATACCTGAGTGGGACTCAACTGGGAGGTCTTATT
ACAGTACTGTGCTTCTTTTTCAACCATGGAGAGGCCACCCGTGTGATGTGGACACCACCTCT
CCGTGAAAGTTTTTCCTATCCTTTCCTTGTACTTCAGATGTGTATTTTAACTTTGATTCTCA
GGACCTCAAGCAATGATAGAAGGCCCTTCATTGCACTCTGTCTTTCCAATGTTGCTTTTATG
CTTCCCTGGCAATTTGCTCAGTTTATACTTTTTACACAGATAGCATCATTATTTCCCATGTA
TGTTGTGGGATACATTGAACCAAGCAAATTTCAGAAGATCATTTATATGAACATGATTTCAGTT
ACCCTTAGTTTCATTTTGATGTTTGGAAATTCAATGTACTTATCTTCTTATTATTCTTCATC
TTTGTTAATGACGTGGGCAATAATTCTAAAGAGAAATGAAATTCAAAAACTGGGAGTATCTA
AACTCAACTTTTGGCTAATTCAAGGTAGTGCCTGGTGGTGTGGAACAATCATTTTGAAATTT
CTGACATCTAAAATCTTAGGCGTTTCAGACCACATTCGCCTGAGTGATCTTATAGCAGCCAG
AATCTTAAGGTATACAGATTTTGATACTTTAATATATACCTGTGCTCCCGAATTTGACTTCA
TGGAAAAAGCGACTCCGCTGAGATACACAAAGACATTATTGCTTCCAGTTGTTATGGTGATT
ACATGTTTTATCTTTAAAAAGACTGTTCGTGATATTTCATATGTTTTAGCTACAAACATTTA
TCTAAGAAAACAGCTCCTTGAACACAGTGAGCTGGCTTTTCACACATTGCAGTTGTTAGTGT
TTACTGCCCTTGCCATTTTAATTATGAGGCTAAAGATGTTTTTGACACCGCACATGTGTGTT
ATGGCTTCCTTGATATGCTCTCGACAGCTCTTTGGCTGGCTTTTTCGCAGAGTTCGTTTTGA
GAAGGTTATCTTTGGCATTTTAACAGTGATGTCAATACAAGGTTATGCAAACCTCCGTAATC
AATGGAGCATAATAGGAGAATTTAATAATTTGCCTCAGGAAGAACTTTTACAGTGGATCAAA
TACAGTACCACATCAGATGCTGTCTTTGCAGGTGCCATGCCTACAATGGCAAGCATCAAGCT
GTCTACACTTCATCCCATTGTGAATCATCCACATTACGAAGATGCAGACTTGAGGGCTCGGA
CAAAAATAGTTTATTCTACATATAGTCGAAAATCTGCCAAAGAAGTAAGAGATAAATTGTTG
GAGTTACATGTGAATTATTATGTTTTAGAAGAGGCATGGTGTGTTGTGAGAACTAAGCCTGG
TTGCAGTATGCTTGAAATCTGGGATGTGGAAGACCCTTCCAATGCAGCTAACCCTCCCTTAT
GTAGCGTCCTGCTCGAAGACGCCAGGCCTTACTTCACCACAGTATTTCAGAATAGTGTGTAC
AGAGTATTAAAGGTTAACTGAGAAGGATACTACCCATTTTACTATGGCACAATGCCGTGTGT
CAAAAACAATCACCCTTTGGCTTATTCACATTAATAAAAATCACAAGCTTTAATAACAGACA
CTTAAAAATAAGATAAAAATGGATTGGAAATTTTTCTGATTACTAAAAGGTAAATTACTTTT
CTGTTCATTGAATGTCAGCCTTATTAAGCTTGTCATATAAGTTATTAAATCATTCATGTCAT
ACTGCATAAACAAATGTTCATTTCAGAATTTTAAAGAGAAATGTATATAAAGAACMATGATT
TTAATAATCAGGGGTATGTAAGTCCTTTTTCATCCAACTAGGTGAATTGCTTCAGATTTTCT
CTAGTACCAGAGGGTACCTCCTCAAACTCTTTGAACCACTTAAGGCAGAAGAATGCAAGCTC
TGAAATGACATCCTTAAAATGCTGATACTGGTCACAGCCTCTTTACCTCTGTGAGGAAATTG
TAACAGTGTGTCTTTTAAGGTGTTTTTATTTTACCAGCCCTTAAGAAAGATCTCTAATACCT
TTTAATACTTTTTTTTAATAATTTCAAGTTGAAGTGTTTTTAAAAACACTTTGTTTTGTAAT
GTTTTGAATCTCTTGAGATGTGTTTACCCCACTAGATACATATTTGCCACTGGTTAGTTCTC
CATCTAAGCTCAAGAGGTTATTCATCTCTCTTTAGATTCCAGTGGCTTTTCTTTTAACATCC
AGGTAAAACAGAAACTGCTATGGTATACAACCAAGTTTTGGGGTTAAACATAATCAGAAAAG

FIGURE 59B

AAAATCCAGTTAAATTTATGAAGTGAGATTTTCAGATCCTAGATCTTGAATAAAGGAAAGGT
CTTTTCATCTTGATGGCCCCAAAGCTTGTTGGTCATGGTCTTTATTTCTGGCCACTATCTTC
TTAAATAATATATTTTTAAGCCCTCATTTATTTTTGGTTTTGGGTGAGGAAAGTCATGTTTT
CTAAGTCCTCTCCCCTAATAAAACCTACCCAACAATAGTGCTTTGAAAAGTGGTAGTTATCT
TGAAGATACTCTTGCCAAATGCAAAGATAAACATTCTTTTTGTCTGCTTTATAAATATGAAA
TATGCCAGATCTATAGTATTTTAATGTGCATCTACTTTAAATGAGTCATCTTGGGGTTTTTA
TAATTCCCTTATGTTCTTGCCCCTCTACACTTGAAATAACAAAATGCCTTAATTTTATGGAT
TAGTTCTCTTATAGTAGACAGGCAGCTATATGCAGCAAAACCAATAAAGTTATTTTTCAACT
TTCATAGTTGTAAAATATCTTATACCAGAATACAAAACAGCTAAGAAAACATGCCACATTTTAT
TTTAGCATTTTCAAATAATTTGTTTTTGGTGTAAGCACAGGATAAAAAAGGAGAGCGTCAAA
GAAAAGAGACATAACACCTAACATTCATAAAAATTAACAAAGTATATTTTGGATGATGTTTT
TACAGGAAATATTTTAAATAAGTTGGTAGAACTTTTAAAATGGTACTGTATTAGCTAATAAA
ATATTCAGTACAAATATATGTTTGGATTTATGCATTAAAAAACTAATAAAATTATTTCCAAC
TTTA

FIGURE 60

></usr/seqdb2/sst/DNA/Dnaseqs.min/ss.DNA138039
><subunit 1 of 1, 758 aa, 1 stop
><MW: 87354, pI: 9.36, NX(S/T): 1
MRKQGVSSKRLQSSGRSQSKGRRGASLAREPEVEEEVEKSVLGGGKLPRGAWRSSPGRIQ
SLKERKGLELEVVAKTFLLGPFQFVRNSLAQLREKVQELQARRFSSRTTLGIAVFVAILH
WLHLVTLFENDRHFSHLSSLEREMTFRTEMGLYYSYFKTIIEAPSFLEGLWMIMNDRLTE
YPLIINAIKRFHLYPEVIIASWYCTFMGIMNLFGLETKTCWNVTRIEPLNEVQSCEGLGD
PACFYVGVIFILNGLMMGLFFMYGAYLSGTQLGGLITVLCFFFNHGEATRVMWTPPLRES
FSYPFLVLQMCILTLILRTSSNDRRPFIALCLSNVAFMLPWQFAQFILFTQIASLFPMYV
VGYIEPSKFQKIIYMNMISVTLSFILMFGNSMYLSSYYSSSLLMTWAIILKRNEIQKLGV
SKLNFWLIQGSAWWCGTIILKFLTSKILGVSDHIRLSDLIAARILRYTDFDTLIYTCAPE
FDFMEKATPLRYTKTLLLPVVMVITCFIFKKTVRDISYVLATNIYLRKQLLEHSELAFHT
LQLLVFTALAILIMRLKMFLTPHMCVMASLICSRQLFGWLFRRVRFEKVIFGILTVMSIQ
GYANLRNQWSIIGEFNNLPQEELLQWIKYSTTSDAVFAGAMPTMASIKLSTLHPIVNHPH
YEDADLRARTKIVYSTYSRKSAKEVRDKLLELHVNYYVLEEAWCVVRTKPGCSMLEIWDV
EDPSNAANPPLCSVLLEDARPYFTTVFQNSVYRVLKVN

Important features of the protein:
Transmembrane domain:
Amino acids 109-124;197-213;241-260;266-283;302-315;336-356;
376-391;430-450;495-509;541-560;584-599;634-647

N-glycosylation site:
Amino acids 222-226 cAMP- and cGMP-dependent protein kinase phosphorylation site:
Amino acids 102-106

Tyrosine kinase phosphorylation site:
Amino acids 511-519

N-myristoylation sites:
Amino acids 24-30;50-56;151-157;254-260;264-270;269-275;
273-279;639-645

Amidation site:
Amino acids 20-24

FIGURE 61

GGCGCGGCCACATCCTTTAAATATGGTCTTTCTTGGGCGCGCGCGACAATGTGAGGAGTGGG
GTGGAGCGTGTGTGGTGTGTGGCTGCGGCCTGGGCAAGAGCCGCCGCGGACCATGAGCTGAG
TAAGTTCTGGAGGGATCCTGCCTCTTGGAGCCTTCGCAGCCAGGCAGCTGTGAACTGTGAGC
TAGAGTGAAGCAGAAATCTAGGAAGATGAGCTCCAAGATGGTCATAAGTGAACCAGGACTGA
ATTGGGATATTTCCCCCAAAAATGGCCTTAAGACATTTTTCTCTCGAGAAAATTATAAAGAT
CATTCCATGGCTCCAAGTTTAAAAGAACTACGTGTTTTATCCAACAGACGTATAGGAGAAAA
TTTGAATGCCTCAGCAAGTTCTGTAGAAAATGAGCCGGCAGTTAGTTCAGCAACTCAAGCAA
AGGAAAAAGTTAAAACCACAATTGGAATGGTTCTTCTTCCAAAACCAAGAGTTCCTTATCCT
CGTTTCTCTCGTTTCTCACAGAGAGAGCAGAGGAGTTATGTGGACTTGTTGGTTAAATACGC
AAAGATTCCTGCAAATTCCAAAGCTGTTGGAATAAATAAAAATGACTACTTGCAGTACTTGG
ATATGAAAAAACATGTGAACGAAGAAGTTACTGAGTTCCTAAAGTTTTTGCAGAATTCTGCA
AAGAAATGTGCGCAGGATTATAATATGCTTTCTGATGATGCCCGTCTCTTCACAGAGAAAAT
TTTAAGAGCTTGCATTGAACAAGTGAAAAAGTATTCAGAATTCTATACTCTCCACGAGGTCA
CCAGCTTAATGGGATTCTTCCCATTCAGAGTAGAGATGGGATTAAAGTTAGAAAAAACTCTT
CTCGCATTGGGCAGTGTAAAATATGTGAAAACAGTATTTCCCTCAATGCCTATAAAGTTGCAG
CTGTCAAAGGACGATATAGCTACCATTGAAACGTCAGAACAAACAGCTGAAGCTATGCATTA
TGATATTAGTAAAGATCCAAATGCAGAGAAGCTTGTTTCCAGATATCACCCTCAGATAGCTC
TAACTAGTCAGTCATTATTTACCTTATTAAATAATCATGGACCAACGTACAAGGAACAGTGG
GAAATTCCAGTGTGTATTCAAGTAATACCTGTTGCAGGTTCAAAACCAGTTAAAGTAATATA
TATTAATTCACCACTTCCCCAAAAGAAAATGACTATGAGAGAGAGAAATCAAATCTTTCATG
AAGTTCCATTAAAATTTATGATGTCCAAAAACACATCTGTTCCAGTCTCTGCAGTCTTTATG
GACAAACCTGAAGAGTTTATATCTGAAATGGACATGTCCTGTGAAGTCAACGAGTGCCGAAA
AATTGAGAGTCTTGAAAACTTGTATTTGGATTTTGATGATGATGTCACAGAACTTGAAACTT
TTGGAGTAACCACCACCAAAGTATCAAAATCACCAAGTCCAGCAAGTACTTCCACAGTACCT
AACATGACAGATGCTCCTACAGCCCCCAAAGCAGGAACTACAACTGTGGCACCAAGTGCACC
AGACATTTCTGCTAATTCTAGAAGTTTATCTCAGATTCTGATGGAACAATTGCAAAAGGAGA
AACAGCTGGTCACTGGTATGGATGGTGGCCCTGAGGAATGCAAAAATAAAGATGATCAGGGA
TTTGAATCATGTGAAAAGGTATCAAATTCTGACAAGCCTTTGATACAAGATAGTGACTTGAA
AACATCTGATGCCTTACAGTTAGAAAATTCTCAGGAAATTGAAACTTCTAATAAAAATGATA
TGACTATAGATATACTACATGCTGATGGTGAAAGACCTAATGTTCTAGAAAACCTAGACAAC
TCAAAGGAAAAGACTGTTGGATCAGAAGCAGCAAAAACTGAAGATACAGTTCTCTGCAGCAG
TGATACAGATGAGGAGTGTTTAATCATTGATACAGAATGTAAAAAAACCAGTTATAACAGTG
TTTAATTTAGATAAGTTTGAGGGAAAATAATCAGTAGGCAAGAGGAACATTTTTCCTGTAGT
AGCTAGAGTGCCTTGAAAAAATGTGTTGGCTATGTGAAGGAATATTTCAACTAAAATGGAAT
GGTATGCTTTTCACCCTTAAAGTTTGAGGAGGATCTTGATATGTTTTAACATTATCATGGCA
GGGAAATATATAAAGAAGAAAAATATTTTTACATTAAACCTTTTCTAAAAATTGTAAATAGA
AAAATAATTTGGTTTTTTATCAAGAACAACACTTATCGTTATGTATTGTGTTAGTTATATTG
CCAGTCTGTTGCGACTGACTCAAAAAGTTAAATGTTGCCACTGCTGAAGATGATTATGAGCA
TCGCAAACTTTGTTTCTGACCCATTTTGACAGTTTTTATATACTCCTTTAAAATGATGAATG
TTACAGGTTAATAAAGTTAATACCTTTAAA

FIGURE 62

></usr/seqdb2/sst/DNA/Dnaseqs.min/ss.DNA139540
><subunit 1 of 1, 592 aa, 1 stop
><MW: 66453, pI: 5.42, NX(S/T): 3
MSSKMVISEPGLNWDISPKNGLKTFFSRENYKDHSMAPSLKELRVLSNRRIGENLNASAS
SVENEPAVSSATQAKEKVKTTIGMVLLPKPRVPYPRFSRFSQREQRSYVDLLVKYAKIPA
NSKAVGINKNDYLQYLDMKKHVNEEVTEFLKFLQNSAKKCAQDYNMLSDDARLFTEKILR
ACIEQVKKYSEFYTLHEVTSLMGFFPFRVEMGLKLEKTLLALGSVKYVKTVFPSMPIKLQ
LSKDDIATIETSEQTAEAMHYDISKDPNAEKLVSRYHPQIALTSQSLFTLLNNHGPTYKE
QWEIPVCIQVIPVAGSKPVKVIYINSPLPQKKMTMRERNQIFHEVPLKFMMSKNTSVPVS
AVFMDKPEEFISEMDMSCEVNECRKIESLENLYLDFDDDVTELETFGVTTTKVSKSPSPA
STSTVPNMTDAPTAPKAGTTTVAPSAPDISANSRSLSQILMEQLQKEKQLVTGMDGGPEE
CKNKDDQGFESCEKVSNSDKPLIQDSDLKTSDALQLENSQEIETSNKNDMTIDILHADGE
RPNVLENLDNSKEKTVGSEAAKTEDTVLCSSDTDEECLIIDTECKKTSYNSV

Important features of the protein:
N-glycosylation sites:
Amino acids 56-60;354-358;427-431 cAMP- and cGMP-dependent protein kinase phosphorylation sites:
Amino acids 187-191;331-335;585-589

N-myristoylation sites:
Amino acids 126-132;407-413;557-563

FIGURE 63

TTTTTAACTTGAACTTCCAAGGCCACGTGCGTCTCCTGGCTCCTGCACGGACTGTGTGACTG
TCCCCGACAGCTTTCCTGTCTCGTCTCATGAGGGGTCCAGCACATGGCATTCTGGGTCGGCA
CCTGAAGTCCACCTCTATGAGACCCTCTGGGAGCGTGACGGGGCCTTGGCATGGGTCGGCCG
AGGCCCTTCTGTCCCAGGTCACTGGTGTGGTCGGCCCAGGCCCTCCTGTCCCACATCACCTG
TGTGGTCGGCCCAGGCCCTCCTGTCCCAGGTCACCGGTGTGGTCGGCCCAGGCCCTCCTGTC
CAGGTCCTCCTGTCCAGGTCACTGGTGTGGTCGGCCCAGGCCCTTCTGTCCCAGGTCACCTG
TGTGGTCGGCCCAGGGCCCTCCTGTACCATGTCACTGTTGAGGGGCTGGCTCTGGAAGAGGG
CAGGGACTTGGCATTGGTGGGGGCAGGGTTCCAAGGTGTGGCCTGTCAGCAGGAAGGGGCAG
GTGGCATGGGTCCAGGCGGGACTCAGGGCTGGGGTGCCACTGCTGGAGACTGTCCGGAGGCC
CCTCCAGGGCACCTTGCCATTGCCATTGTCGCTCATGGCCATCTGGTCCCGTTTCAGGGAAC
AAGAGGAGGATCAGATGCTGCGGGACATGATTGAGAAGCTGGGTGACTGGGCCGGGGATGCT
GAGGGCTGGGCTGGCTGGCTGGGTGGGCCGGGGATGCTGAGTGCTGGGCTGGCTGGCTGGGT
GGACCGGGCCTCCAGCTGGGGTGGGGGGGGCGGGTATCGGGTCCCCCCCTCAGCCTTGG
TGACAGGACAGGCAGGTTCACCCTGAGGGTGAGAGCTCCCTCCCGCCCCTAAGAGAGCCAGG
GGCAGCTGGTGACCGTGTGGTCATGGTGGGGACCAGCCCTCCGGGGCACCCAGTCGGGGCAG
GTTCTCACGTGGGAGGGCACAGGGCTTCCTGCAGGCTCGGAGGCCCAGGGCGGATTGTGGCC
AGTGGAAGGGAAGGATGTTTCTGGCAGGGGGACTTGTGTGGGCCACGGCTGTGCGGCTGCGG
CGTTGAGCACGGCCTCACTGTCCACCTGTCCCCTAGGCCTCCAGAGGAAGAAGTCCAAGTTC
CGCTTGTCCAAGATCTGGTCACCAAAAAGCAAAAGCAGCCCCTCCCAGTAGTAGCCAGTAGG
GCCGTGGGCTCGGCCCGGACCTGGCATCCGGACTTGGACTCGGGGCCATGGGCTTGGCCCGG
ACCCGGAACCCGGACTTGTACTCGGGGCCGTGGGCTCGGCCCGGACCCGGCATTCGGACTTG
GACTCGGGAAGGGCCTCCTGTCCCTACAAGGGGCATGTGGACAGCAGGGACCTGCGCTACCG
TCTGTGGTCTCAATAAAGAAACCGACCACATGGCCCCGGAAAAAAAAAAAAAAAAAAAAA
AAAAAAAAAAAAAAAAAAAAAACA

FIGURE 64

></usr/seqdb2/sst/DNA/Dnaseqs.min/ss.DNA139602
><subunit 1 of 1, 159 aa, 1 stop
><MW: 15900, pI: 8.07, NX(S/T): 0
MGRPRPFCPRSLVWSAQALLSHITCVVGPGPPVPGHRCGRPRPSCPGPPVQVTGVVGPGP
SVPGHLCGRPRALLYHVTVEGLALEEGRDLALVGAGFQGVACQQEGAGGMGPGGTQGWGA
TAGDCPEAPPGHLAIAIVAHGHLVPFQGTRGGSDAAGHD

Important features of the protein:
Signal peptide:
Amino acids 1-25

N-myristoylation sites:
Amino acids 109-115;113-119;119-125;148-154;151-157;152-158

FIGURE 65

GGCGACCACCGCCGCCTCCTCACCTGGCCATTGGTGCAGCCCGTTCCCGGCGGCGAGAGAAG
GCAGGCGCGCTCCTTGCGCCACGCCACACCGTCGGGCCCCCGTCGGGTCCCCCTCGGGCCGCA
ATGGTGGGCTCCGCGCGGCTGGGTCCGGCACTCTTGACCCCCTTTGTAACCACCGCGGCGGG
CACCCAGGGAGTTCGAGCAACGAAGTTGGTGACCTGCCCCGCTCCCAGGCAGTTTGCTGTTG
GGGCTTTCACGGCTGCTGGAAGGGCATGGCTGTTTGTCCCATCACTGGGCGCCAGCTTCTCA
AAGCTACGTTCACAGCAACGCAGTAGGGACTTTCGTGGCAGGCTTTTTTTAAGAGCTGAAAG
AAGGGCGGGAGGGTTTACGTCCTAGGGTGATGATTTCCTCACCAGACAGCGAAGTATCTATT
GGGAAACTCCAGGTGACCGCACCTCCTTCCGACAGTTCGCCCCGGGGCAAGTTTACCAGCTG
CGTCAGAAAGCAGGTTTGCAAAATCCTTGGAGAACGGCCTGAGCTAAGGACTGGGGTCAGGA
GGGTTTTAAACTCATTCTGATTTTCTTGCAATCATATCTCTTGAAAGTTTTTATATTTTCCC
CAATATTTTTCTGAGTTGCTATATCCAATGAAAACAATGCTGATGTAGAGGTCCACCAGCCA
ATGCTTTATTGGAAGTCAACGAATGAGACCGAGGGTGGCCCATAATCAATCTCGGCACGCGG
GAATGTGAACCTCTTCCAAGGTCTGGGCGAGTCCCTAGAGTTACGCAGATGAAGGACATTGG
CCCTCGAGAATCTCACACCAGCAAAGAAGAGCACAACGAAGCGCAAACTACTTATGATCATT
GTGGCTTTGGGCAAGTTGTTGTAGCTCCCAGCAACAATTTCTTCACCTGGAGTGCAGCAATA
AATGATACTGGTGCTGCAGGGCAGCTAATAAGCTTCTGAATAATATATGCAAAGTACTTGGC
ACCATGAGCAGAACTCAGTATACCGTCACTGAAGAAATAGCTTATTTAATGATTACACTTTT
CATATGTGCAAGTAAAAGTTTGACTTTTAGGGAGAGCCTCACCTACGGAATGTCTTTTTTAA
ATTTCTTTTTTAATTATACTTTAAGTTCTGGGATACATGTGCAGAACGTGCAGGTTTGTTAC
ACAGGTATACATGTGCCATGGTGGTTTGCAGCACCCATCAACCCTTCATCTAGGTTTTAAGC
TCCGCATGCATTAGTTATTTGTCCTAATGCTCTCCCTCCCCTTGTCCCCCACCCCCCAACAG
GCCTCAGGGTGTGATGTTCCCCTCCCTGGGTCCATATGTTCTCATTGTTCAACTCCCACTTA
TGATGAGAACATGCAGTGTTTGGTTTTCTGTTCCTGTGTTAGTTTGCTGAGAATGATGGTTT
CCAGCATCATCCACGTCCCTGCAAAGGACATGAATTCATTCTTTTTTATGGCTGCATGGTAT
TCCATGGTGTATATGTGCCACATTTTCTTCATCCAGTCTATCATTGATGGGCACTTGGGTTG
GTTCCAAGACTTTGTTATTGTGAACAGTGCTGCAATAAACATACGTTTGTATGTGTCAAAAA
AAAAAAAAAAAAAAAA

FIGURE 66

></usr/seqdb2/sst/DNA/Dnaseqs.min/ss.DNA139632
><subunit 1 of 1, 90 aa, 1 stop
><MW: 9586, pI: 12.18, NX(S/T): 0
MVGSARLGPALLTPFVTTAAGTQGVRATKLVTCPAPRQFAVGAFTAAGRAWLFVPSLGAS
FSKLRSQQRSRDFRGRLFLRAERRAGGFTS

Important features of the protein:
Signal peptide:
Amino acids 1-24

N-myristoylation sites:
Amino acids 24-30;42-48;58-64

FIGURE 67

CATGTCTAGACTGGGAGCCCTGGGTGGTGCCCGTGCCGGGCTGGGACTGTTGCTGGGTACCG
CCGCCGGCCTTGGATTCCTGTGCCTCCTTTACAGCCAGCGATGGAAACGGACCCAGCGTCAT
GGCCGCAGCCAGAGCCTGCCCAACTCCCTGGACTATACGCAGACTTCAGATCCCGGACGCCA
CGTGATGCTCCTGCGGGCTGTCCCAGGTGGGGCTGGAGATGCCTCAGTGCTGCCCAGCCTTC
CACGGGAAGGACAGGAGAAGGTGCTGGACCGCCTGGACTTTGTGCTGACCAGCCTTGTGGCG
CTGCGGCGGGAGGTGGAGGAGCTGAGAAGCAGCCTGCGAGGGCTTGCGGGGGAGATTGTTGG
GGAGGTCCGATGCCACATGGAAGAGAACCAGAGAGTGGCTCGGCGGCGAAGGTTTCCGTTTG
TCCGGGAGAGGAGTGACTCCACTGGCTCCAGCTCTGTCTACTTCACGGCCTCCTCGGGAGCC
ACGTTCACAGATGCTGAGAGTGAAGGGGGTTACACAACAGCCAATGCGGAGTCTGACAATGA
GCGGGACTCTGACAAAGAAAGTGAGGACGGGGAAGATGAAGTGAGCTGTGAGACTGTGAAGA
TGGGGAGAAAGGATTCTCTTGACTTGGAGGAAGAGGCAGCTTCAGGTGCCTCCAGTGCCCTG
GAGGCTGGAGGTTCCTCAGGCTTGGAGGATGTGCTGCCCCTCCTGCAGCAGGCCGACGAGCT
GCACAGGGGTGATGAGCAAGGCAAGCGGGAGGGCTTCCAGCTGCTGCTCAACAACAAGCTGG
TGTATGGAAGCCGGCAGGACTTTCTCTGGCGCCTGGCCCGAGCCTACAGTGACATGTGTGAG
CTCACTGAGGAGGTGAGCGAGAAGAAGTCATATGCCCTAGATGGAAAAGAAGAAGCAGAGGC
TGCTCTGGAGAAGGGGGATGAGAGTGCTGACTGTCACCTGTGGTATGCGGTGCTTTGTGGTC
AGCTGGCTGAGCATGAGAGCATCCAGAGGCGCATCCAGAGTGGCTTTAGCTTCAAGGAGCAT
GTGGACAAAGCCATTGCTCTCCAGCCAGAAAACCCCATGGCTCACTTTCTTCTTGGCAGGTG
GTGCTATCAGGTCTCTCACCTGAGCTGGCTAGAAAAAAAAACTGCTACAGCCTTGCTTGAAA
GCCCTCTCAGTGCCACTGTGGAAGATGCCCTCCAGAGCTTCCTAAAGGCTGAAGAACTACAG
CCAGGATTTTCCAAAGCAGGAAGGGTATATATTTCCAAGTGCTACAGAGAACTAGGGAAAAA
CTCTGAAGCTAGATGGTGGATGAAGTTGGCCCTGGAGCTGCCAGATGTCACGAAGGAGGATT
TGGCTATCCAGAAGGACCTGGAAGAACTGGAAGTCATTTTACGAGACTAACCACGTTTCACT
GGCCTTCATGACTTGATGCCACTATTTAAGGTGGGGGGGCGGGGAGGCTTTTTTCCTTAGAC
CTTGCTGAGATCAGGAAACCACACAAATCTGTCTCCTGGGTCTGACTGCTACCCACTACCAC
TCCCCATTAGTTAATTTATTCTAACCTCTAACCTAATCTAGAATTGGGGCAGTACTCATGGC
TTCCGTTTCTGTTGTTCTCTCCCTTGAGTAATCTCTTAAAAAAATCAAGATTCACACCTGCC
CCAGGATTACACATGGGTAGAGCCTGCAAGACCTGAGACCTTCCAATTGCTGGTGAGGTGGA
TGAACTTCAAAGCTATAGGAACAAAGCACATAACTTGTCACTTTAATCTTTTTCACTGACTA
ATAGGACTCAGTACATATAGTCTTAAGATCATACCTTACCTACCAAGGTAAAAAGAGGATCA
GAGTGGCCCACAGACATTGCTTTCTTATCACCTATCATGTGAATTCTACCTGTATTCCTGGG
CTGGACCACTTGATAACTTCCAGTGTCCTGGCAGCTTTTGGAATGACAGCAGTGGTATGGGG
TTTATGATGCTATAAAACAATGTCTGAAAAGTTGCCTAGAATATATTTTGTTACAAACTTGA
AATAAACCAAATTTGATGTT

FIGURE 68

></usr/seqdb2/sst/DNA/Dnaseqs.min/ss.DNA139686
><subunit 1 of 1, 470 aa, 1 stop
><MW: 52118, pI: 5.06, NX(S/T): 0
MSRLGALGGARAGLGLLLGTAAGLGFLCLLYSQRWKRTQRHGRSQSLPNSLDYTQTSDPG
RHVMLLRAVPGGAGDASVLPSLPREGQEKVLDRLDFVLTSLVALRREVEELRSSLRGLAG
EIVGEVRCHMEENQRVARRRRFPFVRERSDSTGSSSVYFTASSGATFTDAESEGGYTTAN
AESDNERDSDKESEDGEDEVSCETVKMGRKDSLDLEEEAASGASSALEAGGSSGLEDVLP
LLQQADELHRGDEQGKREGFQLLLNNKLVYGSRQDFLWRLARAYSDMCELTEEVSEKKSY
ALDGKEEAEAALEKGDESADCHLWYAVLCGQLAEHESIQRRIQSGFSFKEHVDKAIALQP
ENPMAHFLLGRWCYQVSHLSWLEKKTATALLESPLSATVEDALQSFLKAEELQPGFSKAG
RVYISKCYRELGKNSEARWWMKLALELPDVTKEDLAIQKDLEELEVILRD

Important features of the protein:
Signal peptide:
Amino acids 1-32 cAMP- and cGMP-dependent protein kinase phosphorylation site:
Amino acids 209-213

N-myristoylation sites:
Amino acids 5-11;8-14;9-15;15-21;19-25;72-78;164-170;
174-180;222-228;230-236

Amidation sites:
Amino acids 207-211;254-258

Cell attachment sequence:
Amino acids 250-253

FIGURE 69

CCCACGCGTCCGAAACACTTTAAACCTGACCAGCTAAATGGATAAACCTAGCCTGCATAGCT
TTTAAACTGGGGTCTCATACAGCACAGGAGGCCTACTTGCTTCAAGAACTGAAAATCCAGAG
GATGAATTGCTTTATCTGGGAATGGCAAAAGCCAGCACAATAAGGAATGCCAGTTTGTATGG
GGCTACTAGCTCACATGCGGGATCAGAATGGTGTGAATGACAGCCGCACTGTGTCATGAAGG
TGGTGGTGGTTTCCGCACAAGAGACCAAATAAGAAGAAAGCTGAGAGAGGGGGGAAACGTTTTT
GGATGACAAAGGATGGGTTTCCATTTAATTACGCAGCTGAAAGGCATGAGTGTGGTGCTGGT
GCTACTTCCTACACTGCTGCTTGTTATGCTCACGGGTGCTCAGAGAGCTTGCCCAAAGAACT
GCAGATGTGATGGCAAAATTGTGTACTGTGAGTCTCATGCTTTCGCAGATATCCCTGAGAAC
ATTTCTGGAGGGTCACAAGGCTTATCATTAAGGTTCAACAGCATTCAGAAGCTCAAATCCAA
TCAGTTTGCCGGCCTTAACCAGCTTATATGGCTTTATCTTGACCATAATTACATTAGCTCAGTG
GATGAAGATGCATTTCAAGGGATCCGTAGACTGAAAGAATTAATTCTAAGCTCCAACAAAAT
TACTTATCTGCACAATAAAACATTTCACCCAGTTCCCAATCTCCGCAATCTGGACCTCTCCT
ACAATAAGCTTCAGACATTGCAATCTGAACAATTTAAAGGCCTTCGGAAACTCATCATTTTG
CACTTGAGATCTAACTCACTAAAGACTGTGCCCATAAGAGTTTTTCAAGACTGTCGGAATCT
TGATTTTTTGGATTTGGGTTACAATCGTCTTCGAAGCTTGTCCCGAAATGCATTTGCTGGCC
TCTTGAAGTTAAAGGAGCTCCACCTGGAGCACAACCAGTTTTCCAAGATCAACTTTGCTCAT
TTTCCACGTCTCTTCAACCTCCGCTCAATTTACTTACAATGGAACAGGATTCGCTCCATTAG
CCAAGGTTTGACATGGACTTGGAGTTCCTTACACAACTTGGATTTATCAGGGAATGACATCC
AAGGAATTGAGCCGGGCACATTTAAATGCCTCCCCAATTTACAAAAATTGAATTTGGATTCC
AACAAGCTCACCAATATCTCACAGGAAACTGTCAATGCGTGGATATCATTAATATCCATCAC
ATTGTCTGGAAATATGTGGGAATGCAGTCGGAGCATTTGTCCTTTATTTTATTGGCTTAAGA
ATTTCAAAGGAAATAAGGAAAGCACCATGATATGTGCGGGACCTAAGCACATCCAGGGTGAA
AAGGTTAGTGATGCAGTGGAAACATATAATATCTGTTCTGAAGTCCAGGTGGTCAACACAGA
AAGATCACACCTGGTGCCCCAAACTCCCCAGAAACCTCTGATTATCCCTAGACCTACCATCT
TCAAACCTGACGTCACCCAATCCACCTTTGAAACACCAAGCCCTTCCCCAGGGTTTCAGATT
CCTGGCGCAGAGCAAGAGTATGAGCATGTTTCATTTCACAAAATTATTGCCGGGAGTGTGGC
TCTCTTTCTCTCAGTGGCCATGATCCTCTTGGTGATCTATGTGTCTTGGAAACGCTACCCAG
CCAGCATGAAACAACTCCAGCAACACTCTCTTATGAAGAGGCGGCGGAAAAAGGCCAGAGAG
TCTGAAAGACAAATGAATTCCCCTTTACAGGAGTATTATGTGGACTACAAGCCTACAAACTC
TGAGACCATGGATATATCGGTTAATGGATCTGGGCCCTGCACATATACCATCTCTGGCTCCA
GGGAATGTGAGATGCCACACCACATGAAGCCCTTGCCATATTACAGCTATGACCAGCCTGTG
ATCGGGTACTGCCAGGCCCACCAGCCACTCCATGTCACCAAGGGCTATGAGACAGTGTCTCC
AGAGCAGGACGAAAGCCCCGGCCTGGAGCTGGGCCGAGACCACAGCTTCATCGCCACCATCG
CCAGGTCGGCAGCACCGGCCATCTACCTAGAGAGAATTGCAAACTAACGCTGAAGCCAACTC
CTCACTGGGGAGCTCCATGGGGGGGAGGGAGGGCCTTCATCTTAAAGGAGAATGGGTGTCCA
CAATCGCGCAATCGAGCAAGCTCATCGTTCCTGTTAAAACATTTATGGCATAGGGAAAAAAA
AAAAAAAAAAAAA

FIGURE 70

></usr/seqdb2/sst/DNA/Dnaseqs.min/ss.DNA142392
><subunit 1 of 1, 590 aa, 1 stop
><MW: 67217, pI: 9.26, NX(S/T): 4
MGFHLITQLKGMSVVLVLLPTLLLVMLTGAQRACPKNCRCDGKIVYCESHAFADIPENIS
GGSQGLSLRFNSIQKLKSNQFAGLNQLIWLYLDHNYISSVDEDAFQGIRRLKELILSSNK
ITYLHNKTFHPVPNLRNLDLSYNKLQTLQSEQFKGLRKLIILHLRSNSLKTVPIRVFQDC
RNLDFLDLGYNRLRSLSRNAFAGLLKLKELHLEHNQFSKINFAHFPRLFNLRSIYLQWNR
IRSISQGLTWTWSSLHNLDLSGNDIQGIEPGTFKCLPNLQKLNLDSNKLTNISQETVNAW
ISLISITLSGNMWECSRSICPLFYWLKNFKGNKESTMICAGPKHIQGEKVSDAVETYNIC
SEVQVVNTERSHLVPQTPQKPLIIPRPTIFKPDVTQSTFETPSPSPGFQIPGAEQEYEHV
SFHKIIAGSVALFLSVAMILLVIYVSWKRYPASMKQLQQHSLMKRRRKKARESERQMNSP
LQEYYVDYKPTNSETMDISVNGSGPCTYTISGSRECEMPHHMKPLPYYSYDQPVIGYCQA
HQPLHVTKGYETVSPEQDESPGLELGRDHSFIATIARSAAPAIYLERIAN

Important features of the protein:
Signal peptide:
Amino acids 1-30

Transmembrane domain:
Amino acids 425-443

N-glycosylation sites:
Amino acids 58-62;126-130;291-295;501-505

Tyrosine kinase phosphorylation site:
Amino acids 136-143

N-myristoylation sites:
Amino acids 29-35;61-67;247-253;267-273;271-277;331-337;
502-508;512-518;562-568

Glycosyl hydrolases family:
Amino acids 310-319

FIGURE 71

TTCCAGTCAGAGTTAAGTTAAAACAGAAAAAAGGAAGATGGCAAGAATATTGTTACTTTTCC
TCCCGGGTCTTGTGGCTGTATGTGCTGTGCATGGAATATTTATGGACCGTCTAGCTTCCAAG
AAGCTCTGTGCAGATGATGAGTGTGTCTATACTATTTCTCTGGCTAGTGCTCAAGAAGATTA
TAATGCCCCGGACTGTAGATTCATTAACGTTAAAAAAGGGCAGCAGATCTATGTGTACTCAA
AGCTGGTAAAAGAAAATGGAGCTGGAGAATTTTGGGCTGGCAGTGTTTATGGTGATGGCCAG
GACGAGATGGGAGTCGTGGGTTATTTCCCCAGGAACTTGGTCAAGGAACAGCGTGTGTACCA
GGAAGCTACCAAGGAAGTTCCCACCACGGATATTGACTTCTTCTGCGAGTAATAAATTAGTT
AAAACTGCAAATAGAAAGAAAACACCAAAAATAAAGAAAAGAGCAAAAGTGGCCAAAAAATG
CATGTCTGTAATTTTGGACTGACGT

FIGURE 72

></usr/seqdb2/sst/DNA/Dnaseqs.min/ss.DNA143076
><subunit 1 of 1, 128 aa, 1 stop
><MW: 14332, pI: 4.83, NX(S/T): 0
MARILLLFLPGLVAVCAVHGIFMDRLASKKLCADDECVYTISLASAQEDYNAPDCRFINV
KKGQQIYVYSKLVKENGAGEFWAGSVYGDGQDEMGVVGYFPRNLVKEQRVYQEATKEVPT
TDIDFFCE

Important features of the protein:
Signal peptide:
Amino acids 1-14

N-myristoylation site:
Amino acids 84-90

FIGURE 73

CTCAGATTTGCCATGGAGAAATTTTCAGTCTCGGCAATCCTGCTTCTTGTGGCCATCTCTGG
TACTCTGGCCAAAGACACCACAGTCAAATCTGGATCCAAAAAGGACCCAAAGGACTCTCGAC
CCAAACTACCCCAGACCCTGTCCAGAGGTTGGGGAGATCAGCTCATCTGGACTCAGACTTAC
GAAGAAGCCTTATACAAATCCAAGACAAGCAACAGACCCTTGATGGTCATTCATCACTTGGA
CGAATGCCCGCACAGTCAAGCTTTAAAGAAAGTGTTTGCTGAAAATAAGGAGATCCAGAAATTG
GCAGAGCAGTTTGTTCTCCTCAACTTGATCTATGAAACAACTGACAAGCACCTTTCTCCTGA
TGGCCAGTACGTCCCCAGAATTGTGTTTGTGGACCCTTCCCTGACGGTGAGGGCAGACATCA
CCGGAAGATACTCAAACCGTCTCTACGCTTATGAACCTTCTGACACAGCTCTGTTGCACGAC
AACATGAAGAAAGCTCTCAAGTTGCTGAAGACAGAGTTGTAGAGTCAACTGTACAGTGCCTC
AGGAGCCGGGAAGGCAGAAGCACTGTGGACCTGCCGATGACATTACAGTTTAATGTTACAAC
AAATGTATTTTTTAAACACCCACGTGTGGGGAAACAATATTATTATCTACTACAGACACATG
ATTTTCTAGAAAATAAAGTCTTGTGAGAACTCCAAA

FIGURE 74

></usr/seqdb2/sst/DNA/Dnaseqs.min/ss.DNA143294
><subunit 1 of 1, 175 aa, 1 stop, 1 unknown
><MW: 19888.97, pI: 9.08, NX(S/T): 0
MEKFSVSAILLLVAISGTLAKDTTVKSGSKKDPKDSRPKLPQTLSRGWGDQLIWTQTYEE
ALYKSKTSNRPLMVIHHLDECPHSQALKKVFAENKEIQKLAEQFVLLNLIYETTDKHLSP
DGQYVPRIVFVDPSLTVRADITGRYSNRLYAYEPSDTALLHDNMKKALKLLKTEL

Important features of the protein:
Signal peptide:
Amino acids 1-20

FIGURE 75

GCCGGCGCCAGGGCAGGCGGGCGGCTGGCAGCTGTGGCGCCGACATGGCTGCGCTGGTGGAG
CCGCTGGGGCTGGAGCGGGACGTGTCCCGGGCGGTTGAGCTCCTCGAGCGGCTCCAGCGCAG
CGGGGAGCTGCCGCCGCAGAAGCTGCAGGCCCTCCAGCGAGTTCTGCAGAGCCGCTTCTGCT
CCGCTATCCGAGAGGTGTATGAGCAGCTTTATGACACGCTGGACATCACCGGCAGCGCCGAG
ATCCGAGCCCATGCCACAGCCAAGGCCACAGTGGCTGCCTTCACAGCCAGCGAGGGCCACGC
ACATCCCAGGGTAGTGGAGCTACCCAAGACGGATGAGGGCCTAGGCTTCAACATCATGGGTG
GCAAAGAGCAAAACTCGCCCATCTACATCTCCCGGGTCATCCCAGGGGGTGTGGCTGACCGC
CATGGAGGCCTCAAGCGTGGGGATCAACTGTTGTCGGTGAACGGTGTGAGCGTTGAGGGTGA
GCAGCATGAGAAGGCGGTGGAGCTGCTGAAGGCGGCCCAGGGCTCGGTGAAGCTGGTTGTCC
GTTACACACCGCGAGTGCTGGAGGAGATGGAGGCCCGGTTCGAGAAGATGCGCTCTGCCCGC
CGGCGCCAACAGCATCAGAGCTACTCGTCCTTGGAGTCTCGAGGTTGAAACCACAGATCTGG
ACGTTCACGTGCACTCTCTTCCTGTACAGTATTTATTGTTCCTGGCACTTTATTTAAAGATA
TTTGACCCTCAAAAAAAAAAAAAAAAAAAAAA

FIGURE 76

></usr/seqdb2/sst/DNA/Dnaseqs.min/ss.DNA143514
><subunit 1 of 1, 207 aa, 1 stop
><MW: 22896, pI: 8.93, NX(S/T): 0
MAALVEPLGLERDVSRAVELLERLQRSGELPPQKLQALQRVLQSRFCSAIREVYEQLYDT
LDITGSAEIRAHATAKATVAAFTASEGHAHPRVVELPKTDEGLGFNIMGGKEQNSPIYIS
RVIPGGVADRHGGLKRGDQLLSVNGVSVEGEQHEKAVELLKAAQGSVKLVVRYTPRVLEE
MEARFEKMRSARRRQQHQSYSSLESRG

Tyrosine kinase phosphorylation site:
Amino acids 51-59

N-myristoylation sites:
Amino acids 102-108;133-139

Cell attachment sequence:
Amino acids 136-139

PDZ domain (Also known as DHR or GLGF):
Amino acids 93-174

FIGURE 77

CTGTCAGCTGAGGATCCAGCCGAAAGAGGAGCCAGGCACTCAGGCCACCTGAGTCTACTCAC
CTGGACAACTGGAATCTGGCACCAATTCTAAACCACTCAGCTTCTCCGAGCTCACACCCCGG
AGATCACCTGAGGACCCGAGCCATTGATGGACTCGGACGAGACCGGGTTCGAGCACTCAGGA
CTGTGGGTTTCTGTGCTGGCTGGTCTGCTGGGAGCCTGCCAGGCACACCCCATCCCTGACTC
CAGTCCTCTCCTGCAATTCGGGGGCCAAGTCCGGCAGCGGTACCTCTACACAGATGATGCCC
AGCAGACAGAAGCCCACCTGGAGATCAGGGAGGATGGGACGGTGGGGGGCGCTGCTGACCAG
AGCCCCGAAAGTCTCCTGCAGCTGAAAGCCTTGAAGCCGGGAGTTATTCAAATCTTGGGAGT
CAAGACATCCAGGTTCCTGTGCCAGCGGCCAGATGGGGCCCTGTATGGATCGCTCCACTTTG
ACCCTGAGGCCTGCAGCTTCCGGGAGCTGCTTCTTGAGGACGGATACAATGTTTACCAGTCC
GAAGCCCACGGCCTCCCGCTGCACCTGCCAGGGAACAAGTCCCCACACCGGGACCCTGCACC
CCGAGGACCAGCTCGCTTCCTGCCACTACCAGGCCTGCCCCCCGCACTCCCGGAGCCACCCG
GAATCCTGGCCCCCCAGCCCCCCGATGTGGGCTCCTCGGACCCTCTGAGCATGGTGGGACCT
TCCCAGGGCCGAAGCCCCAGCTACGCTTCCTGAAGCCAGAGGCTGTTTACTATGACATCTCC
TCTTTATTTATTAGGTTATTTATCTTATTTATTTTTTTATTTTTCTTACTTGAGATAATAAAGA
GTTCCAGAGGAGAAAAAAAAAAAAAAAAAAAAAAAAAAAAAAAAAAAAAAAAAAAAAAAAAAA
AAAAAAG

FIGURE 78

></usr/seqdb2/sst/DNA/Dnaseqs.min/ss.DNA144841
><subunit 1 of 1, 208 aa, 1 stop
><MW: 22187, pI: 5.08, NX(S/T): 1
MDSDETGFEHSGLWVSVLAGLLGACQAHPIPDSSPLLQFGGQVRQRYLYTDDAQQTEAHL
EIREDGTVGGAADQSPESLLQLKALKPGVIQILGVKTSRFLCQRPDGALYGSLHFDPEAC
SFRELLLEDGYNVYQSEAHGLPLHLPGNKSPHRDPAPRGPARFLPLPGLPPALPEPPGIL
APQPPDVGSSDPLSMVGPSQGRSPSYAS

Important features of the protein:
Signal peptide:
Amino acids 1-27

N-myristoylation sites:
Amino acids 12-18;20-26;23-29;66-72;94-100;107-113;168-174

Prokaryotic membrane lipoprotein lipid attachment site:
Amino acids 15-26

HBGF/FGF family proteins:
Amino acids 57-73;80-131

FIGURE 79

AGTCCCAGACGGGCTTTTCCCAGAGAGCTAAAAGAGAAGGGCCAGAGAATGTCGTCCCAG
CCAGCAGGGAACCAGACCTCCCCCGGGGCCACAGAGGACTACTCCTATGGCAGCTGGTAC
ATCGATGAGCCCCAGGGGGGCGAGGAGCTCCAGCCAGAGGGGGAAGTGCCCTCCTGCCAC
ACCAGCATACCACCCGGCCTGTACCACGCCTGCCTGGCCTCGCTGTCAATCCTTGTGCTG
CTGCTCCTGGCCATGCTGGTGAGGCGCCGCCAGCTCTGGCCTGACTGTGTGCGTGGCAGG
CCCGGCCTGCCCAGCCCTGTGGATTTCTTGGCTGGGGACAGGCCCCGGGCAGTGCCTGCT
GCTGTTTTCATGGTCCTCCTGAGCTCCCTGTGTTTGCTGCTCCCCGACGAGGACGCATTG
CCCTTCCTGACTCTCGCCTCAGCACCCAGCCAAGATGGGAAAACTGAGGCTCCAAGAGGG
GCCTGGAAGATACTGGGACTGTTCTATTATGCTGCCCTCTACTACCCTCTGGCTGCCTGT
GCCACGGCTGGCCACACAGCTGCACACCTGCTCGGCAGCACGCTGTCCTGGGCCCACCTT
GGGGTCCAGGTCTGGCAGAGGGCAGAGTGTCCCCAGGTGCCCAAGATCTACAAGTACTAC
TCCCTGCTGGCCTCCCTGCCTCTCCTGCTGGGCCTCGGATTCCTGAGCCTTTGGTACCCT
GTGCAGCTGGTGAGAAGCTTCAGCCGTAGGACAGGAGCAGGCTCCAAGGGGCTGCAGAGC
AGCTACTCTGAGGAATATCTGAGGAACCTCCTTTGCAGGAAGAAGCTGGGAAGCAGCTAC
CACACCTCCAAGCATGGCTTCCTGTCCTGGGCCCGCGTCTGCTTGAGACACTGCATCTAC
ACTCCACAGCCAGGATTCCATCTCCCGCTGAAGCTGGTGCTTTCAGCTACACTGACAGGG
ACGGCCATTTACCAGGTGGCCCTGCTGCTGCTGGTGGGCGTGGTACCCACTATCCAGAAG
GTGAGGGCAGGGGTCACCACGGATGTCTCCTACCTGCTGGCCGGCTTTGGAATCGTGCTC
TCCGAGGACAAGCAGGAGGTGGTGGAGCTGGTGAAGCACCATCTGTGGGCTCTGGAAGTG
TGCTACATCTCAGCCTTGGTCTTGTCCTGCTTACTCACCTTCCTGGTCCTGATGCGCTCA
CTGGTGACACACAGGACCAACCTTCGAGCTCTGCACCGAGGAGCTGCCCTGGACTTGAGT
CCCTTGCATCGGAGTCCCCATCCCTCCCGCCAAGCCATATTCTGTTGGATGAGCTTCAGT
GCCTACCAGACAGCCTTTATCTGCCTTGGGCTCCTGGTGCAGCAGATCATCTTCTTCCTG
GGAACCACGGCCCTGGCCTTCCTGGTGCTCATGCCTGTGCTCCATGGCAGGAACCTCCTG
CTCTTCCGTTCCCTGGAGTCCTCGTGGCCCTTCTGGCTGACTTTGGCCCTGGCTGTGATC
CTGCAGAACATGGCAGCCCATTGGGTCTTCCTGGAGACTCATGATGGACACCCACAGCTG
ACCAACCGGCGAGTGCTCTATGCAGCCACCTTTCTTCTCTTCCCCCTCAATGTGCTGGTG
GGTGCCATGGTGGCCACCTGGCGAGTGCTCCTCTCTGCCCTCTACAACGCCATCCACCTT
GGCCAGATGGACCTCAGCCTGCTGCCACCGAGAGCCGCCACTCTCGACCCCGGCTACTAC
ACGTACCGAAACTTCTTGAAGATTGAAGTCAGCCAGTCGCATCCAGCCATGACAGCCTTC
TGCTCCCTGCTCCTGCAAGCGCAGAGCCTCCTACCCAGGACCATGGCAGCCCCCCAGGAC
AGCCTCAGACCAGGGGAGGAAGACGAAGGGATGCAGCTGCTACAGACAAAGGACTCCATG
GCCAAGGGAGCTAGGCCCGGGGCCAGCCGCGGCAGGGCTCGCTGGGGTCTGGCCTACACG
CTGCTGCACAACCCAACCCTGCAGGTCTTCCGCAAGACGGCCCTGTTGGGTGCCAATGGT
GCCCAGCCCTGAGGGCAGGGAAGGTCAACCCACCTGCCCATCTGTGCTGAGGCATGTTCC
TGCCTACCATCCTCCTCCCTCCCCGGCTCTCCTCCCAGCATCACACCAGCCATGCAGCCA
GCAGGTCCTCCGGATCACTGTGGTTGGGTGGAGGTCTGTCTGCACTGGGAGCCTCAGGAG
GGCTCTGCTCCACCCACTTGGCTATGGGAGAGCCAGCAGGGGTTCTGGAGAAAAAAACTG
GTGGGTTAGGGCCTTGGTCCAGGAGCCAGTTGAGCCAGGGCAGCCACATCCAGGCGTCTC
CCTACCCTGGCTCTGCCATCAGCCTTGAAGGGCCTCGATGAAGCCTTCTCTGGAACCACT
CCAGCCCAGCTCCACCTCAGCCTTGGCCTTCACGCTGTGGAAGCAGCCAAGGCACTTCCT
CACCCCCTCAGCGCCACGGACCTCTCTGGGGAGTGGCCGGAAAGCTCCCGGTCCTCTGGC
CTGCAGGGCAGCCCAAGTCATGACTCAGACCAGGTCCCACACTGAGCTGCCCACACTCGA
GAGCCAGATATTTTTGTAGTTTTTATGCCTTTGGCTATTATGAAAGAGGTTAGTGTGTTC
CCTGCAATAAACTTGTTCCTGAGAAAAAAAAAAAAAAAAAAAAAAAAAAAAAAAAAAAAAA
AAAAAAAAAAAAAAAAAAAAAAAAAAAAAAAAA

FIGURE 80

Protein File:
MW: 73502.97, pI: 9.26
MSSQPAGNQTSPGATEDYSYGSWYIDEPQGGEELQPEGEVPSCHTSIPPGLYHACLASLS
ILVLLLLAMLVRRRQLWPDCVRGRPGLPSPVDFLAGDRPRAVPAAVFMVLLSSLCLLLPD
EDALPFLTLASAPSQDGKTEAPRGAWKILGLFYYAALYYPLAACATAGHTAAHLLGSTLS
WAHLGVQVWQRAECPQVPKIYKYYSLLASLPLLLGLGFLSLWYPVQLVRSFSRRTGAGSK
GLQSSYSEEYLRNLLCRKKLGSSYHTSKHGFLSWARVCLRHCIYTPQPGFHLPLKLVLSA
TLTGTAIYQVALLLLVGVVPTIQKVRAGVTTDVSYLLAGFGIVLSEDKQEVVELVKHHLW
ALEVCYISALVLSCLLTFLVLMRSLVTHRTNLRALHRGAALDLSPLHRSPHPSRQAIFCW
MSFSAYQTAFICLGLLVQQIIFFLGTTALAFLVLMPVLHGRNLLLFRSLESSWPFWLTLA
LAVILQNMAAHWVFLETHDGHPQLTNRRVLYAATFLLFPLNVLVGAMVATWRVLLSALYN
AIHLGQMDLSLLPPRAATLDPGYYTYRNFLKIEVSQSHPAMTAFCSLLLQAQSLLPRTMA
APQDSLRPGEEDEGMQLLQTKDSMAKGARPGASRGRARWGLAYTLLHNPTLQVFRKTALL
GANGAQP

Important features of the protein:
Transmembrane domains:
Amino acids    54-69;102-119;148-166;207-222;301-320;
364-380;431-451;474-489;512-531

N-glycosylation site:
Amino acids    8-12

N-myristoylation sites:
Amino acids    50-56;176-182;241-247;317-323;341-347;525-531;
627-633;631-637;640-646;661-667

Prokaryotic membrane lipoprotein lipid attachment site:
Amino acids    364-375

ATP/GTP-binding site motif A (P-loop):
Amino acids    132-140

FIGURE 81

AAAAAATACAGCAGGTGAAGGAGGTTGGAGAGTAGGGGGTGGAGGGCCCACGCAGCACTTGT
CCTTCACCCTGGAGGGGATCTGTTACATGCCCCAGATTGCTGGTCCCCTAGAAATGTTACTG
AGGCAGCCTCTGCATTTTTGCAGGGATTGTTTTCTACTGTTTGACATTCACGTAACCTCCTA
ACGCTGTCTGGGGAAGATGCTACCCCCTGCTCTCCCCGTCTTTCCTGCACTCTCAGCAATGG
GATGGGCTGACTGATGCCCTGTGGGCTGGAAAGCTGACCACAGTTGCTGCAGACCAGACCCC
CTCACATAGTGAGTGCTGGGCTGAGGAATCCAGGAGAGCCCGAGGGGGGACACTGAAGGTGT
ATCGTTGGCCCTGCCAGCTGCAAGTGAACTGCTTCTGATGAATTTTAATAGGGAGAAAGAAG
TATTTGCTAAGAATGGCAATCCTGACGCTCAGCCTTCAACTCATCTTGTTATTAATACCATC
AATATCCCATGAGGCTCATAAAACGAGTCTTTCTTCTTGGAAACATGACCAAGATTGGGCAA
ACGTCTCCAACATGACTTTCAGCAACGGAAAACTAAGAGTCAAAGGCATTTATTACCGGAAT
GCCGACATTTGCTCTCGACATCGCGTAACCTCAGCAGGCCTAACTCTGCAGGACCTTCAGCT
ATGGTGTAATTTGAGGTCAGTGGCCAGAGGACAGATCCCGTCTACATTATGAGTGAAGCGGAGA
GCTACTGCAGGGTTCTGAGCAGAGTCCTAATTTATATTTTAGAAGAATCATCATGGCTCCTA
GATTAGGAATAAAACGAAGGGGCCCAGGGATGGAAACGATGAGTCCAGTTGGGTTACTGCAA
AGATCCAGGCCAGAAATCCAGGCACAGTGGCACACACCTGAGTCCCAGATAATTCCACCTAC
TGGTCCTGCTCTGTGGCCTACTGGTCCGAGTCCAGCCCCGACTGATTTCTGGGCCTGTAATG
TCTAAAAACGCTCCCTGCTGATGTTTTGCAAGTGACTGTGTTACTTGAAGGCAGTTCCTAGG
ATAAACTAGTCGCTTTATCATTACAGAATCATTCACTGAGCATCAACTATGTAACCAGCATT
GGGTTGGGTGCCAGAGATCCAAAGCTAAGACACCAAAACCTGCTCTCCAGGAAACGAGAGGC
TGAGAA

FIGURE 82

></usr/seqdb2/sst/DNA/Dnaseqs.min/ss.DNA149995
><subunit 1 of 1, 95 aa, 1 stop
><MW: 10704, pI: 10.00, NX(S/T): 2
MAILTLSLQLILLLIPSISHEAHKTSLSSWKHDQDWANVSNMTFSNGKLRVKGIYYRNAD
ICSRHRVTSAGLTLQDLQLWCNLRSVARGQIPSTL

Important features of the protein:
Signal peptide:
Amino acids 1-19

N-glycosylation sites:
Amino acids 38-42;41-45

N-myristoylation site:
Amino acids 89-95

FIGURE 83

AATAGAAGTCCTCAGGACGGAGCAGAGGTGGCCGGCGGGCCCGGCTGACTGCGCCTCTGCTT
TCTTTCCATAACCTTTTCTTTCGGACTCGAATCACGGCTGCTGCGAAGGGTCTAGTTCCGGA
CACTAGGGTGCCCGAACGCGCTGATGCCCCGAGTGCTCGCAGGGCTTCCCGCTAACCATGCT
GCCGCCGCCGCGGCCCGCAGCTGCCTTGGCGCTGCCTGTGCTCCTGCTACTGCTGGTGGTGC
TGACGCCGCCCCCGACCGGCGCAAGGCCATCCCCAGGCCCAGATTACCTGCGGCGCGGCTGG
ATGCGGCTGCTAGCGGAGGGCGAGGGCTGCGCTCCCTGCCGGCCAGAAGAGTGCGCCGCGCC
GCGGGGCTGCCTGGCGGGCAGGGTGCGCGACGCGTGCGGCTGCTGCTGGGAATGCGCCAACC
TCGAGGGCCAGCTCTGCGACCTGGACCCCAGTGCTCACTTCTACGGGCACTGCGGCGAGCAG
CTTGAGTGCCGGCTGGACACAGGCGGCGACCTGAGCCGCGGAGAGGTGCCGGAACCTCTGTG
TGCCTGTCGTTCGCAGAGTCCGCTCTGCGGGTCCGACGGTCACACCTACTCCCAGATCTGCC
GCCTGCAGGAGGCGGCCCGCGCTCGGCCCGATGCCAACCTCACTGTGGCACACCCGGGGCCC
TGCGAATCGGGGCCCCAGATCGTGTCACATCCATATGACACTTGGAATGTGACAGGGCAGGA
TGTGATCTTTGGCTGTGAAGTGTTTGCCTACCCCATGGCCTCCATCGAGTGGAGGAAGGATG
GCTTGGACATCCAGCTGCCAGGGGATGACCCCCACATCTCTGTGCAGTTTAGGGGTGGACCC
CAGAGGTTTGAGGTGACTGGCTGGCTGCAGATCCAGGCTGTGCGTCCCAGTGATGAGGGCAC
TTACCGCTGCCTTGGCCGCAATGCCCTGGGTCAAGTGGAGGCCCCTGCTAGCTTGACAGTGC
TCACACCTGACCAGCTGAACTCTACAGGCATCCCCCAGCTGCGATCACTAAACCTGGTTCCT
GAGGAGGAGGCTGAGAGTGAAGAGAATGACGATTACTACTAGGTCCAGAGCTCTGGCCCATG
GGGGTGGGTGAGCGGCTATAGTGTTCATCCCTGCTCTTGAAAAGACCTGGAAAGGGGAGCAG
GGTCCCTTCATCGACTGCTTTCATGCTGTCAGTAGGGATGATCATGGGAGGCCTATTTGACT
CCAAGGTAGCAGTGTGGTAGGATAGAGACAAAAGCTGGAGGAGGGTAGGGAGAGAAGCTGAG
ACCAGGACCGGTGGGGTACAAAGGGGCCCATGCAGGAGATGCCCTGGCCAGTAGGACCTCCA
ACAGGTTGTTTCCCAGGCTGGGGTGGGGGCCTGAGCAGACACAGAGGTGCAGGCACCAGGAT
TCTCCACTTCTTCCAGCCCTGCTGGGCCACAGTTCTAACTGCCCTTCCTCCCAGGCCCTGGT
TCTTGCTATTTCCTGGTCCCCAACGTTTATCTAGCTTGTTTGCCCTTTCCCCAAACTCATCT
TCCAGAACTTTTCCCTCTCTCCTAAGCCCCAGTTGCACCTACTAACTGCAGTCCCTTTTGCT
GTCTGCCGTCTTTTGTACAAGAGAGAGAGAACAGCGGAGCATGACTTAGTTCAGTGCAGAGAGA
TTT

FIGURE 84

```
></usr/seqdb2/sst/DNA/Dnaseqs.min/ss.DNA167678
><subunit 1 of 1, 304 aa, 1 stop
><MW: 32945, pI: 4.69, NX(S/T): 3
MLPPPRPAAALALPVLLLLLVVLTPPPTGARPSPGPDYLRRGWMRLLAEGEGCAPCRPEE
CAAPRGCLAGRVRDACGCCWECANLEGQLCDLDPSAHFYGHCGEQLECRLDTGGDLSRGE
VPEPLCACRSQSPLCGSDGHTYSQICRLQEAARARPDANLTVAHPGPCESGPQIVSHPYD
TWNVTGQDVIFGCEVFAYPMASIEWRKDGLDIQLPGDDPHISVQFRGGPQRFEVTGWLQI
QAVRPSDEGTYRCLGRNALGQVEAPASLTVLTPDQLNSTGIPQLRSLNLVPEEEAESEEN
DDYY

Important features of the protein:
Signal peptide:
Amino acids    1-30

N-glycosylation sites:
Amino acids    159-163;183-187;277-281

Tyrosine kinase phosphorylation site:
Amino acids    244-252

N-myristoylation sites:
Amino acids    52-58;66-72;113-119;249-255

Kazal-type serine protease inhibitor domain:
Amino acids    121-168

Immunoglobulin domain:
Amino acids    186-255

Insulin-like growth factor binding proteins:
Amino acids    53-90
```

FIGURE 85

CAAAGCGGCGGCTGTCCGCGGTGCCGGCTGGGGGCGGAGAGGCGGCGGTGGGCTCCCTGGGG
TGTGTGAGCCCGGTGATGGAGCCGGGCCCGACAGCCGCGCAGCGGAGGTGTTCGTTGCCGCC
GTGGCTGCCGCTGGGGCTGCTGCTGTGGTCGGGGCTGGCCCTGGGCGCGCTCCCCTTCGGCA
GCAGTCCGCACAGGGTCTTCCACGACCTCCTGTCGGAGCAGCAGTTGCTGGAGGTGGAGGAC
TTGTCCCTGTCCCTCCTGCAGGGTGGAGGGCTGGGGCCTCTGTCGCTGCCCCCGGACCTGCC
GGATCTGGATCCTGAGTGCCGGGAGCTCCTGCTGGACTTCGCCAACAGCAGCGCAGAGCTGA
CAGGGTGTCTGGTGCGCAGCGCCCGGCCCGTGCGCCTCTGTCAGACCTGCTACCCCCTCTTC
CAACAGGTCGTCAGCAAGATGGACAACATCAGCCGAGCCGCGGGGAATACTTCAGAGAGTCAG
AGTTGTGCCAGAAGTCTCTTAATGGCAGATAGAATGCAAATAGTTGTGATTCTCTCAGAATT
TTTTAATACCACATGGCAGGAGGCAAATTGTGCAAATTGTTTAACAAACAACAGTGAAGAAT
TATCAAACAGCACAGTATATTTCCTTAATCTATTTAATCACACCCTGACCTGCTTTGAACAT
AACCTTCAGGGGAATGCACATAGTCTTTTACAGACAAAAAATTATTCAGAAGTATGCAAAAA
CTGCCGTGAAGCATACAAAACTCTGAGTAGTCTGTACAGTGAAATGCAAAAAATGAATGAAC
TTGAGAATAAGGCTGAACCTGGAACACATTTATGCATTGATGTGGAAGATGCAATGAACATC
ACTCGAAAACTATGGAGTCGAACTTTCAACTGTTCAGTCCCTTGCAGTGACACAGTGCCTGT
AATTGCTGTTTCTGTGTTCATTCTCTTTCTACCTGTTGTCTTCTACCTTAGTAGCTTTCTTC
ACTCAGAGCAAAAGAAACGCAAACTCATTCTGCCCAAACGTCTCAAGTCCAGTACCAGTTTT
GCAAATATTCAGGAAAATTCAAACTGAGACCTACAAAATGGAGAATTGACATATCACGTGAA
TGAATGGTGGAAGACACAACTTGGTTTCAGAAAGAAGATAAACTGTGATTTGACAAGTCAAG
CTCTTAAGAAATACAAGGACTTCAGATCCATTTTTAAATAAGAATTTTCGATTTTTCTTTCC
TTTTCCACTTCTTTCTAACAGATTTGGATATTTTTAATTTCCAG

FIGURE 86

```
></usr/seqdb2/sst/DNA/Dnaseqs.min/ss.DNA168028
><subunit 1 of 1, 334 aa, 1 stop
><MW: 37257, pI: 5.95, NX(S/T): 10
MEPGPTAAQRRCSLPPWLPLGLLLWSGLALGALPFGSSPHRVFHDLLSEQQLLEVEDLSL
SLLQGGGLGPLSLPPDLPDLDPECRELLLDFANSSAELTGCLVRSARPVRLCQTCYPLFQ
QVVSKMDNISRAAGNTSESQSCARSLLMADRMQIVVILSEFFNTTWQEANCANCLTNNSE
ELSNSTVYFLNLFNHTLTCFEHNLQGNAHSLLQTKNYSEVCKNCREAYKTLSSLYSEMQK
MNELENKAEPGTHLCIDVEDAMNITRKLWSRTFNCSVPCSDTVPVIAVSVFILFLPVVFY
LSSFLHSEQKKRKLILPKRLKSSTSFANIQENSN
```

Important features of the protein:
Signal peptide:
Amino acids 1-31

Transmembrane domain:
Amino acids 278-300

N-glycosylation sites:
Amino acids 93-97;128-132;135-139;163-167;177-181;
184-188;194-198;216-220;263-267;274-278 cAMP- and cGMP-dependent protein kinase phosphorylation site:
Amino acids 10-14

N-myristoylation sites:
Amino acids 27-33;206-212;251-257

Leucine zipper pattern:
Amino acids 190-212

FIGURE 87

ATGCTGGTAGCCGGCTTCCTGCTGGCGCTGCCGCCGAGCTGGGCCGCGGGCGCCCCCAGGGC
GGGCAGGCGCCCCGCGCGGCCGCGGGGCTGCGCGGACCGGCCGGAGGAGCTACTGGAGCAGC
TGTACGGGCGCCTGGCGGCCGGCGTGCTCAGTGCCTTCCACCACACGCTGCAGCTGGGGCCG
CGTGAGCAGGCGCGCAACGCGAGCTGCCCGGCAGGGGGCAGGCCCGGCGACCGCCGCTTCCG
GCCGCCCACCAACCTGCGCAGCGTGTCGCCCTGGGCCTACAGAATCTCCTACGACCCGGCGA
GGTACCCCAGGTACCTGCCTGAAGCCTACTGCCTGTGCCGGGGCTGCCTGACCGGGCTGTTC
GGCGAGGAGGACGTGCGCTTCCGCAGCGCCCCTGTCTACATGCCCACCGTCGTCCTGCGCCG
CACCCCCGCCTGCGCCGGCGGCCGTTCCGTCTACACCGAGGCCTACGTCACCATCCCCGTGG
GCTGCACCTGCGTCCCCGAGCCGGAGAAGGACGCAGACAGCATCAACTCCAGCATCGACAAA
CAGGGCGCCAAGCTCCTGCTGGGCCCCAACGACGCGCCCGCTGGCCCCTGAGGCCGGTCCTG
CCCCGGGAGGTCTCCCCGGCCCGCATCCCGAGGCGCCCAAGCTGGAGCCGCCTGGAGGGCTC
GGTCGGCGACCTCTGAAGAGAGTGCACCGAGCAAACCAAGTGCCGGAGCACCAGCGCCGCCT
TTCCATGGAGACTCGTAAGCAGCTTCATCTGACACGGGCATCCCTGGCTTGCTTTTAGCTAC
AAGCAAGCAGCGTGGCTGGAAGCTGATGGGAAACGACCCGGCACGGGCATCCTGTGTGCGGC
CCGCATGGAGGGTTTGGAAAAGTTCACGGAGGCTCCCTGAGGAGCCTCTCAGATCGGCTGCT
GCGGGTGCAGGGCGTGACTCACCGCTGGGTGCTTGCCAAAGAGATAGGGACGCATATGCTTT
TTAAAGCAATCTAAAAATAATAATAAGTATAGCGACTATATACCTACTTTTAAAATCAACTG
TTTTGAATAGAGGCAGAGCTATTTTATATTATCAAATGAGAGCTACTCTGTTACATTTCTTA
ACATATAAACATCGTTTTTTACTTCTTCTGGTAGAATTTTTTAAAGCATAATTGGAATCCTT
GGATAAATTTTGTAGCTGGTACACTCTGGCCTGGGTCTCTGAATTCAGCCTGTCACCGATGG
CTGACTGATGAAATGGACACGTCTCATCTGACCCACTCTTCCTTCCACTGAAGGTCTTCACG
GGCCTCCAGGTGGACCAAAGGGATGCACAGGCGGCTCGCATGCCCCAGGGCCAGCTAAGAGT
TCCAAAGATCTCAGATTTGGTTTTAGTCATGAATACATAAACAGTCTCAAACTCGCACAATT
TTTTCCCCCTTTTGAAAGCCACTGGGGCCAATTTGTGGTTAAGAGGTGGTGAGATAAGAAGT
GGAACGTGACATCTTTGCCAGTTGTCAGAAGAATCCAAGCAGGTATTGGCTTAGTTGTAAGG
GCTTTAGGATCAGGCTGAATATGAGGACAAAGTGGGCCACGTTAGCATCTGCAGAGATCAAT
CTGGAGGCTTCTGTTTCTGCATTCTGCCACGAGAGCTAGGTCCTTGATCTTTTCTTTAGATT
GAAAGTCTGTCTCTGAACACAATTATTTGTAAAAGTTAGTAGTTCTTTTTTAAATCATTAAA
AGAGGCTTGCTGAAGGAT

FIGURE 88

></usr/seqdb2/sst/DNA/Dnaseqs.min/ss.DNA173894
><subunit 1 of 1, 202 aa, 1 stop
><MW: 21879, pI: 9.30, NX(S/T): 2
MLVAGFLLALPPSWAAGAPRAGRRPARPRGCADRPEELLEQLYGRLAAGVLSAFHHTLQL
GPREQARNASCPAGGRPGDRRFRPPTNLRSVSPWAYRISYDPARYPRYLPEAYCLCRGCL
TGLFGEEDVRFRSAPVYMPTVVLRRTPACAGGRSVYTEAYVTIPVGCTCVPEPEKDADSI
NSSIDKQGAKLLLGPNDAPAGP

Important features of the protein:
Signal peptide:
Amino acids 1-15

N-glycosylation sites:
Amino acids 68-72;181-185

Tyrosine kinase phosphorylation site:
Amino acids 97-106

N-myristoylation sites:
Amino acids 17-23;49-55;74-80;118-124

Amidation site:
Amino acids 21-25

FIGURE 89

CCGGGGCCTCCGGAGAACGCTGTCCCATGAACGTGCGGGGAGCGGCCCCCGGCGTCCGCGCG
TCCCCGCGTCCCTGGCAATTCCCGACTTCCCAACGGCTTCCCGCTGGCAGCCCCGAAGCCGC
ACCATGTTCCGCCTCTGGTTGCTGCTGGCCGGGCTCTGCGGCCTCCTGGCGTCAAGACCCGGT
TTTCAAAATTCACTTCTACAGATCGTAATTCCAGAGAAAATCCAAACAAATACAAATGACAG
TTCAGAAATAGAATATGAACAAATATCCTATATTATTCCAATAGATGAGAAACTGTACACTG
TGCACCTTAAACAAAGATATTTTTTAGCAGATAATTTTATGATCTATTTGTACAATCAAGGA
TCTATGAATACTTATTCTTCAGATATTCAGACTCAATGCTACTATCAAGGAAATATTGAAGG
ATATCCAGATTCCATGGTCACACTCAGCACGTGCTCTGGACTAAGAGGAATACTGCAATTTG
AAAATGTTTCTTATGGAATTGAGCCTCTGGAATCTGCAGTTGAATTTCAGCATGTTCTTTAC
AAATTAAAGAATGAAGACAATGATATTGCAATTTTTATTGACAGAAGCCTGAAAGAACAACC
AATGGATGACAACATTTTTATAAGTGAAAAATCAGAACCAGCTGTTCCAGATTTATTTCCTC
TTTATCTAGAAATGCATATTGTGGTGGACAAAACTTTGTATGATTACTGGGGCTCTGATAGC
ATGATAGTAACAAATAAAGTCATCGAAATTGTTGGCCTTGCAAATTCAATGTTCACCCAATT
TAAAGTTACTATTGTGCTGTCATCATTGGAGTTATGGTCAGATGAAAATAAGATTTCTACAG
TTGGTGAGGCAGATGAATTATTGCAAAAATTTTTAGAATGGAAACAATCTTATCTTAACCTA
AGGCCTCATGATATTGCATATCTACTAATTTATATGGATTATCCTCGTTATTTGGGAGCAGT
GTTTCCTGGAACAATGTGTATTACTCGTTATTCTGCAGGAGTTGCATTGTACCCCAAGGAGA
TAACTCTGGAGGCATTTGCAGTTATTGTCACCCAGATGCTGGCACTCAGTCTGGGAATATCA
TATGACGACCCAAAGAAATGTCAATGTTCAGAATCCACCTGTATAATGAATCCAGAAGTTGT
GCAATCCAATGGTGTGAAGACTTTTAGCAGTTGCAGTTTGAGGAGCTTTCAAAATTTCATTT
CAAATGTGGGTGTCAAATGTCTTCAGAATAAGCCACAAATGCAAAAAAAATCTCCGAAACCA
GTCTGTGGCAATGGCAGATTGGAGGGAAATGAAATCTGTGATTGTGGTACTGAGGCTCAATG
TGGACCTGCAAGCTGTTGTGATTTTCGAACTTGTGTACTGAAAGACGGAGCAAAATGTTATA
AAGGACTGTGCTGCAAAGACTGTCAAATTTTACAATCAGGCGTTGAATGTAGGCCGAAAGCA
CATCCTGAATGTGACATCGCTGAAAATTGTAATGGAAGCTCACCAGAATGTGGTCCTGACAT
AACTTTAATCAATGGACTTTCATGCAAAAATAATAAGTTTATTTGTTATGACGGAGACTGCC
ATGATCTCGATGCACGTTGTGAGAGTGTATTTGGAAAAGGTTCAAGAAATGCTCCATTTGCC
TGCTATGAAGAAATACAATCTCAATCAGACAGATTTGGGAACTGTGGTAGGGATAGAAATAA
CAAATATGTGTTCTGTGGATGGAGGAATCTTATATGTGGAAGATTAGTTTGTACCTACCCTA
CTCGAAAGCCTTTCCATCAAGAAAATGGTGATGTGATTTATGCTTTCGTACGAGATTCTGTA
TGCATAACTGTAGACTACAAATTGCCTCGAACAGTTCCAGATCCACTGGCTGTCAAAAATGG
CTCTCAGTGTGATATTGGGAGGGTTTGTGTAAATCGTGAATGTGTAGAATCAAGGATAATTAAG
GCTTCAGCACATGTTTGTTCACAACAGTGTTCTGGACATGGAGTGTGTGATTCCAGAAACAA
GTGCCATTGTTCGCCAGGCTATAAGCCTCCAAACTGCCAAATACGTTCCAAAGGATTTTCCA
TATTTCCTGAGGAAGATATGGGTTCAATCATGGAAAGAGCATCTGGGAAGACTGAAAACACC
TGGCTTCTAGGTTTCCTCATTGCTCTTCCTATTCTCATTGTAACAACCGCAATAGTTTTGGC
AAGGAAACAGTTGAAAAAGTGGTTCGCCAAGGAAGAGGAATTCCCAAGTAGCGAATCTAAAT
CGGAAGGTAGCACACAGACATATGCCAGCCAATCCAGCTCAGAAGGCAGCACTCAGACATAT
GCCAGCCAAACCAGATCAGAAAGCAGCAGTCAAGCTGATACTAGCAAATCCAAATCAGAAGA
TAGTGCTGAAGCATATACTAGCAGATCCAAATCACAGGACAGTACCCAAACACAAAGCAGTA
GTAACTAGTGATTCCTTCAGAAGGCAACGGATAACATCGAGAGTCTCGCTAAGAAATGAAAA
TTCTGTCTTTCCTTCCGTGGTCACAGCTGAAAGAAACAATAAATTGAGTGTGGATC

FIGURE 90

></usr/seqdb2/sst/DNA/Dnaseqs.min/ss.DNA176775
><subunit 1 of 1, 787 aa, 1 stop
><MW: 87934, pI: 5.49, NX(S/T): 4
MFRLWLLLAGLCGLLASRPGFQNSLLQIVIPEKIQTNTNDSSEIEYEQISYIIPIDEKLY
TVHLKQRYFLADNFMIYLYNQGSMNTYSSDIQTQCYYQGNIEGYPDSMVTLSTCSGLRGI
LQFENVSYGIEPLESAVEFQHVLYKLKNEDNDIAIFIDRSLKEQPMDDNIFISEKSEPAV
PDLFPLYLEMHIVVDKTLYDYWGSDSMIVTNKVIEIVGLANSMFTQFKVTIVLSSLELWS
DENKISTVGEADELLQKFLEWKQSYLNLRPHDIAYLLIYMDYPRYLGAVFPGTMCITRYS
AGVALYPKEITLEAFAVIVTQMLALSLGISYDDPKKCQCSESTCIMNPEVVQSNGVKTFS
SCSLRSFQNFISNVGVKCLQNKPQMQKKSPKPVCGNGRLEGNEICDCGTEAQCGPASCCD
FRTCVLKDGAKCYKGLCCKDCQILQSGVECRPKAHPECDIAENCNGSSPECGPDITLING
LSCKNNKFICYDGDCHDLDARCESVFGKGSRNAPFACYEEIQSQSDRFGNCGRDRNNKYV
FCGWRNLICGRLVCTYPTRKPFHQENGDVIYAFVRDSVCITVDYKLPRTVPDPLAVKNGS
QCDIGRVCVNRECVESRIIKASAHVCSQQCSGHGVCDSRNKCHCSPGYKPPNCQIRSKGF
SIFPEEDMGSIMERASGKTENTWLLGFLIALPILIVTTAIVLARKQLKKWFAKEEEFPSS
ESKSEGSTQTYASQSSSEGSTQTYASQTRSESSSQADTSKSKSEDSAEAYTSRSKSQDST
QTQSSSN

Important features of the protein:
Signal peptide:
Amino acids 1-16

Transmembrane domain:
Amino acids 309-326;681-705

N-glycosylation sites:
Amino acids 39-43;125-129;465-469;598-602

Glycosaminoglycan attachment site:
Amino acids 631-635

Tyrosine kinase phosphorylation site:
Amino acids 269-276

N-myristoylation sites:
Amino acids 13-19;82-88;99-105;218-224;401-407;634-640;
726-732;739-745

EGF-like domain proteins:
Amino acids 642-654

Disintegrins proteins:
Amino acids 400-407;422-472;403-453;467-517;634-684

Reprolysin (M12B) family zinc metalloprotease:
Amino acids 186-383

Reprolysin family propeptide:
Amino acids 63-176

FIGURE 91

CACCAGACAGCACTCCAGCACTCTGTTTGGGGGGCATTCGAAACAGCAAAATCACTCATAAA
AGGCAAAAAATTGCAAAAAAAAAATAGTAATAACCAGCATGGCACTAAATAGACCATGAAAAG
ACATGTGTGTGCAGTATGAAAATTGAGACAGGAAGGCAGAGTGTCAGCTTGTTCCACCTCAG
CTGGGAATGTGCATCAGGCAACTCAAGTTTTTCACCACGGCATGTGTCTGTGAATGTCCGCA
AAACATTCTCTCTCCCCAGCCTTCATGTGTTAACCTGGGGATGATGTGGACCTGGGCACTGTGG
ATGCTCCCTTCACTCTGCAAATTCAGCCTGGCAGCTCTGCCAGCTAAGCCTGAGAACATTTC
CTGTGTCTACTACTATAGGAAAAATTTAACCTGCACTTGGAGTCCAGGAAAGGAAACCAGTT
ATACCCAGTACACAGTTAAGAGAACTTACGCTTTTGGAGAAAAACATGATAATTGTACAACC
AATAGTTCTACAAGTGAAAATCGTGCTTCGTGCTCTTTTTTCCTTCCAAGAATAACGATCCC
AGATAATTATACCATTGAGGTGGAAGCTGAAAATGGAGATGGTGTAATTAAATCTCATATGA
CATACTGGAGATTAGAGAACATAGCGAAAACTGAACCACCTAAGATTTTCCGTGTGAAACCA
GTTTTGGGCATCAAACGAATGATTCAAATTGAATGGATAAAGCCTGAGTTGGCGCCTGTTTC
ATCTGATTTAAAATACACACTTCGATTCAGGACAGTCAACAGTACCAGCTGGATGGAAGTCA
ACTTCGCTAAGAACCGTAAGGATAAAAACCAAACGTACAACCTCACGGGGCTGCAGCCTTTT
ACAGAATATGTCATAGCTCTGCGATGTGCGGTCAAGGAGTCAAAGTTCTGGAGTGACTGGAG
CCAAGAAAAAATGGGAATGACTGAGGAAGAAGCTCCATGTGGCCTGGAACTGTGGAGAGTCC
TGAAACCAGCTGAGGCGGATGGAAGAAGGCCAGTGCGGTTGTTATGGAAGAAGGCAAGAGGA
GCCCCAGTCCTAGAGAAAACACTTGGCTACAACATATGGTACTATCCAGAAAGCAACACTAA
CCTCACAGAAACAATGAACACTACTAACCAGCAGCTTGAACTGCATCTGGGAGGCGAGAGCT
TTTGGGTGTCTATGATTTCTTATAATTCTCTTGGGAAGTCTCCAGTGGCCACCCTGAGGATT
CCAGCTATTCAAGAAAAATCATTTCAGTGCATTGAGGTCATGCAGGCCTGCGTTGCTGAGGA
CCAGCTAGTGGTGAAGTGGCAAAGCTCTGCTCTAGACGTGAACACTTGGATGATTGAATGGT
TTCCGGATGTGGACTCAGAGCCCACCACCCTTTCCTGGGAATCTGTGTCTCAGGCCACGAAC
TGGACGATCCAGCAAGATAAATTAAAACCTTTCTGGTGCTATAACATCTCTGTGTATCCAAT
GTTGCATGACAAAGTTGGCGAGCCATATTCCATCCAGGCTTATGCCAAAGAAGGCGTTCCAT
CAGAAGGTCCTGAGACCAAGGTGGAGAACATTGGCGTGAAGACGGTCACGATCACATGGAAA
GAGATTCCCAAGAGTGAGAGAAAGGGTATCATCTGCAACTACACCATCTTTTACCAAGCTGA
AGGTGGAAAAGGATTCTGTAAGCACGCCCATAGCGAAGTGGAAAAAAACCCCAAGCCCCAGA
TAGATGCTATGGATAGACCTGTTGTAGGCATGGCTCCCCCATCTCATTGTGACTTGCAACCT
GGCATGAATCACTTAGCTTCTTTAAATCTCTCTGAAAATGGGGCCAAGAGCACCCACCTTTT
GGGGTTTTGGGGGTTAAATGAGAGTGAAGTGACAGTACCTGAGAGGAGAGTCCTGAGGAAAT
GGAAGGAGTTGTTATAATTTGTCCTGGTTAGGCCCTGAATTGACCTCCCGGGAGCTCCCCGA
CCATCATTCCCAGGAATGGCGTGCCTGGCTTAAAGAGTGAGGAGGAACAGACCCTGTCACCA
TGACTTCTACTGCCCCTGCCAAATCATGCTTTTGTTTTTCAGTCCACCTTATCTCCTGACATCT
TAAATACTGGGCAAGGCTTGGATTCTTGCTTAGGCTAAATAATTTTTTCTTATGGTAAAATA
CACGTAAAATATTTTTCCAGTTTAAACATTTGAAAGTGTACAATTTAGTGGCATTAGAAGCA
TTCACAATATTGTGCAACCATCACCACTATTTCCAGAACTCTTCTATTTCTGCCCAAATAGA
AGCCCTATACCCATTCATTAGTCACTCCCCATTCCTCTCCTCCCACAGCCCCTGGCAACTAC
CAAACTGCTTTGTGTCTCTATGGATTGCCTATTTTGGATATTTCATATACATAGAATCATAA
ANTAAAAAAAAAAAAAAAAAAAA

FIGURE 92

></usr/seqdb2/sst/DNA/Dnaseqs.min/ss.DNA177313
><subunit 1 of 1, 582 aa, 1 stop
><MW: 66605, pI: 8.14, NX(S/T): 15
MCIRQLKFFTTACVCECPQNILSPQPSCVNLGMMWTWALWMLPSLCKFSLAALPAKPENI
SCVYYYRKNLTCTWSPGKETSYTQYTVKRTYAFGEKHDNCTTNSSTSENRASCSFFLPRI
TIPDNYTIEVEAENGDGVIKSHMTYWRLENIAKTEPPKIFRVKPVLGIKRMIQIEWIKPE
LAPVSSDLKYTLRFRTVNSTSWMEVNFAKNRKDKNQTYNLTGLQPFTEYVIALRCAVKES
KFWSDWSQEKMGMTEEEAPCGLELWRVLKPAEADGRRPVRLLWKKARGAPVLEKTLGYNI
WYYPESNTNLTETMNTTNQQLELHLGGESFWVSMISYNSLGKSPVATLRIPAIQEKSFQC
IEVMQACVAEDQLVVKWQSSALDVNTWMIEWFPDVDSEPTTLSWESVSQATNWTIQQDKL
KPFWCYNISVYPMLHDKVGEPYSIQAYAKEGVPSEGPETKVENIGVKTVTITWKEIPKSE
RKGIICNYTIFYQAEGGKGFCKHAHSEVEKNPKPQIDAMDRPVVGMAPPSHCDLQPGMNH
LASLNLSENGAKSTHLLGFWGLNESEVTVPERRVLRKWKELL

Important features of the protein:
Signal peptide:
Amino acids 1-46

N-glycosylation sites:
Amino acids 59-63;69-73;99-103;103-107;125-129;198-202;
215-219;219-223;309-313;315-319;412-416;
427-431;487-491;545-549;563-567

N-myristoylation sites:
Amino acids 32-38;137-143;483-489;550-556;561-567

Amidation site:
Amino acids 274-278

Growth factor and cytokines receptors family signature 1:
Amino acids 62-75

Fibronectin type III domain:
Amino acids 54-144;154-247

FIGURE 93

ATTCTCCTAGAGCATCTTTGGAAGCATGAGGCCACGATGCTGCATCTTGGCTCTTGTCTGCT
GGATAACAGTCTTCCTCCTCCAGTGTTCAAAAGGAACTACAGACGCTCCTGTTGGCTCAGGA
CTGTGGCTGTGCCAGCCGACACCCAGGTGTGGGAACAAGATCTACAACCCTTCAGAGCAGTG
CTGTTATGATGATGCCATCTTATCCTTAAAGGAGACCCGCCGCTGTGGCTCCACCTGCACCT
TCTGGCCCTGCTTTGAGCTCTGCTGTCCCGAGTCTTTTGGCCCCCAGCAGAAGTTTCTTGTG
AAGTTGAGGGTTCTGGGTATGAAGTCTCAGTGTCACTTATCTCCCATCTCCCGGAGCTGTAC
CAGGAACAGGAGGCACGTCCTGTACCCATAAAAACCCCAGGCTCCACTGGCAGACGGCAGAC
AAGGGGAGAAGAGACGAAGCAGCTGGACATCGGAGACTACAGTTGAACTTCGGAGAGAAGCA
ACTTGACTTCAGAGGGATGGCTCAATGACATAGCTTTGGAGAGGAGCCCAGCTGGGGATGGC
CAGACTTCAGGGGAAGAATGCCTTCCTGCTTCATCCCCTTTCCAGCTCCCCTTCCCGCTGAG
AGCCACTTTCATCGGCAATAAAATCCCCCACATTTACCATCT

FIGURE 94

</usr/seqdb2/sst/DNA/Dnaseqs.min/ss.DNA57700
<subunit 1 of 1, 125 aa, 1 stop
<MW: 14198, pI: 9.01, NX(S/T): 1
MRPRCCILALVCWITVFLLQCSKGTTDAPVGSGLWLCQPTPRCGNKIYNPSEQCCYDDAI
LSLKETRRCGSTCTFWPCFELCCPESFGPQQKFLVKLRVLGMKSQCHLSPISRSCTRNRR
HVLYP

Important features:
Signal peptide:
Amino acids 1-21

N-myristoylation sites:
Amino acids 33-39;70-76

Anaphylatoxin domain proteins:
Amino acids 50-60

FIGURE 95

GCATTTTTGTCTGTGCTCCCTGATCTTCAGGTCACCACCATGAAGTTCTTAGCAGTCCTGGT
ACTCTTGGGAGTTTCCATCTTTCTGGTCTCTGCCCAGAATCCGACAACAGCTGCTCCAGCTG
ACACGTATCCAGCTACTGGTCCTGCTGATGATGAAGCCCCTGATGCTGAAACCACTGCTGCT
GCAACCACTGCGACCACTGCTGCTCCTACCACTGCAACCACCGCTGCTTCTACCACTGCTCG
TAAAGACATTCCAGTTTTACCCAAATGGGTTGGGGATCTCCCGAATGGTAGAGTGTGTCCCT
GAGATGGAATCAGCTTGAGTCTTCTGCAATTGGTCACAACTATTCATGCTTCCTGTGATTTC
ATCCAACTACTTACCTTGCCTACGATATCCCCTTTATCTCTAATCAGTTTATTTTCTTTCAA
ATAAAAAATAACTATGAGCAACATAAAAAAAAAAAAAA

FIGURE 96

</usr/seqdb2/sst/DNA/Dnaseqs.min/ss.DNA62872
<subunit 1 of 1, 90 aa, 1 stop
<MW: 9039, pI: 4.37, NX(S/T): 1
MKFLAVLVLLGVSIFLVSAQNPTTAAPADTYPATGPADDEAPDAETTAAATTATTAAPTT
ATTAASTTARKDIPVLPKWVGDLPNGRVCP

Important features:
Signal peptide:
Amino acids 1-19

FIGURE 97

GGACTCTGAAGGTCCCAAGCAGCTGCTGAGGCCCCCAAGGAAGTGGTTCCAACCTTGGACCC
CTAGGGGTCTGGATTTGCTGGTTAACAAGATAACCTGAGGGCAGGACCCCATAGGGGAATGC
TACCTCCTGCCCTTCCACCTGCCCTGGTGTTCACGGTGGCCTGGTCCCTCCTTGCCGAGAGA
GTGTCCTGGGTCAGGGACGCAGAGGACGCTCACAGACTCCAGCCCTTTGTTACCGAGAGGAC
ACTTGGCAAGGTCCAGCGATGGTCCGGAGTCCACACACAGACTGGCGGCAGGGCAGGAGGGG
GACAGTTCTGTTGTGCTTGGTTGGACAGTAAGAGGGTCTTGGCCAGTCCAGGGTGGGGGGCG
GCAAACTCCATAAAGAACCAGAGGGTCTGGGCCCCGGCCACAGAGTCATCTGCCCAGCTCCT
CTGCTGCTGGCCAGTGGGAGTGGCACGAGGTGGGGCTTTGTGCCAGTAAAACCACAGGCTGG
ATTTGCCTGCGGGCCATGGTCCCTGTCTAGGGCAGCAATTCTCAACCTTCTTGCTCTCAGGA
CCCCAAAGAGCTTTCATTGTATCTATTGATTTTTACCACATTAGCAATTAAAACTGAGAAAT
GGGCCGGGCACGGTGGCTCACGCCTGTAATCCCAGCACTTTGGGAGGCCGAGGCGGGTGGAT
CACCTGAGATCAGGAGTTCAAGACCAGCCTGGCCAACATGGTGAAACCTTGTCTACTAAAAA
TACAAAAAATTAGCCAGGCACAGTGGTGTGCACTGGTAGTCCCAGTTACTCGGGAGGCTGAG
GCAGGAAAATCGCTTGAACCCAGGAGGCGGACGTTGCGGTGAGCCGAGATCGCGCCGCTGAT
TCCAGCCTGGGCGACAAGAGTGAGACTCCATCTCACACA

FIGURE 98

</usr/seqdb2/sst/DNA/Dnaseqs.min/ss.DNA62876
<subunit 1 of 1, 120 aa, 1 stop
<MW: 12925, pI: 9.46, NX(S/T): 0
MLPPALPPALVFTVAWSLLAERVSWVRDAEDAHRLQPFVTERTLGKVQRWSGVHTQTGGR
AGGGQFCCAWLDSKRVLASPGWGAANSIKNQRVWAPATESSAQLLCCWPVGVARGGALCQ

Important features:
Signal peptide:
Amino acids 1-17

N-myristoylation sites:
Amino acids 58-64;63-69;64-70;83-89;111-117;115-121

FIGURE 99

AATTTTTCACCAGAGTAAACTTGAGAAACCAACTGGACCTTGAGTATTGTACATTTTGCCTC
GTGGACCCAAAGGTAGCAATCTGAAACATGAGGAGTACGATTCTACTGTTTTGTCTTCTAGG
ATCAACTCGGTCATTACCACAGCTCAAACCTGCTTTGGGACTCCCTCCCACAAAACTGGCTC
CGGATCAGGGAACACTACCAAACCAACAGCAGTCAAATCAGGTCTTTCCTTCTTTAAGTCTG
ATACCATTAACACAGATGCTCACACTGGGGCCAGATCTGCATCTGTTAAATCCTGCTGCAGG
AATGACACCTGGTACCCAGACCCACCCATTGACCCTGGGAGGGTTGAATGTACAACAGCAAC
TGCACCCACATGTGTTACCAATTTTTGTCACACAACTTGGAGCCCAGGGCACTATCCTAAGC
TCAGAGGAATTGCCACAAATCTTCACGAGCCTCATCATCCATTCCTTGTTCCCGGGAGGCAT
CCTGCCCACCAGTCAGGCAGGGGCTAATCCAGATGTCCAGGATGGAAGCCTTCCAGCAGGAG
GAGCAGGTGTAAATCCTGCCACCCAGGGAACCCCAGCAGGCCGCCTCCCAACTCCCAGTGGC
ACAGATGACGACTTTGCAGTGACCACCCCTGCAGGCATCCAAAGGAGCACACATGCCATCGA
GGAAGCCACCACAGAATCAGCAAATGGAATTCAGTAAGCTGTTTCAAATTTTTTCAACTAAG
CTGCCTCGAATTTGGTGATACATGTGAATCTTTATCATTGATTATATTATGGAATAGATTGA
GACACATTGGATAGTCTTAGAAGAAATTAATTCTTAATTTACCTGAAAATATTCTTGAAATTT
CAGAAAATATGTTCTATGTAGAGAATCCCAACTTTTAAAAACAATAATTCAATGGATAAATC
TGTCTTTGAAATATAACATTATGCTGCCTGGATGATATGCATATTAAAACATATTTGGAAAA
CTGGAAAAAAAAAAAAAAAAAAAAAAAAAAAAAAAAAAAAAAAAAAAAAAAAAAAAAAAAAA
AAAAAAAAAAAAAAAAAA

FIGURE 100

></usr/seqdb2/sst/DNA/Dnaseqs.min/ss.DNA66660
><subunit 1 of 1, 209 aa, 1 stop
><MW: 21588, pI: 5.50, NX(S/T): 0
MRSTILLFCLLGSTRSLPQLKPALGLPPTKLAPDQGTLPNQQQSNQVFPSLSLIPLTQML
TLGPDLHLLNPAAGMTPGTQTHPLTLGGLNVQQQLHPHVLPIFVTQLGAQGTILSSEELP
QIFTSLIIHSLFPGGILPTSQAGANPDVQDGSLPAGGAGVNPATQGTPAGRLPTPSGTDD
DFAVTTPAGIQRSTHAIEEATTESANGIQ

Important features of the protein:
Signal peptide:
Amino acids 1-16

Leucine zipper patterns:
Amino acids 10-32;17-39

N-myristoylation sites:
Amino acids 12-18;25-31;36-42;74-80;108-114;111-117;
135-141;151-157;159-165;166-172;189-195

FIGURE 101

GGGGTCTCCCTCAGGGCCGGGAGGCACAGCGGTCCCTGCTTGCTGAAGGGCTGGATGTACGC
ATCCGCAGGTTCCCGCGGACTTGGGGGCGCCCGCTGAGCCCCGGCGCCCGCAGAAGACTTGT
GTTTGCCTCCTGCAGCCTCAACCCGGAGGGCAGCGAGGGCCTACCACCATGATCACTGGTGT
GTTCAGCATGCGCTTGTGGACCCCAGTGGGCGTCCTGACCTCGCTGGCGTACTGCCTGCACC
AGCGGCGGGTGGCCCTGGCCGAGCTGCAGGAGGCCGATGGCCAGTGTCCGGTCGACCGCAGC
CTGCTGAAGTTGAAAATGGTGCAGGTCGTGTTTCGACACGGGGCTCGGAGTCCTCTCAAGCC
GCTCCCGCTGGAGGAGCAGGTAGAGTGGAACCCCCAGCTATTAGAGGTCCCACCCCAAACTC
AGTTTGATTACACAGTCACCAATCTAGCTGGTGGTCCGAAACCATATTCTCCTTACGACTCT
CAATACCATGAGACCACCCTGAAGGGGGGCATGTTTGCTGGGCAGCTGACCAAGGTGGGCAT
GCAGCAAATGTTTGCCTTGGGAGAGAGACTGAGGAAGAACTATGTGGAAGACATTCCCTTTC
TTTCACCAACCTTCAACCCACAGGAGGTCTTTATTCGTTCCACTAACATTTTTCGGAATCTG
GAGTCCACCCGTTGTTTGCTGGCTGGGCTTTTCCAGTGTCAGAAAGAAGGACCCATCATCAT
CCACACTGATGAAGCAGATTCAGAAGTCTTGTATCCCAACTACCAAAGCTGCTGGAGCCTGA
GGCAGAGAACCAGAGGCCGGAGGCAGACTGCCTCTTTACAGCCAGGAATCTCAGAGGATTTG
AAAAAGGTGAAGGACAGGATGGGCATTGACAGTAGTGATAAAGTGGACTTCTTCATCCTCCT
GGACAACGTGGCTGCCGAGCAGGCACACAACCTCCCAAGCTGCCCCATGCTGAAGAGATTTG
CACGGATGATCGAACAGAGAGCTGTGGACACATCCTTGTACATACTGCCCAAGGAAGACAGG
GAAAGTCTTCAGATGGCAGTAGGCCCATTCCTCCACATCCTAGAGAGCAACCTGCTGAAAGC
CATGGACTCTGCCACTGCCCCCGACAAGATCAGAAAGCTGTATCTCTATGCGGCTCATGATG
TGACCTTCATACCGCTCTTAATGACCCTGGGGATTTTTGACCACAAATGGCCACCGTTTGCT
GTTGACCTGACCATGGAACTTTACCAGCACCTGGAATCTAAGGAGTGGTTTGTGCAGCTCTA
TTACCACGGGAAGGAGCAGGTGCCGAGAGGTTGCCCTGATGGGCTCTGCCCGCTGGACATGT
TCTTGAATGCCATGTCAGTTTATACCTTAAGCCCAGAAAAATACCATGCACTCTGCTCTCAA
ACTCAGGTGATGGAAGTTGGAAATGAAGAGTAACTGATTTATAAAAGCAGGATGTGTTGATT
TTAAAATAAAGTGCCTTTATACAATG

FIGURE 102

MITGVFSMRLWTPVGVLTSLAYCLHQRRVALAELQEADGQCPVDRSLLKLKMVQVVFRHGARSPLKPLPLEEQV
EWNPQLLEVPPQTQFDYTVTNLAGGPKPYSPYDSQYHETTLKGGMFAGQLTKVGMQQMFALGERLRKNYVEDIP
FLSPTFNPQEVFIRSTNIFRNLESTRCLLAGLFQCQKEGPIIIHTDEADSEVLYPNYQSCWSLRQRTRGRRQTA
SLQPGISEDLKKVKDRMGIDSSDKVDFFILLDNVAAEQAHNLPSCPMLKRFARMIEQRAVDTSLYILPKEDRES
LQMAVGPFLHILESNLLKAMDSATAPDKIRKLYLYAAHDVTFIPLLMTLGIFDHKWPPFAVDLTMELYQHLESK
EWFVQLYYHGKEQVPRGCPDGLCPLDMFLNAMSVYTLSPEKYHALCSQTQVMEVGNEE

Important features:
Signal sequence:
amino acids 1-23 cAMP- and cGMP-dependent protein kinase phosphorylation site.
amino acids 218-222

Casein kinase II phosphorylation site.
amino acids 87-91, 104-108, 320-324

Tyrosine kinase phosphorylation site.
amino acids 280-288

N-myristoylation site.
amino acids 15-21, 117-123, 118-124, 179-185, 240-246, 387-393

Amidation site.
amino acids 216-220

Leucine zipper pattern.
amino acids 10-32

Histidine acid phosphatases phosphohistidine signature.
amino acids 50-65

FIGURE 103

GGGGCGGGTGGACGCGGACTCGAACGCAGTTGCTTCGGGACCCAGGACCCCCTCGGGCCCGA
CCCGCCAGGAAAGACTGAGGCCGCGGCCTGCCCCGCCCGGCTCCCTGCGCCGCCGCCGCCTC
CCGGGACAGAAGATGTGCTCCAGGGTCCCTCTGCTGCTGCCGCTGCTCCTGCTACTGGCCCT
GGGGCCTGGGGTGCAGGGCTGCCCATCCGGCTGCCAGTGCAGCCAGCCACAGACAGTCTTCT
GCACTGCCCGCCAGGGGACCACGGTGCCCCGAGACGTGCCACCCGACACGGTGGGGCTGTAC
GTCTTTGAGAACGGCATCACCATGCTCGACGCAAGCAGCTTTGCCGGCCTGCCGGGCCTGCA
GCTCCTGGACCTGTCACAGAACCAGATCGCCAGCCTGCGCCTGCCCCGCCTGCTGCTGCTGG
ACCTCAGCCACAACAGCCTCCTGGCCCTGGAGCCCGGCATCCTGGACACTGCCAACGTGGAG
GCGCTGCGGCTGGCTGGTCTGGGGCTGCAGCAGCTGGACGAGGGGCTCTTCAGCCGCTTGCG
CAACCTCCACGACCTGGATGTGTCCGACAACCAGCTGGAGCGAGTGCCACCTGTGATCCGAG
GCCTCCGGGGCCTGACGCGCCTGCGGCTGGCCGGCAACACCCGCATTGCCCAGCTGCGGCCC
GAGGACCTGGCCGGCCTGGCTGCCCTGCAGGAGCTGGATGTGAGCAACCTAAGCCTGCAGGC
CCTGCCTGGCGACCTCTCGGGCCTCTTCCCCCGCCTGCGGCTGCTGGCAGCTGCCCGCAACC
CCTTCAACTGCGTGTGCCCCCTGAGCTGGTTTGGCCCCTGGGTGCGCGAGAGCCACGTCACA
CTGGCCAGCCCTGAGGAGACGCGCTGCCACTTCCCGCCCAAGAACGCTGGCCGGCTGCTCCT
GGAGCTTGACTACGCCGACTTTGGCTGCCCAGCCACCACCACCACAGCCACAGTGCCCACCA
CGAGGCCCGTGGTGCGGGAGCCCACAGCCTTGTCTTCTAGCTTGGCTCCTACCTGGCTTAGC
CCCACAGCGCCGGCCACTGAGGCCCCCAGCCCGCCCTCCACTGCCCCACCGACTGTAGGGCC
TGTCCCCCAGCCCCAGGACTGCCCACCGTCCACCTGCCTCAATGGGGGCACATGCCACCTGG
GGACACGGCACCACCTGGCGTGCTTGTGCCCCGAAGGCTTCACGGGCCTGTACTGTGAGAGC
CAGATGGGGCAGGGGACACGGCCCAGCCCTACACCAGTCACGCCGAGGCCACCACGGTCCCT
GACCCTGGGCATCGAGCCGGTGAGCCCCACCTCCCTGCGCGTGGGGCTGCAGCGCTACCTCC
AGGGGAGCTCCGTGCAGCTCAGGAGCCTCCGTCTCACCTATCGCAACCTATCGGGCCCTGAT
AAGCGGCTGGTGACGCTGCGACTGCCTGCCTCGCTCGCTGAGTACACGGTCACCCAGCTGCG
GCCCAACGCCACTTACTCCGTCTGTGTCATGCCTTTGGGGCCCGGGCGGGTGCCGGAGGGCG
AGGAGGCCTGCGGGGAGGCCCATACACCCCCAGCCGTCCACTCCAACCACGCCCCAGTCACC
CAGGCCCGCGAGGGCAACCTGCCGCTCCTCATTGCGCCCGCCCTGGCCGCGGTGCTCCTGGC
CGCGCTGGCTGCGGTGGGGGCAGCCTACTGTGTGCGGCGGGGGCGGGCCATGGCAGCAGCGG
CTCAGGACAAAGGGCAGGTGGGGCCAGGGGCTGGGCCCCTGGAACTGGAGGGAGTGAAGGTC
CCCTTGGAGCCAGGCCCGAAGGCAACAGAGGGCGGTGGAGAGGCCCTGCCCAGCGGGTCTGA
GTGTGAGGTGCCACTCATGGGCTTCCCAGGGCCTGGCCTCCAGTCACCCCTCCACGCAAAGC
CCTACATCTAAGCCAGAGAGAGACAGGGCAGCTGGGGCCGGGCTCTCAGCCAGTGAGATGGC
CAGCCCCCTCCTGCTGCCACACCACGTAAGTTCTCAGTCCCAACCTCGGGGATGTGTGCAGA
CAGGGCTGTGTGACCACAGCTGGGCCCTGTTCCCTCTGGACCTCGGTCTCCTCATCTGTGAG
ATGCTGTGGCCCAGCTGACGAGCCCTAACGTCCCCAGAACCGAGTGCCTATGAGGACAGTGT
CCGCCCTGCCCTCCGCAACGTGCAGTCCCTGGGCACGGCGGGCCCTGCCATGTGCTGGTAAC
GCATGCCTGGGCCCTGCTGGGCTCTCCCACTCCAGGCGGACCCTGGGGGCCAGTGAAGGAAG
CTCCCGGAAAGAGCAGAGGGAGAGCGGGTAGGCGGCTGTGTGACTCTAGTCTTGGCCCCAGG
AAGCGAAGGAACAAAAGAAACTGGAAAGGAAGATGCTTTAGGAACATGTTTTGCTTTTTTAA
AATATATATATATTTATAAGAGATCCTTTCCCATTTATTCTGGGAAGATGTTTTTCAAACTC
AGAGACAAGGACTTTGGTTTTTGTAAGACAAACGATGATATGAAGGCCTTTTGTAAGAAAAA
ATAAAAAAAAAAA

FIGURE 104

</usr/seqdb2/sst/DNA/Dnaseqs.min/ss.DNA44804
<subunit 1 of 1, 598 aa, 1 stop
<MW: 63030, pI: 7.24, NX(S/T): 3
MCSRVPLLLPLLLLLALGPGVQGCPSGCQCSQPQTVFCTARQGTTVPRDVPPDTVGLYVFEN
GITMLDASSFAGLPGLQLLDLSQNQIASLRLPRLLLLDLSHNSLLALEPGILDTANVEALRL
AGLGLQQLDEGLFSRLRNLHDLDVSDNQLERVPPVIRGLRGLTRLRLAGNTRIAQLRPEDLA
GLAALQELDVSNLSLQALPGDLSGLFPRLRLLAAARNPFNCVCPLSWFGPWVRESHVTLASP
EETRCHFPPKNAGRLLLELDYADFGCPATTTTATVPTTRPVVREPTALSSSLAPTWLSPTAP
ATEAPSPPSTAPPTVGPVPQPQDCPPSTCLNGGTCHLGTRHHLACLCPEGFTGLYCESQMGQ
GTRPSPTPVTPRPPRSLTLGIEPVSPTSLRVGLQRYLQGSSVQLRSLRLTYRNLSGPDKRLV
TLRLPASLAEYTVTQLRPNATYSVCVMPLGPGRVPEGEEACGEAHTPPAVHSNHAPVTQARE
GNLPLLIAPALAAVLLAALAAVGAAYCVRRGRAMAAAAQDKGQVGPGAGPLELEGVKVPLEP
GPKATEGGGEALPSGSECEVPLMGFPGPGLQSPLHAKPYI

Signal sequence.
amino acids 1-23

Transmembrane domain.
amino acids 501-522

N-glycosylation sites.
amino acids 198-202, 425-429, 453-457

Tyrosine kinase phosphorylation site.
amino acids 262-270

N-myristoylation sites.
amino acids 23-29, 27-33, 112-118, 273-279, 519-525, 565-571

Prokaryotic membrane lipoprotein lipid attachment site.
amino acids 14-25

EGF-like domain cysteine pattern signature.
amino acids 355-367

Leucine zipper pattern.
amino acids 122-144, 194-216

FIGURE 105

CCCACGCGTCCGAAGGCAGACAAAGGTTCATTTGTAAAGAAGCTCCTTCCAGCACCTCCTCT
CTTCTCCTTTTGCCCAAACTCACCCAGTGAGTGTGAGCATTTAAGAAGCATCCTCTGCCAAG
ACCAAAAGGAAAGAAGAAAAAGGGCCAAAAGCCAAAATGAAACTGATGGTACTTGTTTTCAC
CATTGGGCTAACTTTGCTGCTAGGAGTTCAAGCCATGCCTGCAAATCGCCTCTCTTGCTACA
GAAAGATACTAAAAGATCACAACTGTCACAACCTTCCGGAAGGAGTAGCTGACCTGACACAG
ATTGATGTCAATGTCCAGGATCATTTCTGGGATGGGAAGGGATGTGAGATGATCTGTTACTG
CAACTTCAGCGAATTGCTCTGCTGCCCAAAAGACGTTTTCTTTGGACCAAAGATCTCTTTCG
TGATTCCTTGCAACAATCAATGAGAATCTTCATGTATTCTGGAGAACACCATTCCTGATTTC
CCACAAACTGCACTACATCAGTATAACTGCATTTCTAGTTTCTATATAGTGCAATAGAGCAT
AGATTCTATAAATTCTTACTTGTCTAAGACAAGTAAATCTGTGTTAAACAAGTAGTAATAAA
AGTTAATTCAATCTAAAAAAAAAAAAA

FIGURE 106

</usr/seqdb2/sst/DNA/Dnaseqs.min/ss.DNA52758
<subunit 1 of 1, 98 aa, 1 stop
<MW: 11081, pI: 6.68, NX(S/T): 1
MKLMVLVFTIGLTLLLGVQAMPANRLSCYRKILKDHNCHNLPEGVADLTQIDVNVQDHFW
DGKGCEMICYCNFSELLCCPKDVFFGPKISFVIPCNNQ

Important features:
Signal peptide:
Amino acids 1-20

N-glycosylation site:
Amino acids 72-76

Tyrosine kinase phosphorylation site:
Amino acids 63-71

FIGURE 107

AGTGACTGCAGCCTTCCTAGATCCCCTCCACTCGGTTTCTCTCTTTGCAGGAGCACCGGCAG
CACCAGTGTGTGAGGGGAGCAGGCAGCGGTCCTAGCCAGTTCCTTGATCCTGCCAGACCACC
CAGCCCCCGGCACAGAGCTGCTCCACAGGCACCATGAGGATCATGCTGCTATTCACAGCCAT
CCTGGCCTTCAGCCTAGCTCAGAGCTTTGGGGCTGTCTGTAAGGAGCCACAGGAGGAGGTGG
TTCCTGGCGGGGGCCGCAGCAAGAGGGATCCAGATCTCTACCAGCTGCTCCAGAGACTCTTC
AAAAGCCACTCATCTCTGGAGGGATTGCTCAAAGCCCTGAGCCAGGCTAGCACAGATCCTAA
GGAATCAACATCTCCCGAGAAACGTGACATGCATGACTTCTTTGTGGGACTTATGGGCAAGA
GGAGCGTCCAGCCAGAGGGAAAGACAGGACCTTTCTTACCTTCAGTGAGGGTTCCTCGGCCC
CTTCATCCCAATCAGCTTGGATCCACAGGAAAGTCTTCCCTGGGAACAGAGGAGCAGAGACC
TTTATAAGACTCTCCTACGGATGTGAATCAAGAGAACGTCCCCAGCTTTGGCATCCTCAAGTA
TCCCCCGAGAGCAGAATAGGTACTCCACTTCCGGACTCCTGGACTGCATTAGGAAGACCTCT
TTCCCTGTCCCAATCCCCAGGTGCGCACGCTCCTGTTACCCTTTCTCTTCCCTGTTCTTGTA
ACATTCTTGTGCTTTGACTCCTTCTCCATCTTTTCTACCTGACCCTGGTGTGGAAACTGCAT
AGTGAATATCCCCAACCCCAATGGGCATTGACTGTAGAATACCCTAGAGTTCCTGTAGTGTC
CTACATTAAAAATATAATGTCTCTCTCTATTCCTCAACAATAAAGGATTTTTGCATATGAAA
AAAAAAAAAAAAAAAAAAAAAAAAAAAAAAAAAAAAAAAA

FIGURE 108

</usr/seqdb2/sst/DNA/Dnaseqs.min/ss.DNA59849
<subunit 1 of 1, 135 aa, 1 stop
<MW: 14833, pI: 9.78, NX(S/T): 0
MRIMLLFTAILAFSLAQSFGAVCKEPQEEVVPGGGRSKRDPDLYQLLQRLFKSHSSLEGL
LKALSQASTDPKESTSPEKRDMHDFFVGLMGKRSVQPEGKTGPFLPSVRVPRPLHPNQLG
STGKSSLGTEEQRPL

Important features:
Signal peptide:
Amino acids 1-18

Tyrosine kinase phosphorylation site:
Amino acids 36-45

N-myristoylation sites:
Amino acids 33-39;59-65

Amidation site:
Amino acids 90-94

Leucine zipper pattern:
Amino acids 43-65

Tachykinin family signature:
Amino acids 86-92

FIGURE 109

GCGGCCACACGCAGCTAGCCGGAGCCCGGACCAGGCGCCTGTGCCTCCTCCTCGTCCCTCGC
CGCGTCCGCGAAGCCTGGAGCCGGCGGGAGCCCCGCGCTCGCCATGTCGGGCGAGCTCAGCA
ACAGGTTCCAAGGAGGGAAGGCGTTCGGCTTGCTCAAAGCCCGGCAGGAGAGGAGGCTGGCC
GAGATCAACCGGGAGTTTCTGTGTGACCAGAAGTACAGTGATGAAGAGAACCTTCCAGAAAA
GCTCACAGCCTTCAAAGAGAAGTACATGGAGTTTGACCTGAACAATGAAGGCGAGATTGACC
TGATGTCTTTAAAGAGGATGATGGAGAAGCTTGGTGTCCCCAAGACCCACCTGGAGATGAAG
AAGATGATCTCAGAGGTGACAGGAGGGGTCAGTGACACTATATCCTACCGAGACTTTGTGAA
CATGATGCTGGGGAAACGGTCGGCTGTCCTCAAGTTAGTCATGATGTTTGAAGGAAAAGCCA
ACGAGAGCAGCCCCAAGCCAGTTGGCCCCCCTCCAGAGAGAGACATTGCTAGCCTGCCCTGA
GGACCCCGCCTGGACTCCCCAGCCTTCCCACCCCATACCTCCCTCCCGATCTTGCTGCCCTT
CTTGACACACTGTGATCTCTCTCTCTCTCATTTGTTTGGTCATTGAGGGTTTGTTTGTGTTT
TCATCAATGTCTTTGTAAAGCACAAATTATCTGCCTTAAAGGGGCTCTGGGTCGGGGAATCC
TGAGCCTTGGGTCCCCTCCCTCTCTTCTTCCCTCCTTCCCCGCTCCCTGTGCAGAAGGGCTG
ATATCAAACCAAAAACTAGAGGGGGCAGGGCCAGGGCAGGGAGGCTTCCAGCCTGTGTTCCC
CTCACTTGGAGGAACCAGCACTCTCCATCCTTTCAGAAAGTCTCCAAGCCAAGTTCAGGCTC
ACTGACCTGGCTCTGACGAGGACCCCAGGCCACTCTGAGAAGACCTTGGAGTAGGGACAAGG
CTGCAGGGCCTCTTTCGGGTTTCCTTGGACAGTGCCATGGTTCCAGTGCTCTGGTGTCACCC
AGGACACAGCCACTCGGGGCCCCGCTGCCCCAGCTGATCCCCACTCATTCCACACCTCTTCT
CATCCTCAGTGATGTGAAGGTGGGAAGGAAAGGAGCTTGGCATTGGGAGCCCTTCAAGAAGG
TACCAGAAGGAACCCTCCAGTCCTGCTCTCTGGCCACACCTGTGCAGGCAGCTGAGAGGCAG
CGTGCAGCCCTACTGTCCCTTACTGGGGCAGCAGAGGGCTTCGGAGGCAGAAGTGAGGCCTG
GGGTTTGGGGGGAAAGGTCAGCTCAGTGCTGTTCCACCTTTTAGGGAGGATACTGAGGGGAC
CAGGATGGGAGAATGAGGAGTAAAATGCTCACGGCAAAGTCAGCAGCACTGGTAAGCCAAGA
CTGAGAAATACAAGGTTGCTTGTCTGACCCCAATCTGCTTGAAAAAAAAAAAAAAAAAA

FIGURE 110

MSGELSNRFQGGKAFGLLKARQERRLAEINREFLCDQKYSDEENLPEKLTAFKEKYMEFDLN
NEGEIDLMSLKRMMEKLGVPKTHLEMKKMISEVTGGVSDTISYRDFVNMMLGKRSAVLKLVM
MFEGKANESSPKPVGPPPERDIASLP

FIGURE 111

TAAAACAGCTACAATATTCCAGGGCCAGTCACTTGCCATTTCTCATAACAGCGTCAGAGAGA
AAGAACTGACTGAAACGTTTGAGATGAAGAAAGTTCTCCTCCTGATCACAGCCATCTTGGCA
GTGGCTGTTGGTTTCCCAGTCTCTCAAGACCAGGAACGAGAAAAAAGAAGTATCAGTGACAG
CGATGAATTAGCTTCAGGGTTTTTTGTGTTCCCTTACCCATATCCATTTCGCCCACTTCCAC
CAATTCCATTTCCAAGATTTCCATGGTTTAGACGTAATTTTCCTATTCCAATACCTGAATCT
GCCCCTACAACTCCCCTTCCTAGCGAAAAGTAAACAAGAAGGATAAGTCACGATAAACCTGG
TCACCTGAAATTGAAATTGAGCCACTTCCTTGAAGAATCAAAATTCCTGTTAATAAAAGAAA
AACAAATGTAATTGAAATAGCACACAGCATTCTCTAGTCAATATCTTTAGTGATCTTCTTTA
ATAAACATGAAAGCAAAGATTTTGGTTTCTTAATTTCCACA

FIGURE 112

></usr/seqdb2/sst/DNA/Dnaseqs.min/ss.DNA71290
><subunit 1 of 1, 85 aa, 1 stop
><MW: 9700, pI: 9.55, NX(S/T): 0
MKKVLLLITAILAVAVGFPVSQDQEREKRSISDSDELASGFFVFPYPYPFRPLPPIPFPR
FPWFRRNFPIPIPESAPTTPLPSEK

Important features of the protein:
Signal peptide:
Amino acids 1-17

Homologous region to B3-hordein:
Amino acids 47-85

FIGURE 113

CTCCTCTTAACATACTTGCAGCTAAAACTAAATATTGCTGCTTGGGGACCTCCTTCTAGCCT
TAAATTTCAGCTCATCACCTTCACCTGCCTTGGTC<u>ATG</u>GCTCTGCTATTCTCCTTGATCCTT
GCCATTTGCACCAGACCTGGATTCCTAGCGTCTCCATCTGGAGTGCGGCTGGTGGGGGGCCT
CCACCGCTGTGAAGGGCGGGTGGAGGTGGAACAGAAAGGCCAGTGGGGCACCGTGTGTGATG
ACGGCTGGGACATTAAGGACGTGGCTGTGTTGTGCCGGGAGCTGGGCTGTGGAGCTGCCAGC
GGAACCCCTAGTGGTATTTTGTATGAGCCACCAGCAGAAAAAGAGCAAAAGGTCCTCATCCA
ATCAGTCAGTTGCACAGGAACAGAAGATACATTGGCTCAGTGTGAGCAAGAAGAAGTTTATG
ATTGTTCACATGATGAAGATGCTGGGGCATCGTGTGAGAACCCAGAGAGCTCTTTCTCCCCA
GTCCCAGAGGGTGTCAGGCTGGCTGACGGCCCTGGGCATTGCAAGGGACGCGTGGAAGTGAA
GCACCAGAACCAGTGGTATACCGTGTGCCAGACAGGCTGGAGCCTCCGGGCCGCAAAGGTGG
TGTGCCGGCAGCTGGGATGTGGGAGGGCTGTACTGACTCAAAAACGCTGCAACAAGCATGCC
TATGGCCGAAAACCCATCTGGCTGAGCCAGATGTCATGCTCAGGACGAGAAGCAACCCTTCA
GGATTGCCCTTCTGGGCCTTGGGGGAAGAACACCTGCAACCATGATGAAGACACGTGGGTCG
AATGTGAAGATCCCTTTGACTTGAGACTAGTAGGAGGAGACAACCTCTGCTCTGGGCGACTG
GAGGTGCTGCACAAGGGCGTATGGGGCTCTGTCTGTGATGACAACTGGGGAGAAAAGGAGGA
CCAGGTGGTATGCAAGCAACTGGGCTGTGGGAAGTCCCTCTCTCCCTCCTTCAGAGACCGGA
AATGCTATGGCCCTGGGGTTGGCCGCATCTGGCTGGATAATGTTCGTTGCTCAGGGGAGGAG
CAGTCCCTGGAGCAGTGCCAGCACAGATTTTGGGGGTTTCACGACTGCACCCACCAGGAAGA
TGTGGCTGTCATCTGCTCAGTG<u>TAG</u>GTGGGCATCATCTAATCTGTTGAGTGCCTGAATAGAA
GAAAAACACAGAAGAAGGGAGCATTTACTGTCTACATGACTGCATGGGATGAACACTGATCT
TCTTCTGCCCTTGGACTGGGACTTATACTTGGTGCCCCTGATTCTCAGGCCTTCAGAGTTGG
ATCAGAACTTACAACATCAGGTCTAGTTCTCAGGCCATCAGACATAGTTTGGAACTACATCA
CCACCTTTCCTATGTCTCCACATTGCACACAGCAGATTCCCAGCCTCCATAATTGTGTGTAT
CAACTACTTAAATACATTCTCACACACACACACACACACACACACACACACACACACATA
CACCATTTGTCCTGTTTCTCTGAAGAACTCTGACAAAATACAGATTTTGGTACTGAAAGAGA
TTCTAGAGGAACGGAATTTTAAGGATAAATTTTCTGAATTGGTTATGGGGTTTCTGAAATTG
GCTCTATAATCTAATTAGATATAAAATTCTGGTAACTTTATTTACAATAATAAAGATAGCAC
TATGTGTTCAAA

FIGURE 114

MALLFSLILAICTRPGFLASPSGVRLVGGLHRCEGRVEVEQKGQWGTVCDDGWDIKDVAVLC
RELGCGAASGTPSGILYEPPAEKEQKVLIQSVSCTGTEDTLAQCEQEEVYDCSHDEDAGASC
ENPESSFSPVPEGVRLADGPGHCKGRVEVKHQNQWYTVCQTGWSLRAAKVVCRQLGCGRAVL
TQKRCNKHAYGRKPIWLSQMSCSGREATLQDCPSGPWGKNTCNHDEDTWVECEDPFDLRLVG
GDNLCSGRLEVLHKGVWGSVCDDNWGEKEDQVVCKQLGCGKSLSPSFRDRKCYGPGVGRIWL
DNVRCSGEEQSLEQCQHRFWGFHDCTHQEDVAVICSV

Signal sequence:
amino acids 1-15

Casein kinase II phosphorylation site.
amino acids 47-51, 97-101, 115-119, 209-213, 214-218, 234-238, 267-271, 294-298, 316-320, 336-340

N-myristoylation site.
amino acids 29-35, 43-49, 66-72, 68-74, 72-78, 98-104, 137-143, 180-186, 263-269, 286-292

Amidation site.
amino acids 196-200

Speract receptor repeated domain signature.
amino acids 29-67, 249-287

FIGURE 115

CATTTCCAACAAGAGCACTGGCCAAGTCAGCTTCTTCTGAGAGAGTCTCTAGAAGACATGAT
GCTACACTCAGCTTTGGGTCTCTGCCTCTTACTCGTCACAGTTTCTTCCAACCTTGCCATTG
CAATAAAAAAGGAAAAGAGGCCTCCTCAGACACTCTCAAGAGGATGGGGAGATGACATCACT
TGGGTACAAACTTATGAAGAAGGTCTCTTTTATGCTCAAAAAAGTAAGAAGCCATTAATGGT
TATTCATCACCTGGAGGATTGTCAATACTCTCAAGCACTAAAGAAAGTATTTGCCCAAAATG
AAGAAATACAAGAAATGGCTCAGAATAAGTTCATCATGCTAAACCTTATGCATGAAACCACT
GATAAGAATTTATCACCTGATGGGCAATATGTGCCTAGAATCATGTTTGTAGACCCTTCTTT
AACAGTTAGAGCTGACATAGCTGGAAGATACTCTAACAGATTGTACACATATGAGCCTCGGG
ATTTACCCCTATTGATAGAAAACATGAAGAAAGCATTAAGACTTATTCAGTCAGAGCTATAA
GAGATGATGGAAAAAAGCCTTCACTTCAAAGAAGTCAAATTTCATGAAGAAAACCTCTGGCA
CATTGACAAATACTAAATGTGCAAGTATATAGATTTTGTAATATTACTATTTAGTTTTTTTA
ATGTGTTTGCAATAGTCTTATTAAAATAAATGTTTTTTAAATCTGA

FIGURE 116

</usr/seqdb2/sst/DNA/Dnaseqs.min/ss.DNA64896
<subunit 1 of 1, 166 aa, 1 stop
<MW: 19171, pI: 8.26, NX(S/T): 1
MMLHSALGLCLLLVTVSSNLAIAIKKEKRPPQTLSRGWGDDITWVQTYEEGLFYAQKSKK
PLMVIHHLEDCQYSQALKKVFAQNEEIQEMAQNKFIMLNLMHETTDKNLSPDGQYVPRIM
FVDPSLTVRADIAGRYSNRLYTYEPRDLPLLIENMKKALRLIQSEL

Important features:
Signal peptide:
Amino acids 1-23

N-myristoylation site:
Amino acids 51-57

FIGURE 117

CCTGGAGCCGGAAGCGCGGCTGCAGCAGGGCGAGGCTCCAGGTGGGGTCGGTTCCGCATCCA
GCCTAGCGTGTCCACGATGCGGCTGGGCTCCGGGACTTTCGCTACCTGTTGCGTAGCGATCG
AGGTGCTAGGGATCGCGGTCTTCCTTCGGGGATTCTTCCCGGCTCCCGTTCGTTCCTCTGCC
AGAGCGGAACACGGAGCGGAGCCCCCAGCGCCCGAACCCTCGGCTGGAGCCAGTTCTAACTG
GACCACGCTGCCACCACCTCTCTTCAGTAAAGTTGTTATTGTTCTGATAGATGCCTTGAGAG
ATGATTTTGTGTTTGGGTCAAAGGGTGTGAAATTTATGCCCTACACAACTTACCTTGTGGAA
AAAGGAGCATCTCACAGTTTTGTGGCTGAAGCAAAGCCACCTACAGTTACTATGCCTCGAAT
CAAGGCATTGATGACGGGGAGCCTTCCTGGCTTTGTCGACGTCATCAGGAACCTCAATTCTC
CTGCACTGCTGGAAGACAGTGTGATAAGACAAGCAAAAGCAGCTGGAAAAAGAATAGTCTTT
TATGGAGATGAAACCTGGGTTAAATTATTCCCAAAGCATTTTGTGGAATATGATGGAACAAC
CTCATTTTTCGTGTCAGATTACACAGAGGTGGATAATAATGTCACGAGGCATTTGGATAAAG
TATTAAAAAGAGGAGATTGGGACATATTAATCCTCCACTACCTGGGGCTGGACCACATTGGC
CACATTTCAGGGCCCAACAGCCCCCTGATTGGGCAGAAGCTGAGCGAGATGGACAGCGTGCT
GATGAAGATCCACACCTCACTGCAGTCGAAGGAGAGAGAGACGCCTTTACCCAATTTGCTGG
TTCTTTGTGGTGACCATGGCATGTCTGAAACAGGAAGTCACGGGGCCTCCTCCACCGAGGAG
GTGAATACACCTCTGATTTTAATCAGTTCTGCGTTTGAAAGGAAACCCGGTGATATCCGACA
TCCAAAGCACGTCCAATAGACGGATGTGGCTGCGACACTGGCGATAGCACTTGGCTTACCGA
TTCCAAAAGACAGTGTAGGGAGCCTCCTATTCCCAGTTGTGGAAGGAAGACCAATGAGAGAG
CAGTTGAGATTTTTACATTTGAATACAGTGCAGCTTAGTAAACTGTTGCAAGAGAATGTGCC
GTCATATGAAAAAGATCCTGGGTTTGAGCAGTTTAAAATGTCAGAAAGATTGCATGGGAACT
GGATCAGACTGTACTTGGAGGAAAAGCATTCAGAAGTCCTATTCAACCTGGGCTCCAAGGTT
CTCAGGCAGTACCTGGATGCTCTGAAGACGCTGAGCTTGTCCCTGAGTGCACAAGTGGCCCA
GTTCTCACCCTGCTCCTGCTCAGCGTCCCACAGGCACTGCACAGAAAGGCTGAGCTGGAAGTC
CCACTGTCATCTCCTGGGTTTTCTCTGCTCTTTTATTTGGTGATCCTGGTTCTTTCGGCCGT
TCACGTCATTGTGTGCACCTCAGCTGAAAGTTCGTGCTACTTCTGTGGCCTCTCGTGGCTGG
CGGCAGGCTGCCTTTCGTTTACCAGACTCTGGTTGAACACCTGGTGTGTGCCAAGTGCTGGC
AGTGCCCTGGACAGGGGGCCTCAGGGAAGGACGTGGAGCAGCCTTATCCCAGGCCTCTGGGT
GTCCCGACACAGGTGTTCACATCTGTGCTGTCAGGTCAGATGCCTCAGTTCTTGGAAAGCTA
GGTTCCTGCGACTGTTACCAAGGTGATTGTAAAGAGCTGGCGGTCACAGAGGAACAAGCCCC
CCAGCTGAGGGGGTGTGTGAATCGGACAGCCTCCCAGCAGAGGTGTGGGAGCTGCAGCTGAG
GGAAGAAGAGACAATCGGCCTGGACACTCAGGAGGGTCAAAAGGAGACTTGGTCGCACCACT
CATCCTGCCACCCCCAGAATGCATCCTGCCTCATCAGGTCCAGATTTCTTTCCAAGGCGGAC
GTTTTCTGTTGGAATTCTTAGTCCTTGGCCTCGGACACCTTCATTCGTTAGCTGGGGAGTGG
TGGTGAGGCAGTGAAGAAGAGGCGGATGGTCACACTCAGATCCACAGAGCCCAGGATCAAGG
GACCCACTGCAGTGGCAGCAGGACTGTTGGGCCCCCACCCCAACCCTGCACAGCCCTCATCC
CCTCTTGGCTTGAGCCGTCAGAGGCCCTGTGCTGAGTGTCTGACCGAGACACTCACAGCTTT
GTCATCAGGGCACAGGCTTCCTCGGAGCCAGGATGATCTGTGCCACGCTTGCACCTCGGGCC
CATCTGGGCTCATGCTCTCTCTCCTGCTATTGAATTAGTACCTAGCTGCACACAGTATGTAG
TTACCAAAAGAATAAACGGCAATAATTGAGAAAAAAAA

FIGURE 118

></usr/seqdb2/sst/DNA/Dnaseqs.min/ss.DNA84920
><subunit 1 of 1, 310 aa, 1 stop
><MW: 33875, pI: 7.08, NX(S/T): 2
MRLGSGTFATCCVAIEVLGIAVFLRGFFPAPVRSSARAEHGAEPPAPEPSAGASSNWTTL
PPPLFSKVVIVLIDALRDDFVFGSKGVKFMPYTTYLVEKGASHSFVAEAKPPTVTMPRIK
ALMTGSLPGFVDVIRNLNSPALLEDSVIRQAKAAGKRIVFYGDETWVKLFPKHFVEYDGT
TSFFVSDYTEVDNNVTRHLDKVLKRGDWDILILHYLGLDHIGHISGPNSPLIGQKLSEMD
SVLMKIHTSLQSKERETPLPNLLVLCGDHGMSETGSHGASSTEEVNTPLILISSAFERKP
GDIRHPKHVQ

Important features of the protein:
Signal peptide:
Amino acids 1-34

Transmembrane domain:
Amino acids 58-76

N-glycosylation sites:
Amino acids 56-60;194-198

N-myristoylation sites:
Amino acids 6-12;52-58;100-106;125-131;233-239;270-276;
275-281;278-284

Amidation site:
Amino acids 154-158

Cell attachment sequence:
Amino acids 205-208

FIGURE 119

GCCCACGCGTCCGATGGCGTTCACGTTCGCGGCCTTCTGCTACATGCTGGCGCTGCTGCTCA
CTGCCGCGCTCATCTTCTTCGCCATTTGGCACATTATAGCATTTGATGAGCTGAAGACTGAT
TACAAGAATCCTATAGACCAGTGTAATACCCTGAATCCCCTTGTACTCCCAGAGTACCTCAT
CCACGCTTTCTTCTGTGTCATGTTTCTTTGTGCAGCAGAGTGGCTTACACTGGGTCTCAATA
TGCCCCTCTTGGCATATCATATTTGGAGGTATATGAGTAGACCAGTGATGAGTGGCCCAGGA
CTCTATGACCCTACAACCATCATGAATGCAGATATTCTAGCATATTGTCAGAAGGAAGGATGG
TGCAAATTAGCTTTTTATCTTCTAGCATTTTTTTACTACCTATATGGCATGATCTATGTTTT
GGTGAGCTCTTAGAACAACACACAGAAGAATTGGTCCAGTTAAGTGCATGCAAAAAGCCACC
AAATGAAGGGATTCTATCCAGCAAGATCCTGTCCAAGAGTAGCCTGTGGAATCTGATCAGTT
ACTTTAAAAAATGACTCCTTATTTTTTAAATGTTTCCACATTTTTGCTTGTGGAAAGACTGT
TTTCATATGTTATACTCAGATAAAGATTTTAAATGGTATTACGTATAAATTAATATAAAATG
ATTACCTCTGGTGTTGACAGGTTTGAACTTGCACTTCTTAAGGAACAGCCATAATCCTCTGA
ATGATGCATTAATTACTGACTGTCCTAGTACATTGGAAGCTTTTGTTTATAGGAACTTGTAG
GGCTCATTTTGGTTTCATTGAAACAGTATCTAATTATAAATTAGCTGTAGATATCAGGTGCT
TCTGATGAAGTGAAAATGTATATCTGACTAGTGGGAAACTTCATGGGTTTCCTCATCTGTCA
TGTCGATGATTATATATGGATACATTTACAAAAATAAAAAGCGGGAATTTTCCCTTCGCTTG
AATATTATCCCTGTATATTGCATGAATGAGAGATTTCCCATATTTCCATCAGAGTAATAAAT
ATACTTGCTTTAATTCTTAAGCATAAGTAAACATGATATAAAAATATATGCTGAATTACTTG
TGAAGAATGCATTTAAAGCTATTTTAAATGTGTTTTTATTTGTAAGACATTACTTATTAAGA
AATTGGTTATTATGCTTACTGTTCTAATCTGGTGGTAAAGGTATTCTTAAGAATTTGCAGGT
ACTACAGATTTTCAAAACTGAATGAGAGAAAATTGTATAACCATCCTGCTGTTCCTTTAGTG
CAATACAATAAAACTCTGAAATTAAGACTC

FIGURE 120

</usr/seqdb2/sst/DNA/Dnaseqs.min/ss.DNA23330
<subunit 1 of 1, 144 aa, 1 stop
<MW: 16699, pI: 5.60, NX(S/T): 0
MAFTFAAFCYMLALLLTAALIFFAIWHIIAFDELKTDYKNPIDQCNTLNPLVLPEYLIHA
FFCVMFLCAAEWLTLGLNMPLLAYHIWRYMSRPVMSGPGLYDPTTIMNADILAYCQKEGW
CKLAFYLLAFFYYLYGMIYVLVSS

Important features:
Signal peptide:
Amino acids 1-20

Type II transmembrane domain:
Amino acids 11-31

Other transmembrane domain:
Amino acids 57-77;123-143

Glycosaminoglycan attachment site:
Amino acids 96-100

FIGURE 121

CGGACGCGTGGGCGGACGCGTGGGCGGCCCACGGCGCCCGCGGGCTGGGGCGGTCGCTTCTT
CCTTCTCCGTGGCCTACGAGGGTCCCCAGCCTGGGTAAAGATGGCCCCATGGCCCCCGAAGG
GCCTAGTCCCAGCTGTGCTCTGGGGCCTCAGCCTCTTCCTCAACCTCCCAGGACCTATCTGG
CTCCAGCCCTCTCCACCTCCCCAGTCTTCTCCCCCGCCTCAGCCCCATCCGTGTCATACCTG
CCGGGGACTGGTTGACAGCTTTAACAAGGGCCTGGAGAGAACCATCCGGGACAACTTTGGAG
GTGGAAACACTGCCTGGGAGGAAGAGAATTTGTCCAAATACAAAGACAGTGAGACCCGCCTG
GTAGAGGTGCTGGAGGGTGTGTGCAGCAAGTCAGACTTCGAGTGCCACCGCCTGCTGGAGCT
GAGTGAGGAGCTGGTGGAGAGCTGGTGGTTTCACAAGCAGCAGGAGGCCCCGGACCTCTTCC
AGTGGCTGTGCTCAGATTCCCTGAAGCTCTGCTGCCCCGCAGGCACCTTCGGGCCCTCCTGC
CTTCCCTGTCCTGGGGGAACAGAGAGGCCCTGCGGTGGCTACGGGCAGTGTGAAGGAGAAGG
GACACGAGGGGGCAGCGGGCACTGTGACTGCCAAGCCGGCTACGGGGGTGAGGCCTGTGGCC
AGTGTGGCCTTGGCTACTTTGAGGCAGAACGCAACGCCAGCCATCTGGTATGTTCGGCTTGT
TTTGGCCCCTGTGCCCGATGCTCAGGACCTGAGGAATCAAACTGTTTGCAATGCAAGAAGGG
CTGGGCCCTGCATCACCTCAAGTGTGTAGACATTGATGAGTGTGGCACAGAGGGAGCCAACT
GTGGAGCTGACCAATTCTGCGTGAACACTGAGGGCTCCTATGAGTGCCGAGACTGTGCCAAG
GCCTGCCTAGGCTGCATGGGGGCAGGGCCAGGTCGCTGTAAGAAGTGTAGCCCTGGCTATCA
GCAGGTGGGCTCCAAGTGTCTCGATGTGGATGAGTGTGAGACAGAGGTGTGTCCGGGAGAGA
ACAAGCAGTGTGAAAACACCGAGGGCGGTTATCGCTGCATCTGTGCCGAGGGCTACAAGCAG
ATGGAAGGCATCTGTGTGAAGGAGCAGATCCCAGAGTCAGCAGGCTTCTTCTCAGAGATGAC
AGAAGACGAGTTGGTGGTGCTGCAGCAGATGTTCTTTGGCATCATCATCTGTGCACTGGCCA
CGCTGGCTGCTAAGGGCGACTTGGTGTTCACCGCCATCTTCATTGGGGCTGTGGCGGCCATG
ACTGGCTACTGGTTGTCAGAGCGCAGTGACCGTGTGCTGGAGGGCTTCATCAAGGGCAGATA
ATCGCGGCCACCACCTGTAGGACCTCCTCCCACCCACGCTGCCCCCAGAGCTTGGGCTGCCC
TCCTGCTGGACACTCAGGACAGCTTGGTTTATTTTTGAGAGTGGGGTAAGCACCCCTACCTG
CCTTACAGAGCAGCCCAGGTACCCAGGCCCGGGCAGACAAGGCCCCTGGGGTAAAAAGTAGC
CCTGAAGGTGGATACCATGAGCTCTTCACCTGGCGGGGACTGGCAGGCTTCACAATGTGTGA
ATTTCAAAAGTTTTTCCTTAATGGTGGCTGCTAGAGCTTTGGCCCCTGCTTAGGATTAGGTG
GTCCTCACAGGGGTGGGGCCATCACAGCTCCCTCCTGCCAGCTGCATGCTGCCAGTTCCTGT
TCTGTGTTCACCACATCCCCACACCCCATTGCCACTTATTTATTCATCTCAGGAAATAAAGA
AAGGTCTTGGAAAGTTAAAAAAAAAAAAAAAAAAAAAAAA

FIGURE 122

MAPWPPKGLVPAVLWGLSLFLNLPGPIWLQPSPPPQSSPPPQPHPCHTCRGLVDSFNKGLER
TIRDNFGGGNTAWEEENLSKYKDSETRLVEVLEGVCSKSDFECHRLLELSEELVESWWFHKQ
QEAPDLFQWLCSDSLKLCCPAGTFGPSCLPCPGGTERPCGGYGQCEGEGTRGGSGHCDCQAG
YGGEACGQCGLGYFEAERNASHLVCSACFGPCARCSGPEESNCLQCKKGWALHHLKCVDIDE
CGTEGANCGADQFCVNTEGSYECRDCAKACLGCMGAGPGRCKKCSPGYQQVGSKCLDVDECE
TEVCPGENKQCENTEGGYRCICAEGYKQMEGICVKEQIPESAGFFSEMTEDELVVLQQMFFG
IIICALATLAAKGDLVFTAIFIGAVAAMTGYWLSERSDRVLEGFIKGR

Important features:
Signal peptide:

Amino acids 1-29

Transmembrane domain:

Amino acids 342-392

N-glycosylation sites:

Amino acids 79-83;205-209 cAMP- and cGMP-dependent protein kinase phosphorylation site:
Amino acids 290-294

Aspartic acid and asparagine hydroxylation site:
Amino acids 321-333

EGF-like domain cysteine pattern signature:
Amino acids 181-193

FIGURE 123

GCAAGCCAAGGCGCTGTTTGAGAAGGTGAAGAAGTTCCGGACCCATGTGGAGGAGGGGGACATTGTGTACCGCC
TCTACATGCGGCAGACCATCATCAAGGTGATCAAGTTCATCCTCATCATCTGCTACACCGTCTACTACGTGCAC
AACATCAAGTTCGACGTGGACTGCACCGTGGACATTGAGAGCCTGACGGGCTACCGCACCTACCGCTGTGCCCA
CCCCCTGGCCACACTCTTCAAGATCCTGGCGTCCTTCTACATCAGCCTAGTCATCTTCTACGGCCTCATCTGCA
TGTACACACTGTGGTGGATGCTACGGCGCTCCCTCAAGAAGTACTCGTTTGAGTCGATCCGTGAGGAGAGCAGC
TACAGCGACATCCCCGACGTCAAGAACGACTTCGCCTTCATGCTGCACCTCATTGACCAATACGACCCGCTCTA
CTCCAAGCGCTTCGCCGTCTTCCTGTCGGAGGTGAGTGAGAACAAGCTGCGGCAGCTGAACCTCAACAACGAGT
GGACGCTGGACAAGCTCCGGCAGCGGCTCACCAAGAACGCGCAGGACAAGCTGGAGCTGCACCTGTTCATGCTC
AGTGGCATCCCTGACACTGTGTTTGACCTGGTGGAGCTGGAGGTCCTCAAGCTGGAGCTGATCCCCGACGTGAC
CATCCCGCCCAGCATTGCCCAGCTCACGGGCCTCAAGGAGCTGTGGCTCTACCACACAGCGGCCAAGATTGAAG
CGCCTGCGCTGGCCTTCCTGCGCGAGAACCTGCGGGCGCTGCACATCAAGTTCACCGACATCAAGGAGATCCCG
CTGTGGATCTATAGCCTGAAGACACTGGAGGAGCTGCACCTGACGGGCAACCTGAGCGCGGAGAACAACCGCTA
CATCGTCATCGACGGGCTGCGGGAGCTCAAACGCCTCAAGGTGCTGCGGCTCAAGAGCAACCTAAGCAAGCTGC
CACAGGTGGTCACAGATGTGGGCGTGCACCTGCAGAAGCTGTCCATCAACAATGAGGGCACCAAGCTCATCGTC
CTCAACAGCCTCAAGAAGATGGCGAACCTGACTGAGCTGGAGCTGATCCGCTGCGACCTGGAGCGCATCCCCCA
CTCCATCTTCAGCCTCCACAACCTGCAGGAGATTGACCTCAAGGACAACAACCTCAAGACCATCGAGGAGATCA
TCAGCTTCCAGCACCTGCACCGCCTCACCTGCCTTAAGCTGTGGTACAACCACATCGCCTACATCCCCATCCAG
ATCGGCAACCTCACCAACCTGGAGCGCCTCTACCTGAACCGCAACAAGATCGAGAAGATCCCCACCCAGCTCTT
CTACTGCCGCAAGCTGCGCTACCTGGACCTCAGCCACAACAACCTGACCTTCCTCCCTGCCGACATCGGCCTCC
TGCAGAACCTCCAGAACCTAGCCATCACGGCCAACCGGATCGAGACGCTCCCTCCGGAGCTCTTCCAGTGCCGG
AAGCTGCGGGCCCTGCACCTGGGCAACAACGTGCTGCAGTCACTGCCCTCCAGGGTGGGCGAGCTGACCAACCT
GACGCAGATCGAGCTGCGGGGCAACCGGCTGGAGTGCCTGCCTGTGGAGCTGGGCGAGTGCCCACTGCTCAAGC
GCAGCGGCTTGGTGGTGGAGGAGGACCTGTTCAACACACTGCCACCCGAGGTGAAGGAGCGGCTGTGGAGGGCT
GACAAGGAGCAGGCCTGAGCGAGGCCGGCCCAGCACAGCAAGCAGCAGGACCGCTGCCCAGTCCTCAGGCCCGG
AGGGGCAGGCCTAGCTTCTCCCAGAACTCCCGGACAGCCAGGACAGCCTCGCGGCTGGGCAGGAGCCTGGGGCC
GCTTGTGAGTCAGGCCAGAGCGAGAGGACAGTATCTGTGGGGCTGGCCCCTTTTCTCCCTCTGAGACTCACGTC
CCCCAGGGCAAGTGCTTGTGGAGGAGAGCAAGTCTCAAGAGCGCAGTATTTGGATAATCAGGGTCTCCTCCCTG
GAGGCCAGCTCTGCCCCAGGGGCTGAGCTGCCACCAGAGGTCCTGGGACCCTCACTTTAGTTCTTGGTATTTAT
TTTTCTCCATCTCCCACCTCCTTCATCCAGATAACTTATACATTCCCAAGAAAGTTCAGCCCAGATGGAAGGTG
TTCAGGGAAAGGTGGGCTGCCTTTTCCCCTTGTCCTTATTTAGCGATGCCGCCGGGCATTTAACACCCACCTGG
ACTTCAGCAGAGTGGTCCGGGGCGAACCAGCCATGGGACGGTCACCCAGCAGTGCCGGGCTGGGCTCTGCGGTG
CGGTCCACGGGAGAGCAGGCCTCCAGCTGGAAAGGCCAGGCCTGGAGCTTGCCTCTTCAGTTTTTGTGGCAGTT
TTAGTTTTTTGTTTTTTTTTTTTTTAATCAAAAAACAATTTTTTTTAAAAAAAAGCTTTGAAAATGGATGGTTT
GGGTATTAAAAAGAAAAAAAAAAACTTAAAAAAAAAAAAGACACTAACGGCCAGTGAGTTGGAGTCTCAGGGCAGG
GTGGCAGTTTCCCTTGAGCAAAGCAGCCAGACGTTGAACTGTGTTTCCTTTCCCTGGGCGCAGGGTGCAGGGTG
TCTTCCGGATCTGGTGTGACCTTGGTCCAGGAGTTCTATTTGTTCCTGGGGAGGGAGGTTTTTTTGTTTGTTTT
TTGGGTTTTTTTGGTGTCTTGTTTTCTTTCTCCTCCATGTGTCTTGGCAGGCACTCATTTCTGTGGCTGTCGGC
CAGAGGGAATGTTCTGGAGCTGCCAAGGAGGGAGGAGACTCGGGTTGGCTAATCCCCGGATGAACGGTGCTCCA
TTCGCACCTCCCCTCCTCGTGCCTGCCCTGCCTCTCCACGCACAGTGTTAAGGAGCCAAGAGGAGCCACTTCGC
CCAGACTTTGTTTCCCCACCTCCTGCGGCATGGGTGTGTCCAGTGCCACCGCTGGCCTCCGCTGCTTCCATCAG
CCCTGTCGCCACCTGGTCCTTCATGAAGAGCAGACACTTAGAGGCTGGTCGGGAATGGGGAGGTCGCCCCTGGG
AGGGCAGGCGTTGGTTCCAAGCCGGTTCCCGTCCCTGGCGCCTGGAGTGCACACAGCCCAGTCGGCACCTGGTG
GCTGGAAGCCAACCTGCTTTAGATCACTCGGGTCCCCACCTTAGAAGGGTCCCCGCCTTAGATCAATCACGTGG
ACACTAAGGCACGTTTTAGAGTCTCTTGTCTTAATGATTATGTCCATCCGTCTGTCCGTCCATTTGTGTTTTCT
GCGTCGTGTCATTGGATATAATCCTCAGAAATAATGCACACTAGCCTCTGACAACCATGAAGCAAAAATCCGTT
ACATGTGGGTCTGAACTTGTAGACTCGGTCACAGTATCAAATAAAATCTATAACAGAAAAAAAAAAAAAAA

FIGURE 124

MRQTIIKVIKFILIICYTVYYVHNIKFDVDCTVDIESLTGYRTYRCAHPLATLFKILASFYI
SLVIFYGLICMYTLWWMLRRSLKKYSFESIREESSYSDIPDVKNDFAFMLHLIDQYDPLYSK
RFAVFLSEVSENKLRQLNLNNEWTLDKLRQRLTKNAQDKLELHLFMLSGIPDTVFDLVELEV
LKLELIPDVTIPPSIAQLTGLKELWLYHTAAKIEAPALAFLRENLRALHIKFTDIKEIPLWI
YSLKTLEELHLTGNLSAENNRYIVIDGLRELKRLKVLRLKSNLSKLPQVVTDVGVHLQKLSI
NNEGTKLIVLNSLKKMANLTELELIRCDLERIPHSIFSLHNLQEIDLKDNNLKTIEEIISFQ
HLHRLTCLKLWYNHIAYIPIQIGNLTNLERLYLNRNKIEKIPTQLFYCRKLRYLDLSHNNLT
FLPADIGLLQNLQNLAITANRIETLPPELFQCRKLRALHLGNNVLQSLPSRVGELTNLTQIE
LRGNRLECLPVELGECPLLKRSGLVVEEDLFNTLPPEVKERLWRADKEQA

Transmembrane domain:
amino acids 51-75 (type II)

N-glycosylation site.
amino acids 262-266, 290-294, 328-332, 396-400, 432-436, 491-495 cAMP- and cGMP-dependent protein kinase phosphorylation site.
amino acids 85-89

Casein kinase II phosphorylation site.
amino acids 91-95, 97-101, 177-181, 253-257, 330-334, 364-368, 398-402, 493-497

N-myristoylation site.
amino acids 173-179, 261-267, 395-401, 441-447

FIGURE 125

GTTGTGTCCTTCAGCAAAACAGTGGATTTAAATCTCCTTGCACAAGCTTGAGAGCAACACAA
TCTATCAGGAAAGAAAGAAAGAAAAAAACCGAACCTGACAAAAAAGAAGAAAAAGAAGAAGA
AAAAAAATCATGAAAACCATCCAGCCAAAAATGCACAATTCTATCTCTTGGGCAATCTTCAC
GGGGCTGGCTGCTCTGTGTCTCTTCCAAGGAGTGCCCGTGCGCAGCGGAGATGCCACCTTCC
CCAAAGCTATGGACAACGTGACGGTCCGGCAGGGGGAGAGCGCCACCCTCAGGTGCACTATT
GACAACCGGGTCACCCGGGTGGCCTGGCTAAACCGCAGCACCATCCTCTATGCTGGGAATGA
CAAGTGGTGCCTGGATCCTCGCGTGGTCCTTCTGAGCAACACCCAAACGCAGTACAGCATCG
AGATCCAGAACGTGGATGTGTATGACGAGGGCCCTTACACCTGCTCGGTGCAGACAGACAAC
CACCCAAAGACCTCTAGGGTCCACCTCATTGTGCAAGTATCTCCCAAAATTGTAGAGATTTC
TTCAGATATCTCCATTAATGAAGGGAACAATATTAGCCTCACCTGCATAGCAACTGGTAGAC
CAGAGCCTACGGTTACTTGGAGACACATCTCTCCCAAAGCGGTTGGCTTTGTGAGTGAAGAC
GAATACTTGGAAATTCAGGGCATCACCCGGGAGCAGTCAGGGGACTACGAGTGCAGTGCCTC
CAATGACGTGGCCGCGCCCGTGGTACGGAGAGTAAAGGTCACCGTGAACTATCCACCATACA
TTTCAGAAGCCAAGGGTACAGGTGTCCCCGTGGGACAAAAGGGGACACTGCAGTGTGAAGCC
TCAGCAGTCCCCTCAGCAGAATTCCAGTGGTACAAGGATGACAAAAGACTGATTGAAGGAAA
GAAAGGGGTGAAAGTGGAAAACAGACCTTTCCTCTCAAAACTCATCTTCTTCAATGTCTCTG
AACATGACTATGGGAACTACACTTGCGTGGCCTCCAACAAGCTGGGCCACACCAATGCCAGC
ATCATGCTATTTGGTCCAGGCGCCGTCAGCGAGGTGAGCAACGGCACGTCGAGGAGGGCAGG
CTGCGTCTGGCTGCTGCCTCTTCTGGTCTTGCACCTGCTTCTCAAATTTTGATGTGAGTGCC
ACTTCCCCACCCGGGAAAGGCTGCCGCCACCACCACCACCAACACAACAGCAATGGCAACAC
CGACAGCAACCAATCAGATATATACAAATGAAATTAGAAGAAACACAGCCTCATGGACAGA
AATTTGAGGGAGGGGAACAAAGAATACTTTGGGGGGAAAAGAGTTTTAAAAAAGAAATTGAA
AATTGCCTTGCAGATATTTAGGTACAATGGAGTTTTCTTTTCCCAAACGGGAAGAACACAGC
ACACCCGGCTTGGACCCACTGCAAGCTGCATCGTGCAACCTCTTTGGTGCCAGTGTGGGCAA
GGGCTCAGCCTCTCTGCCCACAGAGTGCCCCCACGTGGAACATTCTGGAGCTGGCCATCCCA
AATTCAATCAGTCCATAGAGACGAACAGAATGAGACCTTCCGGCCCAAGCGTGGCGCTGCGG
GCACTTTGGTAGACTGTGCCACCACGGCGTGTGTTGTGAAACGTGAAATAAAAAGAGCAAAA
AAAAA

FIGURE 126

MKTIQPKMHNSISWAIFTGLAALCLFQGVPVRSGDATFPKAMDNVTVRQGESATLRCTIDNR
VTRVAWLNRSTILYAGNDKWCLDPRVVLLSNTQTQYSIEIQNVDVYDEGPYTCSVQTDNHPK
TSRVHLIVQVSPKIVEISSDISINEGNNISLTCIATGRPEPTVTWRHISPKAVGFVSEDEYL
EIQGITREQSGDYECSASNDVAAPVVRRVKVTVNYPPYISEAKGTGVPVGQKGTLQCEASAV
PSAEFQWYKDDKRLIEGKKGVKVENRPFLSKLIFFNVSEHDYGNYTCVASNKLGHTNASIML
FGPGAVSEVSNGTSRRAGCVWLLPLLVLHLLLKF

Important features:
Signal peptide:
amino acids 1-28

FIGURE 127

GGCGCCGGTGCACCGGGCGGGCTGAGCGCCTCCTGCGGCCCGGCCTGCGCGCCCCGGCCCGCCGCGCCGCCCAC
GCCCCAACCCCGGCCCGCGCCCCCTAGCCCCCGCCCGGGCCCGCGCCCGCGCCCGCGCCCAGGTGAGCGCTCCG
CCCGCCGCGAGGCCCCGCCCCGGCCCGCCCCCGCCCCGCCCCGGCCGGCGGGGGAACCGGGCGGATTCCTCGCG
CGTCAAACCACCTGATCCCATAAAACATTCATCCTCCCGGCGGCCCGCGCTGCGAGCGCCCCGCCAGTCCGCGC
CGCCGCCGCCCTCGCCCTGTGCGCCCTGCGCGCCCTGCGCACCCGCGGCCCGAGCCCAGCCAGAGCCGGGCGGA
GCGGAGCGCGCCGAGCCTCGTCCCGCGGCCGGGCCGGGGCCGGGCCGTAGCGGCGGCGCCTGGATGCGGACCCG
GCCGCGGGGAGACGGGCGCCCGCCCCGAAACGACTTTCAGTCCCCGACGCGCCCCGCCCAACCCCTACGATGAA
GAGGGCGTCCGCTGGAGGGAGCCGGCTGCTGGCATGGGTGCTGTGGCTGCAGGCCTGGCAGGTGGCAGCCCCAT
GCCCAGGTGCCTGCGTATGCTACAATGAGCCCAAGGTGACGACAAGCTGCCCCCAGCAGGGCCTGCAGGCTGTG
CCCGTGGGCATCCCTGCTGCCAGCCAGCGCATCTTCCTGCACGGCAACCGCATCTCGCATGTGCCAGCTGCCAG
CTTCCGTGCCTGCCGCAACCTCACCATCCTGTGGCTGCACTCGAATGTGCTGGCCCGAATTGATGCGGCTGCCT
TCACTGGCCTGGCCCTCCTGGAGCAGCTGGACCTCAGCGATAATGCACAGCTCCGGTCTGTGGACCCTGCCACA
TTCCACGGCCTGGGCCGCCTACACACGCTGCACCTGGACCGCTGCGGCCTGCAGGAGCTGGGCCCGGGGCTGTT
CCGCGGCCTGGCTGCCCTGCAGTACCTCTACCTGCAGGACAACGCGCTGCAGGCACTGCCTGATGACACCTTCC
GCGACCTGGGCAACCTCACACACCTCTTCCTGCACGGCAACCGCATCTCCAGCGTGCCCGAGCGCGCCTTCCGT
GGGCTGCACAGCCTCGACCGTCTCCTACTGCACCAGAACCGCGTGGCCCATGTGCACCCGCATGCCTTCCGTGA
CCTTGGCCGCCTCATGACACTCTATCTGTTTGCCAACAATCTATCAGCGCTGCCCACTGAGGCCCTGGCCCCCC
TGCGTGCCCTGCAGTACCTGAGGCTCAACGACAACCCCTGGGTGTGTGACTGCCGGGCACGCCCACTCTGGGCC
TGGCTGCAGAAGTTCCGCGGCTCCTCCTCCGAGGTGCCCTGCAGCCTCCCGCAACGCCTGGCTGGCCGTGACCT
CAAACGCCTAGCTGCCAATGACCTGCAGGGCTGCGCTGTGGCCACCGGCCCTTACCATCCCATCTGGACCGGCA
GGGCCACCGATGAGGAGCCGCTGGGGCTTCCCAAGTGCTGCCAGCCAGATGCCGCTGACAAGGCCTCAGTACTG
GAGCCTGGAAGACCAGCTTCGGCAGGCAATGCGCTGAAGGGACGCGTGCCGCCCGGTGACAGCCCGCCGGGCAA
CGGCTCTGGCCCACGGCACATCAATGACTCACCCTTTGGGACTCTGCCTGGCTCTGCTGAGCCCCCGCTCACTG
CAGTGCGGCCCGAGGGCTCCGAGCCACCAGGGTTCCCCACCTCGGGCCCTCGCCGGAGGCCAGGCTGTTCACGC
AAGAACCGCACCCGCAGCCACTGCCGTCTGGGCCAGGCAGGCAGCGGGGGTGGCGGGACTGGTGACTCAGAAGG
CTCAGGTGCCCTACCCAGCCTCACCTGCAGCCTCACCCCCCTGGGCCTGGCGCTGGTGCTGTGGACAGTGCTTG
GGCCCTGCTGACCCCCAGCGGACACAAGAGCGTGCTCAGCAGCCAGGTGTGTGTACATACGGGGTCTCTCTCCA
CGCCGCCAAGCCAGCCGGGCGGCCGACCCGTGGGGCAGGCCAGGCCAGGTCCTCCCTGATGGACGCCTGCCGCC
CGCCACCCCCATCTCCACCCCATCATGTTTACAGGGTTCGGCGGCAGCGTTTGTTCCAGAACGCCGCCTCCCAC
CCAGATCGCGGTATATAGAGATATGCATTTTATTTTACTTGTGTAAAAATATCGGACGACGTGGAATAAAGAGC
TCTTTTCTTAAAAAAA

FIGURE 128

MKRASAGGSRLLAWVLWLQAWQVAAPCPGACVCYNEPKVTTSCPQQGLQAVPVGIPAASQRIFLHGNRISHVPA
ASFRACRNLTILWLHSNVLARIDAAAFTGLALLEQLDLSDNAQLRSVDPATFHGLGRLHTLHLDRCGLQELGPG
LFRGLAALQYLYLQDNALQALPDDTFRDLGNLTHLFLHGNRISSVPERAFRGLHSLDRLLLHQNRVAHVHPHAF
RDLGRLMTLYLFANNLSALPTEALAPLRALQYLRLNDNPWVCDCRARPLWAWLQKFRGSSSEVPCSLPQRLAGR
DLKRLAANDLQGCAVATGPYHPIWTGRATDEEPLGLPKCCQPDAADKASVLEPGRPASAGNALKGRVPPGDSPP
GNGSGPRHINDSPFGTLPGSAEPPLTAVRPEGSEPPGFPTSGPRRRPGCSRKNRTRSHCRLGQAGSGGGGTGDS
EGSGALPSLTCSLTPLGLALVLWTVLGPC

Important features:
Signal peptide:
amino acids 1-26

Leucine zipper pattern.
amino acids 135-156

Glycosaminoglycan attachment site.
amino acids 436-439

N-glycosylation site.
amino acids 82-85, 179-183, 237-240, 372-375 and 423-426

VWFC domain
amino acids 411-425

FIGURE 129

GCGCCGGGAGCCCATCTGCCCCCAGGGGCACGGGGCGCGGGGCCGGCTCCCGCCCGGCACATGGCTGCAGCCAC
CTCGCGCGCACCCCGAGGCGCCGCGCCCAGCTCGCCCGAGGTCCGTCGGAGGCGCCCGGCCGCCCCGGAGCCAA
GCAGCAACTGAGCGGGGAAGCGCCCGCGTCCGGGGATCGGGATGTCCCTCCTCCTTCTCCTCTTGCTAGTTTCC
TACTATGTTGGAACCTTGGGGACTCACACTGAGATCAAGAGAGTGGCAGAGGAAAAGGTCACTTTGCCCTGCCA
CCATCAACTGGGGCTTCCAGAAAAAGACACTCTGGATATTGAATGGCTGCTCACCGATAATGAAGGGAACCAAA
AAGTGGTGATCACTTACTCCAGTCGTCATGTCTACAATAACTTGACTGAGGAACAGAAGGGCCGAGTGGCCTTT
GCTTCCAATTTCCTGGCAGGAGATGCCTCCTTGCAGATTGAACCTCTGAAGCCCAGTGATGAGGGCCGGTACAC
CTGTAAGGTTAAGAATTCAGGGCGCTACGTGTGGAGCCATGTCATCTTAAAAGTCTTAGTGAGACCATCCAAGC
CCAAGTGTGAGTTGGAAGGAGAGCTGACAGAAGGAAGTGACCTGACTTTGCAGTGTGAGTCATCCTCTGGCACA
GAGCCCATTGTGTATTACTGGCAGCGAATCCGAGAGAAAGAGGGAGAGGATGAACGTCTGCCTCCCAAATCTAG
GATTGACTACAACCACCCTGGACGAGTTCTGCTGCAGAATCTTACCATGTCCTACTCTGGACTGTACCAGTGCA
CAGCAGGCAACGAAGCTGGGAAGGAAAGCTGTGTGGTGCGAGTAACTGTACAGTATGTACAAAGCATCGGCATG
GTTGCAGGAGCAGTGACAGGCATAGTGGCTGGAGCCCTGCTGATTTTCCTCTTGGTGTGGCTGCTAATCCGAAG
GAAAGACAAAGAAAGATATGAGGAAGAAGAGAGACCTAATGAAATTCGAGAAGATGCTGAAGCTCCAAAAGCCC
GTCTTGTGAAACCCAGCTCCTCTTCCTCAGGCTCTCGGAGCTCACGCTCTGGTTCTTCCTCCACTCGCTCCACA
GCAAATAGTGCCTCACGCAGCCAGCGGACACTGTCAACTGACGCAGCACCCCAGCCAGGGCTGGCCACCCAGGC
ATACAGCCTAGTGGGGCCAGAGGTGAGAGGTTCTGAACCAAAGAAAGTCCACCATGCTAATCTGACCAAAGCAG
AAACCACACCCAGCATGATCCCCAGCCAGAGCAGAGCCTTCCAAACGGTCTGAATTACAATGGACTTGACTCCC
ACGCTTTCCTAGGAGTCAGGGTCTTTGGACTCTTCTCGTCATTGGAGCTCAAGTCACCAGCCACACAACCAGAT
GAGAGGTCATCTAAGTAGCAGTGAGCATTGCACGGAACAGATTCAGATGAGCATTTTCCTTATACAATACCAAA
CAAGCAAAAGGATGTAAGCTGATTCATCTGTAAAAAGGCATCTTATTGTGCCTTTAGACCAGAGTAAGGGAAAG
CAGGAGTCCAAATCTATTTGTTGACCAGGACCTGTGGTGAGAAGGTTGGGGAAAGGTGAGGTGAATATACCTAA
AACTTTTAATGTGGGATATTTTGTATCAGTGCTTTGATTCACAATTTTCAAGAGGAAATGGGATGCTGTTTGTA
AATTTTCTATGCATTTCTGCAAACTTATTGGATTATTAGTTATTCAGACAGTCAAGCAGAACCCACAGCCTTAT
TACACCTGTCTACACCATGTACTGAGCTAACCACTTCTAAGAAACTCCAAAAAAGGAAACATGTGTCTTCTATT
CTGACTTAACTTCATTTGTCATAAGGTTTGGATATTAATTTCAAGGGGAGTTGAAATAGTGGGAGATGGAGAAG
AGTGAATGAGTTTCTCCCACTCTATACTAATCTCACTATTTGTATTGAGCCCAAAATAACTATGAAAGGAGACA
AAAATTTGTGACAAAGGATTGTGAAGAGCTTTCCATCTTCATGATGTTATGAGGATTGTTGACAAACATTAGAA
ATATATAATGGAGCAATTGTGGATTTCCCCTCAAATCAGATGCCTCTAAGGACTTTCCTGCTAGATATTTCTGG
AAGGAGAAAATACAACATGTCATTTATCAACGTCCTTAGAAAGAATTCTTCTAGAGAAAAAGGGATCTAGGAAT
GCTGAAAGATTACCCAACATACCATTATAGTCTCTTCTTTCTGAGAAAATGTGAAACCAGAATTGCAAGACTGG
GTGGACTAGAAAGGGAGATTAGATCAGTTTTCTCTTAATATGTCAAGGAAGGTAGCCGGGCATGGTGCCAGGCA
CCTGTAGGAAAATCCAGCAGGTGGAGGTTGCAGTGAGCCGAGATTATGCCATTGCACTCCAGCCTGGGTGACAG
AGCGGGACTCCGTCTC

FIGURE 130

MSLLLLLLLVSYYVGTLGTHTEIKRVAEEKVTLPCHHQLGLPEKDTLDIEWLLTDNEGNQKVVITYSSRHVYNN
LTEEQKGRVAFASNFLAGDASLQIEPLKPSDEGRYTCKVKNSGRYVWSHVILKVLVRPSKPKCELEGELTEGSD
LTLQCESSSGTEPIVYYWQRIREKEGEDERLPPKSRIDYNHPGRVLLQNLTMSYSGLYQCTAGNEAGKESCVVR
VTVQYVQSIGMVAGAVTGIVAGALLIFLLVWLLIRRKDKERYEEEERPNEIREDAEAPKARLVKPSSSSSGSRS
SRSGSSSTRSTANSASRSQRTLSTDAAPQPGLATQAYSLVGPEVRGSEPKKVHHANLTKAETTPSMIPSQSRAFQTV

Important freatures:
Signal sequence:
amino acids 1-16

Transmembrane domain:
amino acids 232-251

FIGURE 131

GGAAGTCCACGGGGAGCTTGGATGCCAAAGGGAGGACGGCTGGGTCCTCTGGAGAGGACTAC
TCACTGGCATATTTCTGAGGTATCTGTAGAATAACCACAGCCTCAGATACTGGGGACTTTAC
AGTCCCACAGAACCGTCCTCCCAGGAAGCTGAATCCAGCAAGAACAATGGAGGCCAGCGGGA
AGCTCATTTGCAGACAAAGGCAAGTCCTTTTTTCCTTTCTCCTTTTGGGCTTATCTCTGGCG
GGCGCGGCGGAACCTAGAAGCTATTCTGTGGTGGAGGAAACTGAGGGCAGCTCCTTTGTCAC
CAATTTAGCAAAGGACCTGGGTCTGGAGCAGAGGGAATTCTCCAGGCGGGGGGTTAGGGTTG
TTTCCAGAGGGAACAAACTACATTTGCAGCTCAATCAGGAGACCGCGGATTTGTTGCTAAAT
GAGAAATTGGACCGTGAGGATCTGTGCGGTCACACAGAGCCCTGTGTGCTACGTTTCCAAGT
GTTGCTAGAGAGTCCCTTCGAGTTTTTTCAAGCTGAGCTGCAAGTAATAGACATAAACGACC
ACTCTCCAGTATTTCTGGACAAACAAATGTTGGTGAAAGTATCAGAGAGCAGTCCTCCTGGG
ACTACGTTTCCTCTGAAGAATGCCGAAGACTTAGATGTAGGCCAAAACAATATTGAGAACTA
TATAATCAGCCCCAACTCCTATTTTCGGGTCCTCACCCGCAAACGCAGTGATGGCAGGAAAT
ACCCAGAGCTGGTGCTGGACAAAGCGCTGGACCGAGAGGAAGAAGCTGAGCTCAGGTTAACA
CTCACAGCACTGGATGGTGGCTCTCCGCCCAGATCTGGCACTGCTCAGGTCTACATCGAAGT
CCTGGATGTCAACGATAATGCCCCTGAATTTGAGCAGCCTTTCTATAGAGTGCAGATCTCTG
AGGACAGTCCGGTAGGCTTCCTGGTTGTGAAGGTCTCTGCCACGGATGTAGACACAGGAGTC
AACGGAGAGATTTCCTATTCACTTTTCCAAGCTTCAGAAGAGATTGGCAAAACCTTTAAGAT
CAATCCCTTGACAGGAGAAATTGAACTAAAAAAACAACTCGATTTCGAAAAACTTCAGTCCT
ATGAAGTCAATATTGAGGCAAGAGATGCTGGAACCTTTTCTGGAAAATGCACCGTTCTGATT
CAAGTGATAGATGTGAACGACCATGCCCCAGAAGTTACCATGTCTGCATTTACCAGCCCAAT
ACCTGAGAACGCGCCTGAAACTGTGGTTGCACTTTTCAGTGTTTCAGATCTTGATTCAGGAG
AAAATGGGAAAATTAGTTGCTCCATTCAGGAGGATCTACCCTTCCTCCTGAAATCCGCGGAA
AACTTTTACACCCTACTAACGGAGAGACCACTAGACAGAGAAAGCAGAGCGGAATACAACAT
CACTATCACTGTCACTGACTTGGGGACCCCTATGCTGATAACACAGCTCAATATGACCGTGC
TGATCGCCGATGTCAATGACAACGCTCCCGCCTTCACCCAAACCTCCTACACCCTGTTCGTC
CGCGAGAACAACAGCCCCGCCCTGCACATCCGCAGCGTCAGCGCTACAGACAGAGACTCAGG
CACCAACGCCCAGGTCACCTACTCGCTGCTGCCGCCCCAGGACCCGCACCTGCCCCTCACAT
CCCTGGTCTCCATCAACGCGGACAACGGCCACCTGTTCGCCCTCAGGTCTCTGGACTACGAG
GCCCTGCAGGGGTTCCAGTTCCGCGTGGGCGCTTCAGACCACGGCTCCCCGGCGCTGAGCAG
CGAGGCGCTGGTGCGCGTGGTGGTGCTGGACGCCAACGACAACTCGCCCTTCGTGCTGTACC
CGCTGCAGAACGGCTCCGCGCCCTGCACCGAGCTGGTGCCCCGGGCGGCCGAGCCGGGCTAC
CTGGTGACCAAGGTGGTGGCGGTGGACGGCGACTCGGGCCAGAACGCCTGGCTGTCGTACCA
GCTGCTCAAGGCCACGGAGCTCGGTCTGTTCGGCGTGTGGGCGCACAATGGCGAGGTGCGCA
CCGCCAGGCTGCTGAGCGAGCGCGACGCGGCCAAGCACAGGCTGGTGGTGCTGGTCAAGGAC
AATGGCGAGCCTCCGCGCTCGGCCACCGCCACGCTGCACGTGCTCCTGGTGGACGGCTTCTC
CCAGCCCTACCTGCCTCTCCCGGAGGCGGCCCCGACCCAGGCCCAGGCCGACTTGCTCACCG
TCTACCTGGTGGTGGCGTTGGCCTCGGTGTCTTCGCTCTTCCTCTTTTCGGTGCTCCTGTTC
GTGGCGGTGCGGCTGTGTAGGAGGAGCAGGGCGGCCTCGGTGGGTCGCTGCTTGGTGCCCGA
GGGCCCCCTTCCAGGGCATCTTGTGGACATGAGCGGCACCAGGACCCTATCCCAGAGCTACC
AGTATGAGGTGTGTCTGGCAGGAGGCTCAGGGACCAATGAGTTCAAGTTCCTGAAGCCGATT
ATCCCCAACTTCCCTCCCCAGTGCCCTGGGAAAGAAATACAAGGAAATTCTACCTTCCCCAA
TAACTTTGGGTTCAATATTCAGTGACCATAGTTGACTTTTACATTCCATAGGTATTTTATTT
TGTGGCATTTCCATGCCAATGTTTATTTCCCCCAATTTGTGTGTATGTAATATTGTACGGAT
TTACTCTTGATTTTTCTCATGTTCTTTCTCCCTTTGTTTTAAAGTGAACATTTACCTTTATT
CCTGGTTCTT

FIGURE 132

</usr/seqdb2/sst/DNA/Dnaseqs.min/ss.DNA48314
<subunit 1 of 1, 798 aa, 1 stop
<MW: 87552, pI: 4.84, NX(S/T): 5

MEASGKLICRQRQVLFSFLLLGLSLAGAAEPRSYSVVEETEGSSFVTNLAKDLGLEQREFSR
RGVRVVSRGNKLHLQLNQETADLLLNEKLDREDLCGHTEPCVLRFQVLLESPFEFFQAELQV
IDINDHSPVFLDKQMLVKVSESSPPGTTFPLKNAEDLDVGQNNIENYIISPNSYFRVLTRKR
SDGRKYPELVLDKALDREEEAELRLTLTALDGGSPPRSGTAQVYIEVLDVNDNAPEFEQPFY
RVQISEDSPVGFLVVKVSATDVDTGVNGEISYSLFQASEEIGKTFKINPLTGEIELKKQLDF
EKLQSYEVNIEARDAGTFSGKCTVLIQVIDVNDHAPEVTMSAFTSPIPENAPETVVALFSVS
DLDSGENGKISCSIQEDLPFLLKSAENFYTLLTERPLDRESRAEYNITITVTDLGTPMLITQ
LNMTVLIADVNDNAPAFTQTSYTLFVRENNSPALHIRSVSATDRDSGTNAQVTYSLLPPQDP
HLPLTSLVSINADNGHLFALRSLDYEALQGFQFRVGASDHGSPALSSEALVRVVVLDANDNS
PFVLYPLQNGSAPCTELVPRAAEPGYLVTKVVAVDGDSGQNAWLSYQLLKATELGLFGVWAH
NGEVRTARLLSERDAAKHRLVVLVKDNGEPPRSATATLHVLLVDGFSQPYLPLPEAAPTQAQ
ADLLTVYLVVALASVSSLFLFSVLLFVAVRLCRRSRAASVGRCLVPEGPLPGHLVDMSGTRT
LSQSYQYEVCLAGGSGTNEFKFLKPIIPNFPPQCPGKEIQGNSTFPNNFGFNIQ

Important features:
Signal peptide:
amino acids 1-26

Transmembrane domain:
amino acids 685-712

Cadherins extracellular repeated domain signature.
amino acids 122-132, 231-241, 336-346, 439-449 and 549-559

ATP/GTP-binding site motif A (P-loop).
amino acids 285-292

N-glycosylation site.
amino acids 418-421, 436-439, 567-570 and 786-789

FIGURE 133

GGAAGGGGAGGAGCAGGCCACACAGGCACAGGCCGGTGAGGGACCTGCCCAGACCTGGAGGGTCTCGCTCTGTC
ACACAGGCTGGAGTGCAGTGGTGTGATCTTGGCTCATCGTAACCTCCACCTCCCGGGTTCAAGTGATTCTCATG
CCTCAGCCTCCCGAGTAGCTGGGATTACAGGTGGTGACTTCCAAGAGTGACTCCGTCGGAGGAAAATGACTCCC
CAGTCGCTGCTGCAGACGACACTGTTCCTGCTGAGTCTGCTCTTCCTGGTCCAAGGTGCCCACGGCAGGGGCCA
CAGGGAAGACTTTCGCTTCTGCAGCCAGCGGAACCAGACACACAGGAGCAGCCTCCACTACAAACCCACACCAG
ACCTGCGCATCTCCATCGAGAACTCCGAAGAGGCCCTCACAGTCCATGCCCCTTTCCCTGCAGCCCACCCTGCT
TCCCGATCCTTCCCTGACCCCAGGGGCCTCTACCACTTCTGCCTCTACTGGAACCGACATGCTGGGAGATTACA
TCTTCTCTATGGCAAGCGTGACTTCTTGCTGAGTGACAAAGCCTCTAGCCTCCTCTGCTTCCAGCACCAGGAGG
AGAGCCTGGCTCAGGGCCCCCCGCTGTTAGCCACTTCTGTCACCTCCTGGTGGAGCCCTCAGAACATCAGCCTG
CCCAGTGCCGCCAGCTTCACCTTCTCCTTCCACAGTCCTCCCCACACGGCCGCTCACAATGCCTCGGTGGACAT
GTGCGAGCTCAAAAGGGACCTCCAGCTGCTCAGCCAGTTCCTGAAGCATCCCCAGAAGGCCTCAAGGAGGCCCT
CGGCTGCCCCCGCCAGCCAGCAGTTGCAGAGCCTGGAGTCGAAACTGACCTCTGTGAGATTCATGGGGGACATG
GTGTCCTTCGAGGAGGACCGGATCAACGCCACGGTGTGGAAGCTCCAGCCCACAGCCGGCCTCCAGGACCTGCA
CATCCACTCCCGGCAGGAGGAGGAGCAGAGCGAGATCATGGAGTACTCGGTGCTGCTGCCTCGAACACTCTTCC
AGAGGACGAAAGGCCGGAGCGGGGAGGCTGAGAAGAGACTCCTCCTGGTGGACTTCAGCAGCCAAGCCCTGTTC
CAGGACAAGAATTCCAGCCAAGTCCTGGGTGAGAAGGTCTTGGGGATTGTGGTACAGAACACCAAAGTAGCCAA
CCTCACGGAGCCCGTGGTGCTCACTTTCCAGCACCAGCTACAGCCGAAGAATGTGACTCTGCAATGTGTGTTCT
GGGTTGAAGACCCCACATTGAGCAGCCCGGGGCATTGGAGCAGTGCTGGGTGTGAGACCGTCAGGAGAGAAACC
CAAACATCCTGCTTCTGCAACCACTTGACCTACTTTGCAGTGCTGATGGTCTCCTCGGTGGAGGTGGACGCCGT
GCACAAGCACTACCTGAGCCTCCTCTCCTACGTGGGCTGTGTCGTCTCTGCCCTGGCCTGCCTTGTCACCATTG
CCGCCTACCTCTGCTCCAGGGTGCCCCTGCCGTGCAGGAGGAAACCTCGGGACTACACCATCAAGGTGCACATG
AACCTGCTGCTGGCCGTCTTCCTGCTGGACACGAGCTTCCTGCTCAGCGAGCCGGTGGCCCTGACAGGCTCTGA
GGCTGGCTGCCGAGCCAGTGCCATCTTCCTGCACTTCTCCCTGCTCACCTGCCTTTCCTGGATGGGCCTCGAGG
GGTACAACCTCTACCGACTCGTGGTGGAGGTCTTTGGCACCTATGTCCCTGGCTACCTACTCAAGCTGAGCGCC
ATGGGCTGGGGCTTCCCCATCTTTCTGGTGACGCTGGTGGCCCTGGTGGATGTGGACAACTATGGCCCCATCAT
CTTGGCTGTGCATAGGACTCCAGAGGGCGTCATCTACCCTTCCATGTGCTGGATCCGGGACTCCCTGGTCAGCT
ACATCACCAACCTGGGCCTCTTCAGCCTGGTGTTTCTGTTCAACATGGCCATGCTAGCCACCATGGTGGTGCAG
ATCCTGCGGCTGCGCCCCCACACCCAAAAGTGGTCACATGTGCTGACACTGCTGGGCCTCAGCCTGGTCCTTGG
CCTGCCCTGGGCCTTGATCTTCTTCTCCTTTGCTTCTGGCACCTTCCAGCTTGTCGTCCTCTACCTTTTCAGCA
TCATCACCTCCTTCCAAGGCTTCCTCATCTTCATCTGGTACTGGTCCATGCGGCTGCAGGCCCGGGGTGGCCCC
TCCCCTCTGAAGAGCAACTCAGACAGCGCCAGGCTCCCCATCAGCTCGGGCAGCACCTCGTCCAGCCGCATCTA
GGCCTCCAGCCCACCTGCCCATGTGATGAAGCAGAGATGCGGCCTCGTCGCACACTGCCTGTGGCCCCCGAGCC
AGGCCCAGCCCCAGGCCAGTCAGCCGCAGACTTTGGAAAGCCCAACGACCATGGAGAGATGGGCCGTTGCCATG
GTGGACGGACTCCCGGGCTGGGCTTTTGAATTGGCCTTGGGGACTACTCGGCTCTCACTCAGCTCCCACGGGAC
TCAGAAGTGCGCCGCCATGCTGCCTAGGGTACTGTCCCCACATCTGTCCCAACCCAGCTGGAGGCCTGGTCTCT
CCTTACAACCCCTGGGCCCAGCCCTCATTGCTGGGGGCCAGGCCTTGGATCTTGAGGGTCTGGCACATCCTTAA
TCCTGTGCCCCTGCCTGGGACAGAAATGTGGCTCCAGTTGCTCTGTCTCTCGTGGTCACCCTGAGGGCACTCTG
CATCCTCTGTCATTTTAACCTCAGGTGGCACCCAGGGCGAATGGGGCCCAGGGCAGACCTTCAGGGCCAGAGCC
CTGGCGGAGGAGAGGCCCTTTGCCAGGAGCACAGCAGCAGCTCGCCTACCTCTGAGCCCAGGCCCCCTCCCTCC
CTCAGCCCCCCAGTCCTCCCTCCATCTTCCCTGGGGTTCTCCTCCTCTCCCAGGGCCTCCTTGCTCCTTCGTTC
ACAGCTGGGGGTCCCCGATTCCAATGCTGTTTTTTGGGGAGTGGTTTCCAGGAGCTGCCTGGTGTCTGCTGTAA
ATGTTTGTCTACTGCACAAGCCTCGGCCTGCCCCTGAGCCAGGCTCGGTACCGATGCGTGGGCTGGGCTAGGTC
CCTCTGTCCATCTGGGCCTTTGTATGAGCTGCATTGCCCTTGCTCACCCTGACCAAGCACACGCCTCAGAGGGG
CCCTCAGCCTCTCCTGAAGCCCTCTTGTGGCAAGAACTGTGGACCATGCCAGTCCCGTCTGGTTTCCATCCCAC
CACTCCAAGGACTGAGACTGACCTCCTCTGGTGACACTGGCCTAGAGCCTGACACTCTCCTAAGAGGTTCTCTC
CAAGCCCCCAAATAGCTCCAGGCGCCCTCGGCCGCCCATCATGGTTAATTCTGTCCAACAAACACACACGGGTA
GATTGCTGGCCTGTTGTAGGTGGTAGGGACACAGATGACCGACCTGGTCACTCCTCCTGCCAACATTCAGTCTG
GTATGTGAGGCGTGCGTGAAGCAAGAACTCCTGGAGCTACAGGGACAGGGAGCCATCATTCCTGCCTGGGAATC
CTGGAAGACTTCCTGCAGGAGTCAGCGTTCAATCTTGACCTTGAAGATGGGAAGGATGTTCTTTTTACGTACCA
ATTCTTTTGTCTTTTGATATTAAAAAGAAGTACATGTTCATTGTAGAGAATTTGGAAACTGTAGAAGAGAATCA
AGAAGAAAAATAAAAATCAGCTGTTGTAATCGCCTAGCAAAAAAAAAAAAAAAAAAAAAAAAAAAAAAAA
AAAAAAAAAAAAAAAAAAAAAAAAAAAAAAAAAAAAAAAAAA

FIGURE 134

MTPQSLLQTTLFLLSLLFLVQGAHGRGHREDFRFCSQRNQTHRSSLHYKPTPDLRISIENSE
EALTVHAPFPAAHPASRSFPDPRGLYHFCLYWNRHAGRLHLLYGKRDFLLSDKASSLLCFQH
QEESLAQGPPLLATSVTSWWSPQNISLPSAASFTFSFHSPPHTAAHNASVDMCELKRDLQLL
SQFLKHPQKASRRPSAAPASQQLQSLESKLTSVRFMGDMVSFEEDRINATVWKLQPTAGLQD
LHIHSRQEEEQSEIMEYSVLLPRTLFQRTKGRSGEAEKRLLLVDFSSQALFQDKNSSQVLGE
KVLGIVVQNTKVANLTEPVVLTFQHQLQPKNVTLQCVFWVEDPTLSSPGHWSSAGCETVRRE
TQTSCFCNHLTYFAVLMVSSVEVDAVHKHYLSLLSYVGCVVSALACLVTIAAYLCSRVPLPC
RRKPRDYTIKVHMNLLLAVFLLDTSFLLSEPVALTGSEAGCRASAIFLHFSLLTCLSWMGLE
GYNLYRLVVEVFGTYVPGYLLKLSAMGWGFPIFLVTLVALVDVDNYGPIILAVHRTPEGVIY
PSMCWIRDSLVSYITNLGLFSLVFLFNMAMLATMVVQILRLRPHTQKWSHVLTLLGLSLVLG
LPWALIFFSFASGTFQLVVLYLFSIITSFQGFLIFIWYWSMRLQARGGPSPLKSNSDSARLP
ISSGSTSSSRI

Important features:

Signal peptide:

amino acids 1-25

Putative transmembrane domains:

amino acids 382-398, 402-420, 445-468, 473-491, 519-537, 568-590 and 634-657

Microbodies C-terminal targeting signal.

amino acids 691-693 cAMP- and cGMP-dependent protein kinase phosphorylation sites.

amino acids 198-201 and 370-373

N-glycosylation sites.

amino acids 39-42, 148-151, 171-174, 234-237, 303-306, 324-327 and 341-344

G-protein coupled receptors family 2 proteins amino acids 475-504

FIGURE 135

GCCTAGCCAGGCCAAGAATGCAATTGCCCCGGTGGTGGGAGCTGGGAGACCCCTGTGCTTGGACGGGACAGGGTCGG
GGGACACGCAGGATGAGCCCCGCGACCACTGGCACATTCTTGCTGACAGTGTACAGTATTTTCTCCAAGGTACA
CTCCGATCGGAATGTATACCCATCAGCAGGTGTCCTCTTTGTTCATGTTTTGGAAAGAGAATATTTTAAGGGGG
AATTTCCACCTTACCCAAAACCTGGCGAGATTAGTAATGATCCCATAACATTTAATACAAATTTAATGGGTTAC
CCAGACCGACCTGGATGGCTTCGATATATCCAAAGGACACCATATAGTGATGGAGTCCTATATGGGTCCCCAAC
AGCTGAAAATGTGGGGAAGCCAACAATCATTGAGATAACTGCCTACAACAGGCGCACCTTTGAGACTGCAAGGC
ATAATTTGATAATTAATATAATGTCTGCAGAAGACTTCCCGTTGCCATATCAAGCAGAATTCTTCATTAAGAAT
ATGAATGTAGAAGAAATGTTGGCCAGTGAGGTTCTTGGAGACTTTCTTGGCGCAGTGAAAAATGTGTGGCAGCC
AGAGCGCCTGAACGCCATAAACATCACATCGGCCCTAGACAGGGGTGGCAGGGTGCCACTTCCCATTAATGACC
TGAAGGAGGGCGTTTATGTCATGGTTGGTGCAGATGTCCCGTTTTCTTCTTGTTTACGAGAAGTTGAAAATCCA
CAGAATCAATTGAGATGTAGTCAAGAAATGGAGCCTGTAATAACATGTGATAAAAAATTTCGTACTCAATTTTA
CATTGACTGGTGCAAAATTTCATTGGTTGATAAAACAAAGCAAGTGTCCACCTATCAGGAAGTGATTCGTGGAG
AGGGGATTTTACCTGATGGTGGAGAATACAAACCCCCTTCTGATTCTTTGAAAAGCAGAGACTATTACACGGAT
TTCCTAATTACACTGGCTGTGCCCTCGGCAGTGGCACTGGTCCTTTTTCTAATACTTGCTTATATCATGTGCTG
CCGACGGGAAGGCGTGGAAAAGAGAAACATGCAAACACCAGACATCCAACTGGTCCATCACAGTGCTATTCAGA
AATCTACCAAGGAGCTTCGAGACATGTCCAAGAATAGAGAGATAGCATGGCCCCTGTCAACGCTTCCTGTGTTC
CACCCTGTGACTGGGGAAATCATACCTCCTTTACACACAGACAACTATGATAGCACAAACATGCCATTGATGCA
AACGCAGCAGAACTTGCCACATCAGACTCAGATTCCCCAACAGCAGACTACAGGTAAATGGTATCCCTGAAGAA
AGAAAACTGACTGAAGCAATGAATTTATAATCAGACAATATAGCAGTTACATCACATTTCTTTTCTCTTCCAAT
AATGCATGAGCTTTTCTGGCATATGTTATGCATGTTGGCAGTATTAAGTGTATACCAAATAATACAACATAACT
TTCATTTTACTAATGTATTTTTTTGTACTTAAAGCATTTTTGACAATTTGTAAAACATTGATGACTTTATATTT
GTTACAATAAAAGTTGATCTTTAAAATAAATATTATTAATGAAGCCTAAAAAAAAAAA

FIGURE 136

MQLPRWWELGDPCAWTGQGRGTRRMSPATTGTFLLTVYSIFSKVHSDRNVYPSAGVLFVHVLEREYFKGEFPPY
PKPGEISNDPITFNTNLMGYPDRPGWLRYIQRTPYSDGVLYGSPTAENVGKPTIIEITAYNRRTFETARHNLII
NIMSAEDFPLPYQAEFFIKNMNVEEMLASEVLGDFLGAVKNVWQPERLNAINITSALDRGGRVPLPINDLKEGV
YVMVGADVPFSSCLREVENPQNQLRCSQEMEPVITCDKKFRTQFYIDWCKISLVDKTKQVSTYQEVIRGEGILP
DGGEYKPPSDSLKSRDYYTDFLITLAVPSAVALVLFLILAYIMCCRREGVEKRNMQTPDIQLVHHSAIQKSTKE
LRDMSKNREIAWPLSTLPVFHPVTGEIIPPLHTDNYDSTNMPLMQTQQNLPHQTQIPQQQTTGKWYP signal sequence:
Amino acids 1-46 transmembrane domain:
Amino acids 319-338

N-glycosylation site:
Amino acids 200-204 cAMP- and cGMP-dependent protein kinase phosphorylation site:
Amino acids 23-27

Tyrosine kinase phosphorylation site:
Amino acids 43-52

N-myristoylation sites:
Amino acids 17-23;112-118;116-122;

CAGAAGAGGGGGCTAGCTAGCTGTCTCTGCGGACCAGGGAGACCCCCGCGCCCCCCCGGTGT
GAGGCGGCCTCACAGGGCCGGGTGGGCTGGCGAGCCGACGCGGCGGCGGAGGAGGCTGTGAG
GAGTGTGTGGAACAGGACCCGGGACAGAGGAACCATGGCTCCGCAGAACCTGAGCACCTTTT
GCCTGTTGCTGCTATACCTCATCGGGGCGGTGATTGCCGGACGAGATTTCTATAAGATCTTG
GGGGTGCCTCGAAGTGCCTCTATAAAGGATATTAAAAAGGCCTATAGGAAACTAGCCCTGCA
GCTTCATCCCGACCGGAACCCTGATGATCCACAAGCCCAGGAGAAATTCCAGGATCTGGGTG
CTGCTTATGAGGTTCTGTCAGATAGTGAGAAACGGAAACAGTACGATACTTATGGTGAAGAA
GGATTAAAAGATGGTCATCAGAGCTCCCATGGAGACATTTTTTCACACTTCTTTGGGGATTT
TGGTTTCATGTTTGGAGGAACCCCTCGTCAGCAAGACAGAAATATTCCAAGAGGAAGTGATA
TTATTGTAGATCTAGAAGTCACTTTGGAAGAAGTATATGCAGGAAATTTTGTGGAAGTAGTT
AGAAACAAACCTGTGGCAAGGCAGGCTCCTGGCAAACGGAAGTGCAATTGTCGGCAAGAGAT
GCGGACCACCCAGCTGGGCCCTGGGCGCTTCCAAATGACCCAGGAGGTGGTCTGCGACGAAT
GCCCTAATGTCAAACTAGTGAATGAAGAACGAACGCTGGAAGTAGAAATAGAGCCTGGGGTG
AGAGACGGCATGGAGTACCCCTTTATTGGAGAAGGTGAGCCTCACGTGGATGGGGAGCCTGG
AGATTTACGGTTCCGAATCAAAGTTGTCAAGCACCCAATATTTGAAAGGAGAGGAGATGATT
TGTACACAAATGTGACAATCTCATTAGTTGAGTCACTGGTTGGCTTTGAGATGGATATTACT
CACTTGGATGGTCACAAGGTACATATTTCCCGGGATAAGATCACCAGGCCAGGAGCGAAGCT
ATGGAAGAAAGGGGAAGGGCTCCCCAACTTTGACAACAACAATATCAAGGGCTCTTTGATAA
TCACTTTTGATGTGGATTTTCCAAAAGAACAGTTAACAGAGGAAGCGAGAGAAGGTATCAAA
CAGCTACTGAAACAAGGGTCAGTGCAGAAGGTATACAATGGACTGCAAGGATATTGAGAGTG
AATAAAATTGGACTTTGTTTAAAATAAGTGAATAAGCGATATTTATTATCTGCAAGGTTTTT
TTGTGTGTGTTTTTGTTTTTATTTTCAATATGCAAGTTAGGCTTAATTTTTTTATCTAATGA
TCATCATGAAATGAATAAGAGGGCTTAAGAATTTGTCCATTTGCATTCGGAAAAGAATGACC
AGCAAAAGGTTTACTAATACCTCTCCCTTTGGGGATTTAATGTCTGGTGCTGCCGCCTGAGT
TTCAAGAATTAAAGCTGCAAGAGGACTCCAGGAGCAAAAGAAACACAATATAGAGGGTTGGA
GTTGTTAGCAATTTCATTCAAAATGCCAACTGGAGAAGTCTGTTTTTAAATACATTTTGTTG
TTATTTTTA

FIGURE 138

MAPQNLSTFCLLLLYLIGAVIAGRDFYKILGVPRSASIKDIKKAYRKLALQLHPDRNPDDPQAQEKFQDLGAAY
EVLSDSEKRKQYDTYGEEGLKDGHQSSHGDIFSHFFGDFGFMFGGTPRQQDRNIPRGSDIIVDLEVTLEEVYAG
NFVEVVRNKPVARQAPGKRKCNCRQEMRTTQLGPGRFQMTQEVVCDECPNVKLVNEERTLEVEIEPGVRDGMEY
PFIGEGEPHVDGEPGDLRFRIKVVKHPIFERRGDDLYTNVTISLVESLVGFEMDITHLDGHKVHISRDKITRPG
AKLWKKGEGLPNFDNNNIKGSLIITFDVDFPKEQLTEEAREGIKQLLKQGSVQKVYNGLQGY

Important features:
Signal peptide:
amino acids 1-22

Cell attachment sequence.
amino acids 254-257

Nt-dnaJ domain signature.
amino acids 67-87

Homologous region to Nt-dnaJ domain proteins.
amino acids 26-58

N-glycosylation site.
amino acids 5-9, 261-265

Tyrosine kinase phosphorylation site.
amino acids 253-260

N-myristoylation site.
amino acids 18-24, 31-37, 93-99, 215-221

Amidation site.
amino acids 164-168

FIGURE 139

CCAGTCTGTCGCCACCTCACTTGGTGTCTGCTGTCCCCGCCAGGCAAGCCTGGGGTGAGAGC
ACAGAGGAGTGGGCCGGGACCATGCGGGGGACGCGGCTGGCGCTCCTGGCGCTGGTGCTGGC
TGCCTGCGGAGAGCTGGCGCCGGCCCTGCGCTGCTACGTCTGTCCGGAGCCCACAGGAGTGT
CGGACTGTGTCACCATCGCCACCTGCACCACCAACGAAACCATGTGCAAGACCACACTCTAC
TCCCGGGAGATAGTGTACCCCTTCCAGGGGGACTCCACGGTGACCAAGTCCTGTGCCAGCAA
GTGTAAGCCCTCGGATGTGGATGGCATCGGCCAGACCCTGCCCGTGTCCTGCTGCAATACTG
AGCTGTGCAATGTAGACGGGGCGCCCGCTCTGAACAGCCTCCACTGCGGGGCCCTCACGCTC
CTCCCACTCTTGAGCCTCCGACTGTAGAGTCCCCGCCCACCCCCATGGCCCTATGCGGCCCA
GCCCCGAATGCCTTGAAGAAGTGCCCCCTGCACCAGGAAAAAAAAAAAAAAA

FIGURE 140

</usr/seqdb2/sst/DNA/Dnaseqs.min/ss.DNA56405
<subunit 1 of 1, 125 aa, 1 stop
<MW: 13115, pI: 5.90, NX(S/T): 1
MRGTRLALLALVLAACGELAPALRCYVCPEPTGVSDCVTIATCTTNETMCKTTLYSREIVYP
FQGDSTVTKSCASKCKPSDVDGIGQTLPVSCCNTELCNVDGAPALNSLHCGALTLLPLLSLRL

Important features:
Signal peptide:
amino acids 1-17

N-glycosylation site.
amino acids 46-49

FIGURE 141

GGCGCCGCGTAGGCCCGGGAGGCCGGGCCGGCCGGGCTGCGAGCGCCTGCCCCATGCGCCGC
CGCCTCTCCGCACGATGTTCCCCTCGCGGAGGAAAGCGGCGCAGCTGCCCTGGGAGGACGGC
AGGTCCGGGTTGCTCTCCGGCGGCCTCCCTCGGAAGTGTTCCGTCTTCCACCTGTTCGTGGC
CTGCCTCTCGCTGGGCTTCTTCTCCCTACTCTGGCTGCAGCTCAGCTGCTCTGGGGACGTGG
CCCGGGCAGTCAGGGGACAAGGGCAGGAGACCTCGGGCCCTCCCCGTGCCTGCCCCCCAGAG
CCGCCCCCTGAGCACTGGGAAGAAGACGCATCCTGGGGCCCCCACCGCCTGGCAGTGCTGGT
GCCCTTCCGCGAACGCTTCGAGGAGCTCCTGGTCTTCGTGCCCCACATGCGCCGCTTCCTGA
GCAGGAAGAAGATCCGGCACCACATCTACGTGCTCAACCAGGTGGACCACTTCAGGTTCAAC
CGGGCAGCGCTCATCAACGTGGGCTTCCTGGAGAGCAGCAACAGCACGGACTACATTGCCAT
GCACGACGTTGACCTGCTCCCTCTCAACGAGGAGCTGGACTATGGCTTTCCTGAGGCTGGGC
CCTTCCACGTGGCCTCCCCGGAGCTCCACCCTCTCTACCACTACAAGACCTATGTCGGCGGC
ATCCTGCTGCTCTCCAAGCAGCACTACCGGCTGTGCAATGGGATGTCCAACCGCTTCTGGGG
CTGGGGCCGCGAGGACGACGAGTTCTACCGGCGCATTAAGGGAGCTGGGCTCCAGCTTTTCC
GCCCCTCGGGAATCACAACTGGGTACAAGACATTTCGCCACCTGCATGACCCAGCCTGGCGG
AAGAGGGACCAGAAGCGCATCGCAGCTCAAAAACAGGAGCAGTTCAAGGTGGACAGGGAGGG
AGGCCTGAACACTGTGAAGTACCATGTGGCTTCCCGCACTGCCCTGTCTGTGGGCGGGGCCC
CCTGCACTGTCCTCAACATCATGTTGGACTGTGACAAGACCGCCACACCCTGGTGCACATTC
AGCTGAGCTGGATGGACAGTGAGGAAGCCTGTACCTACAGGCCATATTGCTCAGGCTCAGGA
CAAGGCCTCAGGTCGTGGGCCCAGCTCTGACAGGATGTGGAGTGGCCAGGACCAAGACAGCA
AGCTACGCAATTGCAGCCACCCGGCCGCCAAGGCAGGCTTGGGCTGGGCCAGGACACGTGGG
GTGCCTGGGACGCTGCTTGCCATGCACAGTGATCAGAGAGAGGCTGGGGTGTGTCCTGTCCG
GGACCCCCCCTGCCTTCCTGCTCACCCTACTCTGACCTCCTTCACGTGCCCAGGCCTGTGGG
TAGTGGGGAGGGCTGAACAGGACAACCTCTCATCACCCTACTCTGACCTCCTTCACGTGCCC
AGGCCTGTGGGTAGTGGGGAGGGCTGAACAGGACAACCTCTCATCACCCCCAAAAAAAAAAA
AAAAAAAAAAAAAAAAAAAAAAAAAAAAAAAAAAA

FIGURE 142

></usr/seqdb2/sst/DNA/Dnaseqs.min/ss.DNA56531
><subunit 1 of 1, 327 aa, 1 stop
><MW: 37406, pI: 9.30, NX(S/T): 1
MFPSRRKAAQLPWEDGRSGLLSGGLPRKCSVFHLFVACLSLGFFSLLWLQLSCSGDVARAVR
GQGQETSGPPRACPPEPPPEHWEEDASWGPHRLAVLVPFRERFEELLVFVPHMRRFLSRKKI
RHHIYVLNQVDHFRFNRAALINVGFLESSNSTDYIAMHDVDLLPLNEELDYGFPEAGPFHVA
SPELHPLYHYKTYVGGILLLSKQHYRLCNGMSNRFWGWGREDDEFYRRIKGAGLQLFRPSGI
TTGYKTFRHLHDPAWRKRDQKRIAAQKQEQFKVDREGGLNTVKYHVASRTALSVGGAPCTVL
NIMLDCDKTATPWCTFS

Signal peptide:
amino acids 1-42

Transmembrane domain:
amino acids 29-49 (type II)

N-glycosylation site.
amino acids 154-158 cAMP- and cGMP-dependent protein kinase phosphorylation site.
amino acids 27-31

Tyrosine kinase phosphorylation site.
amino acids 226-233

N-myristoylation site.
amino acids 19-25, 65-71, 247-253, 285-291, 303-309, 304-310

FIGURE 143

GTGGGATTTATTTGAGTGCAAGATCGTTTTCTCAGTGGTGGTGGAAGTTGCCTCATCGCAGGCAGATGTTGGGG
CTTTGTCCGAACAGCTCCCCTCTGCCAGCTTCTGTAGATAAGGGTTAAAAACTAATATTTATATGACAGAAGAA
AAAGATGTCATTCCGTAAAGTAAACATCATCATCTTGGTCCTGGCTGTTGCTCTCTTCTTACTGGTTTTGCACC
ATAACTTCCTCAGCTTGAGCAGTTTGTTAAGGAATGAGGTTACAGATTCAGGAATTGTAGGGCCTCAACCTATA
GACTTTGTCCCAAATGCTCTCCGACATGCAGTAGATGGGAGACAAGAGGAGATTCCTGTGGTCATCGCTGCATC
TGAAGACAGGCTTGGGGGGGCCATTGCAGCTATAAACAGCATTCAGCACAACACTCGCTCCAATGTGATTTTCT
ACATTGTTACTCTCAACAATACAGCAGACCATCTCCGGTCCTGGCTCAACAGTGATTCCCTGAAAAGCATCAGA
TACAAAATTGTCAATTTTGACCCTAAACTTTTGGAAGGAAAAGTAAAGGAGGATCCTGACCAGGGGGAATCCAT
GAAACCTTTAACCTTTGCAAGGTTCTACTTGCCAATTCTGGTTCCCAGCGCAAAGAAGGCCATATACATGGATG
ATGATGTAATTGTGCAAGGTGATATTCTTGCCCTTTACAATACAGCACTGAAGCCAGGACATGCAGCTGCATTT
TCAGAAGATTGTGATTCAGCCTCTACTAAAGTTGTCATCCGTGGAGCAGGAAACCAGTACAATTACATTGGCTA
TCTTGACTATAAAAAGGAAAGAATTCGTAAGCTTTCCATGAAAGCCAGCACTTGCTCATTTAATCCTGGAGTTT
TTGTTGCAAACCTGACGGAATGGAAACGACAGAATATAACTAACCAACTGGAAAAATGGATGAAACTCAATGTA
GAAGAGGGACTGTATAGCAGAACCCTGGCTGGTAGCATCACAACACCTCCTCTGCTTATCGTATTTTATCAACA
GCACTCTACCATCGATCCTATGTGGAATGTCCGCCACCTTGGTTCCAGTGCTGGAAAACGATATTCACCTCAGT
TTGTAAAGGCTGCCAAGTTACTCCATTGGAATGGACATTTGAAGCCATGGGGAAGGACTGCTTCATATACTGAT
GTTTGGGAAAAATGGTATATTCCAGACCCAACAGGCAAATTCAACCTAATCCGAAGATATACCGAGATCTCAAA
CATAAAGTGAAACAGAATTTGAACTGTAAGCAAGCATTTCTCAGGAAGTCCTGGAAGATAGCATGCATGGGAAG
TAACAGTTGCTAGGCTTCAATGCCTATCGGTAGCAAGCCATGGAAAAAGATGTGTCAGCTAGGTAAAGATGACA
AACTGCCCTGTCTGGCAGTCAGCTTCCCAGACAGACTATAGACTATAAATATGTCTCCATCTGCCTTACCAAGT
GTTTTCTTACTACAATGCTGAATGACTGGAAAGAAGAACTGATATGGCTAGTTCAGCTAGCTGGTACAGATAAT
TCAAAACTGCTGTTGGTTTTAATTTTGTAACCTGTGGCCTGATCTGTAAATAAAACTTACATTTTTC

FIGURE 144

MSFRKVNIIILVLAVALFLLVLHHNFLSLSSLLRNEVTDSGIVGPQPIDFVPNALRHAVDGR
QEEIPVVIAASEDRLGGAIAAINSIQHNTRSNVIFYIVTLNNTADHLRSWLNSDSLKSIRYK
IVNFDPKLLEGKVKEDPDQGESMKPLTFARFYLPILVPSAKKAIYMDDDVIVQGDILALYNT
ALKPGHAAAFSEDCDSASTKVVIRGAGNQYNYIGYLDYKKERIRKLSMKASTCSFNPGVFVA
NLTEWKRQNITNQLEKWMKLNVEEGLYSRTLAGSITTPPLLIVFYQQHSTIDPMWNVRHLGS
SAGKRYSPQFVKAAKLLHWNGHLKPWGRTASYTDVWEKWYIPDPTGKFNLIRRYTEISNIK

FIGURE 145

AAACTTGACGCCATGAAGATCCCGGTCCTTCCTGCCGTGGTGCTCCTCTCCCTCCTGGTGCT
CCACTCTGCCCAGGGAGCCACCCTGGGTGGTCCTGAGGAAGAAAGCACCATTGAGAATTATG
CGTCACGACCCGAGGCCTTTAACACCCCGTTCCTGAACATCGACAAATTGCGATCTGCGTTT
AAGGCTGATGAGTTCCTGAACTGGCACGCCCTCTTTGAGTCTATCAAAAGGAAACTTCCTTT
CCTCAACTGGGATGCCTTTCCTAAGCTGAAAGGACTGAGGAGCGCAACTCCTGATGCCCAGT
GACCATGACCTCCACTGGAAGAGGGGGCTAGCGTGAGCGCTGATTCTCAACCTACCATAACT
CTTTCCTGCCTCAGGAACTCCAATAAAACATTTTCCATCCAAA

FIGURE 146

MKIPVLPAVVLLSLLVLHSAQGATLGGPEEESTIENYASRPEAFNTPFLNIDKLRSAFKADE
FLNWHALFESIKRKLPFLNWDAFPKLKGLRSATPDAQ

FIGURE 147

CCTCTGTCCACTGCTTTCGTGAAGACAAGATGAAGTTCACAATTGTCTTTGCTGGACTTCTT
GGAGTCTTTCTAGCTCCTGCCCTAGCTAACTATAATATCAACGTCAATGATGACAACAACAA
TGCTGGAAGTGGGCAGCAGTCAGTGAGTGTCAACAATGAACACAATGTGGCCAATGTTGACA
ATAACAACGGATGGGACTCCTGGAATTCCATCTGGGATTATGGAAATGGCTTTGCTGCAACC
AGACTCTTTCAAAAGAAGACATGCATTGTGCACAAAATGAACAAGGAAGTCATGCCCTCCAT
TCAATCCCTTGATGCACTGGTCAAGGAAAAGAAGCTTCAGGGTAAGGGACCAGGAGGACCAC
CTCCCAAGGGCCTGATGTACTCAGTCAACCCAAACAAAGTCGATGACCTGAGCAAGTTCGGA
AAAAACATTGCAAACATGTGTCGTGGGATTCCAACATACATGGCTGAGGAGATGCAAGAGGC
AAGCCTGTTTTTTTACTCAGGAACGTGCTACACGACCAGTGTACTATGGATTGTGGACATTT
CCTTCTGTGGAGACACGGTGGAGAACTAAACAATTTTTTAAAGCCACTATGGATTTAGTCAT
CTGAATATGCTGTGCAGAAAAAATATGGGCTCCAGTGGTTTTTACCATGTCATTCTGAAATT
TTTCTCTACTAGTTATGTTTGATTTCTTTAAGTTTCAATAAAATCATTTAGCATTGAAAAAAA

FIGURE 148

MKFTIVFAGLLGVFLAPALANYNINVNDDNNNAGSGQQSVSVNNEHNVANVDNNNGWDSWNS
IWDYGNGFAATRLFQKKTCIVHKMNKEVMPSIQSLDALVKEKKLQGKGPGGPPPKGLMYSVN
PNKVDDLSKFGKNIANMCRGIPTYMAEEMQEASLFFYSGTCYTTSVLWIVDISFCGDTVEN

Signal Peptide:
amino acids 1-20

N-myristoylation Sites:
amino acids 67-72, 118-123, 163-168

Flavodoxin protein homology:
amino acids 156-174

FIGURE 149

GGCACGAGCCAGGAACTAGGAGGTTCTCACTGCCCGAGCAGAGGCCCTACACCCACCGAGGC
ATGGGGCTCCCTGGGCTGTTCTGCTTGGCCGTGCTGGCTGCCAGCAGCTTCTCCAAGGCACG
GGAGGAAGAAATTACCCCTGTGGTCTCCATTGCCTACAAAGTCCTGGAAGTTTTCCCCAAAG
GCCGCTGGGTGCTCATAACCTGCTGTGCACCCCAGCCACCACCGCCCATCACCTATTCCCTC
TGTGGAACCAAGAACATCAAGGTGGCCAAGAAGGTGGTGAAGACCCACGAGCCGGCCTCCTT
CAACCTCAACGTCACACTCAAGTCCAGTCCAGACCTGCTCACCTACTTCTGCCGGGCGTCCT
CCACCTCAGGTGCCCATGTGGACAGTGCCAGGCTACAGATGCACTGGGAGCTGTGGTCCAAG
CCAGTGTCTGAGCTGCGGGCCAACTTCACTCTGCAGGACAGAGGGGCAGGCCCCAGGGTGGA
GATGATCTGCCAGGCGTCCTCGGGCAGCCCACCTATCACCAACAGCCTGATCGGGAAGGATG
GGCAGGTCCACCTGCAGCAGAGACCATGCCACAGGCAGCCTGCCAACTTCTCCTTCCTGCCG
AGCCAGACATCGGACTGGTTCTGGTGCCAGGCTGCAAACAACGCCAATGTCCAGCACAGCGC
CCTCACAGTGGTGCCCCCAGGTGGTGACCAGAAGATGGAGGACTGGCAGGGTCCCCTGGAGA
GCCCCATCCTTGCCTTGCCGCTCTACAGGAGCACCCGCCGTCTGAGTGAAGAGGAGTTTGGG
GGGTTCAGGATAGGGAATGGGGAGGTCAGAGGACGCAAAGCAGCAGCCATGTAGAATGAACC
GTCCAGAGAGCCAAGCACGGCAGAGGACTGCAGGCCATCAGCGTGCACTGTTCGTATTTGGA
GTTCATGCAAAATGAGTGTGTTTTAGCTGCTCTTGCCACAAAAAAAAAAAAAAAAAAAAAAA

FIGURE 150

MGLPGLFCLAVLAASSFSKAREEEITPVVSIAYKVLEVFPKGRWVLITCCAPQPPPPITYSL
CGTKNIKVAKKVVKTHEPASFNLNVTLKSSPDLLTYFCRASSTSGAHVDSARLQMHWELWSK
PVSELRANFTLQDRGAGPRVEMICQASSGSPPITNSLIGKDGQVHLQQRPCHRQPANFSFLP
SQTSDWFWCQAANNANVQHSALTVVPPGGDQKMEDWQGPLESPILALPLYRSTRRLSEEEFG
GFRIGNGEVRGRKAAAM

Signal Peptide:
amino acids 1-18

N-glycosylation Sites:
amino acids 86-89, 132-135, 181-184

FIGURE 151

GCGTGGGGATGTCTAGGAGCTCGAAGGTGGTGCTGGGCCTCTCGGTGCTGCTGACGGCGGCC
ACAGTGGCCGGCGTACATGTGAAGCAGCAGTGGGACCAGCAGAGGCTTCGTGACGGAGTTAT
CAGAGACATTGAGAGGCAAATTCGGAAAAAAGAAAACATTCGTCTTTTGGGAGAACAGATTA
TTTTGACTGAGCAACTTGAAGCAGAAAGAGAGAAGATGTTATTGGCAAAAGGATCTCAAAAA
TCATGACTTGAATGTGAAATATCTGTTGGACAGACAACACGAGTTTGTGTGTGTGTGTTGAT
GGAGAGTAGCTTAGTAGTATCTTCATCTTTTTTTTTTGGTCACTGTCCTTTTAAACTTGATCA
AATAAAGGACAGTGGGTCATATAAGTTACTGCTTTCAGGGTCCCTTATATCTGAATAAAGGA
GTGTGGGCAGACACTTTTTGGAAGAGTCTGTCTGGGTGATCCTGGTAGAAGCCCCATTAGGG
TCACTGTCCAGTGCTTAGGGTTGTTACTGAGAAGCACTGCCGAGCTTGTGAGAAGGAAGGGA
TGGATAGTAGCATCCACCTGAGTAGTCTGATCAGTCGGCATGATGACGAAGCCACGAGAACA
TCGACCTCAGAAGGACTGGAGGAAGGTGAAGTGGAGGGAGAGACGCTCCTGATCGTCGAATCC

FIGURE 152

MSRSSKVVLGLSVLLTAATVAGVHVKQQWDQQRLRDGVIRDIERQIRKKENIRLLGEQIILT
EQLEAEREKMLLAKGSQKS

FIGURE 153

AATGTGAGAGGGGCTGATGGAAGCTGATAGGCAGGACTGGAGTGTTAGCACCAGTACTGGAT
GTGACAGCAGGCAGAGGAGCACTTAGCAGCTTATTCAGTGTCCGATTCTGATTCCGGCAAGG
ATCCAAGCATGGAATGCTGCCGTCGGGCAACTCCTGGCACACTGCTCCTCTTTCTGGCTTTC
CTGCTCCTGAGTTCCAGGACCGCACGCTCCGAGGAGGACCGGGACGGCCTATGGGATGCCTG
GGGCCCATGGAGTGAATGCTCACGCACCTGCGGGGGAGGGGCCTCCTACTCTCTGAGGCGCT
GCCTGAGCAGCAAGAGCTGTGAAGGAAGAAATATCCGATACAGAACATGCAGTAATGTGGAC
TGCCCACCAGAAGCAGGTGATTTCCGAGCTCAGCAATGCTCAGCTCATAATGATGTCAAGCA
CCATGGCCAGTTTTATGAATGGCTTCCTGTGTCTAATGACCCTGACAACCCATGTTCACTCA
AGTGCCAAGCCAAAGGAACAACCCTGGTTGTTGAACTAGCACCTAAGGTCTTAGATGGTACG
CGTTGCTATACAGAATCTTTGGATATGTGCATCAGTGGTTTATGCCAAATTGTTGGCTGCGA
TCACCAGCTGGGAAGCACCGTCAAGGAAGATAACTGTGGGGTCTGCAACGGAGATGGGTCCA
CCTGCCGGCTGGTCCGAGGGCAGTATAAATCCCAGCTCTCCGCAACCAAATCGGATGATACT
GTGGTTGCACTTCCCTATGGAAGTAGACATATTCGCCTTGTCTTAAAAGGTCCTGATCACTT
ATATCTGGAAACCAAAACCCTCCAGGGGACTAAAGGTGAAAACAGTCTCAGCTCCACAGGAA
CTTTCCTTGTGGACAATTCTAGTGTGGACTTCCAGAAATTTCCAGACAAAGAGATACTGAGA
ATGGCTGGACCACTCACAGCAGATTTCATTGTCAAGATTCGTAACTCGGGCTCCGCTGACAG
TACAGTCCAGTTCATCTTCTATCAACCCATCATCCACCGATGGAGGGAGACGGATTTCTTTC
CTTGCTCAGCAACCTGTGGAGGAGGTTATCAGCTGACATCGGCTGAGTGCTACGATCTGAGG
AGCAACCGTGTGGTTGCTGACCAATACTGTCACTATTACCCAGAGAACATCAAACCCAAACC
CAAGCTTCAGGAGTGCAACTTGGATCCTTGTCCAGCCAGTGACGGATACAAGCAGATCATGC
CTTATGACCTCTACCATCCCCTTCCTCGGTGGGAGGCCACCCCATGGACCGCGTGCTCCTCC
TCGTGTGGGGGGGGCATCCAGAGCCGGGCAGTTTCCTGTGTGGAGGAGGACATCCAGGGGCA
TGTCACTTCAGTGGAAGAGTGGAAATGCATGTACACCCCTAAGATGCCCATCGCGCAGCCCT
GCAACATTTTTGACTGCCCTAAATGGCTGGCACAGGAGTGGTCTCCGTGCACAGTGACATGT
GGCCAGGGCCTCAGATACCGTGTGGTCCTCTGCATCGACCATCGAGGAATGCACACAGGAGG
CTGTAGCCCAAAAACAAAGCCCCACATAAAAGAGGAATGCATCGTACCCACTCCCTGCTATA
AACCCAAAGAGAAACTTCCAGTCGAGGCCAAGTTGCCATGGTTCAAACAAGCTCAAGAGCTA
GAAGAAGGAGCTGCTGTGTCAGAGGAGCCCTCGTAAGTTGTAAAAGCACAGACTGTTCTATA
TTTGAAACTGTTTTGTTTAAAGAAAGCAGTGTCTCACTGGTTGTAGCTTTCATGGGTTCTGA
ACTAAGTGTAATCATCTCACCAAAGCTTTTTGGCTCTCAAATTAAAGATTGATTAGTTTCAA
AAAAAAAAA

FIGURE 154

</usr/seqdb2/sst/DNA/Dnaseqs.min/ss.DNA58847
<subunit 1 of 1, 525 aa, 1 stop
<MW: 58416, pI: 6.62, NX(S/T): 1
MECCRRATPGTLLLFLAFLLLSSRTARSEEDRDGLWDAWGPWSECSRTCGGGASYSLRRCLS
SKSCEGRNIRYRTCSNVDCPPEAGDFRAQQCSAHNDVKHHGQFYEWLPVSNDPDNPCSLKCQ
AKGTTLVVELAPKVLDGTRCYTESLDMCISGLCQIVGCDHQLGSTVKEDNCGVCNGDGSTCR
LVRGQYKSQLSATKSDDTVVALPYGSRHIRLVLKGPDHLYLETKTLQGTKGENSLSSTGTFL
VDNSSVDFQKFPDKEILRMAGPLTADFIVKIRNSGSADSTVQFIFYQPIIHRWRETDFFPCS
ATCGGGYQLTSAECYDLRSNRVVADQYCHYYPENIKPKPKLQECNLDPCPASDGYKQIMPYD
LYHPLPRWEATPWTACSSSCGGGIQSRAVSCVEEDIQGHVTSVEEWKCMYTPKMPIAQPCNI
FDCPKWLAQEWSPCTVTCGQGLRYRVVLCIDHRGMHTGGCSPKTKPHIKEECIVPTPCYKPK
EKLPVEAKLPWFKQAQELEEGAAVSEEPS

Important features:
Signal peptide:
amino acids 1-25

N-glycosylation site.
amino acids 251-254

Thrombospondin 1
amino acids 385-399 von Willebrand factor type C domain proteins
amino acids 385-399, 445-459 and 42-56

FIGURE 155

```
GTGGACTCTGAGAAGCCCAGGCAGTTGAGGACAGGAGAGAGAAGGCTGCAGACCCAGAGGGAGGGAGGACAGGG
AGTCGGAAGGAGGAGGACAGAGGAGGGCACAGAGACGCAGAGCAAGGGCGGCAAGGAGGAGACCCTGGTGGGAG
GAAGACACTCTGGAGAGAGAGGGGGCTGGGCAGAGATGAAGTTCCAGGGGCCCCTGGCCTGCCTCCTGCTGGCC
CTCTGCCTGGGCAGTGGGGAGGCTGGCCCCCTGCAGAGCGGAGAGGAAAGCACTGGGACAAATATTGGGGAGGC
CCTTGGACATGGCCTGGGAGACGCCCTGAGCGAAGGGGTGGGAAAGGCCATTGGCAAAGAGGCCGGAGGGGCAG
CTGGCTCTAAAGTCAGTGAGGCCCTTGGCCAAGGGACCAGAGAAGCAGTTGGCACTGGAGTCAGGCAGGTTCCA
GGCTTTGGCGCAGCAGATGCTTTGGGCAACAGGGTCGGGGAAGCAGCCCATGCTCTGGGAAACACTGGGCACGA
GATTGGCAGACAGGCAGAAGATGTCATTCGACACGGAGCAGATGCTGTCCGCGGCTCCTGGCAGGGGGTGCCTG
GCCACAGTGGTGCTTGGGAAACTTCTGGAGGCCATGGCATCTTTGGCTCTCAAGGTGGCCTTGGAGGCCAGGGC
CAGGGCAATCCTGGAGGTCTGGGGACTCCGTGGGTCCACGGATACCCCGGAAACTCAGCAGGCAGCTTTGGAAT
GAATCCTCAGGGAGCTCCCTGGGGTCAAGGAGGCAATGGAGGGCCACCAAACTTTGGGACCAACACTCAGGGAG
CTGTGGCCCAGCCTGGCTATGGTTCAGTGAGAGCCAGCAACCAGAATGAAGGGTGCACGAATCCCCCACCATCT
GGCTCAGGTGGAGGCTCCAGCAACTCTGGGGGAGGCAGCGGCTCACAGTCGGGCAGCAGTGGCAGTGGCAGCAA
TGGTGACAACAACAATGGCAGCAGCAGTGGTGGCAGCAGCAGTGGCAGCAGCAGTGGCAGCAGCAGTGGCGGCA
GCAGTGGCGGCAGCAGTGGTGGCAGCAGTGGCAACAGTGGTGGCAGCAGAGGTGACAGCGGCAGTGAGTCCTCC
TGGGGATCCAGCACCGGCTCCTCCTCCGGCAACCACGGTGGGAGCGGCGGAGGAAATGGACATAAACCCGGGTG
TGAAAAGCCAGGGAATGAAGCCCGCGGGAGCGGGGAATCTGGGATTCAGGGCTTCAGAGGACAGGGAGTTTCCA
GCAACATGAGGGAAATAAGCAAAGAGGGCAATCGCCTCCTTGGAGGCTCTGGAGACAATTATCGGGGGCAAGGG
TCGAGCTGGGGCAGTGGAGGAGGTGACGCTGTTGGTGGAGTCAATACTGTGAACTCTGAGACGTCTCCTGGGAT
GTTTAACTTTGACACTTTCTGGAAGAATTTTAAATCCAAGCTGGGTTTCATCAACTGGGATGCCATAAACAAGG
ACCAGAGAAGCTCTCGCATCCCGTGACCTCCAGACAAGGAGCCACCAGATTGGATGGGAGCCCCCACACTCCCT
CCTTAAAACACCACCCTCTCATCACTAATCTCAGCCCTTGCCCTTGAAATAAACCTTAGCTGCCCCACAAAAAA
AAAAAAAAAAAAAAAAAAAAAAAAAAAAAAAAAAAAAAAAAAAAAAAAAAAAAAAAAAAAAAAAAAAAAAAAAA
AAAAAAAAAAAAAAAAAAAAAAAAAAAAAA
```

FIGURE 156

></usr/seqdb2/sst/DNA/Dnaseqs.min/ss.DNA59212
><subunit 1 of 1, 440 aa, 1 stop
><MW: 42208, pI: 6.36, NX(S/T): 1
MKFQGPLACLLLALCLGSGEAGPLQSGEESTGTNIGEALGHGLGDALSEGVGKAIGKEAGGA
AGSKVSEALGQGTREAVGTGVRQVPGFGAADALGNRVGEAAHALGNTGHEIGRQAEDVIRHG
ADAVRGSWQGVPGHSGAWETSGGHGIFGSQGGLGGQGQGNPGGLGTPWVHGYPGNSAGSFGM
NPQGAPWGQGGNGGPPNFGTNTQGAVAQPGYGSVRASNQNEGCTNPPPSGSGGGSSNSGGGS
GSQSGSSGSGSNGDNNNGSSSGGSSSGSSSGSSSGGSSGGSSGGSSGNSGGSRGDSGSESSW
GSSTGSSSGNHGGSGGGNGHKPGCEKPGNEARGSGESGIQGFRGQGVSSNMREISKEGNRLL
GGSGDNYRGQGSSWGSGGGDAVGGVNTVNSETSPGMFNFDTFWKNFKSKLGFINWDAINKDQ
RSSRIP

Signal peptide:
amino acids 1-21

N-glycosylation site.
amino acids 265-269

Glycosaminoglycan attachment site.
amino acids 235-239, 237-241, 244-248, 255-259, 324-328, 388-392

Casein kinase II phosphorylation site.
amino acids 26-30, 109-113, 259-263, 300-304, 304-308

N-myristoylation site.
amino acids 17-23, 32-38, 42-48, 50-56, 60-66, 61-67, 64-70, 74-80, 90-96, 96-102, 130-136, 140-146, 149-155, 152-158, 155-161, 159-165, 163-169, 178-184, 190-196, 194-200, 199-205, 218-224, 236-242, 238-244, 239-245, 240-246, 245-251, 246-252, 249-252, 253-259, 256-262, 266-272, 270-276, 271-277, 275-281, 279-285, 283-289, 284-290, 287-293, 288-294, 291-297, 292-298, 295-301, 298-304, 305-311, 311-317, 315-321, 319-325, 322-328, 323-329, 325-331, 343-349, 354-360, 356-362, 374-380, 381-387, 383-389, 387-393, 389-395, 395-401

Cell attachment sequence.
amino acids 301-304

FIGURE 157

CCCACGCGTCCGCCCACGCGTCCGCCCACGCGTCCGCCCACGCGTCCGCCCACGCGTCCGCCCACGCGTCCGCC
CACGCGTCCGGTGCAAGCTCGCGCCGCACACTGCCTGGTGGAGGGAAGGAGCCCGGGCGCCTCTCGCCGCTCCC
CGCGCCGCCGTCCGCACCTCCCCACCGCCCGCCGCCCGCCGCCCGCCGCCCGCAAAGCATGAGTGAGCCCGCTC
TCTGCAGCTGCCCGGGGCGCGAATGGCAGGCTGTTTCCGCGGAGTAAAAGGTGGCGCCGGTCAGTGGTCGTTTC
CAATGACGGACATTAACCAGACTGTCAGATCCTGGGGAGTCGCGAGCCCCGAGTTTGGAGTTTTTTCCCCCCAC
AACGTCACAGTCCGAACTGCAGAGGGAAAGGAAGGCGGCAGGAAGGCGAAGCTCGGGCTCCGGCACGTAGTTGG
GAAACTTGCGGGTCCTAGAAGTCGCCTCCCCGCCTTGCCGGCCGCCCTTGCAGCCCCGAGCCGAGCAGCAAAGT
GAGACATTGTGCGCCTGCCAGATCCGCCGGCCGCGGACCGGGGCTGCCTCGGAAACACAGAGGGGTCTTCTCTC
GCCCTGCATATAATTAGCCTGCACACAAAGGGAGCAGCTGAATGGAGGTTGTCACTCTCTGGAAAAGGATTTCT
GACCGAGCGCTTCCAATGGACATTCTCCAGTCTCTCTGGAAAGATTCTCGCTAATGGATTTCCTGCTGCTCGGT
CTCTGTCTATACTGGCTGCTGAGGAGGCCCTCGGGGGTGGTCTTGTGTCTGCTGGGGGCCTGCTTTCAGATGCT
GCCCGCCGCCCCCAGCGGGTGCCCGCAGCTGTGCCGGTGCGAGGGGCGGCTGCTGTACTGCGAGGCGCTCAACC
TCACCGAGGCGCCCCACAACCTGTCCGGCCTGCTGGGCTTGTCCCTGCGCTACAACAGCCTCTCGGAGCTGCGC
GCCGGCCAGTTCACGGGGTTAATGCAGCTCACGTGGCTCTATCTGGATCACAATCACATCTGCTCCGTGCAGGG
GGACGCCTTTCAGAAACTGCGCCGAGTTAAGGAACTCACGCTGAGTTCCAACCAGATCACCCAACTGCCCAACA
CCACCTTCCGGCCCATGCCCAACCTGCGCAGCGTGGACCTCTCGTACAACAAGCTGCAGGCGCTCGCGCCCGAC
CTCTTCCACGGGCTGCGGAAGCTCACCACGCTGCATATGCGGGCCAACGCCATCCAGTTTGTGCCCGTGCGCAT
CTTCCAGGACTGCCGCAGCCTCAAGTTTCTCGACATCGGATACAATCAGCTCAAGAGTCTGGCGCGCAACTCTT
TCGCCGGCTTGTTTAAGCTCACCGAGCTGCACCTCGAGCACAACGACTTGGTCAAGGTGAACTTCGCCCACTTC
CCGCGCCTCATCTCCCTGCACTCGCTCTGCCTGCGGAGGAACAAGGTGGCCATTGTGGTCAGCTCGCTGGACTG
GGTTTGGAACCTGGAGAAAATGGACTTGTCGGGCAACGAGATCGAGTACATGGAGCCCCATGTGTTCGAGACCG
TGCCGCACCTGCAGTCCCTGCAGCTGGACTCCAACCGCCTCACCTACATCGAGCCCCGGATCCTCAACTCTTGG
AAGTCCCTGACAAGCATCACCCTGGCCGGGAACCTGTGGGATTGCGGGCGCAACGTGTGTGCCCTAGCCTCGTG
GCTCAGCAACTTCCAGGGGCGCTACGATGGCAACTTGCAGTGCGCCAGCCCGGAGTACGCACAGGGCGAGGACG
TCCTGGACGCCGTGTACGCCTTCCACCTGTGCGAGGATGGGGCCGAGCCCACCAGCGGCCACCTGCTCTCGGCC
GTCACCAACCGCAGTGATCTGGGGCCCCCTGCCAGCTCGGCCACCACGCTCGCGGACGGCGGGGAGGGGCAGCA
CGACGGCACATTCGAGCCTGCCACCGTGGCTCTTCCAGGCGGCGAGCACGCCGAGAACGCCGTGCAGATCCACA
AGGTGGTCACGGGCACCATGGCCCTCATCTTCTCCTTCCTCATCGTGGTCCTGGTGCTCTACGTGTCCTGGAAG
TGTTTCCCAGCCAGCCTCAGGCAGCTCAGACAGTGCTTTGTCACGCAGCGCAGGAAGCAAAAGCAGAAACAGAC
CATGCATCAGATGGCTGCCATGTCTGCCCAGGAATACTACGTTGATTACAAACCGAACCACATTGAGGGAGCCC
TGGTGATCATCAACGAGTATGGCTCGTGTACCTGCCACCAGCAGCCCGCGAGGGAATGCGAGGTGTGATTGTCC
CAGTGGCTCTCAACCCATGCGCTACCAAATACGCCTGGGCAGCCGGGACGGCCGGCGGCACCAGGCTGGGGT
CTCCTTGTCTGTGCTCTGATATGCTCCTTGACTGAAACTTTAAGGGGATCTCTCCCAGAGACTTGACATTTTAG
CTTTATTGTGTCTTAAAAACAAAAGCGAATTAAAACACAACAAAAAACCCCACCCCACAACCTTCAGGACAGTC
TATCTTAAATTTCATATGAGAACTCCTTCCTCCCTTTGAAGATCTGTCCATATTCAGGAATCTGAGAGTGTAAA
AAAGGTGGCCATAAGACAGAGAGAGAATAATCGTGCTTTGTTTTATGCTACTCCTCCCACCCTGCCCATGATTA
AACATCATGTATGTAGAAGATCTTAAGTCCATACGCATTTCATGAAGAACCATTGGAAAGAGGAATCTGCAATC
TGGGAGCTTAAGAGCAAATGATGACCATAGAAAGCTATGTTCTTACTTTGTGTGTGTGTCTGTATGTTTCTGCG
TTGTGTGTCTTTGTAGGCAAGCAAACGTTGTCTACACAAACGGGAATTTAGCTCACATCATTTCATGCCCCTGT
GCCTCTAGCTCTGGAGATTGGTGGGGGGAGGTGGGGGGAAACGGCAGGAATAAGGGAAAGTGGTAGTTTTAACT
AAGGTTTTGTAACACTTGAAATCTTTTCTTTCTCAAATTAATTATCTTTAAGCTTCAAGAAACTTGCTCTGACC
CCTCTAAGCAAACTACTAAGCATTTAAAAGAGAATCTAATTTTTAAAGGTGTAGCACCTTTTTTTTTATTCTTC
CCACAGAGGGTGCTAATCTCATTATGCTGTGCTATCTGAAAAGAACTTAAGGCCACAATTCACGTCTCGTCCTG
GGCATTGTGATGGATTGACCCTCCATTTGCAGTACCTTCCCAGCTGATTAAAGTTCAGCAGTGGTATTGAGGTT
TTTCGAATATTTATATAGAAAAAAAGTCTTTTCACATGACAAATGACACTCTCACACCAGTCTTAGCCCTAGTA
GTTTTTTAGGTTGGACCAGAGGAAGCAGGTTAAATGAGACCTGTCCTCTGCTGCACTCAGAAAAAATAGGCAGT
CCCTGATGCTCAGATCTTAGCCTTGATATTAATAGTTGAGACCACCTACCCACAATGCAGCCTATACTCCCAAG
ACTACAAAGTTACCATCGCAAAGGAAAGGTTATTCCAGTAAAAGGAAATAGTTTTCTCAACCATTTAAAAATAT
TCTTCTGAACTCATCAAAGTAGAAGAGCCCCCAACCTTTTCTCTCTGCCTTCAAGAAGGCAGACATTTGGTATG
ATTTAGCATCAACAACACATTTATGAGTATATGTAAGTAATCAGAGGGGCAAATGCCACTTGTTATTCCTCCCA
AGTTTTCCAAGCAAGTACACACAGATCTCTGGTAGGATTAGGGGCCACTTGTGTTTCCGGCTTATTTTAGTCGA
CTTGTCAGCAAGTTTGATGCCTAGTCTATCTGACATGGCCCAGTAGAACAGGGCATTGATGGATCACATGAGAT
GGTAGAAGGAACATCATCACATACCCCTCTCACAGAGAAAATTATCAAAGAACCAGAAATTATATCTGTTTTGG
AGCAAGAGTGTCATAATGTTTCAGGGTAGTCAAAATAAACATAAATTATCTCCTCTAGATGAGTGGCGATGTTG
GCTGATTTGGGTCTGCCATTGACAGAATGTCAAATAAAAAGGAATTAGCTAGAATATGACCATTAAATGTGCTT
CTGAAATATATTTTGAGATAGGTTTAGAATGTCA

FIGURE 158

MDFLLLGLCLYWLLRRPSGVVLCLLGACFQMLPAAPSGCPQLCRCEGRLLYCEALNLTEAPHNLSGLLGLSLRY
NSLSELRAGQFTGLMQLTWLYLDHNHICSVQGDAFQKLRRVKELTLSSNQITQLPNTTFRPMPNLRSVDLSYNK
LQALAPDLFHGLRKLTTLHMRANAIQFVPVRIFQDCRSLKFLDIGYNQLKSLARNSFAGLFKLTELHLEHNDLV
KVNFAHFPRLISLHSLCLRRNKVAIVVSSLDWVWNLEKMDLSGNEIEYMEPHVFETVPHLQSLQLDSNRLTYIE
PRILNSWKSLTSITLAGNLWDCGRNVCALASWLSNFQGRYDGNLQCASPEYAQGEDVLDAVYAFHLCEDGAEPT
SGHLLSAVTNRSDLGPPASSATTLADGGEGQHDGTFEPATVALPGGEHAENAVQIHKVVTGTMALIFSFLIVVL
VLYVSWKCFPASLRQLRQCFVTQRRKQKQKQTMHQMAAMSAQEYYVDYKPNHIEGALVIINEYGSCTCHQQPAR
ECEV

FIGURE 159

CAGAGAGGAGGCTTTGGGAATTGTCCAGCAGAAACAGAGAAGTCTGAGGTGGTGTCAAGACA
AAAGATGCTTCAGCTTTGGAAACTTGTTCTCCTGTGCGGCGTGCTCACTGGGACCTCAGAGTCT
CTTCTTGACAATCTTGGCAATGACCTAAGCAATGTCGTGGATAAGCTGGAACCTGTTCTTCA
CGAGGGACTTGAGACAGTTGACAATACTCTTAAAGGCATCCTTGAGAAACTGAAGGTCGACC
TAGGAGTGCTTCAGAAATCCAGTGCTTGGCAACTGGCCAAGCAGAAGGCCCAGGAAGCTGAG
AAATTGCTGAACAATGTCATTTCTAAGCTGCTTCCAACTAACACGGACATTTTTGGGTTGAA
AATCAGCAACTCCCTCATCCTGGATGTCAAAGCTGAACCGATCGATGATGGCAAAGGCCTTA
ACCTGAGCTTCCCTGTCACCGCGAATGTCACTGTGGCCGGGCCCATCATTGGCCAGATTATC
AACCTGAAAGCCTCCTTGGACCTCCTGACCGCAGTCACAATTGAAACTGATCCCCAGACACA
CCAGCCTGTTGCCGTCCTGGGAGAATGCGCCAGTGACCCAACCAGCATCTCACTTTCCTTGC
TGGACAAACACAGCCAAATCATCAACAAGTTCGTGAATAGCGTGATCAACACGCTGAAAAGC
ACTGTATCCTCCCTGCTGCAGAAGGAGATATGTCCACTGATCCGCATCTTCATCCACTCCCT
GGATGTGAATGTCATTCAGCAGGTCGTCGATAATCCTCAGCACAAAACCCAGCTGCAAACCC
TCATCTGAAGAGGACGAATGAGGAGGACCACTGTGGTGCATGCTGATTGGTTCCCAGTGGCT
TGCCCCACCCCCTTATAGCATCTCCCTCCAGGAAGCTGCTGCCACCACCTAACCAGCGTGAA
AGCCTGAGTCCCACCAGAAGGACCTTCCCAGATACCCCTTCTCCTCACAGTCAGAACAGCAG
CCTCTACACATGTTGTCCTGCCCCTGGCAATAAAGGCCCATTTCTGCACCCTTAA

FIGURE 160

></usr/seqdb2/sst/DNA/Dnaseqs.min/ss.DNA59622
><subunit 1 of 1, 249 aa, 1 stop
><MW: 27011, pI: 5.48, NX(S/T): 2
MLQLWKLVLLCGVLTGTSESLLDNLGNDLSNVVDKLEPVLHEGLETVDNTLKGILEKLKV
DLGVLQKSSAWQLAKQKAQEAEKLLNNVISKLLPTNTDIFGLKISNSLILDVKAEPIDDG
KGLNLSFPVTANVTVAGPIIGQIINLKASLDLLTAVTIETDPQTHQPVAVLGECASDPTS
ISLSLLDKHSQIINKFVNSVINTLKSTVSSLLQKEICPLIRIFIHSLDVNVIQQVVDNPQ
HKTQLQTLI

Important features:
Signal peptide:
Amino acids 1-15

N-glycosylation sites:
Amino acids 124-128;132-136

N-myristoylation sites:
Amino acids 12-18;16-22;26-32;101-107;122-128;141-147

Leucine zipper pattern:
Amino acids 44-66

FIGURE 161

CAGCCACAGACGGGTCATGAGCGCGGTATTACTGCTGGCCCTCCTGGGGTTCATCCTCCCAC
TGCCAGGAGTGCAGGCGCTGCTCTGCCAGTTTGGGACAGTTCAGCATGTGTGGAAGGTGTCC
GACCTACCCCGGCAATGGACCCCTAAGAACACCAGCTGCGACAGCGGCTTGGGGTGCCAGGA
CACGTTGATGCTCATTGAGAGCGGACCCCAAGTGAGCCTGGTGCTCTCCAAGGGCTGCACGG
AGGCCAAGGACCAGGAGCCCCGCGTCACTGAGCACCGGATGGGCCCCGGCCTCTCCCTGATC
TCCTACACCTTCGTGTGCCGCCAGGAGGACTTCTGCAACAACCTCGTTAACTCCCTCCCGCT
TTGGGCCCCACAGCCCCCAGCAGACCCAGGATCCTTGAGGTGCCCAGTCTGCTTGTCTATGG
AAGGCTGTCTGGAGGGGACAACAGAAGAGATCTGCCCCAAGGGGACCACACACTGTTATGAT
GGCCTCCTCAGGCTCAGGGGAGGAGGCATCTTCTCCAATCTGAGAGTCCAGGGATGCATGCC
CCAGCCAGGTTGCAACCTGCTCAATGGGACACAGGAAATTGGGCCCGTGGGTATGACTGAGA
ACTGCAATAGGAAAGATTTTCTGACCTGTCATCGGGGGACCACCATTATGACACACGGAAAC
TTGGCTCAAGAACCCACTGATTGGACCACATCGAATACCGAGATGTGCGAGGTGGGGCAGGT
GTGTCAGGAGACGCTGCTGCTCATAGATGTAGGACTCACATCAACCCTGGTGGGGACAAAAG
GCTGCAGCACTGTTGGGGCTCAAAATTCCCAGAAGACCACCATCCACTCAGCCCCTCCTGGG
GTGCTTGTGGCCTCCTATACCCACTTCTGCTCCTCGGACCTGTGCAATAGTGCCAGCAGCAG
CAGCGTTCTGCTGAACTCCCTCCCTCCTCAAGCTGCCCCTGTCCCAGGAGACCGGCAGTGTC
CTACCTGTGTGCAGCCCCTTGGAACCTGTTCAAGTGGCTCCCCCCGAATGACCTGCCCCAGG
GGCGCCACTCATTGTTATGATGGGTACATTCATCTCTCAGGAGGTGGGCTGTCCACCAAAAT
GAGCATTCAGGGCTGCGTGGCCCAACCTTCCAGCTTCTTGTTGAACCACACCAGACAAATCG
GGATCTTCTCTGCGCGTGAGAAGCGTGATGTGCAGCCTCCTGCCTCTCAGCATGAGGGAGGT
GGGGCTGAGGGCCTGGAGTCTCTCACTTGGGGGGTGGGGCTGGCACTGGCCCCAGCGCTGTG
GTGGGGAGTGGTTTGCCCTTCCTGCTAACTCTATTACCCCCACGATTCTTCACCGCTGCTGA
CCACCCACACTCAACCTCCCTCTGACCTCATAACCTAATGGCCTTGGACACCAGATTCTTTC
CCATTCTGTCCATGAATCATCTTCCCCACACACAATCATTCATATCTACTCACCTAACAGCA
ACACTGGGGAGAGCCTGGAGCATCCGGACTTGCCCTATGGGAGAGGGGACGCTGGAGGAGTG
GCTGCATGTATCTGATAATACAGACCCTGTCCTTTCA

FIGURE 162

```
></usr/seqdb2/sst/DNA/Dnaseqs.min/ss.DNA59847
><subunit 1 of 1, 437 aa, 1 stop
><MW: 46363, pI: 6.22, NX(S/T): 3
MSAVLLLALLGFILPLPGVQALLCQFGTVQHVWKVSDLPRQWTPKNTSCDSGLGCQDTLM
LIESGPQVSLVLSKGCTEAKDQEPRVTEHRMGPGLSLISYTFVCRQEDFCNNLVNSLPLW
APQPPADPGSLRCPVCLSMEGCLEGTTEEICPKGTTHCYDGLLRLRGGGIFSNLRVQGCM
PQPGCNLLNGTQEIGPVGMTENCNRKDFLTCHRGTTIMTHGNLAQEPTDWTTSNTEMCEV
GQVCQETLLLIDVGLTSTLVGTKGCSTVGAQNSQKTTIHSAPPGVLVASYTHFCSSDLCN
SASSSSVLLNSLPPQAAPVPGDRQCPTCVQPLGTCSSGSPRMTCPRGATHCYDGYIHLSG
GGLSTKMSIQGCVAQPSSFLLNHTRQIGIFSAREKRDVQPPASQHEGGGAEGLESLTWGV
GLALAPALWWGVVCPSC
```

Important features of the protein:

Signal peptide:

Amino acids 1-15

Transmembrane domain:

Amino acids 243-260

N-glycosylation sites:

Amino acids 46-50;189-193;382-386

Glycosaminoglycan attachment sites:

Amino acids 51-55;359-363

N-myristoylation sites:

Amino acids 54-60;75-81;141-147;154-160;168-174;169-175;
198-204;254-260;261-267;269-275;284-290;333-339
347-353;360-366;361-367;388-394;408-414;419-425

FIGURE 163

GAGGATTTGCCACAGCAGCGGATAGAGCAGGAGAGCACCACCGGAGCCCTTGAGACATCCTTGAGAAGAGCCAC
AGCATAAGAGACTGCCCTGCTTGGTGTTTTGCAGGATGATGGTGGCCCTTCGAGGAGCTTCTGCATTGCTGGTT
CTGTTCCTTGCAGCTTTTCTGCCCCCGCCGCAGTGTACCCAGGACCCAGCCATGGTGCATTACATCTACCAGCG
CTTTCGAGTCTTGGAGCAAGGGCTGGAAAAATGTACCCAAGCAACGAGGGCATACATTCAAGAATTCCAAGAGT
TCTCAAAAAATATATCTGTCATGCTGGGAAGATGTCAGACCTACACAAGTGAGTACAAGAGTGCAGTGGGTAAC
TTGGCACTGAGAGTTGAACGTGCCCAACGGGAGATTGACTACATACAATACCTTCGAGAGGCTGACGAGTGCAT
CGTATCAGAGGACAAGACACTGGCAGAAATGTTGCTCCAAGAAGCTGAAGAAGAGAAAAAGATCCGGACTCTGC
TGAATGCAAGCTGTGACAACATGCTGATGGGCATAAAGTCTTTGAAAATAGTGAAGAAGATGATGGACACACAT
GGCTCTTGGATGAAAGATGCTGTCTATAACTCTCCAAAGGTGTACTTATTAATTGGATCCAGAAACAACACTGT
TTGGGAATTTGCAAACATACGGGCATTCATGGAGGATAACACCAAGCCAGCTCCCCGGAAGCAAATCCTAACAC
TTTCCTGGCAGGGAACAGGCCAAGTGATCTACAAAGGTTTTCTATTTTTTCATAACCAAGCAACTTCTAATGAG
ATAATCAAATATAACCTGCAGAAGAGGACTGTGGAAGATCGAATGCTGCTCCCAGGAGGGGTAGGCCGAGCATT
GGTTTACCAGCACTCCCCCTCAACTTACATTGACCTGGCTGTGGATGAGCATGGGCTCTGGGCCATCCACTCTG
GGCCAGGCACCCATAGCCATTTGGTTCTCACAAAGATTGAGCCGGGCACACTGGGAGTGGAGCATTCATGGGAT
ACCCCATGCAGAAGCCAGGATGCTGAAGCCTCATTCCTCTTGTGTGGGGTTCTCTATGTGGTCTACAGTACTGG
GGGCCAGGGCCCTCATCGCATCACCTGCATCTATGATCCACTGGGCACTATCAGTGAGGAGGACTTGCCCAACT
TGTTCTTCCCCAAGAGACCAAGAAGTCACTCCATGATCCATTACAACCCCAGAGATAAGCAGCTCTATGCCTGG
AATGAAGGAAACCAGATCATTTACAAACTCCAGACAAAGAGAAAGCTGCCTCTGAAGTAATGCATTACAGCTGT
GAGAAAGAGCACTGTGGCTTTGGCAGCTGTTCTACAGGACAGTGAGGCTATAGCCCCTTCACAATATAGTATCC
CTCTAATCACACACAGGAAGAGTGTGTAGAAGTGGAAATACGTATGCCTCCTTTCCCAAATGTCACTGCCTTAG
GTATCTTCCAAGAGCTTAGATGAGAGCATATCATCAGGAAAGTTTCAACAATGTCCATTACTCCCCCAAACCTC
CTGGCTCTCAAGGATGACCACATTCTGATACAGCCTACTTCAAGCCTTTTGTTTTACTGCTCCCCAGCATTTAC
TGTAACTCTGCCATCTTCCCTCCCACAATTAGAGTTGTATGCCAGCCCCTAATATTCACCACTGGCTTTTCTCT
CCCCTGGCCTTTGCTGAAGCTCTTCCCTCTTTTTCAAATGTCTATTGATATTCTCCCATTTTCACTGCCCAACT
AAAATACTATTAATATTTCTTTCTTTTCTTTTCTTTTTTTTGAGACAAGGTCTCACTATGTTGCCCAGGCTGGT
CTCAAACTCCAGAGCTCAAGAGATCCTCCTGCCTCAGCCTCCTAAGTACCTGGGATTACAGGCATGTGCCACCA
CACCTGGCTTAAAATACTATTTCTTATTGAGGTTTAACCTCTATTTCCCCTAGCCCTGTCCTTCCACTAAGCTT
GGTAGATGTAATAATAAAGTGAAAATATTAACATTTGAATATCGCTTTCCAGGTGTGGAGTGTTTGCACATCAT
TGAATTCTCGTTTCACCTTTGTGAAACATGCACAAGTCTTTACAGCTGTCATTCTAGAGTTTAGGTGAGTAACA
CAATTACAAAGTGAAAGATACAGCTAGAAAATACTACAAATCCCATAGTTTTTCCATTGCCCAAGGAAGCATCA
AATACGTATGTTTGTTCACCTACTCTTATAGTCAATGCGTTCATCGTTTCAGCCTAAAAATAATAGTCTGTCCC
TTTAGCCAGTTTTCATGTCTGCACAAGACCTTTCAATAGGCCTTTCAAATGATAATTCCTCCAGAAAACCAGTC
TAAGGGTGAGGACCCCAACTCTAGCCTCCTCTTGTCTTGCTGTCCTCTGTTTCTCTCTTTCTGCTTTAAATTCA
ATAAAAGTGACACTGAGCAAAAAAAAAAAAAAA

FIGURE 164

MMVALRGASALLVLFLAAFLPPPQCTQDPAMVHYIYQRFRVLEQGLEKCTQATRAYIQEFQEFSKNISVMLGRC
QTYTSEYKSAVGNLALRVERAQREIDYIQYLREADECIVSEDKTLAEMLLQEAEEEKKIRTLLNASCDNMLMGI
KSLKIVKKMMDTHGSWMKDAVYNSPKVYLLIGSRNNTVWEFANIRAFMEDNTKPAPRKQILTLSWQGTGQVIYK
GFLFFHNQATSNEIIKYNLQKRTVEDRMLLPGGVGRALVYQHSPSTYIDLAVDEHGLWAIHSGPGTHSHLVLTK
IEPGTLGVEHSWDTPCRSQDAEASFLLCGVLYVVYSTGGQGPHRITCIYDPLGTISEEDLPNLFFPKRPRSHSM
IHYNPRDKQLYAWNEGNQIIYKLQTKRKLPLK

FIGURE 165

TGGCCTCCCCAGCTTGCCAGGCACAAGGCTGAGCGGGAGGAAGCGAGAGGCATCTAAGCAGGCAGTGTTTTGCC
TTCACCCCAAGTGACCATGAGAGGTGCCACGCGAGTCTCAATCATGCTCCTCCTAGTAACTGTGTCTGACTGTG
CTGTGATCACAGGGGCCTGTGAGCGGGATGTCCAGTGTGGGGCAGGCACCTGCTGTGCCATCAGCCTGTGGCTT
CGAGGGCTGCGGATGTGCACCCCGCTGGGGCGGGAAGGCGAGGAGTGCCACCCCGGCAGCCACAAGGTCCCCTT
CTTCAGGAAACGCAAGCACCACACCTGTCCTTGCTTGCCCAACCTGCTGTGCTCCAGGTTCCCGGACGGCAGGT
ACCGCTGCTCCATGGACTTGAAGAACATCAATTTTTAGGCGCTTGCCTGGTCTCAGGATACCCACCATCCTTTT
CCTGAGCACAGCCTGGATTTTTATTTCTGCCATGAAACCCAGCTCCCATGACTCTCCCAGTCCCTACACTGACT
ACCCTGATCTCTCTTGTCTAGTACGCACATATGCACACAGGCAGACATACCTCCCATCATGACATGGTCCCCAG
GCTGGCCTGAGGATGTCACAGCTTGAGGCTGTGGTGTGAAAGGTGGCCAGCCTGGTTCTCTTCCCTGCTCAGGC
TGCCAGAGAGGTGGTAAATGGCAGAAAGGACATTCCCCCTCCCCTCCCCAGGTGACCTGCTCTCTTTCCTGGGC
CCTGCCCCTCTCCCCACATGTATCCCTCGGTCTGAATTAGACATTCCTGGGCACAGGCTCTTGGGTGCATTGCT
CAGAGTCCCAGGTCCTGGCCTGACCCTCAGGCCCTTCACGTGAGGTCTGTGAGGACCAATTTGTGGGTAGTTCA
TCTTCCCTCGATTGGTTAACTCCTTAGTTTCAGACCACAGACTCAAGATTGGCTCTTCCCAGAGGGCAGCAGAC
AGTCACCCCAAGGCAGGTGTAGGGAGCCCAGGGAGGCCAATCAGCCCCCTGAAGACTCTGGTCCCAGTCAGCCT
GTGGCTTGTGGCCTGTGACCTGTGACCTTCTGCCAGAATTGTCATGCCTCTGAGGCCCCCTCTTACCACACTTT
ACCAGTTAACCACTGAAGCCCCCAATTCCCACAGCTTTTCCATTAAAATGCAAATGGTGGTGGTTCAATCTAAT
CTGATATTGACATATTAGAAGGCAATTAGGGTGTTTCCTTAAACAACTCCTTTCCAAGGATCAGCCCTGAGAGC
AGGTTGGTGACTTTGAGGAGGGCAGTCCTCTGTCCAGATTGGGGTGGGAGCAAGGGACAGGGAGCAGGGCAGGG
GCTGAAAGGGGCACTGATTCAGACCAGGGAGGCAACTACACACCAACATGCTGGCTTTAGAATAAAAGCACCAA
CTGAAAAAA

FIGURE 166

MRGATRVSIMLLLVTVSDCAVITGACERDVQCGAGTCCAISLWLRGLRMCTPLGREGEECHPGSHKVPFFRKRK
HHTCPCLPNLLCSRFPDGRYRCSMDLKNINF

Important feratures:
Signal peptide:
amino acids 1-19

Tyrosine kinase phosphorylation site:
amino acids 88-95

N-myristoylation sites:
amino acids 33-39, 35-41, 46-52

FIGURE 167

AACTCAAACTCCTCTCTCTGGGAAAACGCGGTGCTTGCTCCTCCCGGAGTGGCCTTGGCAGGGTGTTGGAGCCC
TCGGTCTGCCCCGTCCGGTCTCTGGGGCCAAGGCTGGGTTTCCCTCATGTATGGCAAGAGCTCTACTCGTGCGG
TGCTTCTTCTCCTTGGCATACAGCTCACAGCTCTTTGGCCTATAGCAGCTGTGGAAATTTATACCTCCCGGGTG
CTGGAGGCTGTTAATGGGACAGATGCTCGGTTAAAATGCACTTTCTCCAGCTTTGCCCCTGTGGGTGATGCTCT
AACAGTGACCTGGAATTTTCGTCCTCTAGACGGGGGACCTGAGCAGTTTGTATTCTACTACCACATAGATCCCT
TCCAACCCATGAGTGGGCGGTTTAAGGACCGGGTGTCTTGGGATGGGAATCCTGAGCGGTACGATGCCTCCATC
CTTCTCTGGAAACTGCAGTTCGACGACAATGGGACATACACCTGCCAGGTGAAGAACCCACCTGATGTTGATGG
GGTGATAGGGGAGATCCGGCTCAGCGTCGTGCACACTGTACGCTTCTCTGAGATCCACTTCCTGGCTCTGGCCA
TTGGCTCTGCCTGTGCACTGATGATCATAATAGTAATTGTAGTGGTCCTCTTCCAGCATTACCGGAAAAAGCGA
TGGGCCGAAAGAGCTCATAAAGTGGTGGAGATAAAATCAAAAGAAGAGGAAAGGCTCAACCAAGAGAAAAAGGT
CTCTGTTTATTTAGAAGACACAGACTAACAATTTTAGATGGAAGCTGAGATGATTTCCAAGAACAAGAACCCTA
GTATTTCTTGAAGTTAATGGAAACTTTTCTTTGGCTTTTCCAGTTGTGACCCGTTTTCCAACCAGTTCTGCAGC
ATATTAGATTCTAGACAAGCAACACCCCTCTGGAGCCAGCACAGTGCTCCTCCATATCACCAGTCATACACAGC
CTCATTATTAAGGTCTTATTTAATTTCAGAGTGTAAATTTTTTCAAGTGCTCATTAGGTTTTATAAACAAGAAG
CTACATTTTTGCCCTTAAGACACTACTTACAGTGTTATGACTTGTATACACATATATTGGTATCAAAGGGGATA
AAAGCCAATTTGTCTGTTACATTTCCTTTCACGTATTTCTTTTAGCAGCACTTCTGCTACTAAAGTTAATGTGT
TTACTCTCTTTCCTTCCCACATTCTCAATTAAAAGGTGAGCTAAGCCTCCTCGGTGTTTCTGATTAACAGTAAA
TCCTAAATTCAAACTGTTAAATGACATTTTTATTTTTATGTCTCTCCTTAACTATGAGACACATCTTGTTTTAC
TGAATTTCTTTCAATATTCCAGGTGATAGATTTTTGTCG

FIGURE 168

MYGKSSTRAVLLLLGIQLTALWPIAAVEIYTSRVLEAVNGTDARLKCTFSSFAPVGDALTVTWNFRPLDGGPEQ
FVFYYHIDPFQPMSGRFKDRVSWDGNPERYDASILLWKLQFDDNGTYTCQVKNPPDVDGVIGEIRLSVVHTVRF
SEIHFLALAIGSACALMIIIVIVVVLFQHYRKKRWAERAHKVVEIKSKEEERLNQEKKVSVYLEDTD

FIGURE 169

GAGCGAACATGGCAGCGCGTTGGCGGTTTTGGTGTGTCTCTGTGACCATGGTGGTGGCGCTG
CTCATCGTTTGCGACGTTCCCTCAGCCTCTGCCCAAAGAAAGAAGGAGATGGTGTTATCTGA
AAAGGTTAGTCAGCTGATGGAATGGACTAACAAAAGACCTGTAATAAGAATGAATGGAGACA
AGTTCCGTCGCCTTGTGAAAGCCCCACCGAGAAATTACTCCGTTATCGTCATGTTCACTGCT
CTCCAACTGCATAGACAGTGTGTCGTTTGCAAGCAAGCTGATGAAGAATTCCAGATCCTGGC
AAACTCCTGGCGATACTCCAGTGCATTCACCAACAGGATATTTTTTGCCATGGTGGATTTTG
ATGAAGGCTCTGATGTATTTCAGATGCTAAACATGAATTCAGCTCCAACTTTCATCAACTTT
CCTGCAAAAGGGAAACCCAAACGGGGTGATACATATGAGTTACAGGTGCGGGGTTTTTCAGC
TGAGCAGATTGCCCGGTGGATCGCCGACAGAACTGATGTCAATATTAGAGTGATTAGACCCC
CAAATTATGCTGGTCCCCTTATGTTGGGATTGCTTTTGGCTGTTATTGGTGGACTTGTGTAT
CTTCGAAGAAGTAATATGGAATTTCTCTTTAATAAAACTGGATGGGCTTTTGCAGCTTTGTG
TTTTGTGCTTGCTATGACATCTGGTCAAATGTGGAACCATATAAGAGGACCACCATATGCCC
ATAAGAATCCCCACACGGGACATGTGAATTATATCCATGGAAGCAGTCAAGCCCAGTTTGTA
GCTGAAACACACATTGTTCTTCTGTTTAATGGTGGAGTTACCTTAGGAATGGTGCTTTTATG
TGAAGCTGCTACCTCTGACATGGATATTGGAAAGCGAAAGATAATGTGTGTGGCTGGTATTG
GACTTGTTGTATTATTCTTCAGTTGGATGCTCTCTATTTTTAGATCTAAATATCATGGCTAC
CCATACAGCTTTCTGATGAGTTAAAAAGGTCCCAGAGATATATAGACACTGGAGTACTGGAA
ATTGAAAAACGAAAATCGTGTGTGTTTGAAAAGAAGAATGCAACTTGTATATTTTGTATTAC
CTCTTTTTTTCAAGTGATTTAAATAGTTAATCATTTAACCAAAGAAGATGTGTAGTGCCTTA
ACAAGCAATCCTCTGTCAAAATCTGAGGTATTTGAAAATAATTATCCTCTTAACCTTCTCTT
CCCAGTGAACTTTATGGAACATTTAATTTAGTACAATTAAGTATATTATAAAAATTGTAAAA
CTACTACTTTGTTTTAGTTAGAACAAAGCTCAAAACTACTTTAGTTAACTTGGTCATCTGAT
TTTATATTGCCTTATCCAAAGATGGGGAAAGTAAGTCCTGACCAGGTGTTCCCACATATGCC
TGTTACAGATAACTACATTAGGAATTCATTCTTAGCTTCTTCATCTTTGTGTGGATGTGTAT
ACTTTACGCATCTTTCCTTTTGAGTAGAGAAATTATGTGTGTCATGTGGTCTTCTGAAAATG
GAACACCATTCTTCAGAGCACACGTCTAGCCCTCAGCAAGACAGTTGTTTCTCCTCCTCCTT
GCATATTTCCTACTGCGCTCCAGCCTGAGTGATAGAGTGAGACTCTGTCTCAAAAAAAAGTA
TCTCTAAATACAGGATTATAATTTCTGCTTGAGTATGGTGTTAACTACCTTGTATTTAGAAA
GATTTCAGATTCATTCCATCTCCTTAGTTTTCTTTTAAGGTGACCCATCTGTGATAAAAATA
TAGCTTAGTGCTAAAATCAGTGTAACTTATACATGGCCTAAAATGTTTCTACAAATTAGAGT
TTGTCACTTATTCCATTTGTACCTAAGAGAAAAATAGGCTCAGTTAGAAAAGGACTCCCTGG
CCAGGCGCAGTGACTTACGCCTGTAATCTCAGCACTTTGGGAGGCCAAGGCAGGCAGATCAC
GAGGTCAGGAGTTCGAGACCATCCTGGCCAACATGGTGAAACCCCGTCTCTACTAAAAATAT
AAAAATTAGCTGGGTGTGGTGGCAGGAGCCTGTAATCCCAGCTACACAGGAGGCTGAGGCAC
GAGAATCACTTGAACTCAGGAGATGGAGGTTTCAGTGAGCCGAGATCACGCCACTGCACTCC
AGCCTGGCAACAGAGCGAGACTCCATCTCAAAAAAAAAAAAAAA

FIGURE 170

MAARWRFWCVSVTMVVALLIVCDVPSASAQRKKEMVLSEKVSQLMEWTNKRPVIRMNGDKFR
RLVKAPPRNYSVIVMFTALQLHRQCVVCKQADEEFQILANSWRYSSAFTNRIFFAMVDFDEG
SDVFQMLNMNSAPTFINFPAKGKPKRGDTYELQVRGFSAEQIARWIADRTDVNIRVIRPPNY
AGPLMLGLLLAVIGGLVYLRRSNMEFLFNKTGWAFAALCFVLAMTSGQMWNHIRGPPYAHKN
PHTGHVNYIHGSSQAQFVAETHIVLLFNGGVTLGMVLLCEAATSDMDIGKRKIMCVAGIGLV
VLFFSWMLSIFRSKYHGYPYSFLMS

Signal peptide:
amino acids 1-29

Transmembrane domains:
amino acids 183-205, 217-237, 217-287, 301-321

FIGURE 171

CTCCACTGCAACCACCCAGAGCCATGGCTCCCCGAGGCTGCATCGTAGCTGTCTTTGCCATTTTCTGCATCTCC
AGGCTCCTCTGCTCACACGGAGCCCCAGTGGCCCCCATGACTCCTTACCTGATGCTGTGCCAGCCACACAAGAG
ATGTGGGGACAAGTTCTACGACCCCCTGCAGCACTGTTGCTATGATGATGCCGTCGTGCCCTTGGCCAGGACCC
AGACGTGTGGAAACTGCACCTTCAGAGTCTGCTTTGAGCAGTGCTGCCCCTGGACCTTCATGGTGAAGCTGATA
AACCAGAACTGCGACTCAGCCCGGACCTCGGATGACAGGCTTTGTCGCAGTGTCAGCTAATGGAACATCAGGGG
AACGATGACTCCTGGATTCTCCTTCCTGGGTGGGCCTGGAGAAAGAGGCTGGTGTTACCTGAGATCTGGGATGC
TGAGTGGCTGTTTGGGGGCCAGAGAAACACACACTCAACTGCCCACTTCATTCTGTGACCTGTCTGAGGCCCAC
CCTGCAGCTGCCCTGAGGAGGCCCACAGGTCCCCTTCTAGAATTCTGGACAGCATGAGATGCGTGTGCTGATGG
GGGCCCAGGGACTCTGAACCCTCCTGATGACCCCTATGGCCAACATCAACCCGGCACCACCCCAAGGCTGGCTG
GGGAACCCTTCACCCTTCTGTGAGATTTTCCATCATCTCAAGTTCTCTTCTATCCAGGAGCAAAGCACAGGATC
ATAATAAATTTATGTACTTTATAAATGAAAA

FIGURE 172

MAPRGCIVAVFAIFCISRLLCSHGAPVAPMTPYLMLCQPHKRCGDKFYDPLQHCCYDDAVVPLARTQTCGNCTF
RVCFEQCCPWTFMVKLINQNCDSARTSDDRLCRSVS

Important features:
Signal peptide:
amino acids 1-24

FIGURE 173

GGGGGCGGGTGCCTGGAGCACGGCGCTGGGGCCGCCCGCAGCGCTCACTCGCTCGCACTCAG
TCGCGGGAGGCTTCCCCGCGCCGGCCGCGTCCCGCCCGCTCCCCGGCACCAGAAGTTCCTCT
GCGCGTCCGACGGCGACATGGGCGTCCCCACGGCCCTGGAGGCCGGCAGCTGGCGCTGGGGA
TCCCTGCTCTTCGCTCTCTTCCTGGCTGCGTCCCTAGGTCCGGTGGCAGCCTTCAAGGTCGC
CACGCCGTATTCCCTGTATGTCTGTCCCGAGGGGCAGAACGTCACCCTCACCTGCAGGCTCT
TGGGCCCTGTGGACAAAGGGCACGATGTGACCTTCTACAAGACGTGGTACCGCAGCTCGAGG
GGCGAGGTGCAGACCTGCTCAGAGCGCCGGCCCATCCGCAACCTCACGTTCCAGGACCTTCA
CCTGCACCATGGAGGCCACCAGGCTGCCAACACCAGCCACGACCTGGCTCAGCGCCACGGGC
TGGAGTCGGCCTCCGACCACCATGGCAACTTCTCCATCACCATGCGCAACCTGACCCTGCTG
GATAGCGGCCTCTACTGCTGCCTGGTGGTGGAGATCAGGCACCACCACTCGGAGCACAGGGT
CCATGGTGCCATGGAGCTGCAGGTGCAGACAGGCAAAGATGCACCATCCAACTGTGTGGTGT
ACCCATCCTCCTCCCAGGATAGTGAAAACATCACGGCTGCAGCCCTGGCTACGGGTGCCTGC
ATCGTAGGAATCCTCTGCCTCCCCCTCATCCTGCTCCTGGTCTACAAGCAAAGGCAGGCAGC
CTCCAACCGCCGTGCCCAGGAGCTGGTGCGGATGGACAGCAACATTCAAGGGATTGAAAACC
CCGGCTTTGAAGCCTCACCACCTGCCCAGGGGATACCCGAGGCCAAAGTCAGGCACCCCCTG
TCCTATGTGGCCCAGCGGCAGCCTTCTGAGTCTGGGCGGCATCTGCTTTCGGAGCCCAGCAC
CCCCCTGTCTCCTCCAGGCCCCGGAGACGTCTTCTTCCCATCCCTGGACCCTGTCCCTGACT
CTCCAAACTTTGAGGTCATCTAGCCCAGCTGGGGGACAGTGGGCTGTTGTGGCTGGGTCTGG
GGCAGGTGCATTTGAGCCAGGGCTGGCTCTGTGAGTGGCCTCCTTGGCCTCGGCCCTGGTTC
CCTCCCTCCTGCTCTGGGCTCAGATACTGTGACATCCCAGAAGCCCAGCCCCTCAACCCCTC
TGGATGCTACATGGGGATGCTGGACGGCTCAGCCCCTGTTCCAAGGATTTTGGGGTGCTGAG
ATTCTCCCCTAGAGACCTGAAATTCACCAGCTACAGATGCCAAATGACTTACATCTTAAGAA
GTCTCAGAACGTCCAGCCCTTCAGCAGCTCTCGTTCTGAGACATGAGCCTTGGGATGTGGCA
GCATCAGTGGGACAAGATGGACACTGGGCCACCCTCCCAGGCACCAGACACAGGGCACGGTG
GAGAGACTTCTCCCCCGTGGCCGCCTTGGCTCCCCCGTTTTGCCCGAGGCTGCTCTTCTGTC
AGACTTCCTCTTTGTACCACAGTGGCTCTGGGGCCAGGCCTGCCTGCCCACTGGCCATCGCC
ACCTTCCCCAGCTGCCTCCTACCAGCAGTTTCTCTGAAGATCTGTCAACAGGTTAAGTCAAT
CTGGGGCTTCCACTGCCTGCATTCCAGTCCCCAGAGCTTGGTGGTCCCGAAACGGGAAGTAC
ATATTGGGGCATGGTGGCCTCCGTGAGCAAATGGTGTCTTGGGCAATCTGAGGCCAGGACAG
ATGTTGCCCCACCCACTGGAGATGGTGCTGAGGGAGGTGGGTGGGGCCTTCTGGGAAGGTGA
GTGGAGAGGGGCACCTGCCCCCCGCCCTCCCCATCCCCTACTCCCACTGCTCAGCGCGGGCC
ATTGCAAGGGTGCCACACAATGTCTTGTCCACCCTGGGACACTTCTGAGTATGAAGCGGGAT
GCTATTAAAAACTACATGGGGAAAAAAAAAAAAAAAAAAAAAAAAAAAAAAAAAAAAAAAGA

FIGURE 174

></usr/seqdb2/sst/DNA/Dnaseqs.min/ss.DNA64897
><subunit 1 of 1, 311 aa, 1 stop
><MW: 33908, pI: 6.87, NX(S/T): 6
MGVPTALEAGSWRWGSLLFALFLAASLGPVAAFKVATPYSLYVCPEGQNVTLTCRLLGPVDK
GHDVTFYKTWYRSSRGEVQTCSERRPIRNLTFQDLHLHHGGHQAANTSHDLAQRHGLESASD
HHGNFSITMRNLTLLDSGLYCCLVVEIRHHHSEHRVHGAMELQVQTGKDAPSNCVVYPSSSQ
DSENITAAALATGACIVGILCLPLILLLVYKQRQAASNRRAQELVRMDSNIQGIENPGFEAS
PPAQGIPEAKVRHPLSYVAQRQPSESGRHLLSEPSTPLSPPGPGDVFFPSLDPVPDSPNFEVI

Signal peptide:
amino acids 1-28

Transmembrane domain:
amino acids 190-216

FIGURE 175

CTAGCCTGCGCCAAGGGGTAGTGAGACCGCGCGGCAACAGCTTGCGGCTGCGGGGAGCTCCCGTGGGCGCTCCG
CTGGCTGTGCAGGCGGCCATGGATTCCTTGCGGAAAATGCTGATCTCAGTCGCAATGCTGGGCGCAGGGGCTGG
CGTGGGCTACGCGCTCCTCGTTATCGTGACCCCGGGAGAGCGGCGGAAGCAGGAAATGCTAAAGGAGATGCCAC
TGCAGGACCCAAGGAGCAGGGAGGAGGCGGCCAGGACCCAGCAGCTATTGCTGGCCACTCTGCAGGAGGCAGCG
ACCACGCAGGAGAACGTGGCCTGGAGGAAGAACTGGATGGTTGGCGGCGAAGGCGGCGCCAGCGGGAGGTCACC
GTGAGACCGGACTTGCCTCCGTGGGCGCCGGACCTTGGCTTGGGCGCAGGAATCCGAGGCAGCCTTTCTCCTTC
GTGGGCCCAGCGGAGAGTCCGGACCGAGATACCATGCCAGGACTCTCCGGGGTCCTGTGAGCTGCCGTCGGGTG
AGCACGTTTCCCCCAAACCCTGGACTGACTGCTTTAAGGTCCGCAAGGCGGGCCAGGGCCGAGACGCGAGTCGG
ATGTGGTGAACTGAAAGAACCAATAAAATCATGTTCCTCCAAAAAAAAAAAAAAAAAAAAAAAAAAAAAAAAAAA
AAAAAAAAAAAAAAAAAAAAAAAAAAA

FIGURE 176

MDSLRKMLISVAMLGAGAGVGYALLVIVTPGERRKQEMLKEMPLQDPRSREEAARTQQLLLATLQEAATTQENV
AWRKNWMVGGEGGASGRSP

Important features:
Signal peptide:
amino acids 1-18

FIGURE 177

GCCAGGCAGGTGGGCCTCAGGAGGTGCCTCCAGGCGGCCAGTGGGCCTGAGGCCCCAGCAAG
GGCTAGGGTCCATCTCCAGTCCCAGGACACAGCAGCGGCCACCATGGCCACGCCTGGGCTCC
AGCAGCATCAGAGCAGCCCCTGTGGTTGGCAGCAAAGTTCAGCTTGGCTGGGCCCGCTGTGA
GGGGCTTCGCGCTACGCCCTGCGGTGTCCCGAGGGCTGAGGTCTCCTCATCTTCTCCCTAGC
AGTGGATGAGCAACCCAACGGGGGCCCGGGGAGGGGAACTGGCCCCGAGGGAGAGGAACCCC
AAAGCCACATCTGTAGCCAGGATGAGCAGTGTGAATCCAGGCAGCCCCCAGGACCGGGGAGG
CACAGGTGGCCCCCACCACCCGGAGGAGCAGCTCCTGCCCCTGTCCGGGGGATGACTGATTC
TCCTCCGCCAGGCCACCCAGAGGAGAAGGCCACCCCGCCTGGAGGCACAGGCCATGAGGGGC
TCTCAGGAGGTGCTGCTGATGTGGCTTCTGGTGTTGGCAGTGGGCGGCACAGAGCACGCCTA
CCGGCCCGGCCGTAGGGTGTGTGCTGTCCGGGCTCACGGGGACCCTGTCTCCGAGTCGTTCG
TGCAGCGTGTGTACCAGCCCTTCCTCACCACCTGCGACGGGCACCGGGCCTGCAGCACCTAC
CGAACCATCTATAGGACCGCCTACCGCCGCAGCCCTGGGCTGGCCCCTGCCAGGCCTCGCTA
CGCGTGCTGCCCCGGCTGGAAGAGGACCAGCGGGCTTCCTGGGGCCTGTGGAGCAGCAATAT
GCCAGCCGCCATGCCGGAACGGAGGGAGCTGTGTCCAGCCTGGCCGCTGCCGCTGCCCTGCA
GGATGGCGGGGTGACACTTGCCAGTCAGATGTGGATGAATGCAGTGCTAGGAGGGGCGGCTG
TCCCCAGCGCTGCATCAACACCGCCGGCAGTTACTGGTGCCAGTGTTGGGAGGGGCACAGCC
TGTCTGCAGACGGTACACTCTGTGTGCCCAAGGGAGGGCCCCCCAGGGTGGCCCCCAACCCG
ACAGGAGTGGACAGTGCAATGAAGGAAGAAGTGCAGAGGCTGCAGTCCAGGGTGGACCTGCT
GGAGGAGAAGCTGCAGCTGGTGCTGGCCCCACTGCACAGCCTGGCCTCGCAGGCACTGGAGC
ATGGGCTCCCGGACCCCGGCAGCCTCCTGGTGCACTCCTTCCAGCAGCTCGGCCGCATCGAC
TCCCTGAGCGAGCAGATTTCCTTCCTGGAGGAGCAGCTGGGGTCCTGCTCCTGCAAGAAAGA
CTCGTGACTGCCCAGCGCTCCAGGCTGGACTGAGCCCCTCACGCCGCCCTGCAGCCCCCATG
CCCCTGCCCAACATGCTGGGGGTCCAGAAGCCACCTCGGGGTGACTGAGCGGAAGGCCAGGC
AGGGCCTTCCTCCTCTTCCTCCTCCCCTTCCTCGGGAGGCTCCCCAGACCCTGGCATGGGAT
GGGCTGGGATCTTCTCTGTGAATCCACCCCTGGCTACCCCCACCCTGGCTACCCCAACGGCA
TCCCAAGGCCAGGTGGACCCTCAGCTGAGGGAAGGTACGAGCTCCCTGCTGGAGCCTGGGAC
CCATGGCACAGGCCAGGCAGCCCGGAGGCTGGGTGGGGCCTCAGTGGGGGCTGCTGCCTGAC
CCCCAGCACAATAAAAATGAAACGTG

FIGURE 178

MRGSQEVLLMWLLVLAVGGTEHAYRPGRRVCAVRAHGDPVSESFVQRVYQPFLTTCDGHRAC
STYRTIYRTAYRRSPGLAPARPRYACCPGWKRTSGLPGACGAAICQPPCRNGGSCVQPGRCR
CPAGWRGDTCQSDVDECSARRGGCPQRCINTAGSYWCQCWEGHSLSADGTLCVPKGGPPRVA
PNPTGVDSAMKEEVQRLQSRVDLLEEKLQLVLAPLHSLASQALEHGLPDPGSLLVHSFQQLG
RIDSLSEQISFLEEQLGSCSCKKDS

Signal sequence:
1-19

FIGURE 179

GACAGCTGTGTCTCGATGGAGTAGACTCTCAGAACAGCGCAGTTTGCCCTCCGCTCACGCAG
AGCCTCTCCGTGGCTTCCGCACCTTGAGCATTAGGCCAGTTCTCCTCTTCTCTCTAATCCAT
CCGTCACCTCTCCTGTCATCCGTTTCCATGCCGTGAGGTCCATTCACAGAACACATCCATGG
CTCTCATGCTCAGTTTGGTTCTGAGTCTCCTCAAGCTGGGATCAGGGCAGTGGCAGGTGTTT
GGGCCAGACAAGCCTGTCCAGGCCTTGGTGGGGGAGGACGCAGCATTCTCCTGTTTCCTGTC
TCCTAAGACCAATGCAGAGGCCATGGAAGTGCGGTTCTTCAGGGGCCAGTTCTCTAGCGTGG
TCCACCTCTACAGGGACGGGAAGGACCAGCCATTTATGCAGATGCCACAGTATCAAGGCAGG
ACAAAACTGGTGAAGGATTCTATTGCGGAGGGGCGCATCTCTCTGAGGCTGGAAAACATTAC
TGTGTTGGATGCTGGCCTCTATGGGTGCAGGATTAGTTCCCAGTCTTACTACCAGAAGGCCA
TCTGGGAGCTACAGGTGTCAGCACTGGGCTCAGTTCCTCTCATTTCCATCACGGGATATGTT
GATAGAGACATCCAGCTACTCTGTCAGTCCTCGGGCTGGTTCCCCCGGCCCACAGCGAAGTG
GAAAGGTCCACAAGGACAGGATTTGTCCACAGACTCCAGGACAAACAGAGACATGCATGGCC
TGTTTGATGTGGAGATCTCTCTGACCGTCCAAGAGAACGCCGGGAGCATATCCTGTTCCATG
CGGCATGCTCATCTGAGCCGAGAGGTGGAATCCAGGGTACAGATAGGAGATACCTTTTTCGA
GCCTATATCGTGGCACCTGGCTACCAAAGTACTGGGAATACTCTGCTGTGGCCTATTTTTTG
GCATTGTTGGACTGAAGATTTTCTTCTCCAAATTCCAGTGGAAAATCCAGGCGGAACTGGAC
TGGAGAAGAAAGCACGGACAGGCAGAATTGAGAGACGCCCGGAAACACGCAGTGGAGGTGAC
TCTGGATCCAGAGACGGCTCACCCGAAGCTCTGCGTTTCTGATCTGAAAACTGTAACCCATA
GAAAAGCTCCCCAGGAGGTGCCTCACTCTGAGAAGAGATTTACAAGGAAGAGTGTGGTGGCT
TCTCAGAGTTTCCAAGCAGGGAAACATTACTGGGAGGTGGACGGAGGACACAATAAAAGGTG
GCGCGTGGGAGTGTGCCGGGATGATGTGGACAGGAGGAAGGAGTACGTGACTTTGTCTCCCG
ATCATGGGTACTGGGTCCTCAGACTGAATGGAGAACATTTGTATTTCACATTAAATCCCCGT
TTTATCAGCGTCTTCCCCAGGACCCCACCTACAAAAATAGGGGTCTTCCTGGACTATGAGTG
TGGGACCATCTCCTTCTTCAACATAAATGACCAGTCCCTTATTTATACCCTGACATGTCGGT
TTGAAGGCTTATTGAGGCCCTACATTGAGTATCCGTCCTATAATGAGCAAAATGGAACTCCC
ATAGTCATCTGCCCAGTCACCCAGGAATCAGAGAAAGAGGCCTCTTGGCAAAGGGCCTCTGC
AATCCCAGAGACAAGCAACAGTGAGTCCTCCTCACAGGCAACCACGCCCTTCCTCCCCAGGG
GTGAAATGTAGGATGAATCACATCCCACATTCTTCTTTAGGGATATTAAGGTCTCTCTCCCA
GATCCAAAGTCCCGCAGCAGCCGGCCAAGGTGGCTTCCAGATGAAGGGGGACTGGCCTGTCC
ACATGGGAGTCAGGTGTCATGGCTGCCCTGAGCTGGGAGGGAAGAAGGCTGACATTACATTT
AGTTTGCTCTCACTCCATCTGGCTAAGTGATCTTGAAATACCACCTCTCAGGTGAAGAACCG
TCAGGAATTCCCATCTCACAGGCTGTGGTGTAGATTAAGTAGACAAGGAATGTGAATAATGC
TTAGATCTTATTGATGACAGAGTGTATCCTAATGGTTTGTTCATTATATTACACTTTCAGTA
AAAAAA

FIGURE 180

MALMLSLVLSLLKLGSGQWQVFGPDKPVQALVGEDAAFSCFLSPKTNAEAMEVRFFRGQFSS
VVHLYRDGKDQPFMQMPQYQGRTKLVKDSIAEGRISLRLENITVLDAGLYGCRISSQSYYQK
AIWELQVSALGSVPLISITGYVDRDIQLLCQSSGWFPRPTAKWKGPQGQDLSTDSRTNRDMH
GLFDVEISLTVQENAGSISCSMRHAHLSREVESRVQIGDTFFEPISWHLATKVLGILCCGLF
FGIVGLKIFFSKFQWKIQAELDWRRKHGQAELRDARKHAVEVTLDPETAHPKLCVSDLKTVT
HRKAPQEVPHSEKRFTRKSVVASQSFQAGKHYWEVDGGHNKRWRVGVCRDDVDRRKEYVTLS
PDHGYWVLRLNGEHLYFTLNPRFISVFPRTPPTKIGVFLDYECGTISFFNINDQSLIYTLTC
RFEGLLRPYIEYPSYNEQNGTPIVICPVTQESEKEASWQRASAIPETSNSESSSQATTPFLP
RGEM

Signal peptide:
amino acids 1-17

Transmembrane domain:
amino acids 239-255

FIGURE 181

GCGATGGTGCGCCCGGTGGCGGTGGCGGCGGCGGTTGCGGAGGCTTCCTTGGTCGGATTGCAACGAGGAGAAGA
TGACTGACCAACCGACTGGCTGAATGAATGAATGGCGGAGCCGAGCGCGCCATGAGGAGCCTGCCGAGCCTGGG
CGGCCTCGCCCTGTTGTGCTGCGCCGCCGCCGCCGCCGCCGTCGCCTCAGCCGCCTCGGCGGGGAATGTCACCG
GTGGCGGCGGGGCCGCGGGGCAGGTGGACGCGTCGCCGGGCCCCGGGTTGCGGGGCGAGCCCAGCCACCCCTTC
CCTAGGGCGACGGCTCCCACGGCCCAGGCCCCGAGGACCGGGCCCCCGCGCGCCACCGTCCACCGACCCCTGGC
TGCGACTTCTCCAGCCCAGTCCCCGGAGACCACCCCTCTTTGGGCGACTGCTGGACCCTCTTCCACCACCTTTC
AGGCGCCGCTCGGCCCCTCGCCGACCACCCCTCCGGCGGCGGAACGCACTTCGACCACCTCTCAGGCGCCGACC
AGACCCGCGCCGACCACCCTTTCGACGACCACTGGCCCGGCGCCGACCACCCCTGTAGCGACCACCGTACCGGC
GCCCACGACTCCCCGGACCCCGACCCCCGATCTCCCCAGCAGCAGCAACAGCAGCGTCCTCCCCACCCCACCTG
CCACCGAGGCCCCCTCTTCGCCTCCTCCAGAGTATGTATGTAACTGCTCTGTGGTTGGAAGCCTGAATGTGAAT
CGCTGCAACCAGACCACAGGGCAGTGTGAGTGTCGGCCAGGTTATCAGGGGCTTCACTGTGAAACCTGCAAAGA
GGGCTTTTACCTAAATTACACTTCTGGGCTCTGTCAGCCATGTGACTGTAGTCCACATGGAGCTCTCAGCATAC
CGTGCAACAGGTAAGCAACAGAGGGTGGAACTGAAGTTTATTTTATTTTAGCAAGGGAAAAAAAAAGGCTGCTA
CTCTCAAGGACCATACTGGTTTAAACAAAGGAGGATGAGGGTCATAGATTTACAAAATATTTTATATACTTTTA
TTCTCTTACTTTATATGTTATATTTAATGTCAGGATTTAAAAACATCTAATTTACTGATTTAGTTCTTCAAAAG
CACTAGAGTCGCCAATTTTTCTCTGGGATAATTTCTGTAAATTTCATGGGAAAAAATTATTGAAGAATAAATCT
GCTTTCTGGAAGGGCTTTCAGGCATGAAACCTGCTAGGAGGTTTAGAAATGTTCTTATGTTTATTAATATACCA
TTGGAGTTTGAGGAAATTTGTTGTTTGGTTTATTTTTCTCTCTAATCAAAATTCTACATTTGTTTCTTTGGACA
TCTAAAGCTTAACCTGGGGGTACCCTAATTTATTTAACTAGTGGTAAGTAGACTGGTTTTACTCTATTTACCAG
TACATTTTTGAGACCAAAAGTAGATTAAGCAGGAATTATCTTTAAACTATTATGTTATTTGGAGGTAATTTAAT
CTAGTGGAATAATGTACTGTTATCTAAGCATTTGCCTTGTACTGCACTGAAAGTAATTATTCTTTGACCTTATG
TGAGGCACTTGGCTTTTTGTGGACCCCAAGTCAAAAAACTGAAGAGACAGTATTAAATAATGAAAAAAATAATG
ACAGGTTATACTCAGTGTAACCTGGGTATAACCCAAGATCTGCTGCCACTTACGAGCTGTGTTCCTTGGGCAAG
TAATTTCCTTTCACTGAGCTTGTTTCTTCTCAAGGTTGTTGTGAAGATTAAATGAGTTGATATATATAAAATGC
CTAGCACATGTCACTCAATAAATTCTGGTTTGTTTTAATTTCAAAGGAATATTATGGACTGAAATGAGAGAACA
TGTTTTAAGAACTTTTAGCTCCTTGACAAAGAAGTGCTTTATACTTTAGCACTAAATATTTTAAATGCTTTATA
AATGATATTATACTGTTATGGAATATTGTATCATATTGTAGTTTATTAAAAATGTAGAAGAGGCTGGGCGCGGT
GGCTCACGCCTGTAATCCTAGCACTTTGGGAGGCCAAGGCGGGTGGATCACTTGAGGCCAGGAGTTCTAGATGA
GCCTGGCCAGCACAGTGAAACCCCGTCTCTACTAAAAATACAAACAAATTAGCTGGGCGTGGTGGCACACACCT
GTAGTCCCAGCTACTCGGGAGGCTGAGGCAGGAGAATCGGTTGAACCCGGGAGGTGGAGGTTGCAGTGAGCTGA
GATCGCGCCACTGCACTCCAGCCTGGTGAGAGAGGGAGACTCTGTCTTAAAAAAAAAAAAAAAAAAAAAAAAA

FIGURE 182

></usr/seqdb2/sst/DNA/Dnaseqs.min/ss.DNA64952
><subunit 1 of 1, 258 aa, 1 stop
><MW: 25716, pI: 8.13, NX(S/T): 5
MRSLPSLGGLALLCCAAAAAAVASAASAGNVTGGGGAAGQVDASPGPGLRGEPSHPFPRATA
PTAQAPRTGPPRATVHRPLAATSPAQSPETTPLWATAGPSSTTFQAPLGPSPTTPPAAERTS
TTSQAPTRPAPTTLSTTTGPAPTTPVATTVPAPTTPRTPTPDLPSSSNSSVLPTPPATEAPS
SPPPEYVCNCSVVGSLNVNRCNQTTGQCECRPGYQGLHCETCKEGFYLNYTSGLCQPCDCSP
HGALSIPCNR

Important features of the protein:
Signal peptide:
amino acids 1-25

N-glycosylation sites.
amino acids 30-33, 172-175, 195-198, 208-211, 235-238

EGF-like domain cysteine pattern signature.
amino acids 214-226.

FIGURE 183

TGCGGCGCAGTGTAGACCTGGGAGGATGGGCGGCCTGCTGCTGGCTGCTTTTCTGGCTTTGGTCTCGGTGCCCA
GGGCCCAGGCCGTGTGGTTGGGAAGACTGGACCCTGAGCAGCTTCTTGGGCCCTGGTACGTGCTTGCGGTGGCC
TCCCGGGAAAAGGGCTTTGCCATGGAGAAGGACATGAAGAACGTCGTGGGGGTGGTGGTGACCCTCACTCCAGA
AAACAACCTGCGGACGCTGTCCTCTCAGCACGGGCTGGGAGGGTGTGACCAGAGTGTCATGGACCTGATAAAGC
GAAACTCCGGATGGGTGTTTGAGAATCCCTCAATAGGCGTGCTGGAGCTCTGGGTGCTGGCCACCAACTTCAGA
GACTATGCCATCATCTTCACTCAGCTGGAGTTCGGGGACGAGCCCTTCAACACCGTGGAGCTGTACAGTCTGAC
GGAGACAGCCAGCCAGGAGGCCATGGGGCTCTTCACCAAGTGGAGCAGGAGCCTGGGCTTCCTGTCACAGTAGC
AGGCCCAGCTGCAGAAGGACCTCACCTGTGCTCACAAGATCCTTCTGTGAGTGCTGCGTCCCCAGTAGGGATGG
CGCCCACAGGGTCCTGTGACCTCGGCCAGTGTCCACCCACCTCGCTCAGCGGCTCCCGGGGCCCAGCACCAGCT
CAGAATAAAGCGATTCCACAGCA

FIGURE 184

MGGLLLAAFLALVSVPRAQAVWLGRLDPEQLLGPWYVLAVASREKGFAMEKDMKNVVGVVVTLTPENNLRTLSS
QHGLGGCDQSVMDLIKRNSGWVFENPSIGVLELWVLATNFRDYAIIFTQLEFGDEPFNTVELYSLTETASQEAM
GLFTKWSRSLGFLSQ

Important features:
Signal peptide:
amino acids 1-20

FIGURE 185

GTTCCGCAGATGCAGAGGTTGAGGTGGCTGCGGGACTGGAAGTCATCGGGCAGAGGTCTCACAGCAGCCAAGGA
ACCTGGGGCCCGCTCCTCCCCCCTCCAGGCCATGAGGATTCTGCAGTTAATCCTGCTTGCTCTGGCAACAGGGC
TTGTAGGGGGAGAGACCAGGATCATCAAGGGGTTCGAGTGCAAGCCTCACTCCCAGCCCTGGCAGGCAGCCCTG
TTCGAGAAGACGCGGCTACTCTGTGGGGCGACGCTCATCGCCCCCAGATGGCTCCTGACAGCAGCCCACTGCCT
CAAGCCCCGCTACATAGTTCACCTGGGGCAGCACAACCTCCAGAAGGAGGAGGGCTGTGAGCAGACCCGGACAG
CCACTGAGTCCTTCCCCCACCCCGGCTTCAACAACAGCCTCCCCAACAAAGACCACCGCAATGACATCATGCTG
GTGAAGATGGCATCGCCAGTCTCCATCACCTGGGCTGTGCGACCCCTCACCCTCTCCTCACGCTGTGTCACTGC
TGGCACCAGCTGCCTCATTTCCGGCTGGGGCAGCACGTCCAGCCCCCAGTTACGCCTGCCTCACACCTTGCGAT
GCGCCAACATCACCATCATTGAGCACCAGAAGTGTGAGAACGCCTACCCCGGCAACATCACAGACACCATGGTG
TGTGCCAGCGTGCAGGAAGGGGGCAAGGACTCCTGCCAGGGTGACTCCGGGGGCCCTCTGGTCTGTAACCAGTC
TCTTCAAGGCATTATCTCCTGGGGCCAGGATCCGTGTGCGATCACCCGAAAGCCTGGTGTCTACACGAAAGTCT
GCAAATATGTGGACTGGATCCAGGAGACGATGAAGAACAATTAGACTGGACCCACCCACCACAGCCCATCACCC
TCCATTTCCACTTGGTGTTTGGTTCCTGTTCACTCTGTTAATAAGAAACCCTAAGCCAAGACCCTCTACGAACA
TTCTTTGGGCCTCCTGGACTACAGGAGATGCTGTCACTTAATAATCAACCTGGGGTTCGAAATCAGTGAGACCT
GGATTCAAATTCTGCCTTGAAATATTGTGACTCTGGGAATGACAACACCTGGTTTGTTCTCTGTTGTATCCCCA
GCCCCAAAGACAGCTCCTGGCCATATATCAAGGTTTCAATAAATATTTGCTAAATGAAAAAAAAAAAAAAAAAA
AAAAAAAAAAAAAAAAAAAA

FIGURE 186

MRILQLILLALATGLVGGETRIIKGFECKPHSQPWQAALFEKTRLLCGATLIAPRWLLTAAHCLKPRYIVHLGQ
HNLQKEEGCEQTRTATESFPHPGFNNSLPNKDHRNDIMLVKMASPVSITWAVRPLTLSSRCVTAGTSCLISGWG
STSSPQLRLPHTLRCANITIIEHQKCENAYPGNITDTMVCASVQEGGKDSCQGDSGGPLVCNQSLQGIISWGQD
PCAITRKPGVYTKVCKYVDWIQETMKNN

Important features:
Signal peptide:
amino acids 1-18

Serine proteases, trypsin family, histidine active site.
amino acids 58-63

N-glycosylation sites.
amino acids 99-102, 165-168, 181-184, 210-213

Glycosaminoglycan attachment site.
amino acids 145-148

Kringle domain proteins.
amino acids 197-209, 47-64

Serine proteases, trypsin family, histidine protein
amino acids 199-209, 47-63, 220-243

Apple domain proteins
amino acids 222-249, 189-222

FIGURE 187

GCTCAAGTGCCCTGCCTTGCCCCACCCAGCCCAGCCTGGCCAGAGCCCCCTGGAGAAGGAGC
TCTCTTCTTGCTTGGCAGCTGGACCAAGGGAGCCAGTCTTGGGCGCTGGAGGGCCTGTCCTG
ACCATGGTCCCTGCCTGGCTGTGGCTGCTTTGTGTCTCCGTCCCCCAGGCTCTCCCCAAGGC
CCAGCCTGCAGAGCTGTCTGTGGAAGTTCCAGAAAACTATGGTGGAAATTTCCCTTTATACC
TGACCAAGTTGCCGCTGCCCCGTGAGGGGGCTGAAGGCCAGATCGTGCTGTCAGGGGACTCA
GGCAAGGCAACTGAGGGCCCATTTGCTATGGATCCAGATTCTGGCTTCCTGCTGGTGACCAG
GGCCCTGGACCGAGAGGAGCAGGCAGAGTACCAGCTACAGGTCACCCTGGAGATGCAGGATG
GACATGTCTTGTGGGGTCCACAGCCTGTGCTTGTGCACGTGAAGGATGAGAATGACCAGGTG
CCCCATTTCTCTCAAGCCATCTACAGAGCTCGGCTGAGCCGGGGTACCAGGCCTGGCATCCC
CTTCCTCTTCCTTGAGGCTTCAGACCGGGATGAGCCAGGCACAGCCAACTCGGATCTTCGAT
TCCACATCCTGAGCCAGGCTCCAGCCCAGCCTTCCCCAGACATGTTCCAGCTGGAGCCTCGG
CTGGGGGCTCTGGCCCTCAGCCCCAAGGGGAGCACCAGCCTTGACCACGCCCTGGAGAGGAC
CTACCAGCTGTTGGTACAGGTCAAGGACATGGGTGACCAGGCCTCAGGCCACCAGGCCACTG
CCACCGTGGAAGTCTCCATCATAGAGAGCACCTGGGTGTCCCTAGAGCCTATCCACCTGGCA
GAGAATCTCAAAGTCCTATACCCGCACCACATGGCCCAGGTACACTGGAGTGGGGGTGATGT
GCACTATCACCTGGAGAGCCATCCCCCGGGACCCTTTGAAGTGAATGCAGAGGGAAACCTCT
ACGTGACCAGAGAGCTGGACAGAGAAGCCCAGGCTGAGTACCTGCTCCAGGTGCGGGCTCAG
AATTCCCATGGCGAGGACTATGCGGCCCCTCTGGAGCTGCACGTGCTGGTGATGGATGAGAA
TGACAACGTGCCTATCTGCCCTCCCCGTGACCCCACAGTCAGCATCCCTGAGCTCAGTCCAC
CAGGTACTGAAGTGACTAGACTGTCAGCAGAGGATGCAGATGCCCCCGGCTCCCCCAATTCC
CACGTTGTGTATCAGCTCCTGAGCCCTGAGCCTGAGGATGGGGTAGAGGGGAGAGCCTTCCA
GGTGGACCCCACTTCAGGCAGTGTGACGCTGGGGGTGCTCCCACTCCGAGCAGGCCAGAACA
TCCTGCTTCTGGTGCTGGCCATGGACCTGGCAGGCGCAGAGGGTGGCTTCAGCAGCACGTGT
GAAGTCGAAGTCGCAGTCACAGATATCAATGATCACGCCCCTGAGTTCATCACTTCCCAGAT
TGGGCCTATAAGCCTCCCTGAGGATGTGGAGCCCGGGACTCTGGTGGCCATGCTAACAGCCA
TTGATGCTGACCTCGAGCCCGCCTTCCGCCTCATGGATTTTGCCATTGAGAGGGGAGACACA
GAAGGGACTTTTGGCCTGGATTGGGAGCCAGACTCTGGGCATGTTAGACTCAGACTCTGCAA
GAACCTCAGTTATGAGGCAGCTCCAAGTCATGAGGTGGTGGTGGTGGTGCAGAGTGTGGCGA
AGCTGGTGGGGCCAGGCCCAGGCCCTGGAGCCACCGCCACGGTGACTGTGCTAGTGGAGAGA
GTGATGCCACCCCCCAAGTTGGACCAGGAGAGCTACGAGGCCAGTGTCCCCATCAGTGCCCC
AGCCGGCTCTTTCCTGCTGACCATCCAGCCCTCCGACCCCATCAGCCGAACCCTCAGGTTCT
CCCTAGTCAATGACTCAGAGGGCTGGCTCTGCATTGAGAAATTCTCCGGGGAGGTGCACACC
GCCCAGTCCCTGCAGGGCGCCCAGCCTGGGGACACCTACACGGTGCTTGTGGAGGCCCAGGA
TACAGCCCTGACTCTTGCCCCTGTGCCCTCCCAATACCTCTGCACACCCCGCCAAGACCATG
GCTTGATCGTGAGTGGACCCAGCAAGGACCCCGATCTGGCCAGTGGGCACGGTCCCTACAGC
TTCACCCTTGGTCCCAACCCCACGGTGCAACGGGATTGGCGCCTCCAGACTCTCAATGGTTC
CCATGCCTACCTCACCTTGGCCCTGCATTGGGTGGAGCCACGTGAACACATAATCCCCGTGG
TGGTCAGCCACAATGCCCAGATGTGGCAGCTCCTGGTTCGAGTGATCGTGTGTCGCTGCAAC
GTGGAGGGGCAGTGCATGCGCAAGGTGGGCCGCATGAAGGGCATGCCCACGAAGCTGTCGGC
AGTGGGCATCCTTGTAGGCACCCTGGTAGCAATAGGAATCTTCCTCATCCTCATTTTCACCC
ACTGGACCATGTCAAGGAAGAAGGACCCGGATCAACCAGCAGACAGCGTGCCCCTGAAGGCG
ACTGTCTGAATGGCCCAGGCAGCTCTAGCTGGGAGCTTGGCCTCTGGCTCCATCTGAGTCCC
CTGGGAGAGAGCCCAGCACCCAAGATCCAGCAGGGGACAGGACAGAGTAGAAGCCCCTCCAT
CTGCCCTGGGGTGGAGGCACCATCACCATCACCAGGCATGTCTGCAGAGCCTGGACACCAAC
TTTATGGACTGCCCATGGGAGTGCTCCAAATGTCAGGGTGTTTGCCCAATAATAAAGCCCCA
GAGAACTGGGCTGGGCCCTATGGGAAAAAAAAAAAAAAAAAAAAAAAAAAAAAAAAAAAG

FIGURE 188

MVPAWLWLLCVSVPQALPKAQPAELSVEVPENYGGNFPLYLTKLPLPREGAEGQIVLSGDSG
KATEGPFAMDPDSGFLLVTRALDREEQAEYQLQVTLEMQDGHVLWGPQPVLVHVKDENDQVP
HFSQAIYRARLSRGTRPGIPFLFLEASDRDEPGTANSDLRFHILSQAPAQPSPDMFQLEPRL
GALALSPKGSTSLDHALERTYQLLVQVKDMGDQASGHQATATVEVSIIESTWVSLEPIHLAE
NLKVLYPHHMAQVHWSGGDVHYHLESHPPGPFEVNAEGNLYVTRELDREAQAEYLLQVRAQN
SHGEDYAAPLELHVLVMDENDNVPICPPRDPTVSIPELSPPGTEVTRLSAEDADAPGSPNSH
VVYQLLSPEPEDGVEGRAFQVDPTSGSVTLGVLPLRAGQNILLLVLAMDLAGAEGGFSSTCE
VEVAVTDINDHAPEFITSQIGPISLPEDVEPGTLVAMLTAIDADLEPAFRLMDFAIERGDTE
GTFGLDWEPDSGHVRLRLCKNLSYEAAPSHEVVVVVQSVAKLVGPGPGPGATATVTVLVERV
MPPPKLDQESYEASVPISAPAGSFLLTIQPSDPISRTLRFSLVNDSEGWLCIEKFSGEVHTA
QSLQGAQPGDTYTVLVEAQDTALTLAPVPSQYLCTPRQDHGLIVSGPSKDPDLASGHGPYSF
TLGPNPTVQRDWRLQTLNGSHAYLTLALHWVEPREHIIPVVVSHNAQMWQLLVRVIVCRCNV
EGQCMRKVGRMKGMPTKLSAVGILVGTLVAIGIFLILIFTHWTMSRKKDPDQPADSVPLKATV

Signal peptide:
amino acids 1-18

Transmembrane domain:
amino acids 762-784

FIGURE 189

GACTTTGCTTGAATGTTTACATTTTCTGCTCGCTGTCCTACATATCACAATATAGTGTTCACGTTTTGTTAAAA
CTTTGGGGTGTCAGGAGTTGAGCTTGCTCAGCAAGCCAGCATGGCTAGGATGAGCTTTGTTATAGCAGCTTGCC
AATTGGTGCTGGGCCTACTAATGACTTCATTAACCGAGTCTTCCATACAGAATAGTGAGTGTCCACAACTTTGC
GTATGTGAAATTCGTCCCTGGTTTACCCCACAGTCAACTTACAGAGAAGCCACCACTGTTGATTGCAATGACCT
CCGCTTAACAAGGATTCCCAGTAACCTCTCTAGTGACACACAAGTGCTTCTCTTACAGAGCAATAACATCGCGA
AGACTGTGGATGAGCTGCAGCAGCTTTTCAACTTGACTGAACTAGATTTCTCCCAAAACAACTTTACTAACATT
AAGGAGGTCGGGCTGGCAAACCTAACCCAGCTCACAACGCTGCATTTGGAGGAAAATCAGATTACCGAGATGAC
TGATTACTGTCTACAAGACCTCAGCAACCTTCAAGAACTCTACATCAACCACAACCAAATTAGCACTATTTCTG
CTCATGCTTTTGCAGGCTTAAAAAATCTATTAAGGCTCCACCTGAACTCCAACAAATTGAAAGTTATTGATAGT
CGCTGGTTTGATTCTACACCCAACCTGGAAATTCTCATGATCGGAGAAAACCCTGTGATTGGAATTCTGGATAT
GAACTTCAAACCCCTCGCAAATTTGAGAAGCTTAGTTTTGGCAGGAATGTATCTCACTGATATTCCTGGAAATG
CTTTGGTGGGTCTGGATAGCCTTGAGAGCCTGTCTTTTTATGATAACAAACTGGTTAAAGTCCCTCAACTTGCC
CTGCAAAAAGTTCCAAATTTGAAATTCTTAGACCTCAACAAAAACCCCATTCACAAAATCCAAGAAGGGGACTT
CAAAAATATGCTTCGGTTAAAAGAACTGGGAATCAACAATATGGGCGAGCTCGTTTCTGTCGACCGCTATGCCC
TGGATAACTTGCCTGAACTCACAAAGCTGGAAGCCACCAATAACCCTAAACTCTCTTACATCCACCGCTTGGCT
TTCCGAAGTGTCCCTGCTCTGGAAAGCTTGATGCTGAACAACAATGCCTTGAATGCCATTTACCAAAAGACAGT
CGAATCCCTCCCCAATCTGCGTGAGATCAGTATCCATAGCAATCCCCTCAGGTGTGACTGTGTGATCCACTGGA
TTAACTCCAACAAAACCAACATCCGCTTCATGGAGCCCCTGTCCATGTTCTGTGCCATGCCGCCCGAATATAAA
GGGCACCAGGTGAAGGAAGTTTTAATCCAGGATTCGAGTGAACAGTGCCTCCCAATGATATCTCACGACAGCTT
CCCAAATCGTTTAAACGTGGATATCGGCACGACGGTTTTCCTAGACTGTCGAGCCATGGCTGAGCCAGAACCTG
AAATTTACTGGGTCACTCCCATTGGAAATAAGATAACTGTGGAAACCCCTTTCAGATAAATACAAGCTAAGTAGC
GAAGGTACCTTGGAAATATCTAACATACAAATTGAAGACTCAGGAAGATACACATGTGTTGCCCAGAATGTCCA
AGGGGCAGACACTCGGGTGGCAACAATTAAGGTTAACGGGACCCTTCTGGATGGTACCCAGGTGCTAAAAATAT
ACGTCAAGCAGACAGAATCCCATTCCATCTTAGTGTCCTGGAAAGTTAATTCCAATGTCATGACGTCAAACTTA
AAATGGTCGTCTGCCACCATGAAGATTGATAACCCTCACATAACATATACTGCCAGGGTCCCAGTCGATGTCCA
TGAATACAACCTAACGCATCTGCAGCCTTCCACAGATTATGAAGTGTGTCTCACAGTGTCCAATATTCATCAGC
AGACTCAAAAGTCATGCGTAAATGTCACAACCAAAAATGCCGCCTTCGCAGTGGACATCTCTGATCAAGAAACC
AGTACAGCCCTTGCTGCAGTAATGGGGTCTATGTTTGCCGTCATTAGCCTTGCGTCCATTGCTGTGTACTTTGC
CAAAAGATTTAAGAGAAAAAACTACCACCACTCATTAAAAAAGTATATGCAAAAAACCTCTTCAATCCCACTAA
ATGAGCTGTACCCACCACTCATTAACCTCTGGGAAGGTGACAGCGAGAAAGACAAAGATGGTTCTGCAGACACC
AAGCCAACCCAGGTCGACACATCCAGAAGCTATTACATGTGGTAACTCAGAGGATATTTTGCTTCTGGTAGTAA
GGAGCACAAAGACGTTTTTGCTTTATTCTGCAAAAGTGAACAAGTTGAAGACTTTTGTATTTTTGACTTTGCTA
GTTTGTGGCAGAGTGGAGAGGACGGGTGGATATTTCAAATTTTTTTAGTATAGCGTATCGCAAGGGTTTGACAC
GGCTGCCAGCGACTCTAGGCTTCCAGTCTGTGTTTGGTTTTTATTCTTATCATTATTATGATTGTTATTATATT
ATTATTTTATTTTAGTTGTTGTGCTAAACTCAATAATGCTGTTCTAACTACAGTGCTCAATAAAATGATTAATG
ACAGGAAAAAAAAAAAAAAAAAAAAAAAAAAAAAAAAAAAAAAAAAAAAAAAAAAAAAAAAAAAAAAAAAAAAA
AAAA

FIGURE 190

MARMSFVIAACQLVLGLLMTSLTESSIQNSECPQLCVCEIRPWFTPQSTYREATTVDCNDLRLTRIPSNLSSDT
QVLLLQSNNIAKTVDELQQLFNLTELDFSQNNFTNIKEVGLANLTQLTTLHLEENQITEMTDYCLQDLSNLQEL
YINHNQISTISAHAFAGLKNLLRLHLNSNKLKVIDSRWFDSTPNLEILMIGENPVIGILDMNFKPLANLRSLVL
AGMYLTDIPGNALVGLDSLESLSFYDNKLVKVPQLALQKVPNLKFLDLNKNPIHKIQEGDFKNMLRLKELGINN
MGELVSVDRYALDNLPELTKLEATNNPKLSYIHRLAFRSVPALESLMLNNNALNAIYQKTVESLPNLREISIHS
NPLRCDCVIHWINSNKTNIRFMEPLSMFCAMPPEYKGHQVKEVLIQDSSEQCLPMISHDSFPNRLNVDIGTTVF
LDCRAMAEPEPEIYWVTPIGNKITVETLSDKYKLSSEGTLEISNIQIEDSGRYTCVAQNVQGADTRVATIKVNG
TLLDGTQVLKIYVKQTESHSILVSWKVNSNVMTSNLKWSSATMKIDNPHITYTARVPVDVHEYNLTHLQPSTDY
EVCLTVSNIHQQTQKSCVNVTTKNAAFAVDISDQETSTALAAVMGSMFAVISLASIAVYFAKRFKRKNYHHSLK
KYMQKTSSIPLNELYPPLINLWEGDSEKDKDGSADTKPTQVDTSRSYYMW

Important features:
Signal peptide:

Amino acids 1-25

Transmembrane domain:

Amino acids 508-530

N-glycosylation sites:

Amino acids 69-73;96-100;106-110;117-121;385-389;517-521;
582-586;611-615

Tyrosine kinase phosphorylation site:

Amino acids 573-582

N-myristoylation sites:

Amino acids 16-22;224-230;464-470;637-643;698-704

FIGURE 191

GGGAGAGAGGATAAATAGCAGCGTGGCTTCCCTGGCTCCTCTCTGCATCCTTCCCGACCTTC
CCAGCAATATGCATCTTGCACGTCTGGTCGGCTCCTGCTCCCTCCTTCTGCTACTGGGGGCC
CTGTCTGGATGGGCGGCCAGCGATGACCCCATTGAGAAGGTCATTGAAGGGATCAACCGAGG
GCTGAGCAATGCAGAGAGAGAGGTGGGCAAGGCCCTGGATGGCATCAACAGTGGAATCACGC
ATGCCGGAAGGGAAGTGGAGAAGGTTTTCAACGGACTTAGCAACATGGGGAGCCACACCGGC
AAGGAGTTGGACAAAGGCGTCCAGGGGCTCAACCACGGCATGGACAAGGTTGCCCATGAGAT
CAACCATGGTATTGGACAAGCAGGAAAGGAAGCAGAGAAGCTTGGCCATGGGGTCAACAACG
CTGCTGGACAGGCCGGGAAGGAAGCAGACAAAGCGGTCCAAGGGTTCCACACTGGGGTCCAC
CAGGCTGGGAAGGAAGCAGAGAAACTTGGCCAAGGGGTCAACCATGCTGCTGACCAGGCTGG
AAAGGAAGTGGAGAAGCTTGGCCAAGGTGCCCACCATGCTGCTGGCCAGGCCGGGAAGGAGC
TGCAGAATGCTCATAATGGGGTCAACCAAGCCAGCAAGGAGGCCAACCAGCTGCTGAATGGC
AACCATCAAAGCGGATCTTCCAGCCATCAAGGAGGGGCCACAACCACGCCGTTAGCCTCTGG
GGCCTCAGTCAACACGCCTTTCATCAACCTTCCCGCCCTGTGGAGGAGCGTCGCCAACATCA
TGCCCTAAACTGGCATCCGGCCTTGCTGGGAGAATAATGTCGCCGTTGTCACATCAGCTGAC
ATGACCTGGAGGGGTTGGGGGTGGGGGACAGGTTTCTGAAATCCCTGAAGGGGGTTGTACTG
GGATTTGTGAATAAACTTGATACACCA

FIGURE 192

></usr/seqdb2/sst/DNA/Dnaseqs.min/ss.DNA66675
><subunit 1 of 1, 247 aa, 1 stop
><MW: 25335, pI: 7.00, NX(S/T): 0
MHLARLVGSCSLLLLLGALSGWAASDDPIEKVIEGINRGLSNAEREVGKALDGINSGITHAG
REVEKVFNGLSNMGSHTGKELDKGVQGLNHGMDKVAHEINHGIGQAGKEAEKLGHGVNNAAG
QAGKEADKAVQGFHTGVHQAGKEAEKLGQGVNHAADQAGKEVEKLGQGAHHAAGQAGKELQN
AHNGVNQASKEANQLLNGNHQSGSSSHQGGATTTPLASGASVNTPFINLPALWRSVANIMP

Important features of the protein:
Signal peptide:
amino acids 1-25

Homologous region to circumsporozoite (CS) repeats:
amino acids 35-225

FIGURE 193

GAAGTAGAGGTGTTGTGCTGAGCGGCGCTCGGCGAACTGTGTGGACCGTCTGCTGGGACTCC
GGCCCTGCGTCCGCTCAGCCCCGTGGCCCCGCGCACCTACTGCCATGGAGACGCGGCCTCGT
CTCGGGGCCACCTGTTTGCTGGGCTTCAGTTTCCTGCTCCTCGTCATCTCTTCTGATGGACA
TAATGGGCTTGGAAAGGGTTTTGGAGATCATATTCATTGGAGGACACTGGAAGATGGGAAGA
AAGAAGCAGCTGCCAGTGGACTGCCCCTGATGGTGATTATTCATAAATCCTGGTGTGGAGCT
TGCAAAGCTCTAAAGCCCAAATTTGCAGAATCTACGGAAATTTCAGAACTCTCCCATAATTT
TGTTATGGTAAATCTTGAGGATGAAGAGGAACCCAAAGATGAAGATTTCAGCCCTGACGGGG
GTTATATTCCACGAATCCTTTTTCTGGATCCCAGTGGCAAGGTGCATCCTGAAATCATCAAT
GAGAATGGAAACCCCAGCTACAAGTATTTTTATGTCAGTGCCGAGCAAGTTGTTCAGGGGAT
GAAGGAAGCTCAGGAAAGGCTGACGGGTGATGCCTTCAGAAAGAAACATCTTGAAGATGAAT
TGTAACATGAATGTGCCCCTTCTTTCATCAGAGTTAGTGTTCTGGAAGGAAAGCAGCAGGGA
AGGGAATATTGAGGAATCATCTAGAACAATTAAGCCGACCAGGAAACCTCATTCCTACCTAC
ACTGGAAGGAGCGCTCTCACTGTGGAAGAGTTCTGCTAACAGAAGCTGGTCTGCATGTTTGT
GGATCCAGCGGAGAGTGGCAGACTTTCTTCTCCTTTTCCCTCTCACCTAAATGTCAACTTGT
CATTGAATGTAAAGAATGAAACCTTCTGACACAAAA

FIGURE 194

></usr/seqdb2/sst/DNA/Dnaseqs.min/ss.DNA67300
><subunit 1 of 1, 172 aa, 1 stop
><MW: 19206, pI: 5.36, NX(S/T): 1
METRPRLGATCLLGFSFLLLVISSDGHNGLGKGFGDHIHWRTLEDGKKEAAASGLPLMVI
IHKSWCGACKALKPKFAESTEISELSHNFVMVNLEDEEEPKDEDFSPDGGYIPRILFLDP
SGKVHPEIINENGNPSYKYFYVSAEQVVQGMKEAQERLTGDAFRKKHLEDEL

Important features of the protein:
Signal peptide:
Amino acids 1-23

Thioredoxin family proteins:
Amino acids 58-75

N-myristoylation sites:
Amino acids 29-35;67-73;150-156

Amidation site:
Amino acid 45-49

FIGURE 195

CGGCTCGAGTGCAGCTGTGGGGAGATTTCAGTGCATTGCCTCCCCTGGGTGCTCTTCATCTTGGATTTGAAAGT
TGAGAGCAGCATGTTTTGCCCACTGAAACTCATCCTGCTGCCAGTGTTACTGGATTATTCCTTGGGCCTGAATG
ACTTGAATGTTTCCCCGCCTGAGCTAACAGTCCATGTGGGTGATTCAGCTCTGATGGGATGTGTTTTCCAGAGC
ACAGAAGACAAATGTATATTCAAGATAGACTGGACTCTGTCACCAGGAGAGCACGCCAAGGACGAATATGTGCT
ATACTATTACTCCAATCTCAGTGTGCCTATTGGGCGCTTCCAGAACCGCGTACACTTGATGGGGGACATCTTAT
GCAATGATGGCTCTCTCCTGCTCCAAGATGTGCAAGAGGCTGACCAGGGAACCTATATCTGTGAAATCCGCCTC
AAAGGGGAGAGCCAGGTGTTCAAGAAGGCGGTGGTACTGCATGTGCTTCCAGAGGAGCCCAAAGAGCTCATGGT
CCATGTGGGTGGATTGATTCAGATGGGATGTGTTTTCCAGAGCACAGAAGTGAAACACGTGACCAAGGTAGAAT
GGATATTTTCAGGACGGCGCGCAAAGGAGGAGATTGTATTTCGTTACTACCACAAACTCAGGATGTCTGTGGAG
TACTCCCAGAGCTGGGGCCACTTCCAGAATCGTGTGAACCTGGTGGGGGACATTTTCCGCAATGACGGTTCCAT
CATGCTTCAAGGAGTGAGGGAGTCAGATGGAGGAAACTACACCTGCAGTATCCACCTAGGGAACCTGGTGTTCA
AGAAAACCATTGTGCTGCATGTCAGCCCGGAAGAGCCTCGAACACTGGTGACCCCGGCAGCCCTGAGGCCTCTG
GTCTTGGGTGGTAATCAGTTGGTGATCATTGTGGGAATTGTCTGTGCCACAATCCTGCTGCTCCCTGTTCTGAT
ATTGATCGTGAAGAAGACCTGTGGAAATAAGAGTTCAGTGAATTCTACAGTCTTGGTGAAGAACACGAAGAAGA
CTAATCCAGAGATAAAAGAAAAACCCTGCCATTTTGAAAGATGTGAAGGGGAGAAACACATTTACTCCCCAATA
ATTGTACGGGAGGTGATCGAGGAAGAAGAACCAAGTGAAAAATCAGAGGCCACCTACATGACCATGCACCCAGT
TTGGCCTTCTCTGAGGTCAGATCGGAACAACTCACTTGAAAAAAAGTCAGGTGGGGGAATGCCAAAAACACAGC
AAGCCTTTTGAGAAGAATGGAGAGTCCCTTCATCTCAGCAGCGGTGGAGACTCTCTCCTGTGTGTGTCCTGGGC
CACTCTACCAGTGATTTCAGACTCCCGCTCTCCCAGCTGTCCTCCTGTCTCATTGTTTGGTCAATACACTGAAG
ATGGAGAATTTGGAGCCTGGCAGAGAGACTGGACAGCTCTGGAGGAACAGGCCTGCTGAGGGGAGGGGAGCATG
GACTTGGCCTCTGGAGTGGGACACTGGCCCTGGGAACCAGGCTGAGCTGAGTGGCCTCAAACCCCCCGTTGGAT
CAGACCCTCCTGTGGGCAGGGTTCTTAGTGGATGAGTTACTGGGAAGAATCAGAGATAAAAACCAACCCAAATCAA

FIGURE 196

MFCPLKLILLPVLLDYSLGLNDLNVSPPELTVHVGDSALMGCVFQSTEDKCIFKIDWTLSPGEHAKDEYVLYYY
SNLSVPIGRFQNRVHLMGDILCNDGSLLLQDVQEADQGTYICEIRLKGESQVFKKAVVLHVLPEEPKELMVHVG
GLIQMGCVFQSTEVKHVTKVEWIFSGRRAKEEIVFRYYHKLRMSVEYSQSWGHFQNRVNLVGDIFRNDGSIMLQ
GVRESDGGNYTCSIHLGNLVFKKTIVLHVSPEEPRTLVTPAALRPLVLGGNQLVIIVGIVCATILLLPVLILIV
KKTCGNKSSVNSTVLVKNTKKTNPEIKEKPCHFERCEGEKHIYSPIIVREVIEEEEPSEKSEATYMTMHPVWPS
LRSDRNNSLEKKSGGGMPKTQQAF

FIGURE 197

CGCCATGGCCGGGCTATCCCGCGGGTCCGCGCGCACTGCTCGCCGCCCTGCTGGCGTCGACG
CTGTTGGCGCTGCTCGTGTCGCCCGCGCGGGGTCGCGGCGGCCGGGACCACGGGGACTGGGA
CGAGGCCTCCCGGCTGCCGCCGCTACCACCCCGCGAGGACGCGGCGCGCGTGGCCCGCTTCG
TGACGCACGTCTCCGACTGGGGCGCTCTGGCCACCATCTCCACGCTGGAGGCGGTGCGCGGC
CGGCCCTTCGCCGACGTCCTCTCGCTCAGCGACGGGCCCCCGGGCGCGGGCAGCGGCGTGCC
CTATTTCTACCTGAGCCCGCTGCAGCTCTCCGTGAGCAACCTGCAGGAGAATCCATATGCTA
CACTGACCATGACTTTGGCACAGACCAACTTCTGCAAGAAACATGGATTTGATCCACAAAGT
CCCCTTTGTGTTCACATAATGCTGTCAGGAACTGTGACCAAGGTGAATGAAACAGAAATGGA
TATTGCAAAGCATTCGTTATTCATTCGACACCCTGAGATGAAAACCTGGCCTTCCAGCCATA
ATTGGTTCTTTGCTAAGTTGAATATAACCAATATCTGGGTCCTGGACTACTTTGGTGGACCA
AAAATCGTGACACCAGAAGAATATTATAATGTCACAGTTCAGTGAAGCAGACTGTGGTGAAT
TTAGCAACACTTATGAAGTTTCTTAAAGTGGCTCATACACACTTAAAAGGCTTAATGTTTCT
CTGGAAAGCGTCCCAGAATATTAGCCAGTTTTCTGTC

FIGURE 198

></usr/seqdb2/sst/DNA/Dnaseqs.min/ss.DNA71269
><subunit 1 of 1, 220 aa, 1 stop
><MW: 24075, pI: 7.67, NX(S/T): 3
MAGLSRGSARALLAALLASTLLALLVSPARGRGGRDHGDWDEASRLPPLPPREDAARVAR
FVTHVSDWGALATISTLEAVRGRPFADVLSLSDGPPGAGSGVPYFYLSPLQLSVSNLQEN
PYATLTMTLAQTNFCKKHGFDPQSPLCVHIMLSGTVTKVNETEMDIAKHSLFIRHPEMKT
WPSSHNWFFAKLNITNIWVLDYFGGPKIVTPEEYYNVTVQ

Important features of the protein:
Transmembrane domain:
Amino acids
11-29

N-glycosylation sites:
Amino acids
160-164;193-197;216-220

N-myristoylation sites:
Amino acids
3-9;7-13;69-75;97-103

FIGURE 199

TCGCCATGGCCTCTGCCGGAATGCAGATCCTGGGAGTCGTCCTGACACTGCTGGGCTGGGTG
AATGGCCTGGTCTCCTGTGCCCTGCCCATGTGGAAGGTGACCGCTTTCATCGGCAACAGCAT
CGTGGTGGCCCAGGTGGTGTGGGAGGGCCTGTGGATGTCCTGCGTGGTGCAGAGCACCGGCC
AGATGCAGTGCAAGGTGTACGACTCACTGCTGGCGCTGCCACAGGACCTGCAGGCTGCACGT
GCCCTCTGTGTCATCGCCCTCCTTGTGGCCCTGTTCGGCTTGCTGGTCTACCTTGCTGGGGC
CAAGTGTACCACCTGTGTGGAGGAGAAGGATTCCAAGGCCCGCCTGGTGCTCACCTCTGGGA
TTGTCTTTGTCATCTCAGGGGTCCTGACGCTAATCCCCGTGTGCTGGACGGCGCATGCCATC
ATCCGGGACTTCTATAACCCCCTGGTGGCTGAGGCCCAAAAGCGGGAGCTGGGGGCCTCCCT
CTACTTGGGCTGGGCGGCCTCAGGCCTTTTGTTGCTGGGTGGGGGGTTGCTGTGCTGCACTT
GCCCCTCGGGGGGGTCCCAGGGCCCCAGCCATTACATGGCCCGCTACTCAACATCTGCCCCT
GCCATCTCTCGGGGGCCCTCTGAGTACCCTACCAAGAATTACGTCTGACGTGGAGGGGAATG
GGGGCTCCGCTGGCGCTAGAGCCATCCAGAAGTGGCAGTGCCCAACAGCTTTGGGATGGGTT
CGTACCTTTTGTTTCTGCCTCCTGCTATTTTTCTTTTGACTGAGGATATTTAAAATTCATTT
GAAAACTGAGCCAAGGTGTTGACTCAGACTCTCACTTAGGCTCTGCTGTTTCTCACCCTTGG
ATGATGGAGCCAAAGAGGGGATGCTTTGAGATTCTGGATCTTGACATGCCCATCTTAGAAGC
CAGTCAAGCTATGGAACTAATGCGGAGGCTGCTTGCTGTGCTGGCTTTGCAACAAGACAGAC
TGTCCCCAAGAGTTCCTGCTGCTGCTGGGGGCTGGGCTTCCCTAGATGTCACTGGACAGCTG
CCCCCCATCCTACTCAGGTCTCTGGAGCTCCTCTCTTCACCCCTGGAAAAACAAATCATCTG
TTAACAAAGGACTGCCCACCTCCGGAACTTCTGACCTCTGTTTCCTCCGTCCTGATAAGACG
TCCACCCCCCAGGGCCAGGTCCCAGCTATGTAGACCCCCGCCCCCACCTCCAACACTGCACC
CTTCTGCCCTGCCCCCCTCGTCTCACCCCCTTTACACTCACATTTTTATCAAATAAAGCATG
TTTTGTTAGTGCA

FIGURE 200

></usr/seqdb2/sst/DNA/Dnaseqs.min/ss.DNA73736
><subunit 1 of 1, 220 aa, 1 stop
><MW: 23292, pI: 8.43, NX(S/T): 0
MASAGMQILGVVLTLLGWVNGLVSCALPMWKVTAFIGNSIVVAQVVWEGLWMSCVVQSTGQM
QCKVYDSLLALPQDLQAARALCVIALLVALFGLLVYLAGAKCTTCVEEKDSKARLVLTSGIV
FVISGVLTLIPVCWTAHAIIRDFYNPLVAEAQKRELGASLYLGWAASGLLLLGGGLLCCTCP
SGGSQGPSHYMARYSTSAPAISRGPSEYPTKNYV

Transmembrane domains:
amino acids 8-30 (type II), 82-102, 121-140, 166-186

FIGURE 201

AGTGACAATCTCAGAGCAGCTTCTACACCACAGCCATTTCCAGCATGAAGATCACTGGGGGTCTCCTTCTGCTC
TGTACAGTGGTCTATTTCTGTAGCAGCTCAGAAGCTGCTAGTCTGTCTCCAAAAAAAGTGGACTGCAGCATTTA
CAAGAAGTATCCAGTGGTGGCCATCCCCTGCCCCATCACATACCTACCAGTTTGTGGTTCTGACTACATCACCT
ATGGGAATGAATGTCACTTGTGTACCGAGAGCTTGAAAAGTAATGGAAGAGTTCAGTTTCTTCACGATGGAAGT
TGCTAAATTCTCCATGGACATAGAGAGAAAGGAATGATATTCTCATCATCATCTTCATCATCCCAGGCTCTGAC
TGAGTTTCTTTCAGTTTTACTGATGTTCTGGGTGGGGGACAGAGCCAGATTCAGAGTAATCTTGACTGAATGGA
GAAAGTTTCTGTGCTACCCCTACAAACCCATGCCTCACTGACAGACCAGCATTTTTTTTTTAACACGTCAATAA
AAAAATAATCTCCCAGA

FIGURE 202

MKITGGLLLLCTVVYFCSSSEAASLSPKKVDCSIYKKYPVVAIPCPITYLPVCGSDYITYGNECHLCTESLKSN
GRVQFLHDGSC

Important features:
Signal peptide:
amino acids 1-19

FIGURE 203

CGACGATGCTACGCGCGCCCGGCTGCCTCCTCCGGACCTCCGTAGCGCCTGCCGCGGCCCTGGCTGCGGCGCTG
CTCTCGTCGCTTGCGCGCTGCTCTCTTCTAGAGCCGAGGGACCCGGTGGCCTCGTCGCTCAGCCCCTATTTCGG
CACCAAGACTCGCTACGAGGATGTCAACCCCGTGCTATTGTCGGCCCCGAGGCTCCGTGGCGGGACCCTGAGC
TGCTGGAGGGGACCTGCACCCCGGTGCAGCTGGTCGCCCTCATTCGCCACGGCACCCGCTACCCCACGGTCAAA
CAGATCCGCAAGCTGAGGCAGCTGCACGGGTTGCTGCAGGCCCGCGGGTCCAGGGATGGCGGGGCTAGTAGTAC
CGGCAGCCGCGACCTGGGTGCAGCGCTGGCCGACTGGCCTTTGTGGTACGCGGACTGGATGGACGGGCAGCTAG
TAGAGAAGGGACGGCAGGATATGCGACAGCTGGCGCTGCGTCTGGCCTCGCTCTTCCCGGCCCTTTTCAGCCGT
GAGAACTACGGCCGCCTGCGGCTCATCACCAGTTCCAAGCACCGCTGCATGGATAGCAGCGCCGCCTTCCTGCA
GGGGCTGTGGCAGCACTACCACCCTGGCTTGCCGCCGCCGGACGTCGCAGATATGGAGTTTGGACCTCCAACAG
TTAATGATAAACTAATGAGATTTTTTGATCACTGTGAGAAGTTTTTAACTGAAGTAGAAAAAAATGCTACAGCT
CTTTATCACGTGGAAGCCTTCAAAACTGGACCAGAAATGCAGAACATTTTAAAAAAAGTTGCAGCTACTTTGCA
AGTGCCAGTAAATGATTTAAATGCAGATTTAATTCAAGTAGCCTTTTTCACCTGTTCATTTGACCTGGCAATTA
AAGGTGTTAAATCTCCTTGGTGTGATGTTTTTGACATAGATGATGCAAAGGTATTAGAATATTTAAATGATCTG
AAACAATATTGGAAAAGAGGATATGGGTATACTATTAACAGTCGATCCAGCTGCACCTTGTTTCAGGATATCTT
TCAGCACTTGGACAAAGCAGTTGAACAGAAACAAAGGTCTCAGCCAATTTCTTCTCCAGTCATCCTCCAGTTTG
GTCATGCAGAGACTCTTCTTCCACTGCTTTCTCTCATGGGCTACTTCAAAGACAAGGAACCCCTAACAGCGTAC
AATTACAAAAAACAAATGCATCGGAAGTTCCGAAGTGGTCTCATTGTACCTTATGCCTCGAACCTGATATTTGT
GCTTTACCACTGTGAAAATGCTAAGACTCCTAAAGAACAATTCCGAGTGCAGATGTTATTAAATGAAAAGGTGT
TACCTTTGGCTTACTCACAAGAAACTGTTTCATTTTATGAAGATCTGAAGAACCACTACAAGGACATCCTTCAG
AGTTGTCAAACCAGTGAAGAATGTGAATTAGCAAGGGCTAACAGTACATCTGATGAACTATGAGTAACTGAAGA
ACATTTTTAATTCTTTAGGAATCTGCAATGAGTGATTACATGCTTGTAATAGGTAGGCAATTCCTTGATTACAG
GAAGCTTTTATATTACTTGAGTATTTCTGTCTTTTCACAGAAAAACATTGGGTTTCTCTCTGGGTTTGGACATG
AAATGTAAGAAAAGATTTTTCACTGGAGCAGCTCTCTTAAGGAGAAACAAATCTATTTAGAGAAACAGCTGGCC
CTGCAAATGTTTACAGAAATGAAATTCTTCCTACTTATATAAGAAATCTCACACTGAGATAGAATTGTGATTTC
ATAATAACACTTGAAAAGTGCTGGAGTAACAAAATATCTCAGTTGGACCATCCTTAACTTGATTGAACTGTCTA
GGAACTTTACAGATTGTTCTGCAGTTCTCTCTTCTTTTCCTCAGGTAGGACAGCTCTAGCATTTTCTTAATCAG
GAATATTGTGGTAAGCTGGGAGTATCACTCTGGAAGAAAGTAACATCTCCAGATGAGAATTTGAAACAAGAAAC
AGAGTGTTGTAAAAGGACACCTTCACTGAAGCAAGTCGGAAAGTACAATGAAAATAAATATTTTTGGTATTTAT
TTATGAAATATTTGAACATTTTTTCAATAATTCCTTTTTACTTCTAGGAAGTCTCAAAAGACCATCTTAAATTA
TTATATGTTTGGACAATTAGCAACAAGTCAGATAGTTAGAATCGAAGTTTTTCAAATCCATTGCTTAGCTAACT
TTTTCATTCTGTCACTTGGCTTCGATTTTTATATTTTCCTATTATATGAAATGTATCTTTTGGTTGTTTGATTT
TTCTTTCTTTCTTTGTAAATAGTTCTGAGTTCTGTCAAATGCCGTGAAAGTATTTGCTATAATAAAGAAAATTC
TTGTGACTTTAAAAAAAAA

FIGURE 204

MLRAPGCLLRTSVAPAAALAAALLSSLARCSLLEPRDPVASSLSPYFGTKTRYEDVNPVLLSGPEAPWRDPELL
EGTCTPVQLVALIRHGTRYPTVKQIRKLRQLHGLLQARGSRDGGASSTGSRDLGAALADWPLWYADWMDGQLVE
KGRQDMRQLALRLASLFPALFSRENYGRLRLITSSKHRCMDSSAAFLQGLWQHYHPGLPPPDVADMEFGPPTVN
DKLMRFFDHCEKFLTEVEKNATALYHVEAFKTGPEMQNILKKVAATLQVPVNDLNADLIQVAFFTCSFDLAIKG
VKSPWCDVFDIDDAKVLEYLNDLKQYWKRGYGYTINSRSSCTLFQDIFQHLDKAVEQKQRSQPISSPVILQFGH
AETLLPLLSLMGYFKDKEPLTAYNYKKQMHRKFRSGLIVPYASNLIFVLYHCENAKTPKEQFRVQMLLNEKVLP
LAYSQETVSFYEDLKNHYKDILQSCQTSEECELARANSTSDEL

Important features:
Signal sequence
amino acids 1-30

N-glycosylation sites.
amino acids 242-246, 481-485

N-myristoylation sites.
amino acids 107-113, 113-119, 117-123, 118-124, 128-134

Endoplasmic reticulum targeting sequence.
amino acids 484-489

FIGURE 205

GCGACGCGCGGCGGGGCGGCGAGAGGAAACGCGGCGCCGGGCCGGGCCCGGCCCTGGAGATG
GTCCCCGGCGCCGCGGGCTGGTGTTGTCTCGTGCTCTGGCTCCCCGCGTGCGTCGCGGCCCA
CGGCTTCCGTATCCATGATTATTTGTACTTTCAAGTGCTGAGTCCTGGGGACATTCGATACA
TCTTCACAGCCACACCTGCCAAGGACTTTGGTGGTATCTTTCACACAAGGTATGAGCAGATT
CACCTTGTCCCCGCTGAACCTCCAGAGGCCTGCGGGGAACTCAGCAACGGTTTCTTCATCCA
GGACCAGATTGCTCTGGTGGAGAGGGGGGGCTGCTCCTTCCTCTCCAAGACTCGGGTGGTCC
AGGAGCACGGCGGGCGGGCGGTGATCATCTCTGACAACGCAGTTGACAATGACAGCTTCTAC
GTGGAGATGATCCAGGACAGTACCCAGCGCACAGCTGACATCCCCGCCCTCTTCCTGCTCGG
CCGAGACGGCTACATGATCCGCCGCTCTCTGGAACAGCATGGGCTGCCATGGGCCATCATTT
CCATCCCAGTCAATGTCACCAGCATCCCCACCTTTGAGCTGCTGCAACCGCCCTGGACCTTC
TGGTAGAAGAGTTTGTCCCACATTCCAGCCATAAGTGACTCTGAGCTGGGAAGGGGAAACCC
AGGAATTTTGCTACTTGGAATTTGGAGATAGCATCTGGGGACAAGTGGAGCCAGGTAGAGGA
AAAGGGTTTGGGCGTTGCTAGGCTGAAAGGGAAGCCACACCACTGGCCTTCCCTTCCCCAGG
GCCCCCAAGGGTGTCTCATGCTACAAGAAGAGGCAAGAGACAGGCCCCAGGGCTTCTGGCTA
GAACCCGAAACAAAAGGAGCTGAAGGCAGGTGGCCTGAGAGCCATCTGTGACCTGTCACACT
CACCTGGCTCCAGCCTCCCCTACCCAGGGTCTCTGCACAGTGACCTTCACAGCAGTTGTTGG
AGTGGTTTAAAGAGCTGGTGTTTGGGGACTCAATAAACCCTCACTGACTTTTTAGCAATAAA
GCTTCTCATCAGGGTTGCAAAAAAAAAAAAAAAAAAAAAAAAA

FIGURE 206

></usr/seqdb2/sst/DNA/Dnaseqs.min/ss.DNA76532
><subunit 1 of 1, 188 aa, 1 stop
><MW: 21042, pI: 5.36, NX(S/T): 2
MVPGAAGWCCLVLWLPACVAAHGFRIHDYLYFQVLSPGDIRYIFTATPAKDFGGIFHTRYEQ
IHLVPAEPPEACGELSNGFFIQDQIALVERGGCSFLSKTRVVQEHGGRAVIISDNAVDNDSF
YVEMIQDSTQRTADIPALFLLGRDGYMIRRSLEQHGLPWAIISIPVNVTSIPTFELLQPPWTFW

Signal peptide:
amino acids 1-20

FIGURE 207

CTCGCTTCTTCCTTCTGGATGGGGGCCCAGGGGGCCCAGGAGAGTATAAAGGCGATGTGGAG
GGTGCCCGGCACAACCAGACGCCCAGTCACAGGCGAGAGCCCTGGGATGCACCGGCCAGAGG
CCATGCTGCTGCTGCTCACGCTTGCCCTCCTGGGGGGCCCCACCTGGGCAGGGAAGATGTAT
GGCCCTGGAGGAGGCAAGTATTTCAGCACCACTGAAGACTACGACCATGAAATCACAGGGCT
GCGGGTGTCTGTAGGTCTTCTCCTGGTGAAAAGTGTCCAGGTGAAACTTGGAGACTCCTGGG
ACGTGAAACTGGGAGCCTTAGGTGGGAATACCCAGGAAGTCACCCTGCAGCCAGGCGAATAC
ATCACAAAAGTCTTTGTCGCCTTCCAAGCTTTCCTCCGGGGTATGGTCATGTACACCAGCAA
GGACCGCTATTTCTATTTTGGGAAGCTTGATGGCCAGATCTCCTCTGCCTACCCCAGCCAAG
AGGGGCAGGTGCTGGTGGGCATCTATGGCCAGTATCAACTCCTTGGCATCAAGAGCATTGGC
TTTGAATGGAATTATCCACTAGAGGAGCCGACCACTGAGCCACCAGTTAATCTCACATACTC
AGCAAACTCACCCGTGGGTCGCTAGGGTGGGGTATGGGGCCATCCGAGCTGAGGCCATCTGT
GTGGTGGTGGCTGATGGTACTGGAGTAACTGAGTCGGGACGCTGAATCTGAATCCACCAATA
AATAAAGCTTCTGCAGAAAA

FIGURE 208

></usr/seqdb2/sst/DNA/Dnaseqs.min/ss.DNA76541
><subunit 1 of 1, 178 aa, 1 stop
><MW: 19600, pI: 5.89, NX(S/T): 1
MHRPEAMLLLLTLALLGGPTWAGKMYGPGGGKYFSTTEDYDHEITGLRVSVGLLLVKSVQVK
LGDSWDVKLGALGGNTQEVTLQPGEYITKVFVAFQAFLRGMVMYTSKDRYFYFGKLDGQISS
AYPSQEGQVLVGIYGQYQLLGIKSIGFEWNYPLEEPTTEPPVNLTYSANSPVGR

Signal peptide:
amino acids 1-22

FIGURE 209

GGAGAATGGAGAGAGCAGTGAGAGTGGAGTCCGGGGTCCTGGTCGGGGTGGTCTGTCTGCTCCTGGCATGCCCT
GCCACAGCCACTGGGCCCGAAGTTGCTCAGCCTGAAGTAGACACCACCCTGGGTCGTGTGCGAGGCCGGCAGGT
GGGCGTGAAGGGCACAGACCGCCTTGTGAATGTCTTTCTGGGCATTCCATTTGCCCAGCCGCCACTGGGCCCTG
ACCGGTTCTCAGCCCCACACCCAGCACAGCCCTGGGAGGGTGTGCGGGATGCCAGCACTGCGCCCCCAATGTGC
CTACAAGACGTGGAGAGCATGAACAGCAGCAGATTTGTCCTCAACGGAAAACAGCAGATCTTCTCCGTTTCAGA
GGACTGCCTGGTCCTCAACGTCTATAGCCCAGCTGAGGTCCCCGCAGGGTCCGGTAGGCCGGTCATGGTATGGG
TCCATGGAGGCGCTCTGATAACTGGCGCTGCCACCTCCTACGATGGATCAGCTCTGGCTGCCTATGGGGATGTG
GTCGTGGTTACAGTCCAGTACCGCCTTGGGGTCCTTGGCTTCTTCAGCACTGGAGATGAGCATGCACCTGGCAA
CCAGGGCTTCCTAGATGTGGTAGCTGCTTTGCGCTGGGTGCAAGAAAACATCGCCCCCTTCGGGGGTGACCTCA
ACTGTGTCACTGTCTTTGGTGGATCTGCCGGTGGGAGCATCATCTCTGGCCTGGTCCTGTCCCCAGTGGCTGCA
GGGCTGTTCCACAGAGCCATCACACAGAGTGGGGTCATCACCACCCCAGGGATCATCGACTCTCACCCTTGGCC
CCTAGCTCAGAAAATCGCAAACACCTTGGCCTGCAGCTCCAGCTCCCCGGCTGAGATGGTGCAGTGCCTTCAGC
AGAAAGAAGGAGAAGAGCTGGTCCTTAGCAAGAAGCTGAAAAATACTATCTATCCTCTCACCGTTGATGGCACT
GTCTTCCCCAAAAGCCCCAAGGAACTCCTGAAGGAGAAGCCCTTCCACTCTGTGCCCTTCCTCATGGGTGTCAA
CAACCATGAGTTCAGCTGGCTCATCCCCAGGGGCTGGGGTCTCCTGGATACAATGGAGCAGATGAGCCGGGAGG
ACATGCTGGCCATCTCAACACCCGTCTTGACCAGTCTGGATGTGCCCCCTGAGATGATGCCCACCGTCATAGAT
GAATACCTAGGAAGCAACTCGGACGCACAAGCCAAATGCCAGGCGTTCCAGGAATTCATGGGTGACGTATTCAT
CAATGTTCCCACCGTCAGTTTTTCAAGATACCTTCGAGATTCTGGAAGCCCTGTCTTTTTCTATGAGTTCCAGC
ATCGACCCAGTTCTTTTGCGAAGATCAAACCTGCCTGGGTGAAGGCTGATCATGGGGCCGAGGGTGCTTTTGTG
TTCGGAGGTCCCTTCCTCATGGACGAGAGCTCCCGCCTGGCCTTTCCAGAGGCCACAGAGGAGGAGAAGCAGCT
AAGCCTCACCATGATGGCCCAGTGGACCCACTTTGCCCGGACAGGGGACCCCAATAGCAAGGCTCTGCCTCCTT
GGCCCCAATTCAACCAGGCGGAACAATATCTGGAGATCAACCCAGTGCCACGGCCGGACAGAAGTTCAGGGAG
GCCTGGATGCAGTTCTGGTCAGAGACGCTCCCCAGCAAGATACAACAGTGGCACCAGAAGCAGAAGAACAGGAA
GGCCCAGGAGGACCTCTGAGGCCAGGCCTGAACCTTCTTGGCTGGGGCAAACCACTCTTCAAGTGGTGGCAGAG
TCCCAGCACGGCAGCCCGCCTCTCCCCCTGCTGAGACTTTAATCTCCACCAGCCCTTAAAGTGTCGGCCGCTCT
GTGACTGGAGTTATGCTCTTTTGAAATGTCACAAGGCCGCCTCCCACCTCTGGGGCATTGTACAAGTTCTTCCC
TCTCCCTGAAGTGCCTTTCCTGCTTTCTTCGTGGTAGGTTCTAGCACATTCCTCTAGCTTCCTGGAGGACTCAC
TCCCCAGGAAGCCTTCCCTGCCTTCTCTGGGCTGTGCGGCCCCGAGTCTGCGTCCATTAGAGCACAGTCCACCC
GAGGCTAGCACCGTGTCTGTGTCTGTCTCCCCCTCAGAGGAGCTCTCTCAAAATGGGGATTAGCCTAACCCCAC
TCTGTCACCCACACCAGGATCGGGTGGGACCTGGAGCTAGGGGGTGTTTGCTGAGTGAGTGAGTGAAACACAGA
ATATGGGAATGGCAGCTGCTGAACTTGAACCCAGAGCCTTCAGGTGCCAAAGCCATACTCAGGCCCCCACCGAC
ATTGTCCACCCTGGCCAGAAGGGTGCATGCCAATGGCAGAGACCTGGGATGGGAGAAGTCCTGGGGCGCCAGGG
GATCCAGCCTAGAGCAGACCTTAGCCCCTGACTAAGGCCTCAGACTAGGGCGGGAGGGGTCTCCTCCTCTCTGC
TGCCCAGTCCTGGCCCCTGCACAAGACAACAGAATCCATCAGGGCCATGAGTGTCACCCAGACCTGACCCTCAC
CAATTCCAGCCCCTGACCCTCAGGACGCTGGATGCCAGCTCCCAGCCCCAGTGCCGGGTCCTCCCTCCCTTCCT
GGCTTGGGGAGACCAGTTTCTGGGGAGCTTCCAAGAGCACCCACCAAGACACAGCAGGACAGGCCAGGGGAGGG
CATCTGGACCAGGGCATCCGTCGGGCTATTGTCACAGAGAAAAGAAGAGACCCACCCACTCGGGCTGCAAAAGG
TGAAAAGCACCAAGAGGTTTTCAGATGGAAGTGAGAGGTGACAGTGTGCTGGCAGCCCTCACAGCCCTCGCTTG
CTCTCCCTGCCGCCTCTGCCTGGGCTCCCACTTTGGCAGCACTTGAGGAGCCCTTCAACCCGCCGCTGCACTGT
AGGAGCCCCTTTCTGGGCTGGCCAAGGCCGGAGCCAGCTCCCTCAGCTTGCGGGGAGGTGCGGAGGGAGAGGGG
CGGGCAGGAACCGGGGCTGCGCGCAGCGCTTGCGGGCCAGAGTGAGTTCCGGGTGGGCGTGGGCTCGGCGGGGC
CCCACTCAGAGCAGCTGGCCGGCCCCAGGCAGTGAGGGCCTTAGCACCTGGGCCAGCAGCTGCTGTGCTCGATT
TCTCGCTGGGCCTTAGCTGCCTCCCCGCGGGGCAGGGCTCGGGACCTGCAGCCCTCCATGCCTGACCCTCCCCC
CACCCCCCGTGGGCTCCTGTGCGGCCGGAGCCTCCCCAAGGAGCGCCGCCCCCTGCTCCACAGCGCCCAGTCCC
ATCGACCACCCAAGGGCTGAGGAGTGCGGGTGCACAGCGCGGGACTGGCAGGCAGCTCCACCTGCTGCCCCAGT
GCTGGATCCACTGGGTGAAGCCAGCTGGGCTCCTGAGTCTGGTGGGGACTTGGAGAACCTTTATGTCTAGCTAA
GGGATTGTAAATACACCGATGGGCACTCTGTATCTAGCTCAAGGTTTGTAAACACACCAATCAGCACCCTGTGT
CTAGCTCAGTGTTTGTGAATGCACCAATCCACACTCTGTATCTGGCTACTCTGGTGGGGACTTGGAGAACCTTT
GTGTCCACACTCTGTATCTAGCTAATCTAGTGGGGATGTGGAGAACCTTTGTGTCTAGCTCAGGGATCGTAAAC
GCACCAATCAGCACCCTGTCAAAACAGACCACTTGACTCTCTGTAAAATGGACCAATCAGCAGGATGTGGGTGG
GGCGAGACAAGAGAATAAAAGCAGGCTGCCTGAGCCAGCAGTGACAACCCCCCTCGGGTCCCCTCCCACGCCGT
GGAAGCTTTGTTCTTTCGCTCTTTGCAATAAATCTTGCTACTGCCCAAAA

FIGURE 210

MERAVRVESGVLVGVVCLLLACPATATGPEVAQPEVDTTLGRVRGRQVGVKGTDRLVNVFLGIPFAQPPLGPDR
FSAPHPAQPWEGVRDASTAPPMCLQDVESMNSSRFVLNGKQQIFSVSEDCLVLNVYSPAEVPAGSGRPVMVWVH
GGALITGAATSYDGSALAAYGDVVVVTVQYRLGVLGFFSTGDEHAPGNQGFLDVVAALRWVQENIAPFGGDLNC
VTVFGGSAGGSIISGLVLSPVAAGLFHRAITQSGVITTPGIIDSHPWPLAQKIANTLACSSSSPAEMVQCLQQK
EGEELVLSKKLKNTIYPLTVDGTVFPKSPKELLKEKPFHSVPFLMGVNNHEFSWLIPRGWGLLDTMEQMSREDM
LAISTPVLTSLDVPPEMMPTVIDEYLGSNSDAQAKCQAFQEFMGDVFINVPTVSFSRYLRDSGSPVFFYEFQHR
PSSFAKIKPAWVKADHGAEGAFVFGGPFLMDESSRLAFPEATEEEKQLSLTMMAQWTHFARTGDPNSKALPPWP
QFNQAEQYLEINPVPRAGQKFREAWMQFWSETLPSKIQQWHQKQKNRKAQEDL

Important features:
Signal peptide:
amino acids 1-27

Transmembrane domain:
amino acids 226-245

N-glycosylation site.
amino acids 105-109

N-myristoylation sites.
amino acids 10-16, 49-55, 62-68, 86-92, 150-156, 155-161, 162-168, 217-223, 227-233, 228-234, 232-238, 262-268, 357-363, 461-467

Prokaryotic membrane lipoprotein lipid attachment site.
amino acids 12-23

Carboxylesterases type-B serine active site.
amino acids 216-232

FIGURE 211

AACTTCTACATGGGCCTCCTGCTGCTGGTGCTCTTCCTCAGCCTCCTGCCGGTGGCCTACAC
CATCATGTCCCTCCCACCCTCCTTTGACTGCGGGCCGTTCAGGTGCAGAGTCTCAGTTGCCC
GGGAGCACCTCCCCTCCCGAGGCAGTCTGCTCAGAGGGCCTCGGCCCAGAATTCCAGTTCTG
GTTTCATGCCAGCCTGTAAAAGGCCATGGAACTTTGGGTGAATCACCGATGCCATTTAAGAG
GGTTTTCTGCCAGGATGGAAATGTTAGGTCGTTCTGTGTCTGCGCTGTTCATTTCAGTAGCC
ACCAGCCACCTGTGGCCGTTGAGTGCTTGAAATGAGGAACTGAGAAAATTAATTTCTCATGT
ATTTTTCTCATTTATTTATTAATTTTTAACTGATAGTTGTACATATTTGGGGGTACATGTGA
TATTTGGATACATGTATACAATATATAATGATCAAATCAGGGTAACTGGGATATCCATCACA
TCAAACATTTATTTTTTATTCTTTTTAGACAGAGTCTCACTCTGTCACCCAGGCTGGAGTGC
AGTGGTGCCATCTCAGCTTACTGCAACCTCTGCCTGCCAGGTTCAAGCGATTCTCATGCCTC
CACCTCCCAAGTAGCTGGGACTACAGGCATGCACCACAATGCCCAACTAATTTTTGTATTTT
TAGTAGAGACGGGGTTTTGCCATGTTGCCCAGGCTGGCCTTGAACTCCTGGCCTCAAACAAT
CCACTTGCCTCGGCCTCCCAAAGTGTTATGATTACAGGCGTGAGCCACCGTGCCTGGCCTAA
ACATTTATCTTTTCTTTGTGTTGGGAACTTTGAAATTATACAATGAATTATTGTTAACTGTC
ATCTCCCTGCTGTGCTATGGAACACTGGGACTTCTTCCCTCTATCTAACTGTATATTTGTAC
CAGTTAACCAACCGTACTTCATCCCCACTCCTCTCTATCCTTCCCAACCTCTGATCACCTCA
TTCTACTCTCTACCTCCATGAGATCCACTTTTTTAGCTCCCACATGTGAGTAAGAAAATGCA
ATATTTGTCTTTCTGTGCCTGGCTTATTTCACTTAACATAATGACTTCCTGTTCCATCCATG
TTGCTGCAAATGACAGGATTTCGTTCTTAATTTCAATTAAAATAACCACACATGGCAAAAA

FIGURE 212

MGLLLLVLFLSLLPVAYTIMSLPPSFDCGPFRCRVSVAREHLPSRGSLLRGPRPRIPVLVSC
QPVKGHGTLGESPMPFKRVFCQDGNVRSFCVCAVHFSSHQPPVAVECLK

Important features of the protein:
Signal peptide:
amino acids 1-18

N-myristoylation site.
amino acids 86-92

Zinc carboxypeptidases, zinc-binding region 2 signature.
amino acids 68-79

FIGURE 213

AGGGCCCGCGGGTGGAGAGAGCGACGCCCGAGGGGATGGCGGCAGCGTCCCGGAGCGCCTCT
GGCTGGGCGCTACTGCTGCTGGTGGCACTTTGGCAGCAGCGCGCGGCCGGCTCCGGCGTCTT
CCAGCTGCAGCTGCAGGAGTTCATCAACGAGCGCGGCGTACTGGCCAGTGGGCGGCCTTGCG
AGCCCGGCTGCCGGACTTTCTTCCGCGTCTGCCTTAAGCACTTCCAGGCGGTCGTCTCGCCC
GGACCCTGCACCTTCGGGACCGTCTCCACGCCGGTATTGGGCACCAACTCCTTCGCTGTCCG
GGACGACAGTAGCGGCGGGGGGCGCAACCCTCTCCAACTGCCCTTCAATTTCACCTGGCCGG
GTACCTTCTCGCTCATCATCGAAGCTTGGCACGCGCCAGGAGACGACCTGCGGCCAGAGGCC
TTGCCACCAGATGCACTCATCAGCAAGATCGCCATCCAGGGCTCCCTAGCTGTGGGTCAGAA
CTGGTTATTGGATGAGCAAACCAGCACCCTCACAAGGCTGCGCTACTCTTACCGGGTCATCT
GCAGTGACAACTACTATGGAGACAACTGCTCCCGCCTGTGCAAGAAGCGCAATGACCACTTC
GGCCACTATGTGTGCCAGCCAGATGGCAACTTGTCCTGCCTGCCCGGTTGGACTGGGGAATA
TTGCCAACAGCCTATCTGTCTTTCGGGCTGTCATGAACAGAATGGCTACTGCAGCAAGCCAG
CAGAGTGCCTCTGCCGCCCAGGCTGGCAGGGCCGGCTGTGTAACGAATGCATCCCCCACAAT
GGCTGTCGCCACGGCACCTGCAGCACTCCCTGGCAATGTACTTGTGATGAGGGCTGGGGAGG
CCTGTTTTGTGACCAAGATCTCAACTACTGCACCCACCACTCCCCATGCAAGAATGGGGCAA
CGTGCTCCAACAGTGGGCAGCGAAGCTACACCTGCACCTGTCGCCCAGGCTACACTGGTGTG
GACTGTGAGCTGGAGCTCAGCGAGTGTGACAGCAACCCCTGTCGCAATGGAGGCAGCTGTAA
GGACCAGGAGGATGGCTACCACTGCCTGTGTCCTCCGGGCTACTATGGCCTGCACTGTGAAC
ACAGCACCTTGAGCTGCGCCGACTCCCCCTGCTTCAATGGGGGCTCCTGCCGGGAGCGCAAC
CAGGGGGCCAACTATGCTTGTGAATGTCCCCCCAACTTCACCGGCTCCAACTGCGAGAAGAA
AGTGGACAGGTGCACCAGCAACCCCTGTGCCAACGGGGGACAGTGCCTGAACCGAGGTCCAA
GCCGCATGTGCCGCTGCCGTCCTGGATTCACGGGCACCTACTGTGAACTCCACGTCAGCGAC
TGTGCCCGTAACCCTTGCGCCCACGGTGGCACTTGCCATGACCTGGAGAATGGGCTCATGTG
CACCTGCCCTGCCGGCTTCTCTGGCCGACGCTGTGAGGTGCGGACATCCATCGATGCCTGTG
CCTCGAGTCCCTGCTTCAACAGGGCCACCTGCTACACCGACCTCTCCACAGACACCTTTGTG
TGCAACTGCCCTTATGGCTTTGTGGGCAGCCGCTGCGAGTTCCCCGTGGGCTTGCCGCCCAG
CTTCCCCTGGGTGGCCGTCTCGCTGGGTGTGGGGCTGGCAGTGCTGCTGGTACTGCTGGGCA
TGGTGGCAGTGGCTGTGCGGCAGCTGCGGCTTCGACGGCCGGACGACGGCAGCAGGGAAGCC
ATGAACAACTTGTCGGACTTCCAGAAGGACAACCTGATTCCTGCCGCCCAGCTTAAAAACAC
AAACCAGAAGAAGGAGCTGGAAGTGGACTGTGGCCTGGACAAGTCCAACTGTGGCAAACAGC
AAAACCACACATTGGACTATAATCTGGCCCCAGGGCCCCTGGGGCGGGGGACCATGCCAGGA
AAGTTTCCCCACAGTGACAAGAGCTTAGGAGAGAAGGCGCCACTGCGGTTACACAGTGAAAA
GCCAGAGTGTCGGATATCAGCGATATGCTCCCCCAGGGACTCCATGTACCAGTCTGTGTGTT
TGATATCAGAGGAGAGGAATGAATGTGTCATTGCCACGGAGGTATAAGGCAGGAGCCTACCT
GGACATCCCTGCTCAGCCCCGCGGCTGGACCTTCCTTCTGCATTGTTTACA

FIGURE 214

MAAASRSASGWALLLLVALWQQRAAGSGVFQLQLQEFINERGVLASGRPCEPGCRTFFRVCL
KHFQAVVSPGPCTFGTVSTPVLGTNSFAVRDDSSGGGRNPLQLPFNFTWPGTFSLIIEAWHA
PGDDLRPEALPPDALISKIAIQGSLAVGQNWLLDEQTSTLTRLRYSYRVICSDNYYGDNCSR
LCKKRNDHFGHYVCQPDGNLSCLPGWTGEYCQQPICLSGCHEQNGYCSKPAECLCRPGWQGR
LCNECIPHNGCRHGTCSTPWQCTCDEGWGGLFCDQDLNYCTHHSPCKNGATCSNSGQRSYTC
TCRPGYTGVDCELELSECDSNPCRNGGSCKDQEDGYHCLCPPGYYGLHCEHSTLSCADSPCF
NGGSCRERNQGANYACECPPNFTGSNCEKKVDRCTSNPCANGGQCLNRGPSRMCRCRPGFTG
TYCELHVSDCARNPCAHGGTCHDLENGLMCTCPAGFSGRRCEVRTSIDACASSPCFNRATCY
TDLSTDTFVCNCPYGFVGSRCEFPVGLPPSFPWVAVSLGVGLAVLLVLLGMVAVAVRQLRLR
RPDDGSREAMNNLSDFQKDNLIPAAQLKNTNQKKELEVDCGLDKSNCGKQQNHTLDYNLAPG
PLGRGTMPGKFPHSDKSLGEKAPLRLHSEKPECRISAICSPRDSMYQSVCLISEERNECVIA
TEV

Important features of the protein:
Signal peptide:
amino acids 1-26
Transmembrane domain:
amino acids 530-552
N-glycosylation sites.
amino acids 108-112, 183-187, 205-209, 393-397, 570-574, 610-614
Glycosaminoglycan attachment site.
amino acids 96-100
Tyrosine kinase phosphorylation site.
amino acids 340-347
N-myristoylation sites.
amino acids 42-48, 204-210, 258-264, 277-283, 297-303, 383-389, 415-421, 461-467, 522-528, 535-541, 563-569, 599-605, 625-631
Amidation site.
amino acids 471-475
Aspartic acid and asparagine hydroxylation site.
amino acids 339-351
EGF-like domain cysteine pattern signature.
amino acids 173-185, 206-218, 239-251, 270-282, 310-322, 348-360, 388-400, 426-438, 464-476, 506-518
Calcium-binding EGF-like:
amino acids 224-245, 255-276, 295-316, 333-354, 373-394, 411-432, 449-470

FIGURE 215

CGCGAGGCGCGGGGAGCCTGGGACCAGGAGCGAGAGCCGCCTACCTGCAGCCGCCGCCCACG
GCACGGCAGCCACCATGGCGCTCCTGCTGTGCTTCGTGCTCCTGTGCGGAGTAGTGGATTTC
GCCAGAAGTTTGAGTATCACTACTCCTGAAGAGATGATTGAAAAAGCCAAAGGGGAAACTGC
CTATCTGCCATGCAAATTTACGCTTAGTCCCGAAGACCAGGGACCGCTGGACATCGAGTGGC
TGATATCACCAGCTGATAATCAGAAGGTGGATCAAGTGATTATTTTATATTCTGGAGACAAA
ATTTATGATGACTACTATCCAGATCTGAAAGGCCGAGTACATTTTACGAGTAATGATCTCAA
ATCTGGTGATGCATCAATAAATGTAACGAATTTACAACTGTCAGATATTGGCACATATCAGT
GCAAAGTGAAAAAAGCTCCTGGTGTTGCAAATAAGAAGATTCATCTGGTAGTTCTTGTTAAG
CCTTCAGGTGCGAGATGTTACGTTGATGGATCTGAAGAAATTGGAAGTGACTTTAAGATAAA
ATGTGAACCAAAAGAAGGTTCACTTCCATTACAGTATGAGTGGCAAAAATTGTCTGACTCAC
AGAAAATGCCCACTTCATGGTTAGCAGAAATGACTTCATCTGTTATATCTGTAAAAAATGCC
TCTTCTGAGTACTCTGGGACATACAGCTGTACAGTCAGAAACAGAGTGGGCTCTGATCAGTG
CCTGTTGCGTCTAAACGTTGTCCCTCCTTCAAATAAAGCTGGACTAATTGCAGGAGCCATTA
TAGGAACTTTGCTTGCTCTAGCGCTCATTGGTCTTATCATCTTTTGCTGTCGTAAAAAGCGC
AGAGAAGAAAAATATGAAAAGGAAGTTCATCACGATATCAGGGAAGATGTGCCACCTCCAAA
GAGCCGTACGTCCACTGCCAGAAGCTACATCGGCAGTAATCATTCATCCCTGGGGTCCATGT
CTCCTTCCAACATGGAAGGATATTCCAAGACTCAGTATAACCAAGTACCAAGTGAAGACTTT
GAACGCACTCCTCAGAGTCCGACTCTCCCACCTGCTAAGTTCAAGTACCCTTACAAGACTGA
TGGAATTACAGTTGTATAAATATGGACTACTGAAGAATCTGAAGTATTGTATTATTTGACTT
TATTTTAGGCCTCTAGTAAAGACTTAAATGTTTTTTAAAAAAAGCACAAGGCACAGAGATTA
GAGCAGCTGTAAGAACACATCTACTTTATGCAATGGCATTAGACATGTAAGTCAGATGTCAT
GTCAAAATTAGTACGAGCCAAATTCTTTGTTAAAAAACCCTATGTATAGTGACACTGATAGT
TAAAAGATGTTTTATTATATTTTCAATAACTACCACTAACAAATTTTTAACTTTTCATATGC
ATATTCTGATATGTGGTCTTTTAGGAAAAGTATGGTTAATAGTTGATTTTTCAAAGGAAATT
TTAAAATTCTTACGTTCTGTTTAATGTTTTTGCTATTTAGTTAAATACATTGAAGGGAAATA
CCCGTTCTTTTCCCCTTTTATGCACACAACAGAAACACGCGTTGTCATGCCTCAAACTATTT
TTTATTTGCAACTACATGATTTCACACAATTCTCTTAAACAACGACATAAAATAGATTTCCT
TGTATATAAATAACTTACATACGCTCCATAAAGTAAATTCTCAAAGGTGCTAGAACAAATCG
TCCACTTCTACAGTGTTCTCGTATCCAACAGAGTTGATGCACAATATATAAATACTCAAGTC
CAATATTAAAAACTTAGGCACTTGACTAACTTTAATAAAATTTCTCAAACTATATCAATATC
TAAAGTGCATATATTTTTTAAGAAAGATTATTCTCAATAACTTCTATAAAAATAAGTTTGAT
GGTTTGGCCCATCTAACTTCACTACTATTAGTAAGAACTTTTAACTTTTAATGTGTAGTAAG
GTTTATTCTACCTTTTTCTCAACATGACACCAACACAATCAAAAACGAAGTTAGTGAGGTGC
TAACATGTGAGGATTAATCCAGTGATTCCGGTCACAATGCATTCCAGGAGGAGGTACCCATG
TCACTGGAATTGGGCGATATGGTTTATTTTTTCTTCCCTGATTTGGATAACCAAATGGAACA
GGAGGAGGATAGTGATTCTGATGGCCATTCCCTCGATACATTCCTGGCTTTTTTCTGGGCAA
AGGGTGCCACATTGGAAGAGGTGGAAATATAAGTTCTGAAATCTGTAGGGAAGAGAACACAT
TAAGTTAATTCAAAGGAAAAAATCATCATCTATGTTCCAGATTTCTCATTAAAGACAAAGTT
ACCCACAACACTGAGATCACATCTAAGTGACACTCCTATTGTCAGGTCTAAATACATTAAAA
ACCTCATGTGTAATAGGCGTATAATGTATAACAGGTGACCAATGTTTTCTGAATGCATAAAG
AAATGAATAAACTCAAACACAGTACTTCCTAAACAACTTCAACCAAAAAAGACCAAAACATG
GAACGAATGGAAGCTTGTAAGGACATGCTTGTTTTAGTCCAGTGGTTTCCACAGCTGGCTAA
GCCAGGAGTCACTTGGAGGCTTTTAAATACAAAACATTGGAGCTGGAGGCCATTATCCTTAG
CAAACTAATGCAGAAACAGAAAATCAACTACCGCATGTTCTCACTTATAAGTGGGAGGTAAT
GATAAGAACTTATGAACACAAAGAAGGAAACAATAGACATTGGAGTCTATTTGAGAGGGGAG
GGTGGGAGAAGGAAAAGGAGCAGAAAAGATAACTATTGAGTACTGCCTTCACACCTGGGTGA
TGAAATAATATGTACAACAAATCCCTGTGACACATGTTTACCTATGGAACAAACCTTCATGT
GTATCCCTAAACCTAAAATAAAAGTTAAAAAAAAAAAAARAAAAAAAAAAAAAAAAAAAAAA
AAAAAAAAAAAAAAAAAAAAAAAAAAAAAAAAAAAAAAAAAAAAAAAAAAAAAAAAAAAAAA
AAAAAAAAAAAAAAAAAAAAAA

FIGURE 216

></usr/seqdb2/sst/DNA/Dnaseqs.full/ss.DNA82361
><subunit 1 of 1, 352 aa, 1 stop
><MW: 38938, pI: 7.86, NX(S/T): 3
MALLLCFVLLCGVVDFARSLSITTPEEMIEKAKGETAYLPCKFTLSPEDQGPLDIEWLISPA
DNQKVDQVIILYSGDKIYDDYYPDLKGRVHFTSNDLKSGDASINVTNLQLSDIGTYQCKVKK
APGVANKKIHLVVLVKPSGARCYVDGSEEIGSDFKIKCEPKEGSLPLQYEWQKLSDSQKMPT
SWLAEMTSSVISVKNASSEYSGTYSCTVRNRVGSDQCLLRLNVVPPSNKAGLIAGAIIGTLL
ALALIGLIIFCCRKKRREEKYEKEVHHDIREDVPPPKSRTSTARSYIGSNHSSLGSMSPSNM
EGYSKTQYNQVPSEDFERTPQSPTLPPAKFKYPYKTDGITVV

Signal sequence.
amino acids 1-19

Transmembrane domain:
amino acids 236-257

N-glycosylation sites.
amino acids 106-110, 201-205, 298-302

Tyrosine kinase phosphorylation sites.
amino acids 31-39, 78-85, 262-270

N-myristoylation sites.
amino acids 116-122, 208-214, 219-225, 237-243, 241-247, 245-251, 296-302

Myelin P0 protein.
amino acids 96-125

FIGURE 217

GATGGCGCAGCCACAGCTTCTGTGAGATTCGATTTCTCCCCAGTTCCCCTGTGGGTCTGAGG
GGACCAGAAGGGTGAGCTACGTTGGCTTTCTGGAAGGGGAGGCTATATGCGTCAATTCCCCA
AAACAAGTTTTGACATTTCCCCTGAAATGTCATTCTCTATCTATTCACTGCAAGTGCCTGCT
GTTCCAGGCCTTACCTGCTGGGCACTAACGGCGGAGCCAGGATGGGGACAGAATAAAGGAGC
CACGACCTGTGCCACCAACTCGCACTCAGACTCTGAACTCAGACCTGAAATCTTCTCTTCAC
GGGAGGCTTGGCAGTTTTTCTTACTCCTGTGGTCTCCAGATTTCAGGCCTAAGATGAAAGCC
TCTAGTCTTGCCTTCAGCCTTCTCTCTGCTGCGTTTTATCTCCTATGGACTCCTTCCACTGG
ACTGAAGACACTCAATTTGGGAAGCTGTGTGATCGCCACAAACCTTCAGGAAATACGAAATG
GATTTTCTGAGATACGGGGCAGTGTGCAAGCCAAAGATGGAAACATTGACATCAGAATCTTA
AGGAGGACTGAGTCTTTGCAAGACACAAAGCCTGCGAATCGATGCTGCCTCCTGCGCCATTT
GCTAAGACTCTATCTGGACAGGGTATTTAAAAACTACCAGACCCCTGACCATTATACTCTCC
GGAAGATCAGCAGCCTCGCCAATTCCTTTCTTACCATCAAGAAGGACCTCCGGCTCTCTCAT
GCCCACATGACATGCCATTGTGGGGAGGAAGCAATGAAGAAATACAGCCAGATTCTGAGTCA
CTTTGAAAAGCTGGAACCTCAGGCAGCAGTTGTGAAGGCTTTGGGGGAACTAGACATTCTTC
TGCAATGGATGGAGGAGACAGAATAGGAGGAAAGTGATGCTGCTGCTAAGAATATTCGAGGT
CAAGAGCTCCAGTCTTCAATACCTGCAGAGGAGGCATGACCCCAAACCACCATCTCTTTACT
GTACTAGTCTTGTGCTGGTCACAGTGTATCTTATTTATGCATTACTTGCTTCCTTGCATGAT
TGTCTTTATGCATCCCCAATCTTAATTGAGACCATACTTGTATAAGATTTTTGTAATATCTT
TCTGCTATTGGATATATTTATTAGTTAATATATTTATTTATTTTTTGCTATTTAATGTATTT
ATTTTTTTACTTGGACATGAAACTTTAAAAAAATTCACAGATTATATTTATAACCTGACTAG
AGCAGGTGATGTATTTTTATACAGTAAAAAAAAAAAAACCTTGTAAATTCTAGAAGAGTGGCT
AGGGGGGTTATTCATTTGTATTCAACTAAGGACATATTTACTCATGCTGATGCTCTGTGAGA
TATTTGAAATTGAACCAATGACTACTTAGGATGGGTTGTGGAATAAGTTTTGATGTGGAATT
GCACATCTACCTTACAATTACTGACCATCCCCAGTAGACTCCCCAGTCCCATAATTGTGTAT
CTTCCAGCCAGGAATCCTACACGGCCAGCATGTATTTCTACAAATAAAGTTTTCTTTGCATA
CCAAAAAAAAAAAAAAAAAA

FIGURE 218

></usr/seqdb2/sst/DNA/Dnaseqs.min/ss.DNA83500

MKASSLAFSLLSAAFYLLWTPSTGLKTLNLGSCVIATNLQEIRNGFSEIRGSVQAKDGN
IDIRILRRTESLQDTKPANRCCLLRHLLRLYLDRVFKNYQTPDHYTLRKISSLANSFLT
IKKDLRLSHAHMTCHCGEEAMKKYSQILSHFEKLEPQAAVVKALGELDILLQWMEETE

FIGURE 219

CGCGGAGCCCTGCGCTGGGAGGTGCACGGTGTGCACGCTGGACTGGACCCCCATGCAACCCC
GCGCCCTGCGCCTTAACCAGGACTGCTCCGCGCGCCCCTGAGCCTCGGGCTCCGGCCCGGAC
CTGCAGCCTCCCAGGTGGCTGGGAAGAACTCTCCAACAATAAATACATTTGATAAGAAAGAT
GGCTTTAAAAGTGCTACTAGAACAAGAGAAAACGTTTTTCACTCTTTTAGTATTACTAGGCT
ATTTGTCATGTAAAGTGACTTGTGAATCAGGAGACTGTAGACAGCAAGAATTCAGGGATCGG
TCTGGAAACTGTGTTCCCTGCAACCAGTGTGGGCCAGGCATGGAGTTGTCTAAGGAATGTGG
CTTCGGCTATGGGGAGGATGCACAGTGTGTGACGTGCCGGCTGCACAGGTTCAAGGAGGACT
GGGGCTTCCAGAAATGCAAGCCCTGTCTGGACTGCGCAGTGGTGAACCGCTTTCAGAAGGCA
AATTGTTCAGCCACCAGTGATGCCATCTGCGGGGACTGCTTGCCAGGATTTTATAGGAAGAC
GAAACTTGTCGGCTTTCAAGACATGGAGTGTGTGCCTTGTGGAGACCCTCCTCCTCCTTACG
AACCGCACTGTGCCAGCAAGGTCAACCTCGTGAAGATCGCGTCCACGGCCTCCAGCCCACGG
GACACGGCGCTGGCTGCCGTTATCTGCAGCGCTCTGGCCACCGTCCTGCTGGCCCTGCTCAT
CCTCTGTGTCATCTATTGTAAGAGACAGTTTATGGAGAAGAAACCCAGCTGGTCTCTGCGGT
CGCAGGACATTCAGTACAACGGCTCTGAGCTGTCGTGTTTTGACAGACCTCAGCTCCACGAA
TATGCCCACAGAGCCTGCTGCCAGTGCCGCCGTGACTCAGTGCAGACCTGCGGGCCGGTGCG
CTTGCTCCCATCCATGTGCTGTGAGGAGGCCTGCAGCCCCAACCCGGCGACTCTTGGTTGTG
GGGTGCATTCTGCAGCCAGTCTTCAGGCAAGAAACGCAGGCCCAGCCGGGGAGATGGTGCCG
ACTTTCTTCGGATCCCTCACGCAGTCCATCTGTGGCGAGTTTTCAGATGCCTGGCCTCTGAT
GCAGAATCCCATGGGTGGTGACAACATCTCTTTTTGTGACTCTTATCCTGAACTCACTGGAG
AAGACATTCATTCTCTCAATCCAGAACTTGAAAGCTCAACGTCTTTGGATTCAAATAGCAGT
CAAGATTTGGTTGGTGGGGCTGTTCCAGTCCAGTCTCATTCTGAAAACTTTACAGCAGCTAC
TGATTTATCTAGATATAACAACACACTGGTAGAATCAGCATCAACTCAGGATGCACTAACTA
TGAGAAGCCAGCTAGATCAGGAGAGTGGCGCTGTCATCCACCCAGCCACTCAGACGTCCCTC
CAGGAAGCTTAAAGAACCTGCTTCTTTCTGCAGTAGAAGCGTGTGCTGGAACCCAAAGAGTA
CTCCTTTGTTAGGCTTATGGACTGAGCAGTCTGGACCTTGCATGGCTTCTGGGGCAAAAATA
AATCTGAACCAAACTGACGGCATTTGAAGCCTTTCAGCCAGTTGCTTCTGAGCCAGACCAGC
TGTAAGCTGAAACCTCAATGAATAACAAGAAAAGACTCCAGGCCGACTCATGATACTCTGCA
TCTTTCCTACATGAGAAGCTTCTCTGCCACAAAAGTGACTTCAAAGACTGATGGGTTGAGCT
GGCAGCCTATGAGATTGTGGACATATAACAAGAAACAGAAATGCCCTCATGCTTATTTTCAT
GGTGATTGTGGTTTTACAAGACTGAAGACCCAGAGTATACTTTTTCTTTCCAGAAATAATTT
CATACCGCCTATGAAATATCAGATAAATTACCTTAGCTTTTATGTAGAATGGGTTCAAAAGT
GAGTGTTTCTATTTGAGAAGGACACTTTTTCATCATCTAAACTGATTCGCATAGGTGGTTAG
AATGGCCCTCATATTGCCTGCCTAAATCTTGGGTTTATTAGATGAAGTTTACTGAATCAGAG
GAATCAGACAGAGGAGGATAGCTCTTTCCAGAATCCACACTTCTGACCTCAGCCTCGGTCTC
ATGAACACCCGCTGATCTCAGGAGAACACCTGGGCTAGGGAATGTGGTCGAGAAAGGGCAGC
CCATTGCCCAGAATTAACACATATTGTAGAGACTTGTATGCAAAGGTTGGCATATTTATATG
AAAATTAGTTGCTATAGAAACATTTGTTGCATCTGTCCCTCTGCCTGAGCTTAGAAGGTTAT
AGAAAAAGGGTATTTATAAACATAAATGACCTTTTACTTGCATTGTATCTTATACTAAAGGC
TTTAGAAATTACAACATATCAGGTTCCCCTACTACTGAAGTAGCCTTCCGTGAGAACACACC
ACATGTTAGGACTAGAAGAAAATGCACAATTTGTAGGGGTTTGGATGAAGCAGCTGTAACTG
CCCTAGTGTAGTTTGACCAGGACATTGTCGTGCTCCTTCCAATTGTGTAAGATTAGTTAGCA
CATCATCTCCTACTTTAGCCATCCGGTGTTGGATTTAAGAGGACGGTGCTTCTTTCTATTAA
AGTGCTCCATCCCCTACCATCTACACATTAGCATTGTCTCTAGAGCTAAGACAGAAATTAAC
CCCGTTCAGTCACAAAGCAGGGAATGGTTCATTTACTCTTAATCTTTATGCCCTGGAGAAGA
CCTACTTGAACAGGGCATATTTTTTAGACTTCTGAACATCAGTATGTTCGAGGGTACTATGA
TATTTTGGTTTGGAATTGCCCTGCCCAAGTCACTGTCTTTTAACTTTTAAACTGAATATTAA
AATGTATCTGTCTTTCCT

FIGURE 220

></usr/seqdb2/sst/DNA/Dnaseqs.min/ss.DNA84210
><subunit 1 of 1, 417 aa, 1 stop
><MW: 45305, pI: 5.12, NX(S/T): 6
MALKVLLEQEKTFFTLLVLLGYLSCKVTCESGDCRQQEFRDRSGNCVPCNQCGPGMELSK
ECGFGYGEDAQCVTCRLHRFKEDWGFQKCKPCLDCAVVNRFQKANCSATSDAICGDCLPG
FYRKTKLVGFQDMECVPCGDPPPPYEPHCASKVNLVKIASTASSPRDTALAAVICSALAT
VLLALLILCVIYCKRQFMEKKPSWSLRSQDIQYNGSELSCFDRPQLHEYAHRACCQCRRD
SVQTCGPVRLLPSMCCEEACSPNPATLGCGVHSAASLQARNAGPAGEMVPTFFGSLTQSI
CGEFSDAWPLMQNPMGGDNISFCDSYPELTGEDIHSLNPELESSTSLDSNSSQDLVGGAV
PVQSHSENFTAATDLSRYNNTLVESASTQDALTMRSQLDQESGAVIHPATQTSLQEA

Important features of the protein:
Signal peptide:
Amino acids
1-25

Transmembrane domain:
Amino acids
169-192

N-glycosylation sites:
Amino acids
105-109;214-218;319-323;350-354;368-372;379-383 cAMP- and cGMP-dependent protein kinase phosphorylation sites:
Amino acids
200-204;238-242

Tyrosine kinase phosphorylation site:
Amino acids
207-214

N-myristoylation sites:
Amino acids
55-61;215-221;270-276

Prokaryotic membrane lipoprotein lipid attachment site:
Amino acids
259-270

TNFR/NGFR family cysteine-rich region proteins:
Amino acids
89-96

FIGURE 221

CTAGAGAGTATAGGGCAGAAGGATGGCAGATGAGTGACTCCACATCCAGAGCTGCCTCCCTT
TAATCCAGGATCCTGTCCTTCCTGTCCTGTAGGAGTGCCTGTTGCCAGTGTGGGGTGAGACA
AGTTTGTCCCACAGGGCTGTCTGAGCAGATAAGATTAAGGGCTGGGTCTGTGCTCAATTAAC
TCCTGTGGGCACGGGGGCTGGGAAGAGCAAAGTCAGCGGTGCCTACAGTCAGCACCATGCTG
GGCCTGCCGTGGAAGGGAGGTCTGTCCTGGGCGCTGCTGCTGCTTCTCTTAGGCTCCCAGAT
CCTGCTGATCTATGCCTGGCATTTCCACGAGCAAAGGGACTGTGATGAACACAATGTCATGG
CTCGTTACCTCCCTGCCACAGTGGAGTTTGCTGTCCACACATTCAACCAACAGAGCAAGGAC
TACTATGCCTACAGACTGGGGCACATCTTGAATTCCTGGAAGGAGCAGGTGGAGTCCAAGAC
TGTATTCTCAATGGAGCTACTGCTGGGGAGAACTAGGTGTGGGAAATTTGAAGACGACATTG
ACAACTGCCATTTCCAAGAAAGCACAGAGCTGAACAATACTTTCACCTGCTTCTTCACCATC
AGCACCAGGCCCTGGATGACTCAGTTCAGCCTCCTGAACAAGACCTGCTTGGAGGGATTCCA
CTGAGTGAAACCCACTCACAGGCTTGTCCATGTGCTGCTCCCACATTCCGTGGACATCAGCA
CTACTCTCCTGAGGACTCTTCAGTGGCTGAGCAGCTTTGGACTTGTTTGTTATCCTATTTTG
CATGTGTTTGAGATCTCAGATCAGTGTTTTAGAAAATCCACACATCTTGAGCCTAATCATGT
AGTGTAGATCATTAAACATCAGCATTTTAAGAAAAAAAAAAAAAAAAAAAAAAAAAAAAAAAA
AAAAAAAAAAAAAAAAAAAAAAAAAAAAAA

FIGURE 222

MLGLPWKGGLSWALLLLLLGSQILLIYAWHFHEQRDCDEHNVMARYLPATVEFAVHTFNQQS
KDYYAYRLGHILNSWKEQVESKTVFSMELLLGRTRCGKFEDDIDNCHFQESTELNNTFTCFF
TISTRPWMTQFSLLNKTCLEGFH

Important features of the protein:
Signal peptide:
amino acids 1-25

N-glycosylation sites.
amino acids 117-121, 139-143

N-myristoylation site.
amino acids 9-15

FIGURE 223

AATCGGCTGATTCTGCATCTGGAAACTGCCTTCATCTTGAAAGAAAAGCTCCAGGTCCCT
TCTCCAGCCACCCAGCCCCAAGATGGTGATGCTGCTGCTGCTGCTTTCCGCACTGGCTGG
CCTCTTCGGTGCGGCAGAGGGACAAGCATTTCATCTTGGGAAGTGCCCCAATCCTCCGGT
GCAGGAGAATTTTGACGTGAATAAGTATCTCGGAAGATGGTACGAAATTGAGAAGATCCC
AACAACCTTTGAGAATGGACGCTGCATCCAGGCCAACTACTCACTAATGGAAAACGGAAA
GATCAAAGTGTTAAACCAGGAGTTGAGAGCTGATGGAACTGTGAATCAAATCGAAGGTGA
AGCCACCCCAGTTAACCTCACAGAGCCTGCCAAGCTGGAAGTTAAGTTTTCCTGGTTTAT
GCCATCGGCACCGTACTGGATCCTGGCCACCGACTATGAGAACTATGCCCTCGTGTATTC
CTGTACCTGCATCATCCAACTTTTTCACGTGGATTTTGCTTGGATCTTGGCAAGAAACCC
TAATCTCCCTCCAGAAACAGTGGACTCTCTAAAAAATATCCTGACTTCTAATAACATTGA
TGTCAAGAAAATGACGGTCACAGACCAGGTGAACTGCCCCAAGCTCTCGTAACCAGGTTC
TACAGGGAGGCTGCACCCACTCCATGTTACTTCTGCTTCGCTTTCCCCTACCCCACCCCC
CCCCCATAAAGACAAACCAATCAACCACGACAAAGGAAGTTGACCTGAACATGTAACCAT
GCCCTACCCTGTTACCTTGCTAGCTGCAAAATAAACTTGTTGCTGACCTGCTGTGCTCGC
AAAAAA

FIGURE 224

MVMLLLLLSALAGLFGAAEGQAFHLGKCPNPPVQENFDVNKYLGRWYEIEKIPTTFENG
RCIQANYSLMENGKIKVLNQELRADGTVNQIEGEATPVNLTEPAKLEVKFSWFMPSAPY
WILATDYENYALVYSCTCIIQLFHVDFAWILARNPNLPPETVDSLKNILTSNNIDVKKM
TVTDQVNCPKLS

Signal sequence
1-16

N-glycosylation site.

65-68
98-101 cAMP- and cGMP-dependent protein kinase phosphorylation site.

175-178

N-myristoylation site.

13-18
16-21

Lipocalin proteins.

36-47
120-130

Lipocalin / cytosolic fatty-acid binding proteins

GGGTGATTGAACTAAACCTTCGCCGCACCGAGTTTGCAGTACGGCCGTCACCCGCACCGCTG
CCTGCTTGCGGTTGGAGAAATCAAGGCCCTACCGGGCCTCCGTAGTCACCTCTCTATAGTGG
GCGTGGCCGAGGCCGGGGTGACCCTGCCGGAGCCTCCGCTGCCAGCGACATGTTCAAGGTAA
TTCAGAGGTCCGTGGGGCCAGCCAGCCTGAGCTTGCTCACCTTCAAAGTCTATGCAGCACCA
AAAAAGGACTCACCTCCCAAAAATTCCGTGAAGGTTGATGAGCTTTCACTCTACTCAGTTCC
TGAGGGTCAATCGAAGTATGTGGAGGAGGCAAGGAGCCAGCTTGAAGAAAGCATCTCACAGC
TCCGACACTATTGCGAGCCATACACAACCTGGTGTCAGGAAACGTACTCCCAAACTAAGCCC
AAGATGCAAAGTTTGGTTCAATGGGGGTTAGACAGCTATGACTATCTCCAAAATGCACCTCC
TGGATTTTTTCCGAGACTTGGTGTTATTGGTTTTGCTGGCCTTATTGGACTCCTTTTGGCTA
GAGGTTCAAAAATAAAGAAGCTAGTGTATCCGCCTGGTTTCATGGGATTAGCTGCCTCCCTC
TATTATCCACAACAAGCCATCGTGTTTGCCCAGGTCAGTGGGGAGAGATTATATGACTGGGG
TTTACGAGGATATATAGTCATAGAAGATTTGTGGAAGGAGAACTTTCAAAAGCCAGGAAATG
TGAAGAATTCACCTGGAACTAAGTAGAAAACTCCATGCTCTGCCATCTTAATCAGTTATAGG
TAAACATTGGAAACTCCATAGAATAAATCAGTATTTCTACAGAAAAATGGCATAGAAGTCAG
TATTGAATGTATTAAATTGGCTTTCTTCTTCAGGAAAAACTAGACCAGACCTCTGTTATCTT
CTGTGAAATCATCCTACAAGCAAACTAACCTGGAATCCCTTCACCTAGAGATAATGTACAAG
CCTTAGAACTCCTCATTCTCATGTTGCTATTTATGTACCTAATTAAAACCCAAGTTTAAAAA
AAAAAAAAAAAAAAAAAAAAAAAAAAAAAAAAAA

FIGURE 226

MFKVIQRSVGPASLSLLTFKVYAAPKKDSPPKNSVKVDELSLYSVPEGQSKYVEEARSQLEE
SISQLRHYCEPYTTWCQETYSQTKPKMQSLVQWGLDSYDYLQNAPPGFFPRLGVIGFAGLIG
LLLARGSKIKKLVYPPGFMGLAASLYYPQQAIVFAQVSGERLYDWGLRGYIVIEDLWKENFQ
KPGNVKNSPGTK

Important features:
Signal peptide:
Amino acids 1-23

Transmembrane domain:
Amino acids 111-130 cAMP- and cGMP-dependent protein kinase phosphorylation site:
Amino acids 26-30

Tyrosine kinase phosphorylation site:
Amino acids 36-44

N-myristoylation sites:
Amino acids 124-130;144-150;189-195

FIGURE 227

CACCGGAGGGCACGCAGCTGACGGAGCTGCGCTGCGTTCGCCTCGTTTGCCTCGCGCCCTCC
ACTGGAGCTGTTCGCGCCTCCCGGCTCCCACCGCAGCCCACCCGGCAGAGGAGTCGCTACCA
GCGCCCAGTGCGCTCTGTCAGTCCGCAAACTCCTTGCCGCCCGCCCCGGGCTGGGCACCAAA
TACCAGGCTACCATGGTCTACAAGACTCTCTTCGCTCTTTGCATCTTAACTGCAGGATGGAG
GGTACAGAGTCTGCCTACATCAGCTCCTTTGTCTGTTTCTCTTCCGACAAACATTGTACCAC
CGACCACCATCTGGACTAGCTCTCCACAAAACACTGATGCAGACACTGCCTCCCCATCCAAC
GGCACTCACAACAACTCGGTGCTCCCAGTTACAGCATCAGCCCCAACATCTCTGCTTCCTAA
GAACATTTCCATAGAGTCCAGAGAAGAGGAGATCACCAGCCCAGGTTCGAATTGGGAAGGCA
CAAACACAGACCCCTCACCTTCTGGGTTCTCGTCAACAAGCGGTGGAGTCCACTTAACAACC
ACGTTGGAGGAACACAGCTCGGGCACTCCTGAAGCAGGCGTGGCAGCTACACTGTCGCAGTC
CGCTGCTGAGCCTCCCACACTCATCTCCCCTCAAGCTCCAGCCTCATCACCCTCATCCCTAT
CAACCTCACCACCTGAGGTCTTTTCTGCCTCCGTTACTACCAACCATAGCTCCACTGTGACC
AGCACCCAACCCACTGGAGCTCCAACTGCACCAGAGTCCCCGACAGAGGAGTCCAGCTCTGA
CCACACACCCACTTCACATGCCACAGCTGAGCCAGTGCCCCAGGAGAAAACACCCCCAACAA
CTGTGTCAGGCAAAGTGATGTGTGAGCTCATAGACATGGAGACCACCACCACCTTTCCCAGG
GTGATCATGCAGGAAGTAGAACATGCATTAAGTTCAGGCAGCATCGCCGCCATTACCGTGAC
AGTCATTGCCGTGGTGCTGCTGGTGTTTGGAGTTGCAGCCTACCTAAAAATCAGGCATTCCT
CCTATGGAAGACTTTTGGACGACCATGACTACGGGTCCTGGGGAAACTACAACAACCCTCTG
TACGATGACTCCTAACAATGGAATATGGCCTGGGATGAGGATTAACTGTTCTTTATTTATAA
GTGCTTATCCAGTAGAATTAATAAGTACCTGATGCGCATTGAACGACAATCTTAAGCCCTGT
TTTGTTGGTATGGTTGTTTTTGTTTTCCTCCCTCTCCTCTGGCTGCTACAACTTCCCCTTTC
TGGTACAAGAAGAACCATTCTTTAAAGGTGAGTGGAGGCTGATTTGCAGCTGAAGTGGGCCA
GCCTTGCACCAGCCAGGCCAGACCACCATGGTGAAGGCTTCTTTCCCCACTGCAGGACCCAC
TTTGAGAAGGATCGAGGAGGAGGATTTGGGTTGTTTTGTTAGGGGTTACTTTCAGGGGAACA
TTTCATTTGTGTTATTTCTTAAACTTCTATTTAGGAAATTACATTAAGTATTAATGAGGGGA
AAGGAAATGAGCTCTACGAGGATTTCACCTTGCATGGGAGAGAGCAGGGTTTTCTCAGATTC
CTTTTTAATCTCTATTTATCTGGTTGTTTCTGACAGGATGCTGCCTGCTTGGCTCTACGAGC
TGGAAAGCAGCTTCTTAGCTGCCTAATTAATGAAAGATGAAAATAGGAAGTGCCCTGGAGGG
GGCCAGCAGGTCACGGGGCAGAATCTCTCAGGTTGCTGTGGGATCTCAGTGTGCCCCTACCT
GTTCTCCCCTCCAGGCCACCTGTCTCTGTAAAGGATGTCTGCTCTGTTCAAAAGGCAGCTGG
GATCCCAGCCCACAAGTGATCAGCAGAGTTGCATTTCCAAAGAAAAAGGCTATGAGATGAGC
TGAGTTATAGAGAGAAAGGGAGAGGCATGTACGGTGTGGGGAAGTGGAAGAGAAGCTGGCGG
GGGAGAAGGAGGCTAACCTGCACTGAGTACTTCATTAGGACAAGTGAGAATCAGCTATTGAT
AATGGCCAGAGATATCCACAGCTTGGAGGAGCCCAGAGACTGTTTGCTTTATACCCACACAG
CAACTGGTCCACTGCTTTACTGTCTGTTGGATAATGGCTGTAAAATGTTTAAAAAC

FIGURE 228

MVYKTLFALCILTAGWRVQSLPTSAPLSVSLPTNIVPPTTIWTSSPQNTDADTASPSNGTHN
NSVLPVTASAPTSLLPKNISIESREEEITSPGSNWEGTNTDPSPSGFSSTSGGVHLTTTLEE
HSSGTPEAGVAATLSQSAAEPPTLISPQAPASSPSSLSTSPPEVFSASVTTNHSSTVTSTQP
TGAPTAPESPTEESSSDHTPTSHATAEPVPQEKTPPTTVSGKVMCELIDMETTTTFPRVIMQ
EVEHALSSGSIAAITVTVIAVVLLVFGVAAYLKIRHSSYGRLLDDHDYGSWGNYNNPLYDDS

Important features of the protein:
Signal peptide:
amino acids 1-20

Transmembrane domain:
amino acids 258-278

N-glycosylation sites.
amino acids 58-61, 62-65, 80-83, 176-179

Casein kinase II phosphorylation sites.
amino acids 49-52, 85-88, 95-98, 100-103, 120-123, 121-124, 141-144, 164-167, 191-194, 195-198, 200-203

Tyrosine kinase phosphorylation site.
amino acids 289-296

N-myristoylation sites.
amino acids 59-64, 115-120, 128-133, 133-138, 257-262, 297-302

FIGURE 229

CTCCTGCACTAGGCTCTCAGCCAGGGATGATGCGCTGCTGCCGCCGCCGCTGCTGCTGCCGG
CAACCACCCCATGCCCTGAGGCCGTTGCTGTTGCTGCCCCTCGTCCTTTTACCTCCCCTGGC
AGCAGCTGCAGCGGGCCCAAACCGATGTGACACCATATACCAGGGCTTCGCCGAGTGTCTCA
TCCGCTTGGGGGACAGCATGGGCCGCGGAGGCGAGCTGGAGACCATCTGCAGGTCTTGGAAT
GACTTCCATGCCTGTGCCTCTCAGGTCCTGTCAGGCTGTCCGGAGGAGGCAGCTGCAGTGTG
GGAATCACTACAGCAAGAAGCTCGCCAGGCCCCCCGTCCGAATAACTTGCACACTCTGTGCG
GTGCCCCGGTGCATGTTCGGGAGCGCGGCACAGGCTCCGAAACCAACCAGGAGACGCTGCGG
GCTACAGCGCCTGCACTCCCCATGGCCCCTGCGCCCCACTGCTGGCGGCTGCTCTGGCTCTG
GCCTACCTCCTGAGGCCTCTGGCCTAGCTTGTTGGGTTGGGTAGCAGCGCCCGTACCTCCAG
CCCTGCTCTGGCGGTGGTTGTCCAGGCTCTGCAGAGCGCAGCAGGGCTTTTCATTAAAGGTA
TTTATATTTGTA

FIGURE 230

></usr/seqdb2/sst/DNA/Dnaseqs.min/ss.DNA92265
><subunit 1 of 1, 165 aa, 1 stop
><MW: 17786, pI: 8.43, NX(S/T): 0
MMRCCRRRCCCRQPPHALRPLLLLPLVLLPPLAAAAAGPNRCDTIYQGFAECLIRLGDSM
GRGGELETICRSWNDFHACASQVLSGCPEEAAAVWESLQQEARQAPRPNNLHTLCGAPVH
VRERGTGSETNQETLRATAPALPMAPAPPLLAAALALAYLLRPLA

Important features of the protein:
Signal peptide:
Amino acids 1-35

Transmembrane domain:
Amino acids 141-157

N-myristoylation site:
Amino acids 127-133

Prokaryotic membrane lipoprotein lipid attachment site:
Amino acids 77-88

FIGURE 231

AAGTACTTGTGTCCGGGTGGTGGACTGGATTAGCTGCGGAGCCCTGGAAGCTGCCTGTCCTT
CTCCCTGTGCTTAACCAGAGGTGCCCATGGGTTGGACAATGAGGCTGGTCACAGCAGCACTG
TTACTGGGTCTCATGATGGTGGTCACTGGAGACGAGGATGAGAACAGCCCGTGTGCCCATGA
GGCCCTCTTGGACGAGGACACCCTCTTTTGCCAGGGCCTTGAAGTTTTCTACCCAGAGTTGG
GGAACATTGGCTGCAAGGTTGTTCCTGATTGTAACAACTACAGACAGAAGATCACCTCCTGG
ATGGAGCCGATAGTCAAGTTCCCGGGGGCCGTGGACGGCGCAACCTATATCCTGGTGATGGT
GGATCCAGATGCCCCTAGCAGAGCAGAACCCAGACAGAGATTCTGGAGACATTGGCTGGTAA
CAGATATCAAGGGCGCCGACCTGAAGAAAGGGAAGATTCAGGGCCAGGAGTTATCAGCCTAC
CAGGCTCCCTCCCCACCGGCACACAGTGGCTTCCATCGCTACCAGTTCTTTGTCTATCTTCA
GGAAGGAAAAGTCATCTCTCTCCTTCCCAAGGAAAACAAAACTCGAGGCTCTTGGAAAATGG
ACAGATTTCTGAACCGCTTCCACCTGGGCGAACCTGAAGCAAGCACCCAGTTCATGACCCAG
AACTACCAGGACTCACCAACCCTCCAGGCTCCCAGAGGAAGGGCCAGCGAGCCCAAGCACAA
AACCAGGCAGAGATAGCTGCCTGCTAGATAGCCGGCTTTGCCATCCGGGCATGTGGCCACAC
TGCTCACCACCGACGATGTGGGTATGGAACCCCCTCTGGATACAGAACCCCTTCTTTTCCAA
ATTAAAAAAAAAAAATCATCAAA

FIGURE 232

></usr/seqdb2/sst/DNA/Dnaseqs.min/ss.DNA92274
><subunit 1 of 1, 223 aa, 1 stop
><MW: 25402, pI: 8.14, NX(S/T): 1
MGWTMRLVTAALLLGLMMVVTGDEDENSPCAHEALLDEDTLFCQGLEVFYPELGNIGCKVVP
DCNNYRQKITSWMEPIVKFPGAVDGATYILVMVDPDAPSRAEPRQRFWRHWLVTDIKGADLK
KGKIQGQELSAYQAPSPPAHSGFHRYQFFVYLQEGKVISLLPKENKTRGSWKMDRFLNRFHL
GEPEASTQFMTQNYQDSPTLQAPRGRASEPKHKTRQR

Important features of the protein:
Signal peptide:
amino acids 1-22

N-glycosylation site.
amino acids 169-173

Tyrosine kinase phosphorylation site.
amino acids 59-68

N-myristoylation sites.
amino acids 54-60, 83-89, 130-136

Phosphatidylethanolamine signature.
amino acids 113-157

FIGURE 233

AAGGAGCAGCCCGCAAGCACCAAGTGAGAGGCATGAAGTTACAGTGTGTTTCCCTTTGGCTC
CTGGGTACAATACTGATATTGTGCTCAGTAGACAACCACGGTCTCAGGAGATGTCTGATTTC
CACAGACATGCACCATATAGAAGAGAGTTTCCAAGAAATCAAAAGAGCCATCCAAGCTAAGG
ACACCTTCCCAAATGTCACTATCCTGTCCACATTGGAGACTCTGCAGATCATTAAGCCCTTA
GATGTGTGCTGCGTGACCAAGAACCTCCTGGCGTTCTACGTGGACAGGGTGTTCAAGGATCA
TCAGGAGCCAAACCCCAAAATCTTGAGAAAAATCAGCAGCATTGCCAACTCTTTCCTCTACA
TGCAGAAAACTCTGCGGCAATGTCAGGAACAGAGGCAGTGTCACTGCAGGCAGGAAGCCACC
AATGCCACCAGAGTCATCCATGACAACTATGATCAGCTGGAGGTCCACGCTGCTGCCATTAA
ATCCCTGGGAGAGCTCGACGTCTTTCTAGCCTGGATTAATAAGAATCATGAAGTAATGTTCT
CAGCTTGATGACAAGGAACCTGTATAGTGATCCAGGGATGAACACCCCCTGTGCGGTTTACT
GTGGGAGACAGCCCACCTTGAAGGGGAAGGAGATGGGGAAGGCCCCTTGCAGCTGAAAGTCC
CACTGGCTGGCCTCAGGCTGTCTTATTCCGCTTGAAAATAGGCAAAAAGTCTACTGTGGTAT
TTGTAATAAACTCTATCTGCTGAAAGGGCCTGCAGGCCATCCTGGGAGTAAAGGGCTGCCTT
CCCATCTAATTTATTGTAAAGTCATATAGTCCATGTCTGTGATGTGAGCCAAGTGATATCCT
GTAGTACACATTGTACTGAGTGGTTTTTCTGAATAAATTCCATATTTTACCTATGA

FIGURE 234

></usr/seqdb2/sst/DNA/Dnaseqs.full/ss.DNA92282
><subunit 1 of 1, 177 aa, 1 stop
><MW: 20452, pI: 8.00, NX(S/T): 2
MKLQCVSLWLLGTILILCSVDNHGLRRCLISTDMHHIEESFQEIKRAIQAKDTFPNVTILST
LETLQIIKPLDVCCVTKNLLAFYVDRVFKDHQEPNPKILRKISSIANSFLYMQKTLRQCQEQ
RQCHCRQEATNATRVIHDNYDQLEVHAAAIKSLGELDVFLAWINKNHEVMFSA

Signal sequence:
amino acids 1-18

N-glycosylation sites.
amino acids 56-60, 135-139 cAMP- and cGMP-dependent protein kinase phosphorylation site.
amino acids 102-106

N-myristoylation site.
amino acids 24-30

Actinin-type actin-binding domain signature 1.
amino acids 159-169

FIGURE 235

GCCCGGGCGGCTGCCCTTGGGTGCTCCCTTCCCTGCCCGACACCCAGACCGACCTTGACCGC
CCACCTGGCAGGAGCAGGACAGGACGGCCGGACGCGGCCATGGCCGAGCTCCCGGGGCCCTT
TCTCTGCGGGGCCCTGCTAGGCTTCCTGTGCCTGAGTGGGCTGGCCGTGGAGGTGAAGGTAC
CCACAGAGCCGCTGAGCACGCCCCTGGGGAAGACAGCCGAGCTGACCTGCACCTACAGCACG
TCGGTGGGAGACAGCTTCGCCCTGGAGTGGAGCTTTGTGCAGCCTGGGAAACCCATCTCTGA
GTCCCATCCAATCCTGTACTTCACCAATGGCCATCTGTATCCAACTGGTTCTAAGTCAAAGC
GGGTCAGCCTGCTTCAGAACCCCCCCACAGTGGGGGTGGCCACACTGAAACTGACTGACGTC
CACCCCTCAGATACTGGAACCTACCTCTGCCAAGTCAACAACCCACCAGATTTCTACACCAA
TGGGTTGGGGCTAATCAACCTTACTGTGCTGGTTCCCCCCAGTAATCCCTTATGCAGTCAGA
GTGGACAAACCTCTGTGGGAGGCTCTACTGCACTGAGATGCAGCTCTTCCGAGGGGGCTCCT
AAGCCAGTGTACAACTGGGTGCGTCTTGGAACTTTTCCTACACCTTCTCCTGGCAGCATGGT
TCAAGATGAGGTGTCTGGCCAGCTCATTCTCACCAACCTCTCCCTGACCTCCTCGGGCACCT
ACCGCTGTGTGGCCACCAACCAGATGGGCAGTGCATCCTGTGAGCTGACCCTCTCTGTGACC
GAACCCTCCCAAGGCCGAGTGGCCGGAGCTCTGATTGGGGTGCTCCTGGGCGTGCTGTTGCT
GTCAGTTGCTGCGTTCTGCCTGGTCAGGTTCCAGAAAGAGAGGGGGAAGAAGCCCAAGGAGA
CATATGGGGGTAGTGACCTTCGGGAGGATGCCATCGCTCCTGGGATCTCTGAGCACACTTGT
ATGAGGGCTGATTCTAGCAAGGGGTTCCTGGAAAGACCCTCGTCTGCCAGCACCGTGACGAC
CACCAAGTCCAAGCTCCCTATGGTCGTGTGACTTCTCCCGATCCCTGAGGGCGGTGAGGGGG
AATATCAATAATTAAAGTCTGTGGGTACCCTTNAAAAAAAAAAAA

FIGURE 236

></usr/seqdb2/sst/DNA/Dnaseqs.min/ss.DNA108760
><subunit 1 of 1, 327 aa, 1 stop
><MW: 34348, pI: 7.88, NX(S/T): 2
MAELPGPFLCGALLGFLCLSGLAVEVKVPTEPLSTPLGKTAELTCTYSTSVGDSFALEWS
FVQPGKPISESHPILYFTNGHLYPTGSKSKRVSLLQNPPTVGVATLKLTDVHPSDTGTYL
CQVNNPPDFYTNGLGLINLTVLVPPSNPLCSQSGQTSVGGSTALRCSSSEGAPKPVYNWV
RLGTFPTPSPGSMVQDEVSGQLILTNLSLTSSGTYRCVATNQMGSASCELTLSVTEPSQG
RVAGALIGVLLGVLLLSVAAFCLVRFQKERGKKPKETYGGSDLREDAIAPGISEHTCMRA
DSSKGFLERPSSASTVTTTKSKLPMVV

Important features of the protein:
Signal peptide:
Amino acids 1-20

Transmembrane domain:
Amino acids 242-260

N-glycosylation sites:
Amino acids 138-142;206-210 cAMP- and cGMP-dependent protein kinase phosphorylation site:
Amino acids 90-94

N-myristoylation sites:
Amino acids 11-17;117-123;159-165;213-219;224-230;244-250;
248-254

Amidation site:
Amino acids 270-274

Prokaryotic membrane lipoprotein lipid attachment site:
Amino acids 218-229

FIGURE 237

GGATGCAGCAGAGAGGAGCAGCTGGAAGCCGTGGCTGCGCTCTCTTCCCTCTGCTGGGCG
TCCTGTTCTTCCAGGGTGTTTATATCGTCTTTTCCTTGGAGATTCGTGCAGATGCCCATG
TCCGAGGTTATGTTGGAGAAAAGATCAAGTTGAAATGCACTTTCAAGTCAACTTCAGATG
TCACTGACAAGCTTACTATAGACTGGACATATCGCCCTCCCAGCAGCAGCCACACAGTAT
CAATATTTCATTATCAGTCTTTCCAGTACCCAACCACAGCAGGCACATTTCGGGATCGGA
TTTCCTGGGTTGGAAATGTATACAAAGGGGATGCATCTATAAGTATAAGCAACCCTACCA
TAAAGGACAATGGGACATTCAGCTGTGCTGTGAAGAATCCCCCAGATGTGCACCATAATA
TTCCCATGACAGAGCTAACAGTCACAGAAAGGGGTTTTGGCACCATGCTTTCCTCTGTGG
CCCTTCTTTCCATCCTTGTCTTTGTGCCCTCAGCCGTGGTGGTTGCTCTGCTGCTGGTGA
GAATGGGGAGGAAGGCTGCTGGGCTGAAGAAGAGGAGCAGGTCTGGCTATAAGAAGTCAT
CTATTGAGGTTTCCGATGACACTGATCAGGAGGAGGAAGAGGCGTGTATGGCGAGGCTTT
GTGTCCGTTGCGCTGAGTGCCTGGATTCAGACTATGAAGAGACATATTGATGAAAGTCTG
TATGACACAAGAAGAGTCACCTAAAGACAGGAAACATCCCATTCCACTGGCAGCTAAAGC
CTGTCAGAGAAAGTGGAGCTGGCCTGGACCATAGCGATGGACAATCCTGGAGATCATCAG
TAAAGACTTTAGGAACCACTTATTTATTGAATAAATGTTCTTGTTGTATTTATAAACTGT
TCAGGAAGTCTCATAAGAGACTCATGACTTCCCCTTTCAATGAATTATGCTGTAATTGAA
TGAAGAAATTCTTTTCCTGAGCA

FIGURE 238

MQQRGAAGSRGCALFPLLGVLFFQGVYIVFSLEIRADAHVRGYVGEKIKLKCTFKSTSD
VTDKLTIDWTYRPPSSSHTVSIFHYQSFQYPTTAGTFRDRISWVGNVYKGDASISISNP
TIKDNGTFSCAVKNPPDVHHNIPMTELTVTERGFGTMLSSVALLSILVFVPSAVVVALL
LVRMGRKAAGLKKRSRSGYKKSSIEVSDDTDQEEEEACMARLCVRCAECLDSDYEETY

Transmembrane domain
11-30
157-177

N-glycosylation site
123-127 cAMP- and cGMP-dependent protein kinase phosphorylation site
189-193
197-201

Tyrosine kinase phosphorylation site
63-71

N-myristoylation site
5-11
8-14
124-130
153-159

Amidation site
181-185

FIGURE 239

CAGGCGGGCCCCCGCGCGGCAGGGCCCTGGACCCGCGCGGCTCCCGGGGATGGTGAGCAAGGCGCTGCTGCGCC
TCGTGTCTGCCGTCAACCGCAGGAGGATGAAGCTGCTGCTGGGCATCGCCTTGCTGGCCTACGTCGCCTCTGTT
TGGGGCAACTTCGTTAATATGAGGTCTATCCAGGAAAATGGTGAACTAAAAATTGAAAGCAAGATTGAAGAGAT
GGTTGAACCACTAAGAGAGAAAATCAGAGATTTAGAAAAAAGCTTTACCCAGAAATACCCACCAGTAAAGTTTT
TATCAGAAAAGGATCGGAAAAGAATTTTGATAACAGGAGGCGCAGGGTTCGTGGGCTCCCATCTAACTGACAAA
CTCATGATGGACGGCCACGAGGTGACCGTGGTGGACAATTTCTTCACGGGCAGGAAGAGAAACGTGGAGCACTG
GATCGGACATGAGAACTTCGAGTTGATTAACCACGACGTGGTGGAGCCCCTCTACATCGAGGTTGACCAGATAT
ACCATCTGGCATCTCCAGCCTCCCCTCCAAACTACATGTATAATCCTATCAAGACATTAAAGACCAATACGATT
GGGACATTAAACATGTTGGGGCTGGCAAAACGAGTCGGTGCCCGTCTGCTCCTGGCCTCCACATCGGAGGTGTA
TGGAGATCCTGAAGTCCACCCTCAAAGTGAGGATTACTGGGGCCACGTGAATCCAATAGGACCTCGGGCCTGCT
ACGATGAAGGCAAACGTGTTGCAGAGACCATGTGCTATGCCTACATGAAGCAGGAAGGCGTGGAAGTGCGAGTG
GCCAGAATCTTCAACACCTTTGGGCCACGCATGCACATGAACGATGGGCGAGTAGTCAGCAACTTCATCCTGCA
GGCGCTCCAGGGGGAGCCACTCACGGTATACGGATCCGGGTCTCAGACAAGGGCGTTCCAGTACGTCAGCGATC
TAGTGAATGGCCTCGTGGCTCTCATGAACAGCAACGTCAGCAGCCCGGTCAACCTGGGGAACCCAGAAGAACAC
ACAATCCTAGAATTTGCTCAGTTAATTAAAAACCTTGTTGGTAGCGGAAGTGAAATTCAGTTTCTCTCCGAAGC
CCAGGATGACCCACAGAAAAGAAAACCAGACATCAAAAAAGCAAAGCTGATGCTGGGGTGGGAGCCCGTGGTCC
CGCTGGAGGAAGGTTTAAACAAAGCAATTCACTACTTCCGTAAAGAACTCGAGTACCAGGCAAATAATCAGTAC
ATCCCCAAACCAAAGCCTGCCAGAATAAAGAAAGGACGGACTCGCCACAGCTGAACTCCTCACTTTTAGGACAC
AAGACTACCATTGTACACTTGATGGGATGTATTTTTGGCTTTTTTTTGTTGTCGTTTAAAGAAAGACTTTAACA
GGTGTCATGAAGAACAAACTGGAATTTCATTCTGAAGCTTGCTTTAATGAAATGGATGTGCCTAAAAGCTCCCC
TCAAAAAACTGCAGATTTTGCCTTGCACTTTTTGAATCTCTCTTTTTATGTAAAATAGCGTAGATGCATCTCTG
CGTATTTTCAAGTTTTTTTATCTTGCTGTGAGAGCATATGTTGTGACTGTCGTTGACAGTTTTATTTACTGGTT
TCTTTGTGAAGCTGAAAAGGAACATTAAGCGGGACAAAAAATGCCGATTTTATTTATAAAAGTGGGTACTTAAT
AAATGAGTCGTTATACTATGCATAAAGAAAAATCCTAGCAGTATTGTCAGGTGGTGGTGCGCCGGCATTGATTT
TAGGGCAGATAAAAGAATTCTGTGTGAGAGCTTTATGTTTCTCTTTTAATTCAGAGTTTTTCCAAGGTCTACTT
TTGAGTTGCAAACTTGACTTTGAAATATTCCTGTTGGTCATGATCAAGGATATTTGAAATCACTACTGTGTTTT
GCTGCGTATCTGGGGCGGGGGCAGGTTGGGGGGCACAAAGTTAACATATTCTTGGTTAACCATGGTTAAATATG
CTATTTTAATAAAATATTGAAACTCA

FIGURE 240

MVSKALLRLVSAVNRRRMKLLLGIALLAYVASVWGNFVNMRSIQENGELKIESKIEEMVEPL
REKIRDLEKSFTQKYPPVKFLSEKDRKRILITGGAGFVGSHLTDKLMMDGHEVTVVDNFFTG
RKRNVEHWIGHENFELINHDVVEPLYIEVDQIYHLASPASPPNYMYNPIKTLKTNTIGTLNM
LGLAKRVGARLLLASTSEVYGDPEVHPQSEDYWGHVNPIGPRACYDEGKRVAETMCYAYMKQ
EGVEVRVARIFNTFGPRMHMNDGRVVSNFILQALQGEPLTVYGSGSQTRAFQYVSDLVNGLV
ALMNSNVSSPVNLGNPEEHTILEFAQLIKNLVGSGSEIQFLSEAQDDPQKRKPDIKKAKLML
GWEPVVPLEEGLNKAIHYFRKELEYQANNQYIPKPKPARIKKGRTRHS

Important features:
Signal peptide:
amino acids 1-32

N-glycosylation site:
amino acids 316-320

Tyrosine kinase phosphorylation site:
amino acids 235-244

N-myristoylation sites:
amino acids 35-41,101-107,383-389

Amidation sites:
amino acids 123-127,233-237

FIGURE 241

GCCCGGTGGAGAATTAGGTGCTGCTGGGAGCTCCTGCCTCCCACAGGATTCCAGCTGCAGGG
AGCCTCAGGGACTCTGGGCCGCACGGAGTTGGGGGCATTCCCCAGAGAGCGTCGCCATGGTC
TGCAGGGAGCAGTTATCAAAGAATCAGGTCAAGTGGGTGTTTGCCGGCATTACCTGTGTGTC
TGTGGTGGTCATTGCCGCAATAGTCCTTGCCATCACCCTGCGGCGGCCAGGCTGTGAGCTGG
AGGCCTGCAGCCCTGATGCCGACATGCTGGACTACCTGCTGAGCCTGGGCCAGATCAGCCGG
CGAGATGCCTTGGAGGTCACCTGGTACCACGCAGCCAACAGCAAGAAAGCCATGACAGCTGC
CCTGAACAGCAACATCACAGTCCTGGAGGCTGACGTCAATGTAGAAGGGCTCGGCACAGCCA
ATGAGACAGGAGTTCCCATCATGGCACACCCCCCCACTATCTACAGTGACAACACACTGGAG
CAGTGGCTGGACGCTGTGCTGGGCTCTTCCCAAAAGGGCATCAAACTGGACTTCAAGAACAT
CAAGGCAGTGGGCCCCTCCCTGGACCTCCTGCGGCAGCTGACAGAGGAAGGCAAAGTCCGGC
GGCCCATATGGATCAACGCTGACATCTTAAAGGGCCCCAACATGCTCATCTCAACTGAGGTC
AATGCCACACAGTTCCTGGCCCTGGTCCAGGAGAAGTATCCCAAGGCTACCCTATCTCCAGG
CTGGACCACCTTCTACATGTCCACGTCCCCAAACAGGACGTACACCCAAGCCATGGTGGAGA
AGATGCACGAGCTGGTGGGAGGAGTGCCCCAGAGGGTCACCTTCCCTGTACGGTCTTCCATG
GTGCGGGCTGCCTGGCCCCACTTCAGCTGGCTGCTGAGCCAATCTGAGAGGTACAGCCTGAC
GCTGTGGCAGGCTGCCTCGGACCCCATGTCGGTGGAAGATCTGCTCTACGTCCGGGATAACA
CTGCTGTCCACCAAGTCTACTATGACATCTTTGAGCCTCTCCTGTCACAGTTCAAGCAGCTG
GCCTTGAATGCCACACGGAAACCAATGTACTACACGGGAGGCAGCCTGATCCCTCTTCTCCA
GCTGCCTGGGGATGACGGTCTGAATGTGGAGTGGCTGGTTCCTGACGTCCAGGGCAGCGGTA
AAACAGCAACAATGACCCTCCCAGACACAGAAGGCATGATCCTGCTGAACACTGGCCTCGAG
GGAACTGTGGCTGAAAACCCCGTGCCCATTGTTCATACTCCAAGTGGCAACATCCTGACGCT
GGAGTCCTGCCTGCAGCAGCTGGCCACACATCCCGGACACTGGGGCATCCATTTGCAAATAG
TGGAGCCCGCAGCCCTCCGGCCATCCCTGGCCTTGCTGGCACGCCTCTCCAGCCTTGGCCTC
TTGCATTGGCCTGTGTGGGTTGGGGCCAAAATCTCCCACGGGAGTTTTTCGGTCCCCGGCCA
TGTGGCTGGCAGAGAGCTGCTTACAGCTGTGGCTGAGGTCTTCCCCCACGTGACTGTGGCAC
CAGGCTGGCCTGAGGAGGTGCTGGGCAGTGGCTACAGGGAACAGCTGCTCACAGATATGCTA
GAGTTGTGCCAGGGGCTCTGGCAACCTGTGTCCTTCCAGATGCAGGCCATGCTGCTGGGCCA
CAGCACAGCTGGAGCCATAGGCAGGCTGCTGGCATCCTCCCCCCGGGCCACCGTCACAGTGGAG
CACAACCCAGCTGGGGGCGACTATGCCTCTGTGAGGACAGCATTGCTGGCAGCTAGGGCTGT
GGACAGGACCCGAGTCTACTACAGGCTACCCCAGGGCTACCACAAGGACTTGCTGGCTCATG
TTGGTAGAAACTGAGCACCCAGGGGTGGTGGGCCAGCGGACCTCAGGGCGGAGGCTTCCCAC
GGGGAGGCAGGAAGAAATAAAGGTCTTTGGCTTTCTCCAGGCAAAAAAAAAAAAAAAAAAAA
AAAAAAAAAAAAAAAAAAAAAAAAAAAAAAAAAAAAAAAG

FIGURE 242

></usr/seqdb2/sst/DNA/Dnaseqs.min/ss.DNA119514
><subunit 1 of 1, 585 aa, 1 stop
><MW: 64056, pI: 6.58, NX(S/T): 5
MVCREQLSKNQVKWVFAGITCVSVVVIAAIVLAITLRRPGCELEACSPDADMLDYLLSLG
QISRRDALEVTWYHAANSKKAMTAALNSNITVLEADVNVEGLGTANETGVPIMAHPPTIY
SDNTLEQWLDAVLGSSQKGIKLDFKNIKAVGPSLDLLRQLTEEGKVRRPIWINADILKGP
NMLISTEVNATQFLALVQEKYPKATLSPGWTTFYMSTSPNRTYTQAMVEKMHELVGGVPQ
RVTFPVRSSMVRAAWPHFSWLLSQSERYSLTLWQAASDPMSVEDLLYVRDNTAVHQVYYD
IFEPLLSQFKQLALNATRKPMYYTGGSLIPLLQLPGDDGLNVEWLVPDVQGSGKTATMTL
PDTEGMILLNTGLEGTVAENPVPIVHTPSGNILTLESCLQQLATHPGHWGIHLQIVEPAA
LRPSLALLARLSSLGLLHWPVWVGAKISHGSFSVPGHVAGRELLTAVAEVFPHVTVAPGW
PEEVLGSGYREQLLTDMLELCQGLWQPVSFQMQAMLLGHSTAGAIGRLLASSPRATVTVE
HNPAGGDYASVRTALLAARAVDRTRVYYRLPQGYHKDLLAHVGRN

Important features of the protein:
Transmembrane domain:
Amino acids 18-37 (Possible type II)

N-glycosylation sites:
Amino acids 89-93;106-110;189-193;220-224;315-319

Tyrosine kinase phosphorylation site:
Amino acids 65-74

N-myristoylation sites:
Amino acids 101-107;351-357;372-378;390-396;444-450;545-551

Aminotransferases class-V pyridoxal-phosphate attachment site:
Amino acids 312-330

FIGURE 243

CTTCAGAACAGGTTCTCCTTCCCCAGTCACCAGTTGCTCGAGTTAGAATTGTCTGCAATGGC
CGCCCTGCAGAAATCTGTGAGCTCTTTCCTTATGGGGACCCTGGCCACCAGCTGCCTCCTTC
TCTTGGCCCTCTTGGTACAGGGAGGAGCAGCTGCGCCCATCAGCTCCCACTGCAGGCTTGAC
AAGTCCAACTTCCAGCAGCCCTATATCACCAACCGCACCTTCATGCTGGCTAAGGAGGCTAG
CTTGGCTGATAACAACACAGACGTTCGTCTCATTGGGGAGAAACTGTTCCACGGAGTCAGTA
TGAGTGAGCGCTGCTATCTGATGAAGCAGGTGCTGAACTTCACCCTTGAAGAAGTGCTGTTC
CCTCAATCTGATAGGTTCCAGCCTTATATGCAGGAGGTGGTGCCCTTCCTGGCCAGGCTCAG
CAACAGGCTAAGCACATGTCATATTGAAGGTGATGACCTGCATATCCAGAGGAATGTGCAAA
AGCTGAAGGACACAGTGAAAAAGCTTGGAGAGAGTGGAGAGATCAAAGCAATTGGAGAACTG
GATTTGCTGTTTATGTCTCTGAGAAATGCCTGCATTTGACCAGAGCAAAGCTGAAAAATGAA
TAACTAACCCCCTTTCCCTGCTAGAAATAACAATTAGATGCCCCAAAGCGATTTTTTTTAAC
CAAAAGGAAGATGGGAAGCCAAACTCCATCATGATGGGTGGATTCCAAATGAACCCCTGCGT
TAGTTACAAAGGAAACCAATGCCACTTTTGTTTATAAGACCAGAAGGTAGACTTTCTAAGCA
TAGATATTTATTGATAACATTTCATTGTAACTGGTGTTCTATACACAGAAAACAATTTATTT
TTTAAATAATTGTCTTTTTCCATAAAAAAGATTACTTTCCATTCCTTTAGGGGAAAAAACCC
CTAAATAGCTTCATGTTTCCATAATCAGTACTTTATATTTATAAATGTATTTATTATTATTA
TAAGACTGCATTTTATTTATATCATTTTATTAATATGGATTTATTTATAGAAACATCATTCG
ATATTGCTACTTGAGTGTAAGGCTAATATTGATATTTATGACAATAATTATAGAGCTATAAC
ATGTTTATTTGACCTCAATAAACACTTGGATATCCC

FIGURE 244

MAALQKSVSSFLMGTLATSCLLLLALLVQGGAAAPISSHCRLDKSNFQQPYITNRTFMLAKE
ASLADNNTDVRLIGEKLFHGVSMSERCYLMKQVLNFTLEEVLFPQSDRFQPYMQEVVPFLAR
LSNRLSTCHIEGDDLHIQRNVQKLKDTVKKLGESGEIKAIGELDLLFMSLRNACI

Important features of the protein:
Signal peptide:
amino acids 1-33

N-glycosylation sites.
amino acids 54-58, 68-72, 97-101

N-myristoylation sites.
amino acids 14-20, 82-88

Prokaryotic membrane lipoprotein lipid attachment site.
amino acids 10-21

SEQUENCE LISTING

<160> NUMBER OF SEQ ID NOS: 246

<210> SEQ ID NO 1
<211> LENGTH: 4834
<212> TYPE: DNA
<213> ORGANISM: Homo sapiens
<220> FEATURE:
<221> NAME/KEY: Unsure
<222> LOCATION: 3784
<223> OTHER INFORMATION: Unknown base

<400> SEQUENCE: 1
gcagccctag cagggatgga catgatgctg ttggtgcagg gtgcttgttg 50
ctcgaaccag tggctggcgg cggtgctcct cagcctgtgc tgcctgctac 100
cctcctgcct cccggctgga cagagtgtgg acttcccctg ggcggccgtg 150
gacaacatga tggtcagaaa aggggacacg gcggtgctta ggtgttattt 200
ggaagatgga gcttcaaagg gtgcctggct gaaccggtca agtattattt 250
ttgcgggagg tgataagtgg tcagtggatc ctcgagtttc aatttcaaca 300
ttgaataaaa gggactacag cctccagata cagaatgtag atgtgacaga 350
tgatggccca tacacgtgtt ctgttcagac tcaacataca cccagaacaa 400
tgcaggtgca tctaactgtg caagttcctc ctaagatata tgacatctca 450
aatgatatga ccgtcaatga aggaaccaac gtcactctta cttgtttggc 500
cactgggaaa ccagagcctt ccatttcttg gcgacacatc tccccatcag 550
caaaaccatt tgaaaatgga caatatttgg acatttatgg aattacaagg 600
gaccaggctg gggaatatga atgcagtgcg gaaaatgatg tgtcattccc 650
agatgtgagg aaagtaaaag ttgttgtcaa ctttgctcct actattcagg 700
aaattaaatc tggcaccgtg acccccggac gcagtggcct gataagatgt 750
gaaggtgcag gtgtgccgcc tccagccttt gaatggtaca aaggagagaa 800
gaagctcttc aatggccaac aaggaattat tattcaaaat tttagcacaa 850
gatccattct cactgttacc aacgtgacac aggagcactt cggcaattat 900
acttgtgtgg ctgccaacaa gctaggcaca accaatgcga gcctgcctct 950
taaccctcca agtacagccc agtatggaat taccgggagc gctgatgttc 1000
ttttctcctg ctggtacctt gtgttgacac tgtcctcttt caccagcata 1050
ttctacctga agaatgccat tctacaataa attcaaagac ccataaaagg 1100
cttttaagga ttctctgaaa gtgctgatgg ctggatccaa tctggtacag 1150
tttgttaaaa gcagcgtggg atataatcag cagtgcttac atggggatga 1200
tcgccttctg tagaattgct cattatgtaa atactttaat tctactcttt 1250
tttgattagc tacattacct tgtgaagcag tacacattgt cctttttta 1300 agacgtgaaa gctctgaaat tacttttaga ggatattaat tgtgatttca 1350
tgtttgtaat ctacaacttt tcaaaagcat tcagtcatgg tctgctaggt 1400
tgcaggctgt agtttacaaa aacgaatatt gcagtgaata tgtgattctt 1450
taaggctgca atacaagcat tcagttccct gtttcaataa gagtcaatcc 1500
acatttacaa agatgcattt ttttcttttt tgataaaaaa gcaaataata 1550
ttgccttcag attatttctt caaaatataa cacatatcta gatttttctg 1600

-continued

```
ctcgcatgat attcaggttt caggaatgag ccttgtaata taactggctg 1650
tgcagctctg cttctctttc ctgtaagttc agcatgggtg tgccttcata 1700
caataatatt tttctctttg tctccaacta atataaaatg ttttgctaaa 1750
tcttacaatt tgaaagtaaa aataaaccag agtgatcaag ttaaaccata 1800
cactatctct aagtaacgaa ggagctattg gactgtaaaa atctcttcct 1850
gcactgacaa tggggtttga gaattttgcc ccacactaac tcagttcttg 1900
tgatgagaga caatttaata acagtatagt aaatatacca tatgatttct 1950
ttagttgtag ctaaatgtta gatccaccgt gggaaatcat tccctttaaa 2000
atgacagcac agtccactca aaggattgcc tagcaataca gcatcttttc 2050
ctttcactag tccaagccaa aaattttaag atgatttgtc agaaagggca 2100
caaagtccta tcacctaata ttacaagagt tggtaagcgc tcatcattaa 2150
ttttattttg tggcagctaa gttagtatga cagaggcagt gctcctgtgg 2200
acaggagcat tttgcatatt ttccatctga aagtatcact cagttgatag 2250
tctggaatgc atgttatata ttttaaaact tccaaaatat attataacaa 2300
acattctata tcggtatgta gcagaccaat ctctaaaata gctaattctt 2350
caataaaatc tttctatata gccatttcag tgcaaacaag taaaatcaaa 2400
aaagaccatc ctttattttt ccttacatga tatatgtaag atgcgatcaa 2450
ataaagacaa aacaccagtg atgagaatat cttaagataa gtaattatca 2500
aattattgtg aatgttaaat tatttctact ataaagaagc aaaactacat 2550
ttttgaagga aaatgctgtt actctaacat taatttacag gaatagtttg 2600
atggtttcac tctttactaa agaaaggcca tcaccttgaa agccatttta 2650
caggtttgat gaagttacca atttcagtac acctaaattt ctacaaatag 2700
tccccttta caagttgtaa caacaaagac cctataataa aattagatac 2750
aagaaatttt gcagtggtta tacatatttg agatatctag tatgttgccc 2800
tagcagggat ggcttaaaaa ctgtgatttt ttttcttcaa gtaaaactta 2850
gtcccaaagt acatcataaa tcaattttaa ttagaaaaat gaatcttaaa 2900
tgaggggaca taagtatact ctttccacaa aatggcaata ataaggcata 2950
aagctagtaa atctactaac tgtaataaat gtatgacatt attttgattg 3000
atacattaaa aaagagtttt tagaacaaat atggcattta actttattat 3050
ttatttgctt ttaagaaata ttctttgtgg aattgttgaa taaactataa 3100
aatattattt tgtattgcag ctttaaagtg gcacactcca taataatcta 3150
cttactagaa atagtggtgc taccacaaaa aatgttaacc atcagtacca 3200
ttgtttggga gaaagaaaca gatcaagaat gcatattatt cagtgaccgc 3250
tttcctagag ttaaaatacc tcctctttgt aaggtttgta ggtaaattga 3300
ggtataaact atggatgaac caaataatta gttcaaagtg ttgtcatgat 3350
tccaaatttg tggagtctgg tgtttttacc atagaatgtg acagaagtac 3400
agtcatagct cagtagctat atgtatttgc ctttatgtta gaagagactt 3450
tcttgagtga catttttaaa tagaggaggt attcactatg tttttctgta 3500
tcacagcagc attcctagtc cttaggccct cggacagagt gaaatcatga 3550
```

-continued

```
gtatttatga gttcaatatt gtcaaataag gctacagtat ttgctttttt      3600

gtgtgaatgt attgcatata atgttcaagt agatgatttt acatttatgg      3650

acatataaaa tgtctgatta ccccatttta tcagtcctga ctgtacaaga      3700

ttgttgcaat ttcagaatag cagttttata aattgattta tcttttaatc      3750

tataacaatt tgtgttagct gttcatttca ggantatatt ttctacaagt      3800

tccacttgtg ggactccttt tgttgcccct attttttttt aaagaaggaa      3850

gaaagaaaaa taagtagcag tttaaaaatg agaatggaga gaaaagaaaa      3900

agaatgaaaa ggaaaggcag taaagaggga aaaaaaagga aggatggaag      3950

gaatgaagga aggaagggag gaaggggaga aggtaggaag aaagaaagga      4000

tgagagggaa ggaagaatca gagtattagg gtagttaact tacacatttg      4050

cattcttagt ttaactgcaa gtggtgtaac tatgtttttc aatgatcgca      4100

tttgaaacat aagtcctatt ataccattaa gttcctatta tgcagcaatt      4150

atataataaa aagtactgcc caagttatag taatgtgggt gtttttgaga      4200

cactaaaaga tttgagaggg agaatttcaa acttaaagcc acttttgggg      4250

ggtttataac ttaactgaaa aattaatgct tcatcataac atttaagcta      4300

tatctagaaa gtagactgga gaactgagaa aattacccag gtaattcagg      4350

gaaaaaaaaa aatatatata tatataaata cccctacatt tgaagtcaga      4400

aaactctgaa aaactgaatt atcaaagtca atcatctata atgatcaaat      4450

ttactgaaca attgttaatt tatccattgt gcttagcttt gtgacacagc      4500

caaaagttac ctatttaatc ttttcaataa aaattgtttt ttgaaatcca      4550

gaaatgattt aaaaagaggt caggttttta actatttatt gaagtatgtg      4600

gatgtacagt atttcaatag atatgaatat gaataaatgg tatgccttaa      4650

gattctttga atatgtattt actttaaaga ctggaaaaag ctcttcctgt      4700

cttttagtaa aacatccata tttcataacc tgatgtaaaa tatgttgtac      4750

tgtttccaat aggtgaatat aaactcagtt tatcaattaa aaaaaaaaaa      4800

aaaaaaaaaa aaaaaaaaaa aaaaaaaaaa  aaaa                      4834
```

<210> SEQ ID NO 2
<211> LENGTH: 354
<212> TYPE: PRT
<213> ORGANISM: Homo sapiens

<400> SEQUENCE: 2

```
Met Asp Met Met Leu Leu Val Gln Gly Ala Cys Cys Ser Asn Gln
  1               5                  10                  15

Trp Leu Ala Ala Val Leu Leu Ser Leu Cys Cys Leu Leu Pro Ser
                 20                  25                  30

Cys Leu Pro Ala Gly Gln Ser Val Asp Phe Pro Trp Ala Ala Val
                 35                  40                  45

Asp Asn Met Met Val Arg Lys Gly Asp Thr Ala Val Leu Arg Cys
                 50                  55                  60

Tyr Leu Glu Asp Gly Ala Ser Lys Gly Ala Trp Leu Asn Arg Ser
                 65                  70                  75

Ser Ile Ile Phe Ala Gly Gly Asp Lys Trp Ser Val Asp Pro Arg
                 80                  85                  90

Val Ser Ile Ser Thr Leu Asn Lys Arg Asp Tyr Ser Leu Gln Ile
```

-continued

```
                95                  100                 105

Gln Asn Val Asp Val Thr Asp Asp Gly Pro Tyr Thr Cys Ser Val
                110                 115                 120

Gln Thr Gln His Thr Pro Arg Thr Met Gln Val His Leu Thr Val
                125                 130                 135

Gln Val Pro Pro Lys Ile Tyr Asp Ile Ser Asn Asp Met Thr Val
                140                 145                 150

Asn Glu Gly Thr Asn Val Thr Leu Thr Cys Leu Ala Thr Gly Lys
                155                 160                 165

Pro Glu Pro Ser Ile Ser Trp Arg His Ile Ser Pro Ser Ala Lys
                170                 175                 180

Pro Phe Glu Asn Gly Gln Tyr Leu Asp Ile Tyr Gly Ile Thr Arg
                185                 190                 195

Asp Gln Ala Gly Glu Tyr Glu Cys Ser Ala Glu Asn Asp Val Ser
                200                 205                 210

Phe Pro Asp Val Arg Lys Val Lys Val Val Val Asn Phe Ala Pro
                215                 220                 225

Thr Ile Gln Glu Ile Lys Ser Gly Thr Val Thr Pro Gly Arg Ser
                230                 235                 240

Gly Leu Ile Arg Cys Glu Gly Ala Gly Val Pro Pro Pro Ala Phe
                245                 250                 255

Glu Trp Tyr Lys Gly Glu Lys Lys Leu Phe Asn Gly Gln Gln Gly
                260                 265                 270

Ile Ile Ile Gln Asn Phe Ser Thr Arg Ser Ile Leu Thr Val Thr
                275                 280                 285

Asn Val Thr Gln Glu His Phe Gly Asn Tyr Thr Cys Val Ala Ala
                290                 295                 300

Asn Lys Leu Gly Thr Thr Asn Ala Ser Leu Pro Leu Asn Pro Pro
                305                 310                 315

Ser Thr Ala Gln Tyr Gly Ile Thr Gly Ser Ala Asp Val Leu Phe
                320                 325                 330

Ser Cys Trp Tyr Leu Val Leu Thr Leu Ser Ser Phe Thr Ser Ile
                335                 340                 345

Phe Tyr Leu Lys Asn Ala Ile Leu Gln
                350


<210> SEQ ID NO 3
<211> LENGTH: 2506
<212> TYPE: DNA
<213> ORGANISM: Homo sapiens

<400> SEQUENCE: 3

cactgcccgt ccgctcttca gcagccggtc gcgggcggtg gaaaagcgag        50

tgaagagagc gcgacggcgg cggcggcggc ggcgcagcta ttgctggacg       100

gccagtggga gagcgaggcc tgagcctctg cgtctaggat caaaatggtt       150

tcaatcccag aatactatga aggcaagaac gtcctcctca caggagctac       200

cggttttcta gggaaggtgc ttctggaaaa gttgctgagg tcttgtccta       250

aggtgaattc agtatatgtt ttggtgaggc agaaagctgg acagacacca       300

caagagcgag tggaagaagt ccttagtggc aagctttttg acagattgag       350

agatgaaaat ccagatttta gagagaaaat tatagcaatc aacagcgaac       400

tcacccaacc taaactggct ctcagtgaag aagataaaga ggtgatcata       450
```

-continued

```
gattctacca atattatatt ccactgtgca gctacagtaa ggtttaatga           500
aaatttaaga gatgctgttc agttaaatgt gattgcaacg cgacagctta           550
ttctccttgc acaacaaatg aagaatctgg aagtgttcat gcatgtatca           600
acagcatatg cctactgtaa tcgcaagcat attgatgaag tagtctatcc           650
accacctgtg gatcccaaga agctgattga ttctttagag tggatggatg           700
atggcctagt aaatgatatc acgccaaaat tgataggaga cagacctaat           750
acatacatat acacaaaagc attggcagaa tatgttgtac aacaagaagg           800
agcaaaacta aatgtggcaa ttgtaaggcc atcgattgtt ggtgccagtt           850
ggaaagaacc ttttccagga tggattgata actttaatgg accaagtggt           900
ctctttattg cggcagggaa aggaattctt cgaacaatac gtgcctccaa           950
caatgccctt gcagatcttg ttcctgtaga tgtagttgtc aacatgagtc          1000
ttgcggcagc ctggtattcc ggagttaata gaccaagaaa catcatggtg          1050
tataattgta caacaggcag cactaatcct ttccactggg gtgaagttga          1100
gtaccatgta atttccactt tcaagaggaa tcctctcgaa caggccttca          1150
gacggcccaa tgtaaatcta acctccaatc atcttttata tcattactgg          1200
attgctgtaa gccataaggc cccagcattc ctgtatgata tctacctcag          1250
gatgactgga agaagcccaa ggatgatgaa aacaataact cgtcttcaca          1300
aagctatggt gtttcttgaa tatttcacaa gtaattcttg ggtttggaat          1350
actgagaatg tcaatatgtt aatgaatcaa ctaaaccctg aagataaaaa          1400
gaccttcaat attgatgtac ggcagttaca ttgggcagaa tatatagaga          1450
actactgctt gggaactaag aagtacgtat tgaatgaaga aatgtctggc          1500
ctccctgcag ccagaaaaca tctgaacaag ttgcggaata tacgttatgg          1550
ttttaatact atccttgtga tcctcatctg gcgcattttt attgcaagat          1600
cacaaatggc aagaaatatc tggtactttg tggttagtct gtgttacaag          1650
tttttgtcat acttccgagc atccagcact atgagatact gaagaccaag          1700
gattcagcat tagaacatct atacatatgg tgatctaaat gtacaaaatg          1750
taaaatgtat aagtcatctc actttttgtc aagacattaa accatcttag          1800
atcggagtgt gaagtaaatt atggtatatt ttatgtaaca ttttaatgtt          1850
tatgctcata aaacttagtg aacacactgt gttatgccag ctcaaatcta          1900
cagtagccac caaaaccatg acttaatatt ttgagcccta gaagaaaggg          1950
gtgtgctgag gacaagagtg gggaaatagg aacactgacc agtataactg          2000
tgcaattctg gaacatatta attaaaataa tatgccttaa catatagtga          2050
atttctaatt ctaatgttca gtgcaatgga agacatttat ttggacagta          2100
tactagcaaa gttggtagat atttgattct tcatttttg ttttttcat           2150
tagttgaagt gggttttagt tttgtttaaa attataacca gcgtattttc          2200
acatcattct gtaagttaaa tgatatcaaa catgaaagag atgttctcat          2250
ttttcttttt ctgattaaac gtctgatgca tatcattttt ctataagtaa          2300
tcagttgctt ttaaaatcag aaggctatat tattctaatg accctattcg          2350
atctaaatgg gtttgagaat ccatatcagc aacatacgtg ttttttgaca          2400
gaaagtgaaa acaaattccg taaaactgtt agtatcaaaa agaataggaa          2450
```

-continued tacagttttc ttttccacat tatgatcaaa taaaaatctt gtgagattgt 2500
taaaaa 2506

<210> SEQ ID NO 4
<211> LENGTH: 515
<212> TYPE: PRT
<213> ORGANISM: Homo sapiens

<400> SEQUENCE: 4

Met Val Ser Ile Pro Glu Tyr Tyr Glu Gly Lys Asn Val Leu Leu
1 5 10 15

Thr Gly Ala Thr Gly Phe Leu Gly Lys Val Leu Leu Glu Lys Leu
20 25 30

Leu Arg Ser Cys Pro Lys Val Asn Ser Val Tyr Val Leu Val Arg
35 40 45

Gln Lys Ala Gly Gln Thr Pro Gln Glu Arg Val Glu Glu Val Leu
50 55 60

Ser Gly Lys Leu Phe Asp Arg Leu Arg Asp Glu Asn Pro Asp Phe
65 70 75

Arg Glu Lys Ile Ile Ala Ile Asn Ser Glu Leu Thr Gln Pro Lys
80 85 90

Leu Ala Leu Ser Glu Glu Asp Lys Glu Val Ile Ile Asp Ser Thr
95 100 105

Asn Ile Ile Phe His Cys Ala Ala Thr Val Arg Phe Asn Glu Asn
110 115 120

Leu Arg Asp Ala Val Gln Leu Asn Val Ile Ala Thr Arg Gln Leu
125 130 135

Ile Leu Leu Ala Gln Gln Met Lys Asn Leu Glu Val Phe Met His
140 145 150

Val Ser Thr Ala Tyr Ala Tyr Cys Asn Arg Lys His Ile Asp Glu
155 160 165

Val Val Tyr Pro Pro Pro Val Asp Pro Lys Lys Leu Ile Asp Ser
170 175 180

Leu Glu Trp Met Asp Asp Gly Leu Val Asn Asp Ile Thr Pro Lys
185 190 195

Leu Ile Gly Asp Arg Pro Asn Thr Tyr Ile Tyr Thr Lys Ala Leu
200 205 210

Ala Glu Tyr Val Val Gln Gln Glu Gly Ala Lys Leu Asn Val Ala
215 220 225

Ile Val Arg Pro Ser Ile Val Gly Ala Ser Trp Lys Glu Pro Phe
230 235 240

Pro Gly Trp Ile Asp Asn Phe Asn Gly Pro Ser Gly Leu Phe Ile
245 250 255

Ala Ala Gly Lys Gly Ile Leu Arg Thr Ile Arg Ala Ser Asn Asn
260 265 270

Ala Leu Ala Asp Leu Val Pro Val Asp Val Val Val Asn Met Ser
275 280 285

Leu Ala Ala Ala Trp Tyr Ser Gly Val Asn Arg Pro Arg Asn Ile
290 295 300

Met Val Tyr Asn Cys Thr Thr Gly Ser Thr Asn Pro Phe His Trp
305 310 315

Gly Glu Val Glu Tyr His Val Ile Ser Thr Phe Lys Arg Asn Pro
320 325 330

-continued

```
Leu Glu Gln Ala Phe Arg Arg Pro Asn Val Asn Leu Thr Ser Asn
                335                 340                 345

His Leu Leu Tyr His Tyr Trp Ile Ala Val Ser His Lys Ala Pro
                350                 355                 360

Ala Phe Leu Tyr Asp Ile Tyr Leu Arg Met Thr Gly Arg Ser Pro
                365                 370                 375

Arg Met Met Lys Thr Ile Thr Arg Leu His Lys Ala Met Val Phe
                380                 385                 390

Leu Glu Tyr Phe Thr Ser Asn Ser Trp Val Trp Asn Thr Glu Asn
                395                 400                 405

Val Asn Met Leu Met Asn Gln Leu Asn Pro Glu Asp Lys Lys Thr
                410                 415                 420

Phe Asn Ile Asp Val Arg Gln Leu His Trp Ala Glu Tyr Ile Glu
                425                 430                 435

Asn Tyr Cys Leu Gly Thr Lys Lys Tyr Val Leu Asn Glu Glu Met
                440                 445                 450

Ser Gly Leu Pro Ala Ala Arg Lys His Leu Asn Lys Leu Arg Asn
                455                 460                 465

Ile Arg Tyr Gly Phe Asn Thr Ile Leu Val Ile Leu Ile Trp Arg
                470                 475                 480

Ile Phe Ile Ala Arg Ser Gln Met Ala Arg Asn Ile Trp Tyr Phe
                485                 490                 495

Val Val Ser Leu Cys Tyr Lys Phe Leu Ser Tyr Phe Arg Ala Ser
                500                 505                 510

Ser Thr Met Arg Tyr
                515


<210> SEQ ID NO 5
<211> LENGTH: 1759
<212> TYPE: DNA
<213> ORGANISM: Homo sapiens

<400> SEQUENCE: 5

cgatgccggc ggtcagtggt ccaggtccct tattctgcct tctcctcctg          50

ctcctggacc cccacagccc tgagacgggg tgtcctcctc tacgcaggtt         100

tgagtacaag ctcagcttca aaggcccaag gctggcattg cctggggctg         150

gaataccctt ctggagccat catggagacg ccatcctggg cctggaggaa         200

gtgcggctga cgccatccat gaggaaccgg agtggcgccg tgtggagcag         250

ggcctctgtc cccttctctg cctgggaagt agaggtgcag atgagggtga         300

cgggactggg gcgccgggga gcccagggca tggccgtgtg gtacacccgg         350

ggcaggggcc atgtaggctc tgtccttggg gggctggctt cgtgggacgg         400

catcgggatc ttctttgact ctccggcaga ggatactcag gacagtcctg         450

ccatccgtgt gctggccagc gacgggcaca tcccctctga gcagcctggg         500

gatggagcta gccaagggct gggctcctgt cattgggact tccggaaccg         550

gccacactcc ttcagagcac ggatcaccta ctgggggcag aggctgcgca         600

tgtccttgaa cagtggcctc actcccagtg atccaggtga gttctgtgtg         650

gatgtggggc ccctgctttt ggtccctgga ggtttctttg gggtctcagc         700

agccaccggc accctggcag gtgaggatcc cactggacag gttcccccctc         750

agcccttcct ggagatgcag cagctccgcc tggcgaggca gctggaaggg         800
```

-continued

```
ctgtgggcaa ggctgggctt gggcaccagg gaggatgtaa ctccaaaatc          850

agactctgaa gctcaaggag aaggggaaag gctctttgac ctggaggaga          900

cgctgggcag acaccgccgg atcctgcagg ctctgcgggg tctctccaag          950

cagctggccc aggctgagag acaatggaag aagcagctgg ggcccccagg         1000

ccaagccagg cctgacggag gctgggccct ggatgcttcc tgccagattc         1050

catccacccc agggaggggt ggccacctct ccatgtcact caataaggac         1100

tctgccaagg tcggtgccct gctccatgga cagtggactc tgctccaggc         1150

cctgcaagag atgagggatg cagctgtccg catggctgca gaagcccagg         1200

tctcctacct gcctgtgggc attgagcatc atttcttaga gctggaccac         1250

atcctgggcc tcctgcagga ggagcttcgg ggcccggcga aggcagcagc         1300

caaggccccc cgcccacctg gccagccccc aagggcctcc tcgtgcctgc         1350

agcctggcat cttcctgttc tacctcctca ttcagactgt aggcttcttc         1400

ggctacgtgc acttcaggca ggagctgaac aagagccttc aggagtgtct         1450

gtccacaggc agccttcctc tgggtcctgc accacacacc cccagggccc         1500

tggggattct gaggaggcag cctctccctg ccagcatgcc tgcctgaccc         1550

acctcagagc ctgctttgca tcactgggaa gcaggcagtg tcttgggtgg         1600

gggcttggtc agtatcctct ccgtctgggt gcccagctcc cacgcacacc         1650

tgagctttcg gcatgctccc acctcgttaa aggtgatttc cctctcccca         1700

aaaaaaaaaa aaaaaaaaaa aaaaaaaaaa aaaaaaaaaa aaaaaaaaaa         1750

aaaaaaaaa                                                      1759


<210> SEQ ID NO 6
<211> LENGTH: 514
<212> TYPE: PRT
<213> ORGANISM: Homo sapiens

<400> SEQUENCE: 6

Met Pro Ala Val Ser Gly Pro Gly Pro Leu Phe Cys Leu Leu Leu
  1               5                  10                  15

Leu Leu Leu Asp Pro His Ser Pro Glu Thr Gly Cys Pro Pro Leu
                 20                  25                  30

Arg Arg Phe Glu Tyr Lys Leu Ser Phe Lys Gly Pro Arg Leu Ala
                 35                  40                  45

Leu Pro Gly Ala Gly Ile Pro Phe Trp Ser His His Gly Asp Ala
                 50                  55                  60

Ile Leu Gly Leu Glu Glu Val Arg Leu Thr Pro Ser Met Arg Asn
                 65                  70                  75

Arg Ser Gly Ala Val Trp Ser Arg Ala Ser Val Pro Phe Ser Ala
                 80                  85                  90

Trp Glu Val Glu Val Gln Met Arg Val Thr Gly Leu Gly Arg Arg
                 95                 100                 105

Gly Ala Gln Gly Met Ala Val Trp Tyr Thr Arg Gly Arg Gly His
                110                 115                 120

Val Gly Ser Val Leu Gly Gly Leu Ala Ser Trp Asp Gly Ile Gly
                125                 130                 135

Ile Phe Phe Asp Ser Pro Ala Glu Asp Thr Gln Asp Ser Pro Ala
                140                 145                 150

Ile Arg Val Leu Ala Ser Asp Gly His Ile Pro Ser Glu Gln Pro
```

-continued

```
                155                 160                 165

Gly Asp Gly Ala Ser Gln Gly Leu Gly Ser Cys His Trp Asp Phe
                170                 175                 180

Arg Asn Arg Pro His Ser Phe Arg Ala Arg Ile Thr Tyr Trp Gly
                185                 190                 195

Gln Arg Leu Arg Met Ser Leu Asn Ser Gly Leu Thr Pro Ser Asp
                200                 205                 210

Pro Gly Glu Phe Cys Val Asp Val Gly Pro Leu Leu Leu Val Pro
                215                 220                 225

Gly Gly Phe Phe Gly Val Ser Ala Ala Thr Gly Thr Leu Ala Gly
                230                 235                 240

Glu Asp Pro Thr Gly Gln Val Pro Pro Gln Pro Phe Leu Glu Met
                245                 250                 255

Gln Gln Leu Arg Leu Ala Arg Gln Leu Glu Gly Leu Trp Ala Arg
                260                 265                 270

Leu Gly Leu Gly Thr Arg Glu Asp Val Thr Pro Lys Ser Asp Ser
                275                 280                 285

Glu Ala Gln Gly Glu Gly Glu Arg Leu Phe Asp Leu Glu Glu Thr
                290                 295                 300

Leu Gly Arg His Arg Arg Ile Leu Gln Ala Leu Arg Gly Leu Ser
                305                 310                 315

Lys Gln Leu Ala Gln Ala Glu Arg Gln Trp Lys Lys Gln Leu Gly
                320                 325                 330

Pro Pro Gly Gln Ala Arg Pro Asp Gly Gly Trp Ala Leu Asp Ala
                335                 340                 345

Ser Cys Gln Ile Pro Ser Thr Pro Gly Arg Gly Gly His Leu Ser
                350                 355                 360

Met Ser Leu Asn Lys Asp Ser Ala Lys Val Gly Ala Leu Leu His
                365                 370                 375

Gly Gln Trp Thr Leu Leu Gln Ala Leu Gln Glu Met Arg Asp Ala
                380                 385                 390

Ala Val Arg Met Ala Ala Glu Ala Gln Val Ser Tyr Leu Pro Val
                395                 400                 405

Gly Ile Glu His His Phe Leu Glu Leu Asp His Ile Leu Gly Leu
                410                 415                 420

Leu Gln Glu Glu Leu Arg Gly Pro Ala Lys Ala Ala Ala Lys Ala
                425                 430                 435

Pro Arg Pro Pro Gly Gln Pro Pro Arg Ala Ser Ser Cys Leu Gln
                440                 445                 450

Pro Gly Ile Phe Leu Phe Tyr Leu Leu Ile Gln Thr Val Gly Phe
                455                 460                 465

Phe Gly Tyr Val His Phe Arg Gln Glu Leu Asn Lys Ser Leu Gln
                470                 475                 480

Glu Cys Leu Ser Thr Gly Ser Leu Pro Leu Gly Pro Ala Pro His
                485                 490                 495

Thr Pro Arg Ala Leu Gly Ile Leu Arg Arg Gln Pro Leu Pro Ala
                500                 505                 510

Ser Met Pro Ala
```

<210> SEQ ID NO 7
<211> LENGTH: 3010
<212> TYPE: DNA
<213> ORGANISM: Homo sapiens -continued

<400> SEQUENCE: 7
gcccccagca tggcttggca gggctggccc gcggcgtggc agtgggtcgc 50
cggctgctgg ctcctcctcg tccttgtcct cgtcctactt gtgagccccc 100
gcggctgccg agcgcggcgg ggcctccgcg gtctgctcat ggcgcacagc 150
cagcggctgc tcttccgaat cgggtacagc ctgtacaccc gcacctggct 200
cgggtacctc ttctaccgac agcagctgcg cagggctcgg aatcgctacc 250
ctaaaggcca ctcgaaaacc cagccccgcc tcttcaatgg agtgaaggtg 300
cttcccatcc ctgtcctctc ggacaactac agctacctca tcatcgacac 350
ccaggcccag ctggctgtgg ctgtggaccc ttcagaccct cgggctgtgc 400
aggcttccat tgaaaaggaa ggggtcacct tggtcgccat tctgtgtact 450
cacaagcact gggaccacag tggagggaac cgtgacctca gccggcggca 500
ccgggactgt cgggtgtacg ggagccctca ggacggcatc ccctacctca 550
cccatcccct gtgtcatcaa gatgtggtca gcgtgggacg gcttcagatc 600
cgggccctgg ctacacctgg ccacacacaa ggccatctgg tctacctact 650
ggatggggag ccctacaagg gtccctcctg cctcttctca ggggacctgc 700
tcttcctctc tggctgtggg cggacctttg agggcaatgc agagaccatg 750
ctgagctcac tggacactgt gctggggcta ggggatgaca cccttctgtg 800
gcctggtcat gagtatgcag aggagaacct gggctttgca ggtgtggtgg 850
agcccgagaa cctggcccgg gagaggaaga tgcagtgggt gcagcggcag 900
cggctggagc gcaagggcac gtgcccatct accctgggag aggagcgctc 950
ctacaacccg ttcctgagaa cccactgcct ggcgctacag gaggctctgg 1000
ggccggggcc gggccccact ggggatgatg actactcccg ggcccagctc 1050
ctggaagagc tccgccggct gaaggatatg cacaagagca agtgatgccc 1100
ccagcgcccc cagcccagcc cactccccgc atggggaggc cgccaccacc 1150
aacacctcat catccttctc atcgctaaca ccaccacctc catcggcacc 1200
caagcgggca tcatcccccc acactgctca ggggagggga gggatcaggc 1250
gatgagactg tgaggccaaa agaagggggc ctgttggagg ctgggaaccc 1300
cgcagcgcga ggctgcctca tcaacggcaa gaggaaagga ggggtctcgg 1350
gacatctcca gaccctacca actgggaggg tcccctcctc cttccctact 1400
cctgggacgg cagcaaggac atgggggctg ctgttagctt ctccgtcagg 1450
aggcctcatc tcactgtagc cctggaaccc agggtccatc ttgcccttcc 1500
cccatccatg gttgggaaag aagctcagcc cctcacagtg gcctcaagtg 1550
tgatgcctta caaaagcacc actcagatgg gcagctggac tctggtgtcc 1600
tgagactctg ccctcttccc acagcctccc tgccccaccc atccctgcaa 1650
agccattttt cagacagagc cattcctaag aacactgaag ggctggaatg 1700
ctggctggcc actctctgcc tcagtggcct ccctacagcc tggaagaagg 1750
agggtcctga ttgccaagga aacctcctca ttgggctaag gagacactgg 1800
agtctggagt gtggagcccc acagtcttgc aggtcacatg ctctccttgc 1850
acatctggcc tggttgtacc cactggcctc tgcctctgcc ctgggccaaa 1900
agggcccctc cttgccaggg gagagacagc cacggtcctc tttggccgat 1950

-continued

```
gctgtattct cattttggcc cttgttctta ggcccgtctg cccgccctcc        2000

tccatctaac ctttcctgtt ttatccgcag cccttttctt ctttgagtta        2050

gtaaagattt attctgtaac ctgacactca tctggccctt tgcagtttgc        2100

cagccatatt cccatgtgat ttcccactgg atccaggccc ccatccggct        2150

ggcaggaggg ggctctgacg tacaggttgg aaatcagaag tctgtgagag        2200

cgcgggagtg catggcagct ctgggtccca gacctggccc gacccctctg        2250

cttcacctcc agctctgctg ctcctctact cttgggtcga gatccctttg        2300

gagccacagc gaggaaccct gtggtcctca ggcaggtgta ccttgagtca        2350

gccaggagcc ctcttttcct gtgtcaaagc ctgccctcgg gctctgctca        2400

cctctggtga ccctccaaga tgcccctgcc ctcagtttcc cctcatgatc        2450

tggcctctgc cccctctct agccacagcc tctagtacac tttagcaata        2500

ccaccagact agttagagtt ccccactcac caagcaagac atgcagtttc        2550

atgcctctgt gccttcgctc atgctgtttc ttccgactgg aatgccttcc        2600

cctgctcctc ctgccttgtc tgcctggcaa gttcatctct cacgatcccc        2650

tcaaaggccc cctcctccag gaaggcaacc cctgtgcccc tcccctccag        2700

gctacctctg cactttgtca atgcttctct tgtggcactt atcacactgt        2750

attttacttg tttacatgtt tgtctcccct tctagactgt gaatccttaa        2800

gggcatggac tgtatcttat gcatctctgt atttctgcgc ctagcacggt        2850

gcctagcaca cagtaggcgc tcaataaatg ttgaatgaat gaaaaaaaaa        2900

aaaaaaaaaa aaaaaaaaaa aaaaaaaaaa aaaaaaaaaa aaaaaaaaaa        2950

aaaaaaaaaa aaaaaaaaaa aaaaaaaaaa aaaaaaaaaa aaaaaaaaaa        3000

aaaaaaaaaa                                                    3010


<210> SEQ ID NO 8
<211> LENGTH: 361
<212> TYPE: PRT
<213> ORGANISM: Homo sapiens

<400> SEQUENCE: 8

Met Ala Trp Gln Gly Trp Pro Ala Ala Trp Gln Trp Val Ala Gly
  1               5                  10                  15

Cys Trp Leu Leu Leu Val Leu Val Leu Val Leu Leu Val Ser Pro
                 20                  25                  30

Arg Gly Cys Arg Ala Arg Arg Gly Leu Arg Gly Leu Leu Met Ala
                 35                  40                  45

His Ser Gln Arg Leu Leu Phe Arg Ile Gly Tyr Ser Leu Tyr Thr
                 50                  55                  60

Arg Thr Trp Leu Gly Tyr Leu Phe Tyr Arg Gln Gln Leu Arg Arg
                 65                  70                  75

Ala Arg Asn Arg Tyr Pro Lys Gly His Ser Lys Thr Gln Pro Arg
                 80                  85                  90

Leu Phe Asn Gly Val Lys Val Leu Pro Ile Pro Val Leu Ser Asp
                 95                 100                 105

Asn Tyr Ser Tyr Leu Ile Ile Asp Thr Gln Ala Gln Leu Ala Val
                110                 115                 120

Ala Val Asp Pro Ser Asp Pro Arg Ala Val Gln Ala Ser Ile Glu
                125                 130                 135
```

-continued

```
Lys Glu Gly Val Thr Leu Val Ala Ile Leu Cys Thr His Lys His
                140                 145                 150

Trp Asp His Ser Gly Gly Asn Arg Asp Leu Ser Arg Arg His Arg
                155                 160                 165

Asp Cys Arg Val Tyr Gly Ser Pro Gln Asp Gly Ile Pro Tyr Leu
                170                 175                 180

Thr His Pro Leu Cys His Gln Asp Val Val Ser Val Gly Arg Leu
                185                 190                 195

Gln Ile Arg Ala Leu Ala Thr Pro Gly His Thr Gln Gly His Leu
                200                 205                 210

Val Tyr Leu Leu Asp Gly Glu Pro Tyr Lys Gly Pro Ser Cys Leu
                215                 220                 225

Phe Ser Gly Asp Leu Leu Phe Leu Ser Gly Cys Gly Arg Thr Phe
                230                 235                 240

Glu Gly Asn Ala Glu Thr Met Leu Ser Ser Leu Asp Thr Val Leu
                245                 250                 255

Gly Leu Gly Asp Asp Thr Leu Leu Trp Pro Gly His Glu Tyr Ala
                260                 265                 270

Glu Glu Asn Leu Gly Phe Ala Gly Val Val Glu Pro Glu Asn Leu
                275                 280                 285

Ala Arg Glu Arg Lys Met Gln Trp Val Gln Arg Gln Arg Leu Glu
                290                 295                 300

Arg Lys Gly Thr Cys Pro Ser Thr Leu Gly Glu Glu Arg Ser Tyr
                305                 310                 315

Asn Pro Phe Leu Arg Thr His Cys Leu Ala Leu Gln Glu Ala Leu
                320                 325                 330

Gly Pro Gly Pro Gly Pro Thr Gly Asp Asp Asp Tyr Ser Arg Ala
                335                 340                 345

Gln Leu Leu Glu Glu Leu Arg Arg Leu Lys Asp Met His Lys Ser
                350                 355                 360

Lys
```

<210> SEQ ID NO 9
<211> LENGTH: 872
<212> TYPE: DNA
<213> ORGANISM: Homo sapiens

<400> SEQUENCE: 9

```
gctgacaatc cccttgacgt tctatcccgg aagctccacc tggggcccaa        50

tgttgggcgt gatgttcctc gcctgtctct gcctggaaaa ctggtcttcc       100

caagctccac tggcagccac ttctccatgt tgggcatcgg agacatcgtt       150

atgcctggtc tcctactatg ctttgtcctt cgctatgaca actacaaaaa       200

gcaagccagt ggggactcct gtggggcccc tggacctgcc aacatctccg       250

ggcgcatgca gaaggtctcc tactctcact gcaccctcat cggatacttt       300

gtaggcctgc tcactgctac tgtggcgtct cgcattcacc gggccgccca       350

gcccgccctt ctctatttgg tgccatttac tttattgcca ctcctcacga       400

tggcctattt aaagggcgac ctccggcgga tgtggtctga gcctttccac       450

tccaagtcca gcagctcccg attcctggaa gtatgatgga tcacgtggaa       500

agtgaccaga tggccgtcat agtccttttc tctcaactca tggtttgttt       550

cctcttagag ctggcctggt actcagaaat gtacctgtgt ttaaggaact       600
```

-continued

```
gccgtgtgac tggatttggc attgaaaggg agctcgtttg caggagagag        650

gtgctggagc cctgtttggt tccttctctt cctgcggatg tagaggtggg        700

gccccttcca agagggacag gcctctcccc agcgcgcctt cctcccacgt        750

ttttatggat ctgcaccaga ctgttacctt ctgggggaga tggagatttg        800

actgtttaaa aactgaaaac agcgaggagt ctttctagaa cttttgaaca        850

ctaaaaggat gaaaaaatta  gc                                     872


<210> SEQ ID NO 10
<211> LENGTH: 108
<212> TYPE: PRT
<213> ORGANISM: Homo sapiens

<400> SEQUENCE: 10

Met Met Asp His Val Glu Ser Asp Gln Met Ala Val Ile Val Leu
  1               5                  10                  15

Phe Ser Gln Leu Met Val Cys Phe Leu Leu Glu Leu Ala Trp Tyr
                 20                  25                  30

Ser Glu Met Tyr Leu Cys Leu Arg Asn Cys Arg Val Thr Gly Phe
                 35                  40                  45

Gly Ile Glu Arg Glu Leu Val Cys Arg Arg Glu Val Leu Glu Pro
                 50                  55                  60

Cys Leu Val Pro Ser Leu Pro Ala Asp Val Glu Val Gly Pro Leu
                 65                  70                  75

Pro Arg Gly Thr Gly Leu Ser Pro Ala Arg Leu Pro Pro Thr Phe
                 80                  85                  90

Leu Trp Ile Cys Thr Arg Leu Leu Pro Ser Gly Gly Asp Gly Asp
                 95                 100                 105

Leu Thr Val


<210> SEQ ID NO 11
<211> LENGTH: 1739
<212> TYPE: DNA
<213> ORGANISM: Homo sapiens

<400> SEQUENCE: 11

tcgcacactg gtggcttcag aagaaattct caacacctag ctcgccagag         50

agtctatgta tgggattgaa caatctgtaa actaaaggat cctaatcatg        100

aaaataagta tgataaatta taagtcacta ttggcactgt tgtttatatt        150

agcctcctgg atcattttta cagttttcca gaactccaca aaggtttggt        200

ctgctctaaa cttatccatc tccctccatt actggaacaa ctccacaaag        250

tccttattcc ctaaaacacc actgatatca ttaaagccac taacagagac        300

tgaactcaga ataaaggaaa tcatagagaa actagatcag cagatcccac        350

ccagaccttt cacccacgtg aacaccacca ccagcgccac acatagcaca        400

gccaccatcc tcaaccctcg agatacgtac tgcaggggag accagctgca        450

catcctgctg gaggtgaggg accacttggg acgcaggaag caatatggcg        500

gggatttcct gagggccagg atgtcttccc cagcgctgat ggcaggtgct        550

tcaggaaagg tgactgactt caacaacggc acctacctgg tcagcttcac        600

tctgttctgg gagggccagg tctctctgtc tctgctgctc atccacccca        650

gtgaaggggt gtcagctctc tggagtgcaa ggaaccaagg ctatgacagg        700
```

-continued

```
gtgatcttca ctggccagtt tgtcaatggc acttcccaag tccactctga       750
atgtggcctg atcctaaaca caaatgctga attgtgccag tacctggaca       800
acagagacca agaaggcttc tactgtgtga ggcctcaaca catgccctgt       850
gctgcactca ctcacatgta ttctaagaac aagaaagttt cttatcttag       900
caaacaagaa aagagcctct ttgaaaggtc aaatgtgggt gtagagatta       950
tggaaaaatt caatacaatt agtgtctcca aatgcaacaa agaaacagtt      1000
gcaatgaaag agaaatgcaa gtttggaatg acatccacaa tccccagtgg      1050
gcatgtctgg agaaacacat ggaatcctgt ctcctgtagt ttggctacag      1100
tcaaaatgaa ggaatgcctg agaggaaaac tcatatacct aatgggagat      1150
tccacgatcc gccagtggat ggaatacttc aaagccagta tcaacacact      1200
gaagtcagtg gatctgcatg aatctggaaa attgcaacac cagcttgctg      1250
tggatttgga taggaacatc aacatccagt ggcaaaaata ttgttatccc      1300
ttgataggat caatgaccta ttcagtcaaa gagatggagt acctcacccg      1350
ggccattgac agaactggag gagaaaaaaa tactgtcatt gttatttccc      1400
tgggccagca tttcagaccc tttcccattg atgtttttat ccgaagggcc      1450
ctcaatgtcc acaaagccat tcagcatctt cttctgagaa gcccagacac      1500
tatggttatc atcaaaacag aaaacatcag ggagatgtac aatgatgcag      1550
aaagatttag tgactttcat ggttacattc aatatctcat cataaaggac      1600
attttccagg atctcagtgt gagtatcatt gatgcctggg atataacaat      1650
tgcatatggc acaaataatg tacacccacc tcaacatgta gtcggaaatc      1700
agattaatat attattaaac tatatttgtt  aaataacaa                 1739

<210> SEQ ID NO 12
<211> LENGTH: 544
<212> TYPE: PRT
<213> ORGANISM: Homo sapiens

<400> SEQUENCE: 12

Met Lys Ile Ser Met Ile Asn Tyr Lys Ser Leu Leu Ala Leu Leu
  1               5                  10                  15

Phe Ile Leu Ala Ser Trp Ile Ile Phe Thr Val Phe Gln Asn Ser
                 20                  25                  30

Thr Lys Val Trp Ser Ala Leu Asn Leu Ser Ile Ser Leu His Tyr
                 35                  40                  45

Trp Asn Asn Ser Thr Lys Ser Leu Phe Pro Lys Thr Pro Leu Ile
                 50                  55                  60

Ser Leu Lys Pro Leu Thr Glu Thr Glu Leu Arg Ile Lys Glu Ile
                 65                  70                  75

Ile Glu Lys Leu Asp Gln Gln Ile Pro Pro Arg Pro Phe Thr His
                 80                  85                  90

Val Asn Thr Thr Thr Ser Ala Thr His Ser Thr Ala Thr Ile Leu
                 95                 100                 105

Asn Pro Arg Asp Thr Tyr Cys Arg Gly Asp Gln Leu His Ile Leu
                110                 115                 120

Leu Glu Val Arg Asp His Leu Gly Arg Arg Lys Gln Tyr Gly Gly
                125                 130                 135

Asp Phe Leu Arg Ala Arg Met Ser Ser Pro Ala Leu Met Ala Gly
```

-continued

```
                140                 145                 150

Ala Ser Gly Lys Val Thr Asp Phe Asn Asn Gly Thr Tyr Leu Val
                155                 160                 165

Ser Phe Thr Leu Phe Trp Glu Gly Gln Val Ser Leu Ser Leu Leu
                170                 175                 180

Leu Ile His Pro Ser Glu Gly Val Ser Ala Leu Trp Ser Ala Arg
                185                 190                 195

Asn Gln Gly Tyr Asp Arg Val Ile Phe Thr Gly Gln Phe Val Asn
                200                 205                 210

Gly Thr Ser Gln Val His Ser Glu Cys Gly Leu Ile Leu Asn Thr
                215                 220                 225

Asn Ala Glu Leu Cys Gln Tyr Leu Asp Asn Arg Asp Gln Glu Gly
                230                 235                 240

Phe Tyr Cys Val Arg Pro Gln His Met Pro Cys Ala Ala Leu Thr
                245                 250                 255

His Met Tyr Ser Lys Asn Lys Lys Val Ser Tyr Leu Ser Lys Gln
                260                 265                 270

Glu Lys Ser Leu Phe Glu Arg Ser Asn Val Gly Val Glu Ile Met
                275                 280                 285

Glu Lys Phe Asn Thr Ile Ser Val Ser Lys Cys Asn Lys Glu Thr
                290                 295                 300

Val Ala Met Lys Glu Lys Cys Lys Phe Gly Met Thr Ser Thr Ile
                305                 310                 315

Pro Ser Gly His Val Trp Arg Asn Thr Trp Asn Pro Val Ser Cys
                320                 325                 330

Ser Leu Ala Thr Val Lys Met Lys Glu Cys Leu Arg Gly Lys Leu
                335                 340                 345

Ile Tyr Leu Met Gly Asp Ser Thr Ile Arg Gln Trp Met Glu Tyr
                350                 355                 360

Phe Lys Ala Ser Ile Asn Thr Leu Lys Ser Val Asp Leu His Glu
                365                 370                 375

Ser Gly Lys Leu Gln His Gln Leu Ala Val Asp Leu Asp Arg Asn
                380                 385                 390

Ile Asn Ile Gln Trp Gln Lys Tyr Cys Tyr Pro Leu Ile Gly Ser
                395                 400                 405

Met Thr Tyr Ser Val Lys Glu Met Glu Tyr Leu Thr Arg Ala Ile
                410                 415                 420

Asp Arg Thr Gly Gly Glu Lys Asn Thr Val Ile Val Ile Ser Leu
                425                 430                 435

Gly Gln His Phe Arg Pro Phe Pro Ile Asp Val Phe Ile Arg Arg
                440                 445                 450

Ala Leu Asn Val His Lys Ala Ile Gln His Leu Leu Leu Arg Ser
                455                 460                 465

Pro Asp Thr Met Val Ile Ile Lys Thr Glu Asn Ile Arg Glu Met
                470                 475                 480

Tyr Asn Asp Ala Glu Arg Phe Ser Asp Phe His Gly Tyr Ile Gln
                485                 490                 495

Tyr Leu Ile Ile Lys Asp Ile Phe Gln Asp Leu Ser Val Ser Ile
                500                 505                 510

Ile Asp Ala Trp Asp Ile Thr Ile Ala Tyr Gly Thr Asn Asn Val
                515                 520                 525

His Pro Pro Gln His Val Val Gly Asn Gln Ile Asn Ile Leu Leu
                530                 535                 540
```

-continued

Asn Tyr Ile Cys

<210> SEQ ID NO 13
<211> LENGTH: 1893
<212> TYPE: DNA
<213> ORGANISM: Homo sapiens

<400> SEQUENCE: 13
gcaaagagaa gactgaaaga caaacctggg tgcagccaga gaggtccaga 50
tagatgagct tgtggcatcc attccccaag ttcagcctag ggactccacg 100
taccccagct gggtctcatt gttccagaac tgcattagtt aagattaccc 150
agacttggat ttcaaaggaa tactttcatt gttccgtctg taacacgaag 200
taattggggc cagctggatg tcaggatgcg tgtggttacc attgtaatct 250
tgctctgctt ttgcaaagcg gctgagctgc gcaaagcaag cccaggcagt 300
gtgagaagcc gagtgaatca tggccgggcg ggtggaggcc ggagaggctc 350
caacccggtc aaacgctacg caccaggcct cccgtgtgac gtgtacacat 400
atctccatga gaaatactta gattgtcaag aaagaaaatt agtttatgtg 450
ctgcctggtt ggcctcagga tttgctgcac atgctgctag caagaaacaa 500
gatccgcaca ttgaagaaca acatgttttc caagtttaaa aagctgaaaa 550
gcctggatct gcagcagaat gagatctcta aaattgagag tgaggcgttc 600
tttggtttaa acaaactcac caccctctta ctgcagcaca accagatcaa 650
agtcttgacg gaggaagtgt tcatttacac acctctcttg agctacctgc 700
gtctttatga caacccctgg cactgtactt gtgagataga aacgcttatt 750
tcaatgttgc agattcccag gaaccggaat ttggggaact acgccaagtg 800
tgaaagtcca caagaacaaa aaaataaaaa actgcggcag ataaaatctg 850
aacagttgtg taatgaagaa aaggaacaat tggacccgaa accccaagtg 900
tcagggagac ccccagtcat caagcctgag gtggactcaa ctttttgcca 950
caattatgtg tttcccatac aaacactgga ctgcaaaagg aaagagttga 1000
aaaaagtgcc aaacaacatc cctccagata ttgttaaact tgacttgtca 1050
tacaataaaa tcaaccaact tcgacccaag gaatttgaag atgttcatga 1100
gctgaagaaa ttaaacctca gcagcaatgg cattgaattc atcgatcctg 1150
ccgctttttt agggctcaca catttagaag aattagattt atcaaacaac 1200
agtctgcaaa actttgacta tggcgtatta gaagacttgt attttttgaa 1250
actcttgtgg ctcagagata acccttggag atgtgactac aacattcact 1300
acctctacta ctggttaaag caccactaca atgtccattt taatggcctg 1350
gaatgcaaaa cgcctgaaga atacaaagga tggtctgtgg gaaaatatat 1400
tagaagttac tatgaagaat gccccaaaga caagttacca gcatatcctg 1450
agtcatttga ccaagacaca gaagatgatg aatgggaaaa aaaacataga 1500
gatcacaccg caaagaagca aagcgtaata attactatag taggataagg 1550
tagaaattgt tctgattgta attagttttg tattttctat actggtgtta 1600
gaaaacatat gtttacattt gattaactgt gttgcctatt tatgcagggt 1650
aatccagcta aaggaagctt tctttaatta taagtattat tgtgactatt 1700

-continued

```
atagtaatca agagaatgct atcatcctgc ttgcctgtcc atttgtggaa           1750

cagcatctgg tgatatgcaa ttccacactg gtaacctgca gcagttgggt           1800

cctaatgatg gcattagact ttcataatgt cctgtataaa tgtttttact           1850

gcttttagaa aataaagaaa aaaaacttgg ttcatgttta  aaa                 1893


<210> SEQ ID NO 14
<211> LENGTH: 440
<212> TYPE: PRT
<213> ORGANISM: Homo sapiens

<400> SEQUENCE: 14

Met Arg Val Val Thr Ile Val Ile Leu Leu Cys Phe Cys Lys Ala
  1               5                  10                  15

Ala Glu Leu Arg Lys Ala Ser Pro Gly Ser Val Arg Ser Arg Val
                 20                  25                  30

Asn His Gly Arg Ala Gly Gly Gly Arg Arg Gly Ser Asn Pro Val
                 35                  40                  45

Lys Arg Tyr Ala Pro Gly Leu Pro Cys Asp Val Tyr Thr Tyr Leu
                 50                  55                  60

His Glu Lys Tyr Leu Asp Cys Gln Glu Arg Lys Leu Val Tyr Val
                 65                  70                  75

Leu Pro Gly Trp Pro Gln Asp Leu Leu His Met Leu Leu Ala Arg
                 80                  85                  90

Asn Lys Ile Arg Thr Leu Lys Asn Asn Met Phe Ser Lys Phe Lys
                 95                 100                 105

Lys Leu Lys Ser Leu Asp Leu Gln Gln Asn Glu Ile Ser Lys Ile
                110                 115                 120

Glu Ser Glu Ala Phe Phe Gly Leu Asn Lys Leu Thr Thr Leu Leu
                125                 130                 135

Leu Gln His Asn Gln Ile Lys Val Leu Thr Glu Glu Val Phe Ile
                140                 145                 150

Tyr Thr Pro Leu Leu Ser Tyr Leu Arg Leu Tyr Asp Asn Pro Trp
                155                 160                 165

His Cys Thr Cys Glu Ile Glu Thr Leu Ile Ser Met Leu Gln Ile
                170                 175                 180

Pro Arg Asn Arg Asn Leu Gly Asn Tyr Ala Lys Cys Glu Ser Pro
                185                 190                 195

Gln Glu Gln Lys Asn Lys Lys Leu Arg Gln Ile Lys Ser Glu Gln
                200                 205                 210

Leu Cys Asn Glu Glu Lys Glu Gln Leu Asp Pro Lys Pro Gln Val
                215                 220                 225

Ser Gly Arg Pro Pro Val Ile Lys Pro Glu Val Asp Ser Thr Phe
                230                 235                 240

Cys His Asn Tyr Val Phe Pro Ile Gln Thr Leu Asp Cys Lys Arg
                245                 250                 255

Lys Glu Leu Lys Lys Val Pro Asn Asn Ile Pro Pro Asp Ile Val
                260                 265                 270

Lys Leu Asp Leu Ser Tyr Asn Lys Ile Asn Gln Leu Arg Pro Lys
                275                 280                 285

Glu Phe Glu Asp Val His Glu Leu Lys Lys Leu Asn Leu Ser Ser
                290                 295                 300

Asn Gly Ile Glu Phe Ile Asp Pro Ala Ala Phe Leu Gly Leu Thr
                305                 310                 315
```

-continued

His Leu Glu Glu Leu Asp Leu Ser Asn Asn Ser Leu Gln Asn Phe
320 325 330

Asp Tyr Gly Val Leu Glu Asp Leu Tyr Phe Leu Lys Leu Leu Trp
335 340 345

Leu Arg Asp Asn Pro Trp Arg Cys Asp Tyr Asn Ile His Tyr Leu
350 355 360

Tyr Tyr Trp Leu Lys His His Tyr Asn Val His Phe Asn Gly Leu
365 370 375

Glu Cys Lys Thr Pro Glu Glu Tyr Lys Gly Trp Ser Val Gly Lys
380 385 390

Tyr Ile Arg Ser Tyr Tyr Glu Glu Cys Pro Lys Asp Lys Leu Pro
395 400 405

Ala Tyr Pro Glu Ser Phe Asp Gln Asp Thr Glu Asp Asp Glu Trp
410 415 420

Glu Lys Lys His Arg Asp His Thr Ala Lys Lys Gln Ser Val Ile
425 430 435

Ile Thr Ile Val Gly
440

<210> SEQ ID NO 15
<211> LENGTH: 1524
<212> TYPE: DNA
<213> ORGANISM: Homo sapiens

<400> SEQUENCE: 15
gcggcagcag cgcgggcccc agcagcctcg gcagccacag ccgctgcagc 50
cggggcagcc tccgctgctg tcgcctcctc tgatgcgctt gccctctccc 100
ggccccggga ctccgggaga atgtgggtcc taggcatcgc ggcaactttt 150
tgcggattgt tcttgcttcc aggctttgcg ctgcaaatcc agtgctacca 200
gtgtgaagaa ttccagctga acaacgactg ctcctccccc gagttcattg 250
tgaattgcac ggtgaacgtt caagacatgt gtcagaaaga agtgatggag 300
caaagtgccg ggatcatgta ccgcaagtcc tgtgcatcat cagcggcctg 350
tctcatcgcc tctgccgggt accagtcctt ctgctcccca gggaaactga 400
actcagtttg catcagctgc tgcaacaccc ctctttgtaa cgggccaagg 450
cccaagaaaa ggggaagttc tgcctcggcc ctcaggccag ggctccgcac 500
caccatcctg ttcctcaaat tagccctctt ctcggcacac tgctgaagct 550
gaaggagatg ccaccccctc ctgcattgtt cttccagccc tcgcccccaa 600
ccccccacct ccctgagtga gtttcttctg ggtgtccttt tattctgggt 650
agggagcggg agtccgtgtt ctcttttgtt cctgtgcaaa taatgaaaga 700
gctcggtaaa gcattctgaa taaattcagc ctgactgaat tttcagtatg 750
tacttgaagg aaggaggtgg agtgaaagtt cacccccatg tctgtgtaac 800
cggagtcaag gccaggctgg cagagtcagt ccttagaagt cactgaggtg 850
ggcatctgcc ttttgtaaag cctccagtgt ccattccatc cctgatgggg 900
gcatagtttg agactgcaga gtgagagtga cgttttctta gggctggagg 950
gccagttccc actcaaggct ccctcgcttg acattcaaac ttcatgctcc 1000
tgaaaaccat tctctgcagc agaattggct ggtttcgcgc ctgagttggg 1050
ctctagtgac tcgagactca atgactggga cttagactgg ggctcggcct 1100

-continued

```
cgctctgaaa agtgcttaag aaaatcttct cagttctcct tgcagaggac          1150

tggcgccggg acgcgaagag caacgggcgc tgcacaaagc gggcgctgtc          1200

ggtggtggag tgcgcatgta cgcgcaggcg cttctcgtgg ttggcgtgct          1250

gcagcgacag gcggcagcac agcacctgca cgaacacccg ccgaaactgc          1300

tgcgaggaca ccgtgtacag gagcgggttg atgaccgagc tgaggtagaa          1350

aaacgtctcc gagaagggga ggaggatcat gtacgcccgg aagtaggacc          1400

tcgtccagtc gtgcttgggt ttggccgcag ccatgatcct ccgaatctgg          1450

ttgggcatcc agcatacggc caatgtcaca acaatcagcc ctgggcagac          1500

acgagcagga gggagagaca  gaga                                     1524


<210> SEQ ID NO 16
<211> LENGTH: 141
<212> TYPE: PRT
<213> ORGANISM: Homo sapiens

<400> SEQUENCE: 16

Met Trp Val Leu Gly Ile Ala Ala Thr Phe Cys Gly Leu Phe Leu
  1               5                  10                  15

Leu Pro Gly Phe Ala Leu Gln Ile Gln Cys Tyr Gln Cys Glu Glu
                 20                  25                  30

Phe Gln Leu Asn Asn Asp Cys Ser Ser Pro Glu Phe Ile Val Asn
                 35                  40                  45

Cys Thr Val Asn Val Gln Asp Met Cys Gln Lys Glu Val Met Glu
                 50                  55                  60

Gln Ser Ala Gly Ile Met Tyr Arg Lys Ser Cys Ala Ser Ser Ala
                 65                  70                  75

Ala Cys Leu Ile Ala Ser Ala Gly Tyr Gln Ser Phe Cys Ser Pro
                 80                  85                  90

Gly Lys Leu Asn Ser Val Cys Ile Ser Cys Cys Asn Thr Pro Leu
                 95                 100                 105

Cys Asn Gly Pro Arg Pro Lys Lys Arg Gly Ser Ser Ala Ser Ala
                110                 115                 120

Leu Arg Pro Gly Leu Arg Thr Thr Ile Leu Phe Leu Lys Leu Ala
                125                 130                 135

Leu Phe Ser Ala His Cys
                140


<210> SEQ ID NO 17
<211> LENGTH: 1402
<212> TYPE: DNA
<213> ORGANISM: Homo sapiens

<400> SEQUENCE: 17

cgcaaagccg ccctcggggc gctcatggcg ggacgcctcc tgggaaaggc            50

tttagccgcg gtgtctctct ctctggcctt ggcctctgtg actatcaggt           100

cctcgcgctg ccgcggcatc caggcgttca gaaactcgtt ttcatcttct           150

tggtttcatc ttaataccaa cgtcatgtct ggttctaatg gttccaaaga           200

aaattctcac aataaggctc ggacgtctcc ttacccaggt tcaaaagttg           250

aacgaagcca ggttcctaat gagaaagtgg gctggcttgt tgagtggcaa           300

gactataagc ctgtggaata cactgcagtc tctgtcttgg ctggacccag           350

gtgggcagat cctcagatca gtgaaagtaa tttttctccc aagtttaacg           400
```

```
aaaaggatgg gcatgttgag agaaagagca agaatggcct gtatgagatt      450

gaaaatggaa gaccgagaaa tcctgcagga cggactggac tggtgggccg      500

ggggcttttg gggcgatggg gcccaaatca cgctgcagat cccattataa      550

ccagatggaa aagggatagc agtggaaata aaatcatgca tcctgtttct      600

gggaagcata tcttacaatt tgttgcaata aaaaggaaag actgtggaga      650

atgggcaatc ccaggggga tggtggatcc aggagagaag attagtgcca       700

cactgaaaag agaatttggt gaggaagctc tcaactcctt acagaaaacc      750

agtgctgaga agagagaaat agaggaaaag ttgcacaaac tcttcagcca      800

agaccaccta gtgatatata agggatatgt tgatgatcct cgaaacactg      850

ataatgcatg gatggagaca gaagctgtga actaccatga cgaaacaggt      900

gagataatgg ataatcttat gctagaagct ggagatgatg ctggaaaagt      950

gaaatgggtg gacatcaatg ataaactgaa gctttatgcc agtcactctc      1000

aattcatcaa acttgtggct gagaaacgag atgcacactg gagcgaggac      1050

tctgaagctg actgccatgc gttgtagctg atggtctccg tgtaagccaa      1100

aggcccacag aggagcatat actgaaaaga aggcagtatc acagaattta      1150

tactataaaa agggcagggt aggccacttg gcctatttac tttcaaaaca      1200

atttgcattt agagtgtttc gcatcagaat aacatgagta agatgaactg      1250

gaacacaaaa ttttcagctc tttggtcaaa aggaatataa gtaatcatat      1300

tttgtatgta ttcgatttaa gcatggctta aattaaattt aaacaactaa      1350

tgctctttga agaatcataa tcagaataaa gataaattct tgatcagcta      1400

ta                                                          1402
```

<210> SEQ ID NO 18
<211> LENGTH: 350
<212> TYPE: PRT
<213> ORGANISM: Homo sapiens

<400> SEQUENCE: 18

```
Met Ala Gly Arg Leu Leu Gly Lys Ala Leu Ala Ala Val Ser Leu
 1               5                  10                  15

Ser Leu Ala Leu Ala Ser Val Thr Ile Arg Ser Ser Arg Cys Arg
                20                  25                  30

Gly Ile Gln Ala Phe Arg Asn Ser Phe Ser Ser Ser Trp Phe His
                35                  40                  45

Leu Asn Thr Asn Val Met Ser Gly Ser Asn Gly Ser Lys Glu Asn
                50                  55                  60

Ser His Asn Lys Ala Arg Thr Ser Pro Tyr Pro Gly Ser Lys Val
                65                  70                  75

Glu Arg Ser Gln Val Pro Asn Glu Lys Val Gly Trp Leu Val Glu
                80                  85                  90

Trp Gln Asp Tyr Lys Pro Val Glu Tyr Thr Ala Val Ser Val Leu
                95                 100                 105

Ala Gly Pro Arg Trp Ala Asp Pro Gln Ile Ser Glu Ser Asn Phe
               110                 115                 120

Ser Pro Lys Phe Asn Glu Lys Asp Gly His Val Glu Arg Lys Ser
               125                 130                 135

Lys Asn Gly Leu Tyr Glu Ile Glu Asn Gly Arg Pro Arg Asn Pro
```

-continued

```
                140                 145                 150

Ala Gly Arg Thr Gly Leu Val Gly Arg Gly Leu Leu Gly Arg Trp
                155                 160                 165

Gly Pro Asn His Ala Ala Asp Pro Ile Ile Thr Arg Trp Lys Arg
                170                 175                 180

Asp Ser Ser Gly Asn Lys Ile Met His Pro Val Ser Gly Lys His
                185                 190                 195

Ile Leu Gln Phe Val Ala Ile Lys Arg Lys Asp Cys Gly Glu Trp
                200                 205                 210

Ala Ile Pro Gly Gly Met Val Asp Pro Gly Glu Lys Ile Ser Ala
                215                 220                 225

Thr Leu Lys Arg Glu Phe Gly Glu Glu Ala Leu Asn Ser Leu Gln
                230                 235                 240

Lys Thr Ser Ala Glu Lys Arg Glu Ile Glu Glu Lys Leu His Lys
                245                 250                 255

Leu Phe Ser Gln Asp His Leu Val Ile Tyr Lys Gly Tyr Val Asp
                260                 265                 270

Asp Pro Arg Asn Thr Asp Asn Ala Trp Met Glu Thr Glu Ala Val
                275                 280                 285

Asn Tyr His Asp Glu Thr Gly Glu Ile Met Asp Asn Leu Met Leu
                290                 295                 300

Glu Ala Gly Asp Asp Ala Gly Lys Val Lys Trp Val Asp Ile Asn
                305                 310                 315

Asp Lys Leu Lys Leu Tyr Ala Ser His Ser Gln Phe Ile Lys Leu
                320                 325                 330

Val Ala Glu Lys Arg Asp Ala His Trp Ser Glu Asp Ser Glu Ala
                335                 340                 345

Asp Cys His Ala Leu
                350


<210> SEQ ID NO 19
<211> LENGTH: 2138
<212> TYPE: DNA
<213> ORGANISM: Homo sapiens

<400> SEQUENCE: 19

cgagggctcc tgctggtact gtgttcgctg ctgcacagca aggccctgcc                50

acccaccttc aggccatgca gccatgttcc gggagcccta attgcacaga               100

agcccatggg gagctccaga ctggcagccc tgctcctgcc tctcctcctc               150

atagtcatcg acctctctga ctctgctggg attggctttc gccacctgcc               200

ccactggaac acccgctgtc ctctggcctc ccacacggat gacagtttca               250

ctggaagttc tgcctatatc ccttgccgca cctggtgggc cctcttctcc               300

acaaagcctt ggtgtgtgcg agtctggcac tgttcccgct gtttgtgcca               350

gcatctgctg tcaggtggct caggtcttca acggggcctc ttccacctcc               400

tggtgcagaa atccaaaaag tcttccacat tcaagttcta taggagacac               450

aagatgccag cacctgctca gaggaagctg ctgcctcgtc gtcacctgtc               500

tgagaagagc catcacattt ccatcccctc cccagacatc tcccacaagg               550

gacttcgctc taaaaggacc caaccttcgg atccagagac atgggaaagt               600

cttcccagat tggactcaca aaggcatgga ggacccgagt tctcctttga               650

tttgctgcct gaggcccggg ctattcgggt gaccatatct tcaggccctg               700
```

-continued

```
aggtcagcgt gcgtctttgt caccagtggg cactggagtg tgaagagctg          750
agcagtccct atgatgtcca gaaaattgtg tctgggggcc acactgtaga          800
gctgccttat gaattccttc tgccctgtct gtgcatagag gcatcctacc          850
tgcaagagga cactgtgagg cgcaaaaaat gtcccttcca gagctggcca          900
gaagcctatg gctcggactt ctggaagtca gtgcacttca ctgactacag          950
ccagcacact cagatggtca tggccctgac actccgctgc ccactgaagc         1000
tggaagctgc cctctgccag aggcacgact ggcataccct ttgcaaagac         1050
ctcccgaatg ccacggctcg agagtcagat gggtggtatg ttttggagaa         1100
ggtggacctg cacccccagc tctgcttcaa gttctctttt ggaaacagca         1150
gccatgttga atgcccccac cagactgggt ctctcacatc ctggaatgta         1200
agcatggata cccaagccca gcagctgatt cttcacttct cctcaagaat         1250
gcatgccacc ttcagtgctg cctggagcct cccaggcttg gggcaggaca         1300
ctttggtgcc ccccgtgtac actgtcagcc aggcccgggg ctcaagccca         1350
gtgtcactag acctcatcat tcccttcctg aggccagggt gctgtgtcct         1400
ggtgtggcgg tcagatgtcc agtttgcctg gaagcacctc ttgtgtccag         1450
atgtctctta cagacacctg ggctcttga tcctggcact gctggccctc         1500
ctcaccctac tgggtgttgt tctggccctc acctgccggc gcccacagtc         1550
aggcccgggc ccagcgcggc cagtgctcct cctgcacgcg gcggactcgg         1600
aggcgcagcg gcgcctggtg ggagcgctgg ctgaactgct acgggcagcg         1650
ctgggcggcg ggcgcgacgt gatcgtggac ctgtgggagg ggaggcacgt         1700
ggcgcgcgtg ggcccgctgc cgtggctctg ggcggcgcgg acgcgcgtag         1750
cgcgggagca gggcactgtg ctgctgctgt ggagcggcgc cgaccttcgc         1800
ccggtcagcg gccccgaccc ccgcgccgcg cccctgctcg ccctgctcca         1850
cgctgccccg cgcccgctgc tgctgctcgc ttacttcagt cgcctctgcg         1900
ccaagggcga catccccccg ccgctgcgcg ccctgccgcg ctaccgcctg         1950
ctgcgcgacc tgccgcgtct gctgcgggcg ctggacgcgc ggcctttcgc         2000
agaggccacc agctggggcc gccttggggc gcggcagcgc aggcagagcc         2050
gcctagagct gtgcagccgg cttgaacgag aggccgcccg acttgcagac         2100
ctaggttgag cagagctcca ccgcagtccc  gggtgtct                     2138
```

<210> SEQ ID NO 20
<211> LENGTH: 667
<212> TYPE: PRT
<213> ORGANISM: Homo sapiens

<400> SEQUENCE: 20

```
Met Gly Ser Ser Arg Leu Ala Ala Leu Leu Leu Pro Leu Leu Leu
  1               5                  10                  15

Ile Val Ile Asp Leu Ser Asp Ser Ala Gly Ile Gly Phe Arg His
                 20                  25                  30

Leu Pro His Trp Asn Thr Arg Cys Pro Leu Ala Ser His Thr Asp
                 35                  40                  45

Asp Ser Phe Thr Gly Ser Ser Ala Tyr Ile Pro Cys Arg Thr Trp
                 50                  55                  60
```

-continued

```
Trp Ala Leu Phe Ser Thr Lys Pro Trp Cys Val Arg Val Trp His
                65                  70                  75

Cys Ser Arg Cys Leu Cys Gln His Leu Leu Ser Gly Gly Ser Gly
                80                  85                  90

Leu Gln Arg Gly Leu Phe His Leu Leu Val Gln Lys Ser Lys Lys
                95                  100                 105

Ser Ser Thr Phe Lys Phe Tyr Arg Arg His Lys Met Pro Ala Pro
                110                 115                 120

Ala Gln Arg Lys Leu Leu Pro Arg Arg His Leu Ser Glu Lys Ser
                125                 130                 135

His His Ile Ser Ile Pro Ser Pro Asp Ile Ser His Lys Gly Leu
                140                 145                 150

Arg Ser Lys Arg Thr Gln Pro Ser Asp Pro Glu Thr Trp Glu Ser
                155                 160                 165

Leu Pro Arg Leu Asp Ser Gln Arg His Gly Gly Pro Glu Phe Ser
                170                 175                 180

Phe Asp Leu Leu Pro Glu Ala Arg Ala Ile Arg Val Thr Ile Ser
                185                 190                 195

Ser Gly Pro Glu Val Ser Val Arg Leu Cys His Gln Trp Ala Leu
                200                 205                 210

Glu Cys Glu Glu Leu Ser Ser Pro Tyr Asp Val Gln Lys Ile Val
                215                 220                 225

Ser Gly Gly His Thr Val Glu Leu Pro Tyr Glu Phe Leu Leu Pro
                230                 235                 240

Cys Leu Cys Ile Glu Ala Ser Tyr Leu Gln Glu Asp Thr Val Arg
                245                 250                 255

Arg Lys Lys Cys Pro Phe Gln Ser Trp Pro Glu Ala Tyr Gly Ser
                260                 265                 270

Asp Phe Trp Lys Ser Val His Phe Thr Asp Tyr Ser Gln His Thr
                275                 280                 285

Gln Met Val Met Ala Leu Thr Leu Arg Cys Pro Leu Lys Leu Glu
                290                 295                 300

Ala Ala Leu Cys Gln Arg His Asp Trp His Thr Leu Cys Lys Asp
                305                 310                 315

Leu Pro Asn Ala Thr Ala Arg Glu Ser Asp Gly Trp Tyr Val Leu
                320                 325                 330

Glu Lys Val Asp Leu His Pro Gln Leu Cys Phe Lys Phe Ser Phe
                335                 340                 345

Gly Asn Ser Ser His Val Glu Cys Pro His Gln Thr Gly Ser Leu
                350                 355                 360

Thr Ser Trp Asn Val Ser Met Asp Thr Gln Ala Gln Gln Leu Ile
                365                 370                 375

Leu His Phe Ser Ser Arg Met His Ala Thr Phe Ser Ala Ala Trp
                380                 385                 390

Ser Leu Pro Gly Leu Gly Gln Asp Thr Leu Val Pro Pro Val Tyr
                395                 400                 405

Thr Val Ser Gln Ala Arg Gly Ser Ser Pro Val Ser Leu Asp Leu
                410                 415                 420

Ile Ile Pro Phe Leu Arg Pro Gly Cys Cys Val Leu Val Trp Arg
                425                 430                 435

Ser Asp Val Gln Phe Ala Trp Lys His Leu Leu Cys Pro Asp Val
                440                 445                 450

Ser Tyr Arg His Leu Gly Leu Leu Ile Leu Ala Leu Leu Ala Leu
```

-continued

```
                455                 460                 465

Leu Thr Leu Leu Gly Val Val Leu Ala Leu Thr Cys Arg Arg Pro
                470                 475                 480

Gln Ser Gly Pro Gly Pro Ala Arg Pro Val Leu Leu Leu His Ala
                485                 490                 495

Ala Asp Ser Glu Ala Gln Arg Arg Leu Val Gly Ala Leu Ala Glu
                500                 505                 510

Leu Leu Arg Ala Ala Leu Gly Gly Gly Arg Asp Val Ile Val Asp
                515                 520                 525

Leu Trp Glu Gly Arg His Val Ala Arg Val Gly Pro Leu Pro Trp
                530                 535                 540

Leu Trp Ala Ala Arg Thr Arg Val Ala Arg Glu Gln Gly Thr Val
                545                 550                 555

Leu Leu Leu Trp Ser Gly Ala Asp Leu Arg Pro Val Ser Gly Pro
                560                 565                 570

Asp Pro Arg Ala Ala Pro Leu Leu Ala Leu Leu His Ala Ala Pro
                575                 580                 585

Arg Pro Leu Leu Leu Leu Ala Tyr Phe Ser Arg Leu Cys Ala Lys
                590                 595                 600

Gly Asp Ile Pro Pro Pro Leu Arg Ala Leu Pro Arg Tyr Arg Leu
                605                 610                 615

Leu Arg Asp Leu Pro Arg Leu Leu Arg Ala Leu Asp Ala Arg Pro
                620                 625                 630

Phe Ala Glu Ala Thr Ser Trp Gly Arg Leu Gly Ala Arg Gln Arg
                635                 640                 645

Arg Gln Ser Arg Leu Glu Leu Cys Ser Arg Leu Glu Arg Glu Ala
                650                 655                 660

Ala Arg Leu Ala Asp Leu Gly
                665
```

<210> SEQ ID NO 21
<211> LENGTH: 2714
<212> TYPE: DNA
<213> ORGANISM: Homo sapiens

<400> SEQUENCE: 21

```
cggctcgagg ccctttgtga gggctgtgag ctgcgcctga cggtggcacc                50

atgagcagct caggtggggc gcccggggcg tccgccagct ctgcgccgcc               100

cgcgcaggaa gagggcatga cgtggtggta ccgctggctg tgtcgcctgt               150

ctggggtgct gggggcagtc tcttgcgcga tctctggcct cttcaactgc               200

atcaccatcc accctctgaa catcgcggcc ggcgtgtgga tgatcatgaa               250

tgccttcatc ttgttgctgt gtgaggcgcc cttctgctgc cagttcatcg               300

agtttgcaaa cacagtggcg gagaaggtgg accggctgcg ctcctggcag               350

aaggctgtct tctactgcgg gatggcggtc gttcccatcg tcatcagcct               400

gaccctgacc acgctgctgg gcaacgccat cgcctttgct acgggggtgc               450

tgtacggact ctctgctctg ggcaaaaagg gcgatgcgat ctcctatgcc               500

aggatccagc agcagaggca gcaggcggat gaggagaagc tcgcggagac               550

cctggagggg gagctgtgaa gggctgggcg cccctccctc cctgtcccct               600

cttctggctc tgtgtgggtc caagtgaggc ctggactgtc cacgctgagg               650

cacagcctgg agaggggcct ttgcacgtgt ccctacacct ggagtcctct               700
```

-continued

```
gctcctttct ccagactggc ttaagccagg agccactggc tgctggtgtg      750
agggtctggg ctgctggact tgaggcagag cctgcagcag ctgtgtggac      800
actacccagc cctactcctc tgctgggtgg gtctgcagat ctcacaccac      850
agacagggct gcctgtgacc tgctgtgacc tgggagcagc ttcccctgga      900
gatgctggtc ctggcttgag gggaggggca agtgggaccc tgccacctgg      950
gcactgagca gagggacctc ccccagctct cttagcaggt ggagccccag     1000
ggcctgggac agcctgccgc tgccagcaac ctcccactgc tgcctagggt     1050
gcagcgccca ctgtcaccct gccttctgaa gaagcccaca gggctcctaa     1100
ggtgcacccc ggtacctgga actgcagcct tggcagtgac tggacagctg     1150
ggtgggggat gctccctgct ggccctggga accttggaca ggccacctca     1200
aggcccctcg gctgcccctc ctccctgggc ctgctggggc ccctaggttc     1250
tacccatcac cccccgcccc tgctggcctt ggtgctaagg aagtggggag     1300
agcaggctct ccctggcacc gagggtgccc accctctccc tggtgtggcc     1350
ccgtcaacat cagccacagc ccagccccat tagtgggtta gtgggtctga     1400
cctcagcccc actcaggtgc tcctgctggc ctgcccaagc cctgccctca     1450
gggagcttct gccttttaag aactgggcag aggccacagt cacctcccca     1500
cacagagctg tccccactgc cctgggtgcc aggctgtccg gagccaggcc     1550
tacccaggga ggatgcagag agctggtgcc caggatgtgc acccccatat     1600
tccctctgcc ctgtggcctc agcccgctgg cctctctgac cgtgaggctg     1650
gctctcagcc atcgggcagg tgcctggtca ggcctggctt agcccaggtg     1700
gggcttggca gaagcgggcg ggtgtggaag atattccatc tggggccaac     1750
cccaggctgg gcctgcgctg agcttctgga gcgcaggtac tgggtcttgc     1800
taagtgaact gtttcccagg aacacctctc gggcccatct gcgtctgagg     1850
ctgggagtgg catctgaggc cgggagtggc atctgaggcc aggagtggca     1900
ggctggtggg ctgggcgtgg ggttttctgg gccctgccca gtactgccct     1950
ggggacttgg tgggctcctg ggtcagcagc atcccacccc tgggagtctg     2000
gccagctgag ccccagggtg gcaggggcat tatagcctgg tggacatgtg     2050
ccttcagggt tcctccgggg ccaccttcct caggccagtg ctgggttcaa     2100
agggctgtgt gtgtgtgtgt ttgtgtgtgt atgtatatgt gtgtgggtgc     2150
acacatctgt cccatgtatg cagtgagacc tgtctacctc ccacaaggag     2200
caagggctct gcccgccctc tgctcattcc tacccaggta gtgggacccc     2250
gggcccccct ctgcctggct tgcctgcttc tgccctttcc agaggggtct     2300
cactgacagc cagagacagc aggagaaggg ttggctgtgg atcaaggaag     2350
gctgcccctg taccctgtgg ggaaatggtg ggtgcatggc tggatgcaga     2400
ggtggaaggc cctgggccac aggcgagagt gggcgtgtca cctgtcccag     2450
gttcccagca agtctgcagc tgtgcagtcc tggggtccct gaccctgtcg     2500
cccagggggc gtgctgtcca gcaggggccc tgccttgcaa ggaacgtctc     2550
tccggcggct gggccgctcc tgcctggtct gggctgtgtg tggcgccctt     2600
tcctccttgt ttgttcctct gtgttctgtg tgcgtcttaa gcaataaagc     2650
```

-continued

```
gtggccgtgg gaaaaaaaaa aaaaaaaaaa aaaaaaaaaa aaaaaaaaaa            2700

aaaaaaaaaa  aaaa                                                   2714


<210> SEQ ID NO 22
<211> LENGTH: 172
<212> TYPE: PRT
<213> ORGANISM: Homo sapiens

<400> SEQUENCE: 22

Met Ser Ser Ser Gly Gly Ala Pro Gly Ala Ser Ala Ser Ser Ala
  1               5                  10                  15

Pro Pro Ala Gln Glu Glu Gly Met Thr Trp Trp Tyr Arg Trp Leu
                 20                  25                  30

Cys Arg Leu Ser Gly Val Leu Gly Ala Val Ser Cys Ala Ile Ser
                 35                  40                  45

Gly Leu Phe Asn Cys Ile Thr Ile His Pro Leu Asn Ile Ala Ala
                 50                  55                  60

Gly Val Trp Met Ile Met Asn Ala Phe Ile Leu Leu Leu Cys Glu
                 65                  70                  75

Ala Pro Phe Cys Cys Gln Phe Ile Glu Phe Ala Asn Thr Val Ala
                 80                  85                  90

Glu Lys Val Asp Arg Leu Arg Ser Trp Gln Lys Ala Val Phe Tyr
                 95                 100                 105

Cys Gly Met Ala Val Val Pro Ile Val Ile Ser Leu Thr Leu Thr
                110                 115                 120

Thr Leu Leu Gly Asn Ala Ile Ala Phe Ala Thr Gly Val Leu Tyr
                125                 130                 135

Gly Leu Ser Ala Leu Gly Lys Lys Gly Asp Ala Ile Ser Tyr Ala
                140                 145                 150

Arg Ile Gln Gln Gln Arg Gln Gln Ala Asp Glu Glu Lys Leu Ala
                155                 160                 165

Glu Thr Leu Glu Gly Glu Leu
                170


<210> SEQ ID NO 23
<211> LENGTH: 888
<212> TYPE: DNA
<213> ORGANISM: Homo sapiens

<400> SEQUENCE: 23

gtgaaacacc catggtttta tgctctattt ctcttttcct catcttcttc              50

cacatcctct ttctgaatgt atcaaactac ttccttgaag tggggcacca             100

ggagggccac tccagtctcc aatgcaggga ctcaggggca gggatctctg             150

agaaagtggc catctcgtta ttaaagctct gtcctctgct tccctctcac             200

ctcagaagca gcccgtttat tcaacagagc tccaggttgc cagctagggg             250

ttttcgggac catagaccaa gcaaccccga gagactgagt actgacctgc             300

agttgttcca gaaactctgc tgggaattag gttgtgacct agaagtgaac             350

tgacactaac agtgagaagg cagggtaaga atgcagtcta gagcgcaacc             400

tttctccact agacttgtaa gtaatttaag tgaatcctgt ccccctgggg             450

ttctatcctg gctggctctg ctggtgaact tgactggcca gcatagggca             500

cttgatgaga ccctggaatg ctgaggccag ttgggcagca agctttcacc             550

tcatccttct gcccatctat ccagccattc aaacattcat tcgcctgaag             600
```

-continued

```
acatttatca agctcctgca atgggtcagg catctgctag gcactgggga       650

cacagagctc acagtctcct ggagggggtg agagatgact gacaggtggt       700

ctgtggtgca gtgtgacctg ggaatgcaca cagtactgtg gaaacacggg       750

agaggcatct agcacaacct gagagggcca ggggaggctt cctggcaggt       800

ttccctttaa ccatcttaag ggaaagaggc actaggtagg aaaataaagg       850

gacagtggtg tcccagacag agggcactct  acatggaa                  888
```

<210> SEQ ID NO 24
<211> LENGTH: 113
<212> TYPE: PRT
<213> ORGANISM: Homo sapiens

<400> SEQUENCE: 24

```
Met Val Leu Cys Ser Ile Ser Leu Phe Leu Ile Phe Phe His Ile
  1               5                  10                  15

Leu Phe Leu Asn Val Ser Asn Tyr Phe Leu Glu Val Gly His Gln
                 20                  25                  30

Glu Gly His Ser Ser Leu Gln Cys Arg Asp Ser Gly Ala Gly Ile
                 35                  40                  45

Ser Glu Lys Val Ala Ile Ser Leu Leu Lys Leu Cys Pro Leu Leu
                 50                  55                  60

Pro Ser His Leu Arg Ser Ser Pro Phe Ile Gln Gln Ser Ser Arg
                 65                  70                  75

Leu Pro Ala Arg Gly Phe Arg Asp His Arg Pro Ser Asn Pro Glu
                 80                  85                  90

Arg Leu Ser Thr Asp Leu Gln Leu Phe Gln Lys Leu Cys Trp Glu
                 95                 100                 105

Leu Gly Cys Asp Leu Glu Val Asn
                110
```

<210> SEQ ID NO 25
<211> LENGTH: 2534
<212> TYPE: DNA
<213> ORGANISM: Homo sapiens

<400> SEQUENCE: 25

```
cgggctccgc gcggtcccac ttcccggctc ccttcgcctc caggatgcgc        50

tgagccctac aacaccccca gcggccgccg gctcccccac gaggtgtgaa       100

tgacagaggt ggtgccatcc agcgcgctca gcgaggtcag cctgcgcctc       150

ctctgccacg atgacataga cactgtgaag cacctgtgtg gcgactggtt       200

ccccatcgag tacccagact catggtatcg tgatatcaca tccaacaaga       250

agttcttttc ccttgctgca acctacagag gtgccattgt gggaatgata       300

gtagctgaaa ttaagaacag gaccaaaata cataaagagg atggagatat       350

tctagcaacc aacttctctg ttgacacaca agtcgcgtac atcctaagtc       400

tgggcgtcgt gaaagagttc aggaagcacg gcataggttc cctcttactt       450

gaaagtttaa aggatcacat atcaaccacc gcccaggacc actgcaaagc       500

catttacctg catgtcctca ccaccaacaa cacagcaata aacttctatg       550

aaaacagaga cttcaagcag caccactatc tcccctatta ctactccatt       600

cgaggggtcc tcaaagatgg cttcacctat gtcctctaca tcaacggcgg       650
```

-continued

```
gcaccctccc tggacgattt tggactacat ccagcacctg ggctctgcac          700

tagccagcct gagcccctgc tccattccgc acagagtcta ccgccaggcc          750

cacagcctgc tctgcagctt cctgccatgg tcgggcatct cttccaagag          800

tggcatcgag tacagccgga ccatgtgatg tcggctgggc agccgccacc          850

aggccccacc cttcagccgc ccgcagagcc cgccttcctg tccatctgac          900

cccttctgtt ttctgcaagg agctgccagc catctaactg ggctcgtcgg          950

cctgccccag ctgcaggccc ggtgctacac gggctcggga acagaacatc         1000

gtgggcatgc gcagagcatg cccatccgtg gcaggctctt cagctcccct         1050

ccctgcttct ggaaacctct gcctgctgcc ctggccctgc ccccctgcgc         1100

atgcaccatc cccagggctg acccagtgtg gctgcattca ctgggagggg         1150

cctgccctca ctgggcctct cccactccgc tgcctgttct tgcagctcct         1200

tcctggaaag ctggagggga ctttctcctg caagggagga acgcaagtat         1250

tatggacaca cttgaccgta aaggcacagg agcctcggaa caagggggcg         1300

caataaaggg aatggcccgt ccccttccag aaccagccca aagaagcctg         1350

gggggtgagg agtggccccc actcctccat gaggggctga tgaggggtgg         1400

gcagcctggg ggaggctttc ctcgcaagca cagagctctg aggctcagcc         1450

ccctggcaca ggcggtcacg catcaggacg gttcctactc ctcagcacct         1500

tccgtgcagt taccagtgcc ctgggaggtc acactgcccg tcggaccttg         1550

gcatgctcca ttcagctgac ctgctgagga caggcatcgc cgagactcct         1600

tgggtcctcc ccgccctccc tcatgctgcc acaagctgct gctccaaggc         1650

ctggccacat gcagacagga ggaagctgag ctcgacatta ggcctcaagg         1700

ctgccatctg tcttgtaggg cctggccttg tgggcagggg gcagtcctgt         1750

gccttgtggg ccctcagcct ctgagggcag agatgctgtc agtgccgcag         1800

gtgcatcaca tacttctagc atcctctcca ccctgcattc caaatgctgc         1850

ttgctgcctg ccctgccctc cgatgcaggg gtggggtggg gggcggagtc         1900

ccgcccagca tagctgcagt gtcacaaagc catggcagag ggtcctagcg         1950

gcgccaccct gccccagcct gaggaggagg gagagggagg aacaaccctg         2000

ggcagacggg gtctcaggga cctgtgtcct tccgcctcca gagctgccca         2050

gccacgggct ctcagggtgc tggggcagcc ccaggtcccc tcttgaactc         2100

agctggggcc aggggccctc agaatgaagg caggcaccag gcaggagcag         2150

catccccctc cttgacggtg ctggcaggag ggccgcgcca tgctgactgc         2200

ttgaacctct gctgacctga cagtgctggc gggagggccg caccatgctg         2250

actgcctgaa tctctgctga ggctgcctgc ctgccgggcc cagctcagcg         2300

ccctctccac tgcgaatcag tggcgatcat gtgatttcta tttctgcccc         2350

acagggtaag ggacgagtct tctggaaggc tctgccatgg acatttgtcc         2400

tcgggctcag aggccccacc ctgccccaca cctgccccta atcactgcag         2450

tgtccagccc agtgttgaac agattgtagc gttctgtctc attacgagca         2500

aataaataga ctttcattgg gaaaaaaaaa  aaaa                         2534
```

<210> SEQ ID NO 26
<211> LENGTH: 242

-continued

<212> TYPE: PRT
<213> ORGANISM: Homo sapiens

<400> SEQUENCE: 26

```
Met Thr Glu Val Val Pro Ser Ser Ala Leu Ser Glu Val Ser Leu
  1               5                  10                  15

Arg Leu Leu Cys His Asp Asp Ile Asp Thr Val Lys His Leu Cys
                 20                  25                  30

Gly Asp Trp Phe Pro Ile Glu Tyr Pro Asp Ser Trp Tyr Arg Asp
                 35                  40                  45

Ile Thr Ser Asn Lys Lys Phe Phe Ser Leu Ala Ala Thr Tyr Arg
                 50                  55                  60

Gly Ala Ile Val Gly Met Ile Val Ala Glu Ile Lys Asn Arg Thr
                 65                  70                  75

Lys Ile His Lys Glu Asp Gly Asp Ile Leu Ala Thr Asn Phe Ser
                 80                  85                  90

Val Asp Thr Gln Val Ala Tyr Ile Leu Ser Leu Gly Val Val Lys
                 95                 100                 105

Glu Phe Arg Lys His Gly Ile Gly Ser Leu Leu Leu Glu Ser Leu
                110                 115                 120

Lys Asp His Ile Ser Thr Thr Ala Gln Asp His Cys Lys Ala Ile
                125                 130                 135

Tyr Leu His Val Leu Thr Thr Asn Asn Thr Ala Ile Asn Phe Tyr
                140                 145                 150

Glu Asn Arg Asp Phe Lys Gln His His Tyr Leu Pro Tyr Tyr Tyr
                155                 160                 165

Ser Ile Arg Gly Val Leu Lys Asp Gly Phe Thr Tyr Val Leu Tyr
                170                 175                 180

Ile Asn Gly Gly His Pro Pro Trp Thr Ile Leu Asp Tyr Ile Gln
                185                 190                 195

His Leu Gly Ser Ala Leu Ala Ser Leu Ser Pro Cys Ser Ile Pro
                200                 205                 210

His Arg Val Tyr Arg Gln Ala His Ser Leu Leu Cys Ser Phe Leu
                215                 220                 225

Pro Trp Ser Gly Ile Ser Ser Lys Ser Gly Ile Glu Tyr Ser Arg
                230                 235                 240

Thr Met
```

<210> SEQ ID NO 27
<211> LENGTH: 991
<212> TYPE: DNA
<213> ORGANISM: Homo sapiens

<400> SEQUENCE: 27

```
gttgggcagc agccacccgc tcacctccat ccccaggact tagagggacg          50

cagggcgttg ggaacagagg acactccagg cgctgaccct gggaggccag         100

gaccagggcc aaagtcccgt gggcaagagg agtcctcaga ggtccttcat         150

tcagcggttc cgggaggtct gggaagccca cggcctggct ggggcagggt         200

caacgccgcc aggccgccat ggtcctgtgc tggctgctgc ttctggtgat         250

ggctctgccc ccaggcacga cgggcgtcaa ggactgcgtc ttctgtgagc         300

tcaccgactc catgcagtgt cctggtacct acatgcactg tggcgatgac         350

gaggactgct tcacaggcca cggggtcgcc ccgggcactg gtccggtcat         400
```

-continued

```
caacaaaggc tgcctgcgag ccaccagctg cggccttgag gaacccgtca          450

gctacagggg cgtcacctac agcctcacca ccaactgctg caccggccgc          500

ctgtgtaaca gagccccgag cagccagaca gtgggggcca ccaccagcct          550

ggcactgggg ctgggtatgc tgcttcctcc acgtttgctg tgaccaacag          600

ggaggacagg gcctgggact gttctcccag atccgccact ccccatgtcc          650

ccatgtcctt cccccactaa atggccagag aggccctgga caacctcttg          700

cggccctggc ttcatccctt ctaaggctgt ccaccaggag cccggtgcta          750

ggggaagcat ccccaggcct gactgagcgg caggggagca cggcccgtgg          800

gtttgattgt attactctgt tccactggtt ctaagacgca gagcttctca          850

catctcaatc aggatgcttc tctccattgg tagcacttta gagtccatga          900

aatatggtaa aaaatatata tatatcataa taaatgacag ctgatgttca          950

tgggggaaaa aaaaaaaaaa aaaaaaaaaa aaaaaaaaaa  a                  991
```

<210> SEQ ID NO 28
<211> LENGTH: 124
<212> TYPE: PRT
<213> ORGANISM: Homo sapiens

<400> SEQUENCE: 28

```
Met Val Leu Cys Trp Leu Leu Leu Leu Val Met Ala Leu Pro Pro
  1               5                  10                  15

Gly Thr Thr Gly Val Lys Asp Cys Val Phe Cys Glu Leu Thr Asp
                 20                  25                  30

Ser Met Gln Cys Pro Gly Thr Tyr Met His Cys Gly Asp Asp Glu
                 35                  40                  45

Asp Cys Phe Thr Gly His Gly Val Ala Pro Gly Thr Gly Pro Val
                 50                  55                  60

Ile Asn Lys Gly Cys Leu Arg Ala Thr Ser Cys Gly Leu Glu Glu
                 65                  70                  75

Pro Val Ser Tyr Arg Gly Val Thr Tyr Ser Leu Thr Thr Asn Cys
                 80                  85                  90

Cys Thr Gly Arg Leu Cys Asn Arg Ala Pro Ser Ser Gln Thr Val
                 95                 100                 105

Gly Ala Thr Thr Ser Leu Ala Leu Gly Leu Gly Met Leu Leu Pro
                110                 115                 120

Pro Arg Leu Leu
```

<210> SEQ ID NO 29
<211> LENGTH: 2020
<212> TYPE: DNA
<213> ORGANISM: Homo sapiens

<400> SEQUENCE: 29

```
ggcattttga aagcccagtg ttgcccaggg ggcatctcct ttgtgtttat           50

gagagacctg cattctccct ggctcagttc tctcaggctc tccagagctc          100

aggacctctg agaagaatgg agccctcctg gcttcaggaa ctcatggctc          150

accccttctt gctgctgatc ctcctctgca tgtctctgct gctgtttcag          200

gtaatcaggt tgtaccagag gaggagatgg atgatcagag ccctgcacct          250

gtttcctgca ccccctgccc actggttcta tggccacaag gagttttacc          300

cagtaaagga gtttgaggtg tatcataagc tgatggaaaa atacccatgt          350
```

-continued

```
gctgttccct tgtgggttgg accctttacg atgttcttca gtgtccatga          400
cccagactat gccaagattc tcctgaaaag acaagatccc aaaagtgctg          450
ttagccacaa aatccttgaa tcctgggttg gtcgaggact tgtgaccctg          500
gatggttcta aatggaaaaa gcaccgccag attgtgaaac ctggcttcaa          550
catcagcatt ctgaaaatat tcatcaccat gatgtctgag agtgttcgga          600
tgatgctgaa caaatgggag gaacacattg cccaaaactc acgtctggag          650
ctctttcaac atgtctccct gatgaccctg gacagcatca tgaagtgtgc          700
cttcagccac cagggcagca tccagttgga cagtaccctg gactcatacc          750
tgaaagcagt gttcaacctt agcaaaatct ccaaccagcg catgaacaat          800
tttctacatc acaacgacct ggttttcaaa ttcagctctc aaggccaaat          850
cttttctaaa tttaaccaag aacttcatca gttcacagag aaagtaatcc          900
aggaccggaa ggagtctctt aaggataagc taaaacaaga tactactcag          950
aaaaggcgct gggattttct ggacatactt ttgagtgcca aaagcgaaaa         1000
caccaaagat ttctctgaag cagatctcca ggctgaagtg aaaacgttca         1050
tgtttgcagg acatgacacc acatccagtg ctatctcctg gatcctttac         1100
tgcttggcaa agtaccctga gcatcagcag agatgccgag atgaaatcag         1150
ggaactccta ggggatgggt cttctattac ctgggaacac ctgagccaga         1200
tgccttacac cacgatgtgc atcaaggaat gcctccgcct ctacgcaccg         1250
gtagtaaaca tatcccggtt actcgacaaa cccatcacct ttccagatgg         1300
acgctcctta cctgcaggaa taactgtgtt tatcaatatt tgggctcttc         1350
accacaaccc ctatttctgg gaagaccctc aggtctttaa ccccttgaga         1400
ttctccaggg aaaattctga aaaaatacat ccctatgcct tcataccatt         1450
ctcagctgga ttaaggaact gcattgggca gcattttgcc ataattgagt         1500
gtaaagtggc agtggcatta actctgctcc gcttcaagct ggctccagac         1550
cactcaaggc ctccccagcc tgttcgtcaa gttgtcctca agtccaagaa         1600
tggaatccat gtgtttgcaa aaaaagtttg ctaattttaa gtcctttcgt         1650
ataagaatta atgagacaat ttcctaccaa aaggaagaac aaaaggataa         1700
atataataca aaatatatgt atatggttgt ttgacaaatt atataactta         1750
ggatacttct gactggtttt gacatccatt aacagtaatt ttaatttctt         1800
tgctgtatct ggtgaaaccc acaaaaacac ctgaaaaaac tcaagctgac         1850
ttccactgcg aagggaaatt attggtttgt gtaactagtg gtagagtggc         1900
tttcaagcat agtttgatca aaactccact cagtatctgc attactttta         1950
tctctgcaaa tatctgcatg atagctttat tctcagttat ctttccccat         2000
aataaaaaat atctgccaaa                                          2020
```

<210> SEQ ID NO 30
<211> LENGTH: 505
<212> TYPE: PRT
<213> ORGANISM: Homo sapiens

<400> SEQUENCE: 30

```
Met Glu Pro Ser Trp Leu Gln Glu Leu Met Ala His Pro Phe Leu
  1               5                  10                  15
```

-continued

```
Leu Leu Ile Leu Leu Cys Met Ser Leu Leu Leu Phe Gln Val Ile
                20                  25                  30

Arg Leu Tyr Gln Arg Arg Arg Trp Met Ile Arg Ala Leu His Leu
                35                  40                  45

Phe Pro Ala Pro Pro Ala His Trp Phe Tyr Gly His Lys Glu Phe
                50                  55                  60

Tyr Pro Val Lys Glu Phe Glu Val Tyr His Lys Leu Met Glu Lys
                65                  70                  75

Tyr Pro Cys Ala Val Pro Leu Trp Val Gly Pro Phe Thr Met Phe
                80                  85                  90

Phe Ser Val His Asp Pro Asp Tyr Ala Lys Ile Leu Leu Lys Arg
                95                 100                 105

Gln Asp Pro Lys Ser Ala Val Ser His Lys Ile Leu Glu Ser Trp
               110                 115                 120

Val Gly Arg Gly Leu Val Thr Leu Asp Gly Ser Lys Trp Lys Lys
               125                 130                 135

His Arg Gln Ile Val Lys Pro Gly Phe Asn Ile Ser Ile Leu Lys
               140                 145                 150

Ile Phe Ile Thr Met Met Ser Glu Ser Val Arg Met Met Leu Asn
               155                 160                 165

Lys Trp Glu Glu His Ile Ala Gln Asn Ser Arg Leu Glu Leu Phe
               170                 175                 180

Gln His Val Ser Leu Met Thr Leu Asp Ser Ile Met Lys Cys Ala
               185                 190                 195

Phe Ser His Gln Gly Ser Ile Gln Leu Asp Ser Thr Leu Asp Ser
               200                 205                 210

Tyr Leu Lys Ala Val Phe Asn Leu Ser Lys Ile Ser Asn Gln Arg
               215                 220                 225

Met Asn Asn Phe Leu His His Asn Asp Leu Val Phe Lys Phe Ser
               230                 235                 240

Ser Gln Gly Gln Ile Phe Ser Lys Phe Asn Gln Glu Leu His Gln
               245                 250                 255

Phe Thr Glu Lys Val Ile Gln Asp Arg Lys Glu Ser Leu Lys Asp
               260                 265                 270

Lys Leu Lys Gln Asp Thr Thr Gln Lys Arg Arg Trp Asp Phe Leu
               275                 280                 285

Asp Ile Leu Leu Ser Ala Lys Ser Glu Asn Thr Lys Asp Phe Ser
               290                 295                 300

Glu Ala Asp Leu Gln Ala Glu Val Lys Thr Phe Met Phe Ala Gly
               305                 310                 315

His Asp Thr Thr Ser Ser Ala Ile Ser Trp Ile Leu Tyr Cys Leu
               320                 325                 330

Ala Lys Tyr Pro Glu His Gln Gln Arg Cys Arg Asp Glu Ile Arg
               335                 340                 345

Glu Leu Leu Gly Asp Gly Ser Ser Ile Thr Trp Glu His Leu Ser
               350                 355                 360

Gln Met Pro Tyr Thr Thr Met Cys Ile Lys Glu Cys Leu Arg Leu
               365                 370                 375

Tyr Ala Pro Val Val Asn Ile Ser Arg Leu Leu Asp Lys Pro Ile
               380                 385                 390

Thr Phe Pro Asp Gly Arg Ser Leu Pro Ala Gly Ile Thr Val Phe
               395                 400                 405
```

-continued

```
Ile Asn Ile Trp Ala Leu His His Asn Pro Tyr Phe Trp Glu Asp
                410                 415                 420

Pro Gln Val Phe Asn Pro Leu Arg Phe Ser Arg Glu Asn Ser Glu
                425                 430                 435

Lys Ile His Pro Tyr Ala Phe Ile Pro Phe Ser Ala Gly Leu Arg
                440                 445                 450

Asn Cys Ile Gly Gln His Phe Ala Ile Ile Glu Cys Lys Val Ala
                455                 460                 465

Val Ala Leu Thr Leu Leu Arg Phe Lys Leu Ala Pro Asp His Ser
                470                 475                 480

Arg Pro Pro Gln Pro Val Arg Gln Val Val Leu Lys Ser Lys Asn
                485                 490                 495

Gly Ile His Val Phe Ala Lys Lys Val Cys
                500                 505
```

<210> SEQ ID NO 31
<211> LENGTH: 1118
<212> TYPE: DNA
<213> ORGANISM: Homo sapiens

<400> SEQUENCE: 31

```
tccgctgtcg cccagtcccg gccgctggcg ggaactgacc tggagcaagc        50

aggaccttcc ctcccacctc tcccgcctgg cctccgcggg agtcccctac       100

gatcccgctc agcagtgggg cactcgctga ggacagcgag tcctgggagt       150

gagcccaagg ccacccctgg ccagcccagg agagatagcc agggcaggcc       200

cagcagcccg aggccaggct ctggccacgg cggtctccga catggagaga       250

cattgtctgc tttttatcct gttaacctgt cttcggtggt tgtgccacga       300

cattccccag ggttcaggtg cccggtggcc gagggtcagt ccagtggtag       350

agccttgctc tcctaggctc atcctgctgg cggtcctcct gcttctgctg       400

tgtggtgtca cagctggttg tgtccggttc tgctgcctcc ggaagcaggc       450

acaggcccag ccacatctgc caccagcacg gcagccctgc gacgtggcag       500

tcatccctat ggacagtgac agccctgtac acagcactgt gacctcctac       550

agctccgtgc agtacccact gggcatgcgg ttgcccctgc cctttgggga       600

gctggacctg gactccacgg ctcctcctgc ctacagcctg tacaccccgg       650

agcctccacc ctcctacgat gaagctgtca agatggccaa gcccagagag       700

gaaggaccag cactctccca gaaacccagc cctctccttg gggcctcggg       750

cctagagacc actccagtgc cccaggagtc gggccccaat actcaactac       800

caccttgtag ccctggtgcc ccttgaagga ggtaggagaa cggaccagag       850

cttggagaac taatgcttgg agccaagggc cccagcccac cccaccgtcc       900

cacacattgc tgtggcccca acctcggtgc catgttacac cggcccctgg       950

cgtcacccac taggcaggct gctgctttca gcctcagccc ctggcccagc      1000

cccagcaggc cctcagcctg gaagaggccc cttgggccta agcctcgggt      1050

gggagctcag ggccacctgt gacgtctgca tcttcttgga gagagaataa      1100

agtttgtatt  taagtggt                                        1118
```

<210> SEQ ID NO 32
<211> LENGTH: 194
<212> TYPE: PRT

-continued

<213> ORGANISM: Homo sapiens

<400> SEQUENCE: 32

Met Glu Arg His Cys Leu Leu Phe Ile Leu Leu Thr Cys Leu Arg
1 5 10 15

Trp Leu Cys His Asp Ile Pro Gln Gly Ser Gly Ala Arg Trp Pro
20 25 30

Arg Val Ser Pro Val Val Glu Pro Cys Ser Pro Arg Leu Ile Leu
35 40 45

Leu Ala Val Leu Leu Leu Leu Leu Cys Gly Val Thr Ala Gly Cys
50 55 60

Val Arg Phe Cys Cys Leu Arg Lys Gln Ala Gln Ala Gln Pro His
65 70 75

Leu Pro Pro Ala Arg Gln Pro Cys Asp Val Ala Val Ile Pro Met
80 85 90

Asp Ser Asp Ser Pro Val His Ser Thr Val Thr Ser Tyr Ser Ser
95 100 105

Val Gln Tyr Pro Leu Gly Met Arg Leu Pro Leu Pro Phe Gly Glu
110 115 120

Leu Asp Leu Asp Ser Thr Ala Pro Pro Ala Tyr Ser Leu Tyr Thr
125 130 135

Pro Glu Pro Pro Pro Ser Tyr Asp Glu Ala Val Lys Met Ala Lys
140 145 150

Pro Arg Glu Glu Gly Pro Ala Leu Ser Gln Lys Pro Ser Pro Leu
155 160 165

Leu Gly Ala Ser Gly Leu Glu Thr Thr Pro Val Pro Gln Glu Ser
170 175 180

Gly Pro Asn Thr Gln Leu Pro Pro Cys Ser Pro Gly Ala Pro
185 190

<210> SEQ ID NO 33
<211> LENGTH: 1976
<212> TYPE: DNA
<213> ORGANISM: Homo sapiens

<400> SEQUENCE: 33
ccttgcttgg tgcttggcac acacaaatcc agtgggctac acaggttttc 50
cagaagcccc acgaggtggt aatggtgctg ctgattcaga ccctgggggc 100
cctcatgccc tcgctgccct cctgcctcag caacggcgtg gagagggcag 150
ggcccgagca ggagctcacc aggctgctgg agttctacga cgccaccgcc 200
cacttcgcca agggcttgga gatggcactg ctcccccacc tacatgaaca 250
caatctggta aaagtcacgg agctggtgga tgctgtgtat gatccataca 300
aaccctacca gctgaagtat ggcgacatgg aagagagcaa cctcctcatc 350
cagatgagtg ctgtgcctct ggagcatggg gaagtgattg actgtgtgca 400
ggagctgagc cactccgtga acaagctgtt tggtctggcg tctgcagccg 450
ttgacagatg cgtcagattc accaatggcc tggggacctg cggcctgttg 500
tcagccctga aatccctctt tgccaagtat gtgtctgatt tcaccagcac 550
tctccagtcc atacgaaaga agtgcaaact ggaccacatt cctcccaact 600
ccctcttcca ggaagattgg acggcttttc agaactccat taggataata 650
gccacctgtg gagagctttt gcggcattgt ggggacttcg agcagcagct 700

-continued

```
agccaacagg attttgtcca cagctgggaa gtatctatct gattcctgca          750

gcccccggag cctggctggt tttcaggaga gcatcttgac agacaagaag          800

aactctgcca agaacccatg gcaagaatat aattacctcc agaaagataa          850

ccctgctgaa tatgccagtt taatggaaat actttatacc cttaaggaaa          900

aagggtcaag caaccacaac ctgctggctg cacctcgagc agcgctgact          950

cggcttaacc agcaggccca ccagctggct ttcgattccg tgttcctgcg         1000

catcaaacaa cagctgttgc ttatttcgaa gatggacagc tggaatacgg         1050

ctggcatcgg agaaaccctc acagatgaac tgcccgcctt tagtctcacc         1100

cctctcgagt acatcagcaa catcgggcag tacatcatgt ccctcccccct        1150

gaatcttgag ccatttgtga ctcaggagga ctctgcctta gagttggcat         1200

tgcacgctgg aaagctgcca tttcctcctg agcaggggga tgaattgccc         1250

gagctggaca acatggctga caactggctg ggctcgatcg ccagagccac         1300

aatgcagacc tactgtgatg cgatcctaca gatccctgag ctgagcccac         1350

actctgccaa gcagctggcc actgacatcg actatctgat caacgtgatg         1400

gatgccctgg gcctgcagcc gtcccgcacc ctccagcaca tcgtgacgct         1450

actgaagacc aggcctgagg actatagaca ggtcagcaaa ggcctgcccc         1500

gtcgcctggc caccaccgtg gccaccatgc ggagtgtgaa ttactgaccc         1550

caccacacac cggaccacca agagagccag ggctgctgtt tcgtgactca         1600

ccagcacaga tttgctcaga aactctgccc aagattgggc agaagttact         1650

ttaaaaagac ttggttcagc tggtcacggt ggctcacgcc tgtaatccca         1700

gcactttggg aggccaagcc agatggatca tgaggccagg agttcgagac         1750

cagcctgacc aacatggtga aaccccatct ctactaaaaa tacaaaaatt         1800

aacagcagag cgagactctg tctcaaaaaa aaaaaaaaaa agacttggtt         1850

catttgtata atcaaaaaga gttgtaaatt aaagatgtat tatttatcag         1900

agaagacttt ttagataatt tttttaaagg atcagatctt gaaaatggaa         1950

taaataacta ctgtgaaatg  caaaaa                                  1976


<210> SEQ ID NO 34
<211> LENGTH: 491
<212> TYPE: PRT
<213> ORGANISM: Homo sapiens

<400> SEQUENCE: 34

Met Val Leu Leu Ile Gln Thr Leu Gly Ala Leu Met Pro Ser Leu
  1               5                  10                  15

Pro Ser Cys Leu Ser Asn Gly Val Glu Arg Ala Gly Pro Glu Gln
                 20                  25                  30

Glu Leu Thr Arg Leu Leu Glu Phe Tyr Asp Ala Thr Ala His Phe
                 35                  40                  45

Ala Lys Gly Leu Glu Met Ala Leu Leu Pro His Leu His Glu His
                 50                  55                  60

Asn Leu Val Lys Val Thr Glu Leu Val Asp Ala Val Tyr Asp Pro
                 65                  70                  75

Tyr Lys Pro Tyr Gln Leu Lys Tyr Gly Asp Met Glu Glu Ser Asn
                 80                  85                  90

Leu Leu Ile Gln Met Ser Ala Val Pro Leu Glu His Gly Glu Val
```

-continued

```
                95                  100                 105
Ile Asp Cys Val Gln Glu Leu Ser His Ser Val Asn Lys Leu Phe
                110                 115                 120
Gly Leu Ala Ser Ala Ala Val Asp Arg Cys Val Arg Phe Thr Asn
                125                 130                 135
Gly Leu Gly Thr Cys Gly Leu Leu Ser Ala Leu Lys Ser Leu Phe
                140                 145                 150
Ala Lys Tyr Val Ser Asp Phe Thr Ser Thr Leu Gln Ser Ile Arg
                155                 160                 165
Lys Lys Cys Lys Leu Asp His Ile Pro Pro Asn Ser Leu Phe Gln
                170                 175                 180
Glu Asp Trp Thr Ala Phe Gln Asn Ser Ile Arg Ile Ile Ala Thr
                185                 190                 195
Cys Gly Glu Leu Leu Arg His Cys Gly Asp Phe Glu Gln Gln Leu
                200                 205                 210
Ala Asn Arg Ile Leu Ser Thr Ala Gly Lys Tyr Leu Ser Asp Ser
                215                 220                 225
Cys Ser Pro Arg Ser Leu Ala Gly Phe Gln Glu Ser Ile Leu Thr
                230                 235                 240
Asp Lys Lys Asn Ser Ala Lys Asn Pro Trp Gln Glu Tyr Asn Tyr
                245                 250                 255
Leu Gln Lys Asp Asn Pro Ala Glu Tyr Ala Ser Leu Met Glu Ile
                260                 265                 270
Leu Tyr Thr Leu Lys Glu Lys Gly Ser Ser Asn His Asn Leu Leu
                275                 280                 285
Ala Ala Pro Arg Ala Ala Leu Thr Arg Leu Asn Gln Gln Ala His
                290                 295                 300
Gln Leu Ala Phe Asp Ser Val Phe Leu Arg Ile Lys Gln Gln Leu
                305                 310                 315
Leu Leu Ile Ser Lys Met Asp Ser Trp Asn Thr Ala Gly Ile Gly
                320                 325                 330
Glu Thr Leu Thr Asp Glu Leu Pro Ala Phe Ser Leu Thr Pro Leu
                335                 340                 345
Glu Tyr Ile Ser Asn Ile Gly Gln Tyr Ile Met Ser Leu Pro Leu
                350                 355                 360
Asn Leu Glu Pro Phe Val Thr Gln Glu Asp Ser Ala Leu Glu Leu
                365                 370                 375
Ala Leu His Ala Gly Lys Leu Pro Phe Pro Pro Glu Gln Gly Asp
                380                 385                 390
Glu Leu Pro Glu Leu Asp Asn Met Ala Asp Asn Trp Leu Gly Ser
                395                 400                 405
Ile Ala Arg Ala Thr Met Gln Thr Tyr Cys Asp Ala Ile Leu Gln
                410                 415                 420
Ile Pro Glu Leu Ser Pro His Ser Ala Lys Gln Leu Ala Thr Asp
                425                 430                 435
Ile Asp Tyr Leu Ile Asn Val Met Asp Ala Leu Gly Leu Gln Pro
                440                 445                 450
Ser Arg Thr Leu Gln His Ile Val Thr Leu Leu Lys Thr Arg Pro
                455                 460                 465
Glu Asp Tyr Arg Gln Val Ser Lys Gly Leu Pro Arg Arg Leu Ala
                470                 475                 480
Thr Thr Val Ala Thr Met Arg Ser Val Asn Tyr
                485                 490
```

-continued

<210> SEQ ID NO 35
<211> LENGTH: 1227
<212> TYPE: DNA
<213> ORGANISM: Homo sapiens

<400> SEQUENCE: 35
gcaagtgcca ccatgctagt gtgatttgga cttcagtaaa agttagtttg 50
cttccttccc gttgtcccat ctcactcctg ggccacccat ggggctgctg 100
gtagctggtg tgtggctgct gctggactgt gtggcagtcc atccatctgt 150
cagcagccac tgcgggccta cttgctgggt gcccagcacc gcactcacca 200
ctgcaggcgt ggccaggagc gtgagatccc cagagcccat ggccagtgag 250
aggcggccag ggataggtac ccagggaatg ccacaggagt ttgctgggct 300
cacggagctc tttcactggt cagagaggag tgtgtgtagg agaggacttc 350
tacttggtgt tgaaggacag atggggtttg gctgggagag aggaggaatg 400
tgggcgggcc ttataggcag gcgagaaggt gagagccaag gccctctgtg 450
ggcagggcga ggtggcgtgt tgaggagact cgtccagctg ggcagaggct 500
catgttgagg gatgaggcag agctggggga ggagggagcc cagaaatggc 550
aggtccttga atgcaggttt ggaagcaggg acgccctgtg agggtacaga 600
gtctgggctg ttaccttctg tggcttttgc tagaaggtga gatgtcaggg 650
aggaagacag gactccagga tgtctcctgt ctctctctgg aaaaaggagg 700
tgggcccctt tctcagcagt cagctgctgt ttttgaggtc ttctccatgg 750
ataatccacg gtgttggaag tggttaaggt aatggatcct catgggctta 800
ccataaaaat atctggaggc tggaccattt tccttaaaac gttataaaag 850
ctggaattga atgccatcgg tgtcacccct gggaagtgtg ctttctcttg 900
agctcttttg gccccgagat agcagtcact ccatagtttc gtgaagacca 950
gcctggtgtt gcctggtttt ctgccattag ggagcagcta gaggtcttcc 1000
agtagctcct gtgtaaagtg atgaaagaaa agggctgggt gctgactgct 1050
cctggagaaa agcaacacac tcccaaagtc ttaattgcct gcttccaggg 1100
agctgtggtg gtttcccttg ggcagggcac acgccccagt ggttgactta 1150
ataaggatac attttaatca gaggacaaaa atgtgccctg acttgatttc 1200
cgcatgggct tccagcatgg tcaaagg 1227

<210> SEQ ID NO 36
<211> LENGTH: 139
<212> TYPE: PRT
<213> ORGANISM: Homo sapiens

<400> SEQUENCE: 36

Met Gly Leu Leu Val Ala Gly Val Trp Leu Leu Leu Asp Cys Val
1 5 10 15

Ala Val His Pro Ser Val Ser Ser His Cys Gly Pro Thr Cys Trp
20 25 30

Val Pro Ser Thr Ala Leu Thr Thr Ala Gly Val Ala Arg Ser Val
35 40 45

Arg Ser Pro Glu Pro Met Ala Ser Glu Arg Arg Pro Gly Ile Gly
50 55 60

-continued

```
Thr Gln Gly Met Pro Gln Glu Phe Ala Gly Leu Thr Glu Leu Phe
                65                  70                  75

His Trp Ser Glu Arg Ser Val Cys Arg Arg Gly Leu Leu Leu Gly
                80                  85                  90

Val Glu Gly Gln Met Gly Phe Gly Trp Glu Arg Gly Gly Met Trp
                95                  100                 105

Ala Gly Leu Ile Gly Arg Arg Glu Gly Glu Ser Gln Gly Pro Leu
                110                 115                 120

Trp Ala Gly Arg Gly Gly Val Leu Arg Arg Leu Val Gln Leu Gly
                125                 130                 135

Arg Gly Ser Cys
```

<210> SEQ ID NO 37
<211> LENGTH: 1225
<212> TYPE: DNA
<213> ORGANISM: Homo sapiens

<400> SEQUENCE: 37

```
ggccaggaat ggggtccccg ggcatggtgc tgggcctcct ggtgcagatc            50

tgggccctgc aagaagcctc aagcctgagc gtgcagcagg ggcccaactt           100

gctgcaggtg aggcagggca gtcaggcgac cctggtctgc caggtggacc           150

aggccacagc ctgggaacgg ctccgtgtta agtggacaaa ggatggggcc           200

atcctgtgtc aaccgtacat caccaacggc agcctcagcc tgggggtctg           250

cgggccccag ggacggctct cctggcaggc acccagccat ctcaccctgc           300

agctggaccc tgtgagcctc aaccacagcg ggcgtacgt gtgctgggcg            350

gccgtagaga ttcctgagtt ggaggaggct gagggcaaca taacaaggct           400

ctttgtggac ccagatgacc ccacacagaa cagaaaccgg atcgcaagct           450

tcccaggatt cctcttcgtg ctgctggggg tgggaagcat gggtgtggct           500

gcgatcgtgt ggggtgcctg gttctggggc cgccgcagct gccagcaaag           550

ggactcagga aatgcattct acagcaacgt cctataccgg ccccgggggg           600

ccccaaagaa gagtgaggac tgctctggag aggggaagga ccagaggggc           650

cagagcattt attcaacctc cttcccgcaa ccggcccccc gccagccgca           700

cctggcgtca agaccctgcc ccagcccgag accctgcccc agccccaggc           750

ccggccaccc cgtctctatg gtcagggtct ctcctagacc aagccccacc           800

cagcagccga ggccaaaagg gttccccaaa gtgggagagg agtgagagat           850

cccaggagac ctcaacagga ccccacccat aggtacacac aaaaaagggg           900

ggatcgaggc cagacacggt ggctcacgcc tgtaatccca gcagtttggg           950

aagccgaggc gggtggaaca cttgaggtca ggggtttgag accagcctgg          1000

cttgaacctg ggaggcggag gttgcagtga gccgagattg cgccactgca          1050

ctccagcctg ggcgacagag tgagactccg tctcaaaaaa aaaacaaaaa          1100

gcaggaggat tgggagcctg tcagccccat cctgagaccc cgtcctcatt          1150

tctgtaatga tggatctcgc tcccactttc ccccaagaac ctaataaagg          1200

cttgtgaaga aaaaaaaaaa  aaaaa                                    1225
```

<210> SEQ ID NO 38
<211> LENGTH: 278
<212> TYPE: PRT

-continued

<213> ORGANISM: Homo sapiens

<400> SEQUENCE: 38

```
Met Gly Ser Pro Gly Met Val Leu Gly Leu Leu Val Gln Ile Trp
  1               5                  10                  15

Ala Leu Gln Glu Ala Ser Ser Leu Ser Val Gln Gln Gly Pro Asn
                 20                  25                  30

Leu Leu Gln Val Arg Gln Gly Ser Gln Ala Thr Leu Val Cys Gln
                 35                  40                  45

Val Asp Gln Ala Thr Ala Trp Glu Arg Leu Arg Val Lys Trp Thr
                 50                  55                  60

Lys Asp Gly Ala Ile Leu Cys Gln Pro Tyr Ile Thr Asn Gly Ser
                 65                  70                  75

Leu Ser Leu Gly Val Cys Gly Pro Gln Gly Arg Leu Ser Trp Gln
                 80                  85                  90

Ala Pro Ser His Leu Thr Leu Gln Leu Asp Pro Val Ser Leu Asn
                 95                 100                 105

His Ser Gly Ala Tyr Val Cys Trp Ala Ala Val Glu Ile Pro Glu
                110                 115                 120

Leu Glu Glu Ala Glu Gly Asn Ile Thr Arg Leu Phe Val Asp Pro
                125                 130                 135

Asp Asp Pro Thr Gln Asn Arg Asn Arg Ile Ala Ser Phe Pro Gly
                140                 145                 150

Phe Leu Phe Val Leu Leu Gly Val Gly Ser Met Gly Val Ala Ala
                155                 160                 165

Ile Val Trp Gly Ala Trp Phe Trp Gly Arg Arg Ser Cys Gln Gln
                170                 175                 180

Arg Asp Ser Gly Asn Ala Phe Tyr Ser Asn Val Leu Tyr Arg Pro
                185                 190                 195

Arg Gly Ala Pro Lys Lys Ser Glu Asp Cys Ser Gly Glu Gly Lys
                200                 205                 210

Asp Gln Arg Gly Gln Ser Ile Tyr Ser Thr Ser Phe Pro Gln Pro
                215                 220                 225

Ala Pro Arg Gln Pro His Leu Ala Ser Arg Pro Cys Pro Ser Pro
                230                 235                 240

Arg Pro Cys Pro Ser Pro Arg Pro Gly His Pro Val Ser Met Val
                245                 250                 255

Arg Val Ser Pro Arg Pro Ser Pro Thr Gln Gln Pro Arg Pro Lys
                260                 265                 270

Gly Phe Pro Lys Val Gly Glu Glu
                275
```

<210> SEQ ID NO 39
<211> LENGTH: 1837
<212> TYPE: DNA
<213> ORGANISM: Homo sapiens

<400> SEQUENCE: 39

```
accagcagaa ggctgggagt ctgtagtttg ttcctgctgc caggctccac                50

tgaggggaac ggggacctgt ctgaagagaa gatgcccctg ctgacactct               100

acctgctcct cttctggctc tcaggctact ccattgccac tcaaatcacc               150

ggtccaacaa cagtgaatgg cttggagcgg ggctccttga ccgtgcagtg               200

tgtttacaga tcaggctggg agacctactt gaagtggtgg tgtcgaggag               250
```

-continued

```
ctatttggcg tgactgcaag atccttgtta aaaccagtgg gtcagagcag          300

gaggtgaaga gggaccgggt gtccatcaag gacaatcaga aaaaccgcac          350

gttcactgtg accatggagg atctcatgaa aactgatgct gacacttact          400

ggtgtggaat tgagaaaact ggaaatgacc ttggggtcac agttcaagtg          450

accattgacc cagcaccagt cacccaagaa gaaactagca gctccccaac          500

tctgaccggc caccacttgg acaacaggca caagctcctg aagctcagtg          550

tcctcctgcc cctcatcttc accatattgc tgctgctttt ggtggccgcc          600

tcactcttgg cttggaggat gatgaagtac cagcagaaag cagccgggat          650

gtccccagag caggtactgc agcccctgga gggcgacctc tgctatgcag          700

acctgaccct gcagctggcc ggaacctccc cgcgaaaggc taccacgaag          750

ctttcctctg cccaggttga ccaggtggaa gtggaatatg tcaccatggc          800

ttccttgccg aaggaggaca tttcctatgc atctctgacc ttgggtgctg          850

aggatcagga accgacctac tgcaacatgg gccacctcag tagccacctc          900

cccggcaggg gccctgagga gcccacggaa tacagcacca tcagcaggcc          950

ttagcctgca ctccaggctc cttcttggac cccaggctgt gagcacactc         1000

ctgcctcatc gaccgtctgc cccctgctcc cctcatcagg accaacccgg         1050

ggactggtgc ctctgcctga tcagccagca ttgcccctag ctctgggttg         1100

ggcttggggc caagtctcag gggcttcta ggagttgggg ttttctaaac          1150

gtcccctcct ctcctacata gttgaggagg gggctaggga tatgctctgg         1200

ggctttcatg ggaatgatga agatgataat gagaaaaatg ttatcattat         1250

tatcatgaag taccattatc ataatacaat gaacctttat ttattgccta         1300

ccacatgtta tgggctgaat aatggccccc aaagatatct gtgtcctaat         1350

cctcagaact tgtgactgtt accttctgtg gcagaaaggg acagtgcaga         1400

tgtatgtaag ttaaggactt tgagatagag aggttattct tgctgattca         1450

ggtgggccca aaatatcacc acaagggtcc tcataagaaa gaggccagaa         1500

ggtcaaagag gtagagacaa agtgatgatg gaagtggacg tgggtgtgac         1550

gtgagcaggg gccatgaatg ccgcagcctt cagatgccag aaagggaaag         1600

gaatggattc ccctgcctgg agcctccaaa agaaaccagc cctgcccacg         1650

ccttgacttg agcccattga aactgatctt gagctcctgg cctccagaat         1700

tgcaggagaa taaatttgtg ttgtttttaa tgaaaaaaaa aaaaaaaaaa         1750

aaaaaaaaaa aaaaaaaaaa aaaaaaaaaa aaaaaaaaaa aaaaaaaaaa         1800

aaaaaaaaaa aaaaaaaaaa aaaaaaaaaa  aaaaaag                      1837
```

<210> SEQ ID NO 40
<211> LENGTH: 290
<212> TYPE: PRT
<213> ORGANISM: Homo sapiens

<400> SEQUENCE: 40

```
Met Pro Leu Leu Thr Leu Tyr Leu Leu Leu Phe Trp Leu Ser Gly
  1               5                  10                  15

Tyr Ser Ile Ala Thr Gln Ile Thr Gly Pro Thr Thr Val Asn Gly
                 20                  25                  30

Leu Glu Arg Gly Ser Leu Thr Val Gln Cys Val Tyr Arg Ser Gly
```

-continued

```
                35                  40                  45

Trp Glu Thr Tyr Leu Lys Trp Trp Cys Arg Gly Ala Ile Trp Arg
                50                  55                  60

Asp Cys Lys Ile Leu Val Lys Thr Ser Gly Ser Glu Gln Glu Val
                65                  70                  75

Lys Arg Asp Arg Val Ser Ile Lys Asp Asn Gln Lys Asn Arg Thr
                80                  85                  90

Phe Thr Val Thr Met Glu Asp Leu Met Lys Thr Asp Ala Asp Thr
                95                 100                 105

Tyr Trp Cys Gly Ile Glu Lys Thr Gly Asn Asp Leu Gly Val Thr
               110                 115                 120

Val Gln Val Thr Ile Asp Pro Ala Pro Val Thr Gln Glu Glu Thr
               125                 130                 135

Ser Ser Ser Pro Thr Leu Thr Gly His His Leu Asp Asn Arg His
               140                 145                 150

Lys Leu Leu Lys Leu Ser Val Leu Leu Pro Leu Ile Phe Thr Ile
               155                 160                 165

Leu Leu Leu Leu Leu Val Ala Ala Ser Leu Leu Ala Trp Arg Met
               170                 175                 180

Met Lys Tyr Gln Gln Lys Ala Ala Gly Met Ser Pro Glu Gln Val
               185                 190                 195

Leu Gln Pro Leu Glu Gly Asp Leu Cys Tyr Ala Asp Leu Thr Leu
               200                 205                 210

Gln Leu Ala Gly Thr Ser Pro Arg Lys Ala Thr Thr Lys Leu Ser
               215                 220                 225

Ser Ala Gln Val Asp Gln Val Glu Val Glu Tyr Val Thr Met Ala
               230                 235                 240

Ser Leu Pro Lys Glu Asp Ile Ser Tyr Ala Ser Leu Thr Leu Gly
               245                 250                 255

Ala Glu Asp Gln Glu Pro Thr Tyr Cys Asn Met Gly His Leu Ser
               260                 265                 270

Ser His Leu Pro Gly Arg Gly Pro Glu Glu Pro Thr Glu Tyr Ser
               275                 280                 285

Thr Ile Ser Arg Pro
               290
```

<210> SEQ ID NO 41
<211> LENGTH: 2683
<212> TYPE: DNA
<213> ORGANISM: Homo sapiens

<400> SEQUENCE: 41

```
aagaacactg ttgctcttgg tggacgggcc cagaggaatt cagagttaaa          50

ccttgagtgc ctgcgtccgt gagaattcag catggaatgt ctctactatt         100

tcctgggatt tctgctcctg gctgcaagat tgccacttga tgccgccaaa         150

cgatttcatg atgtgctggg caatgaaaga ccttctgctt acatgaggga         200

gcacaatcaa ttaaatggct ggtcttctga tgaaaatgac tggaatgaaa         250

aactctaccc agtgtggaag cggggagaca tgaggtggaa aaactcctgg         300

aagggaggcc gtgtgcaggc ggtcctgacc agtgactcac cagccctcgt         350

gggctcaaat ataacatttg cggtgaacct gatattccct agatgccaaa         400

aggaagatgc caatggcaac atagtctatg agaagaactg cagaaatgag         450
```

-continued

```
gctggtttat ctgctgatcc gtatgtttac aactggacag catggtcaga      500
ggacagtgac ggggaaaatg gcaccggcca aagccatcat aacgtcttcc      550
ctgatgggaa accttttcct caccaccccg gatggagaag atggaatttc      600
atctacgtct tccacacact tggtcagtat ttccagaaat tgggacgatg      650
ttcagtgaga gtttctgtga acacagccaa tgtgacactt gggcctcaac      700
tcatggaagt gactgtctac agaagacatg gacgggcata tgttcccatc      750
gcacaagtga aagatgtgta cgtggtaaca gatcagattc ctgtgtttgt      800
gactatgttc cagaagaacg atcgaaattc atccgacgaa accttcctca      850
aagatctccc cattatgttt gatgtcctga ttcatgatcc tagccacttc      900
ctcaattatt ctaccattaa ctacaagtgg agcttcgggg ataatactgg      950
cctgtttgtt tccaccaatc atactgtgaa tcacacgtat gtgctcaatg     1000
gaaccttcag ccttaacctc actgtgaaag ctgcagcacc aggaccttgt     1050
ccgccaccgc caccaccacc cagaccttca aaacccaccc cttctttagc     1100
aactactcta aaatcttatg attcaaacac cccaggacct actggtgaca     1150
accccctgga gctgagtagg attcctgatg aaaactgcca gattaacaga     1200
tatggccact ttcaagccac catcacaatt gtagagggaa tcttagaggt     1250
taacatcatc cagatgacag acgtcctgat gccggtgcca tggcctgaaa     1300
gctccctaat agactttgtc gtgacctgcc aagggagcat tcccacggag     1350
gtctgtacca tcatttctga ccccacctgc gagatcaccc agaacacagt     1400
ctgcagccct gtggatgtgg atgagatgtg tctgctgact gtgagacgaa     1450
ccttcaatgg gtctgggacg tactgtgtga acctcaccct gggggatgac     1500
acaagcctgg ctctcacgag caccctgatt tctgttcctg acagagaccc     1550
agcctcgcct ttaaggatgg caaacagtgc cctgatctcc gttggctgct     1600
tggccatatt tgtcactgtg atctccctct tggtgtacaa aaaacacaag     1650
gaatacaacc caatagaaaa tagtcctggg aatgtggtca gaagcaaagg     1700
cctgagtgtc tttctcaacc gtgcaaaagc cgtgttcttc ccgggaaacc     1750
aggaaaagga tccgctactc aaaaaccaag aatttaaagg agtttcttaa     1800
atttcgacct tgtttctgaa gctcactttt cagtgccatt gatgtgagat     1850
gtgctggagt ggctattaac cttttttcc taaagattat tgttaaatag     1900
atattgtggt ttggggaagt tgaatttttt ataggttaaa tgtcatttta     1950
gagatgggga gagggattat actgcaggca gcttcagcca tgttgtgaaa     2000
ctgataaaag caacttagca aggcttcttt tcattatttt ttatgtttca     2050
cttataaagt cttaggtaac tagtaggata gaaacactgt gtcccgagag     2100
taaggagaga agctactatt gattagagcc taacccaggt taactgcaag     2150
aagaggcggg atactttcag ctttccatgt aactgtatgc ataaagccaa     2200
tgtagtccag tttctaagat catgttccaa gctaactgaa tcccacttca     2250
atacacactc atgaactcct gatggaacaa taacaggccc aagcctgtgg     2300
tatgatgtgc acacttgcta gactcagaaa aaatactact ctcataaatg     2350
ggtgggagta ttttggtgac aacctacttt gcttggctga gtgaaggaat     2400
gatattcata tattcattta ttccatggac atttagttag tgctttttat     2450
```

-continued

```
ataccaggca tgatgctgag tgacactctt gtgtatattt ccaaattttt          2500

gtacagtcgc tgcacatatt tgaaatcata tattaagact ttccaaagat          2550

gaggtccctg gtttttcatg gcaacttgat cagtaaggat ttcacctctg          2600

tttgtaacta aaaccatcta ctatatgtta gacatgacat tctttttctc          2650

tccttcctga aaaataaagt gtgggaagag  aca                           2683


<210> SEQ ID NO 42
<211> LENGTH: 572
<212> TYPE: PRT
<213> ORGANISM: Homo sapiens

<400> SEQUENCE: 42

Met Glu Cys Leu Tyr Tyr Phe Leu Gly Phe Leu Leu Leu Ala Ala
  1               5                  10                  15

Arg Leu Pro Leu Asp Ala Ala Lys Arg Phe His Asp Val Leu Gly
                 20                  25                  30

Asn Glu Arg Pro Ser Ala Tyr Met Arg Glu His Asn Gln Leu Asn
                 35                  40                  45

Gly Trp Ser Ser Asp Glu Asn Asp Trp Asn Glu Lys Leu Tyr Pro
                 50                  55                  60

Val Trp Lys Arg Gly Asp Met Arg Trp Lys Asn Ser Trp Lys Gly
                 65                  70                  75

Gly Arg Val Gln Ala Val Leu Thr Ser Asp Ser Pro Ala Leu Val
                 80                  85                  90

Gly Ser Asn Ile Thr Phe Ala Val Asn Leu Ile Phe Pro Arg Cys
                 95                 100                 105

Gln Lys Glu Asp Ala Asn Gly Asn Ile Val Tyr Glu Lys Asn Cys
                110                 115                 120

Arg Asn Glu Ala Gly Leu Ser Ala Asp Pro Tyr Val Tyr Asn Trp
                125                 130                 135

Thr Ala Trp Ser Glu Asp Ser Asp Gly Glu Asn Gly Thr Gly Gln
                140                 145                 150

Ser His His Asn Val Phe Pro Asp Gly Lys Pro Phe Pro His His
                155                 160                 165

Pro Gly Trp Arg Arg Trp Asn Phe Ile Tyr Val Phe His Thr Leu
                170                 175                 180

Gly Gln Tyr Phe Gln Lys Leu Gly Arg Cys Ser Val Arg Val Ser
                185                 190                 195

Val Asn Thr Ala Asn Val Thr Leu Gly Pro Gln Leu Met Glu Val
                200                 205                 210

Thr Val Tyr Arg Arg His Gly Arg Ala Tyr Val Pro Ile Ala Gln
                215                 220                 225

Val Lys Asp Val Tyr Val Val Thr Asp Gln Ile Pro Val Phe Val
                230                 235                 240

Thr Met Phe Gln Lys Asn Asp Arg Asn Ser Ser Asp Glu Thr Phe
                245                 250                 255

Leu Lys Asp Leu Pro Ile Met Phe Asp Val Leu Ile His Asp Pro
                260                 265                 270

Ser His Phe Leu Asn Tyr Ser Thr Ile Asn Tyr Lys Trp Ser Phe
                275                 280                 285

Gly Asp Asn Thr Gly Leu Phe Val Ser Thr Asn His Thr Val Asn
                290                 295                 300
```

-continued

```
His Thr Tyr Val Leu Asn Gly Thr Phe Ser Leu Asn Leu Thr Val
                305                 310                 315

Lys Ala Ala Ala Pro Gly Pro Cys Pro Pro Pro Pro Pro Pro Pro
                320                 325                 330

Arg Pro Ser Lys Pro Thr Pro Ser Leu Ala Thr Thr Leu Lys Ser
                335                 340                 345

Tyr Asp Ser Asn Thr Pro Gly Pro Thr Gly Asp Asn Pro Leu Glu
                350                 355                 360

Leu Ser Arg Ile Pro Asp Glu Asn Cys Gln Ile Asn Arg Tyr Gly
                365                 370                 375

His Phe Gln Ala Thr Ile Thr Ile Val Glu Gly Ile Leu Glu Val
                380                 385                 390

Asn Ile Ile Gln Met Thr Asp Val Leu Met Pro Val Pro Trp Pro
                395                 400                 405

Glu Ser Ser Leu Ile Asp Phe Val Val Thr Cys Gln Gly Ser Ile
                410                 415                 420

Pro Thr Glu Val Cys Thr Ile Ile Ser Asp Pro Thr Cys Glu Ile
                425                 430                 435

Thr Gln Asn Thr Val Cys Ser Pro Val Asp Val Asp Glu Met Cys
                440                 445                 450

Leu Leu Thr Val Arg Arg Thr Phe Asn Gly Ser Gly Thr Tyr Cys
                455                 460                 465

Val Asn Leu Thr Leu Gly Asp Asp Thr Ser Leu Ala Leu Thr Ser
                470                 475                 480

Thr Leu Ile Ser Val Pro Asp Arg Asp Pro Ala Ser Pro Leu Arg
                485                 490                 495

Met Ala Asn Ser Ala Leu Ile Ser Val Gly Cys Leu Ala Ile Phe
                500                 505                 510

Val Thr Val Ile Ser Leu Leu Val Tyr Lys Lys His Lys Glu Tyr
                515                 520                 525

Asn Pro Ile Glu Asn Ser Pro Gly Asn Val Val Arg Ser Lys Gly
                530                 535                 540

Leu Ser Val Phe Leu Asn Arg Ala Lys Ala Val Phe Phe Pro Gly
                545                 550                 555

Asn Gln Glu Lys Asp Pro Leu Leu Lys Asn Gln Glu Phe Lys Gly
                560                 565                 570

Val Ser


<210> SEQ ID NO 43
<211> LENGTH: 1434
<212> TYPE: DNA
<213> ORGANISM: Homo sapiens

<400> SEQUENCE: 43

gcatagatga atgtatcagt ggatggatag ttggctagat gggtgggttg          50

gtggatgaat ggcagagctt gcacctgcca gtccatctga catcaaagcc         100

agtgtctcta atggtgacac caccctcctc tgcagcagga ggcagagctg         150

tgggatgaat gaggttcgcc aggtctccct tacctatcct gggtccccag         200

ctccttctca ctctcttccc ttgcagcctc gaagcggagg atccctgtgt         250

cccagccggg catggccgac ccccaccagc ttttcgatga cacaagttca         300

gcccagagcc ggggctatgg ggcccagcgg gcacctggtg gcctgagtta         350

tcctgcagcc tctcccacgc cccatgcagc cttcctggct gacccggtgt         400
```

-continued

```
ccaacatggc catggcctat gggagcagcc tggccgcgca gggcaaggag          450

ctggtggata agaacatcga ccgcttcatc cccatcacca agctcaagta          500

ttactttgct gtggacacca tgtatgtggg cagaaagctg ggcctgctgt          550

tcttccccta cctacaccag gactgggaag tgcagtacca acaggacacc          600

ccggtggccc cccgctttga cgtcaatgcc ccggacctct acattccagc          650

aatggctttc atcacctacg ttttggtggc tggtcttgcg ctggggaccc          700

aggataggtt ctccccagac ctcctggggc tgcaagcgag ctcagccctg          750

gcctggctga ccctggaggt gctggccatc ctgctcagcc tctatctggt          800

cactgtcaac accgacctca ccaccatcga cctggtggcc ttcttgggct          850

acaaatatgt cgggatgatt ggcggggtcc tcatgggcct gctcttcggg          900

aagattggct actacctggt gctgggctgg tgctgcgtag ccatctttgt          950

gttcatgatc cggacgctgc ggctgaagat cttggcagac gcagcagctg         1000

agggggtccc ggtgcgtggg gcccggaacc agctgcgcat gtacctgacc         1050

atggcggtgg cggcggcgca gcctatgctc atgtactggc tcaccttcca         1100

cctggtgcgg tgagcgcgcc cgctgaacct cccgctgctg ctgctgctgc         1150

tgggggccac tgtggccgcc gaactcatct cctgcctgca ggccccaagg         1200

tccaccctgt ctggccacag gcaccgcctc catcccatgt cccgcccagc         1250

cccgccccca acccaaggtg ctgagagatc tccagctgca caggccaccg         1300

ccccagggcg tggccgctgt tacagaaaca ataaaccctg atgggcatgg         1350

caaaaaaaaa aaaaaaaaaa aaaaaaaaaa aaaaaaaaaa aaaaaaaaaa         1400

aaaaaaaaaa aaaaaaaaaa aaaaaaaaaa  aaga                         1434
```

<210> SEQ ID NO 44
<211> LENGTH: 283
<212> TYPE: PRT
<213> ORGANISM: Homo sapiens

<400> SEQUENCE: 44

```
Met Ala Asp Pro His Gln Leu Phe Asp Asp Thr Ser Ser Ala Gln
  1               5                  10                  15

Ser Arg Gly Tyr Gly Ala Gln Arg Ala Pro Gly Gly Leu Ser Tyr
                 20                  25                  30

Pro Ala Ala Ser Pro Thr Pro His Ala Ala Phe Leu Ala Asp Pro
                 35                  40                  45

Val Ser Asn Met Ala Met Ala Tyr Gly Ser Ser Leu Ala Ala Gln
                 50                  55                  60

Gly Lys Glu Leu Val Asp Lys Asn Ile Asp Arg Phe Ile Pro Ile
                 65                  70                  75

Thr Lys Leu Lys Tyr Tyr Phe Ala Val Asp Thr Met Tyr Val Gly
                 80                  85                  90

Arg Lys Leu Gly Leu Leu Phe Phe Pro Tyr Leu His Gln Asp Trp
                 95                 100                 105

Glu Val Gln Tyr Gln Gln Asp Thr Pro Val Ala Pro Arg Phe Asp
                110                 115                 120

Val Asn Ala Pro Asp Leu Tyr Ile Pro Ala Met Ala Phe Ile Thr
                125                 130                 135

Tyr Val Leu Val Ala Gly Leu Ala Leu Gly Thr Gln Asp Arg Phe
```

-continued

```
                140                 145                 150

Ser Pro Asp Leu Leu Gly Leu Gln Ala Ser Ser Ala Leu Ala Trp
                155                 160                 165

Leu Thr Leu Glu Val Leu Ala Ile Leu Leu Ser Leu Tyr Leu Val
                170                 175                 180

Thr Val Asn Thr Asp Leu Thr Thr Ile Asp Leu Val Ala Phe Leu
                185                 190                 195

Gly Tyr Lys Tyr Val Gly Met Ile Gly Gly Val Leu Met Gly Leu
                200                 205                 210

Leu Phe Gly Lys Ile Gly Tyr Tyr Leu Val Leu Gly Trp Cys Cys
                215                 220                 225

Val Ala Ile Phe Val Phe Met Ile Arg Thr Leu Arg Leu Lys Ile
                230                 235                 240

Leu Ala Asp Ala Ala Ala Glu Gly Val Pro Val Arg Gly Ala Arg
                245                 250                 255

Asn Gln Leu Arg Met Tyr Leu Thr Met Ala Val Ala Ala Ala Gln
                260                 265                 270

Pro Met Leu Met Tyr Trp Leu Thr Phe His Leu Val Arg
                275                 280


<210> SEQ ID NO 45
<211> LENGTH: 1205
<212> TYPE: DNA
<213> ORGANISM: Homo sapiens

<400> SEQUENCE: 45

gctgagcacc aacaggaact attccagtga agagcaagtg ctgcccgacc          50

caggaccctg tgccaggctg gcagccctcc agctccctcc agagaggaaa         100

cctctgtctg gctgagggtg ggactagctg ggatgtctca ctccagttgc         150

tcaggttcac ccaggaagct cctccgtgga gtggccagcc tgattctagc         200

cctgtcctct ctggcagcac atgccacacc tgcctgggcc ttctgctccc         250

tgatgcttga tgagcccctg cctcctcaat gtttctcaaa gacagacccc         300

cctgaggcca gcttgaatgt gaagactgct gaagtcagct ggcttcactt         350

gagctgcaga aaaggtggct gggatggccc aggtgcaccc agaggcccca         400

gccctttggc tgcctttggg ttgtgacttg ggttgtctct gaggccctgc         450

cagagctggg cctgcgggtg gtgggcggtc cgacctcggg cagtcagtgc         500

tccgcagcct cagcactgca tcccagaccc agtgtcctca gagggaagag         550

ccagcctccc tgcctcatgg aaccaggagt cccaaaaagt caggagcctg         600

gaggctctga aaggagcagg gattccatag tgcgtgaagc tgaaataggc         650

gccctcctgg ggagccccca gcaaaactgt ttttcatacc cactcccaga         700

actgccccgc tccagctcca gcgccagcgc cagctggttg ccaggcgtca         750

ttggagaggc ctggctgccc caggggcagc agggagtggt ggacctgtat         800

gggctggcag gaggccattg gccatgctga caagtgtcac ctgccttcct         850

agcctggagc cacccctcag gtggcctgct tgcacctcct atccggaggt         900

agcctgcccc acctgtaggc agagggggct cttgcttgag gcctgcacag         950

gaagcaagta tagccccggt gccccagagt gggttccact tagccctggc        1000

gagatggcct gtcctgagat ctctgctccc agaccccacc atctggggag        1050
```

| | |
|---|---:|
| cacagtcctt aggctgcctg gtccaggaag ggggtgcggc tctgtcagga | 1100 |
| aacctggact ctcaaggccc accagcctct ccgtgagtgt tagaaatcac | 1150 |
| agatacagta tatacttaat tacactactc actactcaaa aaaaaaaaaa | 1200 |
| aaaaa | 1205 |

<210> SEQ ID NO 46
<211> LENGTH: 97
<212> TYPE: PRT
<213> ORGANISM: Homo sapiens

<400> SEQUENCE: 46

```
Met Ser His Ser Ser Cys Ser Gly Ser Pro Arg Lys Leu Leu Arg
  1               5                  10                  15

Gly Val Ala Ser Leu Ile Leu Ala Leu Ser Ser Leu Ala Ala His
             20                  25                  30

Ala Thr Pro Ala Trp Ala Phe Cys Ser Leu Met Leu Asp Glu Pro
         35                  40                  45

Leu Pro Pro Gln Cys Phe Ser Lys Thr Asp Pro Pro Glu Ala Ser
     50                  55                  60

Leu Asn Val Lys Thr Ala Glu Val Ser Trp Leu His Leu Ser Cys
 65                  70                  75

Arg Lys Gly Gly Trp Asp Gly Pro Gly Ala Pro Arg Gly Pro Ser
             80                  85                  90

Pro Leu Ala Ala Phe Gly Leu
             95
```

<210> SEQ ID NO 47
<211> LENGTH: 983
<212> TYPE: DNA
<213> ORGANISM: Homo sapiens

<400> SEQUENCE: 47

| | |
|---|---:|
| ttccgggccc tggcgtctcg tctccttacc ctggggctac ccttgcccgg | 50 |
| tcctactgcc cgcggttaac ccgccgcgag ccgcctctcc cctccccgcc | 100 |
| cgactcaacc ctgccctccc ccgtgctttg cagacgccgc ccgggggccc | 150 |
| aggcggctga tgcgtgtggg cctcgcgctg atcttggtgg gccacgtgaa | 200 |
| cctgctgctg ggggccgtgc tgcatggcac cgtcctgcgg cacgtggcca | 250 |
| atccccgcgg cgctgtcacg ccggagtaca ccgtagccaa tgtcatctct | 300 |
| gtcggctcgg ggctgctgag cgtttccgtg ggacttgtgg ccctcctggc | 350 |
| gtccaggaac cttcttcgcc ctccactgca ctgggtcctg ctggcactag | 400 |
| ctctggtgaa cctgctcttg tccgttgcct gctccctggg cctccttctt | 450 |
| gctgtgtcac tcactgtggc caacggtggc cgccgcctta ttgctgactg | 500 |
| ccacccagga ctgctggatc ctctggtacc actggatgag gggccgggac | 550 |
| atactgactg cccctttgac cccacaagaa tctatgatac agccttggct | 600 |
| ctctggatcc cttctttgct catgtctgca ggggaggctg ctctatctgg | 650 |
| ttactgctgt gtggctgcac tcactctacg tggagttggg ccctgcagga | 700 |
| aggacggact tcaggggcag ctagaggaaa tgacagagct tgaatctcct | 750 |
| aaaatgtaaaa ggcaggaaaa tgagcagcta ctggatcaaa atcaagaaat | 800 |
| ccgggcatca cagagaagtt gggtttagga caggtgctgt tccgagactc | 850 |

-continued

```
agtcctaaag ggttttttttt cccactaagc aaggggccct gacctcggga              900

tgagataaca aattgtaata aagtaacttc tcttttcttc taaaaaaaaa              950

aaaaaaaaaa aaaaaaaaaa aaaaaaaaaa  aaa                               983


<210> SEQ ID NO 48
<211> LENGTH: 222
<212> TYPE: PRT
<213> ORGANISM: Homo sapiens

<400> SEQUENCE: 48

Met Arg Val Gly Leu Ala Leu Ile Leu Val Gly His Val Asn Leu
  1               5                  10                  15

Leu Leu Gly Ala Val Leu His Gly Thr Val Leu Arg His Val Ala
                 20                  25                  30

Asn Pro Arg Gly Ala Val Thr Pro Glu Tyr Thr Val Ala Asn Val
                 35                  40                  45

Ile Ser Val Gly Ser Gly Leu Leu Ser Val Ser Val Gly Leu Val
                 50                  55                  60

Ala Leu Leu Ala Ser Arg Asn Leu Leu Arg Pro Pro Leu His Trp
                 65                  70                  75

Val Leu Leu Ala Leu Ala Leu Val Asn Leu Leu Leu Ser Val Ala
                 80                  85                  90

Cys Ser Leu Gly Leu Leu Leu Ala Val Ser Leu Thr Val Ala Asn
                 95                 100                 105

Gly Gly Arg Arg Leu Ile Ala Asp Cys His Pro Gly Leu Leu Asp
                110                 115                 120

Pro Leu Val Pro Leu Asp Glu Gly Pro Gly His Thr Asp Cys Pro
                125                 130                 135

Phe Asp Pro Thr Arg Ile Tyr Asp Thr Ala Leu Ala Leu Trp Ile
                140                 145                 150

Pro Ser Leu Leu Met Ser Ala Gly Glu Ala Ala Leu Ser Gly Tyr
                155                 160                 165

Cys Cys Val Ala Ala Leu Thr Leu Arg Gly Val Gly Pro Cys Arg
                170                 175                 180

Lys Asp Gly Leu Gln Gly Gln Leu Glu Glu Met Thr Glu Leu Glu
                185                 190                 195

Ser Pro Lys Cys Lys Arg Gln Glu Asn Glu Gln Leu Leu Asp Gln
                200                 205                 210

Asn Gln Glu Ile Arg Ala Ser Gln Arg Ser Trp Val
                215                 220


<210> SEQ ID NO 49
<211> LENGTH: 847
<212> TYPE: DNA
<213> ORGANISM: Homo sapiens

<400> SEQUENCE: 49

cgtcagtcta gaaggataag agaaagaaag ttaagcaact acaggaaatg               50

gctttgggag ttccaatatc agtctatctt ttattcaacg caatgacagc              100

actgaccgaa gaggcagccg tgactgtaac acctccaatc acagcccagc              150

aagctgacaa catagaagga cccatagcct tgaagttctc acacctttgc              200

ctggaagatc ataacagtta ctgcatcaac ggtgcttgtg cattccacca              250

tgagctagag aaagccatct gcaggtgttt tactggttat actggagaaa              300
```

-continued

```
ggtgtgagca cttgacttta acttcatatg ctgtggattc ttatgaaaaa              350

tacattgcaa ttgggattgg tgttggatta ctattaagtg gttttcttgt              400

tattttttac tgctatataa gaaagaggta tgaaaaagac aaaatatgaa              450

gtcacttcat atgcaatcgt ttgacaaata gttattcagg ccctataatg              500

tgtcaggcac tgacatgtaa aattttttta attaaaaaag agctgtaatc              550

tggcaaaaag tttctatgta atatttttca tgccttttct cataaaccca              600

gacgagtggt aaaaatttgc cttcagttgt aataggagag ttcaaacgta              650

cagtctccct tcaacctatc tctgtctgcc catatcaaaa ttataaatga              700

ggaggacagc aggccccaag aaagtaggga ctaagtatgt cttgttcaaa              750

attgtatatt cagtgactta cactatgcct agcacacaac acacactgag              800

taaatatttg ttgagtgaaa taaaatcaag aaacaagtaa  aaactga              847
```

<210> SEQ ID NO 50
<211> LENGTH: 133
<212> TYPE: PRT
<213> ORGANISM: Homo sapiens

<400> SEQUENCE: 50

```
Met Ala Leu Gly Val Pro Ile Ser Val Tyr Leu Leu Phe Asn Ala
  1               5                  10                  15

Met Thr Ala Leu Thr Glu Glu Ala Ala Val Thr Val Thr Pro Pro
                 20                  25                  30

Ile Thr Ala Gln Gln Ala Asp Asn Ile Glu Gly Pro Ile Ala Leu
                 35                  40                  45

Lys Phe Ser His Leu Cys Leu Glu Asp His Asn Ser Tyr Cys Ile
                 50                  55                  60

Asn Gly Ala Cys Ala Phe His His Glu Leu Glu Lys Ala Ile Cys
                 65                  70                  75

Arg Cys Phe Thr Gly Tyr Thr Gly Glu Arg Cys Glu His Leu Thr
                 80                  85                  90

Leu Thr Ser Tyr Ala Val Asp Ser Tyr Glu Lys Tyr Ile Ala Ile
                 95                 100                 105

Gly Ile Gly Val Gly Leu Leu Leu Ser Gly Phe Leu Val Ile Phe
                110                 115                 120

Tyr Cys Tyr Ile Arg Lys Arg Tyr Glu Lys Asp Lys Ile
                125                 130
```

<210> SEQ ID NO 51
<211> LENGTH: 978
<212> TYPE: DNA
<213> ORGANISM: Homo sapiens

<400> SEQUENCE: 51

```
ggctcgagct tggctctcag accatcctgg tggaagaaac actagcagtc               50

tgcccaatct gaatgcaaat ccagaataat cttttctttt gttgttacac              100

agttatgagt gcaattttta aatggctgct actctacagc ctgcctgcct              150

tatgctttct cctgggcacg caggaaagtg agagcttcca ctccaaagca              200

gagatcctag tgacactaag tcaggtaata atctctccag ctggacctca              250

tgcactcaca tggacaacac acttctctcc ttcagtgatc atcatccttg              300

taccatgttg gtggcatgct gtaatcgtga ctcaacatcc ggttgccaat              350
```

-continued tgctatgtaa caaaccacct caacattcag tggcttgaat tgaaagcagg 400
gtcttgaaga gatatttgca catttcatcc tcccagcagc attattcaca 450
acagccaata ggcagaagca acccaatgtc caaccataga tgagtggata 500
accaaaatgt agtccatcca tacaatgaaa tatgattcag ccttaacaag 550
gaaggaagtc ccgccacgtg ctacaacatg gatggacctt gaggacacta 600
tgctaagtga agtaagccag gcacaaaagg acaaatactc tatgattcca 650
ttttataggg taccaaagag aatcaaactc acagagatag aaagtagact 700
ggggtggcca gggactcggg gagagaggaa agggcagtta ttgtttaaaa 750
ggtacagagt ttcagtttgg gaagatgaaa atgttctgga aacggttaat 800
ggtgatttta cattgtttat gttaccacga tttgtaaaag agcagctgcg 850
ctgagaatga gcatgcttgt cattggcagc tctctgagat tttcagtgcc 900
tcttactggc ttgttaagaa gacggcaaaa aaaaaaaaaa aaaaaaaaaa 950
aaaaaaaaaa aaaaaaaaaa aaaaaaaa 978

<210> SEQ ID NO 52
<211> LENGTH: 114
<212> TYPE: PRT
<213> ORGANISM: Homo sapiens

<400> SEQUENCE: 52

Met Gln Ile Gln Asn Asn Leu Phe Phe Cys Cys Tyr Thr Val Met
1 5 10 15

Ser Ala Ile Phe Lys Trp Leu Leu Leu Tyr Ser Leu Pro Ala Leu
20 25 30

Cys Phe Leu Leu Gly Thr Gln Glu Ser Glu Ser Phe His Ser Lys
35 40 45

Ala Glu Ile Leu Val Thr Leu Ser Gln Val Ile Ile Ser Pro Ala
50 55 60

Gly Pro His Ala Leu Thr Trp Thr Thr His Phe Ser Pro Ser Val
65 70 75

Ile Ile Ile Leu Val Pro Cys Trp Trp His Ala Val Ile Val Thr
80 85 90

Gln His Pro Val Ala Asn Cys Tyr Val Thr Asn His Leu Asn Ile
95 100 105

Gln Trp Leu Glu Leu Lys Ala Gly Ser
110

<210> SEQ ID NO 53
<211> LENGTH: 1664
<212> TYPE: DNA
<213> ORGANISM: Homo sapiens

<400> SEQUENCE: 53
ttttgaaatg gtttatgacc tcttccccac ttccccgctt gctttgctca 50
ttagtgttcc taggtggctg ctgggtgacg ggcttttcat catctctgat 100
gtgggccagt gcgaaagagc agctgcaaca tctgtttcta attgggtcgt 150
gcctttataa atacttcttg cctatttgtc acattgcttc cctcccaccc 200
tgtcttcctt ggagtactgc agaatctgta agcgtccctg gaatgcacac 250
gtggaccttg tcattcccaa acagactttc tgctggtcag cactttgtaa 300
tgttcggctg ttacaggcat tagtcacttg tgctcagaga gagactgtgg 350

-continued

```
tctttggaaa ctgaagaaaa tgtctttttt gttgttgtta attcttggca    400

tccagttaga tttaacttct caagagttta cacagacttt tagaaaaaca    450

ttctgtctct aagaaaaaag tgctctagct ttgtacagtt tttggatttt    500

cacacttggt ggttgtttgc tgaaatgctg ttttgctagt gattcccctc    550

ctccccctat ctggggttgt aagcagctct ggggctctgt tcacttcgga    600

tacctgtttc tggggactgc ttttcaacag cgtttttcct aagggcatat    650

gagaaattta atttctgatg gaatgaaggt gaaactctag tcccaggtaa    700

acctgggtag gctgtagaga cagaaagggg gctgcaggtc taggtggaag    750

aacgagaacg aatgcagcat ggtatttcca ggccttttag attcggcttc    800

atccacaacc aatgtgagtt cttatctgca aagcgggcct aagtgtaatg    850

gagggaaggt gggccaggca ccagggtcct gggttctccc gcgcctcact    900

ctgtctccac ctggcccatg cataaagaac actagtcaag tagccattgt    950

acctgtttcc ttatctgaaa atgagaaggt tggagagtat gacttctgtt   1000

gaaacaacaa ggcgcttaca aattttggtg aagtcgaatg agggcagcgt   1050

taagagaaat atcaaagtta gtcattggat ttcagggctt agggatggaa   1100

accagctggt agtagactgg ttgtagttat gtccaaaggg cagagtggga   1150

aaaatttggc cgaaaagagt gtggtgggtg accagcaaat gttagaggta   1200

tacatcaggg cacagaggag aaaagctaac atgatactga tgacttcaag   1250

tcttcactgt ccaattcaga ggatagggga gggtttaagc tgattaaaca   1300

gtgggctttt tttctcctgc aagagggtgg aggtctataa ctgtgcagat   1350

tttatcagat gcatgctaat acatgttatt ctgggggact ctcttatacc   1400

ttgaagtaga cattgctgct atttgcgtga aaaaaatagg aggacttatt   1450

tgaattgaga atggggatag gctgagttcc accgagatgt tggcttagag   1500

atgcctgggc catgctgtac agtaggaagc ccagcagagg agattgggct   1550

gtgtgggtca tgacaaaggg agttgttagc ttatggttgg ctattaaagt   1600

catgggcaag gatgggcaag aaaagtgtgt aaaatgagct gacaaaagat   1650

aaatatgtta  atta                                         1664
```

```
<210> SEQ ID NO 54
<211> LENGTH: 102
<212> TYPE: PRT
<213> ORGANISM: Homo sapiens

<400> SEQUENCE: 54

Met Thr Ser Ser Pro Leu Pro Arg Leu Leu Cys Ser Leu Val Phe
  1               5                  10                  15

Leu Gly Gly Cys Trp Val Thr Gly Phe Ser Ser Ser Leu Met Trp
                 20                  25                  30

Ala Ser Ala Lys Glu Gln Leu Gln His Leu Phe Leu Ile Gly Ser
                 35                  40                  45

Cys Leu Tyr Lys Tyr Phe Leu Pro Ile Cys His Ile Ala Ser Leu
                 50                  55                  60

Pro Pro Cys Leu Pro Trp Ser Thr Ala Glu Ser Val Ser Val Pro
                 65                  70                  75

Gly Met His Thr Trp Thr Leu Ser Phe Pro Asn Arg Leu Ser Ala
```

-continued

```
                80                  85                  90

Gly Gln His Phe Val Met Phe Gly Cys Tyr Arg His
                95                  100
```

<210> SEQ ID NO 55
<211> LENGTH: 1824
<212> TYPE: DNA
<213> ORGANISM: Homo sapiens

<400> SEQUENCE: 55

```
acactggcca aacactcgca tcccagggcg tctccggctg ctcccattga        50

gctgtctgct cgctgtgccc gctgtgcctg ctgtgcccgc gctgtcgccg       100

ctgctaccgc gtctgctgga cgcgggagac gccagcgagc tggtgattgg       150

agccctgcgg agagctcaag cgcccagctc tgcccgagga gcccaggctg       200

ccccgtgagt cccatagttg ctgcaggagt ggagccatga gctgcgtcct       250

gggtggtgtc atccccttgg ggctgctgtt cctggtctgc ggatcccaag       300

gctacctcct gcccaacgtc actctcttag aggagctgct cagcaaatac       350

cagcacaacg agtctcactc ccgggtccgc agagccatcc ccagggagga       400

caaggaggag atcctcatgc tgcacaacaa gcttcggggc caggtgcagc       450

ctcaggcctc caacatggag tacatgacct gggatgacga actggagaag       500

tctgctgcag cgtgggccag tcagtgcatc tgggagcacg ggcccaccag       550

tctgctggtg tccatcgggc agaacctggg cgctcactgg ggcaggtatc       600

gctctccggg gttccatgtg cagtcctggt atgacgaggt gaaggactac       650

acctacccct acccgagcga gtgcaacccc tggtgtccag agaggtgctc       700

ggggcctatg tgcacgcact acacacagat agtttgggcc accaccaaca       750

agatcggttg tgctgtgaac acctgccgga agatgactgt ctggggagaa       800

gtttgggaga acgcggtcta ctttgtctgc aattattctc caaaggggaa       850

ctggattgga gaagccccct acaagaatgg ccggccctgc tctgagtgcc       900

cacccagcta tggaggcagc tgcaggaaca acttgtgtta ccgagaagaa       950

acctacactc caaaacctga aacggacgag atgaatgagg tggaaacggc      1000

tcccattcct gaagaaaacc atgtttggct ccaaccgagg gtgatgagac      1050

ccaccaagcc caagaaaacc tctgcggtca actacatgac ccaagtcgtc      1100

agatgtgaca ccaagatgaa ggacaggtgc aaagggtcca cgtgtaacag      1150

gtaccagtgc ccagcaggct gcctgaacca caaggcgaag atctttggaa      1200

gtctgttcta tgaaagctcg tctagcatat gccgcgccgc catccactac      1250

gggatcctgg atgacaaggg aggcctggtg gatatcacca ggaacgggaa      1300

ggtccccttc ttcgtgaagt ctgagagaca cggcgtgcag tccctcagca      1350

aatacaaacc ttccagctca ttcatggtgt caaaagtgaa agtgcaggat      1400

ttggactgct acacgaccgt tgctcagctg tgcccgtttg aaaagccagc      1450

aactcactgc ccaagaatcc attgtccggc acactgcaaa gacgaacctt      1500

cctactgggc tccggtgttt ggaaccaaca tctatgcaga tacctcaagc      1550

atctgcaaga cagctgtgca cgcgggagtc atcagcaacg agagtggggg      1600

tgacgtggac gtgatgcccg tggataaaaa gaagacctac gtgggctcgc      1650
```

-continued

```
tcaggaatgg agttcagtct gaaagcctgg ggactcctcg ggatggaaag          1700

gccttccgga tctttgctgt caggcagtga atttccagca ccaggggaga          1750

aggggcgtct tcaggagggc ttcggggttt tgcttttatt tttattttgt          1800

cattgcgggg tatatggaga  gtca                                     1824


<210> SEQ ID NO 56
<211> LENGTH: 497
<212> TYPE: PRT
<213> ORGANISM: Homo sapiens

<400> SEQUENCE: 56

Met Ser Cys Val Leu Gly Gly Val Ile Pro Leu Gly Leu Leu Phe
  1               5                  10                  15

Leu Val Cys Gly Ser Gln Gly Tyr Leu Leu Pro Asn Val Thr Leu
                 20                  25                  30

Leu Glu Glu Leu Leu Ser Lys Tyr Gln His Asn Glu Ser His Ser
                 35                  40                  45

Arg Val Arg Arg Ala Ile Pro Arg Glu Asp Lys Glu Glu Ile Leu
                 50                  55                  60

Met Leu His Asn Lys Leu Arg Gly Gln Val Gln Pro Gln Ala Ser
                 65                  70                  75

Asn Met Glu Tyr Met Thr Trp Asp Asp Glu Leu Glu Lys Ser Ala
                 80                  85                  90

Ala Ala Trp Ala Ser Gln Cys Ile Trp Glu His Gly Pro Thr Ser
                 95                 100                 105

Leu Leu Val Ser Ile Gly Gln Asn Leu Gly Ala His Trp Gly Arg
                110                 115                 120

Tyr Arg Ser Pro Gly Phe His Val Gln Ser Trp Tyr Asp Glu Val
                125                 130                 135

Lys Asp Tyr Thr Tyr Pro Tyr Pro Ser Glu Cys Asn Pro Trp Cys
                140                 145                 150

Pro Glu Arg Cys Ser Gly Pro Met Cys Thr His Tyr Thr Gln Ile
                155                 160                 165

Val Trp Ala Thr Thr Asn Lys Ile Gly Cys Ala Val Asn Thr Cys
                170                 175                 180

Arg Lys Met Thr Val Trp Gly Glu Val Trp Glu Asn Ala Val Tyr
                185                 190                 195

Phe Val Cys Asn Tyr Ser Pro Lys Gly Asn Trp Ile Gly Glu Ala
                200                 205                 210

Pro Tyr Lys Asn Gly Arg Pro Cys Ser Glu Cys Pro Pro Ser Tyr
                215                 220                 225

Gly Gly Ser Cys Arg Asn Asn Leu Cys Tyr Arg Glu Glu Thr Tyr
                230                 235                 240

Thr Pro Lys Pro Glu Thr Asp Glu Met Asn Glu Val Glu Thr Ala
                245                 250                 255

Pro Ile Pro Glu Glu Asn His Val Trp Leu Gln Pro Arg Val Met
                260                 265                 270

Arg Pro Thr Lys Pro Lys Lys Thr Ser Ala Val Asn Tyr Met Thr
                275                 280                 285

Gln Val Val Arg Cys Asp Thr Lys Met Lys Asp Arg Cys Lys Gly
                290                 295                 300

Ser Thr Cys Asn Arg Tyr Gln Cys Pro Ala Gly Cys Leu Asn His
                305                 310                 315
```

-continued

```
Lys Ala Lys Ile Phe Gly Ser Leu Phe Tyr Glu Ser Ser Ser Ser
                320                 325                 330

Ile Cys Arg Ala Ala Ile His Tyr Gly Ile Leu Asp Asp Lys Gly
                335                 340                 345

Gly Leu Val Asp Ile Thr Arg Asn Gly Lys Val Pro Phe Phe Val
                350                 355                 360

Lys Ser Glu Arg His Gly Val Gln Ser Leu Ser Lys Tyr Lys Pro
                365                 370                 375

Ser Ser Ser Phe Met Val Ser Lys Val Lys Val Gln Asp Leu Asp
                380                 385                 390

Cys Tyr Thr Thr Val Ala Gln Leu Cys Pro Phe Glu Lys Pro Ala
                395                 400                 405

Thr His Cys Pro Arg Ile His Cys Pro Ala His Cys Lys Asp Glu
                410                 415                 420

Pro Ser Tyr Trp Ala Pro Val Phe Gly Thr Asn Ile Tyr Ala Asp
                425                 430                 435

Thr Ser Ser Ile Cys Lys Thr Ala Val His Ala Gly Val Ile Ser
                440                 445                 450

Asn Glu Ser Gly Gly Asp Val Asp Val Met Pro Val Asp Lys Lys
                455                 460                 465

Lys Thr Tyr Val Gly Ser Leu Arg Asn Gly Val Gln Ser Glu Ser
                470                 475                 480

Leu Gly Thr Pro Arg Asp Gly Lys Ala Phe Arg Ile Phe Ala Val
                485                 490                 495

Arg Gln


<210> SEQ ID NO 57
<211> LENGTH: 486
<212> TYPE: DNA
<213> ORGANISM: Homo sapiens

<400> SEQUENCE: 57

gcacgaggcc aaacacagca gcctcaacat gaaggtggtt atggtcctcc              50

tgcttgctgc cctccccctt tactgctatg caggttctgg ttgcgttctt             100

ctggagagcg tcgtggaaaa gaccatcgat ccatcggttt ctgtggagga             150

atacaaagca gatcttcaga ggttcatcga cactgagcaa accgaagcag             200

ctgtagagga gttcaaggag tgcttcctca gccagagcaa tgagactctg             250

gccaacttcc gagtcatggt gcatacgata tatgacagcc tttactgtgc             300

tgcgtattaa ctgtcacaag aactttggct cagaggaatc cagacgatgc             350

tcacaacccg actgtggact ggcagaaatc tcaacttttc cttttgactt             400

tcccctttga tcagtaatat ggaagacgtt gttgaaacct gaagtatagt             450

taatttaaat aaacccactg caagaaaaaa  aaaaaa                           486


<210> SEQ ID NO 58
<211> LENGTH: 93
<212> TYPE: PRT
<213> ORGANISM: Homo sapiens

<400> SEQUENCE: 58

Met Lys Val Val Met Val Leu Leu Leu Ala Ala Leu Pro Leu Tyr
  1               5                  10                  15

Cys Tyr Ala Gly Ser Gly Cys Val Leu Leu Glu Ser Val Val Glu
                 20                  25                  30
```

-continued

```
Lys Thr Ile Asp Pro Ser Val Ser Val Glu Glu Tyr Lys Ala Asp
                35                  40                  45

Leu Gln Arg Phe Ile Asp Thr Glu Gln Thr Glu Ala Ala Val Glu
                50                  55                  60

Glu Phe Lys Glu Cys Phe Leu Ser Gln Ser Asn Glu Thr Leu Ala
                65                  70                  75

Asn Phe Arg Val Met Val His Thr Ile Tyr Asp Ser Leu Tyr Cys
                80                  85                  90

Ala Ala Tyr


<210> SEQ ID NO 59
<211> LENGTH: 3976
<212> TYPE: DNA
<213> ORGANISM: Homo sapiens

<400> SEQUENCE: 59

caagtccgtt gaggctgcca ggcgagtcag gtctctctgg acctcgcctg      50

actcggctgg gctgtgcctg aaattgaccc agctccacca tactccttga     100

ttatgagaaa acaaggagta agctcaaagc ggctgcaatc ttccggccgc     150

agccagtcta aggggcggcg cggggcctcc ctcgcccggg agccggaggt     200

agaggaggag gtggaaaagt cggtcctagg cggcgggaaa ctgccaaggg     250

gcgcctggag gtcctccccg gggaggatcc aaagtctgaa agagcgaaaa     300

ggcttggagc tagaggtggt ggccaagacc tttcttctcg gccccttcca     350

gttcgtccgt aattccctgg cgcagctccg ggaaaaggtg caggaactgc     400

aggcgcggcg gttctccagc agaaccactc tcggcatcgc tgtctttgtg     450

gcaattttac attggttaca tttagtaaca ctttttgaaa atgatcgtca     500

tttctctcac ctctcatctt tggaacggga gatgactttt cgcactgaaa     550

tgggacttta ttattcatac ttcaagacca ttattgaagc accttcgttt     600

ttggaaggac tgtggatgat tatgaatgac aggcttactg aatatcctct     650

tataattaat gcaataaaac gcttccatct ttatccagag gtaatcatag     700

cctcctggta ttgcacattc atgggaataa tgaatttatt tggactagaa     750

actaagacct gctggaatgt caccagaata gaacctctta atgaagttca     800

aagctgtgaa ggattgggag atcctgcttg cttttatgtt ggtgtaatct     850

ttattttaaa tggactaatg atgggattgt tcttcatgta tggagcatac     900

ctgagtggga ctcaactggg aggtcttatt acagtactgt gcttcttttt     950

caaccatgga gaggccaccc gtgtgatgtg gacaccacct ctccgtgaaa    1000

gtttttccta tcctttcctt gtacttcaga tgtgtatttt aactttgatt    1050

ctcaggacct caagcaatga tagaaggccc ttcattgcac tctgtctttc    1100

caatgttgct tttatgcttc cctggcaatt tgctcagttt atacttttta    1150

cacagatagc atcattattt cccatgtatg ttgtgggata cattgaacca    1200

agcaaatttc agaagatcat ttatatgaac atgatttcag ttacccttag    1250

tttcattttg atgtttggaa attcaatgta cttatcttct tattattctt    1300

catctttgtt aatgacgtgg gcaataattc taaagagaaa tgaaattcaa    1350

aaactgggag tatctaaact caacttttgg ctaattcaag gtagtgcctg    1400
```

-continued gtggtgtgga acaatcattt tgaaatttct gacatctaaa atcttaggcg 1450
tttcagacca cattcgcctg agtgatctta tagcagccag aatcttaagg 1500
tatacagatt ttgatacttt aatatatacc tgtgctcccg aatttgactt 1550
catggaaaaa gcgactccgc tgagatacac aaagacatta ttgcttccag 1600
ttgttatggt gattacatgt tttatcttta aaaagactgt tcgtgatatt 1650
tcatatgttt tagctacaaa catttatcta agaaaacagc tccttgaaca 1700
cagtgagctg gcttttcaca cattgcagtt gttagtgttt actgcccttg 1750
ccattttaat tatgaggcta aagatgtttt tgacaccgca catgtgtgtt 1800
atggcttcct tgatatgctc tcgacagctc tttggctggc tttttcgcag 1850
agttcgtttt gagaaggtta tctttggcat tttaacagtg atgtcaatac 1900
aaggttatgc aaacctccgt aatcaatgga gcataatagg agaatttaat 1950
aatttgcctc aggaagaact tttacagtgg atcaaataca gtaccacatc 2000
agatgctgtc tttgcaggtg ccatgcctac aatggcaagc atcaagctgt 2050
ctacacttca tcccattgtg aatcatccac attacgaaga tgcagacttg 2100
agggctcgga caaaaatagt ttattctaca tatagtcgaa aatctgccaa 2150
agaagtaaga gataaattgt tggagttaca tgtgaattat tatgttttag 2200
aagaggcatg gtgtgttgtg agaactaagc ctggttgcag tatgcttgaa 2250
atctgggatg tggaagaccc ttccaatgca gctaaccctc ccttatgtag 2300
cgtcctgctc gaagacgcca ggccttactt caccacagta tttcagaata 2350
gtgtgtacag agtattaaag gttaactgag aaggatacta cccattttac 2400
tatggcacaa tgccgtgtgt caaaaacaat cacccctttgg cttattcaca 2450
ttaataaaaa tcacaagctt taataacaga cacttaaaaa taagataaaa 2500
atggattgga aatttttctg attactaaaa ggtaaattac ttttctgttc 2550
attgaatgtc agccttatta agcttgtcat ataagttatt aaatcattca 2600
tgtcatactg cataaacaaa tgttcatttc agaattttaa agagaaatgt 2650
atataaagaa cmatgatttt aataatcagg ggtatgtaag tcctttttca 2700
tccaactagg tgaattgctt cagattttct ctagtaccag agggtacctc 2750
ctcaaactct ttgaaccact taaggcagaa gaatgcaagc tctgaaatga 2800
catccttaaa atgctgatac tggtcacagc ctctttacct ctgtgaggaa 2850
attgtaacag tgtgtctttt aaggtgtttt tattttacca gcccttaaga 2900
aagatctcta ataccttttta atactttttt ttaataattt caagttgaag 2950
tgtttttaaa aacactttgt tttgtaatgt tttgaatctc ttgagatgtg 3000
tttaccccac tagatacata tttgccactg gttagttctc catctaagct 3050
caagaggtta ttcatctctc tttagattcc agtggctttt cttttaacat 3100
ccaggtaaaa cagaaactgc tatggtatac aaccaagttt tggggttaaa 3150
cataatcaga aaagaaaatc cagttaaatt tatgaagtga gattttcaga 3200
tcctagatct tgaataaagg aaaggtcttt tcatcttgat ggccccaaag 3250
cttgttggtc atggtcttta tttctggcca ctatcttctt aaataatata 3300
tttttaagcc ctcatttatt tttggttttg ggtgaggaaa gtcatgtttt 3350
ctaagtcctc tcccctaata aaacctaccc aacaatagtg ctttgaaaag 3400

-continued

```
tggtagttat cttgaagata ctcttgccaa atgcaaagat aaacattctt          3450

tttgtctgct ttataaatat gaaatatgcc agatctatag tattttaatg          3500

tgcatctact ttaaatgagt catcttgggg tttttataat tcccttatgt          3550

tcttgcccct ctacacttga aataacaaaa tgccttaatt ttatggatta          3600

gttctcttat agtagacagg cagctatatg cagcaaaacc aataaagtta          3650

tttttcaact ttcatagttg taaaatatct tataccagaa tacaaaacag          3700

ctaagaaaac atgccacatt ttattttagc attttcaaat aatttgtttt          3750

tggtgtaagc acaggataaa aaaggagagc gtcaaagaaa agagacataa          3800

cacctaacat tcataaaaat taacaaagta tattttggat gatgttttta          3850

caggaaatat tttaaataag ttggtagaac ttttaaaatg gtactgtatt          3900

agctaataaa atattcagta caaatatatg tttggattta tgcattaaaa          3950

aactaataaa attatttcca  acttta                                   3976
```

```
<210> SEQ ID NO 60
<211> LENGTH: 758
<212> TYPE: PRT
<213> ORGANISM: Homo sapiens

<400> SEQUENCE: 60

Met Arg Lys Gln Gly Val Ser Ser Lys Arg Leu Gln Ser Ser Gly
  1               5                  10                  15

Arg Ser Gln Ser Lys Gly Arg Arg Gly Ala Ser Leu Ala Arg Glu
                 20                  25                  30

Pro Glu Val Glu Glu Glu Val Glu Lys Ser Val Leu Gly Gly Gly
                 35                  40                  45

Lys Leu Pro Arg Gly Ala Trp Arg Ser Ser Pro Gly Arg Ile Gln
                 50                  55                  60

Ser Leu Lys Glu Arg Lys Gly Leu Glu Leu Glu Val Val Ala Lys
                 65                  70                  75

Thr Phe Leu Leu Gly Pro Phe Gln Phe Val Arg Asn Ser Leu Ala
                 80                  85                  90

Gln Leu Arg Glu Lys Val Gln Glu Leu Gln Ala Arg Arg Phe Ser
                 95                 100                 105

Ser Arg Thr Thr Leu Gly Ile Ala Val Phe Val Ala Ile Leu His
                110                 115                 120

Trp Leu His Leu Val Thr Leu Phe Glu Asn Asp Arg His Phe Ser
                125                 130                 135

His Leu Ser Ser Leu Glu Arg Glu Met Thr Phe Arg Thr Glu Met
                140                 145                 150

Gly Leu Tyr Tyr Ser Tyr Phe Lys Thr Ile Ile Glu Ala Pro Ser
                155                 160                 165

Phe Leu Glu Gly Leu Trp Met Ile Met Asn Asp Arg Leu Thr Glu
                170                 175                 180

Tyr Pro Leu Ile Ile Asn Ala Ile Lys Arg Phe His Leu Tyr Pro
                185                 190                 195

Glu Val Ile Ile Ala Ser Trp Tyr Cys Thr Phe Met Gly Ile Met
                200                 205                 210

Asn Leu Phe Gly Leu Glu Thr Lys Thr Cys Trp Asn Val Thr Arg
                215                 220                 225

Ile Glu Pro Leu Asn Glu Val Gln Ser Cys Glu Gly Leu Gly Asp
```

-continued

```
                230                 235                 240
Pro Ala Cys Phe Tyr Val Gly Val Ile Phe Ile Leu Asn Gly Leu
                245                 250                 255
Met Met Gly Leu Phe Phe Met Tyr Gly Ala Tyr Leu Ser Gly Thr
                260                 265                 270
Gln Leu Gly Gly Leu Ile Thr Val Leu Cys Phe Phe Phe Asn His
                275                 280                 285
Gly Glu Ala Thr Arg Val Met Trp Thr Pro Pro Leu Arg Glu Ser
                290                 295                 300
Phe Ser Tyr Pro Phe Leu Val Leu Gln Met Cys Ile Leu Thr Leu
                305                 310                 315
Ile Leu Arg Thr Ser Ser Asn Asp Arg Arg Pro Phe Ile Ala Leu
                320                 325                 330
Cys Leu Ser Asn Val Ala Phe Met Leu Pro Trp Gln Phe Ala Gln
                335                 340                 345
Phe Ile Leu Phe Thr Gln Ile Ala Ser Leu Phe Pro Met Tyr Val
                350                 355                 360
Val Gly Tyr Ile Glu Pro Ser Lys Phe Gln Lys Ile Ile Tyr Met
                365                 370                 375
Asn Met Ile Ser Val Thr Leu Ser Phe Ile Leu Met Phe Gly Asn
                380                 385                 390
Ser Met Tyr Leu Ser Ser Tyr Tyr Ser Ser Ser Leu Leu Met Thr
                395                 400                 405
Trp Ala Ile Ile Leu Lys Arg Asn Glu Ile Gln Lys Leu Gly Val
                410                 415                 420
Ser Lys Leu Asn Phe Trp Leu Ile Gln Gly Ser Ala Trp Trp Cys
                425                 430                 435
Gly Thr Ile Ile Leu Lys Phe Leu Thr Ser Lys Ile Leu Gly Val
                440                 445                 450
Ser Asp His Ile Arg Leu Ser Asp Leu Ile Ala Ala Arg Ile Leu
                455                 460                 465
Arg Tyr Thr Asp Phe Asp Thr Leu Ile Tyr Thr Cys Ala Pro Glu
                470                 475                 480
Phe Asp Phe Met Glu Lys Ala Thr Pro Leu Arg Tyr Thr Lys Thr
                485                 490                 495
Leu Leu Leu Pro Val Val Met Val Ile Thr Cys Phe Ile Phe Lys
                500                 505                 510
Lys Thr Val Arg Asp Ile Ser Tyr Val Leu Ala Thr Asn Ile Tyr
                515                 520                 525
Leu Arg Lys Gln Leu Leu Glu His Ser Glu Leu Ala Phe His Thr
                530                 535                 540
Leu Gln Leu Leu Val Phe Thr Ala Leu Ala Ile Leu Ile Met Arg
                545                 550                 555
Leu Lys Met Phe Leu Thr Pro His Met Cys Val Met Ala Ser Leu
                560                 565                 570
Ile Cys Ser Arg Gln Leu Phe Gly Trp Leu Phe Arg Arg Val Arg
                575                 580                 585
Phe Glu Lys Val Ile Phe Gly Ile Leu Thr Val Met Ser Ile Gln
                590                 595                 600
Gly Tyr Ala Asn Leu Arg Asn Gln Trp Ser Ile Ile Gly Glu Phe
                605                 610                 615
Asn Asn Leu Pro Gln Glu Glu Leu Leu Gln Trp Ile Lys Tyr Ser
                620                 625                 630
```

-continued

Thr Thr Ser Asp Ala Val Phe Ala Gly Ala Met Pro Thr Met Ala
635 640 645

Ser Ile Lys Leu Ser Thr Leu His Pro Ile Val Asn His Pro His
650 655 660

Tyr Glu Asp Ala Asp Leu Arg Ala Arg Thr Lys Ile Val Tyr Ser
665 670 675

Thr Tyr Ser Arg Lys Ser Ala Lys Glu Val Arg Asp Lys Leu Leu
680 685 690

Glu Leu His Val Asn Tyr Tyr Val Leu Glu Glu Ala Trp Cys Val
695 700 705

Val Arg Thr Lys Pro Gly Cys Ser Met Leu Glu Ile Trp Asp Val
710 715 720

Glu Asp Pro Ser Asn Ala Ala Asn Pro Pro Leu Cys Ser Val Leu
725 730 735

Leu Glu Asp Ala Arg Pro Tyr Phe Thr Thr Val Phe Gln Asn Ser
740 745 750

Val Tyr Arg Val Leu Lys Val Asn
755

<210> SEQ ID NO 61
<211> LENGTH: 2449
<212> TYPE: DNA
<213> ORGANISM: Homo sapiens

<400> SEQUENCE: 61
ggcgcggcca catcctttaa atatggtctt tcttgggcgc gcgcgacaat 50
gtgaggagtg gggtggagcg tgtgtggtgt gtggctgcgg cctgggcaag 100
agccgccgcg gaccatgagc tgagtaagtt ctggagggat cctgcctctt 150
ggagccttcg cagccaggca gctgtgaact gtgagctaga gtgaagcaga 200
aatctaggaa gatgagctcc aagatggtca taagtgaacc aggactgaat 250
tgggatattt cccccaaaaa tggccttaag acatttttct ctcgagaaaa 300
ttataaagat cattccatgg ctccaagttt aaaagaacta cgtgttttat 350
ccaacagacg tataggagaa aatttgaatg cctcagcaag ttctgtagaa 400
aatgagccgg cagttagttc agcaactcaa gcaaaggaaa aagttaaaac 450
cacaattgga atggttcttc ttccaaaacc aagagttcct tatcctcgtt 500
tctctcgttt ctcacagaga gagcagagga gttatgtgga cttgttggtt 550
aaatacgcaa agattcctgc aaattccaaa gctgttggaa taaataaaaa 600
tgactacttg cagtacttgg atatgaaaaa acatgtgaac gaagaagtta 650
ctgagttcct aaagtttttg cagaattctg caaagaaatg tgcgcaggat 700
tataatatgc tttctgatga tgcccgtctc ttcacagaga aaattttaag 750
agcttgcatt gaacaagtga aaaagtattc agaattctat actctccacg 800
aggtcaccag cttaatggga ttcttcccat tcagagtaga gatgggatta 850
aagttagaaa aaactcttct cgcattgggc agtgtaaaat atgtgaaaac 900
agtatttccc tcaatgccta taaagttgca gctgtcaaag gacgatatag 950
ctaccattga aacgtcagaa caaacagctg aagctatgca ttatgatatt 1000
agtaaagatc caaatgcaga gaagcttgtt tccagatatc accctcagat 1050
agctctaact agtcagtcat tatttacctt attaaataat catggaccaa 1100

-continued

```
cgtacaagga acagtgggaa attccagtgt gtattcaagt aatacctgtt    1150

gcaggttcaa aaccagttaa agtaatatat attaattcac cacttcccca    1200

aaagaaaatg actatgagag agagaaatca aatctttcat gaagttccat    1250

taaaatttat gatgtccaaa aacacatctg ttccagtctc tgcagtcttt    1300

atggacaaac ctgaagagtt tatatctgaa atggacatgt cctgtgaagt    1350

caacgagtgc cgaaaaattg agagtcttga aaacttgtat ttggattttg    1400

atgatgatgt cacagaactt gaaacttttg gagtaaccac caccaaagta    1450

tcaaaatcac caagtccagc aagtacttcc acagtaccta acatgacaga    1500

tgctcctaca gcccccaaag caggaactac aactgtggca ccaagtgcac    1550

cagacatttc tgctaattct agaagtttat ctcagattct gatggaacaa    1600

ttgcaaaagg agaaacagct ggtcactggt atggatggtg gccctgagga    1650

atgcaaaaat aaagatgatc agggatttga atcatgtgaa aaggtatcaa    1700

attctgacaa gcctttgata caagatagtg acttgaaaac atctgatgcc    1750

ttacagttag aaaattctca ggaaattgaa acttctaata aaaatgatat    1800

gactatagat atactacatg ctgatggtga aagacctaat gttctagaaa    1850

acctagacaa ctcaaaggaa aagactgttg gatcagaagc agcaaaaact    1900

gaagatacag ttctctgcag cagtgataca gatgaggagt gtttaatcat    1950

tgatacagaa tgtaaaaaaa ccagttataa cagtgtttaa tttagataag    2000

tttgagggaa aataatcagt aggcaagagg aacatttttc ctgtagtagc    2050

tagagtgcct tgaaaaaatg tgttggctat gtgaaggaat atttcaacta    2100

aaatggaatg gtatgctttt caccccttaaa gtttgaggag gatcttgata    2150

tgttttaaca ttatcatggc agggaaatat ataaagaaga aaaatatttt    2200

tacattaaac cttttctaaa aattgtaaat agaaaaataa tttggttttt    2250

tatcaagaac aacacttatc gttatgtatt gtgttagtta tattgccagt    2300

ctgttgcgac tgactcaaaa agttaaatgt tgccactgct gaagatgatt    2350

atgagcatcg caaactttgt ttctgaccca ttttgacagt ttttatatac    2400

tcctttaaaa tgatgaatgt tacaggttaa taaagttaat acctttaaa    2449
```

```
<210> SEQ ID NO 62
<211> LENGTH: 592
<212> TYPE: PRT
<213> ORGANISM: Homo sapiens

<400> SEQUENCE: 62

Met Ser Ser Lys Met Val Ile Ser Glu Pro Gly Leu Asn Trp Asp
  1               5                  10                  15

Ile Ser Pro Lys Asn Gly Leu Lys Thr Phe Phe Ser Arg Glu Asn
                 20                  25                  30

Tyr Lys Asp His Ser Met Ala Pro Ser Leu Lys Glu Leu Arg Val
                 35                  40                  45

Leu Ser Asn Arg Arg Ile Gly Glu Asn Leu Asn Ala Ser Ala Ser
                 50                  55                  60

Ser Val Glu Asn Glu Pro Ala Val Ser Ser Ala Thr Gln Ala Lys
                 65                  70                  75

Glu Lys Val Lys Thr Thr Ile Gly Met Val Leu Leu Pro Lys Pro
```

-continued

```
                80                  85                  90

Arg Val Pro Tyr Pro Arg Phe Ser Arg Phe Ser Gln Arg Glu Gln
                95                  100                 105

Arg Ser Tyr Val Asp Leu Leu Val Lys Tyr Ala Lys Ile Pro Ala
                110                 115                 120

Asn Ser Lys Ala Val Gly Ile Asn Lys Asn Asp Tyr Leu Gln Tyr
                125                 130                 135

Leu Asp Met Lys Lys His Val Asn Glu Glu Val Thr Glu Phe Leu
                140                 145                 150

Lys Phe Leu Gln Asn Ser Ala Lys Lys Cys Ala Gln Asp Tyr Asn
                155                 160                 165

Met Leu Ser Asp Asp Ala Arg Leu Phe Thr Glu Lys Ile Leu Arg
                170                 175                 180

Ala Cys Ile Glu Gln Val Lys Lys Tyr Ser Glu Phe Tyr Thr Leu
                185                 190                 195

His Glu Val Thr Ser Leu Met Gly Phe Phe Pro Phe Arg Val Glu
                200                 205                 210

Met Gly Leu Lys Leu Glu Lys Thr Leu Leu Ala Leu Gly Ser Val
                215                 220                 225

Lys Tyr Val Lys Thr Val Phe Pro Ser Met Pro Ile Lys Leu Gln
                230                 235                 240

Leu Ser Lys Asp Asp Ile Ala Thr Ile Glu Thr Ser Glu Gln Thr
                245                 250                 255

Ala Glu Ala Met His Tyr Asp Ile Ser Lys Asp Pro Asn Ala Glu
                260                 265                 270

Lys Leu Val Ser Arg Tyr His Pro Gln Ile Ala Leu Thr Ser Gln
                275                 280                 285

Ser Leu Phe Thr Leu Leu Asn Asn His Gly Pro Thr Tyr Lys Glu
                290                 295                 300

Gln Trp Glu Ile Pro Val Cys Ile Gln Val Ile Pro Val Ala Gly
                305                 310                 315

Ser Lys Pro Val Lys Val Ile Tyr Ile Asn Ser Pro Leu Pro Gln
                320                 325                 330

Lys Lys Met Thr Met Arg Glu Arg Asn Gln Ile Phe His Glu Val
                335                 340                 345

Pro Leu Lys Phe Met Met Ser Lys Asn Thr Ser Val Pro Val Ser
                350                 355                 360

Ala Val Phe Met Asp Lys Pro Glu Glu Phe Ile Ser Glu Met Asp
                365                 370                 375

Met Ser Cys Glu Val Asn Glu Cys Arg Lys Ile Glu Ser Leu Glu
                380                 385                 390

Asn Leu Tyr Leu Asp Phe Asp Asp Asp Val Thr Glu Leu Glu Thr
                395                 400                 405

Phe Gly Val Thr Thr Thr Lys Val Ser Lys Ser Pro Ser Pro Ala
                410                 415                 420

Ser Thr Ser Thr Val Pro Asn Met Thr Asp Ala Pro Thr Ala Pro
                425                 430                 435

Lys Ala Gly Thr Thr Thr Val Ala Pro Ser Ala Pro Asp Ile Ser
                440                 445                 450

Ala Asn Ser Arg Ser Leu Ser Gln Ile Leu Met Glu Gln Leu Gln
                455                 460                 465

Lys Glu Lys Gln Leu Val Thr Gly Met Asp Gly Gly Pro Glu Glu
                470                 475                 480
```

-continued

Cys Lys Asn Lys Asp Asp Gln Gly Phe Glu Ser Cys Glu Lys Val
485 490 495

Ser Asn Ser Asp Lys Pro Leu Ile Gln Asp Ser Asp Leu Lys Thr
500 505 510

Ser Asp Ala Leu Gln Leu Glu Asn Ser Gln Glu Ile Glu Thr Ser
515 520 525

Asn Lys Asn Asp Met Thr Ile Asp Ile Leu His Ala Asp Gly Glu
530 535 540

Arg Pro Asn Val Leu Glu Asn Leu Asp Asn Ser Lys Glu Lys Thr
545 550 555

Val Gly Ser Glu Ala Ala Lys Thr Glu Asp Thr Val Leu Cys Ser
560 565 570

Ser Asp Thr Asp Glu Glu Cys Leu Ile Ile Asp Thr Glu Cys Lys
575 580 585

Lys Thr Ser Tyr Asn Ser Val
590

<210> SEQ ID NO 63
<211> LENGTH: 1451
<212> TYPE: DNA
<213> ORGANISM: Homo sapiens

<400> SEQUENCE: 63
tttttaactt gaacttccaa ggccacgtgc gtctcctggc tcctgcacgg 50
actgtgtgac tgtccccgac agctttcctg tctcgtctca tgaggggtcc 100
agcacatggc attctgggtc ggcacctgaa gtccacctct atgagaccct 150
ctgggagcgt gacggggcct tggcatgggt cggccgaggc ccttctgtcc 200
caggtcactg gtgtggtcgg cccaggccct cctgtcccac atcacctgtg 250
tggtcggccc aggccctcct gtcccaggtc accggtgtgg tcggcccagg 300
ccctcctgtc caggtcctcc tgtccaggtc actggtgtgg tcggcccagg 350
cccttctgtc ccaggtcacc tgtgtggtcg gcccagggcc ctcctgtacc 400
atgtcactgt tgaggggctg gctctggaag agggcaggga cttggcattg 450
gtgggggcag ggttccaagg tgtggcctgt cagcaggaag ggcaggtgg 500 catgggtcca ggcgggactc agggctgggg tgccactgct ggagactgtc 550
cggaggcccc tccagggcac cttgccattg ccattgtcgc tcatggccat 600
ctggtcccgt ttcagggaac aagaggagga tcagatgctg cgggacatga 650
ttgagaagct gggtgactgg gccggggatg ctgagggctg ggctggctgg 700
ctgggtgggc cggggatgct gagtgctggg ctggctggct gggtggaccg 750
ggcctccagc tgggggtggg gggggggcgg gtatcgggtc ccccccctcag 800 ccttggtgac aggacaggca ggttcaccct gagggtgaga gctccctccc 850
gcccctaaga gagccagggg cagctggtga ccgtgtggtc atggtgggga 900
ccagccctcc ggggcaccca gtcggggcag gttctcacgt gggagggcac 950
agggcttcct gcaggctcgg aggcccaggg cggattgtgg ccagtggaag 1000
ggaaggatgt ttctggcagg gggacttgtg tgggccacgg ctgtgcggct 1050
gcggcgttga gcacggcctc actgtccacc tgtcccctag gcctccagag 1100
gaagaagtcc aagttccgct tgtccaagat ctggtcacca aaaagcaaaa 1150

-continued

```
gcagcccctc ccagtagtag ccagtagggc cgtgggctcg gcccggacct      1200

ggcatccgga cttggactcg gggccatggg cttggcccgg acccggaacc      1250

cggacttgta ctcggggccg tgggctcggc ccggacccgg cattcggact      1300

tggactcggg aagggcctcc tgtccctaca aggggcatgt ggacagcagg      1350

gacctgcgct accgtctgtg gtctcaataa agaaaccgac cacatggccc      1400

cggaaaaaaa aaaaaaaaaa aaaaaaaaaa aaaaaaaaaa aaaaaaaaac      1450

a                                                           1451
```

<210> SEQ ID NO 64
<211> LENGTH: 159
<212> TYPE: PRT
<213> ORGANISM: Homo sapiens

<400> SEQUENCE: 64

```
Met Gly Arg Pro Arg Pro Phe Cys Pro Arg Ser Leu Val Trp Ser
  1               5                  10                  15

Ala Gln Ala Leu Leu Ser His Ile Thr Cys Val Val Gly Pro Gly
                 20                  25                  30

Pro Pro Val Pro Gly His Arg Cys Gly Arg Pro Arg Pro Ser Cys
                 35                  40                  45

Pro Gly Pro Pro Val Gln Val Thr Gly Val Val Gly Pro Gly Pro
                 50                  55                  60

Ser Val Pro Gly His Leu Cys Gly Arg Pro Arg Ala Leu Leu Tyr
                 65                  70                  75

His Val Thr Val Glu Gly Leu Ala Leu Glu Glu Gly Arg Asp Leu
                 80                  85                  90

Ala Leu Val Gly Ala Gly Phe Gln Gly Val Ala Cys Gln Gln Glu
                 95                 100                 105

Gly Ala Gly Gly Met Gly Pro Gly Gly Thr Gln Gly Trp Gly Ala
                110                 115                 120

Thr Ala Gly Asp Cys Pro Glu Ala Pro Pro Gly His Leu Ala Ile
                125                 130                 135

Ala Ile Val Ala His Gly His Leu Val Pro Phe Gln Gly Thr Arg
                140                 145                 150

Gly Gly Ser Asp Ala Ala Gly His Asp
                155
```

<210> SEQ ID NO 65
<211> LENGTH: 1629
<212> TYPE: DNA
<213> ORGANISM: Homo sapiens

<400> SEQUENCE: 65

```
ggcgaccacc gccgcctcct cacctggcca ttggtgcagc ccgttcccgg        50

cggcgagaga aggcaggcgc gctccttgcg ccacgccaca ccgtcgggcc       100

cccgtcgggt ccccctcggg ccgcaatggt gggctccgcg cggctgggtc       150

cggcactctt gaccccettt gtaaccaccg cggcgggcac ccagggagtt       200

cgagcaacga agttggtgac ctgccccgct cccaggcagt ttgctgttgg       250

ggctttcacg gctgctggaa gggcatggct gtttgtccca tcactgggcg       300

ccagcttctc aaagctacgt tcacagcaac gcagtaggga ctttcgtggc       350

aggctttttt taagagctga aagaagggcg ggagggttta cgtcctaggg       400
```

-continued

```
tgatgatttc ctcaccagac agcgaagtat ctattgggaa actccaggtg         450

accgcacctc cttccgacag ttcgccccgg ggcaagttta ccagctgcgt         500

cagaaagcag gtttgcaaaa tccttggaga acggcctgag ctaaggactg         550

gggtcaggag ggttttaaac tcattctgat tttcttgcaa tcatatctct         600

tgaaagtttt tatattttcc ccaatatttt tctgagttgc tatatccaat         650

gaaaacaatg ctgatgtaga ggtccaccag ccaatgcttt attggaagtc         700

aacgaatgag accgagggtg gcccataatc aatctcggca cgcgggaatg         750

tgaacctctt ccaaggtctg ggcgagtccc tagagttacg cagatgaagg         800

acattggccc tcgagaatct cacaccagca aagaagagca caacgaagcg         850

caaactactt atgatcattg tggctttggg caagttgttg tagctcccag         900

caacaatttc ttcacctgga gtgcagcaat aaatgatact ggtgctgcag         950

ggcagctaat aagcttctga ataatatatg caaagtactt ggcaccatga        1000

gcagaactca gtataccgtc actgaagaaa tagcttattt aatgattaca        1050

cttttcatat gtgcaagtaa aagtttgact tttagggaga gcctcaccta        1100

cggaatgtct tttttaaatt tctttttaa ttatacttta agttctggga         1150

tacatgtgca gaacgtgcag gtttgttaca caggtataca tgtgccatgg        1200

tggtttgcag cacccatcaa cccttcatct aggttttaag ctccgcatgc        1250

attagttatt tgtcctaatg ctctccctcc ccttgtcccc caccccccaa        1300

caggcctcag ggtgtgatgt tcccctccct gggtccatat gttctcattg        1350

ttcaactccc acttatgatg agaacatgca gtgtttggtt ttctgttcct        1400

gtgttagttt gctgagaatg atggtttcca gcatcatcca cgtccctgca        1450

aaggacatga attcattctt ttttatggct gcatggtatt ccatggtgta        1500

tatgtgccac attttcttca tccagtctat cattgatggg cacttgggtt        1550

ggttccaaga ctttgttatt gtgaacagtg ctgcaataaa catacgtttg        1600

tatgtgtcaa aaaaaaaaaa  aaaaaaaaa                              1629
```

<210> SEQ ID NO 66
<211> LENGTH: 90
<212> TYPE: PRT
<213> ORGANISM: Homo sapiens

<400> SEQUENCE: 66

```
Met Val Gly Ser Ala Arg Leu Gly Pro Ala Leu Leu Thr Pro Phe
  1               5                  10                  15

Val Thr Thr Ala Ala Gly Thr Gln Gly Val Arg Ala Thr Lys Leu
                 20                  25                  30

Val Thr Cys Pro Ala Pro Arg Gln Phe Ala Val Gly Ala Phe Thr
                 35                  40                  45

Ala Ala Gly Arg Ala Trp Leu Phe Val Pro Ser Leu Gly Ala Ser
                 50                  55                  60

Phe Ser Lys Leu Arg Ser Gln Gln Arg Ser Arg Asp Phe Arg Gly
                 65                  70                  75

Arg Leu Phe Leu Arg Ala Glu Arg Arg Ala Gly Gly Phe Thr Ser
                 80                  85                  90
```

<210> SEQ ID NO 67
<211> LENGTH: 2067

-continued

<212> TYPE: DNA
<213> ORGANISM: Homo sapiens

<400> SEQUENCE: 67

```
catgtctaga ctgggagccc tgggtggtgc ccgtgccggg ctgggactgt     50
tgctgggtac cgccgccggc cttggattcc tgtgcctcct ttacagccag    100
cgatggaaac ggacccagcg tcatggccgc agccagagcc tgcccaactc    150
cctggactat acgcagactt cagatcccgg acgccacgtg atgctcctgc    200
gggctgtccc aggtggggct ggagatgcct cagtgctgcc cagccttcca    250
cgggaaggac aggagaaggt gctggaccgc ctggactttg tgctgaccag    300
ccttgtggcg ctgcggcggg aggtggagga gctgagaagc agcctgcgag    350
ggcttgcggg ggagattgtt ggggaggtcc gatgccacat ggaagagaac    400
cagagagtgg ctcggcggcg aaggtttccg tttgtccggg agaggagtga    450
ctccactggc tccagctctg tctacttcac ggcctcctcg ggagccacgt    500
tcacagatgc tgagagtgaa gggggttaca caacagccaa tgcggagtct    550
gacaatgagc gggactctga caaagaaagt gaggacgggg aagatgaagt    600
gagctgtgag actgtgaaga tggggagaaa ggattctctt gacttggagg    650
aagaggcagc ttcaggtgcc tccagtgccc tggaggctgg aggttcctca    700
ggcttggagg atgtgctgcc cctcctgcag caggccgacg agctgcacag    750
gggtgatgag caaggcaagc gggagggctt ccagctgctg ctcaacaaca    800
agctggtgta tggaagccgg caggactttc tctggcgcct ggcccgagcc    850
tacagtgaca tgtgtgagct cactgaggag gtgagcgaga agaagtcata    900
tgccctagat ggaaaagaag aagcagaggc tgctctggag aagggggatg    950
agagtgctga ctgtcacctg tggtatgcgg tgctttgtgg tcagctggct   1000
gagcatgaga gcatccagag gcgcatccag agtggcttta gcttcaagga   1050
gcatgtggac aaagccattg ctctccagcc agaaaacccc atggctcact   1100
ttcttcttgg caggtggtgc tatcaggtct ctcacctgag ctggctagaa   1150
aaaaaaactg ctacagcctt gcttgaaagc cctctcagtg ccactgtgga   1200
agatgccctc cagagcttcc taaaggctga agaactacag ccaggatttt   1250
ccaaagcagg aagggtatat atttccaagt gctacagaga actagggaaa   1300
aactctgaag ctagatggtg gatgaagttg gccctggagc tgccagatgt   1350
cacgaaggag gatttggcta tccagaagga cctggaagaa ctggaagtca   1400
ttttacgaga ctaaccacgt ttcactggcc ttcatgactt gatgccacta   1450
tttaaggtgg gggggcgggg aggctttttt ccttagacct tgctgagatc   1500
aggaaaccac acaaatctgt ctcctgggtc tgactgctac ccactaccac   1550
tccccattag ttaatttatt ctaacctcta acctaatcta gaattggggc   1600
agtactcatg gcttccgttt ctgttgttct ctcccttgag taatctctta   1650
aaaaaatcaa gattcacacc tgccccagga ttacacatgg gtagagcctg   1700
caagacctga gaccttccaa ttgctggtga ggtggatgaa cttcaaagct   1750
ataggaacaa agcacataac ttgtcacttt aatctttttc actgactaat   1800
aggactcagt acatatagtc ttaagatcat accttaccta ccaaggtaaa   1850
```

-continued

```
aagagggatc agagtggccc acagacattg ctttcttatc acctatcatg          1900

tgaattctac ctgtattcct gggctggacc acttgataac ttccagtgtc          1950

ctggcagctt ttggaatgac agcagtggta tggggtttat gatgctataa          2000

aacaatgtct gaaaagttgc ctagaatata ttttgttaca aacttgaaat          2050

aaaccaaatt  tgatgtt                                             2067


<210> SEQ ID NO 68
<211> LENGTH: 470
<212> TYPE: PRT
<213> ORGANISM: Homo sapiens

<400> SEQUENCE: 68

Met Ser Arg Leu Gly Ala Leu Gly Gly Ala Arg Ala Gly Leu Gly
  1               5                  10                  15

Leu Leu Leu Gly Thr Ala Ala Gly Leu Gly Phe Leu Cys Leu Leu
                 20                  25                  30

Tyr Ser Gln Arg Trp Lys Arg Thr Gln Arg His Gly Arg Ser Gln
                 35                  40                  45

Ser Leu Pro Asn Ser Leu Asp Tyr Thr Gln Thr Ser Asp Pro Gly
                 50                  55                  60

Arg His Val Met Leu Leu Arg Ala Val Pro Gly Gly Ala Gly Asp
                 65                  70                  75

Ala Ser Val Leu Pro Ser Leu Pro Arg Glu Gly Gln Glu Lys Val
                 80                  85                  90

Leu Asp Arg Leu Asp Phe Val Leu Thr Ser Leu Val Ala Leu Arg
                 95                 100                 105

Arg Glu Val Glu Glu Leu Arg Ser Ser Leu Arg Gly Leu Ala Gly
                110                 115                 120

Glu Ile Val Gly Glu Val Arg Cys His Met Glu Glu Asn Gln Arg
                125                 130                 135

Val Ala Arg Arg Arg Arg Phe Pro Phe Val Arg Glu Arg Ser Asp
                140                 145                 150

Ser Thr Gly Ser Ser Ser Val Tyr Phe Thr Ala Ser Ser Gly Ala
                155                 160                 165

Thr Phe Thr Asp Ala Glu Ser Glu Gly Gly Tyr Thr Thr Ala Asn
                170                 175                 180

Ala Glu Ser Asp Asn Glu Arg Asp Ser Asp Lys Glu Ser Glu Asp
                185                 190                 195

Gly Glu Asp Glu Val Ser Cys Glu Thr Val Lys Met Gly Arg Lys
                200                 205                 210

Asp Ser Leu Asp Leu Glu Glu Glu Ala Ala Ser Gly Ala Ser Ser
                215                 220                 225

Ala Leu Glu Ala Gly Gly Ser Ser Gly Leu Glu Asp Val Leu Pro
                230                 235                 240

Leu Leu Gln Gln Ala Asp Glu Leu His Arg Gly Asp Glu Gln Gly
                245                 250                 255

Lys Arg Glu Gly Phe Gln Leu Leu Leu Asn Asn Lys Leu Val Tyr
                260                 265                 270

Gly Ser Arg Gln Asp Phe Leu Trp Arg Leu Ala Arg Ala Tyr Ser
                275                 280                 285

Asp Met Cys Glu Leu Thr Glu Glu Val Ser Glu Lys Lys Ser Tyr
                290                 295                 300

Ala Leu Asp Gly Lys Glu Glu Ala Glu Ala Ala Leu Glu Lys Gly
```

-continued

```
                305                 310                 315

Asp Glu Ser Ala Asp Cys His Leu Trp Tyr Ala Val Leu Cys Gly
                320                 325                 330

Gln Leu Ala Glu His Glu Ser Ile Gln Arg Arg Ile Gln Ser Gly
                335                 340                 345

Phe Ser Phe Lys Glu His Val Asp Lys Ala Ile Ala Leu Gln Pro
                350                 355                 360

Glu Asn Pro Met Ala His Phe Leu Leu Gly Arg Trp Cys Tyr Gln
                365                 370                 375

Val Ser His Leu Ser Trp Leu Glu Lys Lys Thr Ala Thr Ala Leu
                380                 385                 390

Leu Glu Ser Pro Leu Ser Ala Thr Val Glu Asp Ala Leu Gln Ser
                395                 400                 405

Phe Leu Lys Ala Glu Glu Leu Gln Pro Gly Phe Ser Lys Ala Gly
                410                 415                 420

Arg Val Tyr Ile Ser Lys Cys Tyr Arg Glu Leu Gly Lys Asn Ser
                425                 430                 435

Glu Ala Arg Trp Trp Met Lys Leu Ala Leu Glu Leu Pro Asp Val
                440                 445                 450

Thr Lys Glu Asp Leu Ala Ile Gln Lys Asp Leu Glu Glu Leu Glu
                455                 460                 465

Val Ile Leu Arg Asp
                470


<210> SEQ ID NO 69
<211> LENGTH: 2250
<212> TYPE: DNA
<213> ORGANISM: Homo sapiens

<400> SEQUENCE: 69

cccacgcgtc cgaaacactt taaacctgac cagctaaatg gataaaccta          50

gcctgcatag cttttaaact ggggtctcat acagcacagg aggcctactt         100

gcttcaagaa ctgaaaatcc agaggatgaa ttgctttatc tgggaatggc         150

aaaagccagc acaataagga atgccagttt gtatggggct actagctcac         200

atgcgggatc agaatggtgt gaatgacagc cgcactgtgt catgaaggtg         250

gtggtggttt ccgcacaaga gaccaaataa gaagaaagct gagagagggg         300

ggaaacgttt ttggatgaca aaggatgggt ttccatttaa ttacgcagct         350

gaaaggcatg agtgtggtgc tggtgctact tcctacactg ctgcttgtta         400

tgctcacggg tgctcagaga gcttgcccaa agaactgcag atgtgatggc         450

aaaattgtgt actgtgagtc tcatgctttc gcagatatcc ctgagaacat         500

ttctggaggg tcacaaggct tatcattaag gttcaacagc attcagaagc         550

tcaaatccaa tcagtttgcc ggccttaacc agcttatatg gctttatctt         600

gaccataatt acattagctc agtggatgaa gatgcatttc aagggatccg         650

tagactgaaa gaattaattc taagctccaa caaaattact tatctgcaca         700

ataaaacatt tcacccagtt cccaatctcc gcaatctgga cctctcctac         750

aataagcttc agacattgca atctgaacaa tttaaaggcc ttcggaaact         800

catcatttg cacttgagat ctaactcact aaagactgtg cccataagag         850

tttttcaaga ctgtcggaat cttgattttt tggatttggg ttacaatcgt         900
```

-continued

```
cttcgaagct tgtcccgaaa tgcatttgct ggcctcttga agttaaagga            950

gctccacctg gagcacaacc agttttccaa gatcaacttt gctcattttc           1000

cacgtctctt caacctccgc tcaatttact tacaatggaa caggattcgc           1050

tccattagcc aaggtttgac atggacttgg agttccttac acaacttgga           1100

tttatcaggg aatgacatcc aaggaattga gccgggcaca tttaaatgcc           1150

tccccaattt acaaaaattg aatttggatt ccaacaagct caccaatatc           1200

tcacaggaaa ctgtcaatgc gtggatatca ttaatatcca tcacattgtc           1250

tggaaatatg tgggaatgca gtcggagcat ttgtccttta ttttattggc           1300

ttaagaattt caaaggaaat aaggaaagca ccatgatatg tgcgggacct           1350

aagcacatcc agggtgaaaa ggttagtgat gcagtggaaa catataatat           1400

ctgttctgaa gtccaggtgg tcaacacaga aagatcacac ctggtgcccc           1450

aaactcccca gaaacctctg attatcccta gacctaccat cttcaaacct           1500

gacgtcaccc aatccacctt tgaaacacca agcccttccc cagggtttca           1550

gattcctggc gcagagcaag agtatgagca tgtttcattt cacaaaatta           1600

ttgccgggag tgtggctctc tttctctcag tggccatgat cctcttggtg           1650

atctatgtgt cttggaaacg ctacccagcc agcatgaaac aactccagca           1700

acactctctt atgaagaggc ggcggaaaaa ggccagagag tctgaaagac           1750

aaatgaattc ccctttacag gagtattatg tggactacaa gcctacaaac           1800

tctgagacca tggatatatc ggttaatgga tctgggccct gcacatatac           1850

catctctggc tccagggaat gtgagatgcc acaccacatg aagcccttgc           1900

catattacag ctatgaccag cctgtgatcg ggtactgcca ggcccaccag           1950

ccactccatg tcaccaaggg ctatgagaca gtgtctccag agcaggacga           2000

aagccccggc ctggagctgg gccgagacca cagcttcatc gccaccatcg           2050

ccaggtcggc agcaccggcc atctacctag agagaattgc aaactaacgc           2100

tgaagccaac tcctcactgg ggagctccat ggggggggagg gagggccttc          2150

atcttaaagg agaatgggtg tccacaatcg cgcaatcgag caagctcatc           2200

gttcctgtta aaacatttat ggcataggga aaaaaaaaaa aaaaaaaaaa           2250


<210> SEQ ID NO 70
<211> LENGTH: 590
<212> TYPE: PRT
<213> ORGANISM: Homo sapiens

<400> SEQUENCE: 70

Met Gly Phe His Leu Ile Thr Gln Leu Lys Gly Met Ser Val Val
  1               5                  10                  15

Leu Val Leu Leu Pro Thr Leu Leu Leu Val Met Leu Thr Gly Ala
                 20                  25                  30

Gln Arg Ala Cys Pro Lys Asn Cys Arg Cys Asp Gly Lys Ile Val
                 35                  40                  45

Tyr Cys Glu Ser His Ala Phe Ala Asp Ile Pro Glu Asn Ile Ser
                 50                  55                  60

Gly Gly Ser Gln Gly Leu Ser Leu Arg Phe Asn Ser Ile Gln Lys
                 65                  70                  75

Leu Lys Ser Asn Gln Phe Ala Gly Leu Asn Gln Leu Ile Trp Leu
                 80                  85                  90
```

-continued

```
Tyr Leu Asp His Asn Tyr Ile Ser Ser Val Asp Glu Asp Ala Phe
                95                  100                 105

Gln Gly Ile Arg Arg Leu Lys Glu Leu Ile Leu Ser Ser Asn Lys
                110                 115                 120

Ile Thr Tyr Leu His Asn Lys Thr Phe His Pro Val Pro Asn Leu
                125                 130                 135

Arg Asn Leu Asp Leu Ser Tyr Asn Lys Leu Gln Thr Leu Gln Ser
                140                 145                 150

Glu Gln Phe Lys Gly Leu Arg Lys Leu Ile Ile Leu His Leu Arg
                155                 160                 165

Ser Asn Ser Leu Lys Thr Val Pro Ile Arg Val Phe Gln Asp Cys
                170                 175                 180

Arg Asn Leu Asp Phe Leu Asp Leu Gly Tyr Asn Arg Leu Arg Ser
                185                 190                 195

Leu Ser Arg Asn Ala Phe Ala Gly Leu Leu Lys Leu Lys Glu Leu
                200                 205                 210

His Leu Glu His Asn Gln Phe Ser Lys Ile Asn Phe Ala His Phe
                215                 220                 225

Pro Arg Leu Phe Asn Leu Arg Ser Ile Tyr Leu Gln Trp Asn Arg
                230                 235                 240

Ile Arg Ser Ile Ser Gln Gly Leu Thr Trp Thr Trp Ser Ser Leu
                245                 250                 255

His Asn Leu Asp Leu Ser Gly Asn Asp Ile Gln Gly Ile Glu Pro
                260                 265                 270

Gly Thr Phe Lys Cys Leu Pro Asn Leu Gln Lys Leu Asn Leu Asp
                275                 280                 285

Ser Asn Lys Leu Thr Asn Ile Ser Gln Glu Thr Val Asn Ala Trp
                290                 295                 300

Ile Ser Leu Ile Ser Ile Thr Leu Ser Gly Asn Met Trp Glu Cys
                305                 310                 315

Ser Arg Ser Ile Cys Pro Leu Phe Tyr Trp Leu Lys Asn Phe Lys
                320                 325                 330

Gly Asn Lys Glu Ser Thr Met Ile Cys Ala Gly Pro Lys His Ile
                335                 340                 345

Gln Gly Glu Lys Val Ser Asp Ala Val Glu Thr Tyr Asn Ile Cys
                350                 355                 360

Ser Glu Val Gln Val Val Asn Thr Glu Arg Ser His Leu Val Pro
                365                 370                 375

Gln Thr Pro Gln Lys Pro Leu Ile Ile Pro Arg Pro Thr Ile Phe
                380                 385                 390

Lys Pro Asp Val Thr Gln Ser Thr Phe Glu Thr Pro Ser Pro Ser
                395                 400                 405

Pro Gly Phe Gln Ile Pro Gly Ala Glu Gln Glu Tyr Glu His Val
                410                 415                 420

Ser Phe His Lys Ile Ile Ala Gly Ser Val Ala Leu Phe Leu Ser
                425                 430                 435

Val Ala Met Ile Leu Leu Val Ile Tyr Val Ser Trp Lys Arg Tyr
                440                 445                 450

Pro Ala Ser Met Lys Gln Leu Gln Gln His Ser Leu Met Lys Arg
                455                 460                 465

Arg Arg Lys Lys Ala Arg Glu Ser Glu Arg Gln Met Asn Ser Pro
                470                 475                 480
```

-continued

Leu Gln Glu Tyr Tyr Val Asp Tyr Lys Pro Thr Asn Ser Glu Thr
485 490 495

Met Asp Ile Ser Val Asn Gly Ser Gly Pro Cys Thr Tyr Thr Ile
500 505 510

Ser Gly Ser Arg Glu Cys Glu Met Pro His His Met Lys Pro Leu
515 520 525

Pro Tyr Tyr Ser Tyr Asp Gln Pro Val Ile Gly Tyr Cys Gln Ala
530 535 540

His Gln Pro Leu His Val Thr Lys Gly Tyr Glu Thr Val Ser Pro
545 550 555

Glu Gln Asp Glu Ser Pro Gly Leu Glu Leu Gly Arg Asp His Ser
560 565 570

Phe Ile Ala Thr Ile Ala Arg Ser Ala Ala Pro Ala Ile Tyr Leu
575 580 585

Glu Arg Ile Ala Asn
590

<210> SEQ ID NO 71
<211> LENGTH: 521
<212> TYPE: DNA
<213> ORGANISM: Homo sapiens

<400> SEQUENCE: 71
ttccagtcag agttaagtta aaacagaaaa aaggaagatg gcaagaatat 50
tgttactttt cctcccgggt cttgtggctg tatgtgctgt gcatggaata 100
tttatggacc gtctagcttc caagaagctc tgtgcagatg atgagtgtgt 150
ctatactatt tctctggcta gtgctcaaga agattataat gccccggact 200
gtagattcat taacgttaaa aaagggcagc agatctatgt gtactcaaag 250
ctggtaaaag aaaatggagc tggagaattt tgggctggca gtgtttatgg 300
tgatggccag gacgagatgg gagtcgtggg ttatttcccc aggaacttgg 350
tcaaggaaca gcgtgtgtac caggaagcta ccaaggaagt tcccaccacg 400
gatattgact tcttctgcga gtaataaatt agttaaaact gcaaatagaa 450
agaaaacacc aaaaataaag aaaagagcaa aagtggccaa aaaatgcatg 500
tctgtaattt tggactgacg t 521

<210> SEQ ID NO 72
<211> LENGTH: 128
<212> TYPE: PRT
<213> ORGANISM: Homo sapiens

<400> SEQUENCE: 72

Met Ala Arg Ile Leu Leu Leu Phe Leu Pro Gly Leu Val Ala Val
1 5 10 15

Cys Ala Val His Gly Ile Phe Met Asp Arg Leu Ala Ser Lys Lys
20 25 30

Leu Cys Ala Asp Asp Glu Cys Val Tyr Thr Ile Ser Leu Ala Ser
35 40 45

Ala Gln Glu Asp Tyr Asn Ala Pro Asp Cys Arg Phe Ile Asn Val
50 55 60

Lys Lys Gly Gln Gln Ile Tyr Val Tyr Ser Lys Leu Val Lys Glu
65 70 75

Asn Gly Ala Gly Glu Phe Trp Ala Gly Ser Val Tyr Gly Asp Gly
80 85 90

-continued

Gln Asp Glu Met Gly Val Val Gly Tyr Phe Pro Arg Asn Leu Val
                95                  100                 105

Lys Glu Gln Arg Val Tyr Gln Glu Ala Thr Lys Glu Val Pro Thr
                110                 115                 120

Thr Asp Ile Asp Phe Phe Cys Glu
                125

<210> SEQ ID NO 73
<211> LENGTH: 720
<212> TYPE: DNA
<213> ORGANISM: Homo sapiens

<400> SEQUENCE: 73
ctcagatttg ccatggagaa attttcagtc tcggcaatcc tgcttcttgt 50
ggccatctct ggtactctgg ccaaagacac cacagtcaaa tctggatcca 100
aaaaggaccc aaaggactct cgacccaaac taccccagac cctgtccaga 150
ggttggggag atcagctcat ctggactcag acttacgaag aagccttata 200
caaatccaag acaagcaaca gacccttgat ggtcattcat cacttggacg 250
aatgcccgca cagtcaagct ttaaagaaag tgtttgctga aaataaggag 300
atccagaaat tggcagagca gtttgttctc ctcaacttga tctatgaaac 350
aactgacaag cacctttctc ctgatggcca gtacgtcccc agaattgtgt 400
ttgtggaccc ttccctgacg gtgagggcag acatcaccgg aagatactca 450
aaccgtctct acgcttatga accttctgac acagctctgt tgcacgacaa 500
catgaagaaa gctctcaagt tgctgaagac agagttgtag agtcaactgt 550
acagtgcctc aggagccggg aaggcagaag cactgtggac ctgccgatga 600
cattacagtt taatgttaca acaaatgtat tttttaaaca cccacgtgtg 650
gggaaacaat attattatct actacagaca catgattttc tagaaaataa 700
agtcttgtga gaactccaaa 720

<210> SEQ ID NO 74
<211> LENGTH: 175
<212> TYPE: PRT
<213> ORGANISM: Homo sapiens

<400> SEQUENCE: 74

Met Glu Lys Phe Ser Val Ser Ala Ile Leu Leu Leu Val Ala Ile
  1             5                   10                  15

Ser Gly Thr Leu Ala Lys Asp Thr Thr Val Lys Ser Gly Ser Lys
                20                  25                  30

Lys Asp Pro Lys Asp Ser Arg Pro Lys Leu Pro Gln Thr Leu Ser
                35                  40                  45

Arg Gly Trp Gly Asp Gln Leu Ile Trp Thr Gln Thr Tyr Glu Glu
                50                  55                  60

Ala Leu Tyr Lys Ser Lys Thr Ser Asn Arg Pro Leu Met Val Ile
                65                  70                  75

His His Leu Asp Glu Cys Pro His Ser Gln Ala Leu Lys Lys Val
                80                  85                  90

Phe Ala Glu Asn Lys Glu Ile Gln Lys Leu Ala Glu Gln Phe Val
                95                  100                 105

Leu Leu Asn Leu Ile Tyr Glu Thr Thr Asp Lys His Leu Ser Pro
                110                 115                 120

```
Asp Gly Gln Tyr Val Pro Arg Ile Val Phe Val Asp Pro Ser Leu
                125                 130                 135

Thr Val Arg Ala Asp Ile Thr Gly Arg Tyr Ser Asn Arg Leu Tyr
                140                 145                 150

Ala Tyr Glu Pro Ser Asp Thr Ala Leu Leu His Asp Asn Met Lys
                155                 160                 165

Lys Ala Leu Lys Leu Leu Lys Thr Glu Leu
                170                 175


<210> SEQ ID NO 75
<211> LENGTH: 776
<212> TYPE: DNA
<213> ORGANISM: Homo sapiens

<400> SEQUENCE: 75

gccggcgcca gggcaggcgg gcggctggca gctgtggcgc cgacatggct          50

gcgctggtgg agccgctggg gctggagcgg gacgtgtccc gggcggttga         100

gctcctcgag cggctccagc gcagcgggga gctgccgccg cagaagctgc         150

aggccctcca gcgagttctg cagagccgct tctgctccgc tatccgagag         200

gtgtatgagc agctttatga cacgctggac atcaccggca gcgccgagat         250

ccgagcccat gccacagcca aggccacagt ggctgccttc acagccagcg         300

agggccacgc acatcccagg gtagtggagc tacccaagac ggatgagggc         350

ctaggcttca acatcatggg tggcaaagag caaaactcgc ccatctacat         400

ctcccgggtc atcccagggg gtgtggctga ccgccatgga ggcctcaagc         450

gtggggatca actgttgtcg gtgaacggtg tgagcgttga gggtgagcag         500

catgagaagg cggtggagct gctgaaggcg gcccagggct cggtgaagct         550

ggttgtccgt tacacaccgc gagtgctgga ggagatggag gcccggttcg         600

agaagatgcg ctctgcccgc cggcgccaac agcatcagag ctactcgtcc         650

ttggagtctc gaggttgaaa ccacagatct ggacgttcac gtgcactctc         700

ttcctgtaca gtatttattg ttcctggcac tttatttaaa gatatttgac         750

cctcaaaaaa aaaaaaaaaa  aaaaaa                                  776


<210> SEQ ID NO 76
<211> LENGTH: 207
<212> TYPE: PRT
<213> ORGANISM: Homo sapiens

<400> SEQUENCE: 76

Met Ala Ala Leu Val Glu Pro Leu Gly Leu Glu Arg Asp Val Ser
  1               5                  10                  15

Arg Ala Val Glu Leu Leu Glu Arg Leu Gln Arg Ser Gly Glu Leu
                 20                  25                  30

Pro Pro Gln Lys Leu Gln Ala Leu Gln Arg Val Leu Gln Ser Arg
                 35                  40                  45

Phe Cys Ser Ala Ile Arg Glu Val Tyr Glu Gln Leu Tyr Asp Thr
                 50                  55                  60

Leu Asp Ile Thr Gly Ser Ala Glu Ile Arg Ala His Ala Thr Ala
                 65                  70                  75

Lys Ala Thr Val Ala Ala Phe Thr Ala Ser Glu Gly His Ala His
                 80                  85                  90
```

-continued

```
Pro Arg Val Val Glu Leu Pro Lys Thr Asp Glu Gly Leu Gly Phe
                95                  100                 105

Asn Ile Met Gly Gly Lys Glu Gln Asn Ser Pro Ile Tyr Ile Ser
                110                 115                 120

Arg Val Ile Pro Gly Gly Val Ala Asp Arg His Gly Gly Leu Lys
                125                 130                 135

Arg Gly Asp Gln Leu Leu Ser Val Asn Gly Val Ser Val Glu Gly
                140                 145                 150

Glu Gln His Glu Lys Ala Val Glu Leu Leu Lys Ala Ala Gln Gly
                155                 160                 165

Ser Val Lys Leu Val Val Arg Tyr Thr Pro Arg Val Leu Glu Glu
                170                 175                 180

Met Glu Ala Arg Phe Glu Lys Met Arg Ser Ala Arg Arg Arg Gln
                185                 190                 195

Gln His Gln Ser Tyr Ser Ser Leu Glu Ser Arg Gly
                200                 205


<210> SEQ ID NO 77
<211> LENGTH: 939
<212> TYPE: DNA
<213> ORGANISM: Homo sapiens

<400> SEQUENCE: 77

ctgtcagctg aggatccagc cgaaagagga gccaggcact caggccacct          50

gagtctactc acctggacaa ctggaatctg gcaccaattc taaaccactc         100

agcttctccg agctcacacc ccggagatca cctgaggacc cgagccattg         150

atggactcgg acgagaccgg gttcgagcac tcaggactgt gggtttctgt         200

gctggctggt ctgctgggag cctgccaggc acaccccatc cctgactcca         250

gtcctctcct gcaattcggg ggccaagtcc ggcagcggta cctctacaca         300

gatgatgccc agcagacaga agcccacctg gagatcaggg aggatgggac         350

ggtgggggc gctgctgacc agagccccga aagtctcctg cagctgaaag          400

ccttgaagcc gggagttatt caaatcttgg gagtcaagac atccaggttc         450

ctgtgccagc ggccagatgg ggccctgtat ggatcgctcc actttgaccc         500

tgaggcctgc agcttccggg agctgcttct tgaggacgga tacaatgttt         550

accagtccga agcccacggc ctcccgctgc acctgccagg gaacaagtcc         600

ccacaccggg accctgcacc ccgaggacca gctcgcttcc tgccactacc         650

aggcctgccc cccgcactcc cggagccacc cggaatcctg gccccccagc         700

cccccgatgt gggctcctcg gaccctctga gcatggtggg accttcccag         750

ggccgaagcc ccagctacgc ttcctgaagc cagaggctgt ttactatgac         800

atctcctctt tatttattag gttatttatc ttatttattt ttttattttt         850

cttacttgag ataataaaga gttccagagg agaaaaaaaa aaaaaaaaaa         900

aaaaaaaaaa aaaaaaaaaa aaaaaaaaaa  aaaaaaaag                    939


<210> SEQ ID NO 78
<211> LENGTH: 208
<212> TYPE: PRT
<213> ORGANISM: Homo sapiens

<400> SEQUENCE: 78

Met Asp Ser Asp Glu Thr Gly Phe Glu His Ser Gly Leu Trp Val
```

-continued

```
1               5                   10                  15

Ser Val Leu Ala Gly Leu Leu Gly Ala Cys Gln Ala His Pro Ile
                20                  25                  30

Pro Asp Ser Ser Pro Leu Leu Gln Phe Gly Gly Gln Val Arg Gln
                35                  40                  45

Arg Tyr Leu Tyr Thr Asp Asp Ala Gln Gln Thr Glu Ala His Leu
                50                  55                  60

Glu Ile Arg Glu Asp Gly Thr Val Gly Gly Ala Ala Asp Gln Ser
                65                  70                  75

Pro Glu Ser Leu Leu Gln Leu Lys Ala Leu Lys Pro Gly Val Ile
                80                  85                  90

Gln Ile Leu Gly Val Lys Thr Ser Arg Phe Leu Cys Gln Arg Pro
                95                  100                 105

Asp Gly Ala Leu Tyr Gly Ser Leu His Phe Asp Pro Glu Ala Cys
                110                 115                 120

Ser Phe Arg Glu Leu Leu Leu Glu Asp Gly Tyr Asn Val Tyr Gln
                125                 130                 135

Ser Glu Ala His Gly Leu Pro Leu His Leu Pro Gly Asn Lys Ser
                140                 145                 150

Pro His Arg Asp Pro Ala Pro Arg Gly Pro Ala Arg Phe Leu Pro
                155                 160                 165

Leu Pro Gly Leu Pro Pro Ala Leu Pro Glu Pro Pro Gly Ile Leu
                170                 175                 180

Ala Pro Gln Pro Pro Asp Val Gly Ser Ser Asp Pro Leu Ser Met
                185                 190                 195

Val Gly Pro Ser Gln Gly Arg Ser Pro Ser Tyr Ala Ser
                200                 205


<210> SEQ ID NO 79
<211> LENGTH: 2732
<212> TYPE: DNA
<213> ORGANISM: Homo sapiens

<400> SEQUENCE: 79

agtcccagac gggcttttcc cagagagcta aaagagaagg gccagagaat        50

gtcgtcccag ccagcaggga accagacctc ccccggggcc acagaggact       100

actcctatgg cagctggtac atcgatgagc cccagggggg cgaggagctc       150

cagccagagg gggaagtgcc ctcctgccac accagcatac caccccggcct       200

gtaccacgcc tgcctggcct cgctgtcaat ccttgtgctg ctgctcctgg       250

ccatgctggt gaggcgccgc cagctctggc ctgactgtgt gcgtggcagg       300

cccggcctgc ccagccctgt ggatttcttg gctggggaca ggccccgggc       350

agtgcctgct gctgttttca tggtcctcct gagctccctg tgtttgctgc       400

tccccgacga ggacgcattg cccttcctga ctctcgcctc agcacccagc       450

caagatggga aaactgaggc tccaagaggg gcctggaaga tactgggact       500

gttctattat gctgccctct actaccctct ggctgcctgt gccacggctg       550

gccacacagc tgcacacctg ctcggcagca cgctgtcctg ggcccacctt       600

ggggtccagg tctggcagag ggcagagtgt ccccaggtgc ccaagatcta       650

caagtactac tccctgctgg cctccctgcc tctcctgctg ggcctcggat       700

tcctgagcct ttggtaccct gtgcagctgg tgagaagctt cagccgtagg       750
```

-continued

```
acaggagcag gctccaaggg gctgcagagc agctactctg aggaatatct        800
gaggaacctc ctttgcagga agaagctggg aagcagctac cacacctcca        850
agcatggctt cctgtcctgg gcccgcgtct gcttgagaca ctgcatctac        900
actccacagc caggattcca tctcccgctg aagctggtgc tttcagctac        950
actgacaggg acggccattt accaggtggc cctgctgctg ctggtgggcg       1000
tggtacccac tatccagaag gtgagggcag gggtcaccac ggatgtctcc       1050
tacctgctgg ccggctttgg aatcgtgctc tccgaggaca agcaggaggt       1100
ggtggagctg gtgaagcacc atctgtgggc tctggaagtg tgctacatct       1150
cagccttggt cttgtcctgc ttactcacct tcctggtcct gatgcgctca       1200
ctggtgacac acaggaccaa ccttcgagct ctgcaccgag gagctgccct       1250
ggacttgagt cccttgcatc ggagtcccca tccctcccgc caagccatat       1300
tctgttggat gagcttcagt gcctaccaga cagcctttat ctgccttggg       1350
ctcctggtgc agcagatcat cttcttcctg ggaaccacgg ccctggcctt       1400
cctggtgctc atgcctgtgc tccatggcag gaacctcctg ctcttccgtt       1450
ccctggagtc ctcgtggccc ttctggctga ctttggccct ggctgtgatc       1500
ctgcagaaca tggcagccca ttgggtcttc ctggagactc atgatggaca       1550
cccacagctg accaaccggc gagtgctcta tgcagccacc tttcttctct       1600
tcccccctcaa tgtgctggtg ggtgccatgg tggccacctg gcgagtgctc      1650
ctctctgccc tctacaacgc catccacctt ggccagatgg acctcagcct       1700
gctgccaccg agagccgcca ctctcgaccc cggctactac acgtaccgaa       1750
acttcttgaa gattgaagtc agccagtcgc atccagccat gacagccttc       1800
tgctccctgc tcctgcaagc gcagagcctc ctacccagga ccatggcagc       1850
cccccaggac agcctcagac caggggagga agacgaaggg atgcagctgc       1900
tacagacaaa ggactccatg gccaagggag ctaggcccgg ggccagccgc       1950
ggcagggctc gctggggtct ggcctacacg ctgctgcaca acccaaccct       2000
gcaggtcttc cgcaagacgg ccctgttggg tgccaatggt gcccagccct       2050
gagggcaggg aaggtcaacc cacctgccca tctgtgctga ggcatgttcc       2100
tgcctaccat cctcctccct ccccggctct cctcccagca tcacaccagc       2150
catgcagcca gcaggtcctc cggatcactg tggttgggtg gaggtctgtc       2200
tgcactggga gcctcaggag ggctctgctc cacccacttg gctatgggag       2250
agccagcagg ggttctggag aaaaaaactg gtgggttagg gccttggtcc       2300
aggagccagt tgagccaggg cagccacatc caggcgtctc cctaccctgg       2350
ctctgccatc agccttgaag ggcctcgatg aagccttctc tggaaccact       2400
ccagcccagc tccacctcag ccttggcctt cacgctgtgg aagcagccaa       2450
ggcacttcct caccccctca gcgccacgga cctctctggg gagtggccgg       2500
aaagctcccg gtcctctggc ctgcagggca gcccaagtca tgactcagac       2550
caggtcccac actgagctgc ccacactcga gagccagata tttttgtagt       2600
ttttatgcct ttggctatta tgaaagaggt tagtgtgttc cctgcaataa       2650
acttgttcct gagaaaaaaa aaaaaaaaaa aaaaaaaaaa aaaaaaaaaa       2700
aaaaaaaaaa aaaaaaaaaa aaaaaaaaaa  aa                         2732
```

<210> SEQ ID NO 80
<211> LENGTH: 667
<212> TYPE: PRT
<213> ORGANISM: Homo sapiens

<400> SEQUENCE: 80

```
Met Ser Ser Gln Pro Ala Gly Asn Gln Thr Ser Pro Gly Ala Thr
  1               5                  10                  15

Glu Asp Tyr Ser Tyr Gly Ser Trp Tyr Ile Asp Glu Pro Gln Gly
                 20                  25                  30

Gly Glu Glu Leu Gln Pro Glu Gly Glu Val Pro Ser Cys His Thr
                 35                  40                  45

Ser Ile Pro Pro Gly Leu Tyr His Ala Cys Leu Ala Ser Leu Ser
                 50                  55                  60

Ile Leu Val Leu Leu Leu Leu Ala Met Leu Val Arg Arg Arg Gln
                 65                  70                  75

Leu Trp Pro Asp Cys Val Arg Gly Arg Pro Gly Leu Pro Ser Pro
                 80                  85                  90

Val Asp Phe Leu Ala Gly Asp Arg Pro Arg Ala Val Pro Ala Ala
                 95                 100                 105

Val Phe Met Val Leu Leu Ser Ser Leu Cys Leu Leu Leu Pro Asp
                110                 115                 120

Glu Asp Ala Leu Pro Phe Leu Thr Leu Ala Ser Ala Pro Ser Gln
                125                 130                 135

Asp Gly Lys Thr Glu Ala Pro Arg Gly Ala Trp Lys Ile Leu Gly
                140                 145                 150

Leu Phe Tyr Tyr Ala Ala Leu Tyr Tyr Pro Leu Ala Ala Cys Ala
                155                 160                 165

Thr Ala Gly His Thr Ala Ala His Leu Leu Gly Ser Thr Leu Ser
                170                 175                 180

Trp Ala His Leu Gly Val Gln Val Trp Gln Arg Ala Glu Cys Pro
                185                 190                 195

Gln Val Pro Lys Ile Tyr Lys Tyr Tyr Ser Leu Leu Ala Ser Leu
                200                 205                 210

Pro Leu Leu Leu Gly Leu Gly Phe Leu Ser Leu Trp Tyr Pro Val
                215                 220                 225

Gln Leu Val Arg Ser Phe Ser Arg Arg Thr Gly Ala Gly Ser Lys
                230                 235                 240

Gly Leu Gln Ser Ser Tyr Ser Glu Glu Tyr Leu Arg Asn Leu Leu
                245                 250                 255

Cys Arg Lys Lys Leu Gly Ser Ser Tyr His Thr Ser Lys His Gly
                260                 265                 270

Phe Leu Ser Trp Ala Arg Val Cys Leu Arg His Cys Ile Tyr Thr
                275                 280                 285

Pro Gln Pro Gly Phe His Leu Pro Leu Lys Leu Val Leu Ser Ala
                290                 295                 300

Thr Leu Thr Gly Thr Ala Ile Tyr Gln Val Ala Leu Leu Leu Leu
                305                 310                 315

Val Gly Val Val Pro Thr Ile Gln Lys Val Arg Ala Gly Val Thr
                320                 325                 330

Thr Asp Val Ser Tyr Leu Leu Ala Gly Phe Gly Ile Val Leu Ser
                335                 340                 345

Glu Asp Lys Gln Glu Val Val Glu Leu Val Lys His His Leu Trp
```

-continued 350 355 360

Ala Leu Glu Val Cys Tyr Ile Ser Ala Leu Val Leu Ser Cys Leu
365 370 375

Leu Thr Phe Leu Val Leu Met Arg Ser Leu Val Thr His Arg Thr
380 385 390

Asn Leu Arg Ala Leu His Arg Gly Ala Ala Leu Asp Leu Ser Pro
395 400 405

Leu His Arg Ser Pro His Pro Ser Arg Gln Ala Ile Phe Cys Trp
410 415 420

Met Ser Phe Ser Ala Tyr Gln Thr Ala Phe Ile Cys Leu Gly Leu
425 430 435

Leu Val Gln Gln Ile Ile Phe Phe Leu Gly Thr Thr Ala Leu Ala
440 445 450

Phe Leu Val Leu Met Pro Val Leu His Gly Arg Asn Leu Leu Leu
455 460 465

Phe Arg Ser Leu Glu Ser Ser Trp Pro Phe Trp Leu Thr Leu Ala
470 475 480

Leu Ala Val Ile Leu Gln Asn Met Ala Ala His Trp Val Phe Leu
485 490 495

Glu Thr His Asp Gly His Pro Gln Leu Thr Asn Arg Arg Val Leu
500 505 510

Tyr Ala Ala Thr Phe Leu Leu Phe Pro Leu Asn Val Leu Val Gly
515 520 525

Ala Met Val Ala Thr Trp Arg Val Leu Leu Ser Ala Leu Tyr Asn
530 535 540

Ala Ile His Leu Gly Gln Met Asp Leu Ser Leu Leu Pro Pro Arg
545 550 555

Ala Ala Thr Leu Asp Pro Gly Tyr Tyr Thr Tyr Arg Asn Phe Leu
560 565 570

Lys Ile Glu Val Ser Gln Ser His Pro Ala Met Thr Ala Phe Cys
575 580 585

Ser Leu Leu Leu Gln Ala Gln Ser Leu Leu Pro Arg Thr Met Ala
590 595 600

Ala Pro Gln Asp Ser Leu Arg Pro Gly Glu Glu Asp Glu Gly Met
605 610 615

Gln Leu Leu Gln Thr Lys Asp Ser Met Ala Lys Gly Ala Arg Pro
620 625 630

Gly Ala Ser Arg Gly Arg Ala Arg Trp Gly Leu Ala Tyr Thr Leu
635 640 645

Leu His Asn Pro Thr Leu Gln Val Phe Arg Lys Thr Ala Leu Leu
650 655 660

Gly Ala Asn Gly Ala Gln Pro
665

<210> SEQ ID NO 81
<211> LENGTH: 1186
<212> TYPE: DNA
<213> ORGANISM: Homo sapiens

<400> SEQUENCE: 81
aaaaaataca gcaggtgaag gaggttggag agtagggggt ggagggccca 50
cgcagcactt gtccttcacc ctggagggga tctgttacat gccccagatt 100
gctggtcccc tagaaatgtt actgaggcag cctctgcatt tttgcaggga 150

-continued

```
ttgttttcta ctgtttgaca ttcacgtaac ctcctaacgc tgtctgggga      200

agatgctacc ccctgctctc cccgtctttc ctgcactctc agcaatggga      250

tgggctgact gatgccctgt gggctggaaa gctgaccaca gttgctgcag      300

accagacccc ctcacatagt gagtgctggg ctgaggaatc caggagagcc      350

cgaggggga cactgaaggt gtatcgttgg ccctgccagc tgcaagtgaa       400

ctgcttctga tgaattttaa tagggagaaa gaagtatttg ctaagaatgg      450

caatcctgac gctcagcctt caactcatct tgttattaat accatcaata      500

tcccatgagg ctcataaaac gagtctttct tcttggaaac atgaccaaga      550

ttgggcaaac gtctccaaca tgactttcag caacggaaaa ctaagagtca      600

aaggcattta ttaccggaat gccgacattt gctctcgaca tcgcgtaacc      650

tcagcaggcc taactctgca ggaccttcag ctatggtgta atttgaggtc      700

agtggccaga ggacagatcc cgtctacatt atgagtgaag cggagagcta      750

ctgcagggtt ctgagcagag tcctaattta tattttagaa gaatcatcat      800

ggctcctaga ttaggaataa aacgaagggg cccagggatg gaaacgatga      850

gtccagttgg gttactgcaa agatccaggc cagaaatcca ggcacagtgg      900

cacacacctg agtcccagat aattccacct actggtcctg ctctgtggcc      950

tactggtccg agtccagccc cgactgattt ctgggcctgt aatgtctaaa     1000

aacgctccct gctgatgttt tgcaagtgac tgtgttactt gaaggcagtt     1050

cctaggataa actagtcgct ttatcattac agaatcattc actgagcatc     1100

aactatgtaa ccagcattgg gttgggtgcc agagatccaa agctaagaca     1150

ccaaaacctg ctctccagga aacgagaggc  tgagaa                   1186
```

<210> SEQ ID NO 82
<211> LENGTH: 95
<212> TYPE: PRT
<213> ORGANISM: Homo sapiens

<400> SEQUENCE: 82

```
Met Ala Ile Leu Thr Leu Ser Leu Gln Leu Ile Leu Leu Leu Ile
  1               5                  10                  15

Pro Ser Ile Ser His Glu Ala His Lys Thr Ser Leu Ser Ser Trp
                 20                  25                  30

Lys His Asp Gln Asp Trp Ala Asn Val Ser Asn Met Thr Phe Ser
                 35                  40                  45

Asn Gly Lys Leu Arg Val Lys Gly Ile Tyr Tyr Arg Asn Ala Asp
                 50                  55                  60

Ile Cys Ser Arg His Arg Val Thr Ser Ala Gly Leu Thr Leu Gln
                 65                  70                  75

Asp Leu Gln Leu Trp Cys Asn Leu Arg Ser Val Ala Arg Gly Gln
                 80                  85                  90

Ile Pro Ser Thr Leu
                 95
```

<210> SEQ ID NO 83
<211> LENGTH: 1677
<212> TYPE: DNA
<213> ORGANISM: Homo sapiens

<400> SEQUENCE: 83

-continued

```
aatagaagtc ctcaggacgg agcagaggtg gccggcgggc ccggctgact          50

gcgcctctgc tttctttcca taaccttttc tttcggactc gaatcacggc         100

tgctgcgaag ggtctagttc cggacactag ggtgcccgaa cgcgctgatg         150

ccccgagtgc tcgcagggct tcccgctaac catgctgccg ccgccgcggc         200

ccgcagctgc cttggcgctg cctgtgctcc tgctactgct ggtggtgctg         250

acgccgcccc cgaccggcgc aaggccatcc ccaggcccag attacctgcg         300

gcgcggctgg atgcggctgc tagcggaggg cgagggctgc gctccctgcc         350

ggccagaaga gtgcgccgcg ccgcggggct gcctggcggg cagggtgcgc         400

gacgcgtgcg gctgctgctg ggaatgcgcc aacctcgagg gccagctctg         450

cgacctggac cccagtgctc acttctacgg gcactgcggc gagcagcttg         500

agtgccggct ggacacaggc ggcgacctga gccgcggaga ggtgccggaa         550

cctctgtgtg cctgtcgttc gcagagtccg ctctgcgggt ccgacggtca         600

cacctactcc cagatctgcc gcctgcagga ggcggcccgc gctcggcccg         650

atgccaacct cactgtggca cacccggggc cctgcgaatc ggggcccccag        700

atcgtgtcac atccatatga cacttggaat gtgacagggc aggatgtgat         750

ctttggctgt gaagtgtttg cctaccccat ggcctccatc gagtggagga         800

aggatggctt ggacatccag ctgccagggg atgaccccca catctctgtg         850

cagtttaggg gtggacccca gaggtttgag gtgactggct ggctgcagat         900

ccaggctgtg cgtcccagtg atgagggcac ttaccgctgc cttggccgca         950

atgccctggg tcaagtggag gcccctgcta gcttgacagt gctcacacct        1000

gaccagctga actctacagg catcccccag ctgcgatcac taaacctggt        1050

tcctgaggag gaggctgaga gtgaagagaa tgacgattac tactaggtcc        1100

agagctctgg cccatggggg tgggtgagcg gctatagtgt tcatccctgc        1150

tcttgaaaag acctggaaag gggagcaggg tcccttcatc gactgctttc        1200

atgctgtcag tagggatgat catgggaggc ctatttgact ccaaggtagc        1250

agtgtggtag gatagagaca aaagctggag gagggtaggg agagaagctg        1300

agaccaggac cggtggggta caaaggggcc catgcaggag atgccctggc        1350

cagtaggacc tccaacaggt tgtttcccag gctggggtgg gggcctgagc        1400

agacacagag gtgcaggcac caggattctc cacttcttcc agccctgctg        1450

ggccacagtt ctaactgccc ttcctcccag gccctggttc ttgctatttc        1500

ctggtcccca acgtttatct agcttgtttg ccctttcccc aaactcatct        1550

tccagaactt ttccctctct cctaagcccc agttgcacct actaactgca        1600

gtccctttttg ctgtctgccg tcttttgtac aagagagaga acagcggagc       1650

atgacttagt tcagtgcaga gagattt                                 1677
```

<210> SEQ ID NO 84
<211> LENGTH: 304
<212> TYPE: PRT
<213> ORGANISM: Homo sapiens

<400> SEQUENCE: 84

```
Met Leu Pro Pro Pro Arg Pro Ala Ala Ala Leu Ala Leu Pro Val
1               5                   10                  15
```

-continued

Leu Leu Leu Leu Leu Val Val Leu Thr Pro Pro Pro Thr Gly Ala
20 25 30

Arg Pro Ser Pro Gly Pro Asp Tyr Leu Arg Arg Gly Trp Met Arg
35 40 45

Leu Leu Ala Glu Gly Glu Gly Cys Ala Pro Cys Arg Pro Glu Glu
50 55 60

Cys Ala Ala Pro Arg Gly Cys Leu Ala Gly Arg Val Arg Asp Ala
65 70 75

Cys Gly Cys Cys Trp Glu Cys Ala Asn Leu Glu Gly Gln Leu Cys
80 85 90

Asp Leu Asp Pro Ser Ala His Phe Tyr Gly His Cys Gly Glu Gln
95 100 105

Leu Glu Cys Arg Leu Asp Thr Gly Gly Asp Leu Ser Arg Gly Glu
110 115 120

Val Pro Glu Pro Leu Cys Ala Cys Arg Ser Gln Ser Pro Leu Cys
125 130 135

Gly Ser Asp Gly His Thr Tyr Ser Gln Ile Cys Arg Leu Gln Glu
140 145 150

Ala Ala Arg Ala Arg Pro Asp Ala Asn Leu Thr Val Ala His Pro
155 160 165

Gly Pro Cys Glu Ser Gly Pro Gln Ile Val Ser His Pro Tyr Asp
170 175 180

Thr Trp Asn Val Thr Gly Gln Asp Val Ile Phe Gly Cys Glu Val
185 190 195

Phe Ala Tyr Pro Met Ala Ser Ile Glu Trp Arg Lys Asp Gly Leu
200 205 210

Asp Ile Gln Leu Pro Gly Asp Asp Pro His Ile Ser Val Gln Phe
215 220 225

Arg Gly Gly Pro Gln Arg Phe Glu Val Thr Gly Trp Leu Gln Ile
230 235 240

Gln Ala Val Arg Pro Ser Asp Glu Gly Thr Tyr Arg Cys Leu Gly
245 250 255

Arg Asn Ala Leu Gly Gln Val Glu Ala Pro Ala Ser Leu Thr Val
260 265 270

Leu Thr Pro Asp Gln Leu Asn Ser Thr Gly Ile Pro Gln Leu Arg
275 280 285

Ser Leu Asn Leu Val Pro Glu Glu Glu Ala Glu Ser Glu Glu Asn
290 295 300

Asp Asp Tyr Tyr

<210> SEQ ID NO 85
<211> LENGTH: 1285
<212> TYPE: DNA
<213> ORGANISM: Homo sapiens

<400> SEQUENCE: 85
caaagcggcg gctgtccgcg gtgccggctg ggggcggaga ggcggcggtg 50
ggctccctgg ggtgtgtgag cccggtgatg gagccgggcc cgacagccgc 100
gcagcggagg tgttcgttgc cgccgtggct gccgctgggg ctgctgctgt 150
ggtcggggct ggccctgggc gcgctcccct tcggcagcag tccgcacagg 200
gtcttccacg acctcctgtc ggagcagcag ttgctggagg tggaggactt 250
gtccctgtcc ctcctgcagg gtggagggct ggggcctctg tcgctgcccc 300

-continued

```
cggacctgcc ggatctggat cctgagtgcc gggagctcct gctggacttc          350

gccaacagca gcgcagagct gacagggtgt ctggtgcgca gcgcccggcc          400

cgtgcgcctc tgtcagacct gctacccccct cttccaacag gtcgtcagca          450

agatggacaa catcagccga gccgcgggga atacttcaga gagtcagagt          500

tgtgccagaa gtctcttaat ggcagataga atgcaaatag ttgtgattct          550

ctcagaattt tttaatacca catggcagga ggcaaattgt gcaaattgtt          600

taacaaacaa cagtgaagaa ttatcaaaca gcacagtata tttccttaat          650

ctatttaatc acaccctgac ctgctttgaa cataaccttc aggggaatgc          700

acatagtctt ttacagacaa aaaattattc agaagtatgc aaaaactgcc          750

gtgaagcata caaaactctg agtagtctgt acagtgaaat gcaaaaaatg          800

aatgaacttg agaataaggc tgaacctgga acacatttat gcattgatgt          850

ggaagatgca atgaacatca ctcgaaaact atggagtcga actttcaact          900

gttcagtccc ttgcagtgac acagtgcctg taattgctgt ttctgtgttc          950

attctctttc tacctgttgt cttctacctt agtagctttc ttcactcaga         1000

gcaaaagaaa cgcaaactca ttctgcccaa acgtctcaag tccagtacca         1050

gttttgcaaa tattcaggaa aattcaaact gagacctaca aaatggagaa         1100

ttgacatatc acgtgaatga atggtggaag acacaacttg gtttcagaaa         1150

gaagataaac tgtgatttga caagtcaagc tcttaagaaa tacaaggact         1200

tcagatccat ttttaaataa gaattttcga tttttctttc cttttccact         1250

tctttctaac agatttggat atttttaatt  tccag                        1285
```

<210> SEQ ID NO 86
<211> LENGTH: 334
<212> TYPE: PRT
<213> ORGANISM: Homo sapiens

<400> SEQUENCE: 86

```
Met Glu Pro Gly Pro Thr Ala Ala Gln Arg Arg Cys Ser Leu Pro
  1               5                  10                  15

Pro Trp Leu Pro Leu Gly Leu Leu Leu Trp Ser Gly Leu Ala Leu
                 20                  25                  30

Gly Ala Leu Pro Phe Gly Ser Ser Pro His Arg Val Phe His Asp
                 35                  40                  45

Leu Leu Ser Glu Gln Gln Leu Leu Glu Val Glu Asp Leu Ser Leu
                 50                  55                  60

Ser Leu Leu Gln Gly Gly Gly Leu Gly Pro Leu Ser Leu Pro Pro
                 65                  70                  75

Asp Leu Pro Asp Leu Asp Pro Glu Cys Arg Glu Leu Leu Leu Asp
                 80                  85                  90

Phe Ala Asn Ser Ser Ala Glu Leu Thr Gly Cys Leu Val Arg Ser
                 95                 100                 105

Ala Arg Pro Val Arg Leu Cys Gln Thr Cys Tyr Pro Leu Phe Gln
                110                 115                 120

Gln Val Val Ser Lys Met Asp Asn Ile Ser Arg Ala Ala Gly Asn
                125                 130                 135

Thr Ser Glu Ser Gln Ser Cys Ala Arg Ser Leu Leu Met Ala Asp
                140                 145                 150

Arg Met Gln Ile Val Val Ile Leu Ser Glu Phe Phe Asn Thr Thr
```

-continued

```
                155                 160                 165

Trp Gln Glu Ala Asn Cys Ala Asn Cys Leu Thr Asn Asn Ser Glu
                170                 175                 180

Glu Leu Ser Asn Ser Thr Val Tyr Phe Leu Asn Leu Phe Asn His
                185                 190                 195

Thr Leu Thr Cys Phe Glu His Asn Leu Gln Gly Asn Ala His Ser
                200                 205                 210

Leu Leu Gln Thr Lys Asn Tyr Ser Glu Val Cys Lys Asn Cys Arg
                215                 220                 225

Glu Ala Tyr Lys Thr Leu Ser Ser Leu Tyr Ser Glu Met Gln Lys
                230                 235                 240

Met Asn Glu Leu Glu Asn Lys Ala Glu Pro Gly Thr His Leu Cys
                245                 250                 255

Ile Asp Val Glu Asp Ala Met Asn Ile Thr Arg Lys Leu Trp Ser
                260                 265                 270

Arg Thr Phe Asn Cys Ser Val Pro Cys Ser Asp Thr Val Pro Val
                275                 280                 285

Ile Ala Val Ser Val Phe Ile Leu Phe Leu Pro Val Val Phe Tyr
                290                 295                 300

Leu Ser Ser Phe Leu His Ser Glu Gln Lys Lys Arg Lys Leu Ile
                305                 310                 315

Leu Pro Lys Arg Leu Lys Ser Ser Thr Ser Phe Ala Asn Ile Gln
                320                 325                 330

Glu Asn Ser Asn


<210> SEQ ID NO 87
<211> LENGTH: 1754
<212> TYPE: DNA
<213> ORGANISM: Homo sapiens

<400> SEQUENCE: 87

atgctggtag ccggcttcct gctggcgctg ccgccgagct gggccgcggg          50

cgcccccagg gcgggcaggc gccccgcgcg gccgcggggc tgcgcggacc         100

ggccggagga gctactggag cagctgtacg ggcgcctggc ggccggcgtg         150

ctcagtgcct tccaccacac gctgcagctg gggccgcgtg agcaggcgcg         200

caacgcgagc tgcccggcag gggcaggcc cggcgaccgc cgcttccggc          250

cgcccaccaa cctgcgcagc gtgtcgccct gggcctacag aatctcctac         300

gacccggcga ggtaccccag gtacctgcct gaagcctact gcctgtgccg         350

gggctgcctg accgggctgt tcggcgagga ggacgtgcgc ttccgcagcg         400

cccctgtcta catgcccacc gtcgtcctgc gccgcacccc cgcctgcgcc         450

ggcggccgtt ccgtctacac cgaggcctac gtcaccatcc ccgtgggctg         500

cacctgcgtc cccgagccgg agaaggacgc agacagcatc aactccagca         550

tcgacaaaca gggcgccaag ctcctgctgg gccccaacga cgcgcccgct         600

ggcccctgag gccggtcctg ccccgggagg tctccccggc ccgcatcccg         650

aggcgcccaa gctggagccg cctggagggc tcggtcggcg acctctgaag         700

agagtgcacc gagcaaacca agtgccggag caccagcgcc gcctttccat         750

ggagactcgt aagcagcttc atctgacacg ggcatccctg gcttgctttt         800

agctacaagc aagcagcgtg gctggaagct gatgggaaac gacccggcac         850
```

-continued

```
gggcatcctg tgtgcggccc gcatggaggg tttggaaaag ttcacggagg            900

ctccctgagg agcctctcag atcggctgct gcgggtgcag ggcgtgactc            950

accgctgggt gcttgccaaa gagataggga cgcatatgct ttttaaagca           1000

atctaaaaat aataataagt atagcgacta tatacctact tttaaaatca           1050

actgttttga atagaggcag agctatttta tattatcaaa tgagagctac           1100

tctgttacat ttcttaacat ataaacatcg tttttttactt cttctggtag           1150

aattttttaa agcataattg gaatccttgg ataaattttg tagctggtac           1200

actctggcct gggtctctga attcagcctg tcaccgatgg ctgactgatg           1250

aaatggacac gtctcatctg acccactctt ccttccactg aaggtcttca           1300

cgggcctcca ggtggaccaa agggatgcac aggcggctcg catgccccag           1350

ggccagctaa gagttccaaa gatctcagat ttggttttag tcatgaatac           1400

ataaacagtc tcaaactcgc acaatttttt ccccctttttg aaagccactg           1450

gggccaattt gtggttaaga ggtggtgaga taagaagtgg aacgtgacat           1500

ctttgccagt tgtcagaaga atccaagcag gtattggctt agttgtaagg           1550

gctttaggat caggctgaat atgaggacaa agtgggccac gttagcatct           1600

gcagagatca atctggaggc ttctgtttct gcattctgcc acgagagcta           1650

ggtccttgat cttttcttta gattgaaagt ctgtctctga acacaattat           1700

ttgtaaaagt tagtagttct tttttaaatc attaaaagag gcttgctgaa           1750

ggat                                                             1754
```

<210> SEQ ID NO 88
<211> LENGTH: 202
<212> TYPE: PRT
<213> ORGANISM: Homo sapiens

<400> SEQUENCE: 88

```
Met Leu Val Ala Gly Phe Leu Leu Ala Leu Pro Pro Ser Trp Ala
  1               5                  10                  15

Ala Gly Ala Pro Arg Ala Gly Arg Arg Pro Ala Arg Pro Arg Gly
                 20                  25                  30

Cys Ala Asp Arg Pro Glu Glu Leu Leu Glu Gln Leu Tyr Gly Arg
                 35                  40                  45

Leu Ala Ala Gly Val Leu Ser Ala Phe His His Thr Leu Gln Leu
                 50                  55                  60

Gly Pro Arg Glu Gln Ala Arg Asn Ala Ser Cys Pro Ala Gly Gly
                 65                  70                  75

Arg Pro Gly Asp Arg Arg Phe Arg Pro Pro Thr Asn Leu Arg Ser
                 80                  85                  90

Val Ser Pro Trp Ala Tyr Arg Ile Ser Tyr Asp Pro Ala Arg Tyr
                 95                 100                 105

Pro Arg Tyr Leu Pro Glu Ala Tyr Cys Leu Cys Arg Gly Cys Leu
                110                 115                 120

Thr Gly Leu Phe Gly Glu Glu Asp Val Arg Phe Arg Ser Ala Pro
                125                 130                 135

Val Tyr Met Pro Thr Val Val Leu Arg Arg Thr Pro Ala Cys Ala
                140                 145                 150

Gly Gly Arg Ser Val Tyr Thr Glu Ala Tyr Val Thr Ile Pro Val
                155                 160                 165
```

-continued

```
Gly Cys Thr Cys Val Pro Glu Pro Glu Lys Asp Ala Asp Ser Ile
                170                 175                 180

Asn Ser Ser Ile Asp Lys Gln Gly Ala Lys Leu Leu Leu Gly Pro
                185                 190                 195

Asn Asp Ala Pro Ala Gly Pro
                200


<210> SEQ ID NO 89
<211> LENGTH: 2601
<212> TYPE: DNA
<213> ORGANISM: Homo sapiens

<400> SEQUENCE: 89

ccggggcctc cggagaacgc tgtcccatga acgtgcgggg agcggccccc          50

ggcgtccgcg cgtccccgcg tccctggcaa ttcccgactt cccaacggct         100

tcccgctggc agccccgaag ccgcaccatg ttccgcctct ggttgctgct         150

ggccgggctc tgcggcctcc tggcgtcaag acccggtttt caaaattcac         200

ttctacagat cgtaattcca gagaaaatcc aaacaaatac aaatgacagt         250

tcagaaatag aatatgaaca aatatcctat attattccaa tagatgagaa         300

actgtacact gtgcacctta aacaaagata ttttttagca gataatttta         350

tgatctattt gtacaatcaa ggatctatga atacttattc ttcagatatt         400

cagactcaat gctactatca aggaaatatt gaaggatatc cagattccat         450

ggtcacactc agcacgtgct ctggactaag aggaatactg caatttgaaa         500

atgtttctta tggaattgag cctctggaat ctgcagttga atttcagcat         550

gttctttaca aattaaagaa tgaagacaat gatattgcaa tttttattga         600

cagaagcctg aaagaacaac caatggatga caacattttt ataagtgaaa         650

aatcagaacc agctgttcca gatttatttc ctctttatct agaaatgcat         700

attgtggtgg acaaaacttt gtatgattac tggggctctg atagcatgat         750

agtaacaaat aaagtcatcg aaattgttgg ccttgcaaat tcaatgttca         800

cccaatttaa agttactatt gtgctgtcat cattggagtt atggtcagat         850

gaaaataaga tttctacagt tggtgaggca gatgaattat tgcaaaaatt         900

tttagaatgg aaacaatctt atcttaacct aaggcctcat gatattgcat         950

atctactaat ttatatggat tatcctcgtt atttgggagc agtgtttcct        1000

ggaacaatgt gtattactcg ttattctgca ggagttgcat tgtaccccaa        1050

ggagataact ctggaggcat ttgcagttat tgtcacccag atgctggcac        1100

tcagtctggg aatatcatat gacgacccaa agaaatgtca atgttcagaa        1150

tccacctgta taatgaatcc agaagttgtg caatccaatg gtgtgaagac        1200

ttttagcagt tgcagtttga ggagctttca aaatttcatt tcaaatgtgg        1250

gtgtcaaatg tcttcagaat aagccacaaa tgcaaaaaaa atctccgaaa        1300

ccagtctgtg gcaatggcag attggaggga aatgaaatct gtgattgtgg        1350

tactgaggct caatgtggac ctgcaagctg ttgtgatttt cgaacttgtg        1400

tactgaaaga cggagcaaaa tgttataaag gactgtgctg caaagactgt        1450

caaattttac aatcaggcgt tgaatgtagg ccgaaagcac atcctgaatg        1500

tgacatcgct gaaaattgta atggaagctc accagaatgt ggtcctgaca        1550
```

-continued

```
taactttaat caatggactt tcatgcaaaa ataataagtt tatttgttat          1600

gacggagact gccatgatct cgatgcacgt tgtgagagtg tatttggaaa          1650

aggttcaaga aatgctccat ttgcctgcta tgaagaaata caatctcaat          1700

cagacagatt tgggaactgt ggtagggata gaaataacaa atatgtgttc          1750

tgtggatgga ggaatcttat atgtggaaga ttagtttgta cctaccctac          1800

tcgaaagcct ttccatcaag aaaatggtga tgtgatttat gctttcgtac          1850

gagattctgt atgcataact gtagactaca aattgcctcg aacagttcca          1900

gatccactgg ctgtcaaaaa tggctctcag tgtgatattg ggagggtttg          1950

tgtaaatcgt gaatgtgtag aatcaaggat aattaaggct tcagcacatg          2000

tttgttcaca acagtgttct ggacatggag tgtgtgattc cagaaacaag          2050

tgccattgtt cgccaggcta taagcctcca aactgccaaa tacgttccaa          2100

aggattttcc atatttcctg aggaagatat gggttcaatc atggaaagag          2150

catctgggaa gactgaaaac acctggcttc taggtttcct cattgctctt          2200

cctattctca ttgtaacaac cgcaatagtt ttggcaagga aacagttgaa          2250

aaagtggttc gccaaggaag aggaattccc aagtagcgaa tctaaatcgg          2300

aaggtagcac acagacatat gccagccaat ccagctcaga aggcagcact          2350

cagacatatg ccagccaaac cagatcagaa agcagcagtc aagctgatac          2400

tagcaaatcc aaatcagaag atagtgctga agcatatact agcagatcca          2450

aatcacagga cagtacccaa acacaaagca gtagtaacta gtgattcctt          2500

cagaaggcaa cggataacat cgagagtctc gctaagaaat gaaaattctg          2550

tctttccttc cgtggtcaca gctgaaagaa acaataaatt gagtgtggat          2600

c                                                               2601
```

<210> SEQ ID NO 90
<211> LENGTH: 787
<212> TYPE: PRT
<213> ORGANISM: Homo sapiens

<400> SEQUENCE: 90

```
Met Phe Arg Leu Trp Leu Leu Leu Ala Gly Leu Cys Gly Leu Leu
  1               5                  10                  15

Ala Ser Arg Pro Gly Phe Gln Asn Ser Leu Leu Gln Ile Val Ile
                 20                  25                  30

Pro Glu Lys Ile Gln Thr Asn Thr Asn Asp Ser Ser Glu Ile Glu
                 35                  40                  45

Tyr Glu Gln Ile Ser Tyr Ile Ile Pro Ile Asp Glu Lys Leu Tyr
                 50                  55                  60

Thr Val His Leu Lys Gln Arg Tyr Phe Leu Ala Asp Asn Phe Met
                 65                  70                  75

Ile Tyr Leu Tyr Asn Gln Gly Ser Met Asn Thr Tyr Ser Ser Asp
                 80                  85                  90

Ile Gln Thr Gln Cys Tyr Tyr Gln Gly Asn Ile Glu Gly Tyr Pro
                 95                 100                 105

Asp Ser Met Val Thr Leu Ser Thr Cys Ser Gly Leu Arg Gly Ile
                110                 115                 120

Leu Gln Phe Glu Asn Val Ser Tyr Gly Ile Glu Pro Leu Glu Ser
                125                 130                 135
```

-continued

```
Ala Val Glu Phe Gln His Val Leu Tyr Lys Leu Lys Asn Glu Asp
                140                 145                 150

Asn Asp Ile Ala Ile Phe Ile Asp Arg Ser Leu Lys Glu Gln Pro
                155                 160                 165

Met Asp Asp Asn Ile Phe Ile Ser Glu Lys Ser Glu Pro Ala Val
                170                 175                 180

Pro Asp Leu Phe Pro Leu Tyr Leu Glu Met His Ile Val Val Asp
                185                 190                 195

Lys Thr Leu Tyr Asp Tyr Trp Gly Ser Asp Ser Met Ile Val Thr
                200                 205                 210

Asn Lys Val Ile Glu Ile Val Gly Leu Ala Asn Ser Met Phe Thr
                215                 220                 225

Gln Phe Lys Val Thr Ile Val Leu Ser Ser Leu Glu Leu Trp Ser
                230                 235                 240

Asp Glu Asn Lys Ile Ser Thr Val Gly Glu Ala Asp Glu Leu Leu
                245                 250                 255

Gln Lys Phe Leu Glu Trp Lys Gln Ser Tyr Leu Asn Leu Arg Pro
                260                 265                 270

His Asp Ile Ala Tyr Leu Leu Ile Tyr Met Asp Tyr Pro Arg Tyr
                275                 280                 285

Leu Gly Ala Val Phe Pro Gly Thr Met Cys Ile Thr Arg Tyr Ser
                290                 295                 300

Ala Gly Val Ala Leu Tyr Pro Lys Glu Ile Thr Leu Glu Ala Phe
                305                 310                 315

Ala Val Ile Val Thr Gln Met Leu Ala Leu Ser Leu Gly Ile Ser
                320                 325                 330

Tyr Asp Asp Pro Lys Lys Cys Gln Cys Ser Glu Ser Thr Cys Ile
                335                 340                 345

Met Asn Pro Glu Val Val Gln Ser Asn Gly Val Lys Thr Phe Ser
                350                 355                 360

Ser Cys Ser Leu Arg Ser Phe Gln Asn Phe Ile Ser Asn Val Gly
                365                 370                 375

Val Lys Cys Leu Gln Asn Lys Pro Gln Met Gln Lys Lys Ser Pro
                380                 385                 390

Lys Pro Val Cys Gly Asn Gly Arg Leu Glu Gly Asn Glu Ile Cys
                395                 400                 405

Asp Cys Gly Thr Glu Ala Gln Cys Gly Pro Ala Ser Cys Cys Asp
                410                 415                 420

Phe Arg Thr Cys Val Leu Lys Asp Gly Ala Lys Cys Tyr Lys Gly
                425                 430                 435

Leu Cys Cys Lys Asp Cys Gln Ile Leu Gln Ser Gly Val Glu Cys
                440                 445                 450

Arg Pro Lys Ala His Pro Glu Cys Asp Ile Ala Glu Asn Cys Asn
                455                 460                 465

Gly Ser Ser Pro Glu Cys Gly Pro Asp Ile Thr Leu Ile Asn Gly
                470                 475                 480

Leu Ser Cys Lys Asn Asn Lys Phe Ile Cys Tyr Asp Gly Asp Cys
                485                 490                 495

His Asp Leu Asp Ala Arg Cys Glu Ser Val Phe Gly Lys Gly Ser
                500                 505                 510

Arg Asn Ala Pro Phe Ala Cys Tyr Glu Glu Ile Gln Ser Gln Ser
                515                 520                 525

Asp Arg Phe Gly Asn Cys Gly Arg Asp Arg Asn Asn Lys Tyr Val
```

-continued

```
                530                 535                 540

Phe Cys Gly Trp Arg Asn Leu Ile Cys Gly Arg Leu Val Cys Thr
                545                 550                 555

Tyr Pro Thr Arg Lys Pro Phe His Gln Glu Asn Gly Asp Val Ile
                560                 565                 570

Tyr Ala Phe Val Arg Asp Ser Val Cys Ile Thr Val Asp Tyr Lys
                575                 580                 585

Leu Pro Arg Thr Val Pro Asp Pro Leu Ala Val Lys Asn Gly Ser
                590                 595                 600

Gln Cys Asp Ile Gly Arg Val Cys Val Asn Arg Glu Cys Val Glu
                605                 610                 615

Ser Arg Ile Ile Lys Ala Ser Ala His Val Cys Ser Gln Gln Cys
                620                 625                 630

Ser Gly His Gly Val Cys Asp Ser Arg Asn Lys Cys His Cys Ser
                635                 640                 645

Pro Gly Tyr Lys Pro Pro Asn Cys Gln Ile Arg Ser Lys Gly Phe
                650                 655                 660

Ser Ile Phe Pro Glu Glu Asp Met Gly Ser Ile Met Glu Arg Ala
                665                 670                 675

Ser Gly Lys Thr Glu Asn Thr Trp Leu Leu Gly Phe Leu Ile Ala
                680                 685                 690

Leu Pro Ile Leu Ile Val Thr Thr Ala Ile Val Leu Ala Arg Lys
                695                 700                 705

Gln Leu Lys Lys Trp Phe Ala Lys Glu Glu Glu Phe Pro Ser Ser
                710                 715                 720

Glu Ser Lys Ser Glu Gly Ser Thr Gln Thr Tyr Ala Ser Gln Ser
                725                 730                 735

Ser Ser Glu Gly Ser Thr Gln Thr Tyr Ala Ser Gln Thr Arg Ser
                740                 745                 750

Glu Ser Ser Ser Gln Ala Asp Thr Ser Lys Ser Lys Ser Glu Asp
                755                 760                 765

Ser Ala Glu Ala Tyr Thr Ser Arg Ser Lys Ser Gln Asp Ser Thr
                770                 775                 780

Gln Thr Gln Ser Ser Ser Asn
                785


<210> SEQ ID NO 91
<211> LENGTH: 2445
<212> TYPE: DNA
<213> ORGANISM: Homo sapiens
<220> FEATURE:
<221> NAME/KEY: Unsure
<222> LOCATION: 2424
<223> OTHER INFORMATION: Unknown base

<400> SEQUENCE: 91

caccagacag cactccagca ctctgtttgg ggggcattcg aaacagcaaa          50

atcactcata aaaggcaaaa aattgcaaaa aaaaatagta ataaccagca         100

tggcactaaa tagaccatga aaagacatgt gtgtgcagta tgaaaattga         150

gacaggaagg cagagtgtca gcttgttcca cctcagctgg gaatgtgcat         200

caggcaactc aagtttttca ccacggcatg tgtctgtgaa tgtccgcaaa         250

acattctctc tccccagcct tcatgtgtta acctggggat gatgtggacc         300

tgggcactgt ggatgctccc ttcactctgc aaattcagcc tggcagctct         350
```

-continued

```
gccagctaag cctgagaaca tttcctgtgt ctactactat aggaaaaatt      400
taacctgcac ttggagtcca ggaaaggaaa ccagttatac ccagtacaca      450
gttaagagaa cttacgcttt tggagaaaaa catgataatt gtacaaccaa      500
tagttctaca agtgaaaatc gtgcttcgtg ctcttttttc cttccaagaa      550
taacgatccc agataattat accattgagg tggaagctga aaatggagat      600
ggtgtaatta aatctcatat gacatactgg agattagaga acatagcgaa      650
aactgaacca cctaagattt tccgtgtgaa accagttttg ggcatcaaac      700
gaatgattca aattgaatgg ataaagcctg agttggcgcc tgtttcatct      750
gatttaaaat acacacttcg attcaggaca gtcaacagta ccagctggat      800
ggaagtcaac ttcgctaaga accgtaagga taaaaaccaa acgtacaacc      850
tcacggggct gcagcctttt acagaatatg tcatagctct gcgatgtgcg      900
gtcaaggagt caaagttctg gagtgactgg agccaagaaa aaatgggaat      950
gactgaggaa gaagctccat gtggcctgga actgtggaga gtcctgaaac     1000
cagctgaggc ggatggaaga aggccagtgc ggttgttatg gaagaaggca     1050
agaggagccc cagtcctaga gaaaacactt ggctacaaca tatggtacta     1100
tccagaaagc aacactaacc tcacagaaac aatgaacact actaaccagc     1150
agcttgaact gcatctggga ggcgagagct tttgggtgtc tatgatttct     1200
tataattctc ttgggaagtc tccagtggcc accctgagga ttccagctat     1250
tcaagaaaaa tcatttcagt gcattgaggt catgcaggcc tgcgttgctg     1300
aggaccagct agtggtgaag tggcaaagct ctgctctaga cgtgaacact     1350
tggatgattg aatggtttcc ggatgtggac tcagagccca ccaccctttc     1400
ctgggaatct gtgtctcagg ccacgaactg gacgatccag caagataaat     1450
taaaaccttt ctggtgctat aacatctctg tgtatccaat gttgcatgac     1500
aaagttggcg agccatattc catccaggct tatgccaaag aaggcgttcc     1550
atcagaaggt cctgagacca aggtggagaa cattggcgtg aagacggtca     1600
cgatcacatg gaaagagatt cccaagagtg agagaaaggg tatcatctgc     1650
aactacacca tcttttacca agctgaaggt ggaaaaggat tctgtaagca     1700
cgcccatagc gaagtggaaa aaaaccccaa gccccagata gatgctatgg     1750
atagacctgt tgtaggcatg gctcccccat ctcattgtga cttgcaacct     1800
ggcatgaatc acttagcttc tttaaatctc tctgaaaatg gggccaagag     1850
cacccacctt ttggggtttt gggggttaaa tgagagtgaa gtgacagtac     1900
ctgagaggag agtcctgagg aaatggaagg agttgttata atttgtcctg     1950
gttaggccct gaattgacct cccgggagct ccccgaccat cattcccagg     2000
aatggcgtgc ctggcttaaa gagtgaggag gaacagaccc tgtcaccatg     2050
acttctactg cccctgccaa atcatgcttt tgtttttcag tccaccttat     2100
ctcctgacat cttaaatact gggcaaggct tggattcttg cttaggctaa     2150
ataatttttt cttatggtaa aatacacgta aaatattttt ccagtttaaa     2200
catttgaaag tgtacaattt agtggcatta gaagcattca caatattgtg     2250
caaccatcac cactatttcc agaactcttc tatttctgcc caaatagaag     2300
ccctataccc attcattagt cactccccat tcctctcctc ccacagcccc     2350
```

-continued

```
tggcaactac caaactgctt tgtgtctcta tggattgcct attttggata             2400

tttcatatac atagaatcat aaantaaaaa aaaaaaaaaa  aaaaa                 2445


<210> SEQ ID NO 92
<211> LENGTH: 582
<212> TYPE: PRT
<213> ORGANISM: Homo sapiens

<400> SEQUENCE: 92

Met Cys Ile Arg Gln Leu Lys Phe Phe Thr Thr Ala Cys Val Cys
  1               5                  10                  15

Glu Cys Pro Gln Asn Ile Leu Ser Pro Gln Pro Ser Cys Val Asn
                 20                  25                  30

Leu Gly Met Met Trp Thr Trp Ala Leu Trp Met Leu Pro Ser Leu
                 35                  40                  45

Cys Lys Phe Ser Leu Ala Ala Leu Pro Ala Lys Pro Glu Asn Ile
                 50                  55                  60

Ser Cys Val Tyr Tyr Tyr Arg Lys Asn Leu Thr Cys Thr Trp Ser
                 65                  70                  75

Pro Gly Lys Glu Thr Ser Tyr Thr Gln Tyr Thr Val Lys Arg Thr
                 80                  85                  90

Tyr Ala Phe Gly Glu Lys His Asp Asn Cys Thr Thr Asn Ser Ser
                 95                 100                 105

Thr Ser Glu Asn Arg Ala Ser Cys Ser Phe Phe Leu Pro Arg Ile
                110                 115                 120

Thr Ile Pro Asp Asn Tyr Thr Ile Glu Val Glu Ala Glu Asn Gly
                125                 130                 135

Asp Gly Val Ile Lys Ser His Met Thr Tyr Trp Arg Leu Glu Asn
                140                 145                 150

Ile Ala Lys Thr Glu Pro Pro Lys Ile Phe Arg Val Lys Pro Val
                155                 160                 165

Leu Gly Ile Lys Arg Met Ile Gln Ile Glu Trp Ile Lys Pro Glu
                170                 175                 180

Leu Ala Pro Val Ser Ser Asp Leu Lys Tyr Thr Leu Arg Phe Arg
                185                 190                 195

Thr Val Asn Ser Thr Ser Trp Met Glu Val Asn Phe Ala Lys Asn
                200                 205                 210

Arg Lys Asp Lys Asn Gln Thr Tyr Asn Leu Thr Gly Leu Gln Pro
                215                 220                 225

Phe Thr Glu Tyr Val Ile Ala Leu Arg Cys Ala Val Lys Glu Ser
                230                 235                 240

Lys Phe Trp Ser Asp Trp Ser Gln Glu Lys Met Gly Met Thr Glu
                245                 250                 255

Glu Glu Ala Pro Cys Gly Leu Glu Leu Trp Arg Val Leu Lys Pro
                260                 265                 270

Ala Glu Ala Asp Gly Arg Arg Pro Val Arg Leu Leu Trp Lys Lys
                275                 280                 285

Ala Arg Gly Ala Pro Val Leu Glu Lys Thr Leu Gly Tyr Asn Ile
                290                 295                 300

Trp Tyr Tyr Pro Glu Ser Asn Thr Asn Leu Thr Glu Thr Met Asn
                305                 310                 315

Thr Thr Asn Gln Gln Leu Glu Leu His Leu Gly Gly Glu Ser Phe
                320                 325                 330
```

-continued

```
Trp Val Ser Met Ile Ser Tyr Asn Ser Leu Gly Lys Ser Pro Val
                335                 340                 345

Ala Thr Leu Arg Ile Pro Ala Ile Gln Glu Lys Ser Phe Gln Cys
                350                 355                 360

Ile Glu Val Met Gln Ala Cys Val Ala Glu Asp Gln Leu Val Val
                365                 370                 375

Lys Trp Gln Ser Ser Ala Leu Asp Val Asn Thr Trp Met Ile Glu
                380                 385                 390

Trp Phe Pro Asp Val Asp Ser Glu Pro Thr Thr Leu Ser Trp Glu
                395                 400                 405

Ser Val Ser Gln Ala Thr Asn Trp Thr Ile Gln Gln Asp Lys Leu
                410                 415                 420

Lys Pro Phe Trp Cys Tyr Asn Ile Ser Val Tyr Pro Met Leu His
                425                 430                 435

Asp Lys Val Gly Glu Pro Tyr Ser Ile Gln Ala Tyr Ala Lys Glu
                440                 445                 450

Gly Val Pro Ser Glu Gly Pro Glu Thr Lys Val Glu Asn Ile Gly
                455                 460                 465

Val Lys Thr Val Thr Ile Thr Trp Lys Glu Ile Pro Lys Ser Glu
                470                 475                 480

Arg Lys Gly Ile Ile Cys Asn Tyr Thr Ile Phe Tyr Gln Ala Glu
                485                 490                 495

Gly Gly Lys Gly Phe Cys Lys His Ala His Ser Glu Val Glu Lys
                500                 505                 510

Asn Pro Lys Pro Gln Ile Asp Ala Met Asp Arg Pro Val Val Gly
                515                 520                 525

Met Ala Pro Pro Ser His Cys Asp Leu Gln Pro Gly Met Asn His
                530                 535                 540

Leu Ala Ser Leu Asn Leu Ser Glu Asn Gly Ala Lys Ser Thr His
                545                 550                 555

Leu Leu Gly Phe Trp Gly Leu Asn Glu Ser Glu Val Thr Val Pro
                560                 565                 570

Glu Arg Arg Val Leu Arg Lys Trp Lys Glu Leu Leu
                575                 580
```

<210> SEQ ID NO 93
<211> LENGTH: 662
<212> TYPE: DNA
<213> ORGANISM: Homo sapiens

<400> SEQUENCE: 93

```
attctcctag agcatctttg gaagcatgag gccacgatgc tgcatcttgg      50

ctcttgtctg ctggataaca gtcttcctcc tccagtgttc aaaaggaact     100

acagacgctc ctgttggctc aggactgtgg ctgtgccagc cgacacccag     150

gtgtgggaac aagatctaca acccttcaga gcagtgctgt tatgatgatg     200

ccatcttatc cttaaaggag acccgccgct gtggctccac ctgcaccttc     250

tggccctgct ttgagctctg ctgtcccgag tcttttggcc cccagcagaa     300

gtttcttgtg aagttgaggg ttctgggtat gaagtctcag tgtcacttat     350

ctcccatctc ccggagctgt accaggaaca ggaggcacgt cctgtaccca     400

taaaaacccc aggctccact ggcagacggc agacaagggg agaagagacg     450

aagcagctgg acatcggaga ctacagttga acttcggaga gaagcaactt     500
```

-continued

```
gacttcagag ggatggctca atgacatagc tttggagagg agcccagctg        550

gggatggcca gacttcaggg gaagaatgcc ttcctgcttc atcccctttc        600

cagctcccct tcccgctgag agccactttc atcggcaata aaatccccca        650

catttaccat  ct                                                662


<210> SEQ ID NO 94
<211> LENGTH: 125
<212> TYPE: PRT
<213> ORGANISM: Homo sapiens

<400> SEQUENCE: 94

Met Arg Pro Arg Cys Cys Ile Leu Ala Leu Val Cys Trp Ile Thr
  1               5                  10                  15

Val Phe Leu Leu Gln Cys Ser Lys Gly Thr Thr Asp Ala Pro Val
                 20                  25                  30

Gly Ser Gly Leu Trp Leu Cys Gln Pro Thr Pro Arg Cys Gly Asn
                 35                  40                  45

Lys Ile Tyr Asn Pro Ser Glu Gln Cys Cys Tyr Asp Asp Ala Ile
                 50                  55                  60

Leu Ser Leu Lys Glu Thr Arg Arg Cys Gly Ser Thr Cys Thr Phe
                 65                  70                  75

Trp Pro Cys Phe Glu Leu Cys Cys Pro Glu Ser Phe Gly Pro Gln
                 80                  85                  90

Gln Lys Phe Leu Val Lys Leu Arg Val Leu Gly Met Lys Ser Gln
                 95                 100                 105

Cys His Leu Ser Pro Ile Ser Arg Ser Cys Thr Arg Asn Arg Arg
                110                 115                 120

His Val Leu Tyr Pro
                125


<210> SEQ ID NO 95
<211> LENGTH: 471
<212> TYPE: DNA
<213> ORGANISM: Homo sapiens

<400> SEQUENCE: 95

gcatttttgt ctgtgctccc tgatcttcag gtcaccacca tgaagttctt         50

agcagtcctg gtactcttgg gagtttccat ctttctggtc tctgcccaga        100

atccgacaac agctgctcca gctgacacgt atccagctac tggtcctgct        150

gatgatgaag cccctgatgc tgaaaccact gctgctgcaa ccactgcgac        200

cactgctgct cctaccactg caaccaccgc tgcttctacc actgctcgta        250

aagacattcc agttttaccc aaatgggttg gggatctccc gaatggtaga        300

gtgtgtccct gagatggaat cagcttgagt cttctgcaat tggtcacaac        350

tattcatgct tcctgtgatt tcatccaact acttaccttg cctacgatat        400

cccctttatc tctaatcagt ttattttctt tcaaataaaa aataactatg        450

agcaacataa aaaaaaaaaa  a                                      471


<210> SEQ ID NO 96
<211> LENGTH: 90
<212> TYPE: PRT
<213> ORGANISM: Homo sapiens

<400> SEQUENCE: 96
```

-continued

```
Met Lys Phe Leu Ala Val Leu Val Leu Leu Gly Val Ser Ile Phe
  1               5                  10                  15

Leu Val Ser Ala Gln Asn Pro Thr Thr Ala Ala Pro Ala Asp Thr
                 20                  25                  30

Tyr Pro Ala Thr Gly Pro Ala Asp Asp Glu Ala Pro Asp Ala Glu
                 35                  40                  45

Thr Thr Ala Ala Ala Thr Thr Ala Thr Thr Ala Ala Pro Thr Thr
                 50                  55                  60

Ala Thr Thr Ala Ala Ser Thr Thr Ala Arg Lys Asp Ile Pro Val
                 65                  70                  75

Leu Pro Lys Trp Val Gly Asp Leu Pro Asn Gly Arg Val Cys Pro
                 80                  85                  90
```

<210> SEQ ID NO 97
<211> LENGTH: 907
<212> TYPE: DNA
<213> ORGANISM: Homo sapiens

<400> SEQUENCE: 97

```
ggactctgaa ggtcccaagc agctgctgag gcccccaagg aagtggttcc      50

aaccttggac ccctaggggt ctggatttgc tggttaacaa gataacctga     100

gggcaggacc ccatagggga atgctacctc ctgcccttcc acctgccctg     150

gtgttcacgg tggcctggtc cctccttgcc gagagagtgt cctgggtcag     200

ggacgcagag gacgctcaca gactccagcc ctttgttacc gagaggacac     250

ttggcaaggt ccagcgatgg tccggagtcc acacacagac tggcggcagg     300

gcaggagggg gacagttctg ttgtgcttgg ttggacagta agagggtctt     350

ggccagtcca gggtgggggg cggcaaactc cataaagaac cagagggtct     400

gggccccggc cacagagtca tctgcccagc tcctctgctg ctggccagtg     450

ggagtggcac gaggtggggc tttgtgccag taaaaccaca ggctggattt     500

gcctgcgggc catggtccct gtctagggca gcaattctca accttcttgc     550

tctcaggacc ccaaagagct ttcattgtat ctattgattt ttaccacatt     600

agcaattaaa actgagaaat gggccgggca cggtggctca cgcctgtaat     650

cccagcactt tgggaggccg aggcgggtgg atcacctgag atcaggagtt     700

caagaccagc ctggccaaca tggtgaaacc ttgtctacta aaaatacaaa     750

aaattagcca ggcacagtgg tgtgcactgg tagtcccagt tactcgggag     800

gctgaggcag gaaaatcgct tgaacccagg aggcggacgt tgcggtgagc     850

cgagatcgcg ccgctgattc cagcctgggc gacaagagtg agactccatc     900

tcacaca                                                    907
```

<210> SEQ ID NO 98
<211> LENGTH: 120
<212> TYPE: PRT
<213> ORGANISM: Homo sapiens

<400> SEQUENCE: 98

```
Met Leu Pro Pro Ala Leu Pro Pro Ala Leu Val Phe Thr Val Ala
  1               5                  10                  15

Trp Ser Leu Leu Ala Glu Arg Val Ser Trp Val Arg Asp Ala Glu
                 20                  25                  30

Asp Ala His Arg Leu Gln Pro Phe Val Thr Glu Arg Thr Leu Gly
```

-continued

```
                35                  40                  45

Lys Val Gln Arg Trp Ser Gly Val His Thr Gln Thr Gly Gly Arg
                50                  55                  60

Ala Gly Gly Gly Gln Phe Cys Cys Ala Trp Leu Asp Ser Lys Arg
                65                  70                  75

Val Leu Ala Ser Pro Gly Trp Gly Ala Ala Asn Ser Ile Lys Asn
                80                  85                  90

Gln Arg Val Trp Ala Pro Ala Thr Glu Ser Ser Ala Gln Leu Leu
                95                  100                 105

Cys Cys Trp Pro Val Gly Val Ala Arg Gly Gly Ala Leu Cys Gln
                110                 115                 120
```

<210> SEQ ID NO 99
<211> LENGTH: 1073
<212> TYPE: DNA
<213> ORGANISM: Homo sapiens

<400> SEQUENCE: 99

```
aatttttcac cagagtaaac ttgagaaacc aactggacct tgagtattgt        50

acattttgcc tcgtggaccc aaaggtagca atctgaaaca tgaggagtac       100

gattctactg ttttgtcttc taggatcaac tcggtcatta ccacagctca       150

aacctgcttt gggactccct cccacaaaac tggctccgga tcagggaaca       200

ctaccaaacc aacagcagtc aaatcaggtc tttccttctt taagtctgat       250

accattaaca cagatgctca cactggggcc agatctgcat ctgttaaatc       300

ctgctgcagg aatgacacct ggtacccaga cccacccatt gaccctggga       350

gggttgaatg tacaacagca actgcaccca catgtgttac caatttttgt       400

cacacaactt ggagcccagg gcactatcct aagctcagag gaattgccac       450

aaatcttcac gagcctcatc atccattcct tgttcccggg aggcatcctg       500

cccaccagtc aggcaggggc taatccagat gtccaggatg gaagccttcc       550

agcaggagga gcaggtgtaa atcctgccac ccagggaacc ccagcaggcc       600

gcctcccaac tcccagtggc acagatgacg actttgcagt gaccacccct       650

gcaggcatcc aaaggagcac acatgccatc gaggaagcca ccacagaatc       700

agcaaatgga attcagtaag ctgtttcaaa ttttttcaac taagctgcct       750

cgaatttggt gatacatgtg aatctttatc attgattata ttatggaata       800

gattgagaca cattggatag tcttagaaga aattaattct taatttacct       850

gaaaatattc ttgaaatttc agaaaatatg ttctatgtag agaatcccaa       900

cttttaaaaa caataattca atggataaat ctgtctttga aatataacat       950

tatgctgcct ggatgatatg catattaaaa catatttgga aaactggaaa      1000

aaaaaaaaaa aaaaaaaaaa aaaaaaaaaa aaaaaaaaaa aaaaaaaaaa      1050

aaaaaaaaaa aaaaaaaaaa  aaa                                  1073
```

<210> SEQ ID NO 100
<211> LENGTH: 209
<212> TYPE: PRT
<213> ORGANISM: Homo sapiens

<400> SEQUENCE: 100

```
Met Arg Ser Thr Ile Leu Leu Phe Cys Leu Leu Gly Ser Thr Arg
  1               5                  10                  15
```

-continued

Ser Leu Pro Gln Leu Lys Pro Ala Leu Gly Leu Pro Pro Thr Lys
20 25 30

Leu Ala Pro Asp Gln Gly Thr Leu Pro Asn Gln Gln Gln Ser Asn
35 40 45

Gln Val Phe Pro Ser Leu Ser Leu Ile Pro Leu Thr Gln Met Leu
50 55 60

Thr Leu Gly Pro Asp Leu His Leu Leu Asn Pro Ala Ala Gly Met
65 70 75

Thr Pro Gly Thr Gln Thr His Pro Leu Thr Leu Gly Gly Leu Asn
80 85 90

Val Gln Gln Gln Leu His Pro His Val Leu Pro Ile Phe Val Thr
95 100 105

Gln Leu Gly Ala Gln Gly Thr Ile Leu Ser Ser Glu Glu Leu Pro
110 115 120

Gln Ile Phe Thr Ser Leu Ile Ile His Ser Leu Phe Pro Gly Gly
125 130 135

Ile Leu Pro Thr Ser Gln Ala Gly Ala Asn Pro Asp Val Gln Asp
140 145 150

Gly Ser Leu Pro Ala Gly Gly Ala Gly Val Asn Pro Ala Thr Gln
155 160 165

Gly Thr Pro Ala Gly Arg Leu Pro Thr Pro Ser Gly Thr Asp Asp
170 175 180

Asp Phe Ala Val Thr Thr Pro Ala Gly Ile Gln Arg Ser Thr His
185 190 195

Ala Ile Glu Glu Ala Thr Thr Glu Ser Ala Asn Gly Ile Gln
200 205

<210> SEQ ID NO 101
<211> LENGTH: 1514
<212> TYPE: DNA
<213> ORGANISM: Homo sapiens

<400> SEQUENCE: 101
ggggtctccc tcagggccgg gaggcacagc ggtccctgct tgctgaaggg 50
ctggatgtac gcatccgcag gttcccgcgg acttgggggc gcccgctgag 100
ccccggcgcc cgcagaagac ttgtgtttgc ctcctgcagc ctcaacccgg 150
agggcagcga gggcctacca ccatgatcac tggtgtgttc agcatgcgct 200
tgtggacccc agtgggcgtc ctgacctcgc tggcgtactg cctgcaccag 250
cggcgggtgg ccctggccga gctgcaggag gccgatggcc agtgtccggt 300
cgaccgcagc ctgctgaagt tgaaaatggt gcaggtcgtg tttcgacacg 350
gggctcggag tcctctcaag ccgctcccgc tggaggagca ggtagagtgg 400
aacccccagc tattagaggt cccaccccaa actcagtttg attacacagt 450
caccaatcta gctggtggtc cgaaaccata ttctccttac gactctcaat 500
accatgagac caccctgaag gggggcatgt ttgctgggca gctgaccaag 550
gtgggcatgc agcaaatgtt tgccttggga gagagactga ggaagaacta 600
tgtggaagac attccctttc tttcaccaac cttcaaccca caggaggtct 650
ttattcgttc cactaacatt tttcggaatc tggagtccac ccgttgtttg 700
ctggctgggc ttttccagtg tcagaaagaa ggacccatca tcatccacac 750
tgatgaagca gattcagaag tcttgtatcc caactaccaa agctgctgga 800

-continued

```
gcctgaggca gagaaccaga ggccggaggc agactgcctc tttacagcca          850

ggaatctcag aggatttgaa aaaggtgaag gacaggatgg gcattgacag          900

tagtgataaa gtggacttct tcatcctcct ggacaacgtg gctgccgagc          950

aggcacacaa cctcccaagc tgccccatgc tgaagagatt tgcacggatg         1000

atcgaacaga gagctgtgga cacatccttg tacatactgc ccaaggaaga         1050

cagggaaagt cttcagatgg cagtaggccc attcctccac atcctagaga         1100

gcaacctgct gaaagccatg gactctgcca ctgcccccga caagatcaga         1150

aagctgtatc tctatgcggc tcatgatgtg accttcatac cgctcttaat         1200

gaccctgggg atttttgacc acaaatggcc accgtttgct gttgacctga         1250

ccatggaact ttaccagcac ctggaatcta aggagtggtt tgtgcagctc         1300

tattaccacg ggaaggagca ggtgccgaga ggttgccctg atgggctctg         1350

cccgctggac atgttcttga atgccatgtc agtttatacc ttaagcccag         1400

aaaaatacca tgcactctgc tctcaaactc aggtgatgga agttggaaat         1450

gaagagtaac tgatttataa aagcaggatg tgttgatttt aaaataaagt         1500

gcctttatac  aatg                                                1514
```

<210> SEQ ID NO 102
<211> LENGTH: 428
<212> TYPE: PRT
<213> ORGANISM: Homo sapiens

<400> SEQUENCE: 102

```
Met Ile Thr Gly Val Phe Ser Met Arg Leu Trp Thr Pro Val Gly
  1               5                  10                  15

Val Leu Thr Ser Leu Ala Tyr Cys Leu His Gln Arg Arg Val Ala
                 20                  25                  30

Leu Ala Glu Leu Gln Glu Ala Asp Gly Gln Cys Pro Val Asp Arg
                 35                  40                  45

Ser Leu Leu Lys Leu Lys Met Val Gln Val Val Phe Arg His Gly
                 50                  55                  60

Ala Arg Ser Pro Leu Lys Pro Leu Pro Leu Glu Glu Gln Val Glu
                 65                  70                  75

Trp Asn Pro Gln Leu Leu Glu Val Pro Pro Gln Thr Gln Phe Asp
                 80                  85                  90

Tyr Thr Val Thr Asn Leu Ala Gly Gly Pro Lys Pro Tyr Ser Pro
                 95                 100                 105

Tyr Asp Ser Gln Tyr His Glu Thr Thr Leu Lys Gly Gly Met Phe
                110                 115                 120

Ala Gly Gln Leu Thr Lys Val Gly Met Gln Gln Met Phe Ala Leu
                125                 130                 135

Gly Glu Arg Leu Arg Lys Asn Tyr Val Glu Asp Ile Pro Phe Leu
                140                 145                 150

Ser Pro Thr Phe Asn Pro Gln Glu Val Phe Ile Arg Ser Thr Asn
                155                 160                 165

Ile Phe Arg Asn Leu Glu Ser Thr Arg Cys Leu Leu Ala Gly Leu
                170                 175                 180

Phe Gln Cys Gln Lys Glu Gly Pro Ile Ile Ile His Thr Asp Glu
                185                 190                 195

Ala Asp Ser Glu Val Leu Tyr Pro Asn Tyr Gln Ser Cys Trp Ser
```

-continued

```
                200                 205                 210

Leu Arg Gln Arg Thr Arg Gly Arg Arg Gln Thr Ala Ser Leu Gln
                215                 220                 225

Pro Gly Ile Ser Glu Asp Leu Lys Lys Val Lys Asp Arg Met Gly
                230                 235                 240

Ile Asp Ser Ser Asp Lys Val Asp Phe Phe Ile Leu Leu Asp Asn
                245                 250                 255

Val Ala Ala Glu Gln Ala His Asn Leu Pro Ser Cys Pro Met Leu
                260                 265                 270

Lys Arg Phe Ala Arg Met Ile Glu Gln Arg Ala Val Asp Thr Ser
                275                 280                 285

Leu Tyr Ile Leu Pro Lys Glu Asp Arg Glu Ser Leu Gln Met Ala
                290                 295                 300

Val Gly Pro Phe Leu His Ile Leu Glu Ser Asn Leu Leu Lys Ala
                305                 310                 315

Met Asp Ser Ala Thr Ala Pro Asp Lys Ile Arg Lys Leu Tyr Leu
                320                 325                 330

Tyr Ala Ala His Asp Val Thr Phe Ile Pro Leu Leu Met Thr Leu
                335                 340                 345

Gly Ile Phe Asp His Lys Trp Pro Pro Phe Ala Val Asp Leu Thr
                350                 355                 360

Met Glu Leu Tyr Gln His Leu Glu Ser Lys Glu Trp Phe Val Gln
                365                 370                 375

Leu Tyr Tyr His Gly Lys Glu Gln Val Pro Arg Gly Cys Pro Asp
                380                 385                 390

Gly Leu Cys Pro Leu Asp Met Phe Leu Asn Ala Met Ser Val Tyr
                395                 400                 405

Thr Leu Ser Pro Glu Lys Tyr His Ala Leu Cys Ser Gln Thr Gln
                410                 415                 420

Val Met Glu Val Gly Asn Glu Glu
                425
```

<210> SEQ ID NO 103
<211> LENGTH: 2555
<212> TYPE: DNA
<213> ORGANISM: Homo sapiens

<400> SEQUENCE: 103

```
ggggcgggtg gacgcggact cgaacgcagt tgcttcggga cccaggaccc          50

cctcgggccc gacccgccag gaaagactga ggccgcggcc tgccccgccc         100

ggctccctgc gccgccgccg cctcccggga cagaagatgt gctccagggt         150

ccctctgctg ctgccgctgc tcctgctact ggccctgggg cctggggtgc         200

agggctgccc atccggctgc cagtgcagcc agccacagac agtcttctgc         250

actgcccgcc aggggaccac ggtgccccga gacgtgccac ccgacacggt         300

ggggctgtac gtctttgaga acggcatcac catgctcgac gcaagcagct         350

ttgccggcct gccgggcctg cagctcctgg acctgtcaca gaaccagatc         400

gccagcctgc gcctgccccg cctgctgctg ctggacctca gccacaacag         450

cctcctggcc ctggagcccg gcatcctgga cactgccaac gtggaggcgc         500

tgcggctggc tggtctgggg ctgcagcagc tggacgaggg gctcttcagc         550

cgcttgcgca acctccacga cctggatgtg tccgacaacc agctggagcg         600
```

-continued

```
agtgccacct gtgatccgag gcctccgggg cctgacgcgc ctgcggctgg       650
ccggcaacac ccgcattgcc cagctgcggc ccgaggacct ggccggcctg       700
gctgccctgc aggagctgga tgtgagcaac ctaagcctgc aggccctgcc       750
tggcgacctc tcgggcctct tcccccgcct gcggctgctg gcagctgccc       800
gcaacccctt caactgcgtg tgcccctga gctggtttgg cccctgggtg        850
cgcgagagcc acgtcacact ggccagccct gaggagacgc gctgccactt       900
cccgcccaag aacgctggcc ggctgctcct ggagcttgac tacgccgact       950
ttggctgccc agccaccacc accacagcca cagtgcccac cacgaggccc      1000
gtggtgcggg agcccacagc cttgtcttct agcttggctc ctacctggct      1050
tagccccaca gcgccggcca ctgaggcccc cagcccgccc tccactgccc      1100
caccgactgt agggcctgtc cccagcccc aggactgccc accgtccacc       1150
tgcctcaatg ggggcacatg ccacctgggg acacggcacc acctggcgtg      1200
cttgtgcccc gaaggcttca cgggcctgta ctgtgagagc cagatggggc      1250
aggggacacg gcccagccct acaccagtca cgccgaggcc accacggtcc      1300
ctgaccctgg gcatcgagcc ggtgagcccc acctccctgc gcgtggggct      1350
gcagcgctac ctccagggga gctccgtgca gctcaggagc ctccgtctca      1400
cctatcgcaa cctatcgggc cctgataagc ggctggtgac gctgcgactg      1450
cctgcctcgc tcgctgagta cacggtcacc cagctgcggc ccaacgccac      1500
ttactccgtc tgtgtcatgc ctttggggcc cgggcgggtg ccggagggcg      1550
aggaggcctg cggggaggcc catacacccc cagccgtcca ctccaaccac      1600
gccccagtca cccaggcccg cgagggcaac ctgccgctcc tcattgcgcc      1650
cgccctggcc gcggtgctcc tggccgcgct ggctgcggtg ggggcagcct      1700
actgtgtgcg gcgggggcgg gccatggcag cagcggctca ggacaaaggg      1750
caggtggggc caggggctgg gcccctggaa ctggagggag tgaaggtccc      1800
cttggagcca ggcccgaagg caacagaggg cggtggagag gccctgccca      1850
gcgggtctga gtgtgaggtg ccactcatgg gcttcccagg gcctggcctc      1900
cagtcacccc tccacgcaaa gccctacatc taagccagag agagacaggg      1950
cagctggggc cgggctctca gccagtgaga tggccagccc cctcctgctg      2000
ccacaccacg taagttctca gtcccaacct cggggatgtg tgcagacagg      2050
gctgtgtgac cacagctggg ccctgttccc tctggacctc ggtctcctca      2100
tctgtgagat gctgtggccc agctgacgag ccctaacgtc cccagaaccg      2150
agtgcctatg aggacagtgt ccgccctgcc ctccgcaacg tgcagtccct      2200
gggcacggcg ggccctgcca tgtgctggta acgcatgcct gggccctgct      2250
gggctctccc actccaggcg gaccctgggg gccagtgaag gaagctcccg      2300
gaaagagcag agggagagcg ggtaggcggc tgtgtgactc tagtcttggc      2350
cccaggaagc gaaggaacaa aagaaactgg aaaggaagat gctttaggaa      2400
catgttttgc ttttttaaaa tatatatata tttataagag atcctttccc      2450
atttattctg ggaagatgtt tttcaaactc agagacaagg actttggttt      2500
ttgtaagaca aacgatgata tgaaggcctt ttgtaagaaa aaataaaaaa      2550
aaaaa                                                       2555
```

<210> SEQ ID NO 104
<211> LENGTH: 598
<212> TYPE: PRT
<213> ORGANISM: Homo sapiens

<400> SEQUENCE: 104

```
Met Cys Ser Arg Val Pro Leu Leu Leu Pro Leu Leu Leu Leu Leu
  1               5                  10                  15

Ala Leu Gly Pro Gly Val Gln Gly Cys Pro Ser Gly Cys Gln Cys
                 20                  25                  30

Ser Gln Pro Gln Thr Val Phe Cys Thr Ala Arg Gln Gly Thr Thr
                 35                  40                  45

Val Pro Arg Asp Val Pro Pro Asp Thr Val Gly Leu Tyr Val Phe
                 50                  55                  60

Glu Asn Gly Ile Thr Met Leu Asp Ala Ser Ser Phe Ala Gly Leu
                 65                  70                  75

Pro Gly Leu Gln Leu Leu Asp Leu Ser Gln Asn Gln Ile Ala Ser
                 80                  85                  90

Leu Arg Leu Pro Arg Leu Leu Leu Leu Asp Leu Ser His Asn Ser
                 95                 100                 105

Leu Leu Ala Leu Glu Pro Gly Ile Leu Asp Thr Ala Asn Val Glu
                110                 115                 120

Ala Leu Arg Leu Ala Gly Leu Gly Leu Gln Gln Leu Asp Glu Gly
                125                 130                 135

Leu Phe Ser Arg Leu Arg Asn Leu His Asp Leu Asp Val Ser Asp
                140                 145                 150

Asn Gln Leu Glu Arg Val Pro Pro Val Ile Arg Gly Leu Arg Gly
                155                 160                 165

Leu Thr Arg Leu Arg Leu Ala Gly Asn Thr Arg Ile Ala Gln Leu
                170                 175                 180

Arg Pro Glu Asp Leu Ala Gly Leu Ala Ala Leu Gln Glu Leu Asp
                185                 190                 195

Val Ser Asn Leu Ser Leu Gln Ala Leu Pro Gly Asp Leu Ser Gly
                200                 205                 210

Leu Phe Pro Arg Leu Arg Leu Leu Ala Ala Ala Arg Asn Pro Phe
                215                 220                 225

Asn Cys Val Cys Pro Leu Ser Trp Phe Gly Pro Trp Val Arg Glu
                230                 235                 240

Ser His Val Thr Leu Ala Ser Pro Glu Glu Thr Arg Cys His Phe
                245                 250                 255

Pro Pro Lys Asn Ala Gly Arg Leu Leu Leu Glu Leu Asp Tyr Ala
                260                 265                 270

Asp Phe Gly Cys Pro Ala Thr Thr Thr Thr Ala Thr Val Pro Thr
                275                 280                 285

Thr Arg Pro Val Val Arg Glu Pro Thr Ala Leu Ser Ser Ser Leu
                290                 295                 300

Ala Pro Thr Trp Leu Ser Pro Thr Ala Pro Ala Thr Glu Ala Pro
                305                 310                 315

Ser Pro Pro Ser Thr Ala Pro Pro Thr Val Gly Pro Val Pro Gln
                320                 325                 330

Pro Gln Asp Cys Pro Pro Ser Thr Cys Leu Asn Gly Gly Thr Cys
                335                 340                 345

His Leu Gly Thr Arg His His Leu Ala Cys Leu Cys Pro Glu Gly
```

-continued

```
                350                 355                 360

Phe Thr Gly Leu Tyr Cys Glu Ser Gln Met Gly Gln Gly Thr Arg
                365                 370                 375

Pro Ser Pro Thr Pro Val Thr Pro Arg Pro Pro Arg Ser Leu Thr
                380                 385                 390

Leu Gly Ile Glu Pro Val Ser Pro Thr Ser Leu Arg Val Gly Leu
                395                 400                 405

Gln Arg Tyr Leu Gln Gly Ser Ser Val Gln Leu Arg Ser Leu Arg
                410                 415                 420

Leu Thr Tyr Arg Asn Leu Ser Gly Pro Asp Lys Arg Leu Val Thr
                425                 430                 435

Leu Arg Leu Pro Ala Ser Leu Ala Glu Tyr Thr Val Thr Gln Leu
                440                 445                 450

Arg Pro Asn Ala Thr Tyr Ser Val Cys Val Met Pro Leu Gly Pro
                455                 460                 465

Gly Arg Val Pro Glu Gly Glu Glu Ala Cys Gly Glu Ala His Thr
                470                 475                 480

Pro Pro Ala Val His Ser Asn His Ala Pro Val Thr Gln Ala Arg
                485                 490                 495

Glu Gly Asn Leu Pro Leu Leu Ile Ala Pro Ala Leu Ala Ala Val
                500                 505                 510

Leu Leu Ala Ala Leu Ala Ala Val Gly Ala Ala Tyr Cys Val Arg
                515                 520                 525

Arg Gly Arg Ala Met Ala Ala Ala Ala Gln Asp Lys Gly Gln Val
                530                 535                 540

Gly Pro Gly Ala Gly Pro Leu Glu Leu Glu Gly Val Lys Val Pro
                545                 550                 555

Leu Glu Pro Gly Pro Lys Ala Thr Glu Gly Gly Gly Glu Ala Leu
                560                 565                 570

Pro Ser Gly Ser Glu Cys Glu Val Pro Leu Met Gly Phe Pro Gly
                575                 580                 585

Pro Gly Leu Gln Ser Pro Leu His Ala Lys Pro Tyr Ile
                590                 595


<210> SEQ ID NO 105
<211> LENGTH: 647
<212> TYPE: DNA
<213> ORGANISM: Homo sapiens

<400> SEQUENCE: 105

cccacgcgtc cgaaggcaga caaaggttca tttgtaaaga agctccttcc          50

agcacctcct ctcttctcct tttgcccaaa ctcacccagt gagtgtgagc         100

atttaagaag catcctctgc caagaccaaa aggaaagaag aaaaagggcc         150

aaaagccaaa atgaaactga tggtacttgt tttcaccatt gggctaactt         200

tgctgctagg agttcaagcc atgcctgcaa atcgcctctc ttgctacaga         250

aagatactaa aagatcacaa ctgtcacaac cttccggaag gagtagctga         300

cctgacacag attgatgtca atgtccagga tcatttctgg gatgggaagg         350

gatgtgagat gatctgttac tgcaacttca gcgaattgct ctgctgccca         400

aaagacgttt tctttggacc aaagatctct ttcgtgattc cttgcaacaa         450

tcaatgagaa tcttcatgta ttctggagaa caccattcct gatttcccac         500

aaactgcact acatcagtat aactgcattt ctagtttcta tatagtgcaa         550
```

-continued

```
tagagcatag attctataaa ttcttacttg tctaagacaa gtaaatctgt            600

gttaaacaag tagtaataaa agttaattca atctaaaaaa  aaaaaaa              647


<210> SEQ ID NO 106
<211> LENGTH: 98
<212> TYPE: PRT
<213> ORGANISM: Homo sapiens

<400> SEQUENCE: 106

Met Lys Leu Met Val Leu Val Phe Thr Ile Gly Leu Thr Leu Leu
  1               5                  10                  15

Leu Gly Val Gln Ala Met Pro Ala Asn Arg Leu Ser Cys Tyr Arg
                 20                  25                  30

Lys Ile Leu Lys Asp His Asn Cys His Asn Leu Pro Glu Gly Val
                 35                  40                  45

Ala Asp Leu Thr Gln Ile Asp Val Asn Val Gln Asp His Phe Trp
                 50                  55                  60

Asp Gly Lys Gly Cys Glu Met Ile Cys Tyr Cys Asn Phe Ser Glu
                 65                  70                  75

Leu Leu Cys Cys Pro Lys Asp Val Phe Phe Gly Pro Lys Ile Ser
                 80                  85                  90

Phe Val Ile Pro Cys Asn Asn Gln
                 95


<210> SEQ ID NO 107
<211> LENGTH: 972
<212> TYPE: DNA
<213> ORGANISM: Homo sapiens

<400> SEQUENCE: 107

agtgactgca gccttcctag atcccctcca ctcggtttct ctctttgcag             50

gagcaccggc agcaccagtg tgtgagggga gcaggcagcg gtcctagcca            100

gttccttgat cctgccagac cacccagccc ccggcacaga gctgctccac            150

aggcaccatg aggatcatgc tgctattcac agccatcctg gccttcagcc            200

tagctcagag ctttggggct gtctgtaagg agccacagga ggaggtggtt            250

cctggcgggg gccgcagcaa gagggatcca gatctctacc agctgctcca            300

gagactcttc aaaagccact catctctgga gggattgctc aaagccctga            350

gccaggctag cacagatcct aaggaatcaa catctcccga gaaacgtgac            400

atgcatgact tctttgtggg acttatgggc aagaggagcg tccagccaga            450

gggaaagaca ggacctttct taccttcagt gagggttcct cggcccccttc           500

atcccaatca gcttggatcc acaggaaagt cttccctggg aacagaggag            550

cagagacctt tataagactc tcctacggat gtgaatcaag agaacgtccc            600

cagctttggc atcctcaagt atcccccgag agcagaatag gtactccact            650

tccggactcc tggactgcat taggaagacc tctttccctg tcccaatccc            700

caggtgcgca cgctcctgtt accctttctc ttccctgttc ttgtaacatt            750

cttgtgcttt gactccttct ccatcttttc tacctgaccc tggtgtggaa            800

actgcatagt gaatatcccc aaccccaatg ggcattgact gtagaatacc            850

ctagagttcc tgtagtgtcc tacattaaaa atataatgtc tctctctatt            900

cctcaacaat aaaggatttt tgcatatgaa aaaaaaaaaa aaaaaaaaaa            950
```

```
aaaaaaaaaa aaaaaaaaaa  aa                                              972


<210> SEQ ID NO 108
<211> LENGTH: 135
<212> TYPE: PRT
<213> ORGANISM: Homo sapiens

<400> SEQUENCE: 108

Met Arg Ile Met Leu Leu Phe Thr Ala Ile Leu Ala Phe Ser Leu
  1               5                  10                  15

Ala Gln Ser Phe Gly Ala Val Cys Lys Glu Pro Gln Glu Glu Val
                 20                  25                  30

Val Pro Gly Gly Gly Arg Ser Lys Arg Asp Pro Asp Leu Tyr Gln
                 35                  40                  45

Leu Leu Gln Arg Leu Phe Lys Ser His Ser Ser Leu Glu Gly Leu
                 50                  55                  60

Leu Lys Ala Leu Ser Gln Ala Ser Thr Asp Pro Lys Glu Ser Thr
                 65                  70                  75

Ser Pro Glu Lys Arg Asp Met His Asp Phe Phe Val Gly Leu Met
                 80                  85                  90

Gly Lys Arg Ser Val Gln Pro Glu Gly Lys Thr Gly Pro Phe Leu
                 95                 100                 105

Pro Ser Val Arg Val Pro Arg Pro Leu His Pro Asn Gln Leu Gly
                110                 115                 120

Ser Thr Gly Lys Ser Ser Leu Gly Thr Glu Glu Gln Arg Pro Leu
                125                 130                 135


<210> SEQ ID NO 109
<211> LENGTH: 1485
<212> TYPE: DNA
<213> ORGANISM: Homo sapiens

<400> SEQUENCE: 109

gcggccacac gcagctagcc ggagcccgga ccaggcgcct gtgcctcctc                 50

ctcgtccctc gccgcgtccg cgaagcctgg agccggcggg agccccgcgc                100

tcgccatgtc gggcgagctc agcaacaggt tccaaggagg gaaggcgttc                150

ggcttgctca aagcccggca ggagaggagg ctggccgaga tcaaccggga                200

gtttctgtgt gaccagaagt acagtgatga agagaacctt ccagaaaagc                250

tcacagcctt caaagagaag tacatggagt ttgacctgaa caatgaaggc                300

gagattgacc tgatgtcttt aaagaggatg atggagaagc ttggtgtccc                350

caagacccac ctggagatga agaagatgat ctcagaggtg acaggagggg                400

tcagtgacac tatatcctac cgagactttg tgaacatgat gctggggaaa                450

cggtcggctg tcctcaagtt agtcatgatg tttgaaggaa aagccaacga                500

gagcagcccc aagccagttg gcccccctcc agagagagac attgctagcc                550

tgccctgagg accccgcctg gactccccag ccttcccacc ccatacctcc                600

ctcccgatct tgctgccctt cttgacacac tgtgatctct ctctctctca                650

tttgtttggt cattgagggt ttgtttgtgt tttcatcaat gtctttgtaa                700

agcacaaatt atctgcctta aaggggctct gggtcgggga atcctgagcc                750

ttgggtcccc tccctctctt cttccctcct tccccgctcc ctgtgcagaa                800

gggctgatat caaaccaaaa actagagggg gcagggccag ggcagggagg                850
```

-continued cttccagcct gtgttcccct cacttggagg aaccagcact ctccatcctt 900
tcagaaagtc tccaagccaa gttcaggctc actgacctgg ctctgacgag 950
gaccccaggc cactctgaga agaccttgga gtagggacaa ggctgcaggg 1000
cctctttcgg gtttccttgg acagtgccat ggttccagtg ctctggtgtc 1050
acccaggaca cagccactcg gggccccgct gccccagctg atccccactc 1100
attccacacc tcttctcatc ctcagtgatg tgaaggtggg aaggaaagga 1150
gcttggcatt gggagccctt caagaaggta ccagaaggaa ccctccagtc 1200
ctgctctctg gccacacctg tgcaggcagc tgagaggcag cgtgcagccc 1250
tactgtccct tactggggca gcagagggct tcggaggcag aagtgaggcc 1300
tggggtttgg ggggaaaggt cagctcagtg ctgttccacc ttttagggag 1350
gatactgagg ggaccaggat gggagaatga ggagtaaaat gctcacggca 1400
aagtcagcag cactggtaag ccaagactga gaaatacaag gttgcttgtc 1450
tgaccccaat ctgcttgaaa aaaaaaaaaa aaaaa 1485

<210> SEQ ID NO 110
<211> LENGTH: 150
<212> TYPE: PRT
<213> ORGANISM: Homo sapiens

<400> SEQUENCE: 110

Met Ser Gly Glu Leu Ser Asn Arg Phe Gln Gly Gly Lys Ala Phe
1 5 10 15

Gly Leu Leu Lys Ala Arg Gln Glu Arg Arg Leu Ala Glu Ile Asn
20 25 30

Arg Glu Phe Leu Cys Asp Gln Lys Tyr Ser Asp Glu Glu Asn Leu
35 40 45

Pro Glu Lys Leu Thr Ala Phe Lys Glu Lys Tyr Met Glu Phe Asp
50 55 60

Leu Asn Asn Glu Gly Glu Ile Asp Leu Met Ser Leu Lys Arg Met
65 70 75

Met Glu Lys Leu Gly Val Pro Lys Thr His Leu Glu Met Lys Lys
80 85 90

Met Ile Ser Glu Val Thr Gly Gly Val Ser Asp Thr Ile Ser Tyr
95 100 105

Arg Asp Phe Val Asn Met Met Leu Gly Lys Arg Ser Ala Val Leu
110 115 120

Lys Leu Val Met Met Phe Glu Gly Lys Ala Asn Glu Ser Ser Pro
125 130 135

Lys Pro Val Gly Pro Pro Pro Glu Arg Asp Ile Ala Ser Leu Pro
140 145 150

<210> SEQ ID NO 111
<211> LENGTH: 537
<212> TYPE: DNA
<213> ORGANISM: Homo sapiens

<400> SEQUENCE: 111
taaaacagct acaatattcc agggccagtc acttgccatt tctcataaca 50
gcgtcagaga gaaagaactg actgaaacgt ttgagatgaa gaaagttctc 100
ctcctgatca cagccatctt ggcagtggct gttggtttcc cagtctctca 150

-continued

```
agaccaggaa cgagaaaaaa gaagtatcag tgacagcgat gaattagctt            200

cagggttttt tgtgttccct tacccatatc catttcgccc acttccacca            250

attccatttc caagatttcc atggtttaga cgtaattttc ctattccaat            300

acctgaatct gcccctacaa ctccccttcc tagcgaaaag taaacaagaa            350

ggataagtca cgataaacct ggtcacctga aattgaaatt gagccacttc            400

cttgaagaat caaaattcct gttaataaaa gaaaaacaaa tgtaattgaa            450

atagcacaca gcattctcta gtcaatatct ttagtgatct tctttaataa            500

acatgaaagc aaagattttg gtttcttaat  ttccaca                         537


<210> SEQ ID NO 112
<211> LENGTH: 85
<212> TYPE: PRT
<213> ORGANISM: Homo sapiens

<400> SEQUENCE: 112

Met Lys Lys Val Leu Leu Leu Ile Thr Ala Ile Leu Ala Val Ala
  1               5                  10                  15

Val Gly Phe Pro Val Ser Gln Asp Gln Glu Arg Glu Lys Arg Ser
                 20                  25                  30

Ile Ser Asp Ser Asp Glu Leu Ala Ser Gly Phe Phe Val Phe Pro
                 35                  40                  45

Tyr Pro Tyr Pro Phe Arg Pro Leu Pro Pro Ile Pro Phe Pro Arg
                 50                  55                  60

Phe Pro Trp Phe Arg Arg Asn Phe Pro Ile Pro Ile Pro Glu Ser
                 65                  70                  75

Ala Pro Thr Thr Pro Leu Pro Ser Glu Lys
                 80                  85


<210> SEQ ID NO 113
<211> LENGTH: 1686
<212> TYPE: DNA
<213> ORGANISM: Homo sapiens

<400> SEQUENCE: 113

ctcctcttaa catacttgca gctaaaacta aatattgctg cttggggacc             50

tccttctagc cttaaatttc agctcatcac cttcacctgc cttggtcatg            100

gctctgctat tctccttgat ccttgccatt tgcaccagac ctggattcct            150

agcgtctcca tctggagtgc ggctggtggg gggcctccac cgctgtgaag            200

ggcgggtgga ggtggaacag aaaggccagt ggggcaccgt gtgtgatgac            250

ggctgggaca ttaaggacgt ggctgtgttg tgccgggagc tgggctgtgg            300

agctgccagc ggaaccccta gtggtatttt gtatgagcca ccagcagaaa            350

aagagcaaaa ggtcctcatc caatcagtca gttgcacagg aacagaagat            400

acattggctc agtgtgagca agaagaagtt tatgattgtt cacatgatga            450

agatgctggg gcatcgtgtg agaacccaga gagctctttc tccccagtcc            500

cagagggtgt caggctggct gacggccctg ggcattgcaa gggacgcgtg            550

gaagtgaagc accagaacca gtggtatacc gtgtgccaga caggctggag            600

cctccgggcc gcaaaggtgg tgtgccggca gctgggatgt gggagggctg            650

tactgactca aaaacgctgc aacaagcatg cctatggccg aaaacccatc            700

tggctgagcc agatgtcatg ctcaggacga gaagcaaccc ttcaggattg            750
```

-continued

```
cccttctggg ccttggggga agaacacctg caaccatgat gaagacacgt         800

gggtcgaatg tgaagatccc tttgacttga gactagtagg aggagacaac         850

ctctgctctg ggcgactgga ggtgctgcac aagggcgtat ggggctctgt         900

ctgtgatgac aactggggag aaaaggagga ccaggtggta tgcaagcaac         950

tgggctgtgg gaagtccctc tctccctcct tcagagaccg gaaatgctat        1000

ggccctgggg ttggccgcat ctggctggat aatgttcgtt gctcagggga        1050

ggagcagtcc ctggagcagt gccagcacag attttggggg tttcacgact        1100

gcacccacca ggaagatgtg gctgtcatct gctcagtgta ggtgggcatc        1150

atctaatctg ttgagtgcct gaatagaaga aaaacacaga agaagggagc        1200

atttactgtc tacatgactg catgggatga acactgatct tcttctgccc        1250

ttggactggg acttatactt ggtgcccctg attctcaggc cttcagagtt        1300

ggatcagaac ttacaacatc aggtctagtt ctcaggccat cagacatagt        1350

ttggaactac atcaccacct ttcctatgtc tccacattgc acacagcaga        1400

ttcccagcct ccataattgt gtgtatcaac tacttaaata cattctcaca        1450

cacacacaca cacacacaca cacacacaca cacacataca ccatttgtcc        1500

tgtttctctg aagaactctg acaaaataca gattttggta ctgaaagaga        1550

ttctagagga acggaatttt aaggataaat tttctgaatt ggttatgggg        1600

tttctgaaat tggctctata atctaattag atataaaatt ctggtaactt        1650

tatttacaat aataaagata gcactatgtg  ttcaaa                      1686
```

<210> SEQ ID NO 114
<211> LENGTH: 347
<212> TYPE: PRT
<213> ORGANISM: Homo sapiens

<400> SEQUENCE: 114

```
Met Ala Leu Leu Phe Ser Leu Ile Leu Ala Ile Cys Thr Arg Pro
  1               5                  10                  15

Gly Phe Leu Ala Ser Pro Ser Gly Val Arg Leu Val Gly Gly Leu
                 20                  25                  30

His Arg Cys Glu Gly Arg Val Glu Val Glu Gln Lys Gly Gln Trp
                 35                  40                  45

Gly Thr Val Cys Asp Asp Gly Trp Asp Ile Lys Asp Val Ala Val
                 50                  55                  60

Leu Cys Arg Glu Leu Gly Cys Gly Ala Ala Ser Gly Thr Pro Ser
                 65                  70                  75

Gly Ile Leu Tyr Glu Pro Pro Ala Glu Lys Glu Gln Lys Val Leu
                 80                  85                  90

Ile Gln Ser Val Ser Cys Thr Gly Thr Glu Asp Thr Leu Ala Gln
                 95                 100                 105

Cys Glu Gln Glu Glu Val Tyr Asp Cys Ser His Asp Glu Asp Ala
                110                 115                 120

Gly Ala Ser Cys Glu Asn Pro Glu Ser Ser Phe Ser Pro Val Pro
                125                 130                 135

Glu Gly Val Arg Leu Ala Asp Gly Pro Gly His Cys Lys Gly Arg
                140                 145                 150

Val Glu Val Lys His Gln Asn Gln Trp Tyr Thr Val Cys Gln Thr
                155                 160                 165
```

-continued

```
Gly Trp Ser Leu Arg Ala Ala Lys Val Val Cys Arg Gln Leu Gly
                170                 175                 180

Cys Gly Arg Ala Val Leu Thr Gln Lys Arg Cys Asn Lys His Ala
                185                 190                 195

Tyr Gly Arg Lys Pro Ile Trp Leu Ser Gln Met Ser Cys Ser Gly
                200                 205                 210

Arg Glu Ala Thr Leu Gln Asp Cys Pro Ser Gly Pro Trp Gly Lys
                215                 220                 225

Asn Thr Cys Asn His Asp Glu Asp Thr Trp Val Glu Cys Glu Asp
                230                 235                 240

Pro Phe Asp Leu Arg Leu Val Gly Gly Asp Asn Leu Cys Ser Gly
                245                 250                 255

Arg Leu Glu Val Leu His Lys Gly Val Trp Gly Ser Val Cys Asp
                260                 265                 270

Asp Asn Trp Gly Glu Lys Glu Asp Gln Val Val Cys Lys Gln Leu
                275                 280                 285

Gly Cys Gly Lys Ser Leu Ser Pro Ser Phe Arg Asp Arg Lys Cys
                290                 295                 300

Tyr Gly Pro Gly Val Gly Arg Ile Trp Leu Asp Asn Val Arg Cys
                305                 310                 315

Ser Gly Glu Glu Gln Ser Leu Glu Gln Cys Gln His Arg Phe Trp
                320                 325                 330

Gly Phe His Asp Cys Thr His Gln Glu Asp Val Ala Val Ile Cys
                335                 340                 345

Ser Val
```

```
<210> SEQ ID NO 115
<211> LENGTH: 728
<212> TYPE: DNA
<213> ORGANISM: Homo sapiens

<400> SEQUENCE: 115

catttccaac aagagcactg gccaagtcag cttcttctga gagagtctct           50

agaagacatg atgctacact cagctttggg tctctgcctc ttactcgtca          100

cagtttcttc caaccttgcc attgcaataa aaaaggaaaa gaggcctcct          150

cagacactct caagaggatg gggagatgac atcacttggg tacaaactta          200

tgaagaaggt ctcttttatg ctcaaaaaag taagaagcca ttaatggtta          250

ttcatcacct ggaggattgt caatactctc aagcactaaa gaaagtattt          300

gcccaaaatg aagaaataca agaaatggct cagaataagt tcatcatgct          350

aaaccttatg catgaaacca ctgataagaa tttatcacct gatgggcaat          400

atgtgcctag aatcatgttt gtagaccctt ctttaacagt tagagctgac          450

atagctggaa gatactctaa cagattgtac acatatgagc ctcgggattt          500

acccctattg atagaaaaca tgaagaaagc attaagactt attcagtcag          550

agctataaga gatgatggaa aaaagccttc acttcaaaga agtcaaattt          600

catgaagaaa acctctggca cattgacaaa tactaaatgt gcaagtatat          650

agattttgta atattactat ttagtttttt taatgtgttt gcaatagtct          700

tattaaaata aatgtttttt  aaatctga                                 728

<210> SEQ ID NO 116
```

-continued

<211> LENGTH: 166
<212> TYPE: PRT
<213> ORGANISM: Homo sapiens

<400> SEQUENCE: 116

Met Met Leu His Ser Ala Leu Gly Leu Cys Leu Leu Leu Val Thr
1 5 10 15

Val Ser Ser Asn Leu Ala Ile Ala Ile Lys Lys Glu Lys Arg Pro
20 25 30

Pro Gln Thr Leu Ser Arg Gly Trp Gly Asp Asp Ile Thr Trp Val
35 40 45

Gln Thr Tyr Glu Glu Gly Leu Phe Tyr Ala Gln Lys Ser Lys Lys
50 55 60

Pro Leu Met Val Ile His His Leu Glu Asp Cys Gln Tyr Ser Gln
65 70 75

Ala Leu Lys Lys Val Phe Ala Gln Asn Glu Glu Ile Gln Glu Met
80 85 90

Ala Gln Asn Lys Phe Ile Met Leu Asn Leu Met His Glu Thr Thr
95 100 105

Asp Lys Asn Leu Ser Pro Asp Gly Gln Tyr Val Pro Arg Ile Met
110 115 120

Phe Val Asp Pro Ser Leu Thr Val Arg Ala Asp Ile Ala Gly Arg
125 130 135

Tyr Ser Asn Arg Leu Tyr Thr Tyr Glu Pro Arg Asp Leu Pro Leu
140 145 150

Leu Ile Glu Asn Met Lys Lys Ala Leu Arg Leu Ile Gln Ser Glu
155 160 165

Leu

<210> SEQ ID NO 117
<211> LENGTH: 2395
<212> TYPE: DNA
<213> ORGANISM: Homo sapiens

<400> SEQUENCE: 117
cctggagccg gaagcgcggc tgcagcaggg cgaggctcca ggtggggtcg 50
gttccgcatc cagcctagcg tgtccacgat gcggctgggc tccgggactt 100
tcgctacctg ttgcgtagcg atcgaggtgc tagggatcgc ggtcttcctt 150
cggggattct tcccggctcc cgttcgttcc tctgccagag cggaacacgg 200
agcggagccc ccagcgcccg aaccctcggc tggagccagt tctaactgga 250
ccacgctgcc accacctctc ttcagtaaag ttgttattgt tctgatagat 300
gccttgagag atgattttgt gtttgggtca aagggtgtga aatttatgcc 350
ctacacaact taccttgtgg aaaaaggagc atctcacagt tttgtggctg 400
aagcaaagcc acctacagtt actatgcctc gaatcaaggc attgatgacg 450
gggagccttc ctggctttgt cgacgtcatc aggaacctca attctcctgc 500
actgctggaa gacagtgtga taagacaagc aaaagcagct ggaaaaagaa 550
tagtctttta tggagatgaa acctgggtta aattattccc aaagcatttt 600
gtggaatatg atggaacaac ctcatttttc gtgtcagatt acacagaggt 650
ggataataat gtcacgaggc atttggataa agtattaaaa agaggagatt 700
gggacatatt aatcctccac tacctggggc tggaccacat tggccacatt 750

-continued

```
tcagggccca acagcccccct gattgggcag aagctgagcg agatggacag          800

cgtgctgatg aagatccaca cctcactgca gtcgaaggag agagagacgc          850

ctttacccaa tttgctggtt ctttgtggtg accatggcat gtctgaaaca          900

ggaagtcacg gggcctcctc caccgaggag gtgaatacac ctctgatttt          950

aatcagttct gcgtttgaaa ggaaacccgg tgatatccga catccaaagc         1000

acgtccaata gacggatgtg gctgcgacac tggcgatagc acttggctta         1050

ccgattccaa aagacagtgt agggagcctc ctattcccag ttgtggaagg         1100

aagaccaatg agagagcagt tgagattttt acatttgaat acagtgcagc         1150

ttagtaaact gttgcaagag aatgtgccgt catatgaaaa agatcctggg         1200

tttgagcagt ttaaaatgtc agaaagattg catgggaact ggatcagact         1250

gtacttggag gaaaagcatt cagaagtcct attcaacctg ggctccaagg         1300

ttctcaggca gtacctggat gctctgaaga cgctgagctt gtccctgagt         1350

gcacaagtgg cccagttctc accctgctcc tgctcagcgt cccacaggca         1400

ctgcacagaa aggctgagct ggaagtccca ctgtcatctc ctgggttttc         1450

tctgctcttt tatttggtga tcctggttct ttcggccgtt cacgtcattg         1500

tgtgcacctc agctgaaagt tcgtgctact tctgtggcct ctcgtggctg         1550

gcggcaggct gcctttcgtt taccagactc tggttgaaca cctggtgtgt         1600

gccaagtgct ggcagtgccc tggacagggg gcctcaggga aggacgtgga         1650

gcagccttat cccaggcctc tgggtgtccc gacacaggtg ttcacatctg         1700

tgctgtcagg tcagatgcct cagttcttgg aaagctaggt tcctgcgact         1750

gttaccaagg tgattgtaaa gagctggcgg tcacagagga acaagccccc         1800

cagctgaggg ggtgtgtgaa tcggacagcc tcccagcaga ggtgtgggag         1850

ctgcagctga gggaagaaga gacaatcggc ctggacactc aggagggtca         1900

aaaggagact tggtcgcacc actcatcctg ccaccccag aatgcatcct          1950

gcctcatcag gtccagattt ctttccaagg cggacgtttt ctgttggaat         2000

tcttagtcct tggcctcgga caccttcatt cgttagctgg ggagtggtgg         2050

tgaggcagtg aagaagaggc ggatggtcac actcagatcc acagagccca         2100

ggatcaaggg acccactgca gtggcagcag gactgttggg cccccacccc         2150

aaccctgcac agccctcatc ccctcttggc ttgagccgtc agaggccctg         2200

tgctgagtgt ctgaccgaga cactcacagc tttgtcatca gggcacaggc         2250

ttcctcggag ccaggatgat ctgtgccacg cttgcacctc gggcccatct         2300

gggctcatgc tctctctcct gctattgaat tagtacctag ctgcacacag         2350

tatgtagtta ccaaaagaat aaacggcaat aattgagaaa  aaaaa             2395
```

<210> SEQ ID NO 118
<211> LENGTH: 310
<212> TYPE: PRT
<213> ORGANISM: Homo sapiens

<400> SEQUENCE: 118

```
Met Arg Leu Gly Ser Gly Thr Phe Ala Thr Cys Cys Val Ala Ile
  1               5                  10                  15

Glu Val Leu Gly Ile Ala Val Phe Leu Arg Gly Phe Phe Pro Ala
                 20                  25                  30
```

-continued

```
Pro Val Arg Ser Ser Ala Arg Ala Glu His Gly Ala Glu Pro Pro
                35                  40                  45

Ala Pro Glu Pro Ser Ala Gly Ala Ser Ser Asn Trp Thr Thr Leu
                50                  55                  60

Pro Pro Pro Leu Phe Ser Lys Val Val Ile Val Leu Ile Asp Ala
                65                  70                  75

Leu Arg Asp Asp Phe Val Phe Gly Ser Lys Gly Val Lys Phe Met
                80                  85                  90

Pro Tyr Thr Thr Tyr Leu Val Glu Lys Gly Ala Ser His Ser Phe
                95                  100                 105

Val Ala Glu Ala Lys Pro Pro Thr Val Thr Met Pro Arg Ile Lys
                110                 115                 120

Ala Leu Met Thr Gly Ser Leu Pro Gly Phe Val Asp Val Ile Arg
                125                 130                 135

Asn Leu Asn Ser Pro Ala Leu Leu Glu Asp Ser Val Ile Arg Gln
                140                 145                 150

Ala Lys Ala Ala Gly Lys Arg Ile Val Phe Tyr Gly Asp Glu Thr
                155                 160                 165

Trp Val Lys Leu Phe Pro Lys His Phe Val Glu Tyr Asp Gly Thr
                170                 175                 180

Thr Ser Phe Phe Val Ser Asp Tyr Thr Glu Val Asp Asn Asn Val
                185                 190                 195

Thr Arg His Leu Asp Lys Val Leu Lys Arg Gly Asp Trp Asp Ile
                200                 205                 210

Leu Ile Leu His Tyr Leu Gly Leu Asp His Ile Gly His Ile Ser
                215                 220                 225

Gly Pro Asn Ser Pro Leu Ile Gly Gln Lys Leu Ser Glu Met Asp
                230                 235                 240

Ser Val Leu Met Lys Ile His Thr Ser Leu Gln Ser Lys Glu Arg
                245                 250                 255

Glu Thr Pro Leu Pro Asn Leu Leu Val Leu Cys Gly Asp His Gly
                260                 265                 270

Met Ser Glu Thr Gly Ser His Gly Ala Ser Ser Thr Glu Glu Val
                275                 280                 285

Asn Thr Pro Leu Ile Leu Ile Ser Ser Ala Phe Glu Arg Lys Pro
                290                 295                 300

Gly Asp Ile Arg His Pro Lys His Val Gln
                305                 310
```

<210> SEQ ID NO 119
<211> LENGTH: 1333
<212> TYPE: DNA
<213> ORGANISM: Homo sapiens

<400> SEQUENCE: 119

```
gcccacgcgt ccgatggcgt tcacgttcgc ggccttctgc tacatgctgg        50

cgctgctgct cactgccgcg ctcatcttct tcgccatttg gcacattata       100

gcatttgatg agctgaagac tgattacaag aatcctatag accagtgtaa       150

taccctgaat ccccttgtac tcccagagta cctcatccac gctttcttct       200

gtgtcatgtt tctttgtgca gcagagtggc ttacactggg tctcaatatg       250

cccctcttgg catatcatat ttggaggtat atgagtagac cagtgatgag       300

tggcccagga ctctatgacc ctacaaccat catgaatgca gatattctag       350
```

-continued

```
catattgtca gaaggaagga tggtgcaaat tagcttttta tcttctagca      400

tttttttact acctatatgg catgatctat gttttggtga gctcttagaa      450

caacacacag aagaattggt ccagttaagt gcatgcaaaa agccaccaaa      500

tgaagggatt ctatccagca agatcctgtc caagagtagc ctgtggaatc      550

tgatcagtta ctttaaaaaa tgactcctta ttttttaaat gtttccacat      600

ttttgcttgt ggaaagactg ttttcatatg ttatactcag ataaagattt      650

taaatggtat tacgtataaa ttaatataaa atgattacct ctggtgttga      700

caggtttgaa cttgcacttc ttaaggaaca gccataatcc tctgaatgat      750

gcattaatta ctgactgtcc tagtacattg gaagcttttg tttataggaa      800

cttgtagggc tcattttggt ttcattgaaa cagtatctaa ttataaatta      850

gctgtagata tcaggtgctt ctgatgaagt gaaaatgtat atctgactag      900

tgggaaactt catgggtttc ctcatctgtc atgtcgatga ttatatatgg      950

atacatttac aaaaataaaa agcgggaatt ttcccttcgc ttgaatatta     1000

tccctgtata ttgcatgaat gagagatttc ccatatttcc atcagagtaa     1050

taaatatact tgctttaatt cttaagcata agtaaacatg atataaaaat     1100

atatgctgaa ttacttgtga agaatgcatt taaagctatt ttaaatgtgt     1150

ttttatttgt aagacattac ttattaagaa attggttatt atgcttactg     1200

ttctaatctg gtggtaaagg tattcttaag aatttgcagg tactacagat     1250

tttcaaaact gaatgagaga aaattgtata accatcctgc tgttccttta     1300

gtgcaataca ataaaactct gaaattaaga  ctc                      1333
```

```
<210> SEQ ID NO 120
<211> LENGTH: 144
<212> TYPE: PRT
<213> ORGANISM: Homo sapiens

<400> SEQUENCE: 120

Met Ala Phe Thr Phe Ala Ala Phe Cys Tyr Met Leu Ala Leu Leu
 1               5                   10                  15

Leu Thr Ala Ala Leu Ile Phe Phe Ala Ile Trp His Ile Ile Ala
                20                  25                  30

Phe Asp Glu Leu Lys Thr Asp Tyr Lys Asn Pro Ile Asp Gln Cys
                35                  40                  45

Asn Thr Leu Asn Pro Leu Val Leu Pro Glu Tyr Leu Ile His Ala
                50                  55                  60

Phe Phe Cys Val Met Phe Leu Cys Ala Ala Glu Trp Leu Thr Leu
                65                  70                  75

Gly Leu Asn Met Pro Leu Leu Ala Tyr His Ile Trp Arg Tyr Met
                80                  85                  90

Ser Arg Pro Val Met Ser Gly Pro Gly Leu Tyr Asp Pro Thr Thr
                95                  100                 105

Ile Met Asn Ala Asp Ile Leu Ala Tyr Cys Gln Lys Glu Gly Trp
                110                 115                 120

Cys Lys Leu Ala Phe Tyr Leu Leu Ala Phe Phe Tyr Tyr Leu Tyr
                125                 130                 135

Gly Met Ile Tyr Val Leu Val Ser Ser
                140
```

-continued

<210> SEQ ID NO 121
<211> LENGTH: 1838
<212> TYPE: DNA
<213> ORGANISM: Homo sapiens

<400> SEQUENCE: 121
cggacgcgtg ggcggacgcg tgggcggccc acggcgcccg cgggctgggg 50
cggtcgcttc ttccttctcc gtggcctacg agggtcccca gcctgggtaa 100
agatggcccc atggcccccg aagggcctag tcccagctgt gctctggggc 150
ctcagcctct tcctcaacct cccaggacct atctggctcc agccctctcc 200
acctccccag tcttctcccc cgcctcagcc ccatccgtgt catacctgcc 250
ggggactggt tgacagcttt aacaagggcc tggagagaac catccgggac 300
aactttggag gtggaaacac tgcctgggag gaagagaatt tgtccaaata 350
caaagacagt gagacccgcc tggtagaggt gctggagggt gtgtgcagca 400
agtcagactt cgagtgccac cgcctgctgg agctgagtga ggagctggtg 450
gagagctggt ggtttcacaa gcagcaggag gccccggacc tcttccagtg 500
gctgtgctca gattccctga agctctgctg ccccgcaggc accttcgggc 550
cctcctgcct tccctgtcct gggggaacag agaggccctg cggtggctac 600
gggcagtgtg aaggagaagg gacacgaggg ggcagcgggc actgtgactg 650
ccaagccggc tacgggggtg aggcctgtgg ccagtgtggc cttggctact 700
ttgaggcaga acgcaacgcc agccatctgg tatgttcggc ttgttttggc 750
ccctgtgccc gatgctcagg acctgaggaa tcaaactgtt tgcaatgcaa 800
gaagggctgg gccctgcatc acctcaagtg tgtagacatt gatgagtgtg 850
gcacagaggg agccaactgt ggagctgacc aattctgcgt gaacactgag 900
ggctcctatg agtgccgaga ctgtgccaag gcctgcctag gctgcatggg 950
ggcagggcca ggtcgctgta agaagtgtag ccctggctat cagcaggtgg 1000
gctccaagtg tctcgatgtg gatgagtgtg agacagaggt gtgtccggga 1050
gagaacaagc agtgtgaaaa caccgagggc ggttatcgct gcatctgtgc 1100
cgagggctac aagcagatgg aaggcatctg tgtgaaggag cagatcccag 1150
agtcagcagg cttcttctca gagatgacag aagacgagtt ggtggtgctg 1200
cagcagatgt tctttggcat catcatctgt gcactggcca cgctggctgc 1250
taagggcgac ttggtgttca ccgccatctt cattggggct gtggcggcca 1300
tgactggcta ctggttgtca gagcgcagtg accgtgtgct ggagggcttc 1350
atcaagggca gataatcgcg gccaccacct gtaggacctc ctcccaccca 1400
cgctgccccc agagcttggg ctgccctcct gctggacact caggacagct 1450
tggtttattt ttgagagtgg ggtaagcacc cctacctgcc ttacagagca 1500
gcccaggtac ccaggcccgg gcagacaagg cccctggggt aaaaagtagc 1550
cctgaaggtg gataccatga gctcttcacc tggcggggac tggcaggctt 1600
cacaatgtgt gaatttcaaa agtttttcct taatggtggc tgctagagct 1650
ttggcccctg cttaggatta ggtggtcctc acaggggtgg ggccatcaca 1700
gctccctcct gccagctgca tgctgccagt tcctgttctg tgttcaccac 1750
atccccacac cccattgcca cttatttatt catctcagga aataaagaaa 1800

-continued

```
ggtcttggaa agttaaaaaa aaaaaaaaaa  aaaaaaaa                          1838


<210> SEQ ID NO 122
<211> LENGTH: 420
<212> TYPE: PRT
<213> ORGANISM: Homo sapiens

<400> SEQUENCE: 122

Met Ala Pro Trp Pro Pro Lys Gly Leu Val Pro Ala Val Leu Trp
  1               5                  10                  15

Gly Leu Ser Leu Phe Leu Asn Leu Pro Gly Pro Ile Trp Leu Gln
                 20                  25                  30

Pro Ser Pro Pro Pro Gln Ser Ser Pro Pro Pro Gln Pro His Pro
                 35                  40                  45

Cys His Thr Cys Arg Gly Leu Val Asp Ser Phe Asn Lys Gly Leu
                 50                  55                  60

Glu Arg Thr Ile Arg Asp Asn Phe Gly Gly Gly Asn Thr Ala Trp
                 65                  70                  75

Glu Glu Glu Asn Leu Ser Lys Tyr Lys Asp Ser Glu Thr Arg Leu
                 80                  85                  90

Val Glu Val Leu Glu Gly Val Cys Ser Lys Ser Asp Phe Glu Cys
                 95                 100                 105

His Arg Leu Leu Glu Leu Ser Glu Glu Leu Val Glu Ser Trp Trp
                110                 115                 120

Phe His Lys Gln Gln Glu Ala Pro Asp Leu Phe Gln Trp Leu Cys
                125                 130                 135

Ser Asp Ser Leu Lys Leu Cys Cys Pro Ala Gly Thr Phe Gly Pro
                140                 145                 150

Ser Cys Leu Pro Cys Pro Gly Gly Thr Glu Arg Pro Cys Gly Gly
                155                 160                 165

Tyr Gly Gln Cys Glu Gly Glu Gly Thr Arg Gly Gly Ser Gly His
                170                 175                 180

Cys Asp Cys Gln Ala Gly Tyr Gly Gly Glu Ala Cys Gly Gln Cys
                185                 190                 195

Gly Leu Gly Tyr Phe Glu Ala Glu Arg Asn Ala Ser His Leu Val
                200                 205                 210

Cys Ser Ala Cys Phe Gly Pro Cys Ala Arg Cys Ser Gly Pro Glu
                215                 220                 225

Glu Ser Asn Cys Leu Gln Cys Lys Lys Gly Trp Ala Leu His His
                230                 235                 240

Leu Lys Cys Val Asp Ile Asp Glu Cys Gly Thr Glu Gly Ala Asn
                245                 250                 255

Cys Gly Ala Asp Gln Phe Cys Val Asn Thr Glu Gly Ser Tyr Glu
                260                 265                 270

Cys Arg Asp Cys Ala Lys Ala Cys Leu Gly Cys Met Gly Ala Gly
                275                 280                 285

Pro Gly Arg Cys Lys Lys Cys Ser Pro Gly Tyr Gln Gln Val Gly
                290                 295                 300

Ser Lys Cys Leu Asp Val Asp Glu Cys Glu Thr Glu Val Cys Pro
                305                 310                 315

Gly Glu Asn Lys Gln Cys Glu Asn Thr Glu Gly Gly Tyr Arg Cys
                320                 325                 330

Ile Cys Ala Glu Gly Tyr Lys Gln Met Glu Gly Ile Cys Val Lys
                335                 340                 345
```

-continued

```
Glu Gln Ile Pro Glu Ser Ala Gly Phe Phe Ser Glu Met Thr Glu
                350                 355                 360

Asp Glu Leu Val Val Leu Gln Gln Met Phe Phe Gly Ile Ile Ile
                365                 370                 375

Cys Ala Leu Ala Thr Leu Ala Ala Lys Gly Asp Leu Val Phe Thr
                380                 385                 390

Ala Ile Phe Ile Gly Ala Val Ala Ala Met Thr Gly Tyr Trp Leu
                395                 400                 405

Ser Glu Arg Ser Asp Arg Val Leu Glu Gly Phe Ile Lys Gly Arg
                410                 415                 420


<210> SEQ ID NO 123
<211> LENGTH: 3401
<212> TYPE: DNA
<213> ORGANISM: Homo sapiens

<400> SEQUENCE: 123

gcaagccaag gcgctgtttg agaaggtgaa gaagttccgg acccatgtgg         50

aggaggggga cattgtgtac cgcctctaca tgcggcagac catcatcaag        100

gtgatcaagt tcatcctcat catctgctac accgtctact acgtgcacaa        150

catcaagttc gacgtggact gcaccgtgga cattgagagc ctgacgggct        200

accgcaccta ccgctgtgcc cacccctgg ccacactctt caagatcctg         250

gcgtccttct acatcagcct agtcatcttc tacggcctca tctgcatgta        300

cacactgtgg tggatgctac ggcgctccct caagaagtac tcgtttgagt        350

cgatccgtga ggagagcagc tacagcgaca tccccgacgt caagaacgac        400

ttcgccttca tgctgcacct cattgaccaa tacgacccgc tctactccaa        450

gcgcttcgcc gtcttcctgt cggaggtgag tgagaacaag ctgcggcagc        500

tgaacctcaa caacgagtgg acgctggaca agctccggca gcggctcacc        550

aagaacgcgc aggacaagct ggagctgcac ctgttcatgc tcagtggcat        600

ccctgacact gtgtttgacc tggtggagct ggaggtcctc aagctggagc        650

tgatccccga cgtgaccatc ccgcccagca ttgcccagct cacgggcctc        700

aaggagctgt ggctctacca cacagcggcc aagattgaag cgcctgcgct        750

ggccttcctg cgcgagaacc tgcgggcgct gcacatcaag ttcaccgaca        800

tcaaggagat cccgctgtgg atctatagcc tgaagacact ggaggagctg        850

cacctgacgg gcaacctgag cgcggagaac aaccgctaca tcgtcatcga        900

cgggctgcgg gagctcaaac gcctcaaggt gctgcggctc aagagcaacc        950

taagcaagct gccacaggtg gtcacagatg tgggcgtgca cctgcagaag       1000

ctgtccatca acaatgaggg caccaagctc atcgtcctca acagcctcaa       1050

gaagatggcg aacctgactg agctggagct gatccgctgc gacctggagc       1100

gcatccccca ctccatcttc agcctccaca acctgcagga gattgacctc       1150

aaggacaaca acctcaagac catcgaggag atcatcagct tccagcacct       1200

gcaccgcctc acctgcctta agctgtggta caaccacatc gcctacatcc       1250

ccatccagat cggcaacctc accaacctgg agcgcctcta cctgaaccgc       1300

aacaagatcg agaagatccc cacccagctc ttctactgcc gcaagctgcg       1350

ctacctggac ctcagccaca acaacctgac cttcctccct gccgacatcg       1400
```

-continued

```
gcctcctgca gaacctccag aacctagcca tcacggccaa ccggatcgag          1450
acgctccctc cggagctctt ccagtgccgg aagctgcggg ccctgcacct          1500
gggcaacaac gtgctgcagt cactgccctc cagggtgggc gagctgacca          1550
acctgacgca gatcgagctg cggggcaacc ggctggagtg cctgcctgtg          1600
gagctgggcg agtgcccact gctcaagcgc agcggcttgg tggtggagga          1650
ggacctgttc aacacactgc cacccgaggt gaaggagcgg ctgtggaggg          1700
ctgacaagga gcaggcctga gcgaggccgg cccagcacag caagcagcag          1750
gaccgctgcc cagtcctcag gcccggaggg gcaggcctag cttctcccag          1800
aactcccgga cagccaggac agcctcgcgg ctgggcagga gcctggggcc          1850
gcttgtgagt caggccagag cgagaggaca gtatctgtgg ggctggcccc          1900
ttttctccct ctgagactca cgtcccccag ggcaagtgct tgtggaggag          1950
agcaagtctc aagagcgcag tatttggata atcagggtct cctccctgga          2000
ggccagctct gccccagggg ctgagctgcc accagaggtc ctgggaccct          2050
cactttagtt cttggtattt atttttctcc atctcccacc tccttcatcc          2100
agataactta tacattccca agaaagttca gcccagatgg aaggtgttca          2150
gggaaaggtg ggctgccttt tccccttgtc cttatttagc gatgccgccg          2200
ggcatttaac acccacctgg acttcagcag agtggtccgg ggcgaaccag          2250
ccatgggacg gtcacccagc agtgccgggc tgggctctgc ggtgcggtcc          2300
acgggagagc aggcctccag ctggaaaggc caggcctgga gcttgcctct          2350
tcagtttttg tggcagtttt agtttttttgt ttttttttt tttaatcaaa          2400
aaacaatttt ttttaaaaaa aagctttgaa aatggatggt ttgggtatta          2450
aaaagaaaaa aaaaacttaa aaaaaaaaag acactaacgg ccagtgagtt          2500
ggagtctcag ggcagggtgg cagtttccct tgagcaaagc agccagacgt          2550
tgaactgtgt ttcctttccc tgggcgcagg gtgcagggtg tcttccggat          2600
ctggtgtgac cttggtccag gagttctatt tgttcctggg gagggaggtt          2650
tttttgtttg ttttttgggt ttttttggtg tcttgttttc tttctcctcc          2700
atgtgtcttg gcaggcactc atttctgtgg ctgtcggcca gagggaatgt          2750
tctggagctg ccaaggaggg aggagactcg ggttggctaa tccccggatg          2800
aacggtgctc cattcgcacc tcccctcctc gtgcctgccc tgcctctcca          2850
cgcacagtgt taaggagcca agaggagcca cttcgcccag actttgtttc          2900
cccacctcct gcggcatggg tgtgtccagt gccaccgctg gcctccgctg          2950
cttccatcag ccctgtcgcc acctggtcct tcatgaagag cagacactta          3000
gaggctggtc gggaatgggg aggtcgcccc tgggagggca ggcgttggtt          3050
ccaagccggt tcccgtccct ggcgcctgga gtgcacacag cccagtcggc          3100
acctggtggc tggaagccaa cctgctttag atcactcggg tccccacctt          3150
agaagggtcc ccgccttaga tcaatcacgt ggacactaag gcacgtttta          3200
gagtctcttg tcttaatgat tatgtccatc cgtctgtccg tccatttgtg          3250
ttttctgcgt cgtgtcattg gatataatcc tcagaaataa tgcacactag          3300
cctctgacaa ccatgaagca aaaatccgtt acatgtgggt ctgaacttgt          3350
```

-continued

```
agactcggtc acagtatcaa ataaaatcta taacagaaaa aaaaaaaaaa          3400

a                                                               3401


<210> SEQ ID NO 124
<211> LENGTH: 546
<212> TYPE: PRT
<213> ORGANISM: Homo sapiens

<400> SEQUENCE: 124

Met Arg Gln Thr Ile Ile Lys Val Ile Lys Phe Ile Leu Ile Ile
  1               5                  10                  15

Cys Tyr Thr Val Tyr Tyr Val His Asn Ile Lys Phe Asp Val Asp
                 20                  25                  30

Cys Thr Val Asp Ile Glu Ser Leu Thr Gly Tyr Arg Thr Tyr Arg
                 35                  40                  45

Cys Ala His Pro Leu Ala Thr Leu Phe Lys Ile Leu Ala Ser Phe
                 50                  55                  60

Tyr Ile Ser Leu Val Ile Phe Tyr Gly Leu Ile Cys Met Tyr Thr
                 65                  70                  75

Leu Trp Trp Met Leu Arg Arg Ser Leu Lys Lys Tyr Ser Phe Glu
                 80                  85                  90

Ser Ile Arg Glu Glu Ser Ser Tyr Ser Asp Ile Pro Asp Val Lys
                 95                 100                 105

Asn Asp Phe Ala Phe Met Leu His Leu Ile Asp Gln Tyr Asp Pro
                110                 115                 120

Leu Tyr Ser Lys Arg Phe Ala Val Phe Leu Ser Glu Val Ser Glu
                125                 130                 135

Asn Lys Leu Arg Gln Leu Asn Leu Asn Asn Glu Trp Thr Leu Asp
                140                 145                 150

Lys Leu Arg Gln Arg Leu Thr Lys Asn Ala Gln Asp Lys Leu Glu
                155                 160                 165

Leu His Leu Phe Met Leu Ser Gly Ile Pro Asp Thr Val Phe Asp
                170                 175                 180

Leu Val Glu Leu Glu Val Leu Lys Leu Glu Leu Ile Pro Asp Val
                185                 190                 195

Thr Ile Pro Pro Ser Ile Ala Gln Leu Thr Gly Leu Lys Glu Leu
                200                 205                 210

Trp Leu Tyr His Thr Ala Ala Lys Ile Glu Ala Pro Ala Leu Ala
                215                 220                 225

Phe Leu Arg Glu Asn Leu Arg Ala Leu His Ile Lys Phe Thr Asp
                230                 235                 240

Ile Lys Glu Ile Pro Leu Trp Ile Tyr Ser Leu Lys Thr Leu Glu
                245                 250                 255

Glu Leu His Leu Thr Gly Asn Leu Ser Ala Glu Asn Asn Arg Tyr
                260                 265                 270

Ile Val Ile Asp Gly Leu Arg Glu Leu Lys Arg Leu Lys Val Leu
                275                 280                 285

Arg Leu Lys Ser Asn Leu Ser Lys Leu Pro Gln Val Val Thr Asp
                290                 295                 300

Val Gly Val His Leu Gln Lys Leu Ser Ile Asn Asn Glu Gly Thr
                305                 310                 315

Lys Leu Ile Val Leu Asn Ser Leu Lys Lys Met Ala Asn Leu Thr
                320                 325                 330

Glu Leu Glu Leu Ile Arg Cys Asp Leu Glu Arg Ile Pro His Ser
```

-continued

```
                335                 340                 345

Ile Phe Ser Leu His Asn Leu Gln Glu Ile Asp Leu Lys Asp Asn
                350                 355                 360

Asn Leu Lys Thr Ile Glu Glu Ile Ile Ser Phe Gln His Leu His
                365                 370                 375

Arg Leu Thr Cys Leu Lys Leu Trp Tyr Asn His Ile Ala Tyr Ile
                380                 385                 390

Pro Ile Gln Ile Gly Asn Leu Thr Asn Leu Glu Arg Leu Tyr Leu
                395                 400                 405

Asn Arg Asn Lys Ile Glu Lys Ile Pro Thr Gln Leu Phe Tyr Cys
                410                 415                 420

Arg Lys Leu Arg Tyr Leu Asp Leu Ser His Asn Asn Leu Thr Phe
                425                 430                 435

Leu Pro Ala Asp Ile Gly Leu Leu Gln Asn Leu Gln Asn Leu Ala
                440                 445                 450

Ile Thr Ala Asn Arg Ile Glu Thr Leu Pro Pro Glu Leu Phe Gln
                455                 460                 465

Cys Arg Lys Leu Arg Ala Leu His Leu Gly Asn Asn Val Leu Gln
                470                 475                 480

Ser Leu Pro Ser Arg Val Gly Glu Leu Thr Asn Leu Thr Gln Ile
                485                 490                 495

Glu Leu Arg Gly Asn Arg Leu Glu Cys Leu Pro Val Glu Leu Gly
                500                 505                 510

Glu Cys Pro Leu Leu Lys Arg Ser Gly Leu Val Val Glu Glu Asp
                515                 520                 525

Leu Phe Asn Thr Leu Pro Pro Glu Val Lys Glu Arg Leu Trp Arg
                530                 535                 540

Ala Asp Lys Glu Gln Ala
                545


<210> SEQ ID NO 125
<211> LENGTH: 1679
<212> TYPE: DNA
<213> ORGANISM: Homo sapiens

<400> SEQUENCE: 125

gttgtgtcct tcagcaaaac agtggattta aatctccttg cacaagcttg        50

agagcaacac aatctatcag gaaagaaaga aagaaaaaaa ccgaacctga       100

caaaaaagaa gaaaaagaag aagaaaaaaa atcatgaaaa ccatccagcc       150

aaaaatgcac aattctatct cttgggcaat cttcacgggg ctggctgctc       200

tgtgtctctt ccaaggagtg cccgtgcgca gcggagatgc caccttcccc       250

aaagctatgg acaacgtgac ggtccggcag ggggagagcg ccaccctcag       300

gtgcactatt gacaaccggg tcacccgggt ggcctggcta aaccgcagca       350

ccatcctcta tgctgggaat gacaagtggt gcctggatcc tcgcgtggtc       400

cttctgagca acacccaaac gcagtacagc atcgagatcc agaacgtgga       450

tgtgtatgac gagggccctt acacctgctc ggtgcagaca gacaaccacc       500

caaagacctc tagggtccac ctcattgtgc aagtatctcc caaaattgta       550

gagatttctt cagatatctc cattaatgaa gggaacaata ttagcctcac       600

ctgcatagca actggtagac cagagcctac ggttacttgg agacacatct       650

ctcccaaagc ggttggcttt gtgagtgaag acgaatactt ggaaattcag       700
```

-continued

```
ggcatcaccc gggagcagtc aggggactac gagtgcagtg cctccaatga           750

cgtggccgcg cccgtggtac ggagagtaaa ggtcaccgtg aactatccac           800

catacatttc agaagccaag ggtacaggtg tccccgtggg acaaaagggg           850

acactgcagt gtgaagcctc agcagtcccc tcagcagaat tccagtggta           900

caaggatgac aaaagactga ttgaaggaaa gaaaggggtg aaagtggaaa           950

acagaccttt cctctcaaaa ctcatcttct tcaatgtctc tgaacatgac          1000

tatgggaact acacttgcgt ggcctccaac aagctgggcc acaccaatgc          1050

cagcatcatg ctatttggtc caggcgccgt cagcgaggtg agcaacggca          1100

cgtcgaggag ggcaggctgc gtctggctgc tgcctcttct ggtcttgcac          1150

ctgcttctca aattttgatg tgagtgccac ttccccaccc gggaaaggct          1200

gccgccacca ccaccaccaa cacaacagca atggcaacac cgacagcaac          1250

caatcagata tatacaaatg aaattagaag aaacacagcc tcatgggaca          1300

gaaatttgag ggaggggaac aaagaatact ttgggggga aagagtttta           1350

aaaaagaaat tgaaaattgc cttgcagata tttaggtaca atggagtttt          1400

cttttcccaa acgggaagaa cacagcacac ccggcttgga cccactgcaa          1450

gctgcatcgt gcaacctctt tggtgccagt gtgggcaagg gctcagcctc          1500

tctgcccaca gagtgccccc acgtggaaca ttctggagct ggccatccca          1550

aattcaatca gtccatagag acgaacagaa tgagaccttc cggcccaagc          1600

gtggcgctgc gggcactttg gtagactgtg ccaccacggc gtgtgttgtg          1650

aaacgtgaaa taaaaagagc  aaaaaaaaa                                1679
```

<210> SEQ ID NO 126
<211> LENGTH: 344
<212> TYPE: PRT
<213> ORGANISM: Homo sapiens

<400> SEQUENCE: 126

```
Met Lys Thr Ile Gln Pro Lys Met His Asn Ser Ile Ser Trp Ala
  1               5                  10                  15

Ile Phe Thr Gly Leu Ala Ala Leu Cys Leu Phe Gln Gly Val Pro
                 20                  25                  30

Val Arg Ser Gly Asp Ala Thr Phe Pro Lys Ala Met Asp Asn Val
                 35                  40                  45

Thr Val Arg Gln Gly Glu Ser Ala Thr Leu Arg Cys Thr Ile Asp
                 50                  55                  60

Asn Arg Val Thr Arg Val Ala Trp Leu Asn Arg Ser Thr Ile Leu
                 65                  70                  75

Tyr Ala Gly Asn Asp Lys Trp Cys Leu Asp Pro Arg Val Val Leu
                 80                  85                  90

Leu Ser Asn Thr Gln Thr Gln Tyr Ser Ile Glu Ile Gln Asn Val
                 95                 100                 105

Asp Val Tyr Asp Glu Gly Pro Tyr Thr Cys Ser Val Gln Thr Asp
                110                 115                 120

Asn His Pro Lys Thr Ser Arg Val His Leu Ile Val Gln Val Ser
                125                 130                 135

Pro Lys Ile Val Glu Ile Ser Ser Asp Ile Ser Ile Asn Glu Gly
                140                 145                 150
```

-continued

```
Asn Asn Ile Ser Leu Thr Cys Ile Ala Thr Gly Arg Pro Glu Pro
                155                 160                 165

Thr Val Thr Trp Arg His Ile Ser Pro Lys Ala Val Gly Phe Val
                170                 175                 180

Ser Glu Asp Glu Tyr Leu Glu Ile Gln Gly Ile Thr Arg Glu Gln
                185                 190                 195

Ser Gly Asp Tyr Glu Cys Ser Ala Ser Asn Asp Val Ala Ala Pro
                200                 205                 210

Val Val Arg Arg Val Lys Val Thr Val Asn Tyr Pro Pro Tyr Ile
                215                 220                 225

Ser Glu Ala Lys Gly Thr Gly Val Pro Val Gly Gln Lys Gly Thr
                230                 235                 240

Leu Gln Cys Glu Ala Ser Ala Val Pro Ser Ala Glu Phe Gln Trp
                245                 250                 255

Tyr Lys Asp Asp Lys Arg Leu Ile Glu Gly Lys Lys Gly Val Lys
                260                 265                 270

Val Glu Asn Arg Pro Phe Leu Ser Lys Leu Ile Phe Phe Asn Val
                275                 280                 285

Ser Glu His Asp Tyr Gly Asn Tyr Thr Cys Val Ala Ser Asn Lys
                290                 295                 300

Leu Gly His Thr Asn Ala Ser Ile Met Leu Phe Gly Pro Gly Ala
                305                 310                 315

Val Ser Glu Val Ser Asn Gly Thr Ser Arg Arg Ala Gly Cys Val
                320                 325                 330

Trp Leu Leu Pro Leu Leu Val Leu His Leu Leu Leu Lys Phe
                335                 340
```

<210> SEQ ID NO 127
<211> LENGTH: 2236
<212> TYPE: DNA
<213> ORGANISM: Homo sapiens

<400> SEQUENCE: 127

```
ggcgccggtg caccgggcgg gctgagcgcc tcctgcggcc cggcctgcgc        50

gccccggccc gccgcgccgc ccacgcccca accccggccc gcgcccccta       100

gcccccgccc gggcccgcgc ccgcgcccgc gcccaggtga gcgctccgcc       150

cgccgcgagg ccccgccccg gcccgccccc gccccgcccc ggccggcggg       200

ggaaccgggc ggattcctcg cgcgtcaaac cacctgatcc cataaaacat       250

tcatcctccc ggcggcccgc gctgcgagcg ccccgccagt ccgcgccgcc       300

gccgccctcg ccctgtgcgc cctgcgcgcc ctgcgcaccc gcggcccgag       350

cccagccaga gccgggcgga gcggagcgcg ccgagcctcg tcccgcggcc       400

gggccggggc cgggccgtag cggcggcgcc tggatgcgga cccggccgcg       450

gggagacggg cgcccgcccc gaaacgactt tcagtccccg acgcgccccg       500

cccaacccct acgatgaaga gggcgtccgc tggagggagc cggctgctgg       550

catgggtgct gtggctgcag gcctggcagg tggcagcccc atgcccaggt       600

gcctgcgtat gctacaatga gcccaaggtg acgacaagct gcccccagca       650

gggcctgcag gctgtgcccg tgggcatccc tgctgccagc cagcgcatct       700

tcctgcacgg caaccgcatc tcgcatgtgc cagctgccag cttccgtgcc       750

tgccgcaacc tcaccatcct gtggctgcac tcgaatgtgc tggcccgaat       800
```

-continued

```
tgatgcggct gccttcactg gcctggccct cctggagcag ctggacctca        850

gcgataatgc acagctccgg tctgtggacc ctgccacatt ccacggcctg        900

ggccgcctac acacgctgca cctggaccgc tgcggcctgc aggagctggg        950

cccggggctg ttccgcggcc tggctgccct gcagtacctc tacctgcagg       1000

acaacgcgct gcaggcactg cctgatgaca ccttccgcga cctgggcaac       1050

ctcacacacc tcttcctgca cggcaaccgc atctccagcg tgcccgagcg       1100

cgccttccgt gggctgcaca gcctcgaccg tctcctactg caccagaacc       1150

gcgtggccca tgtgcacccg catgccttcc gtgaccttgg ccgcctcatg       1200

acactctatc tgtttgccaa caatctatca gcgctgccca ctgaggccct       1250

ggcccccctg cgtgccctgc agtacctgag gctcaacgac aaccccctggg       1300

tgtgtgactg ccgggcacgc ccactctggg cctggctgca gaagttccgc       1350

ggctcctcct ccgaggtgcc ctgcagcctc ccgcaacgcc tggctggccg       1400

tgacctcaaa cgcctagctg ccaatgacct gcagggctgc gctgtggcca       1450

ccggccctta ccatcccatc tggaccggca gggccaccga tgaggagccg       1500

ctggggcttc ccaagtgctg ccagccagat gccgctgaca aggcctcagt       1550

actggagcct ggaagaccag cttcggcagg caatgcgctg aagggacgcg       1600

tgccgcccgg tgacagcccg ccgggcaacg gctctggccc acggcacatc       1650

aatgactcac cctttgggac tctgcctggc tctgctgagc cccgctcac        1700

tgcagtgcgg cccgagggct ccgagccacc agggttcccc acctcgggcc       1750

ctcgccggag gccaggctgt tcacgcaaga accgcacccg cagccactgc       1800

cgtctgggcc aggcaggcag cgggggtggc gggactggtg actcagaagg       1850

ctcaggtgcc ctacccagcc tcacctgcag cctcaccccc ctgggcctgg       1900

cgctggtgct gtggacagtg cttgggccct gctgaccccc agcggacaca       1950

agagcgtgct cagcagccag gtgtgtgtac atacggggtc tctctccacg       2000

ccgccaagcc agccgggcgg ccgacccgtg gggcaggcca ggccaggtcc       2050

tccctgatgg acgcctgccg cccgccaccc ccatctccac cccatcatgt       2100

ttacagggtt cggcggcagc gtttgttcca gaacgccgcc tcccacccag       2150

atcgcggtat atagagatat gcattttatt ttacttgtgt aaaaatatcg       2200

gacgacgtgg aataaagagc tcttttctta  aaaaaa                     2236
```

<210> SEQ ID NO 128
<211> LENGTH: 473
<212> TYPE: PRT
<213> ORGANISM: Homo sapiens

<400> SEQUENCE: 128

```
Met Lys Arg Ala Ser Ala Gly Gly Ser Arg Leu Leu Ala Trp Val
  1               5                  10                  15

Leu Trp Leu Gln Ala Trp Gln Val Ala Ala Pro Cys Pro Gly Ala
                 20                  25                  30

Cys Val Cys Tyr Asn Glu Pro Lys Val Thr Thr Ser Cys Pro Gln
                 35                  40                  45

Gln Gly Leu Gln Ala Val Pro Val Gly Ile Pro Ala Ala Ser Gln
                 50                  55                  60

Arg Ile Phe Leu His Gly Asn Arg Ile Ser His Val Pro Ala Ala
```

-continued

```
                65                  70                  75

Ser Phe Arg Ala Cys Arg Asn Leu Thr Ile Leu Trp Leu His Ser
                80                  85                  90

Asn Val Leu Ala Arg Ile Asp Ala Ala Ala Phe Thr Gly Leu Ala
                95                  100                 105

Leu Leu Glu Gln Leu Asp Leu Ser Asp Asn Ala Gln Leu Arg Ser
                110                 115                 120

Val Asp Pro Ala Thr Phe His Gly Leu Gly Arg Leu His Thr Leu
                125                 130                 135

His Leu Asp Arg Cys Gly Leu Gln Glu Leu Gly Pro Gly Leu Phe
                140                 145                 150

Arg Gly Leu Ala Ala Leu Gln Tyr Leu Tyr Leu Gln Asp Asn Ala
                155                 160                 165

Leu Gln Ala Leu Pro Asp Asp Thr Phe Arg Asp Leu Gly Asn Leu
                170                 175                 180

Thr His Leu Phe Leu His Gly Asn Arg Ile Ser Ser Val Pro Glu
                185                 190                 195

Arg Ala Phe Arg Gly Leu His Ser Leu Asp Arg Leu Leu Leu His
                200                 205                 210

Gln Asn Arg Val Ala His Val His Pro His Ala Phe Arg Asp Leu
                215                 220                 225

Gly Arg Leu Met Thr Leu Tyr Leu Phe Ala Asn Asn Leu Ser Ala
                230                 235                 240

Leu Pro Thr Glu Ala Leu Ala Pro Leu Arg Ala Leu Gln Tyr Leu
                245                 250                 255

Arg Leu Asn Asp Asn Pro Trp Val Cys Asp Cys Arg Ala Arg Pro
                260                 265                 270

Leu Trp Ala Trp Leu Gln Lys Phe Arg Gly Ser Ser Ser Glu Val
                275                 280                 285

Pro Cys Ser Leu Pro Gln Arg Leu Ala Gly Arg Asp Leu Lys Arg
                290                 295                 300

Leu Ala Ala Asn Asp Leu Gln Gly Cys Ala Val Ala Thr Gly Pro
                305                 310                 315

Tyr His Pro Ile Trp Thr Gly Arg Ala Thr Asp Glu Glu Pro Leu
                320                 325                 330

Gly Leu Pro Lys Cys Cys Gln Pro Asp Ala Ala Asp Lys Ala Ser
                335                 340                 345

Val Leu Glu Pro Gly Arg Pro Ala Ser Ala Gly Asn Ala Leu Lys
                350                 355                 360

Gly Arg Val Pro Pro Gly Asp Ser Pro Pro Gly Asn Gly Ser Gly
                365                 370                 375

Pro Arg His Ile Asn Asp Ser Pro Phe Gly Thr Leu Pro Gly Ser
                380                 385                 390

Ala Glu Pro Pro Leu Thr Ala Val Arg Pro Glu Gly Ser Glu Pro
                395                 400                 405

Pro Gly Phe Pro Thr Ser Gly Pro Arg Arg Arg Pro Gly Cys Ser
                410                 415                 420

Arg Lys Asn Arg Thr Arg Ser His Cys Arg Leu Gly Gln Ala Gly
                425                 430                 435

Ser Gly Gly Gly Gly Thr Gly Asp Ser Glu Gly Ser Gly Ala Leu
                440                 445                 450

Pro Ser Leu Thr Cys Ser Leu Thr Pro Leu Gly Leu Ala Leu Val
                455                 460                 465
```

-continued

Leu Trp Thr Val Leu Gly Pro Cys
470

<210> SEQ ID NO 129
<211> LENGTH: 2458
<212> TYPE: DNA
<213> ORGANISM: Homo sapiens

<400> SEQUENCE: 129
gcgccgggag cccatctgcc cccaggggca cggggcgcgg ggccggctcc 50
cgcccggcac atggctgcag ccacctcgcg cgcaccccga ggcgccgcgc 100
ccagctcgcc cgaggtccgt cggaggcgcc cggccgcccc ggagccaagc 150
agcaactgag cggggaagcg cccgcgtccg gggatcggga tgtccctcct 200
ccttctcctc ttgctagttt cctactatgt tggaaccttg gggactcaca 250
ctgagatcaa gagagtggca gaggaaaagg tcactttgcc ctgccaccat 300
caactggggc ttccagaaaa agacactctg gatattgaat ggctgctcac 350
cgataatgaa gggaaccaaa aagtggtgat cacttactcc agtcgtcatg 400
tctacaataa cttgactgag gaacagaagg gccgagtggc ctttgcttcc 450
aatttcctgg caggagatgc ctccttgcag attgaacctc tgaagcccag 500
tgatgagggc cggtacacct gtaaggttaa gaattcaggg cgctacgtgt 550
ggagccatgt catcttaaaa gtcttagtga gaccatccaa gcccaagtgt 600
gagttggaag gagagctgac agaaggaagt gacctgactt tgcagtgtga 650
gtcatcctct ggcacagagc ccattgtgta ttactggcag cgaatccgag 700
agaaagaggg agaggatgaa cgtctgcctc ccaaatctag gattgactac 750
aaccaccctg gacgagttct gctgcagaat cttaccatgt cctactctgg 800
actgtaccag tgcacagcag gcaacgaagc tgggaaggaa agctgtgtgg 850
tgcgagtaac tgtacagtat gtacaaagca tcggcatggt tgcaggagca 900
gtgacaggca tagtggctgg agccctgctg attttcctct tggtgtggct 950
gctaatccga aggaaagaca aagaaagata tgaggaagaa gagagaccta 1000
atgaaattcg agaagatgct gaagctccaa aagcccgtct tgtgaaaccc 1050
agctcctctt cctcaggctc tcggagctca cgctctggtt cttcctccac 1100
tcgctccaca gcaaatagtg cctcacgcag ccagcggaca ctgtcaactg 1150
acgcagcacc ccagccaggg ctggccaccc aggcatacag cctagtgggg 1200
ccagaggtga gaggttctga accaaagaaa gtccaccatg ctaatctgac 1250
caaagcagaa accacaccca gcatgatccc cagccagagc agagccttcc 1300
aaacggtctg aattacaatg gacttgactc ccacgctttc ctaggagtca 1350
gggtctttgg actcttctcg tcattggagc tcaagtcacc agccacacaa 1400
ccagatgaga ggtcatctaa gtagcagtga gcattgcacg gaacagattc 1450
agatgagcat tttccttata caataccaaa caagcaaaag gatgtaagct 1500
gattcatctg taaaaaggca tcttattgtg cctttagacc agagtaaggg 1550
aaagcaggag tccaaatcta tttgttgacc aggacctgtg gtgagaaggt 1600
tggggaaagg tgaggtgaat atacctaaaa cttttaatgt gggatatttt 1650
gtatcagtgc tttgattcac aattttcaag aggaaatggg atgctgtttg 1700

-continued

```
taaattttct atgcatttct gcaaacttat tggattatta gttattcaga              1750

cagtcaagca gaacccacag ccttattaca cctgtctaca ccatgtactg              1800

agctaaccac ttctaagaaa ctccaaaaaa ggaaacatgt gtcttctatt              1850

ctgacttaac ttcatttgtc ataaggtttg gatattaatt tcaaggggag              1900

ttgaaatagt gggagatgga gaagagtgaa tgagtttctc ccactctata              1950

ctaatctcac tatttgtatt gagcccaaaa taactatgaa aggagacaaa              2000

aatttgtgac aaaggattgt gaagagcttt ccatcttcat gatgttatga              2050

ggattgttga caaacattag aaatatataa tggagcaatt gtggatttcc              2100

cctcaaatca gatgcctcta aggactttcc tgctagatat ttctggaagg              2150

agaaaataca acatgtcatt tatcaacgtc cttagaaaga attcttctag              2200

agaaaaaggg atctaggaat gctgaaagat tacccaacat accattatag              2250

tctcttcttt ctgagaaaat gtgaaaccag aattgcaaga ctgggtggac              2300

tagaaaggga gattagatca gttttctctt aatatgtcaa ggaaggtagc              2350

cgggcatggt gccaggcacc tgtaggaaaa tccagcaggt ggaggttgca              2400

gtgagccgag attatgccat tgcactccag cctgggtgac agagcgggac              2450

tccgtctc                                                            2458
```

<210> SEQ ID NO 130
<211> LENGTH: 373
<212> TYPE: PRT
<213> ORGANISM: Homo sapiens

<400> SEQUENCE: 130

```
Met Ser Leu Leu Leu Leu Leu Leu Leu Val Ser Tyr Tyr Val Gly
  1               5                  10                  15

Thr Leu Gly Thr His Thr Glu Ile Lys Arg Val Ala Glu Glu Lys
                 20                  25                  30

Val Thr Leu Pro Cys His His Gln Leu Gly Leu Pro Glu Lys Asp
                 35                  40                  45

Thr Leu Asp Ile Glu Trp Leu Leu Thr Asp Asn Glu Gly Asn Gln
                 50                  55                  60

Lys Val Val Ile Thr Tyr Ser Ser Arg His Val Tyr Asn Asn Leu
                 65                  70                  75

Thr Glu Glu Gln Lys Gly Arg Val Ala Phe Ala Ser Asn Phe Leu
                 80                  85                  90

Ala Gly Asp Ala Ser Leu Gln Ile Glu Pro Leu Lys Pro Ser Asp
                 95                 100                 105

Glu Gly Arg Tyr Thr Cys Lys Val Lys Asn Ser Gly Arg Tyr Val
                110                 115                 120

Trp Ser His Val Ile Leu Lys Val Leu Val Arg Pro Ser Lys Pro
                125                 130                 135

Lys Cys Glu Leu Glu Gly Glu Leu Thr Glu Gly Ser Asp Leu Thr
                140                 145                 150

Leu Gln Cys Glu Ser Ser Ser Gly Thr Glu Pro Ile Val Tyr Tyr
                155                 160                 165

Trp Gln Arg Ile Arg Glu Lys Glu Gly Glu Asp Glu Arg Leu Pro
                170                 175                 180

Pro Lys Ser Arg Ile Asp Tyr Asn His Pro Gly Arg Val Leu Leu
                185                 190                 195
```

-continued

Gln Asn Leu Thr Met Ser Tyr Ser Gly Leu Tyr Gln Cys Thr Ala
200 205 210

Gly Asn Glu Ala Gly Lys Glu Ser Cys Val Val Arg Val Thr Val
215 220 225

Gln Tyr Val Gln Ser Ile Gly Met Val Ala Gly Ala Val Thr Gly
230 235 240

Ile Val Ala Gly Ala Leu Leu Ile Phe Leu Leu Val Trp Leu Leu
245 250 255

Ile Arg Arg Lys Asp Lys Glu Arg Tyr Glu Glu Glu Glu Arg Pro
260 265 270

Asn Glu Ile Arg Glu Asp Ala Glu Ala Pro Lys Ala Arg Leu Val
275 280 285

Lys Pro Ser Ser Ser Ser Ser Gly Ser Arg Ser Ser Arg Ser Gly
290 295 300

Ser Ser Ser Thr Arg Ser Thr Ala Asn Ser Ala Ser Arg Ser Gln
305 310 315

Arg Thr Leu Ser Thr Asp Ala Ala Pro Gln Pro Gly Leu Ala Thr
320 325 330

Gln Ala Tyr Ser Leu Val Gly Pro Glu Val Arg Gly Ser Glu Pro
335 340 345

Lys Lys Val His His Ala Asn Leu Thr Lys Ala Glu Thr Thr Pro
350 355 360

Ser Met Ile Pro Ser Gln Ser Arg Ala Phe Gln Thr Val
365 370

<210> SEQ ID NO 131
<211> LENGTH: 2738
<212> TYPE: DNA
<213> ORGANISM: Homo sapiens

<400> SEQUENCE: 131
ggaagtccac ggggagcttg gatgccaaag ggaggacggc tgggtcctct 50
ggagaggact actcactggc atatttctga ggtatctgta gaataaccac 100
agcctcagat actggggact ttacagtccc acagaaccgt cctcccagga 150
agctgaatcc agcaagaaca atggaggcca gcgggaagct catttgcaga 200
caaaggcaag tcctttttc ctttctcctt ttgggcttat ctctggcggg 250
cgcggcggaa cctagaagct attctgtggt ggaggaaact gagggcagct 300
cctttgtcac caatttagca aaggacctgg gtctggagca gagggaattc 350
tccaggcggg gggttagggt tgtttccaga gggaacaaac tacatttgca 400
gctcaatcag gagaccgcgg atttgttgct aaatgagaaa ttggaccgtg 450
aggatctgtg cggtcacaca gagccctgtg tgctacgttt ccaagtgttg 500
ctagagagtc ccttcgagtt ttttcaagct gagctgcaag taatagacat 550
aaacgaccac tctccagtat ttctggacaa acaaatgttg gtgaaagtat 600
cagagagcag tcctcctggg actacgtttc ctctgaagaa tgccgaagac 650
ttagatgtag gccaaaacaa tattgagaac tatataatca gccccaactc 700
ctattttcgg gtcctcaccc gcaaacgcag tgatggcagg aaatacccag 750
agctggtgct ggacaaagcg ctggaccgag aggaagaagc tgagctcagg 800
ttaacactca cagcactgga tggtggctct ccgcccagat ctggcactgc 850

-continued

```
tcaggtctac atcgaagtcc tggatgtcaa cgataatgcc cctgaatttg         900

agcagccttt ctatagagtg cagatctctg aggacagtcc ggtaggcttc         950

ctggttgtga aggtctctgc cacggatgta gacacaggag tcaacggaga        1000

gatttcctat tcacttttcc aagcttcaga agagattggc aaaaccttta        1050

agatcaatcc cttgacagga gaaattgaac taaaaaaaca actcgatttc        1100

gaaaaacttc agtcctatga agtcaatatt gaggcaagag atgctggaac        1150

cttttctgga aaatgcaccg ttctgattca agtgatagat gtgaacgacc        1200

atgccccaga agttaccatg tctgcattta ccagcccaat acctgagaac        1250

gcgcctgaaa ctgtggttgc acttttcagt gtttcagatc ttgattcagg        1300

agaaaatggg aaaattagtt gctccattca ggaggatcta cccttcctcc        1350

tgaaatccgc ggaaaacttt tacaccctac taacggagag accactagac        1400

agagaaagca gagcggaata caacatcact atcactgtca ctgacttggg        1450

gaccccctatg ctgataacac agctcaatat gaccgtgctg atcgccgatg       1500

tcaatgacaa cgctcccgcc ttcacccaaa cctcctacac cctgttcgtc        1550

cgcgagaaca acagccccgc cctgcacatc cgcagcgtca gcgctacaga        1600

cagagactca ggcaccaacg cccaggtcac ctactcgctg ctgccgcccc        1650

aggacccgca cctgcccctc acatccctgg tctccatcaa cgcggacaac        1700

ggccacctgt tcgccctcag gtctctggac tacgaggccc tgcaggggtt        1750

ccagttccgc gtgggcgctt cagaccacgg ctccccggcg ctgagcagcg        1800

aggcgctggt gcgcgtggtg gtgctggacg ccaacgacaa ctcgcccttc        1850

gtgctgtacc cgctgcagaa cggctccgcg ccctgcaccg agctggtgcc        1900

ccgggcggcc gagccgggct acctggtgac caaggtggtg gcggtggacg        1950

gcgactcggg ccagaacgcc tggctgtcgt accagctgct caaggccacg        2000

gagctcggtc tgttcggcgt gtgggcgcac aatggcgagg tgcgcaccgc        2050

caggctgctg agcgagcgcg acgcggccaa gcacaggctg gtggtgctgg        2100

tcaaggacaa tggcgagcct ccgcgctcgg ccaccgccac gctgcacgtg        2150

ctcctggtgg acggcttctc ccagccctac ctgcctctcc cggaggcggc        2200

cccgacccag gcccaggccg acttgctcac cgtctacctg gtggtggcgt        2250

tggcctcggt gtcttcgctc ttcctctttt cggtgctcct gttcgtggcg        2300

gtgcggctgt gtaggaggag cagggcggcc tcggtgggtc gctgcttggt        2350

gcccgagggc cccccttccag ggcatcttgt ggacatgagc ggcaccagga       2400

ccctatccca gagctaccag tatgaggtgt gtctggcagg aggctcaggg        2450

accaatgagt tcaagttcct gaagccgatt atccccaact tccctcccca        2500

gtgccctggg aaagaaatac aaggaaattc taccttcccc aataactttg        2550

ggttcaatat tcagtgacca tagttgactt ttacattcca taggtatttt        2600

attttgtggc atttccatgc caatgtttat ttcccccaat ttgtgtgtat        2650

gtaatattgt acggatttac tcttgatttt tctcatgttc tttctccctt        2700

tgttttaaag tgaacattta cctttattcc  tggttctt                    2738
```

<210> SEQ ID NO 132
<211> LENGTH: 798

-continued

<212> TYPE: PRT
<213> ORGANISM: Homo sapiens

<400> SEQUENCE: 132

```
Met Glu Ala Ser Gly Lys Leu Ile Cys Arg Gln Arg Gln Val Leu
  1               5                  10                  15

Phe Ser Phe Leu Leu Leu Gly Leu Ser Leu Ala Gly Ala Ala Glu
                 20                  25                  30

Pro Arg Ser Tyr Ser Val Val Glu Glu Thr Glu Gly Ser Ser Phe
                 35                  40                  45

Val Thr Asn Leu Ala Lys Asp Leu Gly Leu Glu Gln Arg Glu Phe
                 50                  55                  60

Ser Arg Arg Gly Val Arg Val Val Ser Arg Gly Asn Lys Leu His
                 65                  70                  75

Leu Gln Leu Asn Gln Glu Thr Ala Asp Leu Leu Leu Asn Glu Lys
                 80                  85                  90

Leu Asp Arg Glu Asp Leu Cys Gly His Thr Glu Pro Cys Val Leu
                 95                 100                 105

Arg Phe Gln Val Leu Leu Glu Ser Pro Phe Glu Phe Phe Gln Ala
                110                 115                 120

Glu Leu Gln Val Ile Asp Ile Asn Asp His Ser Pro Val Phe Leu
                125                 130                 135

Asp Lys Gln Met Leu Val Lys Val Ser Glu Ser Ser Pro Pro Gly
                140                 145                 150

Thr Thr Phe Pro Leu Lys Asn Ala Glu Asp Leu Asp Val Gly Gln
                155                 160                 165

Asn Asn Ile Glu Asn Tyr Ile Ile Ser Pro Asn Ser Tyr Phe Arg
                170                 175                 180

Val Leu Thr Arg Lys Arg Ser Asp Gly Arg Lys Tyr Pro Glu Leu
                185                 190                 195

Val Leu Asp Lys Ala Leu Asp Arg Glu Glu Glu Ala Glu Leu Arg
                200                 205                 210

Leu Thr Leu Thr Ala Leu Asp Gly Gly Ser Pro Pro Arg Ser Gly
                215                 220                 225

Thr Ala Gln Val Tyr Ile Glu Val Leu Asp Val Asn Asp Asn Ala
                230                 235                 240

Pro Glu Phe Glu Gln Pro Phe Tyr Arg Val Gln Ile Ser Glu Asp
                245                 250                 255

Ser Pro Val Gly Phe Leu Val Val Lys Val Ser Ala Thr Asp Val
                260                 265                 270

Asp Thr Gly Val Asn Gly Glu Ile Ser Tyr Ser Leu Phe Gln Ala
                275                 280                 285

Ser Glu Glu Ile Gly Lys Thr Phe Lys Ile Asn Pro Leu Thr Gly
                290                 295                 300

Glu Ile Glu Leu Lys Lys Gln Leu Asp Phe Glu Lys Leu Gln Ser
                305                 310                 315

Tyr Glu Val Asn Ile Glu Ala Arg Asp Ala Gly Thr Phe Ser Gly
                320                 325                 330

Lys Cys Thr Val Leu Ile Gln Val Ile Asp Val Asn Asp His Ala
                335                 340                 345

Pro Glu Val Thr Met Ser Ala Phe Thr Ser Pro Ile Pro Glu Asn
                350                 355                 360

Ala Pro Glu Thr Val Val Ala Leu Phe Ser Val Ser Asp Leu Asp
                365                 370                 375
```

-continued

```
Ser Gly Glu Asn Gly Lys Ile Ser Cys Ser Ile Gln Glu Asp Leu
                380                 385                 390

Pro Phe Leu Leu Lys Ser Ala Glu Asn Phe Tyr Thr Leu Leu Thr
                395                 400                 405

Glu Arg Pro Leu Asp Arg Glu Ser Arg Ala Glu Tyr Asn Ile Thr
                410                 415                 420

Ile Thr Val Thr Asp Leu Gly Thr Pro Met Leu Ile Thr Gln Leu
                425                 430                 435

Asn Met Thr Val Leu Ile Ala Asp Val Asn Asp Asn Ala Pro Ala
                440                 445                 450

Phe Thr Gln Thr Ser Tyr Thr Leu Phe Val Arg Glu Asn Asn Ser
                455                 460                 465

Pro Ala Leu His Ile Arg Ser Val Ser Ala Thr Asp Arg Asp Ser
                470                 475                 480

Gly Thr Asn Ala Gln Val Thr Tyr Ser Leu Leu Pro Pro Gln Asp
                485                 490                 495

Pro His Leu Pro Leu Thr Ser Leu Val Ser Ile Asn Ala Asp Asn
                500                 505                 510

Gly His Leu Phe Ala Leu Arg Ser Leu Asp Tyr Glu Ala Leu Gln
                515                 520                 525

Gly Phe Gln Phe Arg Val Gly Ala Ser Asp His Gly Ser Pro Ala
                530                 535                 540

Leu Ser Ser Glu Ala Leu Val Arg Val Val Val Leu Asp Ala Asn
                545                 550                 555

Asp Asn Ser Pro Phe Val Leu Tyr Pro Leu Gln Asn Gly Ser Ala
                560                 565                 570

Pro Cys Thr Glu Leu Val Pro Arg Ala Ala Glu Pro Gly Tyr Leu
                575                 580                 585

Val Thr Lys Val Val Ala Val Asp Gly Asp Ser Gly Gln Asn Ala
                590                 595                 600

Trp Leu Ser Tyr Gln Leu Leu Lys Ala Thr Glu Leu Gly Leu Phe
                605                 610                 615

Gly Val Trp Ala His Asn Gly Glu Val Arg Thr Ala Arg Leu Leu
                620                 625                 630

Ser Glu Arg Asp Ala Ala Lys His Arg Leu Val Val Leu Val Lys
                635                 640                 645

Asp Asn Gly Glu Pro Pro Arg Ser Ala Thr Ala Thr Leu His Val
                650                 655                 660

Leu Leu Val Asp Gly Phe Ser Gln Pro Tyr Leu Pro Leu Pro Glu
                665                 670                 675

Ala Ala Pro Thr Gln Ala Gln Ala Asp Leu Leu Thr Val Tyr Leu
                680                 685                 690

Val Val Ala Leu Ala Ser Val Ser Ser Leu Phe Leu Phe Ser Val
                695                 700                 705

Leu Leu Phe Val Ala Val Arg Leu Cys Arg Arg Ser Arg Ala Ala
                710                 715                 720

Ser Val Gly Arg Cys Leu Val Pro Glu Gly Pro Leu Pro Gly His
                725                 730                 735

Leu Val Asp Met Ser Gly Thr Arg Thr Leu Ser Gln Ser Tyr Gln
                740                 745                 750

Tyr Glu Val Cys Leu Ala Gly Gly Ser Gly Thr Asn Glu Phe Lys
                755                 760                 765
```

-continued

```
Phe Leu Lys Pro Ile Ile Pro Asn Phe Pro Pro Gln Cys Pro Gly
                770                 775                 780

Lys Glu Ile Gln Gly Asn Ser Thr Phe Pro Asn Asn Phe Gly Phe
                785                 790                 795

Asn Ile Gln


<210> SEQ ID NO 133
<211> LENGTH: 3819
<212> TYPE: DNA
<213> ORGANISM: Homo sapiens

<400> SEQUENCE: 133

ggaaggggag gagcaggcca cacaggcaca ggccggtgag ggacctgccc           50

agacctggag ggtctcgctc tgtcacacag gctggagtgc agtggtgtga          100

tcttggctca tcgtaacctc cacctcccgg gttcaagtga ttctcatgcc          150

tcagcctccc gagtagctgg gattacaggt ggtgacttcc aagagtgact          200

ccgtcggagg aaaatgactc cccagtcgct gctgcagacg acactgttcc          250

tgctgagtct gctcttcctg gtccaaggtg cccacggcag gggccacagg          300

gaagactttc gcttctgcag ccagcggaac cagacacaca ggagcagcct          350

ccactacaaa cccacaccag acctgcgcat ctccatcgag aactccgaag          400

aggccctcac agtccatgcc cctttccctg cagcccaccc tgcttcccga          450

tccttccctg accccagggg cctctaccac ttctgcctct actggaaccg          500

acatgctggg agattacatc ttctctatgg caagcgtgac ttcttgctga          550

gtgacaaagc ctctagcctc ctctgcttcc agcaccagga ggagagcctg          600

gctcagggcc ccccgctgtt agccacttct gtcacctcct ggtggagccc          650

tcagaacatc agcctgccca gtgccgccag cttcaccttc tccttccaca          700

gtcctcccca cacggccgct cacaatgcct cggtggacat gtgcgagctc          750

aaaagggacc tccagctgct cagccagttc ctgaagcatc cccagaaggc          800

ctcaaggagg ccctcggctg cccccgccag ccagcagttg cagagcctgg          850

agtcgaaact gacctctgtg agattcatgg gggacatggt gtccttcgag          900

gaggaccgga tcaacgccac ggtgtggaag ctccagccca cagccggcct          950

ccaggacctg cacatccact cccggcagga ggaggagcag agcgagatca         1000

tggagtactc ggtgctgctg cctcgaacac tcttccagag gacgaaaggc         1050

cggagcgggg aggctgagaa gagactcctc ctggtggact tcagcagcca         1100

agccctgttc caggacaaga attccagcca agtcctgggt gagaaggtct         1150

tggggattgt ggtacagaac accaaagtag ccaacctcac ggagcccgtg         1200

gtgctcactt tccagcacca gctacagccg aagaatgtga ctctgcaatg         1250

tgtgttctgg gttgaagacc ccacattgag cagcccgggg cattggagca         1300

gtgctgggtg tgagaccgtc aggagagaaa cccaaacatc ctgcttctgc         1350

aaccacttga cctactttgc agtgctgatg gtctcctcgg tggaggtgga         1400

cgccgtgcac aagcactacc tgagcctcct ctcctacgtg ggctgtgtcg         1450

tctctgccct ggcctgcctt gtcaccattg ccgcctacct ctgctccagg         1500

gtgcccctgc cgtgcaggag gaaacctcgg gactacacca tcaaggtgca         1550

catgaacctg ctgctggccg tcttcctgct ggacacgagc ttcctgctca         1600
```

-continued

```
gcgagccggt ggccctgaca ggctctgagg ctggctgccg agccagtgcc        1650
atcttcctgc acttctccct gctcacctgc ctttcctgga tgggcctcga        1700
ggggtacaac ctctaccgac tcgtggtgga ggtctttggc acctatgtcc        1750
ctggctacct actcaagctg agcgccatgg gctggggctt ccccatcttt        1800
ctggtgacgc tggtggccct ggtggatgtg gacaactatg gccccatcat        1850
cttggctgtg cataggactc cagagggcgt catctaccct tccatgtgct        1900
ggatccggga ctccctggtc agctacatca ccaacctggg cctcttcagc        1950
ctggtgtttc tgttcaacat ggccatgcta gccaccatgg tggtgcagat        2000
cctgcggctg cgcccccaca cccaaaagtg gtcacatgtg ctgacactgc        2050
tgggcctcag cctggtcctt ggcctgccct gggccttgat cttcttctcc        2100
tttgcttctg gcaccttcca gcttgtcgtc ctctaccttt tcagcatcat        2150
cacctccttc caaggcttcc tcatcttcat ctggtactgg tccatgcggc        2200
tgcaggcccg gggtggcccc tcccctctga agagcaactc agacagcgcc        2250
aggctcccca tcagctcggg cagcacctcg tccagccgca tctaggcctc        2300
cagcccacct gcccatgtga tgaagcagag atgcggcctc gtcgcacact        2350
gcctgtggcc cccgagccag gcccagcccc aggccagtca gccgcagact        2400
ttggaaagcc caacgaccat ggagagatgg gccgttgcca tggtggacgg        2450
actcccgggc tgggcttttg aattggcctt ggggactact cggctctcac        2500
tcagctccca cgggactcag aagtgcgccg ccatgctgcc tagggtactg        2550
tccccacatc tgtcccaacc cagctggagg cctggtctct ccttacaacc        2600
cctgggccca gccctcattg ctgggggcca ggccttggat cttgagggtc        2650
tggcacatcc ttaatcctgt gcccctgcct gggacagaaa tgtggctcca        2700
gttgctctgt ctctcgtggt caccctgagg gcactctgca tcctctgtca        2750
ttttaacctc aggtggcacc cagggcgaat ggggcccagg gcagaccttc        2800
agggccagag ccctggcgga ggagaggccc tttgccagga gcacagcagc        2850
agctcgccta cctctgagcc caggccccct ccctccctca gccccccagt        2900
cctccctcca tcttccctgg ggttctcctc ctctcccagg gcctccttgc        2950
tccttcgttc acagctgggg gtccccgatt ccaatgctgt tttttgggga        3000
gtggtttcca ggagctgcct ggtgtctgct gtaaatgttt gtctactgca        3050
caagcctcgg cctgcccctg agccaggctc ggtaccgatg cgtgggctgg        3100
gctaggtccc tctgtccatc tgggcctttg tatgagctgc attgcccttg        3150
ctcaccctga ccaagcacac gcctcagagg ggccctcagc ctctcctgaa        3200
gccctcttgt ggcaagaact gtggaccatg ccagtcccgt ctggtttcca        3250
tcccaccact ccaaggactg agactgacct cctctggtga cactggccta        3300
gagcctgaca ctctcctaag aggttctctc caagccccca aatagctcca        3350
ggcgccctcg gccgcccatc atggttaatt ctgtccaaca aacacacacg        3400
ggtagattgc tggcctgttg taggtggtag ggacacagat gaccgacctg        3450
gtcactcctc ctgccaacat tcagtctggt atgtgaggcg tgcgtgaagc        3500
aagaactcct ggagctacag ggacagggag ccatcattcc tgcctgggaa        3550
```

-continued

```
tcctggaaga cttcctgcag gagtcagcgt tcaatcttga ccttgaagat            3600

gggaaggatg ttctttttac gtaccaattc ttttgtcttt tgatattaaa            3650

aagaagtaca tgttcattgt agagaatttg gaaactgtag aagagaatca            3700

agaagaaaaa taaaaatcag ctgttgtaat cgcctagcaa aaaaaaaaaa            3750

aaaaaaaaaa aaaaaaaaaa aaaaaaaaaa aaaaaaaaaa aaaaaaaaaa            3800

aaaaaaaaaa  aaaaaaaaa                                             3819
```

<210> SEQ ID NO 134
<211> LENGTH: 693
<212> TYPE: PRT
<213> ORGANISM: Homo sapiens

<400> SEQUENCE: 134

```
Met Thr Pro Gln Ser Leu Leu Gln Thr Thr Leu Phe Leu Leu Ser
  1               5                  10                  15

Leu Leu Phe Leu Val Gln Gly Ala His Gly Arg Gly His Arg Glu
                 20                  25                  30

Asp Phe Arg Phe Cys Ser Gln Arg Asn Gln Thr His Arg Ser Ser
                 35                  40                  45

Leu His Tyr Lys Pro Thr Pro Asp Leu Arg Ile Ser Ile Glu Asn
                 50                  55                  60

Ser Glu Glu Ala Leu Thr Val His Ala Pro Phe Pro Ala Ala His
                 65                  70                  75

Pro Ala Ser Arg Ser Phe Pro Asp Pro Arg Gly Leu Tyr His Phe
                 80                  85                  90

Cys Leu Tyr Trp Asn Arg His Ala Gly Arg Leu His Leu Leu Tyr
                 95                 100                 105

Gly Lys Arg Asp Phe Leu Leu Ser Asp Lys Ala Ser Ser Leu Leu
                110                 115                 120

Cys Phe Gln His Gln Glu Glu Ser Leu Ala Gln Gly Pro Pro Leu
                125                 130                 135

Leu Ala Thr Ser Val Thr Ser Trp Trp Ser Pro Gln Asn Ile Ser
                140                 145                 150

Leu Pro Ser Ala Ala Ser Phe Thr Phe Ser Phe His Ser Pro Pro
                155                 160                 165

His Thr Ala Ala His Asn Ala Ser Val Asp Met Cys Glu Leu Lys
                170                 175                 180

Arg Asp Leu Gln Leu Leu Ser Gln Phe Leu Lys His Pro Gln Lys
                185                 190                 195

Ala Ser Arg Arg Pro Ser Ala Ala Pro Ala Ser Gln Gln Leu Gln
                200                 205                 210

Ser Leu Glu Ser Lys Leu Thr Ser Val Arg Phe Met Gly Asp Met
                215                 220                 225

Val Ser Phe Glu Glu Asp Arg Ile Asn Ala Thr Val Trp Lys Leu
                230                 235                 240

Gln Pro Thr Ala Gly Leu Gln Asp Leu His Ile His Ser Arg Gln
                245                 250                 255

Glu Glu Glu Gln Ser Glu Ile Met Glu Tyr Ser Val Leu Leu Pro
                260                 265                 270

Arg Thr Leu Phe Gln Arg Thr Lys Gly Arg Ser Gly Glu Ala Glu
                275                 280                 285

Lys Arg Leu Leu Leu Val Asp Phe Ser Ser Gln Ala Leu Phe Gln
                290                 295                 300
```

-continued

```
Asp Lys Asn Ser Ser Gln Val Leu Gly Glu Lys Val Leu Gly Ile
                305                 310                 315

Val Val Gln Asn Thr Lys Val Ala Asn Leu Thr Glu Pro Val Val
                320                 325                 330

Leu Thr Phe Gln His Gln Leu Gln Pro Lys Asn Val Thr Leu Gln
                335                 340                 345

Cys Val Phe Trp Val Glu Asp Pro Thr Leu Ser Ser Pro Gly His
                350                 355                 360

Trp Ser Ser Ala Gly Cys Glu Thr Val Arg Arg Glu Thr Gln Thr
                365                 370                 375

Ser Cys Phe Cys Asn His Leu Thr Tyr Phe Ala Val Leu Met Val
                380                 385                 390

Ser Ser Val Glu Val Asp Ala Val His Lys His Tyr Leu Ser Leu
                395                 400                 405

Leu Ser Tyr Val Gly Cys Val Val Ser Ala Leu Ala Cys Leu Val
                410                 415                 420

Thr Ile Ala Ala Tyr Leu Cys Ser Arg Val Pro Leu Pro Cys Arg
                425                 430                 435

Arg Lys Pro Arg Asp Tyr Thr Ile Lys Val His Met Asn Leu Leu
                440                 445                 450

Leu Ala Val Phe Leu Leu Asp Thr Ser Phe Leu Leu Ser Glu Pro
                455                 460                 465

Val Ala Leu Thr Gly Ser Glu Ala Gly Cys Arg Ala Ser Ala Ile
                470                 475                 480

Phe Leu His Phe Ser Leu Leu Thr Cys Leu Ser Trp Met Gly Leu
                485                 490                 495

Glu Gly Tyr Asn Leu Tyr Arg Leu Val Val Glu Val Phe Gly Thr
                500                 505                 510

Tyr Val Pro Gly Tyr Leu Leu Lys Leu Ser Ala Met Gly Trp Gly
                515                 520                 525

Phe Pro Ile Phe Leu Val Thr Leu Val Ala Leu Val Asp Val Asp
                530                 535                 540

Asn Tyr Gly Pro Ile Ile Leu Ala Val His Arg Thr Pro Glu Gly
                545                 550                 555

Val Ile Tyr Pro Ser Met Cys Trp Ile Arg Asp Ser Leu Val Ser
                560                 565                 570

Tyr Ile Thr Asn Leu Gly Leu Phe Ser Leu Val Phe Leu Phe Asn
                575                 580                 585

Met Ala Met Leu Ala Thr Met Val Val Gln Ile Leu Arg Leu Arg
                590                 595                 600

Pro His Thr Gln Lys Trp Ser His Val Leu Thr Leu Leu Gly Leu
                605                 610                 615

Ser Leu Val Leu Gly Leu Pro Trp Ala Leu Ile Phe Phe Ser Phe
                620                 625                 630

Ala Ser Gly Thr Phe Gln Leu Val Val Leu Tyr Leu Phe Ser Ile
                635                 640                 645

Ile Thr Ser Phe Gln Gly Phe Leu Ile Phe Ile Trp Tyr Trp Ser
                650                 655                 660

Met Arg Leu Gln Ala Arg Gly Gly Pro Ser Pro Leu Lys Ser Asn
                665                 670                 675

Ser Asp Ser Ala Arg Leu Pro Ile Ser Ser Gly Ser Thr Ser Ser
                680                 685                 690
```

-continued

Ser Arg Ile

<210> SEQ ID NO 135
<211> LENGTH: 1615
<212> TYPE: DNA
<213> ORGANISM: Homo sapiens

<400> SEQUENCE: 135
gcctagccag gccaagaatg caattgcccc ggtggtggga gctgggagac 50
ccctgtgctt ggacgggaca gggtcggggg acacgcagga tgagccccgc 100
gaccactggc acattcttgc tgacagtgta cagtattttc tccaaggtac 150
actccgatcg gaatgtatac ccatcagcag gtgtcctctt tgttcatgtt 200
ttggaaagag aatattttaa gggggaattt ccaccttacc caaaacctgg 250
cgagattagt aatgatccca taacatttaa tacaaattta atgggttacc 300
cagaccgacc tggatggctt cgatatatcc aaaggacacc atatagtgat 350
ggagtcctat atgggtcccc aacagctgaa aatgtgggga agccaacaat 400
cattgagata actgcctaca acaggcgcac ctttgagact gcaaggcata 450
atttgataat taatataatg tctgcagaag acttcccgtt gccatatcaa 500
gcagaattct tcattaagaa tatgaatgta gaagaaatgt tggccagtga 550
ggttcttgga gactttcttg gcgcagtgaa aaatgtgtgg cagccagagc 600
gcctgaacgc cataaacatc acatcggccc tagacagggg tggcagggtg 650
ccacttccca ttaatgacct gaaggagggc gtttatgtca tggttggtgc 700
agatgtcccg ttttcttctt gtttacgaga agttgaaaat ccacagaatc 750
aattgagatg tagtcaagaa atggagcctg taataacatg tgataaaaaa 800
tttcgtactc aattttacat tgactggtgc aaaatttcat tggttgataa 850
aacaaagcaa gtgtccacct atcaggaagt gattcgtgga gaggggattt 900
tacctgatgg tggagaatac aaacccccctt ctgattcttt gaaaagcaga 950
gactattaca cggatttcct aattacactg gctgtgccct cggcagtggc 1000
actggtcctt tttctaatac ttgcttatat catgtgctgc cgacgggaag 1050
gcgtggaaaa gagaaacatg caaacaccag acatccaact ggtccatcac 1100
agtgctattc agaaatctac caaggagctt cgagacatgt ccaagaatag 1150
agagatagca tggcccctgt caacgcttcc tgtgttccac cctgtgactg 1200
gggaaatcat acctccttta cacacagaca actatgatag cacaaacatg 1250
ccattgatgc aaacgcagca gaacttgcca catcagactc agattcccca 1300
acagcagact acaggtaaat ggtatccctg aagaaagaaa actgactgaa 1350
gcaatgaatt tataatcaga caatatagca gttacatcac atttcttttc 1400
tcttccaata atgcatgagc ttttctggca tatgttatgc atgttggcag 1450
tattaagtgt ataccaaata atacaacata actttcattt tactaatgta 1500
tttttttgta cttaaagcat tttgacaat ttgtaaaaca ttgatgactt 1550
tatatttgtt acaataaaag ttgatcttta aaataaatat tattaatgaa 1600
gcctaaaaaa aaaaa 1615

<210> SEQ ID NO 136
<211> LENGTH: 437

<212> TYPE: PRT
<213> ORGANISM: Homo sapiens

<400> SEQUENCE: 136

```
Met Gln Leu Pro Arg Trp Trp Glu Leu Gly Asp Pro Cys Ala Trp
  1               5                  10                  15

Thr Gly Gln Gly Arg Gly Thr Arg Arg Met Ser Pro Ala Thr Thr
                 20                  25                  30

Gly Thr Phe Leu Leu Thr Val Tyr Ser Ile Phe Ser Lys Val His
                 35                  40                  45

Ser Asp Arg Asn Val Tyr Pro Ser Ala Gly Val Leu Phe Val His
                 50                  55                  60

Val Leu Glu Arg Glu Tyr Phe Lys Gly Glu Phe Pro Pro Tyr Pro
                 65                  70                  75

Lys Pro Gly Glu Ile Ser Asn Asp Pro Ile Thr Phe Asn Thr Asn
                 80                  85                  90

Leu Met Gly Tyr Pro Asp Arg Pro Gly Trp Leu Arg Tyr Ile Gln
                 95                 100                 105

Arg Thr Pro Tyr Ser Asp Gly Val Leu Tyr Gly Ser Pro Thr Ala
                110                 115                 120

Glu Asn Val Gly Lys Pro Thr Ile Ile Glu Ile Thr Ala Tyr Asn
                125                 130                 135

Arg Arg Thr Phe Glu Thr Ala Arg His Asn Leu Ile Ile Asn Ile
                140                 145                 150

Met Ser Ala Glu Asp Phe Pro Leu Pro Tyr Gln Ala Glu Phe Phe
                155                 160                 165

Ile Lys Asn Met Asn Val Glu Glu Met Leu Ala Ser Glu Val Leu
                170                 175                 180

Gly Asp Phe Leu Gly Ala Val Lys Asn Val Trp Gln Pro Glu Arg
                185                 190                 195

Leu Asn Ala Ile Asn Ile Thr Ser Ala Leu Asp Arg Gly Gly Arg
                200                 205                 210

Val Pro Leu Pro Ile Asn Asp Leu Lys Glu Gly Val Tyr Val Met
                215                 220                 225

Val Gly Ala Asp Val Pro Phe Ser Ser Cys Leu Arg Glu Val Glu
                230                 235                 240

Asn Pro Gln Asn Gln Leu Arg Cys Ser Gln Glu Met Glu Pro Val
                245                 250                 255

Ile Thr Cys Asp Lys Lys Phe Arg Thr Gln Phe Tyr Ile Asp Trp
                260                 265                 270

Cys Lys Ile Ser Leu Val Asp Lys Thr Lys Gln Val Ser Thr Tyr
                275                 280                 285

Gln Glu Val Ile Arg Gly Glu Gly Ile Leu Pro Asp Gly Gly Glu
                290                 295                 300

Tyr Lys Pro Pro Ser Asp Ser Leu Lys Ser Arg Asp Tyr Tyr Thr
                305                 310                 315

Asp Phe Leu Ile Thr Leu Ala Val Pro Ser Ala Val Ala Leu Val
                320                 325                 330

Leu Phe Leu Ile Leu Ala Tyr Ile Met Cys Cys Arg Arg Glu Gly
                335                 340                 345

Val Glu Lys Arg Asn Met Gln Thr Pro Asp Ile Gln Leu Val His
                350                 355                 360

His Ser Ala Ile Gln Lys Ser Thr Lys Glu Leu Arg Asp Met Ser
                365                 370                 375
```

-continued

```
Lys Asn Arg Glu Ile Ala Trp Pro Leu Ser Thr Leu Pro Val Phe
                380                 385                 390

His Pro Val Thr Gly Glu Ile Ile Pro Pro Leu His Thr Asp Asn
                395                 400                 405

Tyr Asp Ser Thr Asn Met Pro Leu Met Gln Thr Gln Gln Asn Leu
                410                 415                 420

Pro His Gln Thr Gln Ile Pro Gln Gln Gln Thr Thr Gly Lys Trp
                425                 430                 435

Tyr Pro


<210> SEQ ID NO 137
<211> LENGTH: 1621
<212> TYPE: DNA
<213> ORGANISM: Homo sapiens

<400> SEQUENCE: 137

cagaagaggg ggctagctag ctgtctctgc ggaccaggga gaccccccgcg          50

cccccccggt gtgaggcggc ctcacagggc cgggtgggct ggcgagccga          100

cgcggcggcg gaggaggctg tgaggagtgt gtggaacagg acccgggaca          150

gaggaaccat ggctccgcag aacctgagca ccttttgcct gttgctgcta          200

tacctcatcg gggcggtgat tgccggacga gatttctata agatcttggg          250

ggtgcctcga agtgcctcta taaaggatat taaaaaggcc tataggaaac          300

tagccctgca gcttcatccc gaccggaacc ctgatgatcc acaagcccag          350

gagaaattcc aggatctggg tgctgcttat gaggttctgt cagatagtga          400

gaaacggaaa cagtacgata cttatggtga agaaggatta aaagatggtc          450

atcagagctc ccatggagac attttttcac acttctttgg ggattttggt          500

ttcatgtttg gaggaacccc tcgtcagcaa gacagaaata ttccaagagg          550

aagtgatatt attgtagatc tagaagtcac tttggaagaa gtatatgcag          600

gaaattttgt ggaagtagtt agaaacaaac ctgtggcaag gcaggctcct          650

ggcaaacgga agtgcaattg tcggcaagag atgcggacca cccagctggg          700

ccctgggcgc ttccaaatga cccaggaggt ggtctgcgac gaatgcccta          750

atgtcaaact agtgaatgaa gaacgaacgc tggaagtaga aatagagcct          800

ggggtgagag acggcatgga gtaccccttt attggagaag gtgagcctca          850

cgtggatggg gagcctggag atttacggtt ccgaatcaaa gttgtcaagc          900

acccaatatt tgaaaggaga ggagatgatt tgtacacaaa tgtgacaatc          950

tcattagttg agtcactggt tggctttgag atggatatta ctcacttgga          1000

tggtcacaag gtacatattt cccgggataa gatcaccagg ccaggagcga          1050

agctatggaa gaaaggggaa gggctcccca actttgacaa caacaatatc          1100

aagggctctt tgataatcac ttttgatgtg gattttccaa aagaacagtt          1150

aacagaggaa gcgagagaag gtatcaaaca gctactgaaa caagggtcag          1200

tgcagaaggt atacaatgga ctgcaaggat attgagagtg aataaaattg          1250

gactttgttt aaaataagtg aataagcgat atttattatc tgcaaggttt          1300

ttttgtgtgt gtttttgttt ttattttcaa tatgcaagtt aggcttaatt          1350

tttttatcta atgatcatca tgaaatgaat aagagggctt aagaatttgt          1400
```

-continued

```
ccatttgcat tcggaaaaga atgaccagca aaaggtttac taatacctct          1450

ccctttgggg atttaatgtc tggtgctgcc gcctgagttt caagaattaa          1500

agctgcaaga ggactccagg agcaaaagaa acacaatata gagggttgga          1550

gttgttagca atttcattca aaatgccaac tggagaagtc tgtttttaaa          1600

tacattttgt tgttattttt  a                                        1621


<210> SEQ ID NO 138
<211> LENGTH: 358
<212> TYPE: PRT
<213> ORGANISM: Homo sapiens

<400> SEQUENCE: 138

Met Ala Pro Gln Asn Leu Ser Thr Phe Cys Leu Leu Leu Leu Tyr
  1               5                  10                  15

Leu Ile Gly Ala Val Ile Ala Gly Arg Asp Phe Tyr Lys Ile Leu
                 20                  25                  30

Gly Val Pro Arg Ser Ala Ser Ile Lys Asp Ile Lys Lys Ala Tyr
                 35                  40                  45

Arg Lys Leu Ala Leu Gln Leu His Pro Asp Arg Asn Pro Asp Asp
                 50                  55                  60

Pro Gln Ala Gln Glu Lys Phe Gln Asp Leu Gly Ala Ala Tyr Glu
                 65                  70                  75

Val Leu Ser Asp Ser Glu Lys Arg Lys Gln Tyr Asp Thr Tyr Gly
                 80                  85                  90

Glu Glu Gly Leu Lys Asp Gly His Gln Ser Ser His Gly Asp Ile
                 95                 100                 105

Phe Ser His Phe Phe Gly Asp Phe Gly Phe Met Phe Gly Gly Thr
                110                 115                 120

Pro Arg Gln Gln Asp Arg Asn Ile Pro Arg Gly Ser Asp Ile Ile
                125                 130                 135

Val Asp Leu Glu Val Thr Leu Glu Glu Val Tyr Ala Gly Asn Phe
                140                 145                 150

Val Glu Val Val Arg Asn Lys Pro Val Ala Arg Gln Ala Pro Gly
                155                 160                 165

Lys Arg Lys Cys Asn Cys Arg Gln Glu Met Arg Thr Thr Gln Leu
                170                 175                 180

Gly Pro Gly Arg Phe Gln Met Thr Gln Glu Val Val Cys Asp Glu
                185                 190                 195

Cys Pro Asn Val Lys Leu Val Asn Glu Glu Arg Thr Leu Glu Val
                200                 205                 210

Glu Ile Glu Pro Gly Val Arg Asp Gly Met Glu Tyr Pro Phe Ile
                215                 220                 225

Gly Glu Gly Glu Pro His Val Asp Gly Glu Pro Gly Asp Leu Arg
                230                 235                 240

Phe Arg Ile Lys Val Val Lys His Pro Ile Phe Glu Arg Arg Gly
                245                 250                 255

Asp Asp Leu Tyr Thr Asn Val Thr Ile Ser Leu Val Glu Ser Leu
                260                 265                 270

Val Gly Phe Glu Met Asp Ile Thr His Leu Asp Gly His Lys Val
                275                 280                 285

His Ile Ser Arg Asp Lys Ile Thr Arg Pro Gly Ala Lys Leu Trp
                290                 295                 300

Lys Lys Gly Glu Gly Leu Pro Asn Phe Asp Asn Asn Asn Ile Lys
```

-continued

```
                305                 310                 315

Gly Ser Leu Ile Ile Thr Phe Asp Val Asp Phe Pro Lys Glu Gln
                320                 325                 330

Leu Thr Glu Glu Ala Arg Glu Gly Ile Lys Gln Leu Leu Lys Gln
                335                 340                 345

Gly Ser Val Gln Lys Val Tyr Asn Gly Leu Gln Gly Tyr
                350                 355
```

```
<210> SEQ ID NO 139
<211> LENGTH: 550
<212> TYPE: DNA
<213> ORGANISM: Homo sapiens

<400> SEQUENCE: 139

ccagtctgtc gccacctcac ttggtgtctg ctgtccccgc caggcaagcc               50

tggggtgaga gcacagagga gtgggccggg accatgcggg ggacgcggct              100

ggcgctcctg gcgctggtgc tggctgcctg cggagagctg gcgccggccc              150

tgcgctgcta cgtctgtccg gagcccacag gagtgtcgga ctgtgtcacc              200

atcgccacct gcaccaccaa cgaaaccatg tgcaagacca cactctactc              250

ccgggagata gtgtacccct tccaggggga ctccacggtg accaagtcct              300

gtgccagcaa gtgtaagccc tcggatgtgg atggcatcgg ccagaccctg              350

cccgtgtcct gctgcaatac tgagctgtgc aatgtagacg gggcgcccgc              400

tctgaacagc ctccactgcg ggccctcac gctcctccca ctcttgagcc              450

tccgactgta gagtccccgc ccacccccat ggccctatgc ggcccagccc              500

cgaatgcctt gaagaagtgc cccctgcacc aggaaaaaaa aaaaaaaaaa              550
```

```
<210> SEQ ID NO 140
<211> LENGTH: 125
<212> TYPE: PRT
<213> ORGANISM: Homo sapiens

<400> SEQUENCE: 140

Met Arg Gly Thr Arg Leu Ala Leu Leu Ala Leu Val Leu Ala Ala
  1               5                  10                  15

Cys Gly Glu Leu Ala Pro Ala Leu Arg Cys Tyr Val Cys Pro Glu
                 20                  25                  30

Pro Thr Gly Val Ser Asp Cys Val Thr Ile Ala Thr Cys Thr Thr
                 35                  40                  45

Asn Glu Thr Met Cys Lys Thr Thr Leu Tyr Ser Arg Glu Ile Val
                 50                  55                  60

Tyr Pro Phe Gln Gly Asp Ser Thr Val Thr Lys Ser Cys Ala Ser
                 65                  70                  75

Lys Cys Lys Pro Ser Asp Val Asp Gly Ile Gly Gln Thr Leu Pro
                 80                  85                  90

Val Ser Cys Cys Asn Thr Glu Leu Cys Asn Val Asp Gly Ala Pro
                 95                 100                 105

Ala Leu Asn Ser Leu His Cys Gly Ala Leu Thr Leu Leu Pro Leu
                110                 115                 120

Leu Ser Leu Arg Leu
                125
```

```
<210> SEQ ID NO 141
<211> LENGTH: 1524
```

-continued

<212> TYPE: DNA
<213> ORGANISM: Homo sapiens

<400> SEQUENCE: 141

```
ggcgccgcgt aggcccggga ggccgggccg gccgggctgc gagcgcctgc          50
cccatgcgcc gccgcctctc cgcacgatgt tcccctcgcg gaggaaagcg         100
gcgcagctgc cctgggagga cggcaggtcc gggttgctct ccggcggcct         150
ccctcggaag tgttccgtct tccacctgtt cgtggcctgc ctctcgctgg         200
gcttcttctc cctactctgg ctgcagctca gctgctctgg ggacgtggcc         250
cgggcagtca ggggacaagg gcaggagacc tcgggccctc cccgtgcctg         300
ccccccagag ccgccccctg agcactggga agaagacgca tcctggggcc         350
cccaccgcct ggcagtgctg gtgcccttcc gcgaacgctt cgaggagctc         400
ctggtcttcg tgccccacat gcgccgcttc ctgagcagga agaagatccg         450
gcaccacatc tacgtgctca accaggtgga ccacttcagg ttcaaccggg         500
cagcgctcat caacgtgggc ttcctggaga gcagcaacag cacggactac         550
attgccatgc acgacgttga cctgctccct ctcaacgagg agctggacta         600
tggctttcct gaggctgggc ccttccacgt ggcctccccg gagctccacc         650
ctctctacca ctacaagacc tatgtcggcg gcatcctgct gctctccaag         700
cagcactacc ggctgtgcaa tgggatgtcc aaccgcttct ggggctgggg         750
ccgcgaggac gacgagttct accggcgcat taagggagct gggctccagc         800
ttttccgccc ctcgggaatc acaactgggt acaagacatt tcgccacctg         850
catgacccag cctggcggaa gagggaccag aagcgcatcg cagctcaaaa         900
acaggagcag ttcaaggtgg acagggaggg aggcctgaac actgtgaagt         950
accatgtggc ttcccgcact gccctgtctg tgggcggggc cccctgcact        1000
gtcctcaaca tcatgttgga ctgtgacaag accgccacac cctggtgcac        1050
attcagctga gctggatgga cagtgaggaa gcctgtacct acaggccata        1100
ttgctcaggc tcaggacaag gcctcaggtc gtgggcccag ctctgacagg        1150
atgtggagtg gccaggacca agacagcaag ctacgcaatt gcagccaccc        1200
ggccgccaag gcaggcttgg gctgggccag gacacgtggg gtgcctggga        1250
cgctgcttgc catgcacagt gatcagagag aggctggggt gtgtcctgtc        1300
cgggaccccc cctgccttcc tgctcaccct actctgacct ccttcacgtg        1350
cccaggcctg tgggtagtgg ggagggctga acaggacaac ctctcatcac        1400
cctactctga cctccttcac gtgcccaggc ctgtgggtag tggggagggc        1450
tgaacaggac aacctctcat cacccccaaa aaaaaaaaaa aaaaaaaaaa        1500
aaaaaaaaaa aaaaaaaaaa  aaaa                                   1524
```

<210> SEQ ID NO 142
<211> LENGTH: 327
<212> TYPE: PRT
<213> ORGANISM: Homo sapiens

<400> SEQUENCE: 142

```
Met Phe Pro Ser Arg Arg Lys Ala Ala Gln Leu Pro Trp Glu Asp
  1               5                  10                  15

Gly Arg Ser Gly Leu Leu Ser Gly Gly Leu Pro Arg Lys Cys Ser
```

-continued

```
                20                  25                  30

Val Phe His Leu Phe Val Ala Cys Leu Ser Leu Gly Phe Phe Ser
                35                  40                  45

Leu Leu Trp Leu Gln Leu Ser Cys Ser Gly Asp Val Ala Arg Ala
                50                  55                  60

Val Arg Gly Gln Gly Gln Glu Thr Ser Gly Pro Pro Arg Ala Cys
                65                  70                  75

Pro Pro Glu Pro Pro Pro Glu His Trp Glu Glu Asp Ala Ser Trp
                80                  85                  90

Gly Pro His Arg Leu Ala Val Leu Val Pro Phe Arg Glu Arg Phe
                95                 100                 105

Glu Glu Leu Leu Val Phe Val Pro His Met Arg Arg Phe Leu Ser
               110                 115                 120

Arg Lys Lys Ile Arg His His Ile Tyr Val Leu Asn Gln Val Asp
               125                 130                 135

His Phe Arg Phe Asn Arg Ala Ala Leu Ile Asn Val Gly Phe Leu
               140                 145                 150

Glu Ser Ser Asn Ser Thr Asp Tyr Ile Ala Met His Asp Val Asp
               155                 160                 165

Leu Leu Pro Leu Asn Glu Glu Leu Asp Tyr Gly Phe Pro Glu Ala
               170                 175                 180

Gly Pro Phe His Val Ala Ser Pro Glu Leu His Pro Leu Tyr His
               185                 190                 195

Tyr Lys Thr Tyr Val Gly Gly Ile Leu Leu Leu Ser Lys Gln His
               200                 205                 210

Tyr Arg Leu Cys Asn Gly Met Ser Asn Arg Phe Trp Gly Trp Gly
               215                 220                 225

Arg Glu Asp Asp Glu Phe Tyr Arg Arg Ile Lys Gly Ala Gly Leu
               230                 235                 240

Gln Leu Phe Arg Pro Ser Gly Ile Thr Thr Gly Tyr Lys Thr Phe
               245                 250                 255

Arg His Leu His Asp Pro Ala Trp Arg Lys Arg Asp Gln Lys Arg
               260                 265                 270

Ile Ala Ala Gln Lys Gln Glu Gln Phe Lys Val Asp Arg Glu Gly
               275                 280                 285

Gly Leu Asn Thr Val Lys Tyr His Val Ala Ser Arg Thr Ala Leu
               290                 295                 300

Ser Val Gly Gly Ala Pro Cys Thr Val Leu Asn Ile Met Leu Asp
               305                 310                 315

Cys Asp Lys Thr Ala Thr Pro Trp Cys Thr Phe Ser
               320                 325
```

<210> SEQ ID NO 143
<211> LENGTH: 1621
<212> TYPE: DNA
<213> ORGANISM: Homo sapiens

<400> SEQUENCE: 143

```
gtgggattta tttgagtgca agatcgtttt ctcagtggtg gtggaagttg              50

cctcatcgca ggcagatgtt ggggctttgt ccgaacagct cccctctgcc             100

agcttctgta gataagggtt aaaaactaat atttatatga cagaagaaaa             150

agatgtcatt ccgtaaagta aacatcatca tcttggtcct ggctgttgct             200

ctcttcttac tggttttgca ccataacttc ctcagcttga gcagtttgtt             250
```

aaggaatgag gttacagatt caggaattgt agggcctcaa cctatagact 300
ttgtcccaaa tgctctccga catgcagtag atgggagaca agaggagatt 350
cctgtggtca tcgctgcatc tgaagacagg cttggggggg ccattgcagc 400
tataaacagc attcagcaca acactcgctc caatgtgatt ttctacattg 450
ttactctcaa caatacagca gaccatctcc ggtcctggct caacagtgat 500
tccctgaaaa gcatcagata caaaattgtc aattttgacc ctaaactttt 550
ggaaggaaaa gtaaaggagg atcctgacca gggggaatcc atgaaacctt 600
taacctttgc aaggttctac ttgccaattc tggttcccag cgcaaagaag 650
gccatataca tggatgatga tgtaattgtg caaggtgata ttcttgccct 700
ttacaataca gcactgaagc caggacatgc agctgcattt tcagaagatt 750
gtgattcagc ctctactaaa gttgtcatcc gtggagcagg aaaccagtac 800
aattacattg gctatcttga ctataaaaag gaaagaattc gtaagctttc 850
catgaaagcc agcacttgct catttaatcc tggagttttt gttgcaaacc 900
tgacggaatg gaaacgacag aatataacta accaactgga aaaatggatg 950
aaactcaatg tagaagaggg actgtatagc agaaccctgg ctggtagcat 1000
cacaacacct cctctgctta tcgtatttta tcaacagcac tctaccatcg 1050
atcctatgtg gaatgtccgc caccttggtt ccagtgctgg aaaacgatat 1100
tcacctcagt ttgtaaaggc tgccaagtta ctccattgga atggacattt 1150
gaagccatgg ggaaggactg cttcatatac tgatgtttgg gaaaaatggt 1200
atattccaga cccaacaggc aaattcaacc taatccgaag atataccgag 1250
atctcaaaca taaagtgaaa cagaatttga actgtaagca agcatttctc 1300
aggaagtcct ggaagatagc atgcatggga agtaacagtt gctaggcttc 1350
aatgcctatc ggtagcaagc catggaaaaa gatgtgtcag ctaggtaaag 1400
atgacaaact gccctgtctg gcagtcagct tcccagacag actatagact 1450
ataaatatgt ctccatctgc cttaccaagt gttttcttac tacaatgctg 1500
aatgactgga aagaagaact gatatggcta gttcagctag ctggtacaga 1550
taattcaaaa ctgctgttgg ttttaatttt gtaacctgtg gcctgatctg 1600
taaataaaac ttacattttt c 1621

<210> SEQ ID NO 144
<211> LENGTH: 371
<212> TYPE: PRT
<213> ORGANISM: Homo sapiens

<400> SEQUENCE: 144

Met Ser Phe Arg Lys Val Asn Ile Ile Ile Leu Val Leu Ala Val
1 5 10 15

Ala Leu Phe Leu Leu Val Leu His His Asn Phe Leu Ser Leu Ser
20 25 30

Ser Leu Leu Arg Asn Glu Val Thr Asp Ser Gly Ile Val Gly Pro
35 40 45

Gln Pro Ile Asp Phe Val Pro Asn Ala Leu Arg His Ala Val Asp
50 55 60

Gly Arg Gln Glu Glu Ile Pro Val Val Ile Ala Ala Ser Glu Asp
65 70 75

-continued

```
Arg Leu Gly Gly Ala Ile Ala Ala Ile Asn Ser Ile Gln His Asn
                80                  85                  90

Thr Arg Ser Asn Val Ile Phe Tyr Ile Val Thr Leu Asn Asn Thr
                95                  100                 105

Ala Asp His Leu Arg Ser Trp Leu Asn Ser Asp Ser Leu Lys Ser
                110                 115                 120

Ile Arg Tyr Lys Ile Val Asn Phe Asp Pro Lys Leu Leu Glu Gly
                125                 130                 135

Lys Val Lys Glu Asp Pro Asp Gln Gly Glu Ser Met Lys Pro Leu
                140                 145                 150

Thr Phe Ala Arg Phe Tyr Leu Pro Ile Leu Val Pro Ser Ala Lys
                155                 160                 165

Lys Ala Ile Tyr Met Asp Asp Asp Val Ile Val Gln Gly Asp Ile
                170                 175                 180

Leu Ala Leu Tyr Asn Thr Ala Leu Lys Pro Gly His Ala Ala Ala
                185                 190                 195

Phe Ser Glu Asp Cys Asp Ser Ala Ser Thr Lys Val Val Ile Arg
                200                 205                 210

Gly Ala Gly Asn Gln Tyr Asn Tyr Ile Gly Tyr Leu Asp Tyr Lys
                215                 220                 225

Lys Glu Arg Ile Arg Lys Leu Ser Met Lys Ala Ser Thr Cys Ser
                230                 235                 240

Phe Asn Pro Gly Val Phe Val Ala Asn Leu Thr Glu Trp Lys Arg
                245                 250                 255

Gln Asn Ile Thr Asn Gln Leu Glu Lys Trp Met Lys Leu Asn Val
                260                 265                 270

Glu Glu Gly Leu Tyr Ser Arg Thr Leu Ala Gly Ser Ile Thr Thr
                275                 280                 285

Pro Pro Leu Leu Ile Val Phe Tyr Gln Gln His Ser Thr Ile Asp
                290                 295                 300

Pro Met Trp Asn Val Arg His Leu Gly Ser Ser Ala Gly Lys Arg
                305                 310                 315

Tyr Ser Pro Gln Phe Val Lys Ala Ala Lys Leu Leu His Trp Asn
                320                 325                 330

Gly His Leu Lys Pro Trp Gly Arg Thr Ala Ser Tyr Thr Asp Val
                335                 340                 345

Trp Glu Lys Trp Tyr Ile Pro Asp Pro Thr Gly Lys Phe Asn Leu
                350                 355                 360

Ile Arg Arg Tyr Thr Glu Ile Ser Asn Ile Lys
                365                 370
```

<210> SEQ ID NO 145
<211> LENGTH: 415
<212> TYPE: DNA
<213> ORGANISM: Homo sapiens

<400> SEQUENCE: 145

```
aaacttgacg ccatgaagat cccggtcctt cctgccgtgg tgctcctctc          50

cctcctggtg ctccactctg cccagggagc caccctgggt ggtcctgagg         100

aagaaagcac cattgagaat tatgcgtcac gacccgaggc ctttaacacc         150

ccgttcctga acatcgacaa attgcgatct gcgtttaagg ctgatgagtt         200

cctgaactgg cacgccctct ttgagtctat caaaaggaaa cttcctttcc         250
```

-continued

```
tcaactggga tgcctttcct aagctgaaag gactgaggag cgcaactcct              300

gatgcccagt gaccatgacc tccactggaa gagggggcta gcgtgagcgc              350

tgattctcaa cctaccataa ctctttcctg cctcaggaac tccaataaaa              400

cattttccat  ccaaa                                                   415


<210> SEQ ID NO 146
<211> LENGTH: 99
<212> TYPE: PRT
<213> ORGANISM: Homo sapiens

<400> SEQUENCE: 146

Met Lys Ile Pro Val Leu Pro Ala Val Val Leu Leu Ser Leu Leu
  1               5                  10                  15

Val Leu His Ser Ala Gln Gly Ala Thr Leu Gly Gly Pro Glu Glu
                 20                  25                  30

Glu Ser Thr Ile Glu Asn Tyr Ala Ser Arg Pro Glu Ala Phe Asn
                 35                  40                  45

Thr Pro Phe Leu Asn Ile Asp Lys Leu Arg Ser Ala Phe Lys Ala
                 50                  55                  60

Asp Glu Phe Leu Asn Trp His Ala Leu Phe Glu Ser Ile Lys Arg
                 65                  70                  75

Lys Leu Pro Phe Leu Asn Trp Asp Ala Phe Pro Lys Leu Lys Gly
                 80                  85                  90

Leu Arg Ser Ala Thr Pro Asp Ala Gln
                 95


<210> SEQ ID NO 147
<211> LENGTH: 745
<212> TYPE: DNA
<213> ORGANISM: Homo sapiens

<400> SEQUENCE: 147

cctctgtcca ctgctttcgt gaagacaaga tgaagttcac aattgtcttt               50

gctggacttc ttggagtctt tctagctcct gccctagcta actataatat              100

caacgtcaat gatgacaaca acaatgctgg aagtgggcag cagtcagtga              150

gtgtcaacaa tgaacacaat gtggccaatg ttgacaataa caacggatgg              200

gactcctgga attccatctg ggattatgga aatggctttg ctgcaaccag              250

actctttcaa aagaagacat gcattgtgca caaaatgaac aaggaagtca              300

tgccctccat tcaatccctt gatgcactgg tcaaggaaaa gaagcttcag              350

ggtaagggac caggaggacc acctcccaag ggcctgatgt actcagtcaa              400

cccaaacaaa gtcgatgacc tgagcaagtt cggaaaaaac attgcaaaca              450

tgtgtcgtgg gattccaaca tacatggctg aggagatgca agaggcaagc              500

ctgttttttt actcaggaac gtgctacacg accagtgtac tatggattgt              550

ggacatttcc ttctgtggag acacggtgga gaactaaaca attttttaaa              600

gccactatgg atttagtcat ctgaatatgc tgtgcagaaa aaatatgggc              650

tccagtggtt tttaccatgt cattctgaaa tttttctcta ctagttatgt              700

ttgatttctt taagtttcaa taaaatcatt tagcattgaa  aaaaa                  745


<210> SEQ ID NO 148
<211> LENGTH: 185
<212> TYPE: PRT
```

-continued

<213> ORGANISM: Homo sapiens

<400> SEQUENCE: 148

Met Lys Phe Thr Ile Val Phe Ala Gly Leu Leu Gly Val Phe Leu
1 5 10 15

Ala Pro Ala Leu Ala Asn Tyr Asn Ile Asn Val Asn Asp Asp Asn
20 25 30

Asn Asn Ala Gly Ser Gly Gln Gln Ser Val Ser Val Asn Asn Glu
35 40 45

His Asn Val Ala Asn Val Asp Asn Asn Asn Gly Trp Asp Ser Trp
50 55 60

Asn Ser Ile Trp Asp Tyr Gly Asn Gly Phe Ala Ala Thr Arg Leu
65 70 75

Phe Gln Lys Lys Thr Cys Ile Val His Lys Met Asn Lys Glu Val
80 85 90

Met Pro Ser Ile Gln Ser Leu Asp Ala Leu Val Lys Glu Lys Lys
95 100 105

Leu Gln Gly Lys Gly Pro Gly Gly Pro Pro Pro Lys Gly Leu Met
110 115 120

Tyr Ser Val Asn Pro Asn Lys Val Asp Asp Leu Ser Lys Phe Gly
125 130 135

Lys Asn Ile Ala Asn Met Cys Arg Gly Ile Pro Thr Tyr Met Ala
140 145 150

Glu Glu Met Gln Glu Ala Ser Leu Phe Phe Tyr Ser Gly Thr Cys
155 160 165

Tyr Thr Thr Ser Val Leu Trp Ile Val Asp Ile Ser Phe Cys Gly
170 175 180

Asp Thr Val Glu Asn
185

<210> SEQ ID NO 149
<211> LENGTH: 992
<212> TYPE: DNA
<213> ORGANISM: Homo sapiens

<400> SEQUENCE: 149
ggcacgagcc aggaactagg aggttctcac tgcccgagca gaggccctac 50
acccaccgag gcatggggct ccctgggctg ttctgcttgg ccgtgctggc 100
tgccagcagc ttctccaagg cacgggagga agaaattacc cctgtggtct 150
ccattgccta caaagtcctg gaagttttcc ccaaaggccg ctgggtgctc 200
ataacctgct gtgcacccca gccaccaccg cccatcacct attccctctg 250
tggaaccaag aacatcaagg tggccaagaa ggtggtgaag acccacgagc 300
cggcctcctt caacctcaac gtcacactca agtccagtcc agacctgctc 350
acctacttct gccgggcgtc ctccacctca ggtgcccatg tggacagtgc 400
caggctacag atgcactggg agctgtggtc caagccagtg tctgagctgc 450
gggccaactt cactctgcag gacagagggg caggccccag ggtggagatg 500
atctgccagg cgtcctcggg cagcccacct atcaccaaca gcctgatcgg 550
gaaggatggg caggtccacc tgcagcagag accatgccac aggcagcctg 600
ccaacttctc cttcctgccg agccagacat cggactggtt ctggtgccag 650
gctgcaaaca acgccaatgt ccagcacagc gccctcacag tggtgccccc 700

-continued

```
aggtggtgac cagaagatgg aggactggca gggtcccctg gagagcccca          750

tccttgcctt gccgctctac aggagcaccc gccgtctgag tgaagaggag          800

tttggggggt tcaggatagg gaatggggag gtcagaggac gcaaagcagc          850

agccatgtag aatgaaccgt ccagagagcc aagcacggca gaggactgca          900

ggccatcagc gtgcactgtt cgtatttgga gttcatgcaa aatgagtgtg          950

ttttagctgc tcttgccaca aaaaaaaaaa aaaaaaaaaa  aa                 992
```

<210> SEQ ID NO 150
<211> LENGTH: 265
<212> TYPE: PRT
<213> ORGANISM: Homo sapiens

<400> SEQUENCE: 150

```
Met Gly Leu Pro Gly Leu Phe Cys Leu Ala Val Leu Ala Ala Ser
  1               5                  10                  15

Ser Phe Ser Lys Ala Arg Glu Glu Glu Ile Thr Pro Val Val Ser
                 20                  25                  30

Ile Ala Tyr Lys Val Leu Glu Val Phe Pro Lys Gly Arg Trp Val
                 35                  40                  45

Leu Ile Thr Cys Cys Ala Pro Gln Pro Pro Pro Pro Ile Thr Tyr
                 50                  55                  60

Ser Leu Cys Gly Thr Lys Asn Ile Lys Val Ala Lys Lys Val Val
                 65                  70                  75

Lys Thr His Glu Pro Ala Ser Phe Asn Leu Asn Val Thr Leu Lys
                 80                  85                  90

Ser Ser Pro Asp Leu Leu Thr Tyr Phe Cys Arg Ala Ser Ser Thr
                 95                 100                 105

Ser Gly Ala His Val Asp Ser Ala Arg Leu Gln Met His Trp Glu
                110                 115                 120

Leu Trp Ser Lys Pro Val Ser Glu Leu Arg Ala Asn Phe Thr Leu
                125                 130                 135

Gln Asp Arg Gly Ala Gly Pro Arg Val Glu Met Ile Cys Gln Ala
                140                 145                 150

Ser Ser Gly Ser Pro Pro Ile Thr Asn Ser Leu Ile Gly Lys Asp
                155                 160                 165

Gly Gln Val His Leu Gln Gln Arg Pro Cys His Arg Gln Pro Ala
                170                 175                 180

Asn Phe Ser Phe Leu Pro Ser Gln Thr Ser Asp Trp Phe Trp Cys
                185                 190                 195

Gln Ala Ala Asn Asn Ala Asn Val Gln His Ser Ala Leu Thr Val
                200                 205                 210

Val Pro Pro Gly Gly Asp Gln Lys Met Glu Asp Trp Gln Gly Pro
                215                 220                 225

Leu Glu Ser Pro Ile Leu Ala Leu Pro Leu Tyr Arg Ser Thr Arg
                230                 235                 240

Arg Leu Ser Glu Glu Glu Phe Gly Gly Phe Arg Ile Gly Asn Gly
                245                 250                 255

Glu Val Arg Gly Arg Lys Ala Ala Ala Met
                260                 265
```

<210> SEQ ID NO 151
<211> LENGTH: 683
<212> TYPE: DNA
<213> ORGANISM: Homo sapiens -continued

<400> SEQUENCE: 151
gcgtggggat gtctaggagc tcgaaggtgg tgctgggcct ctcggtgctg 50
ctgacggcgg ccacagtggc cggcgtacat gtgaagcagc agtgggacca 100
gcagaggctt cgtgacggag ttatcagaga cattgagagg caaattcgga 150
aaaaagaaaa cattcgtctt ttgggagaac agattatttt gactgagcaa 200
cttgaagcag aaagagagaa gatgttattg gcaaaaggat ctcaaaaatc 250
atgacttgaa tgtgaaatat ctgttggaca gacaacacga gtttgtgtgt 300
gtgtgttgat ggagagtagc ttagtagtat cttcatcttt ttttttggtc 350
actgtccttt taaacttgat caaataaagg acagtgggtc atataagtta 400
ctgctttcag ggtcccttat atctgaataa aggagtgtgg gcagacactt 450
tttggaagag tctgtctggg tgatcctggt agaagcccca ttagggtcac 500
tgtccagtgc ttagggttgt tactgagaag cactgccgag cttgtgagaa 550
ggaagggatg gatagtagca tccacctgag tagtctgatc agtcggcatg 600
atgacgaagc cacgagaaca tcgacctcag aaggactgga ggaaggtgaa 650
gtggagggag agacgctcct gatcgtcgaa tcc 683

<210> SEQ ID NO 152
<211> LENGTH: 81
<212> TYPE: PRT
<213> ORGANISM: Homo sapiens

<400> SEQUENCE: 152

Met Ser Arg Ser Ser Lys Val Val Leu Gly Leu Ser Val Leu Leu
1 5 10 15

Thr Ala Ala Thr Val Ala Gly Val His Val Lys Gln Gln Trp Asp
20 25 30

Gln Gln Arg Leu Arg Asp Gly Val Ile Arg Asp Ile Glu Arg Gln
35 40 45

Ile Arg Lys Lys Glu Asn Ile Arg Leu Leu Gly Glu Gln Ile Ile
50 55 60

Leu Thr Glu Gln Leu Glu Ala Glu Arg Glu Lys Met Leu Leu Ala
65 70 75

Lys Gly Ser Gln Lys Ser
80

<210> SEQ ID NO 153
<211> LENGTH: 1869
<212> TYPE: DNA
<213> ORGANISM: Homo sapiens

<400> SEQUENCE: 153
aatgtgagag gggctgatgg aagctgatag gcaggactgg agtgttagca 50
ccagtactgg atgtgacagc aggcagagga gcacttagca gcttattcag 100
tgtccgattc tgattccggc aaggatccaa gcatggaatg ctgccgtcgg 150
gcaactcctg gcacactgct cctctttctg gctttcctgc tcctgagttc 200
caggaccgca cgctccgagg aggaccggga cggcctatgg gatgcctggg 250
gcccatggag tgaatgctca cgcacctgcg ggggaggggc ctcctactct 300
ctgaggcgct gcctgagcag caagagctgt gaaggaagaa atatccgata 350

-continued

```
cagaacatgc agtaatgtgg actgcccacc agaagcaggt gatttccgag        400

ctcagcaatg ctcagctcat aatgatgtca agcaccatgg ccagttttat        450

gaatggcttc ctgtgtctaa tgaccctgac aacccatgtt cactcaagtg        500

ccaagccaaa ggaacaaccc tggttgttga actagcacct aaggtcttag        550

atggtacgcg ttgctataca gaatctttgg atatgtgcat cagtggttta        600

tgccaaattg ttggctgcga tcaccagctg ggaagcaccg tcaaggaaga        650

taactgtggg gtctgcaacg gagatgggtc cacctgccgg ctggtccgag        700

ggcagtataa atcccagctc tccgcaacca aatcggatga tactgtggtt        750

gcacttccct atggaagtag acatattcgc cttgtcttaa aaggtcctga        800

tcacttatat ctggaaacca aaaccctcca ggggactaaa ggtgaaaaca        850

gtctcagctc cacaggaact ttccttgtgg acaattctag tgtggacttc        900

cagaaatttc cagacaaaga gatactgaga atggctggac cactcacagc        950

agatttcatt gtcaagattc gtaactcggg ctccgctgac agtacagtcc       1000

agttcatctt ctatcaaccc atcatccacc gatggaggga gacggatttc       1050

tttccttgct cagcaacctg tggaggaggt tatcagctga catcggctga       1100

gtgctacgat ctgaggagca accgtgtggt tgctgaccaa tactgtcact       1150

attacccaga gaacatcaaa cccaaaccca agcttcagga gtgcaacttg       1200

gatccttgtc cagccagtga cggatacaag cagatcatgc cttatgacct       1250

ctaccatccc cttcctcggt gggaggccac cccatggacc gcgtgctcct       1300

cctcgtgtgg gggggcatc cagagccggg cagtttcctg tgtggaggag        1350

gacatccagg ggcatgtcac ttcagtggaa gagtggaaat gcatgtacac       1400

ccctaagatg cccatcgcgc agccctgcaa catttttgac tgccctaaat       1450

ggctggcaca ggagtggtct ccgtgcacag tgacatgtgg ccagggcctc       1500

agataccgtg tggtcctctg catcgaccat cgaggaatgc acacaggagg       1550

ctgtagccca aaaacaaagc cccacataaa agaggaatgc atcgtaccca       1600

ctccctgcta taaacccaaa gagaaacttc cagtcgaggc caagttgcca       1650

tggttcaaac aagctcaaga gctagaagaa ggagctgctg tgtcagagga       1700

gccctcgtaa gttgtaaaag cacagactgt tctatatttg aaactgtttt       1750

gtttaaagaa agcagtgtct cactggttgt agctttcatg ggttctgaac       1800

taagtgtaat catctcacca aagcttttg gctctcaaat taaagattga        1850

ttagtttcaa  aaaaaaaaa                                         1869
```

<210> SEQ ID NO 154
<211> LENGTH: 525
<212> TYPE: PRT
<213> ORGANISM: Homo sapiens

<400> SEQUENCE: 154

```
Met Glu Cys Cys Arg Arg Ala Thr Pro Gly Thr Leu Leu Leu Phe
  1               5                  10                  15

Leu Ala Phe Leu Leu Leu Ser Ser Arg Thr Ala Arg Ser Glu Glu
                 20                  25                  30

Asp Arg Asp Gly Leu Trp Asp Ala Trp Gly Pro Trp Ser Glu Cys
                 35                  40                  45
```

-continued

```
Ser Arg Thr Cys Gly Gly Gly Ala Ser Tyr Ser Leu Arg Arg Cys
                50                  55                  60

Leu Ser Ser Lys Ser Cys Glu Gly Arg Asn Ile Arg Tyr Arg Thr
                65                  70                  75

Cys Ser Asn Val Asp Cys Pro Pro Glu Ala Gly Asp Phe Arg Ala
                80                  85                  90

Gln Gln Cys Ser Ala His Asn Asp Val Lys His His Gly Gln Phe
                95                  100                 105

Tyr Glu Trp Leu Pro Val Ser Asn Asp Pro Asp Asn Pro Cys Ser
                110                 115                 120

Leu Lys Cys Gln Ala Lys Gly Thr Thr Leu Val Val Glu Leu Ala
                125                 130                 135

Pro Lys Val Leu Asp Gly Thr Arg Cys Tyr Thr Glu Ser Leu Asp
                140                 145                 150

Met Cys Ile Ser Gly Leu Cys Gln Ile Val Gly Cys Asp His Gln
                155                 160                 165

Leu Gly Ser Thr Val Lys Glu Asp Asn Cys Gly Val Cys Asn Gly
                170                 175                 180

Asp Gly Ser Thr Cys Arg Leu Val Arg Gly Gln Tyr Lys Ser Gln
                185                 190                 195

Leu Ser Ala Thr Lys Ser Asp Asp Thr Val Val Ala Leu Pro Tyr
                200                 205                 210

Gly Ser Arg His Ile Arg Leu Val Leu Lys Gly Pro Asp His Leu
                215                 220                 225

Tyr Leu Glu Thr Lys Thr Leu Gln Gly Thr Lys Gly Glu Asn Ser
                230                 235                 240

Leu Ser Ser Thr Gly Thr Phe Leu Val Asp Asn Ser Ser Val Asp
                245                 250                 255

Phe Gln Lys Phe Pro Asp Lys Glu Ile Leu Arg Met Ala Gly Pro
                260                 265                 270

Leu Thr Ala Asp Phe Ile Val Lys Ile Arg Asn Ser Gly Ser Ala
                275                 280                 285

Asp Ser Thr Val Gln Phe Ile Phe Tyr Gln Pro Ile Ile His Arg
                290                 295                 300

Trp Arg Glu Thr Asp Phe Phe Pro Cys Ser Ala Thr Cys Gly Gly
                305                 310                 315

Gly Tyr Gln Leu Thr Ser Ala Glu Cys Tyr Asp Leu Arg Ser Asn
                320                 325                 330

Arg Val Val Ala Asp Gln Tyr Cys His Tyr Tyr Pro Glu Asn Ile
                335                 340                 345

Lys Pro Lys Pro Lys Leu Gln Glu Cys Asn Leu Asp Pro Cys Pro
                350                 355                 360

Ala Ser Asp Gly Tyr Lys Gln Ile Met Pro Tyr Asp Leu Tyr His
                365                 370                 375

Pro Leu Pro Arg Trp Glu Ala Thr Pro Trp Thr Ala Cys Ser Ser
                380                 385                 390

Ser Cys Gly Gly Gly Ile Gln Ser Arg Ala Val Ser Cys Val Glu
                395                 400                 405

Glu Asp Ile Gln Gly His Val Thr Ser Val Glu Glu Trp Lys Cys
                410                 415                 420

Met Tyr Thr Pro Lys Met Pro Ile Ala Gln Pro Cys Asn Ile Phe
                425                 430                 435

Asp Cys Pro Lys Trp Leu Ala Gln Glu Trp Ser Pro Cys Thr Val
```

-continued

```
                440                 445                 450

Thr Cys Gly Gln Gly Leu Arg Tyr Arg Val Val Leu Cys Ile Asp
                455                 460                 465

His Arg Gly Met His Thr Gly Gly Cys Ser Pro Lys Thr Lys Pro
                470                 475                 480

His Ile Lys Glu Glu Cys Ile Val Pro Thr Pro Cys Tyr Lys Pro
                485                 490                 495

Lys Glu Lys Leu Pro Val Glu Ala Lys Leu Pro Trp Phe Lys Gln
                500                 505                 510

Ala Gln Glu Leu Glu Glu Gly Ala Ala Val Ser Glu Glu Pro Ser
                515                 520                 525
```

<210> SEQ ID NO 155
<211> LENGTH: 1734
<212> TYPE: DNA
<213> ORGANISM: Homo sapiens

<400> SEQUENCE: 155

```
gtggactctg agaagcccag gcagttgagg acaggagaga gaaggctgca        50

gacccagagg gagggaggac agggagtcgg aaggaggagg acagaggagg       100

gcacagagac gcagagcaag ggcggcaagg aggagaccct ggtgggagga       150

agacactctg gagagagagg gggctgggca gagatgaagt tccaggggcc       200

cctggcctgc ctcctgctgg ccctctgcct gggcagtggg gaggctggcc       250

ccctgcagag cggagaggaa agcactggga caaatattgg ggaggccctt       300

ggacatggcc tgggagacgc cctgagcgaa ggggtgggaa aggccattgg       350

caaagaggcc ggaggggcag ctggctctaa agtcagtgag gcccttggcc       400

aagggaccag agaagcagtt ggcactggag tcaggcaggt tccaggcttt       450

ggcgcagcag atgctttggg caacagggtc ggggaagcag cccatgctct       500

gggaaacact gggcacgaga ttggcagaca ggcagaagat gtcattcgac       550

acggagcaga tgctgtccgc ggctcctggc agggggtgcc tggccacagt       600

ggtgcttggg aaacttctgg aggccatggc atctttggct ctcaaggtgg       650

ccttggaggc cagggccagg gcaatcctgg aggtctgggg actccgtggg       700

tccacggata ccccggaaac tcagcaggca gctttggaat gaatcctcag       750

ggagctccct ggggtcaagg aggcaatgga gggccaccaa actttgggac       800

caacactcag ggagctgtgg cccagcctgg ctatggttca gtgagagcca       850

gcaaccagaa tgaagggtgc acgaatcccc caccatctgg ctcaggtgga       900

ggctccagca actctggggg aggcagcggc tcacagtcgg gcagcagtgg       950

cagtggcagc aatggtgaca acaacaatgg cagcagcagt ggtggcagca      1000

gcagtggcag cagcagtggc agcagcagtg gcggcagcag tggcggcagc      1050

agtggtggca gcagtggcaa cagtggtggc agcagaggtg acagcggcag      1100

tgagtcctcc tggggatcca gcaccggctc ctcctccggc aaccacggtg      1150

ggagcggcgg aggaaatgga cataaacccg ggtgtgaaaa gccagggaat      1200

gaagcccgcg ggagcgggga atctgggatt cagggcttca gaggacaggg      1250

agtttccagc aacatgaggg aaataagcaa agagggcaat cgcctccttg      1300

gaggctctgg agacaattat cgggggcaag ggtcgagctg ggcagtgga      1350
```

-continued

```
ggaggtgacg ctgttggtgg agtcaatact gtgaactctg agacgtctcc      1400

tgggatgttt aactttgaca ctttctggaa gaattttaaa tccaagctgg      1450

gtttcatcaa ctgggatgcc ataaacaagg accagagaag ctctcgcatc      1500

ccgtgacctc cagacaagga gccaccagat tggatgggag cccccacact      1550

ccctccttaa aacaccaccc tctcatcact aatctcagcc cttgcccttg      1600

aaataaacct tagctgcccc acaaaaaaaa aaaaaaaaaa aaaaaaaaaa      1650

aaaaaaaaaa aaaaaaaaaa aaaaaaaaaa aaaaaaaaaa aaaaaaaaaa      1700

aaaaaaaaaa aaaaaaaaaa aaaaaaaaaa  aaaa                      1734
```

```
<210> SEQ ID NO 156
<211> LENGTH: 440
<212> TYPE: PRT
<213> ORGANISM: Homo sapiens

<400> SEQUENCE: 156

Met Lys Phe Gln Gly Pro Leu Ala Cys Leu Leu Leu Ala Leu Cys
  1               5                  10                  15

Leu Gly Ser Gly Glu Ala Gly Pro Leu Gln Ser Gly Glu Glu Ser
                 20                  25                  30

Thr Gly Thr Asn Ile Gly Glu Ala Leu Gly His Gly Leu Gly Asp
                 35                  40                  45

Ala Leu Ser Glu Gly Val Gly Lys Ala Ile Gly Lys Glu Ala Gly
                 50                  55                  60

Gly Ala Ala Gly Ser Lys Val Ser Glu Ala Leu Gly Gln Gly Thr
                 65                  70                  75

Arg Glu Ala Val Gly Thr Gly Val Arg Gln Val Pro Gly Phe Gly
                 80                  85                  90

Ala Ala Asp Ala Leu Gly Asn Arg Val Gly Glu Ala Ala His Ala
                 95                 100                 105

Leu Gly Asn Thr Gly His Glu Ile Gly Arg Gln Ala Glu Asp Val
                110                 115                 120

Ile Arg His Gly Ala Asp Ala Val Arg Gly Ser Trp Gln Gly Val
                125                 130                 135

Pro Gly His Ser Gly Ala Trp Glu Thr Ser Gly Gly His Gly Ile
                140                 145                 150

Phe Gly Ser Gln Gly Gly Leu Gly Gly Gln Gly Gln Gly Asn Pro
                155                 160                 165

Gly Gly Leu Gly Thr Pro Trp Val His Gly Tyr Pro Gly Asn Ser
                170                 175                 180

Ala Gly Ser Phe Gly Met Asn Pro Gln Gly Ala Pro Trp Gly Gln
                185                 190                 195

Gly Gly Asn Gly Gly Pro Pro Asn Phe Gly Thr Asn Thr Gln Gly
                200                 205                 210

Ala Val Ala Gln Pro Gly Tyr Gly Ser Val Arg Ala Ser Asn Gln
                215                 220                 225

Asn Glu Gly Cys Thr Asn Pro Pro Pro Ser Gly Ser Gly Gly Gly
                230                 235                 240

Ser Ser Asn Ser Gly Gly Gly Ser Gly Ser Gln Ser Gly Ser Ser
                245                 250                 255

Gly Ser Gly Ser Asn Gly Asp Asn Asn Asn Gly Ser Ser Ser Gly
                260                 265                 270

Gly Ser Ser Ser Gly Ser Ser Ser Gly Ser Ser Ser Gly Gly Ser
```

-continued

```
                275                 280                 285

Ser Gly Gly Ser Ser Gly Gly Ser Ser Gly Asn Ser Gly Gly Ser
                290                 295                 300

Arg Gly Asp Ser Gly Ser Glu Ser Ser Trp Gly Ser Ser Thr Gly
                305                 310                 315

Ser Ser Ser Gly Asn His Gly Gly Ser Gly Gly Gly Asn Gly His
                320                 325                 330

Lys Pro Gly Cys Glu Lys Pro Gly Asn Glu Ala Arg Gly Ser Gly
                335                 340                 345

Glu Ser Gly Ile Gln Gly Phe Arg Gly Gln Gly Val Ser Ser Asn
                350                 355                 360

Met Arg Glu Ile Ser Lys Glu Gly Asn Arg Leu Leu Gly Gly Ser
                365                 370                 375

Gly Asp Asn Tyr Arg Gly Gln Gly Ser Ser Trp Gly Ser Gly Gly
                380                 385                 390

Gly Asp Ala Val Gly Gly Val Asn Thr Val Asn Ser Glu Thr Ser
                395                 400                 405

Pro Gly Met Phe Asn Phe Asp Thr Phe Trp Lys Asn Phe Lys Ser
                410                 415                 420

Lys Leu Gly Phe Ile Asn Trp Asp Ala Ile Asn Lys Asp Gln Arg
                425                 430                 435

Ser Ser Arg Ile Pro
                440


<210> SEQ ID NO 157
<211> LENGTH: 4104
<212> TYPE: DNA
<213> ORGANISM: Homo sapiens

<400> SEQUENCE: 157

cccacgcgtc cgcccacgcg tccgcccacg cgtccgccca cgcgtccgcc               50

cacgcgtccg cccacgcgtc cgcccacgcg tccggtgcaa gctcgcgccg              100

cacactgcct ggtggaggga aggagcccgg gcgcctctcg ccgctccccg              150

cgccgccgtc cgcacctccc caccgcccgc cgcccgccgc ccgccgcccg              200

caaagcatga gtgagcccgc tctctgcagc tgcccggggc gcgaatggca              250

ggctgtttcc gcggagtaaa aggtggcgcc ggtcagtggt cgtttccaat              300

gacggacatt aaccagactg tcagatcctg gggagtcgcg agccccgagt              350

ttggagtttt ttccccccac aacgtcacag tccgaactgc agagggaaag              400

gaaggcggca ggaaggcgaa gctcgggctc cggcacgtag ttgggaaact              450

tgcgggtcct agaagtcgcc tccccgcctt gccggccgcc cttgcagccc              500

cgagccgagc agcaaagtga gacattgtgc gcctgccaga tccgccggcc              550

gcggaccggg gctgcctcgg aaacacagag ggtcttctc tcgccctgca               600

tataattagc ctgcacacaa agggagcagc tgaatggagg ttgtcactct              650

ctggaaaagg atttctgacc gagcgcttcc aatggacatt ctccagtctc              700

tctggaaaga ttctcgctaa tggatttcct gctgctcggt ctctgtctat              750

actggctgct gaggaggccc tcgggggtgg tcttgtgtct gctgggggcc              800

tgctttcaga tgctgcccgc cgcccccagc gggtgcccgc agctgtgccg              850

gtgcgagggg cggctgctgt actgcgaggc gctcaacctc accgaggcgc              900
```

-continued

```
cccacaacct gtccggcctg ctgggcttgt ccctgcgcta caacagcctc        950
tcggagctgc gcgccggcca gttcacgggg ttaatgcagc tcacgtggct       1000
ctatctggat cacaatcaca tctgctccgt gcagggggac gcctttcaga       1050
aactgcgccg agttaaggaa ctcacgctga gttccaacca gatcacccaa       1100
ctgcccaaca ccaccttccg gcccatgccc aacctgcgca gcgtggacct       1150
ctcgtacaac aagctgcagg cgctcgcgcc cgacctcttc cacgggctgc       1200
ggaagctcac cacgctgcat atgcgggcca acgccatcca gtttgtgccc       1250
gtgcgcatct tccaggactg ccgcagcctc aagtttctcg acatcggata       1300
caatcagctc aagagtctgg cgcgcaactc tttcgccggc ttgtttaagc       1350
tcaccgagct gcacctcgag cacaacgact tggtcaaggt gaacttcgcc       1400
cacttcccgc gcctcatctc cctgcactcg ctctgcctgc ggaggaacaa       1450
ggtggccatt gtggtcagct cgctggactg ggtttggaac ctggagaaaa       1500
tggacttgtc gggcaacgag atcgagtaca tggagcccca tgtgttcgag       1550
accgtgccgc acctgcagtc cctgcagctg gactccaacc gcctcaccta       1600
catcgagccc cggatcctca actcttggaa gtccctgaca agcatcaccc       1650
tggccgggaa cctgtgggat tgcgggcgca acgtgtgtgc cctagcctcg       1700
tggctcagca acttccaggg gcgctacgat ggcaacttgc agtgcgccag       1750
cccggagtac gcacagggcg aggacgtcct ggacgccgtg tacgccttcc       1800
acctgtgcga ggatggggcc gagcccacca gcggccacct gctctcggcc       1850
gtcaccaacc gcagtgatct ggggcccccct gccagctcgg ccaccacgct       1900
cgcggacggc ggggaggggc agcacgacgg cacattcgag cctgccaccg       1950
tggctcttcc aggcggcgag cacgccgaga acgccgtgca gatccacaag       2000
gtggtcacgg gcaccatggc cctcatcttc tccttcctca tcgtggtcct       2050
ggtgctctac gtgtcctgga agtgtttccc agccagcctc aggcagctca       2100
gacagtgctt tgtcacgcag cgcaggaagc aaaagcagaa acagaccatg       2150
catcagatgg ctgccatgtc tgcccaggaa tactacgttg attacaaacc       2200
gaaccacatt gagggagccc tggtgatcat caacgagtat ggctcgtgta       2250
cctgccacca gcagcccgcg agggaatgcg aggtgtgatt gtcccagtgg       2300
ctctcaaccc atgcgctacc aaatacgcct gggcagccgg gacgggccgg       2350
cgggcaccag gctggggtct ccttgtctgt gctctgatat gctccttgac       2400
tgaaacttta aggggatctc tcccagagac ttgacatttt agctttattg       2450
tgtcttaaaa acaaaagcga attaaaacac aacaaaaaac cccaccccac       2500
aaccttcagg acagtctatc ttaaatttca tatgagaact ccttcctccc       2550
tttgaagatc tgtccatatt caggaatctg agagtgtaaa aaaggtggcc       2600
ataagacaga gagagaataa tcgtgctttg ttttatgcta ctcctcccac       2650
cctgcccatg attaaacatc atgtatgtag aagatcttaa gtccatacgc       2700
atttcatgaa gaaccattgg aaagaggaat ctgcaatctg ggagcttaag       2750
agcaaatgat gaccatagaa agctatgttc ttactttgtg tgtgtgtctg       2800
tatgtttctg cgttgtgtgt ctttgtaggc aagcaaacgt tgtctacaca       2850
aacgggaatt tagctcacat catttcatgc ccctgtgcct ctagctctgg       2900
```

-continued agattggtgg ggggaggtgg ggggaaacgg caggaataag ggaaagtggt 2950
agttttaact aaggttttgt aacacttgaa atcttttctt tctcaaatta 3000
attatcttta agcttcaaga aacttgctct gacccctcta agcaaactac 3050
taagcattta aaagagaatc taatttttaa aggtgtagca cctttttttt 3100
tattcttccc acagagggtg ctaatctcat tatgctgtgc tatctgaaaa 3150
gaacttaagg ccacaattca cgtctcgtcc tgggcattgt gatggattga 3200
ccctccattt gcagtacctt cccagctgat taaagttcag cagtggtatt 3250
gaggtttttc gaatatttat atagaaaaaa agtcttttca catgacaaat 3300
gacactctca caccagtctt agccctagta gtttttttagg ttggaccaga 3350 ggaagcaggt taaatgagac ctgtcctctg ctgcactcag aaaaaatagg 3400
cagtccctga tgctcagatc ttagccttga tattaatagt tgagaccacc 3450
tacccacaat gcagcctata ctcccaagac tacaaagtta ccatcgcaaa 3500
ggaaaggtta ttccagtaaa aggaaatagt tttctcaacc atttaaaaat 3550
attcttctga actcatcaaa gtagaagagc ccccaacctt ttctctctgc 3600
cttcaagaag gcagacattt ggtatgattt agcatcaaca acacatttat 3650
gagtatatgt aagtaatcag aggggcaaat gccacttgtt attcctccca 3700
agttttccaa gcaagtacac acagatctct ggtaggatta ggggccactt 3750
gtgtttccgg cttattttag tcgacttgtc agcaagtttg atgcctagtc 3800
tatctgacat ggcccagtag aacagggcat tgatggatca catgagatgg 3850
tagaaggaac atcatcacat accccctctca cagagaaaat tatcaaagaa 3900
ccagaaatta tatctgtttt ggagcaagag tgtcataatg tttcagggta 3950
gtcaaaataa acataaatta tctcctctag atgagtggcg atgttggctg 4000
atttgggtct gccattgaca gaatgtcaaa taaaaaggaa ttagctagaa 4050
tatgaccatt aaatgtgctt ctgaaatata ttttgagata ggtttagaat 4100
gtca 4104

<210> SEQ ID NO 158
<211> LENGTH: 522
<212> TYPE: PRT
<213> ORGANISM: Homo sapiens

<400> SEQUENCE: 158

Met Asp Phe Leu Leu Leu Gly Leu Cys Leu Tyr Trp Leu Leu Arg
1 5 10 15

Arg Pro Ser Gly Val Val Leu Cys Leu Leu Gly Ala Cys Phe Gln
20 25 30

Met Leu Pro Ala Ala Pro Ser Gly Cys Pro Gln Leu Cys Arg Cys
35 40 45

Glu Gly Arg Leu Leu Tyr Cys Glu Ala Leu Asn Leu Thr Glu Ala
50 55 60

Pro His Asn Leu Ser Gly Leu Leu Gly Leu Ser Leu Arg Tyr Asn
65 70 75

Ser Leu Ser Glu Leu Arg Ala Gly Gln Phe Thr Gly Leu Met Gln
80 85 90

Leu Thr Trp Leu Tyr Leu Asp His Asn His Ile Cys Ser Val Gln
95 100 105

-continued

```
Gly Asp Ala Phe Gln Lys Leu Arg Arg Val Lys Glu Leu Thr Leu
                110                 115                 120

Ser Ser Asn Gln Ile Thr Gln Leu Pro Asn Thr Thr Phe Arg Pro
                125                 130                 135

Met Pro Asn Leu Arg Ser Val Asp Leu Ser Tyr Asn Lys Leu Gln
                140                 145                 150

Ala Leu Ala Pro Asp Leu Phe His Gly Leu Arg Lys Leu Thr Thr
                155                 160                 165

Leu His Met Arg Ala Asn Ala Ile Gln Phe Val Pro Val Arg Ile
                170                 175                 180

Phe Gln Asp Cys Arg Ser Leu Lys Phe Leu Asp Ile Gly Tyr Asn
                185                 190                 195

Gln Leu Lys Ser Leu Ala Arg Asn Ser Phe Ala Gly Leu Phe Lys
                200                 205                 210

Leu Thr Glu Leu His Leu Glu His Asn Asp Leu Val Lys Val Asn
                215                 220                 225

Phe Ala His Phe Pro Arg Leu Ile Ser Leu His Ser Leu Cys Leu
                230                 235                 240

Arg Arg Asn Lys Val Ala Ile Val Val Ser Ser Leu Asp Trp Val
                245                 250                 255

Trp Asn Leu Glu Lys Met Asp Leu Ser Gly Asn Glu Ile Glu Tyr
                260                 265                 270

Met Glu Pro His Val Phe Glu Thr Val Pro His Leu Gln Ser Leu
                275                 280                 285

Gln Leu Asp Ser Asn Arg Leu Thr Tyr Ile Glu Pro Arg Ile Leu
                290                 295                 300

Asn Ser Trp Lys Ser Leu Thr Ser Ile Thr Leu Ala Gly Asn Leu
                305                 310                 315

Trp Asp Cys Gly Arg Asn Val Cys Ala Leu Ala Ser Trp Leu Ser
                320                 325                 330

Asn Phe Gln Gly Arg Tyr Asp Gly Asn Leu Gln Cys Ala Ser Pro
                335                 340                 345

Glu Tyr Ala Gln Gly Glu Asp Val Leu Asp Ala Val Tyr Ala Phe
                350                 355                 360

His Leu Cys Glu Asp Gly Ala Glu Pro Thr Ser Gly His Leu Leu
                365                 370                 375

Ser Ala Val Thr Asn Arg Ser Asp Leu Gly Pro Pro Ala Ser Ser
                380                 385                 390

Ala Thr Thr Leu Ala Asp Gly Gly Glu Gly Gln His Asp Gly Thr
                395                 400                 405

Phe Glu Pro Ala Thr Val Ala Leu Pro Gly Gly Glu His Ala Glu
                410                 415                 420

Asn Ala Val Gln Ile His Lys Val Val Thr Gly Thr Met Ala Leu
                425                 430                 435

Ile Phe Ser Phe Leu Ile Val Val Leu Val Leu Tyr Val Ser Trp
                440                 445                 450

Lys Cys Phe Pro Ala Ser Leu Arg Gln Leu Arg Gln Cys Phe Val
                455                 460                 465

Thr Gln Arg Arg Lys Gln Lys Gln Lys Gln Thr Met His Gln Met
                470                 475                 480

Ala Ala Met Ser Ala Gln Glu Tyr Tyr Val Asp Tyr Lys Pro Asn
                485                 490                 495
```

-continued

```
His Ile Glu Gly Ala Leu Val Ile Ile Asn Glu Tyr Gly Ser Cys
                500                 505                 510

Thr Cys His Gln Gln Pro Ala Arg Glu Cys Glu Val
                515                 520
```

<210> SEQ ID NO 159
<211> LENGTH: 1049
<212> TYPE: DNA
<213> ORGANISM: Homo sapiens

<400> SEQUENCE: 159

```
cagagaggag gctttgggaa ttgtccagca gaaacagaga agtctgaggt                50

ggtgtcaaga caaaagatgc ttcagctttg gaaacttgtt ctcctgtgcg               100

gcgtgctcac tgggacctca gagtctcttc ttgacaatct tggcaatgac               150

ctaagcaatg tcgtggataa gctggaacct gttcttcacg agggacttga               200

gacagttgac aatactctta aaggcatcct tgagaaactg aaggtcgacc               250

taggagtgct tcagaaatcc agtgcttggc aactggccaa gcagaaggcc               300

caggaagctg agaaattgct gaacaatgtc atttctaagc tgcttccaac               350

taacacggac atttttgggt tgaaaatcag caactccctc atcctggatg               400

tcaaagctga accgatcgat gatggcaaag gccttaacct gagcttccct               450

gtcaccgcga atgtcactgt ggccgggccc atcattggcc agattatcaa               500

cctgaaagcc tccttggacc tcctgaccgc agtcacaatt gaaactgatc               550

cccagacaca ccagcctgtt gccgtcctgg gagaatgcgc cagtgaccca               600

accagcatct cactttcctt gctggacaaa cacagccaaa tcatcaacaa               650

gttcgtgaat agcgtgatca acacgctgaa aagcactgta tcctccctgc               700

tgcagaagga gatatgtcca ctgatccgca tcttcatcca ctccctggat               750

gtgaatgtca ttcagcaggt cgtcgataat cctcagcaca aaacccagct               800

gcaaaccctc atctgaagag gacgaatgag gaggaccact gtggtgcatg               850

ctgattggtt cccagtggct tgccccaccc ccttatagca tctccctcca               900

ggaagctgct gccaccacct aaccagcgtg aaagcctgag tcccaccaga               950

aggaccttcc cagatacccc ttctcctcac agtcagaaca gcagcctcta              1000

cacatgttgt cctgcccctg gcaataaagg cccatttctg  caccccttaa             1049
```

<210> SEQ ID NO 160
<211> LENGTH: 249
<212> TYPE: PRT
<213> ORGANISM: Homo sapiens

<400> SEQUENCE: 160

```
Met Leu Gln Leu Trp Lys Leu Val Leu Leu Cys Gly Val Leu Thr
  1               5                  10                  15

Gly Thr Ser Glu Ser Leu Leu Asp Asn Leu Gly Asn Asp Leu Ser
                 20                  25                  30

Asn Val Val Asp Lys Leu Glu Pro Val Leu His Glu Gly Leu Glu
                 35                  40                  45

Thr Val Asp Asn Thr Leu Lys Gly Ile Leu Glu Lys Leu Lys Val
                 50                  55                  60

Asp Leu Gly Val Leu Gln Lys Ser Ser Ala Trp Gln Leu Ala Lys
                 65                  70                  75
```

-continued

```
Gln Lys Ala Gln Glu Ala Glu Lys Leu Leu Asn Asn Val Ile Ser
                 80                  85                  90

Lys Leu Leu Pro Thr Asn Thr Asp Ile Phe Gly Leu Lys Ile Ser
                 95                 100                 105

Asn Ser Leu Ile Leu Asp Val Lys Ala Glu Pro Ile Asp Asp Gly
                110                 115                 120

Lys Gly Leu Asn Leu Ser Phe Pro Val Thr Ala Asn Val Thr Val
                125                 130                 135

Ala Gly Pro Ile Ile Gly Gln Ile Ile Asn Leu Lys Ala Ser Leu
                140                 145                 150

Asp Leu Leu Thr Ala Val Thr Ile Glu Thr Asp Pro Gln Thr His
                155                 160                 165

Gln Pro Val Ala Val Leu Gly Glu Cys Ala Ser Asp Pro Thr Ser
                170                 175                 180

Ile Ser Leu Ser Leu Leu Asp Lys His Ser Gln Ile Ile Asn Lys
                185                 190                 195

Phe Val Asn Ser Val Ile Asn Thr Leu Lys Ser Thr Val Ser Ser
                200                 205                 210

Leu Leu Gln Lys Glu Ile Cys Pro Leu Ile Arg Ile Phe Ile His
                215                 220                 225

Ser Leu Asp Val Asn Val Ile Gln Gln Val Val Asp Asn Pro Gln
                230                 235                 240

His Lys Thr Gln Leu Gln Thr Leu Ile
                245
```

<210> SEQ ID NO 161
<211> LENGTH: 1587
<212> TYPE: DNA
<213> ORGANISM: Homo sapiens

<400> SEQUENCE: 161

```
cagccacaga cgggtcatga gcgcggtatt actgctggcc ctcctggggt        50

tcatcctccc actgccagga gtgcaggcgc tgctctgcca gtttgggaca       100

gttcagcatg tgtggaaggt gtccgaccta ccccggcaat ggacccctaa       150

gaacaccagc tgcgacagcg gcttggggtg ccaggacacg ttgatgctca       200

ttgagagcgg accccaagtg agcctggtgc tctccaaggg ctgcacggag       250

gccaaggacc aggagccccg cgtcactgag caccggatgg gccccggcct       300

ctccctgatc tcctacacct tcgtgtgccg ccaggaggac ttctgcaaca       350

acctcgttaa ctccctcccg ctttgggccc cacagccccc agcagaccca       400

ggatccttga ggtgcccagt ctgcttgtct atggaaggct gtctggaggg       450

gacaacagaa gagatctgcc ccaaggggac cacacactgt tatgatggcc       500

tcctcaggct caggggagga ggcatcttct ccaatctgag agtccaggga       550

tgcatgcccc agccaggttg caacctgctc aatgggacac aggaaattgg       600

gcccgtgggt atgactgaga actgcaatag gaaagatttt ctgacctgtc       650

atcgggggac caccattatg acacacggaa acttggctca agaacccact       700

gattggacca catcgaatac cgagatgtgc gaggtggggc aggtgtgtca       750

ggagacgctg ctgctcatag atgtaggact cacatcaacc ctggtgggga       800

caaaaggctg cagcactgtt ggggctcaaa attcccagaa gaccaccatc       850

cactcagccc ctcctggggt gcttgtggcc tcctataccc acttctgctc       900
```

-continued

```
ctcggacctg tgcaatagtg ccagcagcag cagcgttctg ctgaactccc           950

tccctcctca agctgcccct gtcccaggag accggcagtg tcctacctgt          1000

gtgcagcccc ttggaacctg ttcaagtggc tccccccgaa tgacctgccc          1050

caggggcgcc actcattgtt atgatgggta cattcatctc tcaggaggtg          1100

ggctgtccac caaaatgagc attcagggct gcgtggccca accttccagc          1150

ttcttgttga accacaccag acaaatcggg atcttctctg cgcgtgagaa          1200

gcgtgatgtg cagcctcctg cctctcagca tgagggaggt ggggctgagg          1250

gcctggagtc tctcacttgg ggggtggggc tggcactggc cccagcgctg          1300

tggtggggag tggtttgccc ttcctgctaa ctctattacc cccacgattc          1350

ttcaccgctg ctgaccaccc acactcaacc tccctctgac ctcataacct          1400

aatggccttg gacaccagat tctttcccat tctgtccatg aatcatcttc          1450

cccacacaca atcattcata tctactcacc taacagcaac actggggaga          1500

gcctggagca tccggacttg ccctatggga gaggggacgc tggaggagtg          1550

gctgcatgta tctgataata cagaccctgt  cctttca                       1587


<210> SEQ ID NO 162
<211> LENGTH: 437
<212> TYPE: PRT
<213> ORGANISM: Homo sapiens

<400> SEQUENCE: 162

Met Ser Ala Val Leu Leu Leu Ala Leu Leu Gly Phe Ile Leu Pro
  1               5                  10                  15

Leu Pro Gly Val Gln Ala Leu Leu Cys Gln Phe Gly Thr Val Gln
                 20                  25                  30

His Val Trp Lys Val Ser Asp Leu Pro Arg Gln Trp Thr Pro Lys
                 35                  40                  45

Asn Thr Ser Cys Asp Ser Gly Leu Gly Cys Gln Asp Thr Leu Met
                 50                  55                  60

Leu Ile Glu Ser Gly Pro Gln Val Ser Leu Val Leu Ser Lys Gly
                 65                  70                  75

Cys Thr Glu Ala Lys Asp Gln Glu Pro Arg Val Thr Glu His Arg
                 80                  85                  90

Met Gly Pro Gly Leu Ser Leu Ile Ser Tyr Thr Phe Val Cys Arg
                 95                 100                 105

Gln Glu Asp Phe Cys Asn Asn Leu Val Asn Ser Leu Pro Leu Trp
                110                 115                 120

Ala Pro Gln Pro Pro Ala Asp Pro Gly Ser Leu Arg Cys Pro Val
                125                 130                 135

Cys Leu Ser Met Glu Gly Cys Leu Glu Gly Thr Thr Glu Glu Ile
                140                 145                 150

Cys Pro Lys Gly Thr Thr His Cys Tyr Asp Gly Leu Leu Arg Leu
                155                 160                 165

Arg Gly Gly Gly Ile Phe Ser Asn Leu Arg Val Gln Gly Cys Met
                170                 175                 180

Pro Gln Pro Gly Cys Asn Leu Leu Asn Gly Thr Gln Glu Ile Gly
                185                 190                 195

Pro Val Gly Met Thr Glu Asn Cys Asn Arg Lys Asp Phe Leu Thr
                200                 205                 210
```

-continued

```
Cys His Arg Gly Thr Thr Ile Met Thr His Gly Asn Leu Ala Gln
                215                 220                 225

Glu Pro Thr Asp Trp Thr Thr Ser Asn Thr Glu Met Cys Glu Val
                230                 235                 240

Gly Gln Val Cys Gln Glu Thr Leu Leu Leu Ile Asp Val Gly Leu
                245                 250                 255

Thr Ser Thr Leu Val Gly Thr Lys Gly Cys Ser Thr Val Gly Ala
                260                 265                 270

Gln Asn Ser Gln Lys Thr Thr Ile His Ser Ala Pro Pro Gly Val
                275                 280                 285

Leu Val Ala Ser Tyr Thr His Phe Cys Ser Ser Asp Leu Cys Asn
                290                 295                 300

Ser Ala Ser Ser Ser Ser Val Leu Leu Asn Ser Leu Pro Pro Gln
                305                 310                 315

Ala Ala Pro Val Pro Gly Asp Arg Gln Cys Pro Thr Cys Val Gln
                320                 325                 330

Pro Leu Gly Thr Cys Ser Ser Gly Ser Pro Arg Met Thr Cys Pro
                335                 340                 345

Arg Gly Ala Thr His Cys Tyr Asp Gly Tyr Ile His Leu Ser Gly
                350                 355                 360

Gly Gly Leu Ser Thr Lys Met Ser Ile Gln Gly Cys Val Ala Gln
                365                 370                 375

Pro Ser Ser Phe Leu Leu Asn His Thr Arg Gln Ile Gly Ile Phe
                380                 385                 390

Ser Ala Arg Glu Lys Arg Asp Val Gln Pro Pro Ala Ser Gln His
                395                 400                 405

Glu Gly Gly Gly Ala Glu Gly Leu Glu Ser Leu Thr Trp Gly Val
                410                 415                 420

Gly Leu Ala Leu Ala Pro Ala Leu Trp Trp Gly Val Val Cys Pro
                425                 430                 435

Ser Cys
```

<210> SEQ ID NO 163
<211> LENGTH: 2475
<212> TYPE: DNA
<213> ORGANISM: Homo sapiens

<400> SEQUENCE: 163

```
gaggatttgc cacagcagcg gatagagcag gagagcacca ccggagccct        50

tgagacatcc ttgagaagag ccacagcata agagactgcc ctgcttggtg       100

ttttgcagga tgatggtggc ccttcgagga gcttctgcat tgctggttct       150

gttccttgca gcttttctgc ccccgccgca gtgtacccag gacccagcca       200

tggtgcatta catctaccag cgctttcgag tcttggagca agggctggaa       250

aaatgtaccc aagcaacgag ggcatacatt caagaattcc aagagttctc       300

aaaaaatata tctgtcatgc tgggaagatg tcagacctac acaagtgagt       350

acaagagtgc agtgggtaac ttggcactga gagttgaacg tgcccaacgg       400

gagattgact acatacaata ccttcgagag gctgacgagt gcatcgtatc       450

agaggacaag acactggcag aaatgttgct ccaagaagct gaagaagaga       500

aaaagatccg gactctgctg aatgcaagct gtgacaacat gctgatgggc       550

ataaagtctt tgaaaatagt gaagaagatg atggacacac atggctcttg       600
```

-continued

```
gatgaaagat gctgtctata actctccaaa ggtgtactta ttaattggat      650
ccagaaacaa cactgtttgg gaatttgcaa acatacgggc attcatggag      700
gataacacca agccagctcc ccggaagcaa atcctaacac tttcctggca      750
gggaacaggc caagtgatct acaaaggttt tctatttttt cataaccaag      800
caacttctaa tgagataatc aaatataacc tgcagaagag gactgtggaa      850
gatcgaatgc tgctcccagg aggggtaggc cgagcattgg tttaccagca      900
ctccccctca acttacattg acctggctgt ggatgagcat gggctctggg      950
ccatccactc tgggccaggc acccatagcc atttggttct cacaaagatt     1000
gagccgggca cactgggagt ggagcattca tgggataccc catgcagaag     1050
ccaggatgct gaagcctcat tcctcttgtg tggggttctc tatgtggtct     1100
acagtactgg gggccagggc cctcatcgca tcacctgcat ctatgatcca     1150
ctgggcacta tcagtgagga ggacttgccc aacttgttct tccccaagag     1200
accaagaagt cactccatga tccattacaa ccccagagat aagcagctct     1250
atgcctggaa tgaaggaaac cagatcattt acaaactcca gacaaagaga     1300
aagctgcctc tgaagtaatg cattacagct gtgagaaaga gcactgtggc     1350
tttggcagct gttctacagg acagtgaggc tatagcccct tcacaatata     1400
gtatccctct aatcacacac aggaagagtg tgtagaagtg gaaatacgta     1450
tgcctccttt cccaaatgtc actgccttag gtatcttcca agagcttaga     1500
tgagagcata tcatcaggaa agtttcaaca atgtccatta ctcccccaaa     1550
cctcctggct ctcaaggatg accacattct gatacagcct acttcaagcc     1600
ttttgtttta ctgctcccca gcatttactg taactctgcc atcttccctc     1650
ccacaattag agttgtatgc cagcccctaa tattcaccac tggcttttct     1700
ctcccctggc ctttgctgaa gctcttccct ctttttcaaa tgtctattga     1750
tattctccca ttttcactgc ccaactaaaa tactattaat atttctttct     1800
tttcttttct tttttttgag acaaggtctc actatgttgc ccaggctggt     1850
ctcaaactcc agagctcaag agatcctcct gcctcagcct cctaagtacc     1900
tgggattaca ggcatgtgcc accacacctg gcttaaaata ctatttctta     1950
ttgaggttta acctctattt cccctagccc tgtccttcca ctaagcttgg     2000
tagatgtaat aataaagtga aaatattaac atttgaatat cgctttccag     2050
gtgtggagtg tttgcacatc attgaattct cgtttcacct ttgtgaaaca     2100
tgcacaagtc tttacagctg tcattctaga gtttaggtga gtaacacaat     2150
tacaaagtga aagatacagc tagaaaatac tacaaatccc atagtttttc     2200
cattgcccaa ggaagcatca aatacgtatg tttgttcacc tactcttata     2250
gtcaatgcgt tcatcgtttc agcctaaaaa taatagtctg tccctttagc     2300
cagttttcat gtctgcacaa gacctttcaa taggcctttc aaatgataat     2350
tcctccagaa aaccagtcta agggtgagga ccccaactct agcctcctct     2400
tgtcttgctg tcctctgttt ctctctttct gctttaaatt caataaaagt     2450
gacactgagc aaaaaaaaaa  aaaaa                               2475
```

<210> SEQ ID NO 164
<211> LENGTH: 402

<212> TYPE: PRT
<213> ORGANISM: Homo sapiens

<400> SEQUENCE: 164

Met Met Val Ala Leu Arg Gly Ala Ser Ala Leu Leu Val Leu Phe
1 5 10 15

Leu Ala Ala Phe Leu Pro Pro Pro Gln Cys Thr Gln Asp Pro Ala
20 25 30

Met Val His Tyr Ile Tyr Gln Arg Phe Arg Val Leu Glu Gln Gly
35 40 45

Leu Glu Lys Cys Thr Gln Ala Thr Arg Ala Tyr Ile Gln Glu Phe
50 55 60

Gln Glu Phe Ser Lys Asn Ile Ser Val Met Leu Gly Arg Cys Gln
65 70 75

Thr Tyr Thr Ser Glu Tyr Lys Ser Ala Val Gly Asn Leu Ala Leu
80 85 90

Arg Val Glu Arg Ala Gln Arg Glu Ile Asp Tyr Ile Gln Tyr Leu
95 100 105

Arg Glu Ala Asp Glu Cys Ile Val Ser Glu Asp Lys Thr Leu Ala
110 115 120

Glu Met Leu Leu Gln Glu Ala Glu Glu Glu Lys Lys Ile Arg Thr
125 130 135

Leu Leu Asn Ala Ser Cys Asp Asn Met Leu Met Gly Ile Lys Ser
140 145 150

Leu Lys Ile Val Lys Lys Met Met Asp Thr His Gly Ser Trp Met
155 160 165

Lys Asp Ala Val Tyr Asn Ser Pro Lys Val Tyr Leu Leu Ile Gly
170 175 180

Ser Arg Asn Asn Thr Val Trp Glu Phe Ala Asn Ile Arg Ala Phe
185 190 195

Met Glu Asp Asn Thr Lys Pro Ala Pro Arg Lys Gln Ile Leu Thr
200 205 210

Leu Ser Trp Gln Gly Thr Gly Gln Val Ile Tyr Lys Gly Phe Leu
215 220 225

Phe Phe His Asn Gln Ala Thr Ser Asn Glu Ile Ile Lys Tyr Asn
230 235 240

Leu Gln Lys Arg Thr Val Glu Asp Arg Met Leu Leu Pro Gly Gly
245 250 255

Val Gly Arg Ala Leu Val Tyr Gln His Ser Pro Ser Thr Tyr Ile
260 265 270

Asp Leu Ala Val Asp Glu His Gly Leu Trp Ala Ile His Ser Gly
275 280 285

Pro Gly Thr His Ser His Leu Val Leu Thr Lys Ile Glu Pro Gly
290 295 300

Thr Leu Gly Val Glu His Ser Trp Asp Thr Pro Cys Arg Ser Gln
305 310 315

Asp Ala Glu Ala Ser Phe Leu Leu Cys Gly Val Leu Tyr Val Val
320 325 330

Tyr Ser Thr Gly Gly Gln Gly Pro His Arg Ile Thr Cys Ile Tyr
335 340 345

Asp Pro Leu Gly Thr Ile Ser Glu Glu Asp Leu Pro Asn Leu Phe
350 355 360

Phe Pro Lys Arg Pro Arg Ser His Ser Met Ile His Tyr Asn Pro
365 370 375

-continued

```
Arg Asp Lys Gln Leu Tyr Ala Trp Asn Glu Gly Asn Gln Ile Ile
                380                 385                 390

Tyr Lys Leu Gln Thr Lys Arg Lys Leu Pro Leu Lys
                395                 400
```

<210> SEQ ID NO 165
<211> LENGTH: 1415
<212> TYPE: DNA
<213> ORGANISM: Homo sapiens

<400> SEQUENCE: 165

```
tggcctcccc agcttgccag gcacaaggct gagcgggagg aagcgagagg      50

catctaagca ggcagtgttt tgccttcacc ccaagtgacc atgagaggtg     100

ccacgcgagt ctcaatcatg ctcctcctag taactgtgtc tgactgtgct     150

gtgatcacag gggcctgtga gcgggatgtc cagtgtgggg caggcacctg     200

ctgtgccatc agcctgtggc ttcgagggct gcggatgtgc accccgctgg     250

ggcgggaagg cgaggagtgc caccccggca gccacaaggt ccccttcttc     300

aggaaacgca agcaccacac ctgtccttgc ttgcccaacc tgctgtgctc     350

caggttcccg gacggcaggt accgctgctc catggacttg aagaacatca     400

atttttaggc gcttgcctgg tctcaggata cccaccatcc ttttcctgag     450

cacagcctgg atttttattt ctgccatgaa acccagctcc catgactctc     500

ccagtcccta cactgactac cctgatctct cttgtctagt acgcacatat     550

gcacacaggc agacatacct cccatcatga catggtcccc aggctggcct     600

gaggatgtca cagcttgagg ctgtggtgtg aaaggtggcc agcctggttc     650

tcttccctgc tcaggctgcc agagaggtgg taaatggcag aaaggacatt     700

ccccctcccc tccccaggtg acctgctctc tttcctgggc cctgcccctc     750

tccccacatg tatccctcgg tctgaattag acattcctgg gcacaggctc     800

ttgggtgcat tgctcagagt cccaggtcct ggcctgaccc tcaggccctt     850

cacgtgaggt ctgtgaggac caatttgtgg gtagttcatc ttccctcgat     900

tggttaactc cttagtttca gaccacagac tcaagattgg ctcttcccag     950

agggcagcag acagtcaccc caaggcaggt gtagggagcc cagggaggcc    1000

aatcagcccc ctgaagactc tggtcccagt cagcctgtgg cttgtggcct    1050

gtgacctgtg accttctgcc agaattgtca tgcctctgag gccccctctt    1100

accacacttt accagttaac cactgaagcc cccaattccc acagcttttc    1150

cattaaaatg caaatggtgg tggttcaatc taatctgata ttgacatatt    1200

agaaggcaat tagggtgttt ccttaaacaa ctcctttcca aggatcagcc    1250

ctgagagcag gttggtgact ttgaggaggg cagtcctctg tccagattgg    1300

ggtgggagca agggacaggg agcagggcag gggctgaaag gggcactgat    1350

tcagaccagg gaggcaacta cacaccaaca tgctggcttt agaataaaag    1400

caccaactga  aaaaa                                         1415
```

<210> SEQ ID NO 166
<211> LENGTH: 105
<212> TYPE: PRT
<213> ORGANISM: Homo sapiens -continued

<400> SEQUENCE: 166

```
Met Arg Gly Ala Thr Arg Val Ser Ile Met Leu Leu Leu Val Thr
  1               5                  10                  15

Val Ser Asp Cys Ala Val Ile Thr Gly Ala Cys Glu Arg Asp Val
                 20                  25                  30

Gln Cys Gly Ala Gly Thr Cys Cys Ala Ile Ser Leu Trp Leu Arg
                 35                  40                  45

Gly Leu Arg Met Cys Thr Pro Leu Gly Arg Glu Gly Glu Glu Cys
                 50                  55                  60

His Pro Gly Ser His Lys Val Pro Phe Phe Arg Lys Arg Lys His
                 65                  70                  75

His Thr Cys Pro Cys Leu Pro Asn Leu Leu Cys Ser Arg Phe Pro
                 80                  85                  90

Asp Gly Arg Tyr Arg Cys Ser Met Asp Leu Lys Asn Ile Asn Phe
                 95                 100                 105
```

<210> SEQ ID NO 167
<211> LENGTH: 1371
<212> TYPE: DNA
<213> ORGANISM: Homo sapiens

<400> SEQUENCE: 167

```
aactcaaact cctctctctg ggaaaacgcg gtgcttgctc ctcccggagt     50
ggccttggca gggtgttgga gccctcggtc tgccccgtcc ggtctctggg    100
gccaaggctg ggtttccctc atgtatggca agagctctac tcgtgcggtg    150
cttcttctcc ttggcataca gctcacagct ctttggccta tagcagctgt    200
ggaaatttat acctcccggg tgctggaggc tgttaatggg acagatgctc    250
ggttaaaatg cactttctcc agctttgccc ctgtgggtga tgctctaaca    300
gtgacctgga attttcgtcc tctagacggg ggacctgagc agtttgtatt    350
ctactaccac atagatccct tccaacccat gagtgggcgg tttaaggacc    400
gggtgtcttg ggatgggaat cctgagcggt acgatgcctc catccttctc    450
tggaaactgc agttcgacga caatgggaca tacacctgcc aggtgaagaa    500
cccacctgat gttgatgggg tgatagggga gatccggctc agcgtcgtgc    550
acactgtacg cttctctgag atccacttcc tggctctggc cattggctct    600
gcctgtgcac tgatgatcat aatagtaatt gtagtggtcc tcttccagca    650
ttaccggaaa aagcgatggg ccgaaagagc tcataaagtg gtggagataa    700
aatcaaaaga agaggaaagg ctcaaccaag agaaaaaggt ctctgtttat    750
ttagaagaca cagactaaca attttagatg gaagctgaga tgatttccaa    800
gaacaagaac cctagtattt cttgaagtta atggaaactt ttctttggct    850
tttccagttg tgacccgttt tccaaccagt tctgcagcat attagattct    900
agacaagcaa cacccctctg gagccagcac agtgctcctc catatcacca    950
gtcatacaca gcctcattat taaggtctta tttaatttca gagtgtaaat   1000
tttttcaagt gctcattagg ttttataaac aagaagctac atttttgccc   1050
ttaagacact acttacagtg ttatgacttg tatacacata tattggtatc   1100
aaaggggata aaagccaatt tgtctgttac atttcctttc acgtatttct   1150
tttagcagca cttctgctac taaagttaat gtgtttactc tctttccttc   1200
```

-continued

```
ccacattctc aattaaaagg tgagctaagc ctcctcggtg tttctgatta       1250

acagtaaatc ctaaattcaa actgttaaat gacattttta tttttatgtc       1300

tctccttaac tatgagacac atcttgtttt actgaatttc tttcaatatt       1350

ccaggtgata gatttttgtc  g                                     1371


<210> SEQ ID NO 168
<211> LENGTH: 215
<212> TYPE: PRT
<213> ORGANISM: Homo sapiens

<400> SEQUENCE: 168

Met Tyr Gly Lys Ser Ser Thr Arg Ala Val Leu Leu Leu Leu Gly
  1               5                  10                  15

Ile Gln Leu Thr Ala Leu Trp Pro Ile Ala Ala Val Glu Ile Tyr
                 20                  25                  30

Thr Ser Arg Val Leu Glu Ala Val Asn Gly Thr Asp Ala Arg Leu
                 35                  40                  45

Lys Cys Thr Phe Ser Ser Phe Ala Pro Val Gly Asp Ala Leu Thr
                 50                  55                  60

Val Thr Trp Asn Phe Arg Pro Leu Asp Gly Gly Pro Glu Gln Phe
                 65                  70                  75

Val Phe Tyr Tyr His Ile Asp Pro Phe Gln Pro Met Ser Gly Arg
                 80                  85                  90

Phe Lys Asp Arg Val Ser Trp Asp Gly Asn Pro Glu Arg Tyr Asp
                 95                 100                 105

Ala Ser Ile Leu Leu Trp Lys Leu Gln Phe Asp Asp Asn Gly Thr
                110                 115                 120

Tyr Thr Cys Gln Val Lys Asn Pro Pro Asp Val Asp Gly Val Ile
                125                 130                 135

Gly Glu Ile Arg Leu Ser Val Val His Thr Val Arg Phe Ser Glu
                140                 145                 150

Ile His Phe Leu Ala Leu Ala Ile Gly Ser Ala Cys Ala Leu Met
                155                 160                 165

Ile Ile Ile Val Ile Val Val Val Leu Phe Gln His Tyr Arg Lys
                170                 175                 180

Lys Arg Trp Ala Glu Arg Ala His Lys Val Val Glu Ile Lys Ser
                185                 190                 195

Lys Glu Glu Glu Arg Leu Asn Gln Glu Lys Lys Val Ser Val Tyr
                200                 205                 210

Leu Glu Asp Thr Asp
                215


<210> SEQ ID NO 169
<211> LENGTH: 2213
<212> TYPE: DNA
<213> ORGANISM: Homo sapiens

<400> SEQUENCE: 169

gagcgaacat ggcagcgcgt tggcggtttt ggtgtgtctc tgtgaccatg         50

gtggtggcgc tgctcatcgt ttgcgacgtt ccctcagcct ctgcccaaag        100

aaagaaggag atggtgttat ctgaaaaggt tagtcagctg atggaatgga        150

ctaacaaaag acctgtaata agaatgaatg gagacaagtt ccgtcgcctt        200

gtgaaagccc caccgagaaa ttactccgtt atcgtcatgt tcactgctct        250
```

-continued

```
ccaactgcat agacagtgtg tcgtttgcaa gcaagctgat gaagaattcc        300

agatcctggc aaactcctgg cgatactcca gtgcattcac caacaggata        350

tttttgcca tggtggattt tgatgaaggc tctgatgtat ttcagatgct         400

aaacatgaat tcagctccaa ctttcatcaa ctttcctgca aaagggaaac        450

ccaaacgggg tgatacatat gagttacagg tgcggggttt ttcagctgag        500

cagattgccc ggtggatcgc cgacagaact gatgtcaata ttagagtgat        550

tagaccccca aattatgctg gtccccttat gttgggattg cttttggctg        600

ttattggtgg acttgtgtat cttcgaagaa gtaatatgga atttctcttt        650

aataaaactg gatgggcttt tgcagctttg tgttttgtgc ttgctatgac        700

atctggtcaa atgtggaacc atataagagg accaccatat gcccataaga        750

atccccacac gggacatgtg aattatatcc atggaagcag tcaagcccag        800

tttgtagctg aaacacacat tgttcttctg tttaatggtg gagttacctt        850

aggaatggtg cttttatgtg aagctgctac ctctgacatg gatattggaa        900

agcgaaagat aatgtgtgtg gctggtattg gacttgttgt attattcttc        950

agttggatgc tctctatttt tagatctaaa tatcatggct acccatacag       1000

ctttctgatg agttaaaaag gtcccagaga tatatagaca ctggagtact       1050

ggaaattgaa aaacgaaaat cgtgtgtgtt tgaaaagaag aatgcaactt       1100

gtatattttg tattacctct ttttttcaag tgatttaaat agttaatcat       1150

ttaaccaaag aagatgtgta gtgccttaac aagcaatcct ctgtcaaaat       1200

ctgaggtatt tgaaaataat tatcctctta accttctctt cccagtgaac       1250

tttatggaac atttaattta gtacaattaa gtatattata aaaattgtaa       1300

aactactact ttgttttagt tagaacaaag ctcaaaacta ctttagttaa       1350

cttggtcatc tgattttata ttgccttatc caaagatggg gaaagtaagt       1400

cctgaccagg tgttcccaca tatgcctgtt acagataact acattaggaa       1450

ttcattctta gcttcttcat ctttgtgtgg atgtgtatac tttacgcatc       1500

tttccttttg agtagagaaa ttatgtgtgt catgtggtct tctgaaaatg       1550

gaacaccatt cttcagagca cacgtctagc cctcagcaag acagttgttt       1600

ctcctcctcc ttgcatattt cctactgcgc tccagcctga gtgatagagt       1650

gagactctgt ctcaaaaaaa agtatctcta aatacaggat tataatttct       1700

gcttgagtat ggtgttaact accttgtatt tagaaagatt tcagattcat       1750

tccatctcct tagttttctt ttaaggtgac ccatctgtga taaaaatata       1800

gcttagtgct aaaatcagtg taacttatac atggcctaaa atgtttctac       1850

aaattagagt ttgtcactta ttccatttgt acctaagaga aaaataggct       1900

cagttagaaa aggactccct ggccaggcgc agtgacttac gcctgtaatc       1950

tcagcacttt gggaggccaa ggcaggcaga tcacgaggtc aggagttcga       2000

gaccatcctg gccaacatgg tgaaaccccg tctctactaa aaatataaaa       2050

attagctggg tgtggtggca ggagcctgta atcccagcta cacaggaggc       2100

tgaggcacga gaatcacttg aactcaggag atggaggttt cagtgagccg       2150

agatcacgcc actgcactcc agcctggcaa cagagcgaga ctccatctca       2200

aaaaaaaaaa  aaa                                              2213
```

<210> SEQ ID NO 170
<211> LENGTH: 335
<212> TYPE: PRT
<213> ORGANISM: Homo sapiens

<400> SEQUENCE: 170

```
Met Ala Ala Arg Trp Arg Phe Trp Cys Val Ser Val Thr Met Val
  1               5                  10                  15

Val Ala Leu Leu Ile Val Cys Asp Val Pro Ser Ala Ser Ala Gln
                 20                  25                  30

Arg Lys Lys Glu Met Val Leu Ser Glu Lys Val Ser Gln Leu Met
                 35                  40                  45

Glu Trp Thr Asn Lys Arg Pro Val Ile Arg Met Asn Gly Asp Lys
                 50                  55                  60

Phe Arg Arg Leu Val Lys Ala Pro Pro Arg Asn Tyr Ser Val Ile
                 65                  70                  75

Val Met Phe Thr Ala Leu Gln Leu His Arg Gln Cys Val Val Cys
                 80                  85                  90

Lys Gln Ala Asp Glu Glu Phe Gln Ile Leu Ala Asn Ser Trp Arg
                 95                 100                 105

Tyr Ser Ser Ala Phe Thr Asn Arg Ile Phe Phe Ala Met Val Asp
                110                 115                 120

Phe Asp Glu Gly Ser Asp Val Phe Gln Met Leu Asn Met Asn Ser
                125                 130                 135

Ala Pro Thr Phe Ile Asn Phe Pro Ala Lys Gly Lys Pro Lys Arg
                140                 145                 150

Gly Asp Thr Tyr Glu Leu Gln Val Arg Gly Phe Ser Ala Glu Gln
                155                 160                 165

Ile Ala Arg Trp Ile Ala Asp Arg Thr Asp Val Asn Ile Arg Val
                170                 175                 180

Ile Arg Pro Pro Asn Tyr Ala Gly Pro Leu Met Leu Gly Leu Leu
                185                 190                 195

Leu Ala Val Ile Gly Gly Leu Val Tyr Leu Arg Arg Ser Asn Met
                200                 205                 210

Glu Phe Leu Phe Asn Lys Thr Gly Trp Ala Phe Ala Ala Leu Cys
                215                 220                 225

Phe Val Leu Ala Met Thr Ser Gly Gln Met Trp Asn His Ile Arg
                230                 235                 240

Gly Pro Pro Tyr Ala His Lys Asn Pro His Thr Gly His Val Asn
                245                 250                 255

Tyr Ile His Gly Ser Ser Gln Ala Gln Phe Val Ala Glu Thr His
                260                 265                 270

Ile Val Leu Leu Phe Asn Gly Gly Val Thr Leu Gly Met Val Leu
                275                 280                 285

Leu Cys Glu Ala Ala Thr Ser Asp Met Asp Ile Gly Lys Arg Lys
                290                 295                 300

Ile Met Cys Val Ala Gly Ile Gly Leu Val Val Leu Phe Phe Ser
                305                 310                 315

Trp Met Leu Ser Ile Phe Arg Ser Lys Tyr His Gly Tyr Pro Tyr
                320                 325                 330

Ser Phe Leu Met Ser
                335
```

-continued

<210> SEQ ID NO 171
<211> LENGTH: 771
<212> TYPE: DNA
<213> ORGANISM: Homo sapiens

<400> SEQUENCE: 171
ctccactgca accacccaga gccatggctc cccgaggctg catcgtagct 50
gtctttgcca ttttctgcat ctccaggctc ctctgctcac acggagcccc 100
agtggccccc atgactcctt acctgatgct gtgccagcca cacaagagat 150
gtggggacaa gttctacgac cccctgcagc actgttgcta tgatgatgcc 200
gtcgtgccct tggccaggac ccagacgtgt ggaaactgca ccttcagagt 250
ctgctttgag cagtgctgcc cctggacctt catggtgaag ctgataaacc 300
agaactgcga ctcagcccgg acctcggatg acaggctttg tcgcagtgtc 350
agctaatgga acatcagggg aacgatgact cctggattct ccttcctggg 400
tgggcctgga gaaagaggct ggtgttacct gagatctggg atgctgagtg 450
gctgtttggg ggccagagaa acacacactc aactgcccac ttcattctgt 500
gacctgtctg aggcccaccc tgcagctgcc ctgaggaggc ccacaggtcc 550
ccttctagaa ttctggacag catgagatgc gtgtgctgat gggggcccag 600
ggactctgaa ccctcctgat gacccctatg gccaacatca acccggcacc 650
accccaaggc tggctgggga acccttcacc cttctgtgag attttccatc 700
atctcaagtt ctcttctatc caggagcaaa gcacaggatc ataataaatt 750
tatgtacttt ataaatgaaa a 771

<210> SEQ ID NO 172
<211> LENGTH: 110
<212> TYPE: PRT
<213> ORGANISM: Homo sapiens

<400> SEQUENCE: 172

Met Ala Pro Arg Gly Cys Ile Val Ala Val Phe Ala Ile Phe Cys
1 5 10 15

Ile Ser Arg Leu Leu Cys Ser His Gly Ala Pro Val Ala Pro Met
20 25 30

Thr Pro Tyr Leu Met Leu Cys Gln Pro His Lys Arg Cys Gly Asp
35 40 45

Lys Phe Tyr Asp Pro Leu Gln His Cys Cys Tyr Asp Asp Ala Val
50 55 60

Val Pro Leu Ala Arg Thr Gln Thr Cys Gly Asn Cys Thr Phe Arg
65 70 75

Val Cys Phe Glu Gln Cys Cys Pro Trp Thr Phe Met Val Lys Leu
80 85 90

Ile Asn Gln Asn Cys Asp Ser Ala Arg Thr Ser Asp Asp Arg Leu
95 100 105

Cys Arg Ser Val Ser
110

<210> SEQ ID NO 173
<211> LENGTH: 2044
<212> TYPE: DNA
<213> ORGANISM: Homo sapiens

<400> SEQUENCE: 173

-continued

```
gggggcgggt gcctggagca cggcgctggg gccgcccgca gcgctcactc     50
gctcgcactc agtcgcggga ggcttccccg cgccggccgc gtcccgcccg    100
ctccccggca ccagaagttc ctctgcgcgt ccgacggcga catgggcgtc    150
cccacggccc tggaggccgg cagctggcgc tggggatccc tgctcttcgc    200
tctcttcctg gctgcgtccc taggtccggt ggcagccttc aaggtcgcca    250
cgccgtattc cctgtatgtc tgtcccgagg ggcagaacgt caccctcacc    300
tgcaggctct tgggccctgt ggacaaaggg cacgatgtga ccttctacaa    350
gacgtggtac cgcagctcga ggggcgaggt gcagacctgc tcagagcgcc    400
ggcccatccg caacctcacg ttccaggacc ttcacctgca ccatggaggc    450
caccaggctg ccaacaccag ccacgacctg gctcagcgcc acgggctgga    500
gtcggcctcc gaccaccatg gcaacttctc catcaccatg cgcaacctga    550
ccctgctgga tagcggcctc tactgctgcc tggtggtgga gatcaggcac    600
caccactcgg agcacagggt ccatggtgcc atggagctgc aggtgcagac    650
aggcaaagat gcaccatcca actgtgtggt gtacccatcc tcctcccagg    700
atagtgaaaa catcacggct gcagccctgg ctacgggtgc ctgcatcgta    750
ggaatcctct gcctccccct catcctgctc ctggtctaca agcaaaggca    800
ggcagcctcc aaccgccgtg cccaggagct ggtgcggatg gacagcaaca    850
ttcaagggat tgaaaacccc ggctttgaag cctcaccacc tgcccagggg    900
atacccgagg ccaaagtcag gcaccccctg tcctatgtgg cccagcggca    950
gccttctgag tctgggcggc atctgctttc ggagcccagc acccccctgt   1000
ctcctccagg ccccggagac gtcttcttcc catccctgga ccctgtccct   1050
gactctccaa actttgaggt catctagccc agctggggga cagtgggctg   1100
ttgtggctgg gtctggggca ggtgcatttg agccagggct ggctctgtga   1150
gtggcctcct tggcctcggc cctggttccc tccctcctgc tctgggctca   1200
gatactgtga catcccagaa gcccagcccc tcaacccctc tggatgctac   1250
atggggatgc tggacggctc agcccctgtt ccaaggattt tggggtgctg   1300
agattctccc ctagagacct gaaattcacc agctacagat gccaaatgac   1350
ttacatctta agaagtctca gaacgtccag cccttcagca gctctcgttc   1400
tgagacatga gccttgggat gtggcagcat cagtgggaca agatggacac   1450
tgggccaccc tcccaggcac cagacacagg gcacggtgga gagacttctc   1500
ccccgtggcc gccttggctc ccccgttttg cccgaggctg ctcttctgtc   1550
agacttcctc tttgtaccac agtggctctg gggccaggcc tgcctgccca   1600
ctggccatcg ccaccttccc cagctgcctc ctaccagcag tttctctgaa   1650
gatctgtcaa caggttaagt caatctgggg cttccactgc ctgcattcca   1700
gtccccagag cttggtggtc ccgaaacggg aagtacatat tggggcatgg   1750
tggcctccgt gagcaaatgg tgtcttgggc aatctgaggc caggacagat   1800
gttgccccac ccactggaga tggtgctgag ggaggtgggt ggggccttct   1850
gggaaggtga gtggagaggg gcacctgccc cccgccctcc ccatccccta   1900
ctcccactgc tcagcgcggg ccattgcaag ggtgccacac aatgtcttgt   1950
ccaccctggg acacttctga gtatgaagcg ggatgctatt aaaaactaca   2000
```

tggggaaaaa aaaaaaaaaa aaaaaaaaaa aaaaaaaaaa aaga 2044

<210> SEQ ID NO 174
<211> LENGTH: 311
<212> TYPE: PRT
<213> ORGANISM: Homo sapiens

<400> SEQUENCE: 174

Met Gly Val Pro Thr Ala Leu Glu Ala Gly Ser Trp Arg Trp Gly
1 5 10 15

Ser Leu Leu Phe Ala Leu Phe Leu Ala Ala Ser Leu Gly Pro Val
20 25 30

Ala Ala Phe Lys Val Ala Thr Pro Tyr Ser Leu Tyr Val Cys Pro
35 40 45

Glu Gly Gln Asn Val Thr Leu Thr Cys Arg Leu Leu Gly Pro Val
50 55 60

Asp Lys Gly His Asp Val Thr Phe Tyr Lys Thr Trp Tyr Arg Ser
65 70 75

Ser Arg Gly Glu Val Gln Thr Cys Ser Glu Arg Arg Pro Ile Arg
80 85 90

Asn Leu Thr Phe Gln Asp Leu His Leu His His Gly Gly His Gln
95 100 105

Ala Ala Asn Thr Ser His Asp Leu Ala Gln Arg His Gly Leu Glu
110 115 120

Ser Ala Ser Asp His His Gly Asn Phe Ser Ile Thr Met Arg Asn
125 130 135

Leu Thr Leu Leu Asp Ser Gly Leu Tyr Cys Cys Leu Val Val Glu
140 145 150

Ile Arg His His His Ser Glu His Arg Val His Gly Ala Met Glu
155 160 165

Leu Gln Val Gln Thr Gly Lys Asp Ala Pro Ser Asn Cys Val Val
170 175 180

Tyr Pro Ser Ser Ser Gln Asp Ser Glu Asn Ile Thr Ala Ala Ala
185 190 195

Leu Ala Thr Gly Ala Cys Ile Val Gly Ile Leu Cys Leu Pro Leu
200 205 210

Ile Leu Leu Leu Val Tyr Lys Gln Arg Gln Ala Ala Ser Asn Arg
215 220 225

Arg Ala Gln Glu Leu Val Arg Met Asp Ser Asn Ile Gln Gly Ile
230 235 240

Glu Asn Pro Gly Phe Glu Ala Ser Pro Pro Ala Gln Gly Ile Pro
245 250 255

Glu Ala Lys Val Arg His Pro Leu Ser Tyr Val Ala Gln Arg Gln
260 265 270

Pro Ser Glu Ser Gly Arg His Leu Leu Ser Glu Pro Ser Thr Pro
275 280 285

Leu Ser Pro Pro Gly Pro Gly Asp Val Phe Phe Pro Ser Leu Asp
290 295 300

Pro Val Pro Asp Ser Pro Asn Phe Glu Val Ile
305 310

<210> SEQ ID NO 175
<211> LENGTH: 693
<212> TYPE: DNA
<213> ORGANISM: Homo sapiens -continued

<400> SEQUENCE: 175
ctagcctgcg ccaaggggta gtgagaccgc gcggcaacag cttgcggctg 50
cggggagctc ccgtgggcgc tccgctggct gtgcaggcgg ccatggattc 100
cttgcggaaa atgctgatct cagtcgcaat gctgggcgca ggggctggcg 150
tgggctacgc gctcctcgtt atcgtgaccc cgggagagcg gcggaagcag 200
gaaatgctaa aggagatgcc actgcaggac ccaaggagca gggaggaggc 250
ggccaggacc cagcagctat tgctggccac tctgcaggag gcagcgacca 300
cgcaggagaa cgtggcctgg aggaagaact ggatggttgg cggcgaaggc 350
ggcgccagcg ggaggtcacc gtgagaccgg acttgcctcc gtgggcgccg 400
gaccttggct tgggcgcagg aatccgaggc agcctttctc cttcgtgggc 450
ccagcggaga gtccggaccg agataccatg ccaggactct ccggggtcct 500
gtgagctgcc gtcgggtgag cacgtttccc ccaaaccctg gactgactgc 550
tttaaggtcc gcaaggcggg ccagggccga gacgcgagtc ggatgtggtg 600
aactgaaaga accaataaaa tcatgttcct ccaaaaaaaa aaaaaaaaaa 650
aaaaaaaaaa aaaaaaaaaa aaaaaaaaaa aaaaaaaaaa aaa 693

<210> SEQ ID NO 176
<211> LENGTH: 93
<212> TYPE: PRT
<213> ORGANISM: Homo sapiens

<400> SEQUENCE: 176

Met Asp Ser Leu Arg Lys Met Leu Ile Ser Val Ala Met Leu Gly
1 5 10 15

Ala Gly Ala Gly Val Gly Tyr Ala Leu Leu Val Ile Val Thr Pro
20 25 30

Gly Glu Arg Arg Lys Gln Glu Met Leu Lys Glu Met Pro Leu Gln
35 40 45

Asp Pro Arg Ser Arg Glu Glu Ala Ala Arg Thr Gln Gln Leu Leu
50 55 60

Leu Ala Thr Leu Gln Glu Ala Ala Thr Thr Gln Glu Asn Val Ala
65 70 75

Trp Arg Lys Asn Trp Met Val Gly Gly Glu Gly Gly Ala Ser Gly
80 85 90

Arg Ser Pro

<210> SEQ ID NO 177
<211> LENGTH: 1700
<212> TYPE: DNA
<213> ORGANISM: Homo sapiens

<400> SEQUENCE: 177
gccaggcagg tgggcctcag gaggtgcctc caggcggcca gtgggcctga 50
ggccccagca agggctaggg tccatctcca gtcccaggac acagcagcgg 100
ccaccatggc cacgcctggg ctccagcagc atcagagcag cccctgtggt 150
tggcagcaaa gttcagcttg gctgggcccg ctgtgagggg cttcgcgcta 200
cgccctgcgg tgtcccgagg gctgaggtct cctcatcttc tccctagcag 250
tggatgagca acccaacggg ggcccgggga ggggaactgg ccccgaggga 300

-continued

```
gaggaacccc aaagccacat ctgtagccag gatgagcagt gtgaatccag        350

gcagccccca ggaccgggga ggcacaggtg gcccccacca cccggaggag        400

cagctcctgc ccctgtccgg gggatgactg attctcctcc gccaggccac        450

ccagaggaga aggccacccc gcctggaggc acaggccatg aggggctctc        500

aggaggtgct gctgatgtgg cttctggtgt tggcagtggg cggcacagag        550

cacgcctacc ggcccggccg tagggtgtgt gctgtccggg ctcacgggga        600

ccctgtctcc gagtcgttcg tgcagcgtgt gtaccagccc ttcctcacca        650

cctgcgacgg gcaccgggcc tgcagcacct accgaaccat ctataggacc        700

gcctaccgcc gcagccctgg gctggcccct gccaggcctc gctacgcgtg        750

ctgccccggc tggaagagga ccagcgggct tcctggggcc tgtggagcag        800

caatatgcca gccgccatgc cggaacggag ggagctgtgt ccagcctggc        850

cgctgccgct gccctgcagg atggcggggt gacacttgcc agtcagatgt        900

ggatgaatgc agtgctagga ggggcggctg tccccagcgc tgcatcaaca        950

ccgccggcag ttactggtgc cagtgttggg aggggcacag cctgtctgca       1000

gacggtacac tctgtgtgcc caagggaggg ccccccaggg tggcccccaa       1050

cccgacagga gtggacagtg caatgaagga agaagtgcag aggctgcagt       1100

ccagggtgga cctgctggag gagaagctgc agctggtgct ggccccactg       1150

cacagcctgg cctcgcaggc actggagcat gggctcccgg accccggcag       1200

cctcctggtg cactccttcc agcagctcgg ccgcatcgac tccctgagcg       1250

agcagatttc cttcctggag gagcagctgg ggtcctgctc ctgcaagaaa       1300

gactcgtgac tgcccagcgc tccaggctgg actgagcccc tcacgccgcc       1350

ctgcagcccc catgcccctg cccaacatgc tgggggtcca gaagccacct       1400

cggggtgact gagcggaagg ccaggcaggg ccttcctcct cttcctcctc       1450

cccttcctcg ggaggctccc cagaccctgg catgggatgg gctgggatct       1500

tctctgtgaa tccacccctg gctaccccca ccctggctac cccaacggca       1550

tcccaaggcc aggtggaccc tcagctgagg gaaggtacga gctccctgct       1600

ggagcctggg acccatggca caggccaggc agcccggagg ctgggtgggg       1650

cctcagtggg ggctgctgcc tgacccccag cacaataaaa atgaaacgtg       1700
```

<210> SEQ ID NO 178
<211> LENGTH: 273
<212> TYPE: PRT
<213> ORGANISM: Homo sapiens

<400> SEQUENCE: 178

```
Met Arg Gly Ser Gln Glu Val Leu Leu Met Trp Leu Leu Val Leu
  1               5                  10                  15

Ala Val Gly Gly Thr Glu His Ala Tyr Arg Pro Gly Arg Arg Val
                 20                  25                  30

Cys Ala Val Arg Ala His Gly Asp Pro Val Ser Glu Ser Phe Val
                 35                  40                  45

Gln Arg Val Tyr Gln Pro Phe Leu Thr Thr Cys Asp Gly His Arg
                 50                  55                  60

Ala Cys Ser Thr Tyr Arg Thr Ile Tyr Arg Thr Ala Tyr Arg Arg
                 65                  70                  75
```

-continued

```
Ser Pro Gly Leu Ala Pro Ala Arg Pro Arg Tyr Ala Cys Cys Pro
                80                  85                  90

Gly Trp Lys Arg Thr Ser Gly Leu Pro Gly Ala Cys Gly Ala Ala
                95                  100                 105

Ile Cys Gln Pro Pro Cys Arg Asn Gly Gly Ser Cys Val Gln Pro
                110                 115                 120

Gly Arg Cys Arg Cys Pro Ala Gly Trp Arg Gly Asp Thr Cys Gln
                125                 130                 135

Ser Asp Val Asp Glu Cys Ser Ala Arg Arg Gly Gly Cys Pro Gln
                140                 145                 150

Arg Cys Ile Asn Thr Ala Gly Ser Tyr Trp Cys Gln Cys Trp Glu
                155                 160                 165

Gly His Ser Leu Ser Ala Asp Gly Thr Leu Cys Val Pro Lys Gly
                170                 175                 180

Gly Pro Pro Arg Val Ala Pro Asn Pro Thr Gly Val Asp Ser Ala
                185                 190                 195

Met Lys Glu Glu Val Gln Arg Leu Gln Ser Arg Val Asp Leu Leu
                200                 205                 210

Glu Glu Lys Leu Gln Leu Val Leu Ala Pro Leu His Ser Leu Ala
                215                 220                 225

Ser Gln Ala Leu Glu His Gly Leu Pro Asp Pro Gly Ser Leu Leu
                230                 235                 240

Val His Ser Phe Gln Gln Leu Gly Arg Ile Asp Ser Leu Ser Glu
                245                 250                 255

Gln Ile Ser Phe Leu Glu Glu Gln Leu Gly Ser Cys Ser Cys Lys
                260                 265                 270

Lys Asp Ser


<210> SEQ ID NO 179
<211> LENGTH: 2052
<212> TYPE: DNA
<213> ORGANISM: Homo sapiens

<400> SEQUENCE: 179

gacagctgtg tctcgatgga gtagactctc agaacagcgc agtttgccct          50

ccgctcacgc agagcctctc cgtggcttcc gcaccttgag cattaggcca         100

gttctcctct tctctctaat ccatccgtca cctctcctgt catccgtttc         150

catgccgtga ggtccattca cagaacacat ccatggctct catgctcagt         200

ttggttctga gtctcctcaa gctgggatca gggcagtggc aggtgtttgg         250

gccagacaag cctgtccagg ccttggtggg ggaggacgca gcattctcct         300

gtttcctgtc tcctaagacc aatgcagagg ccatggaagt gcggttcttc         350

aggggccagt tctctagcgt ggtccacctc tacagggacg ggaaggacca         400

gccatttatg cagatgccac agtatcaagg caggacaaaa ctggtgaagg         450

attctattgc ggaggggcgc atctctctga ggctggaaaa cattactgtg         500

ttggatgctg gcctctatgg gtgcaggatt agttcccagt cttactacca         550

gaaggccatc tgggagctac aggtgtcagc actgggctca gttcctctca         600

tttccatcac gggatatgtt gatagagaca tccagctact ctgtcagtcc         650

tcgggctggt tcccccggcc cacagcgaag tggaaaggtc cacaaggaca         700

ggatttgtcc acagactcca ggacaaacag agacatgcat ggcctgtttg         750
```

-continued

```
atgtggagat ctctctgacc gtccaagaga acgccgggag catatcctgt             800

tccatgcggc atgctcatct gagccgagag gtggaatcca gggtacagat             850

aggagatacc tttttcgagc ctatatcgtg gcacctggct accaaagtac             900

tgggaatact ctgctgtggc ctatttttg gcattgttgg actgaagatt              950

ttcttctcca aattccagtg gaaaatccag gcggaactgg actggagaag            1000

aaagcacgga caggcagaat tgagagacgc ccggaaacac gcagtggagg            1050

tgactctgga tccagagacg gctcacccga agctctgcgt ttctgatctg            1100

aaaactgtaa cccatagaaa agctccccag gaggtgcctc actctgagaa            1150

gagatttaca aggaagagtg tggtggcttc tcagagtttc caagcaggga            1200

aacattactg ggaggtggac ggaggacaca ataaaaggtg gcgcgtggga            1250

gtgtgccggg atgatgtgga caggaggaag gagtacgtga ctttgtctcc            1300

cgatcatggg tactgggtcc tcagactgaa tggagaacat ttgtatttca            1350

cattaaatcc ccgttttatc agcgtcttcc ccaggacccc acctacaaaa            1400

ataggggtct tcctggacta tgagtgtggg accatctcct tcttcaacat            1450

aaatgaccag tcccttattt ataccctgac atgtcggttt gaaggcttat            1500

tgaggcccta cattgagtat ccgtcctata atgagcaaaa tggaactccc            1550

atagtcatct gcccagtcac ccaggaatca gagaaagagg cctcttggca            1600

aagggcctct gcaatcccag agacaagcaa cagtgagtcc tcctcacagg            1650

caaccacgcc cttcctcccc aggggtgaaa tgtaggatga atcacatccc            1700

acattcttct ttagggatat taaggtctct ctcccagatc caaagtcccg            1750

cagcagccgg ccaaggtggc ttccagatga agggggactg gcctgtccac            1800

atgggagtca ggtgtcatgg ctgccctgag ctgggaggga agaaggctga            1850

cattacattt agtttgctct cactccatct ggctaagtga tcttgaaata            1900

ccacctctca ggtgaagaac cgtcaggaat tcccatctca caggctgtgg            1950

tgtagattaa gtagacaagg aatgtgaata atgcttagat cttattgatg            2000

acagagtgta tcctaatggt ttgttcatta tattacactt tcagtaaaaa            2050

aa                                                                 2052
```

```
<210> SEQ ID NO 180
<211> LENGTH: 500
<212> TYPE: PRT
<213> ORGANISM: Homo sapiens

<400> SEQUENCE: 180

Met Ala Leu Met Leu Ser Leu Val Leu Ser Leu Leu Lys Leu Gly
  1               5                  10                  15

Ser Gly Gln Trp Gln Val Phe Gly Pro Asp Lys Pro Val Gln Ala
                 20                  25                  30

Leu Val Gly Glu Asp Ala Ala Phe Ser Cys Phe Leu Ser Pro Lys
                 35                  40                  45

Thr Asn Ala Glu Ala Met Glu Val Arg Phe Phe Arg Gly Gln Phe
                 50                  55                  60

Ser Ser Val Val His Leu Tyr Arg Asp Gly Lys Asp Gln Pro Phe
                 65                  70                  75

Met Gln Met Pro Gln Tyr Gln Gly Arg Thr Lys Leu Val Lys Asp
                 80                  85                  90
```

-continued

```
Ser Ile Ala Glu Gly Arg Ile Ser Leu Arg Leu Glu Asn Ile Thr
                 95                 100                 105

Val Leu Asp Ala Gly Leu Tyr Gly Cys Arg Ile Ser Ser Gln Ser
                110                 115                 120

Tyr Tyr Gln Lys Ala Ile Trp Glu Leu Gln Val Ser Ala Leu Gly
                125                 130                 135

Ser Val Pro Leu Ile Ser Ile Thr Gly Tyr Val Asp Arg Asp Ile
                140                 145                 150

Gln Leu Leu Cys Gln Ser Ser Gly Trp Phe Pro Arg Pro Thr Ala
                155                 160                 165

Lys Trp Lys Gly Pro Gln Gly Gln Asp Leu Ser Thr Asp Ser Arg
                170                 175                 180

Thr Asn Arg Asp Met His Gly Leu Phe Asp Val Glu Ile Ser Leu
                185                 190                 195

Thr Val Gln Glu Asn Ala Gly Ser Ile Ser Cys Ser Met Arg His
                200                 205                 210

Ala His Leu Ser Arg Glu Val Glu Ser Arg Val Gln Ile Gly Asp
                215                 220                 225

Thr Phe Phe Glu Pro Ile Ser Trp His Leu Ala Thr Lys Val Leu
                230                 235                 240

Gly Ile Leu Cys Cys Gly Leu Phe Phe Gly Ile Val Gly Leu Lys
                245                 250                 255

Ile Phe Phe Ser Lys Phe Gln Trp Lys Ile Gln Ala Glu Leu Asp
                260                 265                 270

Trp Arg Arg Lys His Gly Gln Ala Glu Leu Arg Asp Ala Arg Lys
                275                 280                 285

His Ala Val Glu Val Thr Leu Asp Pro Glu Thr Ala His Pro Lys
                290                 295                 300

Leu Cys Val Ser Asp Leu Lys Thr Val Thr His Arg Lys Ala Pro
                305                 310                 315

Gln Glu Val Pro His Ser Glu Lys Arg Phe Thr Arg Lys Ser Val
                320                 325                 330

Val Ala Ser Gln Ser Phe Gln Ala Gly Lys His Tyr Trp Glu Val
                335                 340                 345

Asp Gly Gly His Asn Lys Arg Trp Arg Val Gly Val Cys Arg Asp
                350                 355                 360

Asp Val Asp Arg Arg Lys Glu Tyr Val Thr Leu Ser Pro Asp His
                365                 370                 375

Gly Tyr Trp Val Leu Arg Leu Asn Gly Glu His Leu Tyr Phe Thr
                380                 385                 390

Leu Asn Pro Arg Phe Ile Ser Val Phe Pro Arg Thr Pro Pro Thr
                395                 400                 405

Lys Ile Gly Val Phe Leu Asp Tyr Glu Cys Gly Thr Ile Ser Phe
                410                 415                 420

Phe Asn Ile Asn Asp Gln Ser Leu Ile Tyr Thr Leu Thr Cys Arg
                425                 430                 435

Phe Glu Gly Leu Leu Arg Pro Tyr Ile Glu Tyr Pro Ser Tyr Asn
                440                 445                 450

Glu Gln Asn Gly Thr Pro Ile Val Ile Cys Pro Val Thr Gln Glu
                455                 460                 465

Ser Glu Lys Glu Ala Ser Trp Gln Arg Ala Ser Ala Ile Pro Glu
                470                 475                 480
```

-continued

```
Thr Ser Asn Ser Glu Ser Ser Ser Gln Ala Thr Thr Pro Phe Leu
                485                 490                 495

Pro Arg Gly Glu Met
                500
```

```
<210> SEQ ID NO 181
<211> LENGTH: 2294
<212> TYPE: DNA
<213> ORGANISM: Homo sapiens

<400> SEQUENCE: 181

gcgatggtgc gcccggtggc ggtggcggcg gcggttgcgg aggcttcctt              50

ggtcggattg caacgaggag aagatgactg accaaccgac tggctgaatg             100

aatgaatggc ggagccgagc gcgccatgag gagcctgccg agcctgggcg             150

gcctcgccct gttgtgctgc gccgccgccg ccgccgccgt cgcctcagcc             200

gcctcggcgg ggaatgtcac cggtggcggc ggggccgcgg ggcaggtgga             250

cgcgtcgccg ggcccccgggt tgcggggcga gcccagccac cccttcccta             300

gggcgacggc tcccacggcc caggccccga ggaccgggcc cccgcgcgcc             350

accgtccacc gacccctggc tgcgacttct ccagcccagt ccccggagac             400

cacccctctt tgggcgactg ctggaccctc ttccaccacc tttcaggcgc             450

cgctcggccc ctcgccgacc acccctccgg cggcggaacg cacttcgacc             500

acctctcagg cgccgaccag acccgcgccg accacccttt cgacgaccac             550

tggcccggcg ccgaccaccc ctgtagcgac caccgtaccg gcgcccacga             600

ctccccggac cccgaccccc gatctcccca gcagcagcaa cagcagcgtc             650

ctccccaccc cacctgccac cgaggccccc tcttcgcctc ctccagagta             700

tgtatgtaac tgctctgtgg ttggaagcct gaatgtgaat cgctgcaacc             750

agaccacagg gcagtgtgag tgtcggccag gttatcaggg gcttcactgt             800

gaaacctgca aagagggctt ttacctaaat tacacttctg ggctctgtca             850

gccatgtgac tgtagtccac atggagctct cagcataccg tgcaacaggt             900

aagcaacaga gggtggaact gaagtttatt ttattttagc aagggaaaaa             950

aaaaggctgc tactctcaag gaccatactg gtttaaacaa aggaggatga            1000

gggtcataga tttacaaaat attttatata cttttattct cttactttat            1050

atgttatatt taatgtcagg atttaaaaac atctaattta ctgatttagt            1100

tcttcaaaag cactagagtc gccaattttt ctctgggata atttctgtaa            1150

atttcatggg aaaaaattat tgaagaataa atctgctttc tggaagggct            1200

ttcaggcatg aaacctgcta ggaggtttag aaatgttctt atgtttatta            1250

atataccatt ggagtttgag gaaatttgtt gtttggttta tttttctctc            1300

taatcaaaat tctacatttg tttctttgga catctaaagc ttaacctggg            1350

ggtaccctaa tttatttaac tagtggtaag tagactggtt ttactctatt            1400

taccagtaca tttttgagac caaaagtaga ttaagcagga attatcttta            1450

aactattatg ttatttggag gtaatttaat ctagtggaat aatgtactgt            1500

tatctaagca tttgccttgt actgcactga aagtaattat tctttgacct            1550

tatgtgaggc acttggcttt ttgtggaccc caagtcaaaa aactgaagag            1600

acagtattaa ataatgaaaa aaataatgac aggttatact cagtgtaacc            1650
```

-continued

```
tgggtataac ccaagatctg ctgccactta cgagctgtgt tccttgggca        1700

agtaatttcc tttcactgag cttgtttctt ctcaaggttg ttgtgaagat        1750

taaatgagtt gatatatata aaatgcctag cacatgtcac tcaataaatt        1800

ctggtttgtt ttaatttcaa aggaatatta tggactgaaa tgagagaaca        1850

tgttttaaga acttttagct ccttgacaaa gaagtgcttt atactttagc        1900

actaaatatt ttaaatgctt tataaatgat attatactgt tatggaatat        1950

tgtatcatat tgtagtttat taaaaatgta gaagaggctg ggcgcggtgg        2000

ctcacgcctg taatcctagc actttgggag gccaaggcgg gtggatcact        2050

tgaggccagg agttctagat gagcctggcc agcacagtga aaccccgtct        2100

ctactaaaaa tacaaacaaa ttagctgggc gtggtggcac acacctgtag        2150

tcccagctac tcgggaggct gaggcaggag aatcggttga acccgggagg        2200

tggaggttgc agtgagctga gatcgcgcca ctgcactcca gcctggtgag        2250

agagggagac tctgtcttaa aaaaaaaaaa aaaaaaaaaa  aaaa             2294
```

<210> SEQ ID NO 182
<211> LENGTH: 258
<212> TYPE: PRT
<213> ORGANISM: Homo sapiens

<400> SEQUENCE: 182

```
Met Arg Ser Leu Pro Ser Leu Gly Gly Leu Ala Leu Leu Cys Cys
  1               5                  10                  15

Ala Ala Ala Ala Ala Ala Val Ala Ser Ala Ala Ser Ala Gly Asn
                 20                  25                  30

Val Thr Gly Gly Gly Gly Ala Ala Gly Gln Val Asp Ala Ser Pro
                 35                  40                  45

Gly Pro Gly Leu Arg Gly Glu Pro Ser His Pro Phe Pro Arg Ala
                 50                  55                  60

Thr Ala Pro Thr Ala Gln Ala Pro Arg Thr Gly Pro Pro Arg Ala
                 65                  70                  75

Thr Val His Arg Pro Leu Ala Ala Thr Ser Pro Ala Gln Ser Pro
                 80                  85                  90

Glu Thr Thr Pro Leu Trp Ala Thr Ala Gly Pro Ser Ser Thr Thr
                 95                 100                 105

Phe Gln Ala Pro Leu Gly Pro Ser Pro Thr Thr Pro Pro Ala Ala
                110                 115                 120

Glu Arg Thr Ser Thr Thr Ser Gln Ala Pro Thr Arg Pro Ala Pro
                125                 130                 135

Thr Thr Leu Ser Thr Thr Thr Gly Pro Ala Pro Thr Thr Pro Val
                140                 145                 150

Ala Thr Thr Val Pro Ala Pro Thr Thr Pro Arg Thr Pro Thr Pro
                155                 160                 165

Asp Leu Pro Ser Ser Ser Asn Ser Ser Val Leu Pro Thr Pro Pro
                170                 175                 180

Ala Thr Glu Ala Pro Ser Ser Pro Pro Pro Glu Tyr Val Cys Asn
                185                 190                 195

Cys Ser Val Val Gly Ser Leu Asn Val Asn Arg Cys Asn Gln Thr
                200                 205                 210

Thr Gly Gln Cys Glu Cys Arg Pro Gly Tyr Gln Gly Leu His Cys
                215                 220                 225
```

-continued

Glu Thr Cys Lys Glu Gly Phe Tyr Leu Asn Tyr Thr Ser Gly Leu
230 235 240

Cys Gln Pro Cys Asp Cys Ser Pro His Gly Ala Leu Ser Ile Pro
245 250 255

Cys Asn Arg

<210> SEQ ID NO 183
<211> LENGTH: 689
<212> TYPE: DNA
<213> ORGANISM: Homo sapiens

<400> SEQUENCE: 183
tgcggcgcag tgtagacctg ggaggatggg cggcctgctg ctggctgctt 50
ttctggcttt ggtctcggtg cccagggccc aggccgtgtg gttgggaaga 100
ctggaccctg agcagcttct tgggccctgg tacgtgcttg cggtggcctc 150
ccgggaaaag ggctttgcca tggagaagga catgaagaac gtcgtggggg 200
tggtggtgac cctcactcca gaaaacaacc tgcggacgct gtcctctcag 250
cacgggctgg gagggtgtga ccagagtgtc atggacctga taaagcgaaa 300
ctccggatgg gtgtttgaga atccctcaat aggcgtgctg gagctctggg 350
tgctggccac caacttcaga gactatgcca tcatcttcac tcagctggag 400
ttcggggacg agcccttcaa caccgtggag ctgtacagtc tgacggagac 450
agccagccag gaggccatgg ggctcttcac caagtggagc aggagcctgg 500
gcttcctgtc acagtagcag gcccagctgc agaaggacct cacctgtgct 550
cacaagatcc ttctgtgagt gctgcgtccc cagtagggat ggcgcccaca 600
gggtcctgtg acctcggcca gtgtccaccc acctcgctca gcggctcccg 650
gggcccagca ccagctcaga ataaagcgat tccacagca 689

<210> SEQ ID NO 184
<211> LENGTH: 163
<212> TYPE: PRT
<213> ORGANISM: Homo sapiens

<400> SEQUENCE: 184

Met Gly Gly Leu Leu Leu Ala Ala Phe Leu Ala Leu Val Ser Val
1 5 10 15

Pro Arg Ala Gln Ala Val Trp Leu Gly Arg Leu Asp Pro Glu Gln
20 25 30

Leu Leu Gly Pro Trp Tyr Val Leu Ala Val Ala Ser Arg Glu Lys
35 40 45

Gly Phe Ala Met Glu Lys Asp Met Lys Asn Val Val Gly Val Val
50 55 60

Val Thr Leu Thr Pro Glu Asn Asn Leu Arg Thr Leu Ser Ser Gln
65 70 75

His Gly Leu Gly Gly Cys Asp Gln Ser Val Met Asp Leu Ile Lys
80 85 90

Arg Asn Ser Gly Trp Val Phe Glu Asn Pro Ser Ile Gly Val Leu
95 100 105

Glu Leu Trp Val Leu Ala Thr Asn Phe Arg Asp Tyr Ala Ile Ile
110 115 120

Phe Thr Gln Leu Glu Phe Gly Asp Glu Pro Phe Asn Thr Val Glu
125 130 135

-continued

```
Leu Tyr Ser Leu Thr Glu Thr Ala Ser Gln Glu Ala Met Gly Leu
                140                 145                 150

Phe Thr Lys Trp Ser Arg Ser Leu Gly Phe Leu Ser Gln
                155                 160
```

<210> SEQ ID NO 185
<211> LENGTH: 1204
<212> TYPE: DNA
<213> ORGANISM: Homo sapiens

<400> SEQUENCE: 185

```
gttccgcaga tgcagaggtt gaggtggctg cgggactgga agtcatcggg          50
cagaggtctc acagcagcca aggaacctgg ggcccgctcc tccccccctcc        100
aggccatgag gattctgcag ttaatcctgc ttgctctggc aacagggctt         150
gtagggggag agaccaggat catcaagggg ttcgagtgca agcctcactc         200
ccagccctgg caggcagccc tgttcgagaa gacgcggcta ctctgtgggg         250
cgacgctcat cgcccccaga tggctcctga cagcagccca ctgcctcaag         300
ccccgctaca tagttcacct ggggcagcac aacctccaga aggaggaggg         350
ctgtgagcag acccggacag ccactgagtc cttcccccac cccggcttca         400
acaacagcct ccccaacaaa gaccaccgca atgacatcat gctggtgaag         450
atggcatcgc cagtctccat cacctgggct gtgcgacccc tcaccctctc         500
ctcacgctgt gtcactgctg gcaccagctg cctcatttcc ggctggggca         550
gcacgtccag cccccagtta cgcctgcctc acaccttgcg atgcgccaac         600
atcaccatca ttgagcacca gaagtgtgag aacgcctacc ccggcaacat         650
cacagacacc atggtgtgtg ccagcgtgca ggaagggggc aaggactcct         700
gccagggtga ctccgggggc cctctggtct gtaaccagtc tcttcaaggc         750
attatctcct ggggccagga tccgtgtgcg atcacccgaa agcctggtgt         800
ctacacgaaa gtctgcaaat atgtggactg gatccaggag acgatgaaga         850
acaattagac tggacccacc caccacagcc catcaccctc catttccact         900
tggtgtttgg ttcctgttca ctctgttaat aagaaaccct aagccaagac         950
cctctacgaa cattctttgg gcctcctgga ctacaggaga tgctgtcact        1000
taataatcaa cctggggttc gaaatcagtg agacctggat tcaaattctg        1050
ccttgaaata ttgtgactct gggaatgaca acacctggtt tgttctctgt        1100
tgtatcccca gccccaaaga cagctcctgg ccatatatca aggtttcaat        1150
aaatatttgc taaatgaaaa aaaaaaaaaa aaaaaaaaaa aaaaaaaaaa        1200
aaaa                                                            1204
```

<210> SEQ ID NO 186
<211> LENGTH: 250
<212> TYPE: PRT
<213> ORGANISM: Homo sapiens

<400> SEQUENCE: 186

```
Met Arg Ile Leu Gln Leu Ile Leu Leu Ala Leu Ala Thr Gly Leu
  1               5                  10                  15

Val Gly Gly Glu Thr Arg Ile Ile Lys Gly Phe Glu Cys Lys Pro
                 20                  25                  30
```

-continued

```
His Ser Gln Pro Trp Gln Ala Ala Leu Phe Glu Lys Thr Arg Leu
                35                  40                  45

Leu Cys Gly Ala Thr Leu Ile Ala Pro Arg Trp Leu Leu Thr Ala
                50                  55                  60

Ala His Cys Leu Lys Pro Arg Tyr Ile Val His Leu Gly Gln His
                65                  70                  75

Asn Leu Gln Lys Glu Glu Gly Cys Glu Gln Thr Arg Thr Ala Thr
                80                  85                  90

Glu Ser Phe Pro His Pro Gly Phe Asn Asn Ser Leu Pro Asn Lys
                95                  100                 105

Asp His Arg Asn Asp Ile Met Leu Val Lys Met Ala Ser Pro Val
                110                 115                 120

Ser Ile Thr Trp Ala Val Arg Pro Leu Thr Leu Ser Ser Arg Cys
                125                 130                 135

Val Thr Ala Gly Thr Ser Cys Leu Ile Ser Gly Trp Gly Ser Thr
                140                 145                 150

Ser Ser Pro Gln Leu Arg Leu Pro His Thr Leu Arg Cys Ala Asn
                155                 160                 165

Ile Thr Ile Ile Glu His Gln Lys Cys Glu Asn Ala Tyr Pro Gly
                170                 175                 180

Asn Ile Thr Asp Thr Met Val Cys Ala Ser Val Gln Glu Gly Gly
                185                 190                 195

Lys Asp Ser Cys Gln Gly Asp Ser Gly Gly Pro Leu Val Cys Asn
                200                 205                 210

Gln Ser Leu Gln Gly Ile Ile Ser Trp Gly Gln Asp Pro Cys Ala
                215                 220                 225

Ile Thr Arg Lys Pro Gly Val Tyr Thr Lys Val Cys Lys Tyr Val
                230                 235                 240

Asp Trp Ile Gln Glu Thr Met Lys Asn Asn
                245                 250
```

<210> SEQ ID NO 187
<211> LENGTH: 2848
<212> TYPE: DNA
<213> ORGANISM: Homo sapiens

<400> SEQUENCE: 187

```
gctcaagtgc cctgccttgc cccacccagc ccagcctggc cagagccccc      50

tggagaagga gctctcttct tgcttggcag ctggaccaag ggagccagtc     100

ttgggcgctg gagggcctgt cctgaccatg gtccctgcct ggctgtggct     150

gctttgtgtc tccgtccccc aggctctccc caaggcccag cctgcagagc     200

tgtctgtgga agttccagaa aactatggtg gaaatttccc tttatacctg     250

accaagttgc cgctgccccg tgagggggct gaaggccaga tcgtgctgtc     300

aggggactca ggcaaggcaa ctgagggccc atttgctatg gatccagatt     350

ctggcttcct gctggtgacc agggccctgg accgagagga gcaggcagag     400

taccagctac aggtcaccct ggagatgcag gatggacatg tcttgtgggg     450

tccacagcct gtgcttgtgc acgtgaagga tgagaatgac caggtgcccc     500

atttctctca agccatctac agagctcggc tgagccgggg taccaggcct     550

ggcatcccct tcctcttcct tgaggcttca gaccgggatg agccaggcac     600

agccaactcg gatcttcgat tccacatcct gagccaggct ccagcccagc     650
```

-continued

```
cttccccaga catgttccag ctggagcctc ggctgggggc tctggccctc      700
agccccaagg ggagcaccag ccttgaccac gccctggaga ggacctacca      750
gctgttggta caggtcaagg acatgggtga ccaggcctca ggccaccagg      800
ccactgccac cgtggaagtc tccatcatag agagcacctg ggtgtcccta      850
gagcctatcc acctggcaga gaatctcaaa gtcctatacc cgcaccacat      900
ggcccaggta cactggagtg ggggtgatgt gcactatcac ctggagagcc      950
atcccccggg accctttgaa gtgaatgcag agggaaacct ctacgtgacc     1000
agagagctgg acagagaagc ccaggctgag tacctgctcc aggtgcgggc     1050
tcagaattcc catggcgagg actatgcggc ccctctggag ctgcacgtgc     1100
tggtgatgga tgagaatgac aacgtgccta tctgccctcc ccgtgacccc     1150
acagtcagca tccctgagct cagtccacca ggtactgaag tgactagact     1200
gtcagcagag gatgcagatg cccccggctc ccccaattcc cacgttgtgt     1250
atcagctcct gagccctgag cctgaggatg gggtagaggg gagagccttc     1300
caggtggacc ccacttcagg cagtgtgacg ctgggggtgc tcccactccg     1350
agcaggccag aacatcctgc ttctggtgct ggccatggac ctggcaggcg     1400
cagagggtgg cttcagcagc acgtgtgaag tcgaagtcgc agtcacagat     1450
atcaatgatc acgcccctga gttcatcact tcccagattg ggcctataag     1500
cctccctgag gatgtggagc ccgggactct ggtggccatg ctaacagcca     1550
ttgatgctga cctcgagccc gccttccgcc tcatggattt tgccattgag     1600
aggggagaca cagaagggac ttttggcctg gattgggagc cagactctgg     1650
gcatgttaga ctcagactct gcaagaacct cagttatgag gcagctccaa     1700
gtcatgaggt ggtggtggtg gtgcagagtg tggcgaagct ggtggggcca     1750
ggcccaggcc ctggagccac cgccacggtg actgtgctag tggagagagt     1800
gatgccaccc cccaagttgg accaggagag ctacgaggcc agtgtcccca     1850
tcagtgcccc agccggctct ttcctgctga ccatccagcc ctccgacccc     1900
atcagccgaa ccctcaggtt ctccctagtc aatgactcag agggctggct     1950
ctgcattgag aaattctccg gggaggtgca caccgcccag tccctgcagg     2000
gcgcccagcc tggggacacc tacacggtgc ttgtggaggc ccaggataca     2050
gccctgactc ttgcccctgt gccctcccaa tacctctgca caccccgcca     2100
agaccatggc ttgatcgtga gtggacccag caaggacccc gatctggcca     2150
gtgggcacgg tccctacagc ttcacccttg gtcccaaccc cacggtgcaa     2200
cgggattggc gcctccagac tctcaatggt tcccatgcct acctcacctt     2250
ggccctgcat tgggtggagc cacgtgaaca cataatcccc gtggtggtca     2300
gccacaatgc ccagatgtgg cagctcctgg ttcgagtgat cgtgtgtcgc     2350
tgcaacgtgg aggggcagtg catgcgcaag gtgggccgca tgaagggcat     2400
gcccacgaag ctgtcggcag tgggcatcct tgtaggcacc ctggtagcaa     2450
taggaatctt cctcatcctc attttcaccc actggaccat gtcaaggaag     2500
aaggacccgg atcaaccagc agacagcgtg cccctgaagg cgactgtctg     2550
aatggcccag gcagctctag ctgggagctt ggcctctggc tccatctgag     2600
tcccctggga gagagcccag cacccaagat ccagcagggg acaggacaga     2650
```

-continued

```
gtagaagccc ctccatctgc cctggggtgg aggcaccatc accatcacca             2700

ggcatgtctg cagagcctgg acaccaactt tatggactgc ccatgggagt             2750

gctccaaatg tcagggtgtt tgcccaataa taaagcccca gagaactggg             2800

ctgggcccta tgggaaaaaa aaaaaaaaaa aaaaaaaaaa  aaaaaaag              2848


<210> SEQ ID NO 188
<211> LENGTH: 807
<212> TYPE: PRT
<213> ORGANISM: Homo sapiens

<400> SEQUENCE: 188

Met Val Pro Ala Trp Leu Trp Leu Leu Cys Val Ser Val Pro Gln
  1               5                  10                  15

Ala Leu Pro Lys Ala Gln Pro Ala Glu Leu Ser Val Glu Val Pro
                 20                  25                  30

Glu Asn Tyr Gly Gly Asn Phe Pro Leu Tyr Leu Thr Lys Leu Pro
                 35                  40                  45

Leu Pro Arg Glu Gly Ala Glu Gly Gln Ile Val Leu Ser Gly Asp
                 50                  55                  60

Ser Gly Lys Ala Thr Glu Gly Pro Phe Ala Met Asp Pro Asp Ser
                 65                  70                  75

Gly Phe Leu Leu Val Thr Arg Ala Leu Asp Arg Glu Glu Gln Ala
                 80                  85                  90

Glu Tyr Gln Leu Gln Val Thr Leu Glu Met Gln Asp Gly His Val
                 95                 100                 105

Leu Trp Gly Pro Gln Pro Val Leu Val His Val Lys Asp Glu Asn
                110                 115                 120

Asp Gln Val Pro His Phe Ser Gln Ala Ile Tyr Arg Ala Arg Leu
                125                 130                 135

Ser Arg Gly Thr Arg Pro Gly Ile Pro Phe Leu Phe Leu Glu Ala
                140                 145                 150

Ser Asp Arg Asp Glu Pro Gly Thr Ala Asn Ser Asp Leu Arg Phe
                155                 160                 165

His Ile Leu Ser Gln Ala Pro Ala Gln Pro Ser Pro Asp Met Phe
                170                 175                 180

Gln Leu Glu Pro Arg Leu Gly Ala Leu Ala Leu Ser Pro Lys Gly
                185                 190                 195

Ser Thr Ser Leu Asp His Ala Leu Glu Arg Thr Tyr Gln Leu Leu
                200                 205                 210

Val Gln Val Lys Asp Met Gly Asp Gln Ala Ser Gly His Gln Ala
                215                 220                 225

Thr Ala Thr Val Glu Val Ser Ile Ile Glu Ser Thr Trp Val Ser
                230                 235                 240

Leu Glu Pro Ile His Leu Ala Glu Asn Leu Lys Val Leu Tyr Pro
                245                 250                 255

His His Met Ala Gln Val His Trp Ser Gly Gly Asp Val His Tyr
                260                 265                 270

His Leu Glu Ser His Pro Pro Gly Pro Phe Glu Val Asn Ala Glu
                275                 280                 285

Gly Asn Leu Tyr Val Thr Arg Glu Leu Asp Arg Glu Ala Gln Ala
                290                 295                 300

Glu Tyr Leu Leu Gln Val Arg Ala Gln Asn Ser His Gly Glu Asp
                305                 310                 315
```

-continued

```
Tyr Ala Ala Pro Leu Glu Leu His Val Leu Val Met Asp Glu Asn
                320                 325                 330

Asp Asn Val Pro Ile Cys Pro Pro Arg Asp Pro Thr Val Ser Ile
                335                 340                 345

Pro Glu Leu Ser Pro Pro Gly Thr Glu Val Thr Arg Leu Ser Ala
                350                 355                 360

Glu Asp Ala Asp Ala Pro Gly Ser Pro Asn Ser His Val Val Tyr
                365                 370                 375

Gln Leu Leu Ser Pro Glu Pro Glu Asp Gly Val Glu Gly Arg Ala
                380                 385                 390

Phe Gln Val Asp Pro Thr Ser Gly Ser Val Thr Leu Gly Val Leu
                395                 400                 405

Pro Leu Arg Ala Gly Gln Asn Ile Leu Leu Leu Val Leu Ala Met
                410                 415                 420

Asp Leu Ala Gly Ala Glu Gly Gly Phe Ser Ser Thr Cys Glu Val
                425                 430                 435

Glu Val Ala Val Thr Asp Ile Asn Asp His Ala Pro Glu Phe Ile
                440                 445                 450

Thr Ser Gln Ile Gly Pro Ile Ser Leu Pro Glu Asp Val Glu Pro
                455                 460                 465

Gly Thr Leu Val Ala Met Leu Thr Ala Ile Asp Ala Asp Leu Glu
                470                 475                 480

Pro Ala Phe Arg Leu Met Asp Phe Ala Ile Glu Arg Gly Asp Thr
                485                 490                 495

Glu Gly Thr Phe Gly Leu Asp Trp Glu Pro Asp Ser Gly His Val
                500                 505                 510

Arg Leu Arg Leu Cys Lys Asn Leu Ser Tyr Glu Ala Ala Pro Ser
                515                 520                 525

His Glu Val Val Val Val Val Gln Ser Val Ala Lys Leu Val Gly
                530                 535                 540

Pro Gly Pro Gly Pro Gly Ala Thr Ala Thr Val Thr Val Leu Val
                545                 550                 555

Glu Arg Val Met Pro Pro Pro Lys Leu Asp Gln Glu Ser Tyr Glu
                560                 565                 570

Ala Ser Val Pro Ile Ser Ala Pro Ala Gly Ser Phe Leu Leu Thr
                575                 580                 585

Ile Gln Pro Ser Asp Pro Ile Ser Arg Thr Leu Arg Phe Ser Leu
                590                 595                 600

Val Asn Asp Ser Glu Gly Trp Leu Cys Ile Glu Lys Phe Ser Gly
                605                 610                 615

Glu Val His Thr Ala Gln Ser Leu Gln Gly Ala Gln Pro Gly Asp
                620                 625                 630

Thr Tyr Thr Val Leu Val Glu Ala Gln Asp Thr Ala Leu Thr Leu
                635                 640                 645

Ala Pro Val Pro Ser Gln Tyr Leu Cys Thr Pro Arg Gln Asp His
                650                 655                 660

Gly Leu Ile Val Ser Gly Pro Ser Lys Asp Pro Asp Leu Ala Ser
                665                 670                 675

Gly His Gly Pro Tyr Ser Phe Thr Leu Gly Pro Asn Pro Thr Val
                680                 685                 690

Gln Arg Asp Trp Arg Leu Gln Thr Leu Asn Gly Ser His Ala Tyr
                695                 700                 705
```

-continued

```
Leu Thr Leu Ala Leu His Trp Val Glu Pro Arg Glu His Ile Ile
                710                 715                 720

Pro Val Val Val Ser His Asn Ala Gln Met Trp Gln Leu Leu Val
                725                 730                 735

Arg Val Ile Val Cys Arg Cys Asn Val Glu Gly Gln Cys Met Arg
                740                 745                 750

Lys Val Gly Arg Met Lys Gly Met Pro Thr Lys Leu Ser Ala Val
                755                 760                 765

Gly Ile Leu Val Gly Thr Leu Val Ala Ile Gly Ile Phe Leu Ile
                770                 775                 780

Leu Ile Phe Thr His Trp Thr Met Ser Arg Lys Lys Asp Pro Asp
                785                 790                 795

Gln Pro Ala Asp Ser Val Pro Leu Lys Ala Thr Val
                800                 805
```

<210> SEQ ID NO 189
<211> LENGTH: 2668
<212> TYPE: DNA
<213> ORGANISM: Homo sapiens

<400> SEQUENCE: 189

```
gactttgctt gaatgtttac attttctgct cgctgtccta catatcacaa        50

tatagtgttc acgttttgtt aaaactttgg ggtgtcagga gttgagcttg       100

ctcagcaagc cagcatggct aggatgagct ttgttatagc agcttgccaa       150

ttggtgctgg gcctactaat gacttcatta accgagtctt ccatacagaa       200

tagtgagtgt ccacaacttt gcgtatgtga aattcgtccc tggtttaccc       250

cacagtcaac ttacagagaa gccaccactg ttgattgcaa tgacctccgc       300

ttaacaagga ttcccagtaa cctctctagt gacacacaag tgcttctctt       350

acagagcaat aacatcgcga agactgtgga tgagctgcag cagcttttca       400

acttgactga actagatttc tcccaaaaca actttactaa cattaaggag       450

gtcgggctgg caaacctaac ccagctcaca acgctgcatt tggaggaaaa       500

tcagattacc gagatgactg attactgtct acaagacctc agcaaccttc       550

aagaactcta catcaaccac aaccaaatta gcactatttc tgctcatgct       600

tttgcaggct taaaaaatct attaaggctc cacctgaact ccaacaaatt       650

gaaagttatt gatagtcgct ggtttgattc tacacccaac ctggaaattc       700

tcatgatcgg agaaaaccct gtgattggaa ttctggatat gaacttcaaa       750

cccctcgcaa atttgagaag cttagttttg gcaggaatgt atctcactga       800

tattcctgga aatgctttgg tgggtctgga tagccttgag agcctgtctt       850

tttatgataa caaactggtt aaagtccctc aacttgccct gcaaaaagtt       900

ccaaatttga aattcttaga cctcaacaaa aaccccattc acaaaatcca       950

agaaggggac ttcaaaaata tgcttcggtt aaaagaactg ggaatcaaca      1000

atatgggcga gctcgtttct gtcgaccgct atgccctgga taacttgcct      1050

gaactcacaa agctggaagc caccaataac cctaaactct cttacatcca      1100

ccgcttggct ttccgaagtg tccctgctct ggaaagcttg atgctgaaca      1150

acaatgcctt gaatgccatt taccaaaaga cagtcgaatc cctccccaat      1200

ctgcgtgaga tcagtatcca tagcaatccc ctcaggtgtg actgtgtgat      1250
```

-continued

```
ccactggatt aactccaaca aaaccaacat ccgcttcatg gagcccctgt          1300

ccatgttctg tgccatgccg cccgaatata aagggcacca ggtgaaggaa          1350

gttttaatcc aggattcgag tgaacagtgc ctcccaatga tatctcacga          1400

cagcttccca aatcgtttaa acgtggatat cggcacgacg gttttcctag          1450

actgtcgagc catggctgag ccagaacctg aaatttactg ggtcactccc          1500

attggaaata agataactgt ggaaaccctt tcagataaat acaagctaag          1550

tagcgaaggt accttggaaa tatctaacat acaaattgaa gactcaggaa          1600

gatacacatg tgttgcccag aatgtccaag ggcagacac tcgggtggca           1650

acaattaagg ttaacgggac ccttctggat ggtacccagg tgctaaaaat          1700

atacgtcaag cagacagaat cccattccat cttagtgtcc tggaaagtta          1750

attccaatgt catgacgtca aacttaaaat ggtcgtctgc caccatgaag          1800

attgataacc ctcacataac atatactgcc agggtcccag tcgatgtcca          1850

tgaatacaac ctaacgcatc tgcagccttc cacagattat gaagtgtgtc          1900

tcacagtgtc caatattcat cagcagactc aaaagtcatg cgtaaatgtc          1950

acaaccaaaa atgccgcctt cgcagtggac atctctgatc aagaaaccag          2000

tacagccctt gctgcagtaa tggggtctat gtttgccgtc attagccttg          2050

cgtccattgc tgtgtacttt gccaaaagat ttaagagaaa aaactaccac          2100

cactcattaa aaaagtatat gcaaaaaacc tcttcaatcc cactaaatga          2150

gctgtaccca ccactcatta acctctggga aggtgacagc gagaaagaca          2200

aagatggttc tgcagacacc aagccaaccc aggtcgacac atccagaagc          2250

tattacatgt ggtaactcag aggatatttt gcttctggta gtaaggagca          2300

caaagacgtt tttgctttat tctgcaaaag tgaacaagtt gaagactttt          2350

gtatttttga ctttgctagt ttgtggcaga gtggagagga cgggtggata          2400

tttcaaattt ttttagtata gcgtatcgca agggtttgac acggctgcca          2450

gcgactctag gcttccagtc tgtgtttggt ttttattctt atcattatta          2500

tgattgttat tatattatta ttttatttta gttgttgtgc taaactcaat          2550

aatgctgttc taactacagt gctcaataaa atgattaatg acaggaaaaa          2600

aaaaaaaaaa aaaaaaaaaa aaaaaaaaaa aaaaaaaaaa aaaaaaaaaa          2650

aaaaaaaaaa  aaaaaaaa                                            2668
```

<210> SEQ ID NO 190
<211> LENGTH: 716
<212> TYPE: PRT
<213> ORGANISM: Homo sapiens

<400> SEQUENCE: 190

```
Met Ala Arg Met Ser Phe Val Ile Ala Ala Cys Gln Leu Val Leu
  1               5                  10                  15

Gly Leu Leu Met Thr Ser Leu Thr Glu Ser Ser Ile Gln Asn Ser
                 20                  25                  30

Glu Cys Pro Gln Leu Cys Val Cys Glu Ile Arg Pro Trp Phe Thr
                 35                  40                  45

Pro Gln Ser Thr Tyr Arg Glu Ala Thr Thr Val Asp Cys Asn Asp
                 50                  55                  60

Leu Arg Leu Thr Arg Ile Pro Ser Asn Leu Ser Ser Asp Thr Gln
```

-continued

```
                65                  70                  75

Val Leu Leu Leu Gln Ser Asn Asn Ile Ala Lys Thr Val Asp Glu
                80                  85                  90

Leu Gln Gln Leu Phe Asn Leu Thr Glu Leu Asp Phe Ser Gln Asn
                95                 100                 105

Asn Phe Thr Asn Ile Lys Glu Val Gly Leu Ala Asn Leu Thr Gln
               110                 115                 120

Leu Thr Thr Leu His Leu Glu Glu Asn Gln Ile Thr Glu Met Thr
               125                 130                 135

Asp Tyr Cys Leu Gln Asp Leu Ser Asn Leu Gln Glu Leu Tyr Ile
               140                 145                 150

Asn His Asn Gln Ile Ser Thr Ile Ser Ala His Ala Phe Ala Gly
               155                 160                 165

Leu Lys Asn Leu Leu Arg Leu His Leu Asn Ser Asn Lys Leu Lys
               170                 175                 180

Val Ile Asp Ser Arg Trp Phe Asp Ser Thr Pro Asn Leu Glu Ile
               185                 190                 195

Leu Met Ile Gly Glu Asn Pro Val Ile Gly Ile Leu Asp Met Asn
               200                 205                 210

Phe Lys Pro Leu Ala Asn Leu Arg Ser Leu Val Leu Ala Gly Met
               215                 220                 225

Tyr Leu Thr Asp Ile Pro Gly Asn Ala Leu Val Gly Leu Asp Ser
               230                 235                 240

Leu Glu Ser Leu Ser Phe Tyr Asp Asn Lys Leu Val Lys Val Pro
               245                 250                 255

Gln Leu Ala Leu Gln Lys Val Pro Asn Leu Lys Phe Leu Asp Leu
               260                 265                 270

Asn Lys Asn Pro Ile His Lys Ile Gln Glu Gly Asp Phe Lys Asn
               275                 280                 285

Met Leu Arg Leu Lys Glu Leu Gly Ile Asn Asn Met Gly Glu Leu
               290                 295                 300

Val Ser Val Asp Arg Tyr Ala Leu Asp Asn Leu Pro Glu Leu Thr
               305                 310                 315

Lys Leu Glu Ala Thr Asn Asn Pro Lys Leu Ser Tyr Ile His Arg
               320                 325                 330

Leu Ala Phe Arg Ser Val Pro Ala Leu Glu Ser Leu Met Leu Asn
               335                 340                 345

Asn Asn Ala Leu Asn Ala Ile Tyr Gln Lys Thr Val Glu Ser Leu
               350                 355                 360

Pro Asn Leu Arg Glu Ile Ser Ile His Ser Asn Pro Leu Arg Cys
               365                 370                 375

Asp Cys Val Ile His Trp Ile Asn Ser Asn Lys Thr Asn Ile Arg
               380                 385                 390

Phe Met Glu Pro Leu Ser Met Phe Cys Ala Met Pro Pro Glu Tyr
               395                 400                 405

Lys Gly His Gln Val Lys Glu Val Leu Ile Gln Asp Ser Ser Glu
               410                 415                 420

Gln Cys Leu Pro Met Ile Ser His Asp Ser Phe Pro Asn Arg Leu
               425                 430                 435

Asn Val Asp Ile Gly Thr Thr Val Phe Leu Asp Cys Arg Ala Met
               440                 445                 450

Ala Glu Pro Glu Pro Glu Ile Tyr Trp Val Thr Pro Ile Gly Asn
               455                 460                 465
```

-continued

```
Lys Ile Thr Val Glu Thr Leu Ser Asp Lys Tyr Lys Leu Ser Ser
                470                 475                 480

Glu Gly Thr Leu Glu Ile Ser Asn Ile Gln Ile Glu Asp Ser Gly
                485                 490                 495

Arg Tyr Thr Cys Val Ala Gln Asn Val Gln Gly Ala Asp Thr Arg
                500                 505                 510

Val Ala Thr Ile Lys Val Asn Gly Thr Leu Leu Asp Gly Thr Gln
                515                 520                 525

Val Leu Lys Ile Tyr Val Lys Gln Thr Glu Ser His Ser Ile Leu
                530                 535                 540

Val Ser Trp Lys Val Asn Ser Asn Val Met Thr Ser Asn Leu Lys
                545                 550                 555

Trp Ser Ser Ala Thr Met Lys Ile Asp Asn Pro His Ile Thr Tyr
                560                 565                 570

Thr Ala Arg Val Pro Val Asp Val His Glu Tyr Asn Leu Thr His
                575                 580                 585

Leu Gln Pro Ser Thr Asp Tyr Glu Val Cys Leu Thr Val Ser Asn
                590                 595                 600

Ile His Gln Gln Thr Gln Lys Ser Cys Val Asn Val Thr Thr Lys
                605                 610                 615

Asn Ala Ala Phe Ala Val Asp Ile Ser Asp Gln Glu Thr Ser Thr
                620                 625                 630

Ala Leu Ala Ala Val Met Gly Ser Met Phe Ala Val Ile Ser Leu
                635                 640                 645

Ala Ser Ile Ala Val Tyr Phe Ala Lys Arg Phe Lys Arg Lys Asn
                650                 655                 660

Tyr His His Ser Leu Lys Lys Tyr Met Gln Lys Thr Ser Ser Ile
                665                 670                 675

Pro Leu Asn Glu Leu Tyr Pro Pro Leu Ile Asn Leu Trp Glu Gly
                680                 685                 690

Asp Ser Glu Lys Asp Lys Asp Gly Ser Ala Asp Thr Lys Pro Thr
                695                 700                 705

Gln Val Asp Thr Ser Arg Ser Tyr Tyr Met Trp
                710                 715
```

<210> SEQ ID NO 191
<211> LENGTH: 957
<212> TYPE: DNA
<213> ORGANISM: Homo sapiens

<400> SEQUENCE: 191

```
gggagagagg ataaatagca gcgtggcttc cctggctcct ctctgcatcc          50

ttcccgacct tcccagcaat atgcatcttg cacgtctggt cggctcctgc         100

tccctccttc tgctactggg ggccctgtct ggatgggcgg ccagcgatga         150

ccccattgag aaggtcattg aagggatcaa ccgagggctg agcaatgcag         200

agagagaggt gggcaaggcc ctggatggca tcaacagtgg aatcacgcat         250

gccggaaggg aagtggagaa ggttttcaac ggacttagca acatggggag         300

ccacaccggc aaggagttgg acaaaggcgt ccaggggctc aaccacggca         350

tggacaaggt tgcccatgag atcaaccatg gtattggaca agcaggaaag         400

gaagcagaga agcttggcca tggggtcaac aacgctgctg gacaggccgg         450

gaaggaagca gacaaagcgg tccaagggtt ccacactggg gtccaccagg         500
```

-continued

```
ctgggaagga agcagagaaa cttggccaag gggtcaacca tgctgctgac          550

caggctggaa aggaagtgga gaagcttggc caaggtgccc accatgctgc          600

tggccaggcc gggaaggagc tgcagaatgc tcataatggg gtcaaccaag          650

ccagcaagga ggccaaccag ctgctgaatg gcaaccatca aagcggatct          700

tccagccatc aaggaggggc cacaaccacg ccgttagcct ctggggcctc          750

agtcaacacg cctttcatca accttcccgc cctgtggagg agcgtcgcca          800

acatcatgcc ctaaactggc atccggcctt gctgggagaa taatgtcgcc          850

gttgtcacat cagctgacat gacctggagg ggttgggggt gggggacagg          900

tttctgaaat ccctgaaggg ggttgtactg ggatttgtga ataaacttga          950

tacacca                                                         957
```

<210> SEQ ID NO 192
<211> LENGTH: 247
<212> TYPE: PRT
<213> ORGANISM: Homo sapiens

<400> SEQUENCE: 192

```
Met His Leu Ala Arg Leu Val Gly Ser Cys Ser Leu Leu Leu Leu
  1               5                  10                  15

Leu Gly Ala Leu Ser Gly Trp Ala Ala Ser Asp Asp Pro Ile Glu
                 20                  25                  30

Lys Val Ile Glu Gly Ile Asn Arg Gly Leu Ser Asn Ala Glu Arg
                 35                  40                  45

Glu Val Gly Lys Ala Leu Asp Gly Ile Asn Ser Gly Ile Thr His
                 50                  55                  60

Ala Gly Arg Glu Val Glu Lys Val Phe Asn Gly Leu Ser Asn Met
                 65                  70                  75

Gly Ser His Thr Gly Lys Glu Leu Asp Lys Gly Val Gln Gly Leu
                 80                  85                  90

Asn His Gly Met Asp Lys Val Ala His Glu Ile Asn His Gly Ile
                 95                 100                 105

Gly Gln Ala Gly Lys Glu Ala Glu Lys Leu Gly His Gly Val Asn
                110                 115                 120

Asn Ala Ala Gly Gln Ala Gly Lys Glu Ala Asp Lys Ala Val Gln
                125                 130                 135

Gly Phe His Thr Gly Val His Gln Ala Gly Lys Glu Ala Glu Lys
                140                 145                 150

Leu Gly Gln Gly Val Asn His Ala Ala Asp Gln Ala Gly Lys Glu
                155                 160                 165

Val Glu Lys Leu Gly Gln Gly Ala His His Ala Ala Gly Gln Ala
                170                 175                 180

Gly Lys Glu Leu Gln Asn Ala His Asn Gly Val Asn Gln Ala Ser
                185                 190                 195

Lys Glu Ala Asn Gln Leu Leu Asn Gly Asn His Gln Ser Gly Ser
                200                 205                 210

Ser Ser His Gln Gly Gly Ala Thr Thr Thr Pro Leu Ala Ser Gly
                215                 220                 225

Ala Ser Val Asn Thr Pro Phe Ile Asn Leu Pro Ala Leu Trp Arg
                230                 235                 240

Ser Val Ala Asn Ile Met Pro
                245
```

-continued

<210> SEQ ID NO 193
<211> LENGTH: 904
<212> TYPE: DNA
<213> ORGANISM: Homo sapiens

<400> SEQUENCE: 193

```
gaagtagagg tgttgtgctg agcggcgctc ggcgaactgt gtggaccgtc        50

tgctgggact ccggccctgc gtccgctcag ccccgtggcc ccgcgcacct       100

actgccatgg agacgcggcc tcgtctcggg gccacctgtt tgctgggctt       150

cagtttcctg ctcctcgtca tctcttctga tggacataat gggcttggaa       200

agggttttgg agatcatatt cattggagga cactggaaga tgggaagaaa       250

gaagcagctg ccagtggact gcccctgatg gtgattattc ataaatcctg       300

gtgtggagct tgcaaagctc taaagcccaa atttgcagaa tctacggaaa       350

tttcagaact ctcccataat tttgttatgg taaatcttga ggatgaagag       400

gaacccaaag atgaagattt cagccctgac gggggttata ttccacgaat       450

cctttttctg gatcccagtg gcaaggtgca tcctgaaatc atcaatgaga       500

atggaaaccc cagctacaag tatttttatg tcagtgccga gcaagttgtt       550

caggggatga aggaagctca ggaaaggctg acgggtgatg ccttcagaaa       600

gaaacatctt gaagatgaat tgtaacatga atgtgcccct tctttcatca       650

gagttagtgt tctggaagga aagcagcagg gaagggaata ttgaggaatc       700

atctagaaca attaagccga ccaggaaacc tcattcctac ctacactgga       750

aggagcgctc tcactgtgga agagttctgc taacagaagc tggtctgcat       800

gtttgtggat ccagcggaga gtggcagact ttcttctcct tttccctctc       850

acctaaatgt caacttgtca ttgaatgtaa agaatgaaac cttctgacac       900

aaaa                                                         904
```

<210> SEQ ID NO 194
<211> LENGTH: 172
<212> TYPE: PRT
<213> ORGANISM: Homo sapiens

<400> SEQUENCE: 194

```
Met Glu Thr Arg Pro Arg Leu Gly Ala Thr Cys Leu Leu Gly Phe
1               5                   10                  15

Ser Phe Leu Leu Leu Val Ile Ser Ser Asp Gly His Asn Gly Leu
                20                  25                  30

Gly Lys Gly Phe Gly Asp His Ile His Trp Arg Thr Leu Glu Asp
                35                  40                  45

Gly Lys Lys Glu Ala Ala Ala Ser Gly Leu Pro Leu Met Val Ile
                50                  55                  60

Ile His Lys Ser Trp Cys Gly Ala Cys Lys Ala Leu Lys Pro Lys
                65                  70                  75

Phe Ala Glu Ser Thr Glu Ile Ser Glu Leu Ser His Asn Phe Val
                80                  85                  90

Met Val Asn Leu Glu Asp Glu Glu Glu Pro Lys Asp Glu Asp Phe
                95                  100                 105

Ser Pro Asp Gly Gly Tyr Ile Pro Arg Ile Leu Phe Leu Asp Pro
                110                 115                 120
```

-continued

```
Ser Gly Lys Val His Pro Glu Ile Ile Asn Glu Asn Gly Asn Pro
                125                 130                 135

Ser Tyr Lys Tyr Phe Tyr Val Ser Ala Glu Gln Val Val Gln Gly
                140                 145                 150

Met Lys Glu Ala Gln Glu Arg Leu Thr Gly Asp Ala Phe Arg Lys
                155                 160                 165

Lys His Leu Glu Asp Glu Leu
                170


<210> SEQ ID NO 195
<211> LENGTH: 1630
<212> TYPE: DNA
<213> ORGANISM: Homo sapiens

<400> SEQUENCE: 195

cggctcgagt gcagctgtgg ggagatttca gtgcattgcc tcccctgggt           50

gctcttcatc ttggatttga aagttgagag cagcatgttt tgcccactga          100

aactcatcct gctgccagtg ttactggatt attccttggg cctgaatgac          150

ttgaatgttt ccccgcctga gctaacagtc catgtgggtg attcagctct          200

gatgggatgt gttttccaga gcacagaaga caaatgtata ttcaagatag          250

actggactct gtcaccagga gagcacgcca aggacgaata tgtgctatac          300

tattactcca atctcagtgt gcctattggg cgcttccaga accgcgtaca          350

cttgatgggg gacatcttat gcaatgatgg ctctctcctg ctccaagatg          400

tgcaagaggc tgaccaggga acctatatct gtgaaatccg cctcaaaggg          450

gagagccagg tgttcaagaa ggcggtggta ctgcatgtgc ttccagagga          500

gcccaaagag ctcatggtcc atgtgggtgg attgattcag atgggatgtg          550

ttttccagag cacagaagtg aaacacgtga ccaaggtaga atggatattt          600

tcaggacggc gcgcaaagga ggagattgta tttcgttact accacaaact          650

caggatgtct gtggagtact cccagagctg gggccacttc cagaatcgtg          700

tgaacctggt gggggacatt ttccgcaatg acggttccat catgcttcaa          750

ggagtgaggg agtcagatgg aggaaactac acctgcagta tccacctagg          800

gaacctggtg ttcaagaaaa ccattgtgct gcatgtcagc ccggaagagc          850

ctcgaacact ggtgaccccg gcagccctga ggcctctggt cttgggtggt          900

aatcagttgg tgatcattgt gggaattgtc tgtgccacaa tcctgctgct          950

ccctgttctg atattgatcg tgaagaagac ctgtggaaat aagagttcag         1000

tgaattctac agtcttggtg aagaacacga agaagactaa tccagagata         1050

aaagaaaaac cctgccattt tgaaagatgt gaaggggaga aacacattta         1100

ctccccaata attgtacggg aggtgatcga ggaagaagaa ccaagtgaaa         1150

aatcagaggc cacctacatg accatgcacc cagtttggcc ttctctgagg         1200

tcagatcgga acaactcact tgaaaaaaag tcaggtgggg gaatgccaaa         1250

aacacagcaa gccttttgag aagaatggag agtcccttca tctcagcagc         1300

ggtggagact ctctcctgtg tgtgtcctgg gccactctac cagtgatttc         1350

agactcccgc tctcccagct gtcctcctgt ctcattgttt ggtcaataca         1400

ctgaagatgg agaatttgga gcctggcaga gagactggac agctctggag         1450

gaacaggcct gctgagggga ggggagcatg gacttggcct ctggagtggg         1500
```

```
acactggccc tgggaaccag gctgagctga gtggcctcaa accccccgtt      1550

ggatcagacc ctcctgtggg cagggttctt agtggatgag ttactgggaa      1600

gaatcagaga taaaaaccaa cccaaatcaa                            1630

<210> SEQ ID NO 196
<211> LENGTH: 394
<212> TYPE: PRT
<213> ORGANISM: Homo sapiens

<400> SEQUENCE: 196

Met Phe Cys Pro Leu Lys Leu Ile Leu Leu Pro Val Leu Leu Asp
  1               5                  10                  15

Tyr Ser Leu Gly Leu Asn Asp Leu Asn Val Ser Pro Pro Glu Leu
                 20                  25                  30

Thr Val His Val Gly Asp Ser Ala Leu Met Gly Cys Val Phe Gln
                 35                  40                  45

Ser Thr Glu Asp Lys Cys Ile Phe Lys Ile Asp Trp Thr Leu Ser
                 50                  55                  60

Pro Gly Glu His Ala Lys Asp Glu Tyr Val Leu Tyr Tyr Tyr Ser
                 65                  70                  75

Asn Leu Ser Val Pro Ile Gly Arg Phe Gln Asn Arg Val His Leu
                 80                  85                  90

Met Gly Asp Ile Leu Cys Asn Asp Gly Ser Leu Leu Leu Gln Asp
                 95                 100                 105

Val Gln Glu Ala Asp Gln Gly Thr Tyr Ile Cys Glu Ile Arg Leu
                110                 115                 120

Lys Gly Glu Ser Gln Val Phe Lys Lys Ala Val Val Leu His Val
                125                 130                 135

Leu Pro Glu Glu Pro Lys Glu Leu Met Val His Val Gly Gly Leu
                140                 145                 150

Ile Gln Met Gly Cys Val Phe Gln Ser Thr Glu Val Lys His Val
                155                 160                 165

Thr Lys Val Glu Trp Ile Phe Ser Gly Arg Arg Ala Lys Glu Glu
                170                 175                 180

Ile Val Phe Arg Tyr Tyr His Lys Leu Arg Met Ser Val Glu Tyr
                185                 190                 195

Ser Gln Ser Trp Gly His Phe Gln Asn Arg Val Asn Leu Val Gly
                200                 205                 210

Asp Ile Phe Arg Asn Asp Gly Ser Ile Met Leu Gln Gly Val Arg
                215                 220                 225

Glu Ser Asp Gly Gly Asn Tyr Thr Cys Ser Ile His Leu Gly Asn
                230                 235                 240

Leu Val Phe Lys Lys Thr Ile Val Leu His Val Ser Pro Glu Glu
                245                 250                 255

Pro Arg Thr Leu Val Thr Pro Ala Ala Leu Arg Pro Leu Val Leu
                260                 265                 270

Gly Gly Asn Gln Leu Val Ile Ile Val Gly Ile Val Cys Ala Thr
                275                 280                 285

Ile Leu Leu Leu Pro Val Leu Ile Leu Ile Val Lys Lys Thr Cys
                290                 295                 300

Gly Asn Lys Ser Ser Val Asn Ser Thr Val Leu Val Lys Asn Thr
                305                 310                 315

Lys Lys Thr Asn Pro Glu Ile Lys Glu Lys Pro Cys His Phe Glu
```

-continued

```
                320                 325                 330

Arg Cys Glu Gly Glu Lys His Ile Tyr Ser Pro Ile Ile Val Arg
                335                 340                 345

Glu Val Ile Glu Glu Glu Glu Pro Ser Glu Lys Ser Glu Ala Thr
                350                 355                 360

Tyr Met Thr Met His Pro Val Trp Pro Ser Leu Arg Ser Asp Arg
                365                 370                 375

Asn Asn Ser Leu Glu Lys Lys Ser Gly Gly Gly Met Pro Lys Thr
                380                 385                 390

Gln Gln Ala Phe


<210> SEQ ID NO 197
<211> LENGTH: 783
<212> TYPE: DNA
<213> ORGANISM: Homo sapiens

<400> SEQUENCE: 197

cgccatggcc gggctatccc gcgggtccgc gcgcgcactg ctcgccgccc          50

tgctggcgtc gacgctgttg gcgctgctcg tgtcgcccgc gcggggtcgc         100

ggcggccggg accacgggga ctgggacgag gcctcccggc tgccgccgct         150

accaccccgc gaggacgcgg cgcgcgtggc ccgcttcgtg acgcacgtct         200

ccgactgggg cgctctggcc accatctcca cgctggaggc ggtgcgcggc         250

cggcccttcg ccgacgtcct ctcgctcagc gacgggcccc cgggcgcggg         300

cagcggcgtg ccctatttct acctgagccc gctgcagctc tccgtgagca         350

acctgcagga gaatccatat gctacactga ccatgacttt ggcacagacc         400

aacttctgca agaaacatgg atttgatcca caaagtcccc tttgtgttca         450

cataatgctg tcaggaactg tgaccaaggt gaatgaaaca gaaatggata         500

ttgcaaagca ttcgttattc attcgacacc ctgagatgaa aacctggcct         550

tccagccata attggttctt tgctaagttg aatataacca atatctgggt         600

cctggactac tttggtggac caaaaatcgt gacaccagaa gaatattata         650

atgtcacagt tcagtgaagc agactgtggt gaatttagca acacttatga         700

agtttcttaa agtggctcat acacacttaa aaggcttaat gtttctctgg         750

aaagcgtccc agaatattag ccagttttct  gtc                          783


<210> SEQ ID NO 198
<211> LENGTH: 220
<212> TYPE: PRT
<213> ORGANISM: Homo sapiens

<400> SEQUENCE: 198

Met Ala Gly Leu Ser Arg Gly Ser Ala Arg Ala Leu Leu Ala Ala
  1               5                  10                  15

Leu Leu Ala Ser Thr Leu Leu Ala Leu Leu Val Ser Pro Ala Arg
                 20                  25                  30

Gly Arg Gly Gly Arg Asp His Gly Asp Trp Asp Glu Ala Ser Arg
                 35                  40                  45

Leu Pro Pro Leu Pro Pro Arg Glu Asp Ala Ala Arg Val Ala Arg
                 50                  55                  60

Phe Val Thr His Val Ser Asp Trp Gly Ala Leu Ala Thr Ile Ser
                 65                  70                  75
```

-continued

```
Thr Leu Glu Ala Val Arg Gly Arg Pro Phe Ala Asp Val Leu Ser
                80                  85                  90

Leu Ser Asp Gly Pro Pro Gly Ala Gly Ser Gly Val Pro Tyr Phe
                95                  100                 105

Tyr Leu Ser Pro Leu Gln Leu Ser Val Ser Asn Leu Gln Glu Asn
                110                 115                 120

Pro Tyr Ala Thr Leu Thr Met Thr Leu Ala Gln Thr Asn Phe Cys
                125                 130                 135

Lys Lys His Gly Phe Asp Pro Gln Ser Pro Leu Cys Val His Ile
                140                 145                 150

Met Leu Ser Gly Thr Val Thr Lys Val Asn Glu Thr Glu Met Asp
                155                 160                 165

Ile Ala Lys His Ser Leu Phe Ile Arg His Pro Glu Met Lys Thr
                170                 175                 180

Trp Pro Ser Ser His Asn Trp Phe Phe Ala Lys Leu Asn Ile Thr
                185                 190                 195

Asn Ile Trp Val Leu Asp Tyr Phe Gly Gly Pro Lys Ile Val Thr
                200                 205                 210

Pro Glu Glu Tyr Tyr Asn Val Thr Val Gln
                215                 220


<210> SEQ ID NO 199
<211> LENGTH: 1315
<212> TYPE: DNA
<213> ORGANISM: Homo sapiens

<400> SEQUENCE: 199

tcgccatggc ctctgccgga atgcagatcc tgggagtcgt cctgacactg          50

ctgggctggg tgaatggcct ggtctcctgt gccctgccca tgtggaaggt         100

gaccgctttc atcggcaaca gcatcgtggt ggcccaggtg gtgtgggagg         150

gcctgtggat gtcctgcgtg gtgcagagca ccggccagat gcagtgcaag         200

gtgtacgact cactgctggc gctgccacag gacctgcagg ctgcacgtgc         250

cctctgtgtc atcgccctcc ttgtggccct gttcggcttg ctggtctacc         300

ttgctggggc caagtgtacc acctgtgtgg aggagaagga ttccaaggcc         350

cgcctggtgc tcacctctgg gattgtcttt gtcatctcag ggtcctgac          400

gctaatcccc gtgtgctgga cggcgcatgc catcatccgg gacttctata         450

accccctggt ggctgaggcc caaaagcggg agctgggggc ctccctctac         500

ttgggctggg cggcctcagg ccttttgttg ctgggtgggg ggttgctgtg         550

ctgcacttgc cctcgggggg ggtcccaggg ccccagccat tacatggccc         600

gctactcaac atctgcccct gccatctctc gggggccctc tgagtaccct         650

accaagaatt acgtctgacg tggaggggaa tgggggctcc gctggcgcta         700

gagccatcca gaagtggcag tgcccaacag ctttgggatg ggttcgtacc         750

ttttgtttct gcctcctgct atttttcttt tgactgagga tatttaaaat         800

tcatttgaaa actgagccaa ggtgttgact cagactctca cttaggctct         850

gctgtttctc acccttggat gatggagcca aagaggggat gctttgagat         900

tctggatctt gacatgccca tcttagaagc cagtcaagct atggaactaa         950

tgcggaggct gcttgctgtg ctggctttgc aacaagacag actgtcccca        1000

agagttcctg ctgctgctgg gggctgggct tccctagatg tcactggaca        1050
```

-continued

```
gctgcccccc atcctactca ggtctctgga gctcctctct tcacccctgg         1100

aaaaacaaat catctgttaa caaaggactg cccacctccg gaacttctga         1150

cctctgtttc ctccgtcctg ataagacgtc caccccccag ggccaggtcc         1200

cagctatgta gacccccgcc cccacctcca acactgcacc cttctgccct         1250

gcccccctcg tctcaccccc tttacactca catttttatc aaataaagca         1300

tgttttgtta  gtgca                                              1315
```

```
<210> SEQ ID NO 200
<211> LENGTH: 220
<212> TYPE: PRT
<213> ORGANISM: Homo sapiens

<400> SEQUENCE: 200

Met Ala Ser Ala Gly Met Gln Ile Leu Gly Val Val Leu Thr Leu
  1               5                  10                  15

Leu Gly Trp Val Asn Gly Leu Val Ser Cys Ala Leu Pro Met Trp
                 20                  25                  30

Lys Val Thr Ala Phe Ile Gly Asn Ser Ile Val Val Ala Gln Val
                 35                  40                  45

Val Trp Glu Gly Leu Trp Met Ser Cys Val Val Gln Ser Thr Gly
                 50                  55                  60

Gln Met Gln Cys Lys Val Tyr Asp Ser Leu Leu Ala Leu Pro Gln
                 65                  70                  75

Asp Leu Gln Ala Ala Arg Ala Leu Cys Val Ile Ala Leu Leu Val
                 80                  85                  90

Ala Leu Phe Gly Leu Leu Val Tyr Leu Ala Gly Ala Lys Cys Thr
                 95                 100                 105

Thr Cys Val Glu Glu Lys Asp Ser Lys Ala Arg Leu Val Leu Thr
                110                 115                 120

Ser Gly Ile Val Phe Val Ile Ser Gly Val Leu Thr Leu Ile Pro
                125                 130                 135

Val Cys Trp Thr Ala His Ala Ile Ile Arg Asp Phe Tyr Asn Pro
                140                 145                 150

Leu Val Ala Glu Ala Gln Lys Arg Glu Leu Gly Ala Ser Leu Tyr
                155                 160                 165

Leu Gly Trp Ala Ala Ser Gly Leu Leu Leu Leu Gly Gly Gly Leu
                170                 175                 180

Leu Cys Cys Thr Cys Pro Ser Gly Gly Ser Gln Gly Pro Ser His
                185                 190                 195

Tyr Met Ala Arg Tyr Ser Thr Ser Ala Pro Ala Ile Ser Arg Gly
                200                 205                 210

Pro Ser Glu Tyr Pro Thr Lys Asn Tyr Val
                215                 220
```

```
<210> SEQ ID NO 201
<211> LENGTH: 535
<212> TYPE: DNA
<213> ORGANISM: Homo sapiens

<400> SEQUENCE: 201

agtgacaatc tcagagcagc ttctacacca cagccatttc cagcatgaag           50

atcactgggg gtctccttct gctctgtaca gtggtctatt tctgtagcag          100

ctcagaagct gctagtctgt ctccaaaaaa agtggactgc agcatttaca          150
```

-continued

```
agaagtatcc agtggtggcc atcccctgcc ccatcacata cctaccagtt          200

tgtggttctg actacatcac ctatgggaat gaatgtcact tgtgtaccga          250

gagcttgaaa agtaatggaa gagttcagtt tcttcacgat ggaagttgct          300

aaattctcca tggacataga gagaaaggaa tgatattctc atcatcatct          350

tcatcatccc aggctctgac tgagtttctt tcagttttac tgatgttctg          400

ggtgggggac agagccagat tcagagtaat cttgactgaa tggagaaagt          450

ttctgtgcta cccctacaaa cccatgcctc actgacagac cagcattttt          500

tttttaacac gtcaataaaa aaataatctc  ccaga                         535
```

<210> SEQ ID NO 202
<211> LENGTH: 85
<212> TYPE: PRT
<213> ORGANISM: Homo sapiens

<400> SEQUENCE: 202

```
Met Lys Ile Thr Gly Gly Leu Leu Leu Leu Cys Thr Val Val Tyr
  1               5                  10                  15

Phe Cys Ser Ser Ser Glu Ala Ala Ser Leu Ser Pro Lys Lys Val
                 20                  25                  30

Asp Cys Ser Ile Tyr Lys Lys Tyr Pro Val Val Ala Ile Pro Cys
                 35                  40                  45

Pro Ile Thr Tyr Leu Pro Val Cys Gly Ser Asp Tyr Ile Thr Tyr
                 50                  55                  60

Gly Asn Glu Cys His Leu Cys Thr Glu Ser Leu Lys Ser Asn Gly
                 65                  70                  75

Arg Val Gln Phe Leu His Asp Gly Ser Cys
                 80                  85
```

<210> SEQ ID NO 203
<211> LENGTH: 2387
<212> TYPE: DNA
<213> ORGANISM: Homo sapiens

<400> SEQUENCE: 203

```
cgacgatgct acgcgcgccc ggctgcctcc tccggacctc cgtagcgcct           50

gccgcggccc tggctgcggc gctgctctcg tcgcttgcgc gctgctctct          100

tctagagccg agggacccgg tggcctcgtc gctcagcccc tatttcggca          150

ccaagactcg ctacgaggat gtcaaccccg tgctattgtc gggccccgag          200

gctccgtggc gggaccctga gctgctggag gggacctgca ccccggtgca          250

gctggtcgcc ctcattcgcc acggcacccg ctaccccacg gtcaaacaga          300

tccgcaagct gaggcagctg cacgggttgc tgcaggcccg cgggtccagg          350

gatggcgggg ctagtagtac cggcagccgc gacctgggtg cagcgctggc          400

cgactggcct ttgtggtacg cggactggat ggacgggcag ctagtagaga          450

agggacggca ggatatgcga cagctggcgc tgcgtctggc ctcgctcttc          500

ccggcccttt tcagccgtga gaactacggc cgcctgcggc tcatcaccag          550

ttccaagcac cgctgcatgg atagcagcgc cgccttcctg caggggctgt          600

ggcagcacta ccaccctggc ttgccgccgc cggacgtcgc agatatggag          650

tttggacctc caacagttaa tgataaacta atgagatttt ttgatcactg          700
```

-continued

```
tgagaagttt ttaactgaag tagaaaaaaa tgctacagct ctttatcacg        750
tggaagcctt caaaactgga ccagaaatgc agaacatttt aaaaaaagtt        800
gcagctactt tgcaagtgcc agtaaatgat ttaaatgcag atttaattca        850
agtagccttt ttcacctgtt catttgacct ggcaattaaa ggtgttaaat        900
ctccttggtg tgatgttttt gacatagatg atgcaaaggt attagaatat        950
ttaaatgatc tgaaacaata ttggaaaaga ggatatgggt atactattaa       1000
cagtcgatcc agctgcacct tgtttcagga tatctttcag cacttggaca       1050
aagcagttga acagaaacaa aggtctcagc caatttcttc tccagtcatc       1100
ctccagtttg gtcatgcaga gactcttctt ccactgcttt ctctcatggg       1150
ctacttcaaa gacaaggaac ccctaacagc gtacaattac aaaaaacaaa       1200
tgcatcggaa gttccgaagt ggtctcattg taccttatgc ctcgaacctg       1250
atatttgtgc tttaccactg tgaaaatgct aagactccta aagaacaatt       1300
ccgagtgcag atgttattaa atgaaaaggt gttacctttg gcttactcac       1350
aagaaactgt ttcattttat gaagatctga agaaccacta caaggacatc       1400
cttcagagtt gtcaaaccag tgaagaatgt gaattagcaa gggctaacag       1450
tacatctgat gaactatgag taactgaaga acatttttaa ttctttagga       1500
atctgcaatg agtgattaca tgcttgtaat aggtaggcaa ttccttgatt       1550
acaggaagct tttatattac ttgagtattt ctgtcttttc acagaaaaac       1600
attgggtttc tctctgggtt tggacatgaa atgtaagaaa agatttttca       1650
ctggagcagc tctcttaagg agaaacaaat ctatttagag aaacagctgg       1700
ccctgcaaat gtttacagaa atgaaattct tcctacttat ataagaaatc       1750
tcacactgag atagaattgt gatttcataa taacacttga aaagtgctgg       1800
agtaacaaaa tatctcagtt ggaccatcct taacttgatt gaactgtcta       1850
ggaactttac agattgttct gcagttctct cttcttttcc tcaggtagga       1900
cagctctagc attttcttaa tcaggaatat tgtggtaagc tgggagtatc       1950
actctggaag aaagtaacat ctccagatga gaatttgaaa caagaaacag       2000
agtgttgtaa aaggacacct tcactgaagc aagtcggaaa gtacaatgaa       2050
aataaatatt tttggtattt atttatgaaa tatttgaaca ttttttcaat       2100
aattcctttt tacttctagg aagtctcaaa agaccatctt aaattattat       2150
atgtttggac aattagcaac aagtcagata gttagaatcg aagtttttca       2200
aatccattgc ttagctaact ttttcattct gtcacttggc ttcgattttt       2250
atattttcct attatatgaa atgtatcttt tggttgtttg atttttcttt       2300
ctttctttgt aaatagttct gagttctgtc aaatgccgtg aaagtatttg       2350
ctataataaa gaaaattctt gtgactttaa  aaaaaaa                    2387
```

<210> SEQ ID NO 204
<211> LENGTH: 487
<212> TYPE: PRT
<213> ORGANISM: Homo sapiens

<400> SEQUENCE: 204

```
Met Leu Arg Ala Pro Gly Cys Leu Leu Arg Thr Ser Val Ala Pro
  1               5                  10                  15
```

-continued

```
Ala Ala Ala Leu Ala Ala Ala Leu Leu Ser Ser Leu Ala Arg Cys
                20                  25                  30

Ser Leu Leu Glu Pro Arg Asp Pro Val Ala Ser Ser Leu Ser Pro
                35                  40                  45

Tyr Phe Gly Thr Lys Thr Arg Tyr Glu Asp Val Asn Pro Val Leu
                50                  55                  60

Leu Ser Gly Pro Glu Ala Pro Trp Arg Asp Pro Glu Leu Leu Glu
                65                  70                  75

Gly Thr Cys Thr Pro Val Gln Leu Val Ala Leu Ile Arg His Gly
                80                  85                  90

Thr Arg Tyr Pro Thr Val Lys Gln Ile Arg Lys Leu Arg Gln Leu
                95                 100                 105

His Gly Leu Leu Gln Ala Arg Gly Ser Arg Asp Gly Gly Ala Ser
               110                 115                 120

Ser Thr Gly Ser Arg Asp Leu Gly Ala Ala Leu Ala Asp Trp Pro
               125                 130                 135

Leu Trp Tyr Ala Asp Trp Met Asp Gly Gln Leu Val Glu Lys Gly
               140                 145                 150

Arg Gln Asp Met Arg Gln Leu Ala Leu Arg Leu Ala Ser Leu Phe
               155                 160                 165

Pro Ala Leu Phe Ser Arg Glu Asn Tyr Gly Arg Leu Arg Leu Ile
               170                 175                 180

Thr Ser Ser Lys His Arg Cys Met Asp Ser Ser Ala Ala Phe Leu
               185                 190                 195

Gln Gly Leu Trp Gln His Tyr His Pro Gly Leu Pro Pro Pro Asp
               200                 205                 210

Val Ala Asp Met Glu Phe Gly Pro Pro Thr Val Asn Asp Lys Leu
               215                 220                 225

Met Arg Phe Phe Asp His Cys Glu Lys Phe Leu Thr Glu Val Glu
               230                 235                 240

Lys Asn Ala Thr Ala Leu Tyr His Val Glu Ala Phe Lys Thr Gly
               245                 250                 255

Pro Glu Met Gln Asn Ile Leu Lys Lys Val Ala Ala Thr Leu Gln
               260                 265                 270

Val Pro Val Asn Asp Leu Asn Ala Asp Leu Ile Gln Val Ala Phe
               275                 280                 285

Phe Thr Cys Ser Phe Asp Leu Ala Ile Lys Gly Val Lys Ser Pro
               290                 295                 300

Trp Cys Asp Val Phe Asp Ile Asp Asp Ala Lys Val Leu Glu Tyr
               305                 310                 315

Leu Asn Asp Leu Lys Gln Tyr Trp Lys Arg Gly Tyr Gly Tyr Thr
               320                 325                 330

Ile Asn Ser Arg Ser Ser Cys Thr Leu Phe Gln Asp Ile Phe Gln
               335                 340                 345

His Leu Asp Lys Ala Val Glu Gln Lys Gln Arg Ser Gln Pro Ile
               350                 355                 360

Ser Ser Pro Val Ile Leu Gln Phe Gly His Ala Glu Thr Leu Leu
               365                 370                 375

Pro Leu Leu Ser Leu Met Gly Tyr Phe Lys Asp Lys Glu Pro Leu
               380                 385                 390

Thr Ala Tyr Asn Tyr Lys Lys Gln Met His Arg Lys Phe Arg Ser
               395                 400                 405

Gly Leu Ile Val Pro Tyr Ala Ser Asn Leu Ile Phe Val Leu Tyr
```

-continued

```
                410                 415                 420

His Cys Glu Asn Ala Lys Thr Pro Lys Glu Gln Phe Arg Val Gln
                425                 430                 435

Met Leu Leu Asn Glu Lys Val Leu Pro Leu Ala Tyr Ser Gln Glu
                440                 445                 450

Thr Val Ser Phe Tyr Glu Asp Leu Lys Asn His Tyr Lys Asp Ile
                455                 460                 465

Leu Gln Ser Cys Gln Thr Ser Glu Glu Cys Glu Leu Ala Arg Ala
                470                 475                 480

Asn Ser Thr Ser Asp Glu Leu
                485


<210> SEQ ID NO 205
<211> LENGTH: 1098
<212> TYPE: DNA
<213> ORGANISM: Homo sapiens

<400> SEQUENCE: 205

gcgacgcgcg gcggggcggc gagaggaaac gcggcgccgg gccgggcccg              50

gccctggaga tggtccccgg cgccgcgggc tggtgttgtc tcgtgctctg             100

gctccccgcg tgcgtcgcgg cccacggctt ccgtatccat gattatttgt             150

actttcaagt gctgagtcct ggggacattc gatacatctt cacagccaca             200

cctgccaagg actttggtgg tatctttcac acaaggtatg agcagattca             250

ccttgtcccc gctgaacctc cagaggcctg cggggaactc agcaacggtt             300

tcttcatcca ggaccagatt gctctggtgg agagggggg ctgctccttc              350

ctctccaaga ctcgggtggt ccaggagcac ggcgggcggg cggtgatcat             400

ctctgacaac gcagttgaca atgacagctt ctacgtggag atgatccagg             450

acagtaccca gcgcacagct gacatccccg ccctcttcct gctcggccga             500

gacggctaca tgatccgccg ctctctggaa cagcatgggc tgccatgggc             550

catcatttcc atcccagtca atgtcaccag catccccacc tttgagctgc             600

tgcaaccgcc ctggaccttc tggtagaaga gtttgtccca cattccagcc             650

ataagtgact ctgagctggg aaggggaaac ccaggaattt tgctacttgg             700

aatttggaga tagcatctgg ggacaagtgg agccaggtag aggaaaaggg             750

tttgggcgtt gctaggctga aagggaagcc acaccactgg ccttcccttc             800

cccagggccc ccaagggtgt ctcatgctac aagaagaggc aagagacagg             850

ccccagggct tctggctaga acccgaaaca aaaggagctg aaggcaggtg             900

gcctgagagc catctgtgac ctgtcacact cacctggctc cagcctcccc             950

tacccagggt ctctgcacag tgaccttcac agcagttgtt ggagtggttt            1000

aaagagctgg tgtttgggga ctcaataaac cctcactgac tttttagcaa            1050

taaagcttct catcagggtt gcaaaaaaaa aaaaaaaaaa  aaaaaaaa             1098


<210> SEQ ID NO 206
<211> LENGTH: 188
<212> TYPE: PRT
<213> ORGANISM: Homo sapiens

<400> SEQUENCE: 206

Met Val Pro Gly Ala Ala Gly Trp Cys Cys Leu Val Leu Trp Leu
  1               5                  10                  15
```

-continued

```
Pro Ala Cys Val Ala Ala His Gly Phe Arg Ile His Asp Tyr Leu
                20                  25                  30

Tyr Phe Gln Val Leu Ser Pro Gly Asp Ile Arg Tyr Ile Phe Thr
                35                  40                  45

Ala Thr Pro Ala Lys Asp Phe Gly Gly Ile Phe His Thr Arg Tyr
                50                  55                  60

Glu Gln Ile His Leu Val Pro Ala Glu Pro Pro Glu Ala Cys Gly
                65                  70                  75

Glu Leu Ser Asn Gly Phe Phe Ile Gln Asp Gln Ile Ala Leu Val
                80                  85                  90

Glu Arg Gly Gly Cys Ser Phe Leu Ser Lys Thr Arg Val Val Gln
                95                  100                 105

Glu His Gly Gly Arg Ala Val Ile Ile Ser Asp Asn Ala Val Asp
                110                 115                 120

Asn Asp Ser Phe Tyr Val Glu Met Ile Gln Asp Ser Thr Gln Arg
                125                 130                 135

Thr Ala Asp Ile Pro Ala Leu Phe Leu Leu Gly Arg Asp Gly Tyr
                140                 145                 150

Met Ile Arg Arg Ser Leu Glu Gln His Gly Leu Pro Trp Ala Ile
                155                 160                 165

Ile Ser Ile Pro Val Asn Val Thr Ser Ile Pro Thr Phe Glu Leu
                170                 175                 180

Leu Gln Pro Pro Trp Thr Phe Trp
                185
```

<210> SEQ ID NO 207
<211> LENGTH: 764
<212> TYPE: DNA
<213> ORGANISM: Homo sapiens

<400> SEQUENCE: 207

```
ctcgcttctt ccttctggat gggggcccag ggggcccagg agagtataaa        50

ggcgatgtgg agggtgcccg gcacaaccag acgcccagtc acaggcgaga       100

gccctgggat gcaccggcca gaggccatgc tgctgctgct cacgcttgcc       150

ctcctggggg gccccacctg ggcagggaag atgtatggcc ctggaggagg       200

caagtatttc agcaccactg aagactacga ccatgaaatc acagggctgc       250

gggtgtctgt aggtcttctc ctggtgaaaa gtgtccaggt gaaacttgga       300

gactcctggg acgtgaaact gggagcctta ggtgggaata cccaggaagt       350

caccctgcag ccaggcgaat acatcacaaa agtctttgtc gccttccaag       400

ctttcctccg ggtatggtc atgtacacca gcaaggaccg ctatttctat        450

tttgggaagc ttgatggcca gatctcctct gcctacccca gccaagaggg       500

gcaggtgctg gtgggcatct atggccagta tcaactcctt ggcatcaaga       550

gcattggctt tgaatggaat tatccactag aggagccgac cactgagcca       600

ccagttaatc tcacatactc agcaaactca cccgtgggtc gctagggtgg       650

ggtatggggc catccgagct gaggccatct gtgtggtggt ggctgatggt       700

actggagtaa ctgagtcggg acgctgaatc tgaatccacc aataaataaa       750

gcttctgcag  aaaa                                             764
```

<210> SEQ ID NO 208

<211> LENGTH: 178
<212> TYPE: PRT
<213> ORGANISM: Homo sapiens

<400> SEQUENCE: 208

Met His Arg Pro Glu Ala Met Leu Leu Leu Leu Thr Leu Ala Leu
1 5 10 15

Leu Gly Gly Pro Thr Trp Ala Gly Lys Met Tyr Gly Pro Gly Gly
20 25 30

Gly Lys Tyr Phe Ser Thr Thr Glu Asp Tyr Asp His Glu Ile Thr
35 40 45

Gly Leu Arg Val Ser Val Gly Leu Leu Leu Val Lys Ser Val Gln
50 55 60

Val Lys Leu Gly Asp Ser Trp Asp Val Lys Leu Gly Ala Leu Gly
65 70 75

Gly Asn Thr Gln Glu Val Thr Leu Gln Pro Gly Glu Tyr Ile Thr
80 85 90

Lys Val Phe Val Ala Phe Gln Ala Phe Leu Arg Gly Met Val Met
95 100 105

Tyr Thr Ser Lys Asp Arg Tyr Phe Tyr Phe Gly Lys Leu Asp Gly
110 115 120

Gln Ile Ser Ser Ala Tyr Pro Ser Gln Glu Gly Gln Val Leu Val
125 130 135

Gly Ile Tyr Gly Gln Tyr Gln Leu Leu Gly Ile Lys Ser Ile Gly
140 145 150

Phe Glu Trp Asn Tyr Pro Leu Glu Glu Pro Thr Thr Glu Pro Pro
155 160 165

Val Asn Leu Thr Tyr Ser Ala Asn Ser Pro Val Gly Arg
170 175

<210> SEQ ID NO 209
<211> LENGTH: 3824
<212> TYPE: DNA
<213> ORGANISM: Homo sapiens

<400> SEQUENCE: 209
ggagaatgga gagagcagtg agagtggagt ccggggtcct ggtcggggtg 50
gtctgtctgc tcctggcatg ccctgccaca gccactgggc ccgaagttgc 100
tcagcctgaa gtagacacca ccctgggtcg tgtgcgaggc cggcaggtgg 150
gcgtgaaggg cacagaccgc cttgtgaatg tctttctggg cattccattt 200
gcccagccgc cactgggccc tgaccggttc tcagccccac acccagcaca 250
gccctgggag ggtgtgcggg atgccagcac tgcgccccca atgtgcctac 300
aagacgtgga gagcatgaac agcagcagat ttgtcctcaa cggaaaacag 350
cagatcttct ccgtttcaga ggactgcctg gtcctcaacg tctatagccc 400
agctgaggtc cccgcagggt ccggtaggcc ggtcatggta tgggtccatg 450
gaggcgctct gataactggc gctgccacct cctacgatgg atcagctctg 500
gctgcctatg gggatgtggt cgtggttaca gtccagtacc gccttggggt 550
ccttggcttc ttcagcactg gagatgagca tgcacctggc aaccagggct 600
tcctagatgt ggtagctgct ttgcgctggg tgcaagaaaa catcgccccc 650
ttcgggggtg acctcaactg tgtcactgtc tttggtggat ctgccggtgg 700
gagcatcatc tctggcctgg tcctgtcccc agtggctgca gggctgttcc 750

-continued

```
acagagccat cacacagagt ggggtcatca ccaccccagg gatcatcgac      800
tctcaccctt ggcccctagc tcagaaaatc gcaaacacct tggcctgcag      850
ctccagctcc ccggctgaga tggtgcagtg ccttcagcag aaagaaggag      900
aagagctggt ccttagcaag aagctgaaaa atactatcta tcctctcacc      950
gttgatggca ctgtcttccc caaaagcccc aaggaactcc tgaaggagaa     1000
gcccttccac tctgtgccct tcctcatggg tgtcaacaac catgagttca     1050
gctggctcat ccccaggggc tggggtctcc tggatacaat ggagcagatg     1100
agccgggagg acatgctggc catctcaaca cccgtcttga ccagtctgga     1150
tgtgcccccct gagatgatgc ccaccgtcat agatgaatac ctaggaagca     1200
actcggacgc acaagccaaa tgccaggcgt tccaggaatt catgggtgac     1250
gtattcatca atgttcccac cgtcagtttt tcaagatacc ttcgagattc     1300
tggaagccct gtctttttct atgagttcca gcatcgaccc agttcttttg     1350
cgaagatcaa acctgcctgg gtgaaggctg atcatggggc cgagggtgct     1400
tttgtgttcg gaggtccctt cctcatggac gagagctccc gcctggcctt     1450
tccagaggcc acagaggagg agaagcagct aagcctcacc atgatggccc     1500
agtggaccca ctttgcccgg acaggggacc ccaatagcaa ggctctgcct     1550
ccttggcccc aattcaacca ggcggaacaa tatctggaga tcaacccagt     1600
gccacgggcc ggacagaagt tcagggaggc ctggatgcag ttctggtcag     1650
agacgctccc cagcaagata caacagtggc accagaagca gaagaacagg     1700
aaggcccagg aggacctctg aggccaggcc tgaaccttct tggctggggc     1750
aaaccactct tcaagtggtg gcagagtccc agcacggcag cccgcctctc     1800
cccctgctga gactttaatc tccaccagcc cttaaagtgt cggccgctct     1850
gtgactggag ttatgctctt ttgaaatgtc acaaggccgc ctcccacctc     1900
tggggcattg tacaagttct tccctctccc tgaagtgcct ttcctgcttt     1950
cttcgtggta ggttctagca cattcctcta gcttcctgga ggactcactc     2000
cccaggaagc cttccctgcc ttctctgggc tgtgcggccc cgagtctgcg     2050
tccattagag cacagtccac ccgaggctag caccgtgtct gtgtctgtct     2100
ccccctcaga ggagctctct caaaatgggg attagcctaa ccccactctg     2150
tcacccacac caggatcggg tgggacctgg agctaggggg tgtttgctga     2200
gtgagtgagt gaaacacaga atatgggaat ggcagctgct gaacttgaac     2250
ccagagcctt caggtgccaa agccatactc aggcccccac cgacattgtc     2300
caccctggcc agaagggtgc atgccaatgg cagagacctg ggatgggaga     2350
agtcctgggg cgccagggga tccagcctag agcagacctt agcccctgac     2400
taaggcctca gactagggcg ggaggggtct cctcctctct gctgcccagt     2450
cctggcccct gcacaagaca acagaatcca tcagggccat gagtgtcacc     2500
cagacctgac cctcaccaat tccagcccct gaccctcagg acgctggatg     2550
ccagctccca gccccagtgc cgggtcctcc ctcccttcct ggcttgggga     2600
gaccagtttc tggggagctt ccaagagcac ccaccaagac acagcaggac     2650
aggccagggg agggcatctg gaccagggca tccgtcgggc tattgtcaca     2700
```

-continued

```
gagaaaagaa gagacccacc cactcgggct gcaaaaggtg aaaagcacca           2750

agaggttttc agatggaagt gagaggtgac agtgtgctgg cagccctcac           2800

agccctcgct tgctctccct gccgcctctg cctgggctcc cactttggca           2850

gcacttgagg agcccttcaa cccgccgctg cactgtagga gccccttct            2900

gggctggcca aggccggagc cagctccctc agcttgcggg gaggtgcgga           2950

gggagagggg cgggcaggaa ccggggctgc gcgcagcgct tgcgggccag           3000

agtgagttcc gggtgggcgt gggctcggcg gggccccact cagagcagct           3050

ggccggcccc aggcagtgag ggccttagca cctgggccag cagctgctgt           3100

gctcgatttc tcgctgggcc ttagctgcct ccccgcgggg cagggctcgg           3150

gacctgcagc cctccatgcc tgaccctccc cccacccccc gtgggctcct           3200

gtgcggccgg agcctcccca aggagcgccg ccccctgctc cacagcgccc           3250

agtcccatcg accacccaag ggctgaggag tgcgggtgca cagcgcggga           3300

ctggcaggca gctccacctg ctgccccagt gctggatcca ctgggtgaag           3350

ccagctgggc tcctgagtct ggtggggact tggagaacct ttatgtctag           3400

ctaagggatt gtaaatacac cgatgggcac tctgtatcta gctcaaggtt           3450

tgtaaacaca ccaatcagca ccctgtgtct agctcagtgt ttgtgaatgc           3500

accaatccac actctgtatc tggctactct ggtggggact tggagaacct           3550

ttgtgtccac actctgtatc tagctaatct agtggggatg tggagaacct           3600

ttgtgtctag ctcagggatc gtaaacgcac caatcagcac cctgtcaaaa           3650

cagaccactt gactctctgt aaaatggacc aatcagcagg atgtgggtgg           3700

ggcgagacaa gagaataaaa gcaggctgcc tgagccagca gtgacaaccc           3750

ccctcgggtc ccctcccacg ccgtggaagc tttgttcttt cgctctttgc           3800

aataaatctt gctactgccc  aaaa                                      3824
```

<210> SEQ ID NO 210
<211> LENGTH: 571
<212> TYPE: PRT
<213> ORGANISM: Homo sapiens

<400> SEQUENCE: 210

```
Met Glu Arg Ala Val Arg Val Glu Ser Gly Val Leu Val Gly Val
  1               5                  10                  15

Val Cys Leu Leu Leu Ala Cys Pro Ala Thr Ala Thr Gly Pro Glu
                 20                  25                  30

Val Ala Gln Pro Glu Val Asp Thr Thr Leu Gly Arg Val Arg Gly
                 35                  40                  45

Arg Gln Val Gly Val Lys Gly Thr Asp Arg Leu Val Asn Val Phe
                 50                  55                  60

Leu Gly Ile Pro Phe Ala Gln Pro Pro Leu Gly Pro Asp Arg Phe
                 65                  70                  75

Ser Ala Pro His Pro Ala Gln Pro Trp Glu Gly Val Arg Asp Ala
                 80                  85                  90

Ser Thr Ala Pro Pro Met Cys Leu Gln Asp Val Glu Ser Met Asn
                 95                 100                 105

Ser Ser Arg Phe Val Leu Asn Gly Lys Gln Gln Ile Phe Ser Val
                110                 115                 120

Ser Glu Asp Cys Leu Val Leu Asn Val Tyr Ser Pro Ala Glu Val
```

-continued

```
                125                 130                 135

Pro Ala Gly Ser Gly Arg Pro Val Met Val Trp Val His Gly Gly
                140                 145                 150

Ala Leu Ile Thr Gly Ala Ala Thr Ser Tyr Asp Gly Ser Ala Leu
                155                 160                 165

Ala Ala Tyr Gly Asp Val Val Val Val Thr Val Gln Tyr Arg Leu
                170                 175                 180

Gly Val Leu Gly Phe Phe Ser Thr Gly Asp Glu His Ala Pro Gly
                185                 190                 195

Asn Gln Gly Phe Leu Asp Val Val Ala Ala Leu Arg Trp Val Gln
                200                 205                 210

Glu Asn Ile Ala Pro Phe Gly Gly Asp Leu Asn Cys Val Thr Val
                215                 220                 225

Phe Gly Gly Ser Ala Gly Gly Ser Ile Ile Ser Gly Leu Val Leu
                230                 235                 240

Ser Pro Val Ala Ala Gly Leu Phe His Arg Ala Ile Thr Gln Ser
                245                 250                 255

Gly Val Ile Thr Thr Pro Gly Ile Ile Asp Ser His Pro Trp Pro
                260                 265                 270

Leu Ala Gln Lys Ile Ala Asn Thr Leu Ala Cys Ser Ser Ser Ser
                275                 280                 285

Pro Ala Glu Met Val Gln Cys Leu Gln Gln Lys Glu Gly Glu Glu
                290                 295                 300

Leu Val Leu Ser Lys Lys Leu Lys Asn Thr Ile Tyr Pro Leu Thr
                305                 310                 315

Val Asp Gly Thr Val Phe Pro Lys Ser Pro Lys Glu Leu Leu Lys
                320                 325                 330

Glu Lys Pro Phe His Ser Val Pro Phe Leu Met Gly Val Asn Asn
                335                 340                 345

His Glu Phe Ser Trp Leu Ile Pro Arg Gly Trp Gly Leu Leu Asp
                350                 355                 360

Thr Met Glu Gln Met Ser Arg Glu Asp Met Leu Ala Ile Ser Thr
                365                 370                 375

Pro Val Leu Thr Ser Leu Asp Val Pro Pro Glu Met Met Pro Thr
                380                 385                 390

Val Ile Asp Glu Tyr Leu Gly Ser Asn Ser Asp Ala Gln Ala Lys
                395                 400                 405

Cys Gln Ala Phe Gln Glu Phe Met Gly Asp Val Phe Ile Asn Val
                410                 415                 420

Pro Thr Val Ser Phe Ser Arg Tyr Leu Arg Asp Ser Gly Ser Pro
                425                 430                 435

Val Phe Phe Tyr Glu Phe Gln His Arg Pro Ser Ser Phe Ala Lys
                440                 445                 450

Ile Lys Pro Ala Trp Val Lys Ala Asp His Gly Ala Glu Gly Ala
                455                 460                 465

Phe Val Phe Gly Gly Pro Phe Leu Met Asp Glu Ser Ser Arg Leu
                470                 475                 480

Ala Phe Pro Glu Ala Thr Glu Glu Glu Lys Gln Leu Ser Leu Thr
                485                 490                 495

Met Met Ala Gln Trp Thr His Phe Ala Arg Thr Gly Asp Pro Asn
                500                 505                 510

Ser Lys Ala Leu Pro Pro Trp Pro Gln Phe Asn Gln Ala Glu Gln
                515                 520                 525
```

-continued

```
Tyr Leu Glu Ile Asn Pro Val Pro Arg Ala Gly Gln Lys Phe Arg
                530                 535                 540

Glu Ala Trp Met Gln Phe Trp Ser Glu Thr Leu Pro Ser Lys Ile
                545                 550                 555

Gln Gln Trp His Gln Lys Gln Lys Asn Arg Lys Ala Gln Glu Asp
                560                 565                 570

Leu


<210> SEQ ID NO 211
<211> LENGTH: 1177
<212> TYPE: DNA
<213> ORGANISM: Homo sapiens

<400> SEQUENCE: 211

aacttctaca tgggcctcct gctgctggtg ctcttcctca gcctcctgcc             50

ggtggcctac accatcatgt ccctcccacc ctcctttgac tgcgggccgt            100

tcaggtgcag agtctcagtt gcccgggagc acctcccctc ccgaggcagt            150

ctgctcagag ggcctcggcc cagaattcca gttctggttt catgccagcc            200

tgtaaaaggc catggaactt tgggtgaatc accgatgcca tttaagaggg            250

ttttctgcca ggatggaaat gttaggtcgt tctgtgtctg cgctgttcat            300

ttcagtagcc accagccacc tgtggccgtt gagtgcttga aatgaggaac            350

tgagaaaatt aatttctcat gtatttttct catttattta ttaattttta            400

actgatagtt gtacatattt gggggtacat gtgatatttg gatacatgta            450

tacaatatat aatgatcaaa tcagggtaac tgggatatcc atcacatcaa            500

acatttattt tttattcttt ttagacagag tctcactctg tcacccaggc            550

tggagtgcag tggtgccatc tcagcttact gcaacctctg cctgccaggt            600

tcaagcgatt ctcatgcctc cacctcccaa gtagctggga ctacaggcat            650

gcaccacaat gcccaactaa tttttgtatt tttagtagag acggggtttt            700

gccatgttgc ccaggctggc cttgaactcc tggcctcaaa caatccactt            750

gcctcggcct cccaaagtgt tatgattaca ggcgtgagcc accgtgcctg            800

gcctaaacat ttatcttttc tttgtgttgg gaactttgaa attatacaat            850

gaattattgt taactgtcat ctccctgctg tgctatggaa cactgggact            900

tcttccctct atctaactgt atatttgtac cagttaacca accgtacttc            950

atccccactc ctctctatcc ttcccaacct ctgatcacct cattctactc           1000

tctacctcca tgagatccac ttttttagct cccacatgtg agtaagaaaa           1050

tgcaatattt gtctttctgt gcctggctta tttcacttaa cataatgact           1100

tcctgttcca tccatgttgc tgcaaatgac aggatttcgt tcttaatttc           1150

aattaaaata accacacatg  gcaaaaa                                   1177


<210> SEQ ID NO 212
<211> LENGTH: 111
<212> TYPE: PRT
<213> ORGANISM: Homo sapiens

<400> SEQUENCE: 212

Met Gly Leu Leu Leu Leu Val Leu Phe Leu Ser Leu Leu Pro Val
  1               5                  10                  15
```

-continued

```
Ala Tyr Thr Ile Met Ser Leu Pro Pro Ser Phe Asp Cys Gly Pro
                20                  25                  30

Phe Arg Cys Arg Val Ser Val Ala Arg Glu His Leu Pro Ser Arg
                35                  40                  45

Gly Ser Leu Leu Arg Gly Pro Arg Pro Arg Ile Pro Val Leu Val
                50                  55                  60

Ser Cys Gln Pro Val Lys Gly His Gly Thr Leu Gly Glu Ser Pro
                65                  70                  75

Met Pro Phe Lys Arg Val Phe Cys Gln Asp Gly Asn Val Arg Ser
                80                  85                  90

Phe Cys Val Cys Ala Val His Phe Ser Ser His Gln Pro Pro Val
                95                  100                 105

Ala Val Glu Cys Leu Lys
                110


<210> SEQ ID NO 213
<211> LENGTH: 2159
<212> TYPE: DNA
<213> ORGANISM: Homo sapiens

<400> SEQUENCE: 213

agggcccgcg ggtggagaga gcgacgcccg aggggatggc ggcagcgtcc          50

cggagcgcct ctggctgggc gctactgctg ctggtggcac tttggcagca         100

gcgcgcggcc ggctccggcg tcttccagct gcagctgcag gagttcatca         150

acgagcgcgg cgtactggcc agtgggcggc cttgcgagcc cggctgccgg         200

actttcttcc gcgtctgcct taagcacttc caggcggtcg tctcgcccgg         250

accctgcacc ttcgggaccg tctccacgcc ggtattgggc accaactcct         300

tcgctgtccg ggacgacagt agcggcgggg ggcgcaaccc tctccaactg         350

cccttcaatt tcacctggcc gggtaccttc tcgctcatca tcgaagcttg         400

gcacgcgcca ggagacgacc tgcggccaga ggccttgcca ccagatgcac         450

tcatcagcaa gatcgccatc cagggctccc tagctgtggg tcagaactgg         500

ttattggatg agcaaaccag caccctcaca aggctgcgct actcttaccg         550

ggtcatctgc agtgacaact actatggaga caactgctcc cgcctgtgca         600

agaagcgcaa tgaccacttc ggccactatg tgtgccagcc agatggcaac         650

ttgtcctgcc tgcccggttg gactggggaa tattgccaac agcctatctg         700

tctttcgggc tgtcatgaac agaatggcta ctgcagcaag ccagcagagt         750

gcctctgccg cccaggctgg cagggccggc tgtgtaacga atgcatcccc         800

cacaatggct gtcgccacgg cacctgcagc actccctggc aatgtacttg         850

tgatgagggc tggggaggcc tgttttgtga ccaagatctc aactactgca         900

cccaccactc cccatgcaag aatggggcaa cgtgctccaa cagtgggcag         950

cgaagctaca cctgcacctg tcgcccaggc tacactggtg tggactgtga        1000

gctggagctc agcgagtgtg acagcaaccc ctgtcgcaat ggaggcagct        1050

gtaaggacca ggaggatggc taccactgcc tgtgtcctcc gggctactat        1100

ggcctgcact gtgaacacag caccttgagc tgcgccgact ccccctgctt        1150

caatgggggc tcctgccggg agcgcaacca gggggccaac tatgcttgtg        1200

aatgtccccc caacttcacc ggctccaact gcgagaagaa agtggacagg        1250
```

-continued

```
tgcaccagca acccctgtgc caacggggga cagtgcctga accgaggtcc           1300

aagccgcatg tgccgctgcc gtcctggatt cacgggcacc tactgtgaac           1350

tccacgtcag cgactgtgcc cgtaaccctt gcgcccacgg tggcacttgc           1400

catgacctgg agaatgggct catgtgcacc tgccctgccg gcttctctgg           1450

ccgacgctgt gaggtgcgga catccatcga tgcctgtgcc tcgagtccct           1500

gcttcaacag ggccacctgc tacaccgacc tctccacaga cacctttgtg           1550

tgcaactgcc cttatggctt tgtgggcagc cgctgcgagt tccccgtggg           1600

cttgccgccc agcttcccct gggtggccgt ctcgctgggt gtggggctgg           1650

cagtgctgct ggtactgctg ggcatggtgg cagtggctgt gcggcagctg           1700

cggcttcgac ggccggacga cggcagcagg gaagccatga acaacttgtc           1750

ggacttccag aaggacaacc tgattcctgc cgcccagctt aaaaacacaa           1800

accagaagaa ggagctggaa gtggactgtg gcctggacaa gtccaactgt           1850

ggcaaacagc aaaaccacac attggactat aatctggccc cagggcccct           1900

ggggcggggg accatgccag gaaagtttcc ccacagtgac aagagcttag           1950

gagagaaggc gccactgcgg ttacacagtg aaaagccaga gtgtcggata           2000

tcagcgatat gctcccccag ggactccatg taccagtctg tgtgtttgat           2050

atcagaggag aggaatgaat gtgtcattgc cacggaggta taaggcagga           2100

gcctacctgg acatccctgc tcagccccgc ggctggacct tccttctgca           2150

ttgtttaca                                                        2159


<210> SEQ ID NO 214
<211> LENGTH: 685
<212> TYPE: PRT
<213> ORGANISM: Homo sapiens

<400> SEQUENCE: 214

Met Ala Ala Ala Ser Arg Ser Ala Ser Gly Trp Ala Leu Leu Leu
1               5                   10                  15

Leu Val Ala Leu Trp Gln Gln Arg Ala Ala Gly Ser Gly Val Phe
                20                  25                  30

Gln Leu Gln Leu Gln Glu Phe Ile Asn Glu Arg Gly Val Leu Ala
                35                  40                  45

Ser Gly Arg Pro Cys Glu Pro Gly Cys Arg Thr Phe Phe Arg Val
                50                  55                  60

Cys Leu Lys His Phe Gln Ala Val Val Ser Pro Gly Pro Cys Thr
                65                  70                  75

Phe Gly Thr Val Ser Thr Pro Val Leu Gly Thr Asn Ser Phe Ala
                80                  85                  90

Val Arg Asp Asp Ser Ser Gly Gly Gly Arg Asn Pro Leu Gln Leu
                95                  100                 105

Pro Phe Asn Phe Thr Trp Pro Gly Thr Phe Ser Leu Ile Ile Glu
                110                 115                 120

Ala Trp His Ala Pro Gly Asp Asp Leu Arg Pro Glu Ala Leu Pro
                125                 130                 135

Pro Asp Ala Leu Ile Ser Lys Ile Ala Ile Gln Gly Ser Leu Ala
                140                 145                 150

Val Gly Gln Asn Trp Leu Leu Asp Glu Gln Thr Ser Thr Leu Thr
                155                 160                 165
```

-continued

```
Arg Leu Arg Tyr Ser Tyr Arg Val Ile Cys Ser Asp Asn Tyr Tyr
                170                 175                 180

Gly Asp Asn Cys Ser Arg Leu Cys Lys Lys Arg Asn Asp His Phe
                185                 190                 195

Gly His Tyr Val Cys Gln Pro Asp Gly Asn Leu Ser Cys Leu Pro
                200                 205                 210

Gly Trp Thr Gly Glu Tyr Cys Gln Gln Pro Ile Cys Leu Ser Gly
                215                 220                 225

Cys His Glu Gln Asn Gly Tyr Cys Ser Lys Pro Ala Glu Cys Leu
                230                 235                 240

Cys Arg Pro Gly Trp Gln Gly Arg Leu Cys Asn Glu Cys Ile Pro
                245                 250                 255

His Asn Gly Cys Arg His Gly Thr Cys Ser Thr Pro Trp Gln Cys
                260                 265                 270

Thr Cys Asp Glu Gly Trp Gly Gly Leu Phe Cys Asp Gln Asp Leu
                275                 280                 285

Asn Tyr Cys Thr His His Ser Pro Cys Lys Asn Gly Ala Thr Cys
                290                 295                 300

Ser Asn Ser Gly Gln Arg Ser Tyr Thr Cys Thr Cys Arg Pro Gly
                305                 310                 315

Tyr Thr Gly Val Asp Cys Glu Leu Glu Leu Ser Glu Cys Asp Ser
                320                 325                 330

Asn Pro Cys Arg Asn Gly Gly Ser Cys Lys Asp Gln Glu Asp Gly
                335                 340                 345

Tyr His Cys Leu Cys Pro Pro Gly Tyr Tyr Gly Leu His Cys Glu
                350                 355                 360

His Ser Thr Leu Ser Cys Ala Asp Ser Pro Cys Phe Asn Gly Gly
                365                 370                 375

Ser Cys Arg Glu Arg Asn Gln Gly Ala Asn Tyr Ala Cys Glu Cys
                380                 385                 390

Pro Pro Asn Phe Thr Gly Ser Asn Cys Glu Lys Lys Val Asp Arg
                395                 400                 405

Cys Thr Ser Asn Pro Cys Ala Asn Gly Gly Gln Cys Leu Asn Arg
                410                 415                 420

Gly Pro Ser Arg Met Cys Arg Cys Arg Pro Gly Phe Thr Gly Thr
                425                 430                 435

Tyr Cys Glu Leu His Val Ser Asp Cys Ala Arg Asn Pro Cys Ala
                440                 445                 450

His Gly Gly Thr Cys His Asp Leu Glu Asn Gly Leu Met Cys Thr
                455                 460                 465

Cys Pro Ala Gly Phe Ser Gly Arg Arg Cys Glu Val Arg Thr Ser
                470                 475                 480

Ile Asp Ala Cys Ala Ser Ser Pro Cys Phe Asn Arg Ala Thr Cys
                485                 490                 495

Tyr Thr Asp Leu Ser Thr Asp Thr Phe Val Cys Asn Cys Pro Tyr
                500                 505                 510

Gly Phe Val Gly Ser Arg Cys Glu Phe Pro Val Gly Leu Pro Pro
                515                 520                 525

Ser Phe Pro Trp Val Ala Val Ser Leu Gly Val Gly Leu Ala Val
                530                 535                 540

Leu Leu Val Leu Leu Gly Met Val Ala Val Ala Val Arg Gln Leu
                545                 550                 555

Arg Leu Arg Arg Pro Asp Asp Gly Ser Arg Glu Ala Met Asn Asn
```

-continued

```
                560                 565                 570

Leu Ser Asp Phe Gln Lys Asp Asn Leu Ile Pro Ala Ala Gln Leu
                575                 580                 585

Lys Asn Thr Asn Gln Lys Lys Glu Leu Glu Val Asp Cys Gly Leu
                590                 595                 600

Asp Lys Ser Asn Cys Gly Lys Gln Gln Asn His Thr Leu Asp Tyr
                605                 610                 615

Asn Leu Ala Pro Gly Pro Leu Gly Arg Gly Thr Met Pro Gly Lys
                620                 625                 630

Phe Pro His Ser Asp Lys Ser Leu Gly Glu Lys Ala Pro Leu Arg
                635                 640                 645

Leu His Ser Glu Lys Pro Glu Cys Arg Ile Ser Ala Ile Cys Ser
                650                 655                 660

Pro Arg Asp Ser Met Tyr Gln Ser Val Cys Leu Ile Ser Glu Glu
                665                 670                 675

Arg Asn Glu Cys Val Ile Ala Thr Glu Val
                680                 685


<210> SEQ ID NO 215
<211> LENGTH: 3060
<212> TYPE: DNA
<213> ORGANISM: Homo sapiens

<400> SEQUENCE: 215

cgcgaggcgc ggggagcctg ggaccaggag cgagagccgc ctacctgcag      50

ccgccgccca cggcacggca gccaccatgg cgctcctgct gtgcttcgtg     100

ctcctgtgcg gagtagtgga tttcgccaga agtttgagta tcactactcc     150

tgaagagatg attgaaaaag ccaaagggga aactgcctat ctgccatgca     200

aatttacgct tagtcccgaa gaccagggac cgctggacat cgagtggctg     250

atatcaccag ctgataatca gaaggtggat caagtgatta ttttatattc     300

tggagacaaa atttatgatg actactatcc agatctgaaa ggccgagtac     350

attttacgag taatgatctc aaatctggtg atgcatcaat aaatgtaacg     400

aatttacaac tgtcagatat tggcacatat cagtgcaaag tgaaaaaagc     450

tcctggtgtt gcaaataaga agattcatct ggtagttctt gttaagcctt     500

caggtgcgag atgttacgtt gatggatctg aagaaattgg aagtgacttt     550

aagataaaat gtgaaccaaa agaaggttca cttccattac agtatgagtg     600

gcaaaaattg tctgactcac agaaaatgcc cacttcatgg ttagcagaaa     650

tgacttcatc tgttatatct gtaaaaaatg cctcttctga gtactctggg     700

acatacagct gtacagtcag aaacagagtg ggctctgatc agtgcctgtt     750

gcgtctaaac gttgtccctc cttcaaataa agctggacta attgcaggag     800

ccattatagg aactttgctt gctctagcgc tcattggtct tatcatcttt     850

tgctgtcgta aaaagcgcag agaagaaaaa tatgaaaagg aagttcatca     900

cgatatcagg gaagatgtgc cacctccaaa gagccgtacg tccactgcca     950

gaagctacat cggcagtaat cattcatccc tggggtccat gtctccttcc    1000

aacatggaag gatattccaa gactcagtat aaccaagtac caagtgaaga    1050

ctttgaacgc actcctcaga gtccgactct cccacctgct aagttcaagt    1100

acccttacaa gactgatgga attacagttg tataaatatg gactactgaa    1150
```

-continued

```
gaatctgaag tattgtatta tttgacttta ttttaggcct ctagtaaaga          1200
cttaaatgtt ttttaaaaaa agcacaaggc acagagatta gagcagctgt          1250
aagaacacat ctactttatg caatggcatt agacatgtaa gtcagatgtc          1300
atgtcaaaat tagtacgagc caaattcttt gttaaaaaac cctatgtata          1350
gtgacactga tagttaaaag atgttttatt atattttcaa taactaccac          1400
taacaaattt ttaacttttc atatgcatat tctgatatgt ggtcttttag          1450
gaaaagtatg gttaatagtt gatttttcaa aggaaatttt aaaattctta          1500
cgttctgttt aatgtttttg ctatttagtt aaatacattg aagggaaata          1550
cccgttcttt tcccctttta tgcacacaac agaaacacgc gttgtcatgc          1600
ctcaaactat tttttatttg caactacatg atttcacaca attctcttaa          1650
acaacgacat aaaatagatt tccttgtata taaataactt acatacgctc          1700
cataaagtaa attctcaaag gtgctagaac aaatcgtcca cttctacagt          1750
gttctcgtat ccaacagagt tgatgcacaa tatataaata ctcaagtcca          1800
atattaaaaa cttaggcact tgactaactt taataaaatt tctcaaacta          1850
tatcaatatc taaagtgcat atattttta agaaagatta ttctcaataa          1900
cttctataaa aataagtttg atggtttggc ccatctaact tcactactat          1950
tagtaagaac ttttaacttt taatgtgtag taaggtttat tctacctttt          2000
tctcaacatg acaccaacac aatcaaaaac gaagttagtg aggtgctaac          2050
atgtgaggat taatccagtg attccggtca caatgcattc caggaggagg          2100
tacccatgtc actggaattg ggcgatatgg tttatttttt cttccctgat          2150
ttggataacc aaatggaaca ggaggaggat agtgattctg atggccattc          2200
cctcgataca ttcctggctt ttttctgggc aaagggtgcc acattggaag          2250
aggtggaaat ataagttctg aaatctgtag ggaagagaac acattaagtt          2300
aattcaaagg aaaaaatcat catctatgtt ccagatttct cattaaagac          2350
aaagttaccc acaacactga gatcacatct aagtgacact cctattgtca          2400
ggtctaaata cattaaaaac ctcatgtgta ataggcgtat aatgtataac          2450
aggtgaccaa tgttttctga atgcataaag aaatgaataa actcaaacac          2500
agtacttcct aaacaacttc aaccaaaaaa gaccaaaaca tggaacgaat          2550
ggaagcttgt aaggacatgc ttgttttagt ccagtggttt ccacagctgg          2600
ctaagccagg agtcacttgg aggcttttaa atacaaaaca ttggagctgg          2650
aggccattat ccttagcaaa ctaatgcaga aacagaaaat caactaccgc          2700
atgttctcac ttataagtgg gaggtaatga taagaactta tgaacacaaa          2750
gaaggaaaca atagacattg gagtctattt gagaggggag ggtgggagaa          2800
ggaaaaggag cagaaaagat aactattgag tactgccttc acacctgggt          2850
gatgaaataa tatgtacaac aaatccctgt gacacatgtt tacctatgga          2900
acaaaccttc atgtgtatcc ctaaacctaa aataaaagtt aaaaaaaaaa          2950
aaaraaaaaa aaaaaaaaaa aaaaaaaaaa aaaaaaaaaa aaaaaaaaaa          3000
aaaaaaaaaa aaaaaaaaaa aaaaaaaaaa aaaaaaaaaa aaaaaaaaaa          3050
aaaaaaaaaa                                                      3060
```

-continued

<210> SEQ ID NO 216
<211> LENGTH: 352
<212> TYPE: PRT
<213> ORGANISM: Homo sapiens

<400> SEQUENCE: 216

```
Met Ala Leu Leu Leu Cys Phe Val Leu Leu Cys Gly Val Val Asp
  1               5                  10                  15

Phe Ala Arg Ser Leu Ser Ile Thr Thr Pro Glu Glu Met Ile Glu
                 20                  25                  30

Lys Ala Lys Gly Glu Thr Ala Tyr Leu Pro Cys Lys Phe Thr Leu
                 35                  40                  45

Ser Pro Glu Asp Gln Gly Pro Leu Asp Ile Glu Trp Leu Ile Ser
                 50                  55                  60

Pro Ala Asp Asn Gln Lys Val Asp Gln Val Ile Ile Leu Tyr Ser
                 65                  70                  75

Gly Asp Lys Ile Tyr Asp Asp Tyr Tyr Pro Asp Leu Lys Gly Arg
                 80                  85                  90

Val His Phe Thr Ser Asn Asp Leu Lys Ser Gly Asp Ala Ser Ile
                 95                 100                 105

Asn Val Thr Asn Leu Gln Leu Ser Asp Ile Gly Thr Tyr Gln Cys
                110                 115                 120

Lys Val Lys Lys Ala Pro Gly Val Ala Asn Lys Lys Ile His Leu
                125                 130                 135

Val Val Leu Val Lys Pro Ser Gly Ala Arg Cys Tyr Val Asp Gly
                140                 145                 150

Ser Glu Glu Ile Gly Ser Asp Phe Lys Ile Lys Cys Glu Pro Lys
                155                 160                 165

Glu Gly Ser Leu Pro Leu Gln Tyr Glu Trp Gln Lys Leu Ser Asp
                170                 175                 180

Ser Gln Lys Met Pro Thr Ser Trp Leu Ala Glu Met Thr Ser Ser
                185                 190                 195

Val Ile Ser Val Lys Asn Ala Ser Ser Glu Tyr Ser Gly Thr Tyr
                200                 205                 210

Ser Cys Thr Val Arg Asn Arg Val Gly Ser Asp Gln Cys Leu Leu
                215                 220                 225

Arg Leu Asn Val Val Pro Pro Ser Asn Lys Ala Gly Leu Ile Ala
                230                 235                 240

Gly Ala Ile Ile Gly Thr Leu Leu Ala Leu Ala Leu Ile Gly Leu
                245                 250                 255

Ile Ile Phe Cys Cys Arg Lys Lys Arg Arg Glu Glu Lys Tyr Glu
                260                 265                 270

Lys Glu Val His His Asp Ile Arg Glu Asp Val Pro Pro Pro Lys
                275                 280                 285

Ser Arg Thr Ser Thr Ala Arg Ser Tyr Ile Gly Ser Asn His Ser
                290                 295                 300

Ser Leu Gly Ser Met Ser Pro Ser Asn Met Glu Gly Tyr Ser Lys
                305                 310                 315

Thr Gln Tyr Asn Gln Val Pro Ser Glu Asp Phe Glu Arg Thr Pro
                320                 325                 330

Gln Ser Pro Thr Leu Pro Pro Ala Lys Phe Lys Tyr Pro Tyr Lys
                335                 340                 345

Thr Asp Gly Ile Thr Val Val
                350
```

-continued

<210> SEQ ID NO 217
<211> LENGTH: 1571
<212> TYPE: DNA
<213> ORGANISM: Homo sapiens

<400> SEQUENCE: 217
gatggcgcag ccacagcttc tgtgagattc gatttctccc cagttcccct 50
gtgggtctga ggggaccaga agggtgagct acgttggctt tctggaaggg 100
gaggctatat gcgtcaattc cccaaaacaa gttttgacat ttcccctgaa 150
atgtcattct ctatctattc actgcaagtg cctgctgttc caggccttac 200
ctgctgggca ctaacggcgg agccaggatg ggacagaat aaaggagcca 250 cgacctgtgc caccaactcg cactcagact ctgaactcag acctgaaatc 300
ttctcttcac gggaggcttg gcagtttttc ttactcctgt ggtctccaga 350
tttcaggcct aagatgaaag cctctagtct tgccttcagc cttctctctg 400
ctgcgtttta tctcctatgg actccttcca ctggactgaa gacactcaat 450
ttgggaagct gtgtgatcgc cacaaacctt caggaaatac gaaatggatt 500
ttctgagata cggggcagtg tgcaagccaa agatggaaac attgacatca 550
gaatcttaag gaggactgag tctttgcaag acacaaagcc tgcgaatcga 600
tgctgcctcc tgcgccattt gctaagactc tatctggaca gggtatttaa 650
aaactaccag acccctgacc attatactct ccggaagatc agcagcctcg 700
ccaattcctt tcttaccatc aagaaggacc tccggctctc tcatgcccac 750
atgacatgcc attgtgggga ggaagcaatg aagaaataca gccagattct 800
gagtcacttt gaaaagctgg aacctcaggc agcagttgtg aaggctttgg 850
gggaactaga cattcttctg caatggatgg aggagacaga ataggaggaa 900
agtgatgctg ctgctaagaa tattcgaggt caagagctcc agtcttcaat 950
acctgcagag gaggcatgac cccaaaccac catctcttta ctgtactagt 1000
cttgtgctgg tcacagtgta tcttatttat gcattacttg cttccttgca 1050
tgattgtctt tatgcatccc caatcttaat tgagaccata cttgtataag 1100
atttttgtaa tatctttctg ctattggata tatttattag ttaatatatt 1150
tatttatttt ttgctattta atgtatttat ttttttactt ggacatgaaa 1200
ctttaaaaaa attcacagat tatatttata acctgactag agcaggtgat 1250
gtatttttat acagtaaaaa aaaaaaacct tgtaaattct agaagagtgg 1300 ctagggggggt tattcatttg tattcaacta aggacatatt tactcatgct 1350
gatgctctgt gagatatttg aaattgaacc aatgactact taggatgggt 1400
tgtggaataa gttttgatgt ggaattgcac atctacctta caattactga 1450
ccatccccag tagactcccc agtcccataa ttgtgtatct tccagccagg 1500
aatcctacac ggccagcatg tatttctaca aataaagttt tctttgcata 1550
ccaaaaaaaa aaaaaaaaaa a 1571

<210> SEQ ID NO 218
<211> LENGTH: 176
<212> TYPE: PRT
<213> ORGANISM: Homo sapiens -continued

<400> SEQUENCE: 218

```
Met Lys Ala Ser Ser Leu Ala Phe Ser Leu Leu Ser Ala Ala Phe
  1               5                  10                  15

Tyr Leu Leu Trp Thr Pro Ser Thr Gly Leu Lys Thr Leu Asn Leu
                 20                  25                  30

Gly Ser Cys Val Ile Ala Thr Asn Leu Gln Glu Ile Arg Asn Gly
                 35                  40                  45

Phe Ser Glu Ile Arg Gly Ser Val Gln Ala Lys Asp Gly Asn Ile
                 50                  55                  60

Asp Ile Arg Ile Leu Arg Arg Thr Glu Ser Leu Gln Asp Thr Lys
                 65                  70                  75

Pro Ala Asn Arg Cys Cys Leu Leu Arg His Leu Leu Arg Leu Tyr
                 80                  85                  90

Leu Asp Arg Val Phe Lys Asn Tyr Gln Thr Pro Asp His Tyr Thr
                 95                 100                 105

Leu Arg Lys Ile Ser Ser Leu Ala Asn Ser Phe Leu Thr Ile Lys
                110                 115                 120

Lys Asp Leu Arg Leu Ser His Ala His Met Thr Cys His Cys Gly
                125                 130                 135

Glu Glu Ala Met Lys Lys Tyr Ser Gln Ile Leu Ser His Phe Glu
                140                 145                 150

Lys Leu Glu Pro Gln Ala Ala Val Val Lys Ala Leu Gly Glu Leu
                155                 160                 165

Asp Ile Leu Leu Gln Trp Met Glu Glu Thr Glu
                170                 175
```

<210> SEQ ID NO 219
<211> LENGTH: 2870
<212> TYPE: DNA
<213> ORGANISM: Homo sapiens

<400> SEQUENCE: 219

```
cgcggagccc tgcgctggga ggtgcacggt gtgcacgctg gactggaccc       50

ccatgcaacc ccgcgccctg cgccttaacc aggactgctc cgcgcgcccc      100

tgagcctcgg gctccggccc ggacctgcag cctcccaggt ggctgggaag      150

aactctccaa caataaatac atttgataag aaagatggct ttaaaagtgc      200

tactagaaca agagaaaacg tttttcactc ttttagtatt actaggctat      250

ttgtcatgta aagtgacttg tgaatcagga gactgtagac agcaagaatt      300

cagggatcgg tctggaaact gtgttccctg caaccagtgt gggccaggca      350

tggagttgtc taaggaatgt ggcttcggct atggggagga tgcacagtgt      400

gtgacgtgcc ggctgcacag gttcaaggag gactggggct tccagaaatg      450

caagccctgt ctggactgcg cagtggtgaa ccgctttcag aaggcaaatt      500

gttcagccac cagtgatgcc atctgcgggg actgcttgcc aggattttat      550

aggaagacga aacttgtcgg ctttcaagac atggagtgtg tgccttgtgg      600

agaccctcct cctccttacg aaccgcactg tgccagcaag gtcaacctcg      650

tgaagatcgc gtccacggcc tccagcccac gggacacggc gctggctgcc      700

gttatctgca gcgctctggc caccgtcctg ctggccctgc tcatcctctg      750

tgtcatctat tgtaagagac agtttatgga gaagaaaccc agctggtctc      800

tgcggtcgca ggacattcag tacaacggct ctgagctgtc gtgttttgac      850
```

-continued

```
agacctcagc tccacgaata tgcccacaga gcctgctgcc agtgccgccg      900
tgactcagtg cagacctgcg ggccggtgcg cttgctccca tccatgtgct      950
gtgaggaggc ctgcagcccc aacccggcga ctcttggttg tggggtgcat     1000
tctgcagcca gtcttcaggc aagaaacgca ggcccagccg gggagatggt     1050
gccgactttc ttcggatccc tcacgcagtc catctgtggc gagttttcag     1100
atgcctggcc tctgatgcag aatcccatgg gtggtgacaa catctctttt     1150
tgtgactctt atcctgaact cactggagaa gacattcatt ctctcaatcc     1200
agaacttgaa agctcaacgt ctttggattc aaatagcagt caagatttgg     1250
ttggtggggc tgttccagtc cagtctcatt ctgaaaactt tacagcagct     1300
actgatttat ctagatataa caacacactg gtagaatcag catcaactca     1350
ggatgcacta actatgagaa gccagctaga tcaggagagt ggcgctgtca     1400
tccacccagc cactcagacg tccctccagg aagcttaaag aacctgcttc     1450
tttctgcagt agaagcgtgt gctggaaccc aaagagtact cctttgttag     1500
gcttatggac tgagcagtct ggaccttgca tggcttctgg ggcaaaaata     1550
aatctgaacc aaactgacgg catttgaagc ctttcagcca gttgcttctg     1600
agccagacca gctgtaagct gaaacctcaa tgaataacaa gaaaagactc     1650
caggccgact catgatactc tgcatctttc ctacatgaga agcttctctg     1700
ccacaaaagt gacttcaaag actgatgggt tgagctggca gcctatgaga     1750
ttgtggacat ataacaagaa acagaaatgc cctcatgctt attttcatgg     1800
tgattgtggt tttacaagac tgaagaccca gagtatactt tttctttcca     1850
gaaataattt cataccgcct atgaaatatc agataaatta ccttagcttt     1900
tatgtagaat gggttcaaaa gtgagtgttt ctatttgaga aggacacttt     1950
ttcatcatct aaactgattc gcataggtgg ttagaatggc cctcatattg     2000
cctgcctaaa tcttgggttt attagatgaa gtttactgaa tcagaggaat     2050
cagacagagg aggatagctc tttccagaat ccacacttct gacctcagcc     2100
tcggtctcat gaacacccgc tgatctcagg agaacacctg ggctagggaa     2150
tgtggtcgag aaagggcagc ccattgccca gaattaacac atattgtaga     2200
gacttgtatg caaaggttgg catatttata tgaaaattag ttgctataga     2250
aacatttgtt gcatctgtcc ctctgcctga gcttagaagg ttatagaaaa     2300
agggtattta taaacataaa tgacctttta cttgcattgt atcttatact     2350
aaaggcttta gaaattacaa catatcaggt tcccctacta ctgaagtagc     2400
cttccgtgag aacacaccac atgttaggac tagaagaaaa tgcacaattt     2450
gtaggggttt ggatgaagca gctgtaactg ccctagtgta gtttgaccag     2500
gacattgtcg tgctccttcc aattgtgtaa gattagttag cacatcatct     2550
cctactttag ccatccggtg ttggatttaa gaggacggtg cttctttcta     2600
ttaaagtgct ccatccccta ccatctacac attagcattg tctctagagc     2650
taagacagaa attaaccccg ttcagtcaca aagcagggaa tggttcattt     2700
actcttaatc tttatgccct ggagaagacc tacttgaaca gggcatattt     2750
tttagacttc tgaacatcag tatgttcgag ggtactatga tattttggtt     2800
```

-continued

```
tggaattgcc ctgcccaagt cactgtcttt taacttttaa actgaatatt          2850

aaaatgtatc tgtctttcct                                          2870


<210> SEQ ID NO 220
<211> LENGTH: 417
<212> TYPE: PRT
<213> ORGANISM: Homo sapiens

<400> SEQUENCE: 220

Met Ala Leu Lys Val Leu Leu Glu Gln Glu Lys Thr Phe Phe Thr
  1               5                  10                  15

Leu Leu Val Leu Leu Gly Tyr Leu Ser Cys Lys Val Thr Cys Glu
                 20                  25                  30

Ser Gly Asp Cys Arg Gln Gln Glu Phe Arg Asp Arg Ser Gly Asn
                 35                  40                  45

Cys Val Pro Cys Asn Gln Cys Gly Pro Gly Met Glu Leu Ser Lys
                 50                  55                  60

Glu Cys Gly Phe Gly Tyr Gly Glu Asp Ala Gln Cys Val Thr Cys
                 65                  70                  75

Arg Leu His Arg Phe Lys Glu Asp Trp Gly Phe Gln Lys Cys Lys
                 80                  85                  90

Pro Cys Leu Asp Cys Ala Val Val Asn Arg Phe Gln Lys Ala Asn
                 95                 100                 105

Cys Ser Ala Thr Ser Asp Ala Ile Cys Gly Asp Cys Leu Pro Gly
                110                 115                 120

Phe Tyr Arg Lys Thr Lys Leu Val Gly Phe Gln Asp Met Glu Cys
                125                 130                 135

Val Pro Cys Gly Asp Pro Pro Pro Pro Tyr Glu Pro His Cys Ala
                140                 145                 150

Ser Lys Val Asn Leu Val Lys Ile Ala Ser Thr Ala Ser Ser Pro
                155                 160                 165

Arg Asp Thr Ala Leu Ala Ala Val Ile Cys Ser Ala Leu Ala Thr
                170                 175                 180

Val Leu Leu Ala Leu Leu Ile Leu Cys Val Ile Tyr Cys Lys Arg
                185                 190                 195

Gln Phe Met Glu Lys Lys Pro Ser Trp Ser Leu Arg Ser Gln Asp
                200                 205                 210

Ile Gln Tyr Asn Gly Ser Glu Leu Ser Cys Phe Asp Arg Pro Gln
                215                 220                 225

Leu His Glu Tyr Ala His Arg Ala Cys Cys Gln Cys Arg Arg Asp
                230                 235                 240

Ser Val Gln Thr Cys Gly Pro Val Arg Leu Leu Pro Ser Met Cys
                245                 250                 255

Cys Glu Glu Ala Cys Ser Pro Asn Pro Ala Thr Leu Gly Cys Gly
                260                 265                 270

Val His Ser Ala Ala Ser Leu Gln Ala Arg Asn Ala Gly Pro Ala
                275                 280                 285

Gly Glu Met Val Pro Thr Phe Phe Gly Ser Leu Thr Gln Ser Ile
                290                 295                 300

Cys Gly Glu Phe Ser Asp Ala Trp Pro Leu Met Gln Asn Pro Met
                305                 310                 315

Gly Gly Asp Asn Ile Ser Phe Cys Asp Ser Tyr Pro Glu Leu Thr
                320                 325                 330

Gly Glu Asp Ile His Ser Leu Asn Pro Glu Leu Glu Ser Ser Thr
```

-continued

```
                335                 340                 345

Ser Leu Asp Ser Asn Ser Ser Gln Asp Leu Val Gly Gly Ala Val
                350                 355                 360

Pro Val Gln Ser His Ser Glu Asn Phe Thr Ala Ala Thr Asp Leu
                365                 370                 375

Ser Arg Tyr Asn Asn Thr Leu Val Glu Ser Ala Ser Thr Gln Asp
                380                 385                 390

Ala Leu Thr Met Arg Ser Gln Leu Asp Gln Glu Ser Gly Ala Val
                395                 400                 405

Ile His Pro Ala Thr Gln Thr Ser Leu Gln Glu Ala
                410                 415
```

<210> SEQ ID NO 221
<211> LENGTH: 961
<212> TYPE: DNA
<213> ORGANISM: Homo sapiens

<400> SEQUENCE: 221

```
ctagagagta tagggcagaa ggatggcaga tgagtgactc cacatccaga              50

gctgcctccc tttaatccag gatcctgtcc ttcctgtcct gtaggagtgc             100

ctgttgccag tgtggggtga gacaagtttg tcccacaggg ctgtctgagc             150

agataagatt aagggctggg tctgtgctca attaactcct gtgggcacgg             200

gggctgggaa gagcaaagtc agcggtgcct acagtcagca ccatgctggg             250

cctgccgtgg aagggaggtc tgtcctgggc gctgctgctg cttctcttag             300

gctcccagat cctgctgatc tatgcctggc atttccacga gcaaagggac             350

tgtgatgaac acaatgtcat ggctcgttac ctccctgcca cagtggagtt             400

tgctgtccac acattcaacc aacagagcaa ggactactat gcctacagac             450

tggggcacat cttgaattcc tggaaggagc aggtggagtc caagactgta             500

ttctcaatgg agctactgct ggggagaact aggtgtggga aatttgaaga             550

cgacattgac aactgccatt tccaagaaag cacagagctg aacaatactt             600

tcacctgctt cttcaccatc agcaccaggc cctggatgac tcagttcagc             650

ctcctgaaca agacctgctt ggagggattc cactgagtga aacccactca             700

caggcttgtc catgtgctgc tcccacattc cgtggacatc agcactactc             750

tcctgaggac tcttcagtgg ctgagcagct ttggacttgt ttgttatcct             800

attttgcatg tgtttgagat ctcagatcag tgttttagaa aatccacaca             850

tcttgagcct aatcatgtag tgtagatcat taaacatcag cattttaaga             900

aaaaaaaaaa aaaaaaaaaa aaaaaaaaaa aaaaaaaaaa aaaaaaaaaa             950

aaaaaaaaaa a                                                       961
```

<210> SEQ ID NO 222
<211> LENGTH: 147
<212> TYPE: PRT
<213> ORGANISM: Homo sapiens

<400> SEQUENCE: 222

```
Met Leu Gly Leu Pro Trp Lys Gly Gly Leu Ser Trp Ala Leu Leu
  1               5                  10                  15

Leu Leu Leu Leu Gly Ser Gln Ile Leu Leu Ile Tyr Ala Trp His
                 20                  25                  30
```

-continued

```
Phe His Glu Gln Arg Asp Cys Asp Glu His Asn Val Met Ala Arg
                35                  40                  45

Tyr Leu Pro Ala Thr Val Glu Phe Ala Val His Thr Phe Asn Gln
                50                  55                  60

Gln Ser Lys Asp Tyr Tyr Ala Tyr Arg Leu Gly His Ile Leu Asn
                65                  70                  75

Ser Trp Lys Glu Gln Val Glu Ser Lys Thr Val Phe Ser Met Glu
                80                  85                  90

Leu Leu Leu Gly Arg Thr Arg Cys Gly Lys Phe Glu Asp Asp Ile
                95                 100                 105

Asp Asn Cys His Phe Gln Glu Ser Thr Glu Leu Asn Asn Thr Phe
               110                 115                 120

Thr Cys Phe Phe Thr Ile Ser Thr Arg Pro Trp Met Thr Gln Phe
               125                 130                 135

Ser Leu Leu Asn Lys Thr Cys Leu Glu Gly Phe His
               140                 145
```

<210> SEQ ID NO 223
<211> LENGTH: 846
<212> TYPE: DNA
<213> ORGANISM: Homo sapiens

<400> SEQUENCE: 223

```
aatcggctga ttctgcatct ggaaactgcc ttcatcttga aagaaaagct              50

ccaggtccct tctccagcca cccagcccca agatggtgat gctgctgctg             100

ctgctttccg cactggctgg cctcttcggt gcggcagagg gacaagcatt             150

tcatcttggg aagtgcccca atcctccggt gcaggagaat tttgacgtga             200

ataagtatct cggaagatgg tacgaaattg agaagatccc aacaaccttt             250

gagaatggac gctgcatcca ggccaactac tcactaatgg aaaacggaaa             300

gatcaaagtg ttaaaccagg agttgagagc tgatggaact gtgaatcaaa             350

tcgaaggtga agccacccca gttaacctca cagagcctgc caagctggaa             400

gttaagtttt cctggtttat gccatcggca ccgtactgga tcctggccac             450

cgactatgag aactatgccc tcgtgtattc ctgtacctgc atcatccaac             500

tttttcacgt ggattttgct tggatcttgg caagaaaccc taatctccct             550

ccagaaacag tggactctct aaaaaatatc ctgacttcta ataacattga             600

tgtcaagaaa atgacggtca cagaccaggt gaactgcccc aagctctcgt             650

aaccaggttc tacagggagg ctgcacccac tccatgttac ttctgcttcg             700

ctttccccta ccccaccccc cccccataaa gacaaaccaa tcaaccacga             750

caaaggaagt tgacctgaac atgtaaccat gccctaccct gttaccttgc             800

tagctgcaaa ataaacttgt tgctgacctg ctgtgctcgc  aaaaaa                846
```

<210> SEQ ID NO 224
<211> LENGTH: 189
<212> TYPE: PRT
<213> ORGANISM: Homo sapiens

<400> SEQUENCE: 224

```
Met Val Met Leu Leu Leu Leu Leu Ser Ala Leu Ala Gly Leu Phe
  1               5                  10                  15

Gly Ala Ala Glu Gly Gln Ala Phe His Leu Gly Lys Cys Pro Asn
                20                  25                  30
```

-continued

```
Pro Pro Val Gln Glu Asn Phe Asp Val Asn Lys Tyr Leu Gly Arg
                35                  40                  45

Trp Tyr Glu Ile Glu Lys Ile Pro Thr Thr Phe Glu Asn Gly Arg
                50                  55                  60

Cys Ile Gln Ala Asn Tyr Ser Leu Met Glu Asn Gly Lys Ile Lys
                65                  70                  75

Val Leu Asn Gln Glu Leu Arg Ala Asp Gly Thr Val Asn Gln Ile
                80                  85                  90

Glu Gly Glu Ala Thr Pro Val Asn Leu Thr Glu Pro Ala Lys Leu
                95                  100                 105

Glu Val Lys Phe Ser Trp Phe Met Pro Ser Ala Pro Tyr Trp Ile
                110                 115                 120

Leu Ala Thr Asp Tyr Glu Asn Tyr Ala Leu Val Tyr Ser Cys Thr
                125                 130                 135

Cys Ile Ile Gln Leu Phe His Val Asp Phe Ala Trp Ile Leu Ala
                140                 145                 150

Arg Asn Pro Asn Leu Pro Pro Glu Thr Val Asp Ser Leu Lys Asn
                155                 160                 165

Ile Leu Thr Ser Asn Asn Ile Asp Val Lys Lys Met Thr Val Thr
                170                 175                 180

Asp Gln Val Asn Cys Pro Lys Leu Ser
                185
```

<210> SEQ ID NO 225
<211> LENGTH: 1088
<212> TYPE: DNA
<213> ORGANISM: Homo sapiens

<400> SEQUENCE: 225

```
gggtgattga actaaacctt cgccgcaccg agtttgcagt acggccgtca        50
cccgcaccgc tgcctgcttg cggttggaga aatcaaggcc ctaccgggcc       100
tccgtagtca cctctctata gtgggcgtgg ccgaggccgg ggtgaccctg       150
ccggagcctc cgctgccagc gacatgttca aggtaattca gaggtccgtg       200
gggccagcca gcctgagctt gctcaccttc aaagtctatg cagcaccaaa       250
aaaggactca cctcccaaaa attccgtgaa ggttgatgag ctttcactct       300
actcagttcc tgagggtcaa tcgaagtatg tggaggaggc aaggagccag       350
cttgaagaaa gcatctcaca gctccgacac tattgcgagc catacacaac       400
ctggtgtcag gaaacgtact cccaaactaa gcccaagatg caaagtttgg       450
ttcaatgggg gttagacagc tatgactatc tccaaaatgc acctcctgga       500
ttttttccga gacttggtgt tattggtttt gctggcctta ttggactcct       550
tttggctaga ggttcaaaaa taaagaagct agtgtatccg cctggtttca       600
tgggattagc tgcctccctc tattatccac aacaagccat cgtgtttgcc       650
caggtcagtg gggagagatt atatgactgg ggtttacgag gatatatagt       700
catagaagat ttgtggaagg agaactttca aaagccagga aatgtgaaga       750
attcacctgg aactaagtag aaaactccat gctctgccat cttaatcagt       800
tataggtaaa cattggaaac tccatagaat aaatcagtat ttctacagaa       850
aaatggcata gaagtcagta ttgaatgtat taaattggct ttcttcttca       900
ggaaaaacta gaccagacct ctgttatctt ctgtgaaatc atcctacaag       950
```

-continued caaactaacc tggaatccct tcacctagag ataatgtaca agccttagaa 1000
ctcctcattc tcatgttgct atttatgtac ctaattaaaa cccaagttta 1050
aaaaaaaaaa aaaaaaaaaa aaaaaaaaaa aaaaaaaa 1088

<210> SEQ ID NO 226
<211> LENGTH: 198
<212> TYPE: PRT
<213> ORGANISM: Homo sapiens

<400> SEQUENCE: 226

Met Phe Lys Val Ile Gln Arg Ser Val Gly Pro Ala Ser Leu Ser
1 5 10 15

Leu Leu Thr Phe Lys Val Tyr Ala Ala Pro Lys Lys Asp Ser Pro
20 25 30

Pro Lys Asn Ser Val Lys Val Asp Glu Leu Ser Leu Tyr Ser Val
35 40 45

Pro Glu Gly Gln Ser Lys Tyr Val Glu Glu Ala Arg Ser Gln Leu
50 55 60

Glu Glu Ser Ile Ser Gln Leu Arg His Tyr Cys Glu Pro Tyr Thr
65 70 75

Thr Trp Cys Gln Glu Thr Tyr Ser Gln Thr Lys Pro Lys Met Gln
80 85 90

Ser Leu Val Gln Trp Gly Leu Asp Ser Tyr Asp Tyr Leu Gln Asn
95 100 105

Ala Pro Pro Gly Phe Phe Pro Arg Leu Gly Val Ile Gly Phe Ala
110 115 120

Gly Leu Ile Gly Leu Leu Leu Ala Arg Gly Ser Lys Ile Lys Lys
125 130 135

Leu Val Tyr Pro Pro Gly Phe Met Gly Leu Ala Ala Ser Leu Tyr
140 145 150

Tyr Pro Gln Gln Ala Ile Val Phe Ala Gln Val Ser Gly Glu Arg
155 160 165

Leu Tyr Asp Trp Gly Leu Arg Gly Tyr Ile Val Ile Glu Asp Leu
170 175 180

Trp Lys Glu Asn Phe Gln Lys Pro Gly Asn Val Lys Asn Ser Pro
185 190 195

Gly Thr Lys

<210> SEQ ID NO 227
<211> LENGTH: 2164
<212> TYPE: DNA
<213> ORGANISM: Homo sapiens

<400> SEQUENCE: 227
caccggaggg cacgcagctg acggagctgc gctgcgttcg cctcgtttgc 50
ctcgcgccct ccactggagc tgttcgcgcc tcccggctcc caccgcagcc 100
cacccggcag aggagtcgct accagcgccc agtgcgctct gtcagtccgc 150
aaactccttg ccgcccgccc cgggctgggc accaaatacc aggctaccat 200
ggtctacaag actctcttcg ctctttgcat cttaactgca ggatggaggg 250
tacagagtct gcctacatca gctcctttgt ctgtttctct tccgacaaac 300
attgtaccac cgaccaccat ctggactagc tctccacaaa acactgatgc 350
agacactgcc tccccatcca acggcactca caacaactcg gtgctcccag 400

-continued

```
ttacagcatc agccccaaca tctctgcttc ctaagaacat ttccatagag      450
tccagagaag aggagatcac cagcccaggt tcgaattggg aaggcacaaa      500
cacagacccc tcaccttctg ggttctcgtc aacaagcggt ggagtccact      550
taacaaccac gttggaggaa cacagctcgg gcactcctga agcaggcgtg      600
gcagctacac tgtcgcagtc cgctgctgag cctcccacac tcatctcccc      650
tcaagctcca gcctcatcac cctcatccct atcaacctca ccacctgagg      700
tcttttctgc ctccgttact accaaccata gctccactgt gaccagcacc      750
caacccactg gagctccaac tgcaccagag tccccgacag aggagtccag      800
ctctgaccac acacccactt cacatgccac agctgagcca gtgccccagg      850
agaaaacacc cccaacaact gtgtcaggca aagtgatgtg tgagctcata      900
gacatggaga ccaccaccac ctttcccagg gtgatcatgc aggaagtaga      950
acatgcatta agttcaggca gcatcgccgc cattaccgtg acagtcattg     1000
ccgtggtgct gctggtgttt ggagttgcag cctacctaaa aatcaggcat     1050
tcctcctatg gaagactttt ggacgaccat gactacgggt cctggggaaa     1100
ctacaacaac cctctgtacg atgactccta acaatggaat atggcctggg     1150
atgaggatta actgttcttt atttataagt gcttatccag tagaattaat     1200
aagtacctga tgcgcattga acgacaatct taagccctgt tttgttggta     1250
tggttgtttt tgttttcctc cctctcctct ggctgctaca acttcccctt     1300
tctggtacaa gaagaaccat tctttaaagg tgagtggagg ctgatttgca     1350
gctgaagtgg gccagccttg caccagccag gccagaccac catggtgaag     1400
gcttctttcc ccactgcagg acccactttg agaaggatcg aggaggagga     1450
tttgggttgt tttgttaggg gttactttca ggggaacatt tcatttgtgt     1500
tatttcttaa acttctattt aggaaattac attaagtatt aatgagggga     1550
aaggaaatga gctctacgag gatttcacct tgcatgggag agagcagggt     1600
tttctcagat tcctttttaa tctctattta tctggttgtt tctgacagga     1650
tgctgcctgc ttggctctac gagctggaaa gcagcttctt agctgcctaa     1700
ttaatgaaag atgaaaatag gaagtgccct ggagggggcc agcaggtcac     1750
ggggcagaat ctctcaggtt gctgtgggat ctcagtgtgc cctacctgt      1800
tctcccctcc aggccacctg tctctgtaaa ggatgtctgc tctgttcaaa     1850
aggcagctgg gatcccagcc cacaagtgat cagcagagtt gcatttccaa     1900
agaaaaaggc tatgagatga gctgagttat agagagaaag ggagaggcat     1950
gtacggtgtg gggaagtgga agagaagctg gcgggggaga aggaggctaa     2000
cctgcactga gtacttcatt aggacaagtg agaatcagct attgataatg     2050
gccagagata tccacagctt ggaggagccc agagactgtt tgctttatac     2100
ccacacagca actggtccac tgctttactg tctgttggat aatggctgta     2150
aaatgtttaa  aaac                                           2164
```

<210> SEQ ID NO 228
<211> LENGTH: 310
<212> TYPE: PRT
<213> ORGANISM: Homo sapiens -continued

<400> SEQUENCE: 228

```
Met Val Tyr Lys Thr Leu Phe Ala Leu Cys Ile Leu Thr Ala Gly
  1               5                  10                  15

Trp Arg Val Gln Ser Leu Pro Thr Ser Ala Pro Leu Ser Val Ser
                 20                  25                  30

Leu Pro Thr Asn Ile Val Pro Pro Thr Thr Ile Trp Thr Ser Ser
                 35                  40                  45

Pro Gln Asn Thr Asp Ala Asp Thr Ala Ser Pro Ser Asn Gly Thr
                 50                  55                  60

His Asn Asn Ser Val Leu Pro Val Thr Ala Ser Ala Pro Thr Ser
                 65                  70                  75

Leu Leu Pro Lys Asn Ile Ser Ile Glu Ser Arg Glu Glu Glu Ile
                 80                  85                  90

Thr Ser Pro Gly Ser Asn Trp Glu Gly Thr Asn Thr Asp Pro Ser
                 95                 100                 105

Pro Ser Gly Phe Ser Ser Thr Ser Gly Gly Val His Leu Thr Thr
                110                 115                 120

Thr Leu Glu Glu His Ser Ser Gly Thr Pro Glu Ala Gly Val Ala
                125                 130                 135

Ala Thr Leu Ser Gln Ser Ala Ala Glu Pro Pro Thr Leu Ile Ser
                140                 145                 150

Pro Gln Ala Pro Ala Ser Ser Pro Ser Ser Leu Ser Thr Ser Pro
                155                 160                 165

Pro Glu Val Phe Ser Ala Ser Val Thr Thr Asn His Ser Ser Thr
                170                 175                 180

Val Thr Ser Thr Gln Pro Thr Gly Ala Pro Thr Ala Pro Glu Ser
                185                 190                 195

Pro Thr Glu Glu Ser Ser Ser Asp His Thr Pro Thr Ser His Ala
                200                 205                 210

Thr Ala Glu Pro Val Pro Gln Glu Lys Thr Pro Pro Thr Thr Val
                215                 220                 225

Ser Gly Lys Val Met Cys Glu Leu Ile Asp Met Glu Thr Thr Thr
                230                 235                 240

Thr Phe Pro Arg Val Ile Met Gln Glu Val Glu His Ala Leu Ser
                245                 250                 255

Ser Gly Ser Ile Ala Ala Ile Thr Val Thr Val Ile Ala Val Val
                260                 265                 270

Leu Leu Val Phe Gly Val Ala Ala Tyr Leu Lys Ile Arg His Ser
                275                 280                 285

Ser Tyr Gly Arg Leu Leu Asp Asp His Asp Tyr Gly Ser Trp Gly
                290                 295                 300

Asn Tyr Asn Asn Pro Leu Tyr Asp Asp Ser
                305                 310
```

<210> SEQ ID NO 229
<211> LENGTH: 633
<212> TYPE: DNA
<213> ORGANISM: Homo sapiens

<400> SEQUENCE: 229

```
ctcctgcact aggctctcag ccagggatga tgcgctgctg ccgccgccgc               50

tgctgctgcc ggcaaccacc ccatgccctg aggccgttgc tgttgctgcc              100

cctcgtcctt ttacctcccc tggcagcagc tgcagcgggc ccaaaccgat              150
```

-continued

```
gtgacaccat ataccagggc ttcgccgagt gtctcatccg cttgggggac              200

agcatgggcc gcggaggcga gctggagacc atctgcaggt cttggaatga              250

cttccatgcc tgtgcctctc aggtcctgtc aggctgtccg gaggaggcag              300

ctgcagtgtg ggaatcacta cagcaagaag ctcgccaggc cccccgtccg              350

aataacttgc acactctgtg cggtgccccg gtgcatgttc gggagcgcgg              400

cacaggctcc gaaaccaacc aggagacgct gcgggctaca gcgcctgcac              450

tccccatggc ccctgcgccc ccactgctgg cggctgctct ggctctggcc              500

tacctcctga ggcctctggc ctagcttgtt gggttgggta gcagcgcccg              550

tacctccagc cctgctctgg cggtggttgt ccaggctctg cagagcgcag              600

cagggctttt cattaaaggt atttatattt  gta                               633
```

<210> SEQ ID NO 230
<211> LENGTH: 165
<212> TYPE: PRT
<213> ORGANISM: Homo sapiens

<400> SEQUENCE: 230

```
Met Met Arg Cys Cys Arg Arg Arg Cys Cys Cys Arg Gln Pro Pro
  1               5                  10                  15

His Ala Leu Arg Pro Leu Leu Leu Leu Pro Leu Val Leu Leu Pro
                 20                  25                  30

Pro Leu Ala Ala Ala Ala Ala Gly Pro Asn Arg Cys Asp Thr Ile
                 35                  40                  45

Tyr Gln Gly Phe Ala Glu Cys Leu Ile Arg Leu Gly Asp Ser Met
                 50                  55                  60

Gly Arg Gly Gly Glu Leu Glu Thr Ile Cys Arg Ser Trp Asn Asp
                 65                  70                  75

Phe His Ala Cys Ala Ser Gln Val Leu Ser Gly Cys Pro Glu Glu
                 80                  85                  90

Ala Ala Ala Val Trp Glu Ser Leu Gln Gln Glu Ala Arg Gln Ala
                 95                 100                 105

Pro Arg Pro Asn Asn Leu His Thr Leu Cys Gly Ala Pro Val His
                110                 115                 120

Val Arg Glu Arg Gly Thr Gly Ser Glu Thr Asn Gln Glu Thr Leu
                125                 130                 135

Arg Ala Thr Ala Pro Ala Leu Pro Met Ala Pro Ala Pro Pro Leu
                140                 145                 150

Leu Ala Ala Ala Leu Ala Leu Ala Tyr Leu Leu Arg Pro Leu Ala
                155                 160                 165
```

<210> SEQ ID NO 231
<211> LENGTH: 890
<212> TYPE: DNA
<213> ORGANISM: Homo sapiens

<400> SEQUENCE: 231

```
aagtacttgt gtccgggtgg tggactggat tagctgcgga gccctggaag               50

ctgcctgtcc ttctccctgt gcttaaccag aggtgcccat gggttggaca              100

atgaggctgg tcacagcagc actgttactg ggtctcatga tggtggtcac              150

tggagacgag gatgagaaca gcccgtgtgc ccatgaggcc ctcttggacg              200

aggacaccct cttttgccag ggccttgaag ttttctaccc agagttgggg              250
```

-continued

```
aacattggct gcaaggttgt tcctgattgt aacaactaca gacagaagat          300

cacctcctgg atggagccga tagtcaagtt cccgggggcc gtggacggcg          350

caacctatat cctggtgatg gtggatccag atgcccctag cagagcagaa          400

cccagacaga gattctggag acattggctg gtaacagata tcaagggcgc          450

cgacctgaag aaagggaaga ttcagggcca ggagttatca gcctaccagg          500

ctccctcccc accggcacac agtggcttcc atcgctacca gttctttgtc          550

tatcttcagg aaggaaaagt catctctctc cttcccaagg aaaacaaaac          600

tcgaggctct tggaaaatgg acagatttct gaaccgcttc cacctgggcg          650

aacctgaagc aagcacccag ttcatgaccc agaactacca ggactcacca          700

accctccagg ctcccagagg aagggccagc gagcccaagc acaaaaccag          750

gcagagatag ctgcctgcta gatagccggc tttgccatcc gggcatgtgg          800

ccacactgct caccaccgac gatgtgggta tggaaccccc tctggataca          850

gaacccccttc ttttccaaat taaaaaaaaa aatcatcaaa                      890
```

<210> SEQ ID NO 232
<211> LENGTH: 223
<212> TYPE: PRT
<213> ORGANISM: Homo sapiens

<400> SEQUENCE: 232

```
Met Gly Trp Thr Met Arg Leu Val Thr Ala Ala Leu Leu Leu Gly
  1               5                  10                  15

Leu Met Met Val Val Thr Gly Asp Glu Asp Glu Asn Ser Pro Cys
                 20                  25                  30

Ala His Glu Ala Leu Leu Asp Glu Asp Thr Leu Phe Cys Gln Gly
                 35                  40                  45

Leu Glu Val Phe Tyr Pro Glu Leu Gly Asn Ile Gly Cys Lys Val
                 50                  55                  60

Val Pro Asp Cys Asn Asn Tyr Arg Gln Lys Ile Thr Ser Trp Met
                 65                  70                  75

Glu Pro Ile Val Lys Phe Pro Gly Ala Val Asp Gly Ala Thr Tyr
                 80                  85                  90

Ile Leu Val Met Val Asp Pro Asp Ala Pro Ser Arg Ala Glu Pro
                 95                 100                 105

Arg Gln Arg Phe Trp Arg His Trp Leu Val Thr Asp Ile Lys Gly
                110                 115                 120

Ala Asp Leu Lys Lys Gly Lys Ile Gln Gly Gln Glu Leu Ser Ala
                125                 130                 135

Tyr Gln Ala Pro Ser Pro Pro Ala His Ser Gly Phe His Arg Tyr
                140                 145                 150

Gln Phe Phe Val Tyr Leu Gln Glu Gly Lys Val Ile Ser Leu Leu
                155                 160                 165

Pro Lys Glu Asn Lys Thr Arg Gly Ser Trp Lys Met Asp Arg Phe
                170                 175                 180

Leu Asn Arg Phe His Leu Gly Glu Pro Glu Ala Ser Thr Gln Phe
                185                 190                 195

Met Thr Gln Asn Tyr Gln Asp Ser Pro Thr Leu Gln Ala Pro Arg
                200                 205                 210

Gly Arg Ala Ser Glu Pro Lys His Lys Thr Arg Gln Arg
                215                 220
```

-continued

<210> SEQ ID NO 233
<211> LENGTH: 924
<212> TYPE: DNA
<213> ORGANISM: Homo sapiens

<400> SEQUENCE: 233
aaggagcagc ccgcaagcac caagtgagag gcatgaagtt acagtgtgtt 50
tccctttggc tcctgggtac aatactgata ttgtgctcag tagacaacca 100
cggtctcagg agatgtctga tttccacaga catgcaccat atagaagaga 150
gtttccaaga aatcaaaaga gccatccaag ctaaggacac cttcccaaat 200
gtcactatcc tgtccacatt ggagactctg cagatcatta agcccttaga 250
tgtgtgctgc gtgaccaaga acctcctggc gttctacgtg gacagggtgt 300
tcaaggatca tcaggagcca aaccccaaaa tcttgagaaa aatcagcagc 350
attgccaact ctttcctcta catgcagaaa actctgcggc aatgtcagga 400
acagaggcag tgtcactgca ggcaggaagc caccaatgcc accagagtca 450
tccatgacaa ctatgatcag ctggaggtcc acgctgctgc cattaaatcc 500
ctgggagagc tcgacgtctt tctagcctgg attaataaga atcatgaagt 550
aatgttctca gcttgatgac aaggaacctg tatagtgatc cagggatgaa 600 cacccctgt gcggtttact gtgggagaca gcccaccttg aaggggaagg 650
agatggggaa ggccccttgc agctgaaagt cccactggct ggcctcaggc 700
tgtcttattc cgcttgaaaa taggcaaaaa gtctactgtg gtatttgtaa 750
taaactctat ctgctgaaag ggcctgcagg ccatcctggg agtaaagggc 800
tgccttccca tctaatttat tgtaaagtca tatagtccat gtctgtgatg 850
tgagccaagt gatatcctgt agtacacatt gtactgagtg gtttttctga 900
ataaattcca tattttacct atga 924

<210> SEQ ID NO 234
<211> LENGTH: 177
<212> TYPE: PRT
<213> ORGANISM: Homo sapiens

<400> SEQUENCE: 234

Met Lys Leu Gln Cys Val Ser Leu Trp Leu Leu Gly Thr Ile Leu
1 5 10 15

Ile Leu Cys Ser Val Asp Asn His Gly Leu Arg Arg Cys Leu Ile
20 25 30

Ser Thr Asp Met His His Ile Glu Glu Ser Phe Gln Glu Ile Lys
35 40 45

Arg Ala Ile Gln Ala Lys Asp Thr Phe Pro Asn Val Thr Ile Leu
50 55 60

Ser Thr Leu Glu Thr Leu Gln Ile Ile Lys Pro Leu Asp Val Cys
65 70 75

Cys Val Thr Lys Asn Leu Leu Ala Phe Tyr Val Asp Arg Val Phe
80 85 90

Lys Asp His Gln Glu Pro Asn Pro Lys Ile Leu Arg Lys Ile Ser
95 100 105

Ser Ile Ala Asn Ser Phe Leu Tyr Met Gln Lys Thr Leu Arg Gln
110 115 120

Cys Gln Glu Gln Arg Gln Cys His Cys Arg Gln Glu Ala Thr Asn

-continued

```
                125                 130                 135

Ala Thr Arg Val Ile His Asp Asn Tyr Asp Gln Leu Glu Val His
                140                 145                 150

Ala Ala Ala Ile Lys Ser Leu Gly Glu Leu Asp Val Phe Leu Ala
                155                 160                 165

Trp Ile Asn Lys Asn His Glu Val Met Phe Ser Ala
                170                 175
```

<210> SEQ ID NO 235
<211> LENGTH: 1161
<212> TYPE: DNA
<213> ORGANISM: Homo sapiens
<220> FEATURE:
<221> NAME/KEY: Unsure
<222> LOCATION: 1149
<223> OTHER INFORMATION: Unknown base

<400> SEQUENCE: 235

```
gcccgggcgg ctgcccttgg gtgctccctt ccctgcccga cacccagacc           50

gaccttgacc gcccacctgg caggagcagg acaggacggc cggacgcggc          100

catggccgag ctcccggggc cctttctctg cggggccctg ctaggcttcc          150

tgtgcctgag tgggctggcc gtggaggtga aggtacccac agagccgctg          200

agcacgcccc tggggaagac agccgagctg acctgcacct acagcacgtc          250

ggtgggagac agcttcgccc tggagtggag ctttgtgcag cctgggaaac          300

ccatctctga gtcccatcca atcctgtact tcaccaatgg ccatctgtat          350

ccaactggtt ctaagtcaaa gcgggtcagc ctgcttcaga acccccccac          400

agtgggggtg gccacactga aactgactga cgtccacccc tcagatactg          450

gaacctacct ctgccaagtc aacaacccac cagatttcta caccaatggg          500

ttggggctaa tcaaccttac tgtgctggtt ccccccagta atcccttatg          550

cagtcagagt ggacaaacct ctgtgggagg ctctactgca ctgagatgca          600

gctcttccga gggggctcct aagccagtgt acaactgggt gcgtcttgga          650

acttttccta caccttctcc tggcagcatg gttcaagatg aggtgtctgg          700

ccagctcatt ctcaccaacc tctccctgac ctcctcgggc acctaccgct          750

gtgtggccac caaccagatg ggcagtgcat cctgtgagct gaccctctct          800

gtgaccgaac cctcccaagg ccgagtggcc ggagctctga ttggggtgct          850

cctgggcgtg ctgttgctgt cagttgctgc gttctgcctg gtcaggttcc          900

agaaagagag gggaagaag cccaaggaga catatggggg tagtgacctt          950

cgggaggatg ccatcgctcc tgggatctct gagcacactt gtatgagggc         1000

tgattctagc aaggggttcc tggaaagacc ctcgtctgcc agcaccgtga         1050

cgaccaccaa gtccaagctc cctatggtcg tgtgacttct cccgatccct         1100

gagggcggtg agggggaata tcaataatta aagtctgtgg gtacccttna         1150

aaaaaaaaaa  a                                                  1161
```

<210> SEQ ID NO 236
<211> LENGTH: 327
<212> TYPE: PRT
<213> ORGANISM: Homo sapiens

<400> SEQUENCE: 236

-continued

```
Met Ala Glu Leu Pro Gly Pro Phe Leu Cys Gly Ala Leu Leu Gly
  1               5                  10                  15

Phe Leu Cys Leu Ser Gly Leu Ala Val Glu Val Lys Val Pro Thr
                 20                  25                  30

Glu Pro Leu Ser Thr Pro Leu Gly Lys Thr Ala Glu Leu Thr Cys
                 35                  40                  45

Thr Tyr Ser Thr Ser Val Gly Asp Ser Phe Ala Leu Glu Trp Ser
                 50                  55                  60

Phe Val Gln Pro Gly Lys Pro Ile Ser Glu Ser His Pro Ile Leu
                 65                  70                  75

Tyr Phe Thr Asn Gly His Leu Tyr Pro Thr Gly Ser Lys Ser Lys
                 80                  85                  90

Arg Val Ser Leu Leu Gln Asn Pro Pro Thr Val Gly Val Ala Thr
                 95                 100                 105

Leu Lys Leu Thr Asp Val His Pro Ser Asp Thr Gly Thr Tyr Leu
                110                 115                 120

Cys Gln Val Asn Asn Pro Pro Asp Phe Tyr Thr Asn Gly Leu Gly
                125                 130                 135

Leu Ile Asn Leu Thr Val Leu Val Pro Pro Ser Asn Pro Leu Cys
                140                 145                 150

Ser Gln Ser Gly Gln Thr Ser Val Gly Gly Ser Thr Ala Leu Arg
                155                 160                 165

Cys Ser Ser Ser Glu Gly Ala Pro Lys Pro Val Tyr Asn Trp Val
                170                 175                 180

Arg Leu Gly Thr Phe Pro Thr Pro Ser Pro Gly Ser Met Val Gln
                185                 190                 195

Asp Glu Val Ser Gly Gln Leu Ile Leu Thr Asn Leu Ser Leu Thr
                200                 205                 210

Ser Ser Gly Thr Tyr Arg Cys Val Ala Thr Asn Gln Met Gly Ser
                215                 220                 225

Ala Ser Cys Glu Leu Thr Leu Ser Val Thr Glu Pro Ser Gln Gly
                230                 235                 240

Arg Val Ala Gly Ala Leu Ile Gly Val Leu Leu Gly Val Leu Leu
                245                 250                 255

Leu Ser Val Ala Ala Phe Cys Leu Val Arg Phe Gln Lys Glu Arg
                260                 265                 270

Gly Lys Lys Pro Lys Glu Thr Tyr Gly Gly Ser Asp Leu Arg Glu
                275                 280                 285

Asp Ala Ile Ala Pro Gly Ile Ser Glu His Thr Cys Met Arg Ala
                290                 295                 300

Asp Ser Ser Lys Gly Phe Leu Glu Arg Pro Ser Ser Ala Ser Thr
                305                 310                 315

Val Thr Thr Thr Lys Ser Lys Leu Pro Met Val Val
                320                 325
```

<210> SEQ ID NO 237
<211> LENGTH: 983
<212> TYPE: DNA
<213> ORGANISM: Homo sapiens

<400> SEQUENCE: 237

```
ggatgcagca gagaggagca gctggaagcc gtggctgcgc tctcttccct          50

ctgctgggcg tcctgttctt ccagggtgtt tatatcgtct tttccttgga         100

gattcgtgca gatgcccatg tccgaggtta tgttggagaa aagatcaagt         150
```

-continued

```
tgaaatgcac tttcaagtca acttcagatg tcactgacaa gcttactata          200

gactggacat atcgccctcc cagcagcagc cacacagtat caatatttca          250

ttatcagtct ttccagtacc caaccacagc aggcacattt cgggatcgga          300

tttcctgggt tggaaatgta tacaaagggg atgcatctat aagtataagc          350

aaccctacca taaaggacaa tgggacattc agctgtgctg tgaagaatcc          400

cccagatgtg caccataata ttcccatgac agagctaaca gtcacagaaa          450

ggggttttgg caccatgctt tcctctgtgg cccttctttc catccttgtc          500

tttgtgccct cagccgtggt ggttgctctg ctgctggtga gaatggggag          550

gaaggctgct gggctgaaga agaggagcag gtctggctat aagaagtcat          600

ctattgaggt ttccgatgac actgatcagg aggaggaaga ggcgtgtatg          650

gcgaggcttt gtgtccgttg cgctgagtgc ctggattcag actatgaaga          700

gacatattga tgaaagtctg tatgacacaa gaagagtcac ctaaagacag          750

gaaacatccc attccactgg cagctaaagc ctgtcagaga aagtggagct          800

ggcctggacc atagcgatgg acaatcctgg agatcatcag taaagacttt          850

aggaaccact tatttattga ataaatgttc ttgttgtatt tataaactgt          900

tcaggaagtc tcataagaga ctcatgactt cccctttcaa tgaattatgc          950

tgtaattgaa tgaagaaatt cttttcctga  gca                           983
```

<210> SEQ ID NO 238
<211> LENGTH: 235
<212> TYPE: PRT
<213> ORGANISM: Homo sapiens

<400> SEQUENCE: 238

```
Met Gln Gln Arg Gly Ala Ala Gly Ser Arg Gly Cys Ala Leu Phe
  1               5                  10                  15

Pro Leu Leu Gly Val Leu Phe Phe Gln Gly Val Tyr Ile Val Phe
                 20                  25                  30

Ser Leu Glu Ile Arg Ala Asp Ala His Val Arg Gly Tyr Val Gly
                 35                  40                  45

Glu Lys Ile Lys Leu Lys Cys Thr Phe Lys Ser Thr Ser Asp Val
                 50                  55                  60

Thr Asp Lys Leu Thr Ile Asp Trp Thr Tyr Arg Pro Pro Ser Ser
                 65                  70                  75

Ser His Thr Val Ser Ile Phe His Tyr Gln Ser Phe Gln Tyr Pro
                 80                  85                  90

Thr Thr Ala Gly Thr Phe Arg Asp Arg Ile Ser Trp Val Gly Asn
                 95                 100                 105

Val Tyr Lys Gly Asp Ala Ser Ile Ser Ile Ser Asn Pro Thr Ile
                110                 115                 120

Lys Asp Asn Gly Thr Phe Ser Cys Ala Val Lys Asn Pro Pro Asp
                125                 130                 135

Val His His Asn Ile Pro Met Thr Glu Leu Thr Val Thr Glu Arg
                140                 145                 150

Gly Phe Gly Thr Met Leu Ser Ser Val Ala Leu Leu Ser Ile Leu
                155                 160                 165

Val Phe Val Pro Ser Ala Val Val Val Ala Leu Leu Leu Val Arg
                170                 175                 180
```

-continued

```
Met Gly Arg Lys Ala Ala Gly Leu Lys Lys Arg Ser Arg Ser Gly
                185                 190                 195

Tyr Lys Lys Ser Ser Ile Glu Val Ser Asp Asp Thr Asp Gln Glu
                200                 205                 210

Glu Glu Glu Ala Cys Met Ala Arg Leu Cys Val Arg Cys Ala Glu
                215                 220                 225

Cys Leu Asp Ser Asp Tyr Glu Glu Thr Tyr
                230                 235


<210> SEQ ID NO 239
<211> LENGTH: 2024
<212> TYPE: DNA
<213> ORGANISM: Homo sapiens

<400> SEQUENCE: 239

caggcgggcc cccgcgcggc agggccctgg acccgcgcgg ctcccgggga          50

tggtgagcaa ggcgctgctg cgcctcgtgt ctgccgtcaa ccgcaggagg         100

atgaagctgc tgctgggcat cgccttgctg gcctacgtcg cctctgtttg         150

gggcaacttc gttaatatga ggtctatcca ggaaaatggt gaactaaaaa         200

ttgaaagcaa gattgaagag atggttgaac cactaagaga gaaaatcaga         250

gatttagaaa aaagctttac ccagaaatac ccaccagtaa agtttttatc         300

agaaaaggat cggaaaagaa ttttgataac aggaggcgca gggttcgtgg         350

gctcccatct aactgacaaa ctcatgatgg acggccacga ggtgaccgtg         400

gtggacaatt tcttcacggg caggaagaga aacgtggagc actggatcgg         450

acatgagaac ttcgagttga ttaaccacga cgtggtggag cccctctaca         500

tcgaggttga ccagatatac catctggcat ctccagcctc ccctccaaac         550

tacatgtata atcctatcaa gacattaaag accaatacga ttgggacatt         600

aaacatgttg gggctggcaa aacgagtcgg tgcccgtctg ctcctggcct         650

ccacatcgga ggtgtatgga gatcctgaag tccaccctca aagtgaggat         700

tactggggcc acgtgaatcc aataggacct cgggcctgct acgatgaagg         750

caaacgtgtt gcagagacca tgtgctatgc ctacatgaag caggaaggcg         800

tggaagtgcg agtggccaga atcttcaaca cctttgggcc acgcatgcac         850

atgaacgatg ggcgagtagt cagcaacttc atcctgcagg cgctccaggg         900

ggagccactc acggtatacg gatccgggtc tcagacaagg gcgttccagt         950

acgtcagcga tctagtgaat ggcctcgtgg ctctcatgaa cagcaacgtc        1000

agcagcccgg tcaacctggg gaacccagaa gaacacacaa tcctagaatt        1050

tgctcagtta attaaaaacc ttgttggtag cggaagtgaa attcagtttc        1100

tctccgaagc ccaggatgac ccacagaaaa gaaaaccaga catcaaaaaa        1150

gcaaagctga tgctggggtg ggagcccgtg gtcccgctgg aggaaggttt        1200

aaacaaagca attcactact tccgtaaaga actcgagtac caggcaaata        1250

atcagtacat ccccaaacca aagcctgcca gaataaagaa aggacggact        1300

cgccacagct gaactcctca cttttaggac acaagactac cattgtacac        1350

ttgatgggat gtatttttgg cttttttttg ttgtcgttta aagaaagact        1400

ttaacaggtg tcatgaagaa caaactggaa tttcattctg aagcttgctt        1450

taatgaaatg gatgtgccta aaagctcccc tcaaaaaact gcagattttg        1500
```

```
ccttgcactt tttgaatctc tctttttatg taaaatagcg tagatgcatc            1550

tctgcgtatt ttcaagtttt tttatcttgc tgtgagagca tatgttgtga            1600

ctgtcgttga cagttttatt tactggtttc tttgtgaagc tgaaaaggaa            1650

cattaagcgg gacaaaaaat gccgatttta tttataaaag tgggtactta            1700

ataaatgagt cgttatacta tgcataaaga aaaatcctag cagtattgtc            1750

aggtggtggt gcgccggcat tgattttagg gcagataaaa gaattctgtg            1800

tgagagcttt atgtttctct tttaattcag agtttttcca aggtctactt            1850

ttgagttgca aacttgactt tgaaatattc ctgttggtca tgatcaagga            1900

tatttgaaat cactactgtg ttttgctgcg tatctggggc gggggcaggt            1950

tggggggcac aaagttaaca tattcttggt taaccatggt taaatatgct            2000

attttaataa aatattgaaa  ctca                                       2024


<210> SEQ ID NO 240
<211> LENGTH: 420
<212> TYPE: PRT
<213> ORGANISM: Homo sapiens

<400> SEQUENCE: 240

Met Val Ser Lys Ala Leu Leu Arg Leu Val Ser Ala Val Asn Arg
  1               5                  10                  15

Arg Arg Met Lys Leu Leu Leu Gly Ile Ala Leu Leu Ala Tyr Val
                 20                  25                  30

Ala Ser Val Trp Gly Asn Phe Val Asn Met Arg Ser Ile Gln Glu
                 35                  40                  45

Asn Gly Glu Leu Lys Ile Glu Ser Lys Ile Glu Glu Met Val Glu
                 50                  55                  60

Pro Leu Arg Glu Lys Ile Arg Asp Leu Glu Lys Ser Phe Thr Gln
                 65                  70                  75

Lys Tyr Pro Pro Val Lys Phe Leu Ser Glu Lys Asp Arg Lys Arg
                 80                  85                  90

Ile Leu Ile Thr Gly Gly Ala Gly Phe Val Gly Ser His Leu Thr
                 95                 100                 105

Asp Lys Leu Met Met Asp Gly His Glu Val Thr Val Val Asp Asn
                110                 115                 120

Phe Phe Thr Gly Arg Lys Arg Asn Val Glu His Trp Ile Gly His
                125                 130                 135

Glu Asn Phe Glu Leu Ile Asn His Asp Val Val Glu Pro Leu Tyr
                140                 145                 150

Ile Glu Val Asp Gln Ile Tyr His Leu Ala Ser Pro Ala Ser Pro
                155                 160                 165

Pro Asn Tyr Met Tyr Asn Pro Ile Lys Thr Leu Lys Thr Asn Thr
                170                 175                 180

Ile Gly Thr Leu Asn Met Leu Gly Leu Ala Lys Arg Val Gly Ala
                185                 190                 195

Arg Leu Leu Leu Ala Ser Thr Ser Glu Val Tyr Gly Asp Pro Glu
                200                 205                 210

Val His Pro Gln Ser Glu Asp Tyr Trp Gly His Val Asn Pro Ile
                215                 220                 225

Gly Pro Arg Ala Cys Tyr Asp Glu Gly Lys Arg Val Ala Glu Thr
                230                 235                 240
```

-continued

```
Met Cys Tyr Ala Tyr Met Lys Gln Glu Gly Val Glu Val Arg Val
                245                 250                 255

Ala Arg Ile Phe Asn Thr Phe Gly Pro Arg Met His Met Asn Asp
                260                 265                 270

Gly Arg Val Val Ser Asn Phe Ile Leu Gln Ala Leu Gln Gly Glu
                275                 280                 285

Pro Leu Thr Val Tyr Gly Ser Gly Ser Gln Thr Arg Ala Phe Gln
                290                 295                 300

Tyr Val Ser Asp Leu Val Asn Gly Leu Val Ala Leu Met Asn Ser
                305                 310                 315

Asn Val Ser Ser Pro Val Asn Leu Gly Asn Pro Glu Glu His Thr
                320                 325                 330

Ile Leu Glu Phe Ala Gln Leu Ile Lys Asn Leu Val Gly Ser Gly
                335                 340                 345

Ser Glu Ile Gln Phe Leu Ser Glu Ala Gln Asp Asp Pro Gln Lys
                350                 355                 360

Arg Lys Pro Asp Ile Lys Lys Ala Lys Leu Met Leu Gly Trp Glu
                365                 370                 375

Pro Val Val Pro Leu Glu Glu Gly Leu Asn Lys Ala Ile His Tyr
                380                 385                 390

Phe Arg Lys Glu Leu Glu Tyr Gln Ala Asn Asn Gln Tyr Ile Pro
                395                 400                 405

Lys Pro Lys Pro Ala Arg Ile Lys Lys Gly Arg Thr Arg His Ser
                410                 415                 420
```

<210> SEQ ID NO 241
<211> LENGTH: 2025
<212> TYPE: DNA
<213> ORGANISM: Homo sapiens

<400> SEQUENCE: 241

```
gcccggtgga gaattaggtg ctgctgggag ctcctgcctc ccacaggatt        50

ccagctgcag ggagcctcag ggactctggg ccgcacggag ttgggggcat       100

tccccagaga gcgtcgccat ggtctgcagg gagcagttat caaagaatca       150

ggtcaagtgg gtgtttgccg gcattacctg tgtgtctgtg gtggtcattg       200

ccgcaatagt ccttgccatc accctgcggc ggccaggctg tgagctggag       250

gcctgcagcc ctgatgccga catgctggac tacctgctga gcctgggcca       300

gatcagccgg cgagatgcct tggaggtcac ctggtaccac gcagccaaca       350

gcaagaaagc catgacagct gccctgaaca gcaacatcac agtcctggag       400

gctgacgtca atgtagaagg gctcggcaca gccaatgaga caggagttcc       450

catcatggca caccccccca ctatctacag tgacaacaca ctggagcagt       500

ggctggacgc tgtgctgggc tcttcccaaa agggcatcaa actggacttc       550

aagaacatca aggcagtggg cccctccctg gacctcctgc ggcagctgac       600

agaggaaggc aaagtccggc ggcccatatg gatcaacgct gacatcttaa       650

agggccccaa catgctcatc tcaactgagg tcaatgccac acagttcctg       700

gccctggtcc aggagaagta tcccaaggct accctatctc caggctggac       750

caccttctac atgtccacgt ccccaaacag gacgtacacc caagccatgg       800

tggagaagat gcacgagctg gtgggaggag tgccccagag ggtcaccttc       850

cctgtacggt cttccatggt gcgggctgcc tggccccact tcagctggct       900
```

-continued

```
gctgagccaa tctgagaggt acagcctgac gctgtggcag gctgcctcgg          950
accccatgtc ggtggaagat ctgctctacg tccgggataa cactgctgtc         1000
caccaagtct actatgacat ctttgagcct ctcctgtcac agttcaagca         1050
gctggccttg aatgccacac ggaaaccaat gtactacacg ggaggcagcc         1100
tgatccctct tctccagctg cctggggatg acggtctgaa tgtggagtgg         1150
ctggttcctg acgtccaggg cagcggtaaa acagcaacaa tgaccctccc         1200
agacacagaa ggcatgatcc tgctgaacac tggcctcgag ggaactgtgg         1250
ctgaaaaccc cgtgcccatt gttcatactc caagtggcaa catcctgacg         1300
ctggagtcct gcctgcagca gctggccaca catcccggac actggggcat         1350
ccatttgcaa atagtggagc ccgcagccct ccggccatcc ctggccttgc         1400
tggcacgcct ctccagcctt ggcctcttgc attggcctgt gtgggttggg         1450
gccaaaatct cccacgggag tttttcggtc cccggccatg tggctggcag         1500
agagctgctt acagctgtgg ctgaggtctt cccccacgtg actgtggcac         1550
caggctggcc tgaggaggtg ctgggcagtg gctacaggga acagctgctc         1600
acagatatgc tagagttgtg ccaggggctc tggcaacctg tgtccttcca         1650
gatgcaggcc atgctgctgg gccacagcac agctggagcc ataggcaggc         1700
tgctggcatc ctcccccccgg gccaccgtca cagtggagca caacccagct        1750
gggggcgact atgcctctgt gaggacagca ttgctggcag ctagggctgt         1800
ggacaggacc cgagtctact acaggctacc ccagggctac cacaaggact         1850
tgctggctca tgttggtaga aactgagcac ccaggggtgg tgggccagcg         1900
gacctcaggg cggaggcttc ccacggggag gcaggaagaa ataaaggtct         1950
ttggctttct ccaggcaaaa aaaaaaaaaa aaaaaaaaaa aaaaaaaaaa         2000
aaaaaaaaaa aaaaaaaaaa  aaaag                                   2025
```

<210> SEQ ID NO 242
<211> LENGTH: 585
<212> TYPE: PRT
<213> ORGANISM: Homo sapiens

<400> SEQUENCE: 242

```
Met Val Cys Arg Glu Gln Leu Ser Lys Asn Gln Val Lys Trp Val
  1               5                  10                  15

Phe Ala Gly Ile Thr Cys Val Ser Val Val Val Ile Ala Ala Ile
                 20                  25                  30

Val Leu Ala Ile Thr Leu Arg Arg Pro Gly Cys Glu Leu Glu Ala
                 35                  40                  45

Cys Ser Pro Asp Ala Asp Met Leu Asp Tyr Leu Leu Ser Leu Gly
                 50                  55                  60

Gln Ile Ser Arg Arg Asp Ala Leu Glu Val Thr Trp Tyr His Ala
                 65                  70                  75

Ala Asn Ser Lys Lys Ala Met Thr Ala Ala Leu Asn Ser Asn Ile
                 80                  85                  90

Thr Val Leu Glu Ala Asp Val Asn Val Glu Gly Leu Gly Thr Ala
                 95                 100                 105

Asn Glu Thr Gly Val Pro Ile Met Ala His Pro Pro Thr Ile Tyr
                110                 115                 120
```

-continued

```
Ser Asp Asn Thr Leu Glu Gln Trp Leu Asp Ala Val Leu Gly Ser
                125                 130                 135

Ser Gln Lys Gly Ile Lys Leu Asp Phe Lys Asn Ile Lys Ala Val
                140                 145                 150

Gly Pro Ser Leu Asp Leu Leu Arg Gln Leu Thr Glu Glu Gly Lys
                155                 160                 165

Val Arg Arg Pro Ile Trp Ile Asn Ala Asp Ile Leu Lys Gly Pro
                170                 175                 180

Asn Met Leu Ile Ser Thr Glu Val Asn Ala Thr Gln Phe Leu Ala
                185                 190                 195

Leu Val Gln Glu Lys Tyr Pro Lys Ala Thr Leu Ser Pro Gly Trp
                200                 205                 210

Thr Thr Phe Tyr Met Ser Thr Ser Pro Asn Arg Thr Tyr Thr Gln
                215                 220                 225

Ala Met Val Glu Lys Met His Glu Leu Val Gly Gly Val Pro Gln
                230                 235                 240

Arg Val Thr Phe Pro Val Arg Ser Ser Met Val Arg Ala Ala Trp
                245                 250                 255

Pro His Phe Ser Trp Leu Leu Ser Gln Ser Glu Arg Tyr Ser Leu
                260                 265                 270

Thr Leu Trp Gln Ala Ala Ser Asp Pro Met Ser Val Glu Asp Leu
                275                 280                 285

Leu Tyr Val Arg Asp Asn Thr Ala Val His Gln Val Tyr Tyr Asp
                290                 295                 300

Ile Phe Glu Pro Leu Leu Ser Gln Phe Lys Gln Leu Ala Leu Asn
                305                 310                 315

Ala Thr Arg Lys Pro Met Tyr Tyr Thr Gly Gly Ser Leu Ile Pro
                320                 325                 330

Leu Leu Gln Leu Pro Gly Asp Asp Gly Leu Asn Val Glu Trp Leu
                335                 340                 345

Val Pro Asp Val Gln Gly Ser Gly Lys Thr Ala Thr Met Thr Leu
                350                 355                 360

Pro Asp Thr Glu Gly Met Ile Leu Leu Asn Thr Gly Leu Glu Gly
                365                 370                 375

Thr Val Ala Glu Asn Pro Val Pro Ile Val His Thr Pro Ser Gly
                380                 385                 390

Asn Ile Leu Thr Leu Glu Ser Cys Leu Gln Gln Leu Ala Thr His
                395                 400                 405

Pro Gly His Trp Gly Ile His Leu Gln Ile Val Glu Pro Ala Ala
                410                 415                 420

Leu Arg Pro Ser Leu Ala Leu Leu Ala Arg Leu Ser Ser Leu Gly
                425                 430                 435

Leu Leu His Trp Pro Val Trp Val Gly Ala Lys Ile Ser His Gly
                440                 445                 450

Ser Phe Ser Val Pro Gly His Val Ala Gly Arg Glu Leu Leu Thr
                455                 460                 465

Ala Val Ala Glu Val Phe Pro His Val Thr Val Ala Pro Gly Trp
                470                 475                 480

Pro Glu Glu Val Leu Gly Ser Gly Tyr Arg Glu Gln Leu Leu Thr
                485                 490                 495

Asp Met Leu Glu Leu Cys Gln Gly Leu Trp Gln Pro Val Ser Phe
                500                 505                 510

Gln Met Gln Ala Met Leu Leu Gly His Ser Thr Ala Gly Ala Ile
```

-continued

```
515 520 525

Gly Arg Leu Leu Ala Ser Ser Pro Arg Ala Thr Val Thr Val Glu
                530                 535                 540

His Asn Pro Ala Gly Gly Asp Tyr Ala Ser Val Arg Thr Ala Leu
                545                 550                 555

Leu Ala Ala Arg Ala Val Asp Arg Thr Arg Val Tyr Tyr Arg Leu
                560                 565                 570

Pro Gln Gly Tyr His Lys Asp Leu Leu Ala His Val Gly Arg Asn
                575                 580                 585


<210> SEQ ID NO 243
<211> LENGTH: 1152
<212> TYPE: DNA
<213> ORGANISM: Homo sapiens

<400> SEQUENCE: 243

cttcagaaca ggttctcctt ccccagtcac cagttgctcg agttagaatt        50

gtctgcaatg gccgccctgc agaaatctgt gagctctttc cttatgggga       100

ccctggccac cagctgcctc cttctcttgg ccctcttggt acagggagga       150

gcagctgcgc ccatcagctc ccactgcagg cttgacaagt ccaacttcca       200

gcagccctat atcaccaacc gcaccttcat gctggctaag gaggctagct       250

tggctgataa caacacagac gttcgtctca ttggggagaa actgttccac       300

ggagtcagta tgagtgagcg ctgctatctg atgaagcagg tgctgaactt       350

caccettgaa gaagtgctgt tccctcaatc tgataggttc cagccttata       400

tgcaggaggt ggtgcccttc ctggccaggc tcagcaacag gctaagcaca       450

tgtcatattg aaggtgatga cctgcatatc cagaggaatg tgcaaaagct       500

gaaggacaca gtgaaaaagc ttggagagag tggagagatc aaagcaattg       550

gagaactgga tttgctgttt atgtctctga gaaatgcctg catttgacca       600

gagcaaagct gaaaaatgaa taactaaccc cctttccctg ctagaaataa       650

caattagatg ccccaaagcg atttttttta accaaaagga agatgggaag       700

ccaaactcca tcatgatggg tggattccaa atgaacccct gcgttagtta       750

caaaggaaac caatgccact tttgtttata agaccagaag gtagactttc       800

taagcataga tatttattga taacatttca ttgtaactgg tgttctatac       850

acagaaaaca atttattttt taaataattg tctttttcca taaaaaagat       900

tactttccat tcctttaggg gaaaaaaccc ctaaatagct tcatgtttcc       950

ataatcagta ctttatattt ataaatgtat ttattattat tataagactg      1000

cattttattt atatcatttt attaatatgg atttatttat agaaacatca      1050

ttcgatattg ctacttgagt gtaaggctaa tattgatatt tatgacaata      1100

attatagagc tataacatgt ttatttgacc tcaataaaca cttggatatc      1150

cc                                                          1152


<210> SEQ ID NO 244
<211> LENGTH: 179
<212> TYPE: PRT
<213> ORGANISM: Homo sapiens

<400> SEQUENCE: 244

Met Ala Ala Leu Gln Lys Ser Val Ser Ser Phe Leu Met Gly Thr
```

-continued

```
  1               5                   10                  15

Leu Ala Thr Ser Cys Leu Leu Leu Leu Ala Leu Leu Val Gln Gly
                20                  25                  30

Gly Ala Ala Ala Pro Ile Ser Ser His Cys Arg Leu Asp Lys Ser
                35                  40                  45

Asn Phe Gln Gln Pro Tyr Ile Thr Asn Arg Thr Phe Met Leu Ala
                50                  55                  60

Lys Glu Ala Ser Leu Ala Asp Asn Asn Thr Asp Val Arg Leu Ile
                65                  70                  75

Gly Glu Lys Leu Phe His Gly Val Ser Met Ser Glu Arg Cys Tyr
                80                  85                  90

Leu Met Lys Gln Val Leu Asn Phe Thr Leu Glu Glu Val Leu Phe
                95                  100                 105

Pro Gln Ser Asp Arg Phe Gln Pro Tyr Met Gln Glu Val Val Pro
                110                 115                 120

Phe Leu Ala Arg Leu Ser Asn Arg Leu Ser Thr Cys His Ile Glu
                125                 130                 135

Gly Asp Asp Leu His Ile Gln Arg Asn Val Gln Lys Leu Lys Asp
                140                 145                 150

Thr Val Lys Lys Leu Gly Glu Ser Gly Glu Ile Lys Ala Ile Gly
                155                 160                 165

Glu Leu Asp Leu Leu Phe Met Ser Leu Arg Asn Ala Cys Ile
                170                 175
```

<210> SEQ ID NO 245
<211> LENGTH: 43
<212> TYPE: DNA
<213> ORGANISM: Artificial Sequence
<220> FEATURE:
<223> OTHER INFORMATION: Synthetic Oligonucleotide Probe

<400> SEQUENCE: 245
tgtaaaacga cggccagtta aatagacctg caattattaa tct 43

<210> SEQ ID NO 246
<211> LENGTH: 41
<212> TYPE: DNA
<213> ORGANISM: Artificial Sequence
<220> FEATURE:
<223> OTHER INFORMATION: Synthetic Oligonucleotide Probe

<400> SEQUENCE: 246
caggaaacag ctatgaccac ctgcacacct gcaaatccat t 41

METHOD OF DETECTING PRO9917

RELATED APPLICATIONS

This application is a divisional of, and claims priority under 35 USC §120 to, U.S. application Ser. No. 11/552,437, filed Oct. 24, 2006, now U.S. Pat. No. 7,476,723, which is a continuation of, and claims priority under 35 USC §120 to, U.S. application Ser. No. 10/216,168, filed Aug. 9, 2002, now U.S. Pat. No. 7,157,558, which is a continuation of, and claims priority under 35 USC §120 to, U.S. application Ser. No. 10/119,480 filed Apr. 9, 2002, now abandoned, which is a continuation of, and claims priority under 35 USC §120 to, International Application PCT/US01/21066 filed Jun. 29, 2001, which is a continuation-in-part of, and claims priority under 35 USC §120 to, International Application PCT/US01/17800 filed Jun. 1, 2001. The entire disclosures of the foregoing applications are incorporated by reference herein.

FIELD OF THE INVENTION

The present invention relates generally to the identification and isolation of novel DNA and to the recombinant production of novel polypeptides.

BACKGROUND OF THE INVENTION

Extracellular proteins play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. These secreted polypeptides or signaling molecules normally pass through the cellular secretory pathway to reach their site of action in the extracellular environment.

Secreted proteins have various industrial applications, including as pharmaceuticals, diagnostics, biosensors and bioreactors. Most protein drugs available at present, such as thrombolytic agents, interferons, interleukins, erythropoietins, colony stimulating factors, and various other cytokines, are secretory proteins. Their receptors, which are membrane proteins, also have potential as therapeutic or diagnostic agents. Efforts are being undertaken by both industry and academia to identify new, native secreted proteins. Many efforts are focused on the screening of mammalian recombinant DNA libraries to identify the coding sequences for novel secreted proteins. Examples of screening methods and techniques are described in the literature [see, for example, Klein et al., *Proc. Natl. Acad. Sci.* 93:7108-7113 (1996); U.S. Pat. No. 5,536,637)].

Membrane-bound proteins and receptors can play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. Such membrane-bound proteins and cell receptors include, but are not limited to, cytokine receptors, receptor kinases, receptor phosphatases, receptors involved in cell-cell interactions, and cellular adhesin molecules like selectins and integrins. For instance, transduction of signals that regulate cell growth and differentiation is regulated in part by phosphorylation of various cellular proteins. Protein tyrosine kinases, enzymes that catalyze that process, can also act as growth factor receptors. Examples include fibroblast growth factor receptor and nerve growth factor receptor.

Membrane-bound proteins and receptor molecules have various industrial applications, including as pharmaceutical and diagnostic agents. Receptor immunoadhesins, for instance, can be employed as therapeutic agents to block receptor-ligand interactions. The membrane-bound proteins can also be employed for screening of potential peptide or small molecule inhibitors of the relevant receptor/ligand interaction.

Efforts are being undertaken by both industry and academia to identify new, native receptor or membrane-bound proteins. Many efforts are focused on the screening of mammalian recombinant DNA libraries to identify the coding sequences for novel receptor or membrane-bound proteins.

SUMMARY OF THE INVENTION

In one embodiment, the invention provides an isolated nucleic acid molecule comprising a nucleotide sequence that encodes a PRO polypeptide.

In one aspect, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule encoding a PRO polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein, or (b) the complement of the DNA molecule of (a).

In other aspects, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule comprising the coding sequence of a full-length PRO polypeptide cDNA as disclosed herein, the coding sequence of a PRO polypeptide lacking the signal peptide as disclosed herein, the coding sequence of an extracellular domain of a transmembrane PRO polypeptide, with or without the signal peptide, as disclosed herein or the coding sequence of any other specifically defined fragment of the full-length amino acid sequence as disclosed herein, or (b) the complement of the DNA molecule of (a).

In a further aspect, the invention concerns an isolated nucleic acid molecule comprising a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule that encodes the same mature polypeptide encoded by any of the human protein cDNAs deposited with the ATCC® (American Type Culture Collection, Manassas, Va.) as disclosed herein, or (b) the complement of the DNA molecule of (a).

Another aspect the invention provides an isolated nucleic acid molecule comprising a nucleotide sequence encoding a PRO polypeptide which is either transmembrane domain-deleted or transmembrane domain-inactivated, or is complementary to such encoding nucleotide sequence, wherein the transmembrane domain(s) of such polypeptide are disclosed herein. Therefore, soluble extracellular domains of the herein described PRO polypeptides are contemplated.

Another embodiment is directed to fragments of a PRO polypeptide coding sequence, or the complement thereof, that may find use as, for example, hybridization probes, for encoding fragments of a PRO polypeptide that may optionally encode a polypeptide comprising a binding site for an anti-PRO antibody or as antisense oligonucleotide probes. Such nucleic acid fragments are usually at least about 10 nucleotides in length, alternatively at least about 15 nucleotides in length, alternatively at least about 20 nucleotides in length, alternatively at least about 30 nucleotides in length, alternatively at least about 40 nucleotides in length, alternatively at least about 50 nucleotides in length, alternatively at least about 60 nucleotides in length, alternatively at least about 70 nucleotides in length, alternatively at least about 80 nucleotides in length, alternatively at least about 90 nucleotides in length, alternatively at least about 100 nucleotides in length, alternatively at least about 110 nucleotides in length, alternatively at least about 120 nucleotides in length, alternatively at least about 130 nucleotides in length, alternatively at least about 140 nucleotides in length, alternatively at least about 150 nucleotides in length, alternatively at least about 160 nucleotides in length, alternatively at least about 170 nucleotides in length, alternatively at least about 180 nucleotides in length, alternatively at least about 190 nucleotides in length, alternatively at least about 200 nucleotides in length, alternatively at least about 250 nucleotides in length, alternatively at least about 300 nucleotides in length, alternatively at least about 350 nucleotides in length, alternatively at least about 400 nucleotides in length, alternatively at least about 450 nucleotides in length, alternatively at least about 500 nucleotides in length, alternatively at least about 600 nucleotides in length, alternatively at least about 700 nucleotides in length, alternatively at least about 800 nucleotides in length, alternatively at least about 900 nucleotides in length and alternatively at least about 1000 nucleotides in length, wherein in this context the term "about" means the referenced nucleotide sequence length plus or minus 10% of that referenced length. It is noted that novel fragments of a PRO polypeptide-encoding nucleotide sequence may be determined in a routine manner by aligning the PRO polypeptide-encoding nucleotide sequence with other known nucleotide sequences using any of a number of well known sequence alignment programs and determining which PRO polypeptide-encoding nucleotide sequence fragment(s) are novel. All of such PRO polypeptide-encoding nucleotide sequences are contemplated herein. Also contemplated are the PRO polypeptide fragments encoded by these nucleotide molecule fragments, preferably those PRO polypeptide fragments that comprise a binding site for an anti-PRO antibody.

In another embodiment, the invention provides isolated PRO polypeptide encoded by any of the isolated nucleic acid sequences hereinabove identified.

In a certain aspect, the invention concerns an isolated PRO polypeptide, comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a PRO polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein.

In a further aspect, the invention concerns an isolated PRO polypeptide comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to an amino acid sequence encoded by any of the human protein cDNAs deposited with the ATCC® as disclosed herein.

In a specific aspect, the invention provides an isolated PRO polypeptide without the N-terminal signal sequence and/or the initiating methionine and is encoded by a nucleotide sequence that encodes such an amino acid sequence as hereinbefore described. Processes for producing the same are also herein described, wherein those processes comprise culturing a host cell comprising a vector which comprises the appropriate encoding nucleic acid molecule under conditions suitable for expression of the PRO polypeptide and recovering the PRO polypeptide from the cell culture.

Another aspect the invention provides an isolated PRO polypeptide which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the PRO polypeptide and recovering the PRO polypeptide from the cell culture.

In yet another embodiment, the invention concerns agonists and antagonists of a native PRO polypeptide as defined herein. In a particular embodiment, the agonist or antagonist is an anti-PRO antibody or a small molecule.

In a further embodiment, the invention concerns a method of identifying agonists or antagonists to a PRO polypeptide which comprise contacting the PRO polypeptide with a candidate molecule and monitoring a biological activity mediated by said PRO polypeptide. Preferably, the PRO polypeptide is a native PRO polypeptide.

In a still further embodiment, the invention concerns a composition of matter comprising a PRO polypeptide, or an agonist or antagonist of a PRO polypeptide as herein described, or an anti-PRO antibody, in combination with a carrier. Optionally, the carrier is a pharmaceutically acceptable carrier.

Another embodiment of the present invention is directed to the use of a PRO polypeptide, or an agonist or antagonist thereof as hereinbefore described, or an anti-PRO antibody, for the preparation of a medicament useful in the treatment of a condition which is responsive to the PRO polypeptide, an agonist or antagonist thereof or an anti-PRO antibody.

In other embodiments of the present invention, the invention provides vectors comprising DNA encoding any of the herein described polypeptides. Host cell comprising any such vector are also provided. By way of example, the host cells may be CHO cells, *E. coli*, or yeast. A process for producing any of the herein described polypeptides is further provided and comprises culturing host cells under conditions suitable for expression of the desired polypeptide and recovering the desired polypeptide from the cell culture.

In other embodiments, the invention provides chimeric molecules comprising any of the herein described polypeptides fused to a heterologous polypeptide or amino acid sequence. Example of such chimeric molecules comprise any of the herein described polypeptides fused to an epitope tag sequence or a Fc region of an immunoglobulin.

In another embodiment, the invention provides an antibody which binds, preferably specifically, to any of the above or below described polypeptides. Optionally, the antibody is a monoclonal antibody, humanized antibody, antibody fragment or single-chain antibody.

In yet other embodiments, the invention provides oligonucleotide probes which may be useful for isolating genomic and cDNA nucleotide sequences, measuring or detecting expression of an associated gene or as antisense probes, wherein those probes may be derived from any of the above or below described nucleotide sequences. Preferred probe lengths are described above.

In yet other embodiments, the present invention is directed to methods of using the PRO polypeptides of the present invention for a variety of uses based upon the functional biological assay data presented in the Examples below.

BRIEF DESCRIPTION OF THE DRAWINGS

FIGS. 1A-1B show a nucleotide sequence (SEQ ID NO:1) of a native sequence PRO6004 cDNA, wherein SEQ ID NO:1 is a clone designated herein as "DNA92259".

FIG. 2 shows the amino acid sequence (SEQ ID NO:2) derived from the coding sequence of SEQ ID NO:1 shown in FIGS. 1A-1B.

FIG. 3 shows a nucleotide sequence (SEQ ID NO:3) of a native sequence PRO4981 cDNA, wherein SEQ ID NO:3 is a clone designated herein as "DNA94849-2960".

FIG. 4 shows the amino acid sequence (SEQ ID NO:4) derived from the coding sequence of SEQ ID NO:3 shown in FIG. 3.

FIG. 5 shows a nucleotide sequence (SEQ ID NO:5) of a native sequence PRO7174 cDNA, wherein SEQ ID NO:5 is a clone designated herein as "DNA96883-2745".

FIG. 6 shows the amino acid sequence (SEQ ID NO:6) derived from the coding sequence of SEQ ID NO:5 shown in FIG. 5.

FIG. 7 shows a nucleotide sequence (SEQ ID NO:7) of a native sequence PRO5778 cDNA, wherein SEQ ID NO:7 is a clone designated herein as "DNA96894-2675".

FIG. 8 shows the amino acid sequence (SEQ ID NO:8) derived from the coding sequence of SEQ ID NO:7 shown in FIG. 7.

FIG. 9 shows a nucleotide sequence (SEQ ID NO:9) of a native sequence PRO4332 cDNA, wherein SEQ ID NO:9 is a clone designated herein as "DNA100272-2969".

FIG. 10 shows the amino acid sequence (SEQ ID NO:10) derived from the coding sequence of SEQ ID NO:9 shown in FIG. 9.

FIG. 11 shows a nucleotide sequence (SEQ ID NO:11) of a native sequence PRO9799 cDNA, wherein SEQ ID NO:11 is a clone designated herein as "DNA108696-2966".

FIG. 12 shows the amino acid sequence (SEQ ID NO:12) derived from the coding sequence of SEQ ID NO:11 shown in FIG. 11.

FIG. 13 shows a nucleotide sequence (SEQ ID NO:13) of a native sequence PRO9909 cDNA, wherein SEQ ID NO:13 is a clone designated herein as "DNA117935-2801".

FIG. 14 shows the amino acid sequence (SEQ ID NO:14) derived from the coding sequence of SEQ ID NO:13 shown in FIG. 13.

FIG. 15 shows a nucleotide sequence (SEQ ID NO:15) of a native sequence PRO9917 cDNA, wherein SEQ ID NO:15 is a clone designated herein as "DNA119474-2803".

FIG. 16 shows the amino acid sequence (SEQ ID NO:16) derived from the coding sequence of SEQ ID NO:15 shown in FIG. 15.

FIG. 17 shows a nucleotide sequence (SEQ ID NO:17) of a native sequence PRO9771 cDNA, wherein SEQ ID NO:17 is a clone designated herein as "DNA119498-2965".

FIG. 18 shows the amino acid sequence (SEQ ID NO:18) derived from the coding sequence of SEQ ID NO:17 shown in FIG. 17.

FIG. 19 shows a nucleotide sequence (SEQ ID NO:19) of a native sequence PRO9877 cDNA, wherein SEQ ID NO:19 is a clone designated herein as "DNA119502-2789".

FIG. 20 shows the amino acid sequence (SEQ ID NO:20) derived from the coding sequence of SEQ ID NO:19 shown in FIG. 19.

FIG. 21 shows a nucleotide sequence (SEQ ID NO:21) of a native sequence PRO9903 cDNA, wherein SEQ ID NO:21 is a clone designated herein as "DNA119516-2797".

FIG. 22 shows the amino acid sequence (SEQ ID NO:22) derived from the coding sequence of SEQ ID NO:21 shown in FIG. 21.

FIG. 23 shows a nucleotide sequence (SEQ ID NO:23) of a native sequence PRO9830 cDNA, wherein SEQ ID NO:23 is a clone designated herein as "DNA119530-2968".

FIG. 24 shows the amino acid sequence (SEQ ID NO:24) derived from the coding sequence of SEQ ID NO:23 shown in FIG. 23.

FIG. 25 shows a nucleotide sequence (SEQ ID NO:25) of a native sequence PRO7155 cDNA, wherein SEQ ID NO:25 is a clone designated herein as "DNA121772-2741".

FIG. 26 shows the amino acid sequence (SEQ ID NO:26) derived from the coding sequence of SEQ ID NO:25 shown in FIG. 25.

FIG. 27 shows a nucleotide sequence (SEQ ID NO:27) of a native sequence PRO9862 cDNA, wherein SEQ ID NO:27 is a clone designated herein as "DNA125148-2782".

FIG. 28 shows the amino acid sequence (SEQ ID NO:28) derived from the coding sequence of SEQ ID NO:27 shown in FIG. 27.

FIG. 29 shows a nucleotide sequence (SEQ ID NO:29) of a native sequence PRO9882 cDNA, wherein SEQ ID NO:29 is a clone designated herein as "DNA125150-2793".

FIG. 30 shows the amino acid sequence (SEQ ID NO:30) derived from the coding sequence of SEQ ID NO:29 shown in FIG. 29.

FIG. 31 shows a nucleotide sequence (SEQ ID NO:31) of a native sequence PRO9864 cDNA, wherein SEQ ID NO:31 is a clone designated herein as "DNA125151-2784".

FIG. 32 shows the amino acid sequence (SEQ ID NO:32) derived from the coding sequence of SEQ ID NO:31 shown in FIG. 31.

FIG. 33 shows a nucleotide sequence (SEQ ID NO:33) of a native sequence PRO10013 cDNA, wherein SEQ ID NO:33 is a clone designated herein as "DNA125181-2804".

FIG. 34 shows the amino acid sequence (SEQ ID NO:34) derived from the coding sequence of SEQ ID NO:33 shown in FIG. 33.

FIG. 35 shows a nucleotide sequence (SEQ ID NO:35) of a native sequence PRO9885 cDNA, wherein SEQ ID NO:35 is a clone designated herein as "DNA125192-2794".

FIG. 36 shows the amino acid sequence (SEQ ID NO:36) derived from the coding sequence of SEQ ID NO:35 shown in FIG. 35.

FIG. 37 shows a nucleotide sequence (SEQ ID NO:37) of a native sequence PRO9879 cDNA, wherein SEQ ID NO:37 is a clone designated herein as "DNA125196-2792".

FIG. 38 shows the amino acid sequence (SEQ ID NO:38) derived from the coding sequence of SEQ ID NO:37 shown in FIG. 37.

FIG. 39 shows a nucleotide sequence (SEQ ID NO:39) of a native sequence PRO10111 cDNA, wherein SEQ ID NO:39 is a clone designated herein as "DNA125200-2810".

FIG. 40 shows the amino acid sequence (SEQ ID NO:40) derived from the coding sequence of SEQ ID NO:39 shown in FIG. 39.

FIG. 41 shows a nucleotide sequence (SEQ ID NO:41) of a native sequence PRO9925 cDNA, wherein SEQ ID NO:41 is a clone designated herein as "DNA125214-2814".

FIG. 42 shows the amino acid sequence (SEQ ID NO:42) derived from the coding sequence of SEQ ID NO:41 shown in FIG. 41.

FIG. 43 shows a nucleotide sequence (SEQ ID NO:43) of a native sequence PRO9905 cDNA, wherein SEQ ID NO:43 is a clone designated herein as "DNA125219-2799".

FIG. 44 shows the amino acid sequence (SEQ ID NO:44) derived from the coding sequence of SEQ ID NO:43 shown in FIG. 43.

FIG. 45 shows a nucleotide sequence (SEQ ID NO:45) of a native sequence PRO10276 cDNA, wherein SEQ ID NO:45 is a clone designated herein as "DNA128309-2825".

FIG. 46 shows the amino acid sequence (SEQ ID NO:46) derived from the coding sequence of SEQ ID NO:45 shown in FIG. 45.

FIG. 47 shows a nucleotide sequence (SEQ ID NO:47) of a native sequence PRO9898 cDNA, wherein SEQ ID NO:47 is a clone designated herein as "DNA129535-2796".

FIG. 48 shows the amino acid sequence (SEQ ID NO:48) derived from the coding sequence of SEQ ID NO:47 shown in FIG. 47.

FIG. 49 shows a nucleotide sequence (SEQ ID NO:49) of a native sequence PRO9904 cDNA, wherein SEQ ID NO:49 is a clone designated herein as "DNA129549-2798".

FIG. 50 shows the amino acid sequence (SEQ ID NO:50) derived from the coding sequence of SEQ ID NO:49 shown in FIG. 49.

FIG. 51 shows a nucleotide sequence (SEQ ID NO:51) of a native sequence PRO19632 cDNA, wherein SEQ ID NO:51 is a clone designated herein as "DNA129580-2863".

FIG. 52 shows the amino acid sequence (SEQ ID NO:52) derived from the coding sequence of SEQ ID NO:51 shown in FIG. 51.

FIG. 53 shows a nucleotide sequence (SEQ ID NO:53) of a native sequence PRO19672 cDNA, wherein SEQ ID NO:53 is a clone designated herein as "DNA129794-2967".

FIG. 54 shows the amino acid sequence (SEQ ID NO:54) derived from the coding sequence of SEQ ID NO:53 shown in FIG. 53.

FIG. 55 shows a nucleotide sequence (SEQ ID NO:55) of a native sequence PRO9783 cDNA, wherein SEQ ID NO:55 is a clone designated herein as "DNA131590-2962".

FIG. 56 shows the amino acid sequence (SEQ ID NO:56) derived from the coding sequence of SEQ ID NO:55 shown in FIG. 55.

FIG. 57 shows a nucleotide sequence (SEQ ID NO:57) of a native sequence PRO10112 cDNA, wherein SEQ ID NO:57 is a clone designated herein as "DNA135173-2811".

FIG. 58 shows the amino acid sequence (SEQ ID NO:58) derived from the coding sequence of SEQ ID NO:57 shown in FIG. 57.

FIGS. 59A-59B show a nucleotide sequence (SEQ ID NO:59) of a native sequence PRO10284 cDNA, wherein SEQ ID NO:59 is a clone designated herein as "DNA138039-2828".

FIG. 60 shows the amino acid sequence (SEQ ID NO:60) derived from the coding sequence of SEQ ID NO:59 shown in FIGS. 59A-59B.

FIG. 61 shows a nucleotide sequence (SEQ ID NO:61) of a native sequence PRO10100 cDNA, wherein SEQ ID NO:61 is a clone designated herein as "DNA139540-2807".

FIG. 62 shows the amino acid sequence (SEQ ID NO:62) derived from the coding sequence of SEQ ID NO:61 shown in FIG. 61.

FIG. 63 shows a nucleotide sequence (SEQ ID NO:63) of a native sequence PRO19628 cDNA, wherein SEQ ID NO:63 is a clone designated herein as "DNA139602-2859".

FIG. 64 shows the amino acid sequence (SEQ ID NO:64) derived from the coding sequence of SEQ ID NO:63 shown in FIG. 63.

FIG. 65 shows a nucleotide sequence (SEQ ID NO:65) of a native sequence PRO19684 cDNA, wherein SEQ ID NO:65 is a clone designated herein as "DNA139632-2880".

FIG. 66 shows the amino acid sequence (SEQ ID NO:66) derived from the coding sequence of SEQ ID NO:65 shown in FIG. 65.

FIG. 67 shows a nucleotide sequence (SEQ ID NO:67) of a native sequence PRO10274 cDNA, wherein SEQ ID NO:67 is a clone designated herein as "DNA139686-2823".

FIG. 68 shows the amino acid sequence (SEQ ID NO:68) derived from the coding sequence of SEQ ID NO:67 shown in FIG. 67.

FIG. 69 shows a nucleotide sequence (SEQ ID NO:69) of a native sequence PRO9907 cDNA, wherein SEQ ID NO:69 is a clone designated herein as "DNA142392-2800".

FIG. 70 shows the amino acid sequence (SEQ ID NO:70) derived from the coding sequence of SEQ ID NO:69 shown in FIG. 69.

FIG. 71 shows a nucleotide sequence (SEQ ID NO:71) of a native sequence PRO9873 cDNA, wherein SEQ ID NO:71 is a clone designated herein as "DNA143076-2787".

FIG. 72 shows the amino acid sequence (SEQ ID NO:72) derived from the coding sequence of SEQ ID NO:71 shown in FIG. 71.

FIG. 73 shows a nucleotide sequence (SEQ ID NO:73) of a native sequence PRO10201 cDNA, wherein SEQ ID NO:73 is a clone designated herein as "DNA143294-2818".

FIG. 74 shows the amino acid sequence (SEQ ID NO:74) derived from the coding sequence of SEQ ID NO:73 shown in FIG. 73.

FIG. 75 shows a nucleotide sequence (SEQ ID NO:75) of a native sequence PRO10200 cDNA, wherein SEQ ID NO:75 is a clone designated herein as "DNA143514-2817".

FIG. 76 shows the amino acid sequence (SEQ ID NO:76) derived from the coding sequence of SEQ ID NO:75 shown in FIG. 75.

FIG. 77 shows a nucleotide sequence (SEQ ID NO:77) of a native sequence PRO10196 cDNA, wherein SEQ ID NO:77 is a clone designated herein as "DNA144841-2816".

FIG. 78 shows the amino acid sequence (SEQ ID NO:78) derived from the coding sequence of SEQ ID NO:77 shown in FIG. 77.

FIG. 79 shows a nucleotide sequence (SEQ ID NO:79) of a native sequence PRO10282 cDNA, wherein SEQ ID NO:79 is a clone designated herein as "DNA148380-2827".

FIG. 80 shows the amino acid sequence (SEQ ID NO:80) derived from the coding sequence of SEQ ID NO:79 shown in FIG. 79.

FIG. 81 shows a nucleotide sequence (SEQ ID NO:81) of a native sequence PRO19650 cDNA, wherein SEQ ID NO:81 is a clone designated herein as "DNA149995-2871".

FIG. 82 shows the amino acid sequence (SEQ ID NO:82) derived from the coding sequence of SEQ ID NO:81 shown in FIG. 81.

FIG. 83 shows a nucleotide sequence (SEQ ID NO:83) of a native sequence PRO21184 cDNA, wherein SEQ ID NO:83 is a clone designated herein as "DNA167678-2963".

FIG. 84 shows the amino acid sequence (SEQ ID NO:84) derived from the coding sequence of SEQ ID NO:83 shown in FIG. 83.

FIG. 85 shows a nucleotide sequence (SEQ ID NO:85) of a native sequence PRO21201 cDNA, wherein SEQ ID NO:85 is a clone designated herein as "DNA168028-2956".

FIG. 86 shows the amino acid sequence (SEQ ID NO:86) derived from the coding sequence of SEQ ID NO:85 shown in FIG. 85.

FIG. 87 shows a nucleotide sequence (SEQ ID NO:87) of a native sequence PRO21175 cDNA, wherein SEQ ID NO:87 is a clone designated herein as "DNA173894-2947".

FIG. 88 shows the amino acid sequence (SEQ ID NO:88) derived from the coding sequence of SEQ ID NO:87 shown in FIG. 87.

FIG. 89 shows a nucleotide sequence (SEQ ID NO:89) of a native sequence PRO21340 cDNA, wherein SEQ ID NO:89 is a clone designated herein as "DNA176775-2957".

FIG. 90 shows the amino acid sequence (SEQ ID NO:90) derived from the coding sequence of SEQ ID NO:89 shown in FIG. 89.

FIG. 91 shows a nucleotide sequence (SEQ ID NO:91) of a native sequence PRO21384 cDNA, wherein SEQ ID NO:91 is a clone designated herein as "DNA177313-2982".

FIG. 92 shows the amino acid sequence (SEQ ID NO:92) derived from the coding sequence of SEQ ID NO:91 shown in FIG. 91.

FIG. 93 shows a nucleotide sequence (SEQ ID NO:93) of a native sequence PRO982 cDNA, wherein SEQ ID NO:93 is a clone designated herein as "DNA57700-1408".

FIG. 94 shows the amino acid sequence (SEQ ID NO:94) derived from the coding sequence of SEQ ID NO:93 shown in FIG. 93.

FIG. 95 shows a nucleotide sequence (SEQ ID NO:95) of a native sequence PRO1160 cDNA, wherein SEQ ID NO:95 is a clone designated herein as "DNA62872-1509".

FIG. 96 shows the amino acid sequence (SEQ ID NO:96) derived from the coding sequence of SEQ ID NO:95 shown in FIG. 95.

FIG. 97 shows a nucleotide sequence (SEQ ID NO:97) of a native sequence PRO1187 cDNA, wherein SEQ ID NO:97 is a clone designated herein as "DNA62876-1517".

FIG. 98 shows the amino acid sequence (SEQ ID NO:98) derived from the coding sequence of SEQ ID NO:97 shown in FIG. 97.

FIG. 99 shows a nucleotide sequence (SEQ ID NO:99) of a native sequence PRO1329 cDNA, wherein SEQ ID NO:99 is a clone designated herein as "DNA66660-1585".

FIG. 100 shows the amino acid sequence (SEQ ID NO:100) derived from the coding sequence of SEQ ID NO:99 shown in FIG. 99.

FIG. 101 shows a nucleotide sequence (SEQ ID NO:101) of a native sequence PRO231 cDNA, wherein SEQ ID NO:101 is a clone designated herein as "DNA34434-1139".

FIG. 102 shows the amino acid sequence (SEQ ID NO:102) derived from the coding sequence of SEQ ID NO:101 shown in FIG. 101.

FIG. 103 shows a nucleotide sequence (SEQ ID NO:103) of a native sequence PRO357 cDNA, wherein SEQ ID NO:103 is a clone designated herein as "DNA44804-1248".

FIG. 104 shows the amino acid sequence (SEQ ID NO:104) derived from the coding sequence of SEQ ID NO:103 shown in FIG. 103.

FIG. 105 shows a nucleotide sequence (SEQ ID NO:105) of a native sequence PRO725 cDNA, wherein SEQ ID NO:105 is a clone designated herein as "DNA52758-1399".

FIG. 106 shows the amino acid sequence (SEQ ID NO:106) derived from the coding sequence of SEQ ID NO:105 shown in FIG. 105.

FIG. 107 shows a nucleotide sequence (SEQ ID NO:107) of a native sequence PRO1155 cDNA, wherein SEQ ID NO:107 is a clone designated herein as "DNA59849-1504".

FIG. 108 shows the amino acid sequence (SEQ ID NO:108) derived from the coding sequence of SEQ ID NO:107 shown in FIG. 107.

FIG. 109 shows a nucleotide sequence (SEQ ID NO:109) of a native sequence PRO1306 cDNA, wherein SEQ ID NO:109 is a clone designated herein as "DNA65410-1569".

FIG. 110 shows the amino acid sequence (SEQ ID NO:110) derived from the coding sequence of SEQ ID NO:109 shown in FIG. 109.

FIG. 111 shows a nucleotide sequence (SEQ ID NO:111) of a native sequence PRO1419 cDNA, wherein SEQ ID NO:111 is a clone designated herein as "DNA71290-1630".

FIG. 112 shows the amino acid sequence (SEQ ID NO:112) derived from the coding sequence of SEQ ID NO:111 shown in FIG. 111.

FIG. 113 shows a nucleotide sequence (SEQ ID NO:113) of a native sequence PRO229 cDNA, wherein SEQ ID NO:113 is a clone designated herein as "DNA33100-1159".

FIG. 114 shows the amino acid sequence (SEQ ID NO:114) derived from the coding sequence of SEQ ID NO:113 shown in FIG. 113.

FIG. 115 shows a nucleotide sequence (SEQ ID NO:115) of a native sequence PRO1272 cDNA, wherein SEQ ID NO:115 is a clone designated herein as "DNA64896-1539".

FIG. 116 shows the amino acid sequence (SEQ ID NO:116) derived from the coding sequence of SEQ ID NO:115 shown in FIG. 115.

FIG. 117 shows a nucleotide sequence (SEQ ID NO:117) of a native sequence PRO4405 cDNA, wherein SEQ ID NO:117 is a clone designated herein as "DNA84920-2614".

FIG. 118 shows the amino acid sequence (SEQ ID NO:118) derived from the coding sequence of SEQ ID NO:117 shown in FIG. 117.

FIG. 119 shows a nucleotide sequence (SEQ ID NO:119) of a native sequence PRO181 cDNA, wherein SEQ ID NO:119 is a clone designated herein as "DNA23330-1390".

FIG. 120 shows the amino acid sequence (SEQ ID NO:120) derived from the coding sequence of SEQ ID NO:119 shown in FIG. 119.

FIG. 121 shows a nucleotide sequence (SEQ ID NO:121) of a native sequence PRO214 cDNA, wherein SEQ ID NO:121 is a clone designated herein as "DNA32286-1191".

FIG. 122 shows the amino acid sequence (SEQ ID NO:122) derived from the coding sequence of SEQ ID NO:121 shown in FIG. 121.

FIG. 123 shows a nucleotide sequence (SEQ ID NO:123) of a native sequence PRO247 cDNA, wherein SEQ ID NO:123 is a clone designated herein as "DNA35673-1201".

FIG. 124 shows the amino acid sequence (SEQ ID NO:124) derived from the coding sequence of SEQ ID NO:123 shown in FIG. 123.

FIG. 125 shows a nucleotide sequence (SEQ ID NO:125) of a native sequence PRO337 cDNA, wherein SEQ ID NO:125 is a clone designated herein as "DNA43316-1237".

FIG. 126 shows the amino acid sequence (SEQ ID NO:126) derived from the coding sequence of SEQ ID NO:125 shown in FIG. 125.

FIG. 127 shows a nucleotide sequence (SEQ ID NO:127) of a native sequence PRO526 cDNA, wherein SEQ ID NO:127 is a clone designated herein as "DNA44184-1319".

FIG. 128 shows the amino acid sequence (SEQ ID NO:128) derived from the coding sequence of SEQ ID NO:127 shown in FIG. 127.

FIG. 129 shows a nucleotide sequence (SEQ ID NO:129) of a native sequence PRO363 cDNA, wherein SEQ ID NO:129 is a clone designated herein as "DNA45419-1252".

FIG. 130 shows the amino acid sequence (SEQ ID NO:130) derived from the coding sequence of SEQ ID NO:129 shown in FIG. 129.

FIG. 131 shows a nucleotide sequence (SEQ ID NO:131) of a native sequence PRO531 cDNA, wherein SEQ ID NO:131 is a clone designated herein as "DNA48314-1320".

FIG. 132 shows the amino acid sequence (SEQ ID NO:132) derived from the coding sequence of SEQ ID NO:131 shown in FIG. 131.

FIG. 133 shows a nucleotide sequence (SEQ ID NO:133) of a native sequence PRO1083 cDNA, wherein SEQ ID NO:133 is a clone designated herein as "DNA50921-1458".

FIG. 134 shows the amino acid sequence (SEQ ID NO:134) derived from the coding sequence of SEQ ID NO:133 shown in FIG. 133.

FIG. 135 shows a nucleotide sequence (SEQ ID NO:135) of a native sequence PRO840 cDNA, wherein SEQ ID NO:135 is a clone designated herein as "DNA53987".

FIG. 136 shows the amino acid sequence (SEQ ID NO:136) derived from the coding sequence of SEQ ID NO:135 shown in FIG. 135.

FIG. 137 shows a nucleotide sequence (SEQ ID NO:137) of a native sequence PRO1080 cDNA, wherein SEQ ID NO:137 is a clone designated herein as "DNA56047-1456".

FIG. 138 shows the amino acid sequence (SEQ ID NO:138) derived from the coding sequence of SEQ ID NO:137 shown in FIG. 137.

FIG. 139 shows a nucleotide sequence (SEQ ID NO:139) of a native sequence PRO788 cDNA, wherein SEQ ID NO:139 is a clone designated herein as "DNA56405-1357".

FIG. 140 shows the amino acid sequence (SEQ ID NO:140) derived from the coding sequence of SEQ ID NO:139 shown in FIG. 139.

FIG. 141 shows a nucleotide sequence (SEQ ID NO:141) of a native sequence PRO1478 cDNA, wherein SEQ ID NO:141 is a clone designated herein as “DNA56531-1648”.

FIG. 142 shows the amino acid sequence (SEQ ID NO:142) derived from the coding sequence of SEQ ID NO:141 shown in FIG. 141.

FIG. 143 shows a nucleotide sequence (SEQ ID NO:143) of a native sequence PRO1134 cDNA, wherein SEQ ID NO:143 is a clone designated herein as “DNA56865-1491”.

FIG. 144 shows the amino acid sequence (SEQ ID NO:144) derived from the coding sequence of SEQ ID NO:143 shown in FIG. 143.

FIG. 145 shows a nucleotide sequence (SEQ ID NO:145) of a native sequence PRO826 cDNA, wherein SEQ ID NO:145 is a clone designated herein as “DNA57694-1341”.

FIG. 146 shows the amino acid sequence (SEQ ID NO:146) derived from the coding sequence of SEQ ID NO:145 shown in FIG. 145.

FIG. 147 shows a nucleotide sequence (SEQ ID NO:147) of a native sequence PRO1005 cDNA, wherein SEQ ID NO:147 is a clone designated herein as “DNA57708-1411”.

FIG. 148 shows the amino acid sequence (SEQ ID NO:148) derived from the coding sequence of SEQ ID NO:147 shown in FIG. 147.

FIG. 149 shows a nucleotide sequence (SEQ ID NO:149) of a native sequence PRO809 cDNA, wherein SEQ ID NO:149 is a clone designated herein as “DNA57836-1338”.

FIG. 150 shows the amino acid sequence (SEQ ID NO:150) derived from the coding sequence of SEQ ID NO:149 shown in FIG. 149.

FIG. 151 shows a nucleotide sequence (SEQ ID NO:151) of a native sequence PRO1194 cDNA, wherein SEQ ID NO:151 is a clone designated herein as “DNA57841-1522”.

FIG. 152 shows the amino acid sequence (SEQ ID NO:152) derived from the coding sequence of SEQ ID NO:151 shown in FIG. 151.

FIG. 153 shows a nucleotide sequence (SEQ ID NO:153) of a native sequence PRO1071 cDNA, wherein SEQ ID NO:153 is a clone designated herein as “DNA58847-1383”.

FIG. 154 shows the amino acid sequence (SEQ ID NO:154) derived from the coding sequence of SEQ ID NO:153 shown in FIG. 153.

FIG. 155 shows a nucleotide sequence (SEQ ID NO:155) of a native sequence PRO1411 cDNA, wherein SEQ ID NO:155 is a clone designated herein as “DNA59212-1627”.

FIG. 156 shows the amino acid sequence (SEQ ID NO:156) derived from the coding sequence of SEQ ID NO:155 shown in FIG. 155.

FIG. 157 shows a nucleotide sequence (SEQ ID NO:157) of a native sequence PRO1309 cDNA, wherein SEQ ID NO:157 is a clone designated herein as “DNA59588-1571”.

FIG. 158 shows the amino acid sequence (SEQ ID NO:158) derived from the coding sequence of SEQ ID NO:157 shown in FIG. 157.

FIG. 159 shows a nucleotide sequence (SEQ ID NO:159) of a native sequence PRO1025 cDNA, wherein SEQ ID NO:159 is a clone designated herein as “DNA59622-1334”.

FIG. 160 shows the amino acid sequence (SEQ ID NO:160) derived from the coding sequence of SEQ ID NO:159 shown in FIG. 159.

FIG. 161 shows a nucleotide sequence (SEQ ID NO:161) of a native sequence PRO1181 cDNA, wherein SEQ ID NO:161 is a clone designated herein as “DNA59847-2510”.

FIG. 162 shows the amino acid sequence (SEQ ID NO:162) derived from the coding sequence of SEQ ID NO:161 shown in FIG. 161.

FIG. 163 shows a nucleotide sequence (SEQ ID NO:163) of a native sequence PRO1126 cDNA, wherein SEQ ID NO:163 is a clone designated herein as “DNA60615-1483”.

FIG. 164 shows the amino acid sequence (SEQ ID NO:164) derived from the coding sequence of SEQ ID NO:163 shown in FIG. 163.

FIG. 165 shows a nucleotide sequence (SEQ ID NO:165) of a native sequence PRO1186 cDNA, wherein SEQ ID NO:165 is a clone designated herein as “DNA60621-1516”.

FIG. 166 shows the amino acid sequence (SEQ ID NO:166) derived from the coding sequence of SEQ ID NO:165 shown in FIG. 165.

FIG. 167 shows a nucleotide sequence (SEQ ID NO:167) of a native sequence PRO1192 cDNA, wherein SEQ ID NO:167 is a clone designated herein as “DNA62814-1521”.

FIG. 168 shows the amino acid sequence (SEQ ID NO:168) derived from the coding sequence of SEQ ID NO:167 shown in FIG. 167.

FIG. 169 shows a nucleotide sequence (SEQ ID NO:169) of a native sequence PRO1244 cDNA, wherein SEQ ID NO:169 is a clone designated herein as “DNA64883-1526”.

FIG. 170 shows the amino acid sequence (SEQ ID NO:170) derived from the coding sequence of SEQ ID NO:169 shown in FIG. 169.

FIG. 171 shows a nucleotide sequence (SEQ ID NO:171) of a native sequence PRO1274 cDNA, wherein SEQ ID NO:171 is a clone designated herein as “DNA64889-1541”.

FIG. 172 shows the amino acid sequence (SEQ ID NO:172) derived from the coding sequence of SEQ ID NO:171 shown in FIG. 171.

FIG. 173 shows a nucleotide sequence (SEQ ID NO:173) of a native sequence PRO1412 cDNA, wherein SEQ ID NO:173 is a clone designated herein as “DNA64897-1628”.

FIG. 174 shows the amino acid sequence (SEQ ID NO:174) derived from the coding sequence of SEQ ID NO:173 shown in FIG. 173.

FIG. 175 shows a nucleotide sequence (SEQ ID NO:175) of a native sequence PRO1286 cDNA, wherein SEQ ID NO:175 is a clone designated herein as “DNA64903-1553”.

FIG. 176 shows the amino acid sequence (SEQ ID NO:176) derived from the coding sequence of SEQ ID NO:175 shown in FIG. 175.

FIG. 177 shows a nucleotide sequence (SEQ ID NO:177) of a native sequence PRO1330 cDNA, wherein SEQ ID NO:177 is a clone designated herein as “DNA64907-1163-1”.

FIG. 178 shows the amino acid sequence (SEQ ID NO:178) derived from the coding sequence of SEQ ID NO:177 shown in FIG. 177.

FIG. 179 shows a nucleotide sequence (SEQ ID NO:179) of a native sequence PRO1347 cDNA, wherein SEQ ID NO:179 is a clone designated herein as “DNA64950-1590”.

FIG. 180 shows the amino acid sequence (SEQ ID NO:180) derived from the coding sequence of SEQ ID NO:179 shown in FIG. 179.

FIG. 181 shows a nucleotide sequence (SEQ ID NO:181) of a native sequence PRO1305 cDNA, wherein SEQ ID NO:181 is a clone designated herein as “DNA64952-1568”.

FIG. 182 shows the amino acid sequence (SEQ ID NO:182) derived from the coding sequence of SEQ ID NO:181 shown in FIG. 181.

FIG. 183 shows a nucleotide sequence (SEQ ID NO:183) of a native sequence PRO1273 cDNA, wherein SEQ ID NO:183 is a clone designated herein as “DNA65402-1540”.

FIG. 184 shows the amino acid sequence (SEQ ID NO:184) derived from the coding sequence of SEQ ID NO:183 shown in FIG. 183.

FIG. 185 shows a nucleotide sequence (SEQ ID NO:185) of a native sequence PRO1279 cDNA, wherein SEQ ID NO:185 is a clone designated herein as "DNA65405-1547".

FIG. 186 shows the amino acid sequence (SEQ ID NO:186) derived from the coding sequence of SEQ ID NO:185 shown in FIG. 185.

FIG. 187 shows a nucleotide sequence (SEQ ID NO:187) of a native sequence PRO1340 cDNA, wherein SEQ ID NO:187 is a clone designated herein as "DNA66663-1598".

FIG. 188 shows the amino acid sequence (SEQ ID NO:188) derived from the coding sequence of SEQ ID NO:187 shown in FIG. 187.

FIG. 189 shows a nucleotide sequence (SEQ ID NO:189) of a native sequence PRO1338 cDNA, wherein SEQ ID NO:189 is a clone designated herein as "DNA66667".

FIG. 190 shows the amino acid sequence (SEQ ID NO:190) derived from the coding sequence of SEQ ID NO:189 shown in FIG. 189.

FIG. 191 shows a nucleotide sequence (SEQ ID NO:191) of a native sequence PRO1343 cDNA, wherein SEQ ID NO:191 is a clone designated herein as "DNA66675-1587".

FIG. 192 shows the amino acid sequence (SEQ ID NO:192) derived from the coding sequence of SEQ ID NO:191 shown in FIG. 191.

FIG. 193 shows a nucleotide sequence (SEQ ID NO:193) of a native sequence PRO1376 cDNA, wherein SEQ ID NO:193 is a clone designated herein as "DNA67300-1605".

FIG. 194 shows the amino acid sequence (SEQ ID NO:194) derived from the coding sequence of SEQ ID NO:193 shown in FIG. 193.

FIG. 195 shows a nucleotide sequence (SEQ ID NO:195) of a native sequence PRO1387 cDNA, wherein SEQ ID NO:195 is a clone designated herein as "DNA68872-1620".

FIG. 196 shows the amino acid sequence (SEQ ID NO:196) derived from the coding sequence of SEQ ID NO:195 shown in FIG. 195.

FIG. 197 shows a nucleotide sequence (SEQ ID NO:197) of a native sequence PRO1409 cDNA, wherein SEQ ID NO:197 is a clone designated herein as "DNA71269-1621".

FIG. 198 shows the amino acid sequence (SEQ ID NO:198) derived from the coding sequence of SEQ ID NO:197 shown in FIG. 197.

FIG. 199 shows a nucleotide sequence (SEQ ID NO:199) of a native sequence PRO1488 cDNA, wherein SEQ ID NO:199 is a clone designated herein as "DNA73736-1657".

FIG. 200 shows the amino acid sequence (SEQ ID NO:200) derived from the coding sequence of SEQ ID NO:199 shown in FIG. 199.

FIG. 201 shows a nucleotide sequence (SEQ ID NO:201) of a native sequence PRO1474 cDNA, wherein SEQ ID NO:201 is a clone designated herein as "DNA73739-1645".

FIG. 202 shows the amino acid sequence (SEQ ID NO:202) derived from the coding sequence of SEQ ID NO:201 shown in FIG. 201.

FIG. 203 shows a nucleotide sequence (SEQ ID NO:203) of a native sequence PRO1917 cDNA, wherein SEQ ID NO:203 is a clone designated herein as "DNA76400-2528".

FIG. 204 shows the amino acid sequence (SEQ ID NO:204) derived from the coding sequence of SEQ ID NO:203 shown in FIG. 203.

FIG. 205 shows a nucleotide sequence (SEQ ID NO:205) of a native sequence PRO1760 cDNA, wherein SEQ ID NO:205 is a clone designated herein as "DNA76532-1702".

FIG. 206 shows the amino acid sequence (SEQ ID NO:206) derived from the coding sequence of SEQ ID NO:205 shown in FIG. 205.

FIG. 207 shows a nucleotide sequence (SEQ ID NO:207) of a native sequence PRO1567 cDNA, wherein SEQ ID NO:207 is a clone designated herein as "DNA76541-1675".

FIG. 208 shows the amino acid sequence (SEQ ID NO:208) derived from the coding sequence of SEQ ID NO:207 shown in FIG. 207.

FIG. 209 shows a nucleotide sequence (SEQ ID NO:209) of a native sequence PRO1887 cDNA, wherein SEQ ID NO:209 is a clone designated herein as "DNA79862-2522".

FIG. 210 shows the amino acid sequence (SEQ ID NO:210) derived from the coding sequence of SEQ ID NO:209 shown in FIG. 209.

FIG. 211 shows a nucleotide sequence (SEQ ID NO:211) of a native sequence PRO1928 cDNA, wherein SEQ ID NO:211 is a clone designated herein as "DNA81754-2532".

FIG. 212 shows the amino acid sequence (SEQ ID NO:212) derived from the coding sequence of SEQ ID NO:211 shown in FIG. 211.

FIG. 213 shows a nucleotide sequence (SEQ ID NO:213) of a native sequence PRO4341 cDNA, wherein SEQ ID NO:213 is a clone designated herein as "DNA81761-2583".

FIG. 214 shows the amino acid sequence (SEQ ID NO:214) derived from the coding sequence of SEQ ID NO:213 shown in FIG. 213.

FIG. 215 shows a nucleotide sequence (SEQ ID NO:215) of a native sequence PRO5723 cDNA, wherein SEQ ID NO:215 is a clone designated herein as "DNA82361".

FIG. 216 shows the amino acid sequence (SEQ ID NO:216) derived from the coding sequence of SEQ ID NO:215 shown in FIG. 215.

FIG. 217 shows a nucleotide sequence (SEQ ID NO:217) of a native sequence PRO1801 cDNA, wherein SEQ ID NO:217 is a clone designated herein as "DNA83500-2506".

FIG. 218 shows the amino acid sequence (SEQ ID NO:218) derived from the coding sequence of SEQ ID NO:217 shown in FIG. 217.

FIG. 219 shows a nucleotide sequence (SEQ ID NO:219) of a native sequence PRO4333 cDNA, wherein SEQ ID NO:219 is a clone designated herein as "DNA84210-2576".

FIG. 220 shows the amino acid sequence (SEQ ID NO:220) derived from the coding sequence of SEQ ID NO:219 shown in FIG. 219.

FIG. 221 shows a nucleotide sequence (SEQ ID NO:221) of a native sequence PRO3543 cDNA, wherein SEQ ID NO:221 is a clone designated herein as "DNA86571-2551".

FIG. 222 shows the amino acid sequence (SEQ ID NO:222) derived from the coding sequence of SEQ ID NO:221 shown in FIG. 221.

FIG. 223 shows a nucleotide sequence (SEQ ID NO:223) of a native sequence PRO3444 cDNA, wherein SEQ ID NO:223 is a clone designated herein as "DNA87997".

FIG. 224 shows the amino acid sequence (SEQ ID NO:224) derived from the coding sequence of SEQ ID NO:223 shown in FIG. 223.

FIG. 225 shows a nucleotide sequence (SEQ ID NO:225) of a native sequence PRO4302 cDNA, wherein SEQ ID NO:225 is a clone designated herein as "DNA92218-2554".

FIG. 226 shows the amino acid sequence (SEQ ID NO:226) derived from the coding sequence of SEQ ID NO:225 shown in FIG. 225.

FIG. 227 shows a nucleotide sequence (SEQ ID NO:227) of a native sequence PRO4322 cDNA, wherein SEQ ID NO:227 is a clone designated herein as "DNA92223-2567".

FIG. 228 shows the amino acid sequence (SEQ ID NO:228) derived from the coding sequence of SEQ ID NO:227 shown in FIG. 227.

FIG. 229 shows a nucleotide sequence (SEQ ID NO:229) of a native sequence PRO5725 cDNA, wherein SEQ ID NO:229 is a clone designated herein as "DNA92265-2669".

FIG. 230 shows the amino acid sequence (SEQ ID NO:230) derived from the coding sequence of SEQ ID NO:229 shown in FIG. 229.

FIG. 231 shows a nucleotide sequence (SEQ ID NO:231) of a native sequence PRO4408 cDNA, wherein SEQ ID NO:231 is a clone designated herein as "DNA92274-2617".

FIG. 232 shows the amino acid sequence (SEQ ID NO:232) derived from the coding sequence of SEQ ID NO:231 shown in FIG. 231.

FIG. 233 shows a nucleotide sequence (SEQ ID NO:233) of a native sequence PRO9940 cDNA, wherein SEQ ID NO:223 is a clone designated herein as "DNA92282".

FIG. 234 shows the amino acid sequence (SEQ ID NO:234) derived from the coding sequence of SEQ ID NO:233 shown in FIG. 233.

FIG. 235 shows a nucleotide sequence (SEQ ID NO:235) of a native sequence PRO7154 cDNA, wherein SEQ ID NO:235 is a clone designated herein as "DNA108760-2740".

FIG. 236 shows the amino acid sequence (SEQ ID NO:236) derived from the coding sequence of SEQ ID NO:235 shown in FIG. 235.

FIG. 237 shows a nucleotide sequence (SEQ ID NO:237) of a native sequence PRO7425 cDNA, wherein SEQ ID NO:237 is a clone designated herein as "DNA108792-2753".

FIG. 238 shows the amino acid sequence (SEQ ID NO:238) derived from the coding sequence of SEQ ID NO:237 shown in FIG. 237.

FIG. 239 shows a nucleotide sequence (SEQ ID NO:239) of a native sequence PRO6079 cDNA, wherein SEQ ID NO:239 is a clone designated herein as "DNA111750-2706".

FIG. 240 shows the amino acid sequence (SEQ ID NO:240) derived from the coding sequence of SEQ ID NO:239 shown in FIG. 239.

FIG. 241 shows a nucleotide sequence (SEQ ID NO:241) of a native sequence PRO9836 cDNA, wherein SEQ ID NO:241 is a clone designated herein as "DNA119514-2772".

FIG. 242 shows the amino acid sequence (SEQ ID NO:242) derived from the coding sequence of SEQ ID NO:241 shown in FIG. 241.

FIG. 243 shows a nucleotide sequence (SEQ ID NO:243) of a native sequence PRO10096 cDNA, wherein SEQ ID NO:243 is a clone designated herein as "DNA125185-2806".

FIG. 244 shows the amino acid sequence (SEQ ID NO:244) derived from the coding sequence of SEQ ID NO:243 shown in FIG. 243.

DETAILED DESCRIPTION OF THE PREFERRED EMBODIMENTS

I. Definitions

The terms "PRO polypeptide" and "PRO" as used herein and when immediately followed by a numerical designation refer to various polypeptides, wherein the complete designation (i.e., PRO/number) refers to specific polypeptide sequences as described herein. The terms "PRO/number polypeptide" and "PRO/number" wherein the term "number" is provided as an actual numerical designation as used herein encompass native sequence polypeptides and polypeptide variants (which are further defined herein). The PRO polypeptides described herein may be isolated from a variety of sources, such as from human tissue types or from another source, or prepared by recombinant or synthetic methods. The term "PRO polypeptide" refers to each individual PRO/number polypeptide disclosed herein. All disclosures in this specification which refer to the "PRO polypeptide" refer to each of the polypeptides individually as well as jointly. For example, descriptions of the preparation of, purification of, derivation of, formation of antibodies to or against, administration of, compositions containing, treatment of a disease with, etc., pertain to each polypeptide of the invention individually. The term "PRO polypeptide" also includes variants of the PRO/number polypeptides disclosed herein.

A "native sequence PRO polypeptide" comprises a polypeptide having the same amino acid sequence as the corresponding PRO polypeptide derived from nature. Such native sequence PRO polypeptides can be isolated from nature or can be produced by recombinant or synthetic means. The term "native sequence PRO polypeptide" specifically encompasses naturally-occurring truncated or secreted forms of the specific PRO polypeptide (e.g., an extracellular domain sequence), naturally-occurring variant forms (e.g., alternatively spliced forms) and naturally-occurring allelic variants of the polypeptide. In various embodiments of the invention, the native sequence PRO polypeptides disclosed herein are mature or full-length native sequence polypeptides comprising the full-length amino acids sequences shown in the accompanying figures. Start and stop codons are shown in bold font and underlined in the figures. However, while the PRO polypeptide disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the PRO polypeptides.

The PRO polypeptide "extracellular domain" or "ECD" refers to a form of the PRO polypeptide which is essentially free of the transmembrane and cytoplasmic domains. Ordinarily, a PRO polypeptide ECD will have less than 1% of such transmembrane and/or cytoplasmic domains and preferably, will have less than 0.5% of such domains. It will be understood that any transmembrane domains identified for the PRO polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified herein. Optionally, therefore, an extracellular domain of a PRO polypeptide may contain from about 5 or fewer amino acids on either side of the transmembrane domain/extracellular domain boundary as identified in the Examples or specification and such polypeptides, with or without the associated signal peptide, and nucleic acid encoding them, are comtemplated by the present invention.

The approximate location of the "signal peptides" of the various PRO polypeptides disclosed herein are shown in the present specification and/or the accompanying figures. It is noted, however, that the C-terminal boundary of a signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., *Prot. Eng.* 10:1-6 (1997) and von Heinje et al., *Nucl. Acids. Res.* 14:4683-4690 (1986)). Moreover, it is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

"PRO polypeptide variant" means an active PRO polypeptide as defined above or below having at least about 80% amino acid sequence identity with a full-length native sequence PRO polypeptide sequence as disclosed herein, a PRO polypeptide sequence lacking the signal peptide as disclosed herein, an extracellular domain of a PRO polypeptide, with or without the signal peptide, as disclosed herein or any other fragment of a full-length PRO polypeptide sequence as disclosed herein. Such PRO polypeptide variants include, for instance, PRO polypeptides wherein one or more amino acid residues are added, or deleted, at the N- or C-terminus of the full-length native amino acid sequence. Ordinarily, a PRO polypeptide variant will have at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a full-length native sequence PRO polypeptide sequence as disclosed herein, a PRO polypeptide sequence lacking the signal peptide as disclosed herein, an extracellular domain of a PRO polypeptide, with or without the signal peptide, as disclosed herein or any other specifically defined fragment of a full-length PRO polypeptide sequence as disclosed herein. Ordinarily, PRO variant polypeptides are at least about 10 amino acids in length, alternatively at least about 20 amino acids in length, alternatively at least about 30 amino acids in length, alternatively at least about 40 amino acids in length, alternatively at least about 50 amino acids in length, alternatively at least about 60 amino acids in length, alternatively at least about 70 amino acids in length, alternatively at least about 80 amino acids in length, alternatively at least about 90 amino acids in length, alternatively at least about 100 amino acids in length, alternatively at least about 150 amino acids in length, alternatively at least about 200 amino acids in length, alternatively at least about 300 amino acids in length, or more.

"Percent (%) amino acid sequence identity" with respect to the PRO polypeptide sequences identified herein is defined as the percentage of amino acid residues in a candidate sequence that are identical with the amino acid residues in the specific PRO polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 demonstrate how to calculate the % amino acid sequence identity of the amino acid sequence designated "Comparison Protein" to the amino acid sequence designated "PRO", wherein "PRO" represents the amino acid sequence of a hypothetical PRO polypeptide of interest, "Comparison Protein" represents the amino acid sequence of a polypeptide against which the "PRO" polypeptide of interest is being compared, and "X, "Y" and "Z" each represent different hypothetical amino acid residues.

Unless specifically stated otherwise, all % amino acid sequence identity values used herein are obtained as described in the immediately preceding paragraph using the ALIGN-2 computer program. However, % amino acid sequence identity values may also be obtained as described below by using the WU-BLAST-2 computer program (Altschul et al., *Methods in Enzymology* 266:460-480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % amino acid sequence identity value is determined by dividing (a) the number of matching identical amino acid residues between the amino acid sequence of the PRO polypeptide of interest having a sequence derived from the native PRO polypeptide and the comparison amino acid sequence of interest (i.e., the sequence against which the PRO polypeptide of interest is being compared which may be a PRO variant polypeptide) as determined by WU-BLAST-2 by (b) the total number of amino acid residues of the PRO polypeptide of interest. For example, in the statement "a polypeptide comprising an the amino acid sequence A which has or having at least 80% amino acid sequence identity to the amino acid sequence B", the amino acid sequence A is the comparison amino acid sequence of interest and the amino acid sequence B is the amino acid sequence of the PRO polypeptide of interest.

Percent amino acid sequence identity may also be determined using the sequence comparison program NCBI-BLAST2 (Altschul et al., *Nucleic Acids Res.* 25:3389-3402 (1997)). The NCBI-BLAST2 sequence comparison program may be obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

"PRO variant polynucleotide" or "PRO variant nucleic acid sequence" means a nucleic acid molecule which encodes an active PRO polypeptide as defined below and which has at least about 80% nucleic acid sequence identity with a nucleotide acid sequence encoding a full-length native sequence PRO polypeptide sequence as disclosed herein, a full-length native sequence PRO polypeptide sequence lacking the signal peptide as disclosed herein, an extracellular domain of a PRO polypeptide, with or without the signal peptide, as disclosed herein or any other fragment of a full-length PRO polypeptide sequence as disclosed herein. Ordinarily, a PRO variant polynucleotide will have at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity with a nucleic acid sequence encoding a full-length native sequence PRO polypeptide sequence as disclosed herein, a full-length native sequence PRO polypeptide sequence lacking the signal peptide as disclosed herein, an extracellular domain of a PRO polypeptide, with or without the signal sequence, as disclosed herein or any other fragment of a full-length PRO polypeptide sequence as disclosed herein. Variants do not encompass the native nucleotide sequence.

Ordinarily, PRO variant polynucleotides are at least about 30 nucleotides in length, alternatively at least about 60 nucleotides in length, alternatively at least about 90 nucleotides in length, alternatively at least about 120 nucleotides in length, alternatively at least about 150 nucleotides in length, alternatively at least about 180 nucleotides in length, alternatively at least about 210 nucleotides in length, alternatively at least about 240 nucleotides in length, alternatively at least about 270 nucleotides in length, alternatively at least about 300 nucleotides in length, alternatively at least about 450 nucleotides in length, alternatively at least about 600 nucleotides in length, alternatively at least about 900 nucleotides in length, or more.

"Percent (%) nucleic acid sequence identity" with respect to PRO-encoding nucleic acid sequences identified herein is defined as the percentage of nucleotides in a candidate sequence that are identical with the nucleotides in the PRO nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5, demonstrate how to calculate the % nucleic acid sequence identity of the nucleic acid sequence designated "Comparison DNA" to the nucleic acid sequence designated "PRO-DNA", wherein "PRO-DNA" represents a hypothetical PRO-encoding nucleic acid sequence of interest, "Comparison DNA" represents the nucleotide sequence of a nucleic acid molecule against which the "PRO-DNA" nucleic acid molecule of interest is being compared, and "N", "L" and "V" each represent different hypothetical nucleotides.

Unless specifically stated otherwise, all % nucleic acid sequence identity values used herein are obtained as described in the immediately preceding paragraph using the ALIGN-2 computer program. However, % nucleic acid sequence identity values may also be obtained as described below by using the WU-BLAST-2 computer program (Altschul et al., *Methods in Enzymology* 266:460-480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % nucleic acid sequence identity value is determined by dividing (a) the number of matching identical nucleotides between the nucleic acid sequence of the PRO polypeptide-encoding nucleic acid molecule of interest having a sequence derived from the native sequence PRO polypeptide-encoding nucleic acid and the comparison nucleic acid molecule of interest (i.e., the sequence against which the PRO polypeptide-encoding nucleic acid molecule of interest is being compared which may be a variant PRO polynucleotide) as determined by WU-BLAST-2 by (b) the total number of nucleotides of the PRO polypeptide-encoding nucleic acid molecule of interest. For example, in the statement "an isolated nucleic acid molecule comprising a nucleic acid sequence A which has or having at least 80% nucleic acid sequence identity to the nucleic acid sequence B", the nucleic acid sequence A is the comparison nucleic acid molecule of interest and the nucleic acid sequence B is the nucleic acid sequence of the PRO polypeptide-encoding nucleic acid molecule of interest.

Percent nucleic acid sequence identity may also be determined using the sequence comparison program NCBI-BLAST2 (Altschul et al., *Nucleic Acids Res.* 25:3389-3402 (1997)). The NCBI-BLAST2 sequence comparison program may be obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program NCBI-BLAST2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

In other embodiments, PRO variant polynucleotides are nucleic acid molecules that encode an active PRO polypeptide and which are capable of hybridizing, preferably under stringent hybridization and wash conditions, to nucleotide sequences encoding a full-length PRO polypeptide as disclosed herein. PRO variant polypeptides may be those that are encoded by a PRO variant polynucleotide.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the PRO polypeptide natural environment will not be present. Ordinarily, however, isolated polypeptide will be prepared by at least one purification step.

An "isolated" PRO polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers, for example, single anti-PRO monoclonal antibodies (including agonist, antagonist, and neutralizing antibodies), anti-PRO antibody compositions with polyepitopic specificity, single chain anti-PRO antibodies, and fragments of anti-PRO antibodies (see below). The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a PRO polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

"Active" or "activity" for the purposes herein refers to form(s) of a PRO polypeptide which retain a biological and/or an immunological activity of native or naturally-occurring PRO, wherein "biological" activity refers to a biological function (either inhibitory or stimulatory) caused by a native or naturally-occurring PRO other than the ability to induce the production of an antibody against an antigenic epitope possessed by a native or naturally-occurring PRO and an "immunological" activity refers to the ability to induce the production of an antibody against an antigenic epitope possessed by a native or naturally-occurring PRO.

The term "antagonist" is used in the broadest sense, and includes any molecule that partially or fully blocks, inhibits, or neutralizes a biological activity of a native PRO polypeptide disclosed herein. In a similar manner, the term "agonist" is used in the broadest sense and includes any molecule that mimics a biological activity of a native PRO polypeptide disclosed herein. Suitable agonist or antagonist molecules specifically include agonist or antagonist antibodies or antibody fragments, fragments or amino acid sequence variants of native PRO polypeptides, peptides, antisense oligonucleotides, small organic molecules, etc. Methods for identifying agonists or antagonists of a PRO polypeptide may comprise contacting a PRO polypeptide with a candidate agonist or antagonist molecule and measuring a detectable change in one or more biological activities normally associated with the PRO polypeptide.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI Americas Inc., Bridgewater, N.J.), polyethylene glycol (PEG), and PLURONICS® (BASF Corporation, Mount Olive, N.J.).

"Antibody fragments" comprise a portion of an intact antibody, preferably the antigen binding or variable region of the intact antibody. Examples of antibody fragments include Fab, Fab', $F(ab')_2$, and Fv fragments; diabodies; linear antibodies (Zapata et al., *Protein Eng.* 8(10): 1057-1062 [1995]); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an $F(ab')_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA,* 90:6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a PRO polypeptide or antibody thereto) to a mammal. The components of the liposome are commonly arranged in a bilayer formation, similar to the lipid arrangement of biological membranes.

A "small molecule" is defined herein to have a molecular weight below about 500 Daltons.

An "effective amount" of a polypeptide disclosed herein or an agonist or antagonist thereof is an amount sufficient to carry out a specifically stated purpose. An "effective amount" may be determined empirically and in a routine manner, in relation to the stated purpose.

TABLE 1

```
/*
 *
 * C-C increased from 12 to 15
 * Z is average of EQ
 * B is average of ND
 * match with stop is _M; stop-stop = 0; J (joker) match = 0
 */
#define _M      −8      /* value of a match with a stop */
int     _day[26][26] = {
/*      A B C D E F G H I J K L M N O P Q R S T U V W X Y Z */
/* A */ { 2, 0,−2, 0, 0,−4, 1,−1,−1, 0,−1,−2,−1, 0,_M, 1, 0,−2, 1, 1, 0, 0,−6, 0,−3, 0},
/* B */ { 0, 3,−4, 3, 2,−5, 0, 1,−2, 0, 0,−3,−2, 2,_M,−1, 1, 0, 0, 0, 0,−2,−5, 0,−3, 1},
/* C */ {−2,−4,15,−5,−5,−4,−3,−3,−2, 0,−5,−6,−5,−4,_M,−3,−5,−4, 0,−2, 0,−2,−8, 0, 0,−5},
/* D */ { 0, 3,−5, 4, 3,−6, 1, 1,−2, 0, 0,−4,−3, 2,_M,−1, 2,−1, 0, 0, 0,−2,−7, 0,−4, 2},
/* E */ { 0, 2,−5, 3, 4,−5, 0, 1,−2, 0, 0,−3,−2, 1,_M,−1, 2,−1, 0, 0, 0,−2,−7, 0,−4, 3},
/* F */ {−4,−5,−4,−6,−5, 9,−5,−2, 1, 0,−5, 2, 0,−4,_M,−5,−5,−4,−3,−3, 0,−1, 0, 0, 7,−5},
/* G */ { 1, 0,−3, 1, 0,−5, 5,−2,−3, 0,−2,−4,−3, 0,_M,−1,−1,−3, 1, 0, 0,−1,−7, 0,−5, 0},
/* H */ {−1, 1,−3, 1, 1,−2,−2, 6,−2, 0, 0,−2,−2, 2,_M, 0, 3, 2,−1,−1, 0,−2,−3, 0, 0, 2},
/* I */ {−1,−2,−2,−2,−2, 1,−3,−2, 5, 0,−2, 2, 2,−2,_M,−2,−2,−2,−1, 0, 0, 4,−5, 0,−1,−2},
/* J */ { 0, 0, 0, 0, 0, 0, 0, 0, 0, 0, 0, 0, 0, 0,_M, 0, 0, 0, 0, 0, 0, 0, 0, 0, 0, 0},
/* K */ {−1, 0,−5, 0, 0,−5,−2, 0,−2, 0, 5,−3, 0, 1,_M,−1, 1, 3, 0, 0, 0,−2,−3, 0,−4, 0},
/* L */ {−2,−3,−6,−4,−3, 2,−4,−2, 2, 0,−3, 6, 4,−3,_M,−3,−2,−3,−3,−1, 0, 2,−2, 0,−1,−2},
/* M */ {−1,−2,−5,−3,−2, 0,−3,−2, 2, 0, 0, 4, 6,−2,_M,−2,−1, 0,−2,−1, 0, 2,−4, 0,−2,−1},
/* N */ { 0, 2,−4, 2, 1,−4, 0, 2,−2, 0, 1,−3,−2, 2,_M,−1, 1, 0, 1, 0, 0,−2,−4, 0,−2, 1},
/* O */ {_M,_M,_M,_M,_M,_M,_M,_M,_M,_M,_M,_M,_M,_M, 0,_M,_M,_M,_M,_M,_M,_M,_M,_M,_M,_M},
/* P */ { 1,−1,−3,−1,−1,−5,−1, 0,−2, 0,−1,−3,−2,−1,_M, 6, 0, 0, 1, 0, 0,−1,−6, 0,−5, 0},
/* Q */ { 0, 1,−5, 2, 2,−5,−1, 3,−2, 0, 1,−2,−1, 1,_M, 0, 4, 1,−1,−1, 0,−2,−5, 0,−4, 3},
/* R */ {−2, 0,−4,−1,−1,−4,−3, 2,−2, 0, 3,−3, 0, 0,_M, 0, 1, 6, 0,−1, 0,−2, 2, 0,−4, 0},
/* S */ { 1, 0, 0, 0, 0,−3, 1,−1,−1, 0, 0,−3,−2, 1,_M, 1,−1, 0, 2, 1, 0,−1,−2, 0,−3, 0},
/* T */ { 1, 0,−2, 0, 0,−3, 0,−1, 0, 0, 0,−1,−1, 0,_M, 0,−1,−1, 1, 3, 0, 0,−5, 0,−3, 0},
/* U */ { 0, 0, 0, 0, 0, 0, 0, 0, 0, 0, 0, 0, 0, 0,_M, 0, 0, 0, 0, 0, 0, 0, 0, 0, 0, 0},
/* V */ { 0,−2,−2,−2,−2,−1,−1,−2, 4, 0,−2, 2, 2,−2,_M,−1,−2,−2,−1, 0, 0, 4,−6, 0,−2,−2},
/* W */ {−6,−5,−8,−7,−7, 0,−7,−3,−5, 0,−3,−2,−4,−4,_M,−6,−5, 2,−2,−5, 0,−6,17, 0, 0,−6},
/* X */ { 0, 0, 0, 0, 0, 0, 0, 0, 0, 0, 0, 0, 0, 0,_M, 0, 0, 0, 0, 0, 0, 0, 0, 0, 0, 0},
/* Y */ {−3,−3, 0,−4,−4, 7,−5, 0,−1, 0,−4,−1,−2,−2,_M,−5,−4,−4,−3,−3, 0,−2, 0, 0,10,−4},
/* Z */ { 0, 1,−5, 2, 3,−5, 0, 2,−2, 0, 0,−2,−1, 1,_M, 0, 3, 0, 0, 0, 0,−2,−6, 0,−4, 4}
};
/*
 */
#include <stdio.h>
#include <ctype.h>
#define  MAXJMP     16      /* max jumps in a diag */
#define  MAXGAP     24      /* don't continue to penalize gaps larger than this */
#define  JMPS       1024    /* max jmps in an path */
#define  MX         4       /* save if there's at least MX−1 bases since last jmp */
#define  DMAT       3       /* value of matching bases */
#define  DMIS       0       /* penalty for mismatched bases */
#define  DINS0      8       /* penalty for a gap */
#define  DINS1      1       /* penalty per base */
#define  PINS0      8       /* penalty for a gap */
#define  PINS1      4       /* penalty per residue */
struct jmp {
        short           n[MAXJMP];      /* size of jmp (neg for dely) */
        unsigned short  x[MAXJMP];      /* base no. of jmp in seq x */
};                                      /* limits seq to 2^16 −1 */
struct diag {
        int             score;          /* score at last jmp */
        long            offset;         /* offset of prev block */
        short           ijmp;           /* current jmp index */
        struct jmp      jp;             /* list of jmps */
};
struct path {
        int     spc;            /* number of leading spaces */
        short   n[JMPS]; /* size of jmp (gap) */
        int     x[JMPS]; /* loc of jmp (last elem before gap) */
};
char    *ofile;                 /* output file name */
char    *namex[2];              /* seq names: getseqs( ) */
char    *prog;                  /* prog name for err msgs */
char    *seqx[2];               /* seqs: getseqs( ) */
int     dmax;                   /* best diag: nw( ) */
int     dmax0;                  /* final diag */
int     dna;                    /* set if dna: main( ) */
int     endgaps;                /* set if penalizing end gaps */
int     gapx, gapy;             /* total gaps in seqs */
int     len0, len1;             /* seq lens */
int     ngapx, ngapy;           /* total size of gaps */
int     smax;                   /* max score: nw( ) */
int     *xbm;                   /* bitmap for matching */
```

TABLE 1-continued

```
long                offset;                       /* current offset in jmp file */
struct    diag      *dx;                          /* holds diagonals */
struct    path      pp[2];                        /* holds path for seqs */
char                *calloc( ), *malloc( ), *index( ), *strcpy( );
char                *getseq( ), *g_calloc( );
/* Needleman-Wunsch alignment program
 *
 * usage: progs file1 file2
 *   where file1 and file2 are two dna or two protein sequences.
 *   The sequences can be in upper- or lower-case an may contain ambiguity
 *   Any lines beginning with ';', '>' or '<' are ignored
 *   Max file length is 65535 (limited by unsigned short x in the jmp struct)
 *   A sequence with 1/3 or more of its elements ACGTU is assumed to be DNA
 *   Output is in the file "align.out"
 *
 * The program may create a tmp file in /tmp to hold info about traceback.
 * Original version developed under BSD 4.3 on a vax 8650
 */
#include "nw.h"
#include "day.h"
static    _dbval[26] = {
          1,14,2,13,0,0,4,11,0,0,12,0,3,15,0,0,0,5,6,8,8,7,9,0,10,0
};
static    _pbval[26] = {
          1, 2|(1<<('D'-'A'))|(1<<('N'-'A')), 4, 8, 16, 32, 64,
          128, 256, 0xFFFFFFF, 1<<10, 1<<11, 1<<12, 1<<13, 1<<14,
          1<<15, 1<<16, 1<<17, 1<<18, 1<<19, 1<<20, 1<<21, 1<<22,
          1<<23, 1<<24, 1<<25|(1<<('E'-'A'))|(1<<('Q'-'A'))
};
main(ac, av)                                                                  main
          int       ac;
          char      *av[ ];
{
          prog = av[0];
          if (ac != 3) {
                    fprintf(stderr,"usage: %s file1 file2\n", prog);
                    fprintf(stderr,"where file1 and file2 are two dna or two protein sequences.\n");
                    fprintf(stderr,"The sequences can be in upper- or lower-case\n");
                    fprintf(stderr,"Any lines beginning with ';' or '<' are ignored\n");
                    fprintf(stderr,"Output is in the file \"align.out\"\n");
                    exit(1);
          }
          namex[0] = av[1];
          namex[1] = av[2];
          seqx[0] = getseq(namex[0], &len0);
          seqx[1] = getseq(namex[1], &len1);
          xbm = (dna)? _dbval : _pbval;
          endgaps = 0;                            /* 1 to penalize endgaps */
          ofile = "align.out";                    /* output file */
          nw( );              /* fill in the matrix, get the possible jmps */
          readjmps( );        /* get the actual jmps */
          print( );           /* print stats, alignment */
          cleanup(0);         /* unlink any tmp files */
}
/* do the alignment, return best score: main( )
 * dna: values in Fitch and Smith, PNAS, 80, 1382-1386, 1983
 * pro: PAM 250 values
 * When scores are equal, we prefer mismatches to any gap, prefer
 * a new gap to extending an ongoing gap, and prefer a gap in seqx
 * to a gap in seq y.
 */
nw( )                                                                         nw
{
          char          *px, *py;           /* seqs and ptrs */
          int           *ndely, *dely;      /* keep track of dely */
          int           ndelx, delx;        /* keep track of delx */
          int           *tmp;               /* for swapping row0, row1 */
          int           mis;                /* score for each type */
          int           ins0, ins1;         /* insertion penalties */
          register      id;                 /* diagonal index */
          register      ij;                 /* jmp index */
          register      *col0, *col1;       /* score for curr, last row */
          register      xx, yy;             /* index into seqs */
          dx = (struct diag *)g_calloc("to get diags", len0+len1+1, sizeof(struct diag));
          ndely = (int *)g_calloc("to get ndely", len1+1, sizeof(int));
          dely = (int *)g_calloc("to get dely", len1+1, sizeof(int));
          col0 = (int *)g_calloc("to get col0", len1+1, sizeof(int));
          col1 = (int *)g_calloc("to get col1", len1+1, sizeof(int));
          ins0 = (dna)? DINS0 : PINS0;
```

TABLE 1-continued

```
ins1 = (dna)? DINS1 : PINS1;
smax = −10000;
if (endgaps) {
        for (col0[0] = dely[0] = −ins0, yy = 1; yy <= len1; yy++) {
                col0[yy] = dely[yy] = col0[yy−1] − ins1;
                ndely[yy] = yy;
        }
        col0[0] = 0;        /* Waterman Bull Math Biol 84 */
}
else
        for (yy = 1; yy <= len1; yy++)
                dely[yy] = −ins0;
/* fill in match matrix
 */
for (px = seqx[0], xx = 1; xx <= len0; px++, xx++) {
        /* initialize first entry in col
         */
        if (endgaps) {
                if (xx == 1)
                        col1[0] = delx = −(ins0+ins1);
                else
                        col1[0] = delx = col0[0] − ins1;
                ndelx = xx;
        }
        else {
                col1[0] = 0;
                delx = −ins0;
                ndelx = 0;
        }
                                                                        . . .nw
        for (py = seqx[1], yy = 1; yy <= len1; py++, yy++) {
                mis = col0[yy−1];
                if (dna)
                        mis += (xbm[*px−'A']&xbm[*py−'A'])? DMAT : DMIS;
                else
                        mis += _day[*px−'A'][*py−'A'];
                /* update penalty for del in x seq;
                 * favor new del over ongong del
                 * ignore MAXGAP if weighting endgaps
                 */
                if (endgaps || ndely[yy] < MAXGAP) {
                        if (col0[yy] − ins0 >= dely[yy]) {
                                dely[yy] = col0[yy] − (ins0+ins1);
                                ndely[yy] = 1;
                        } else {
                                dely[yy] −= ins1;
                                ndely[yy]++;
                        }
                } else {
                        if (col0[yy] − (ins0+ins1) >= dely[yy]) {
                                dely[yy] = col0[yy] − (ins0+ins1);
                                ndely[yy] = 1;
                        } else
                                ndely[yy]++;
                }
                /* update penalty for del in y seq;
                 * favor new del over ongong del
                 */
                if (endgaps || ndelx < MAXGAP) {
                        if (col1[yy−1] − ins0 >= delx) {
                                delx = col1[yy−1] − (ins0+ins1);
                                ndelx = 1;
                        } else {
                                delx −= ins1;
                                ndelx++;
                        }
                } else {
                        if (col1[yy−1] − (ins0+ins1) >= delx) {
                                delx = col1[yy−1] − (ins0+ins1);
                                ndelx = 1;
                        } else
                                ndelx++;
                }
                /* pick the maximum score; we're favoring
                 * mis over any del and delx over dely
                 */
                                                                        . . .nw
                id = xx − yy + len1 − 1;
                if (mis >= delx && mis >= dely[yy])
```

TABLE 1-continued

```
                        col1[yy] = mis;
                else if (delx >= dely[yy]) {
                        col1[yy] = delx;
                        ij = dx[id].ijmp;
                        if (dx[id].jp.n[0] && (!dna || (ndelx >= MAXJMP
                        && xx > dx[id].jp.x[ij]+MX) || mis > dx[id].score+DINS0)) {
                                dx[id].ijmp++;
                                if (++ij >= MAXJMP) {
                                        writejmps(id);
                                        ij = dx[id].ijmp = 0;
                                        dx[id].offset = offset;
                                        offset += sizeof(struct jmp) + sizeof(offset);
                                }
                        }
                        dx[id].jp.n[ij] = ndelx;
                        dx[id].jp.x[ij] = xx;
                        dx[id].score = delx;
                }
                else {
                        col1[yy] = dely[yy];
                        ij = dx[id].ijmp;
        if (dx[id].jp.n[0] && (!dna || (ndely[yy] >= MAXJMP
                        && xx > dx[id].jp.x[ij]+MX) || mis > dx[id].score+DINS0)) {
                                dx[id].ijmp++;
                                if (++ij >= MAXJMP) {
                                        writejmps(id);
                                        ij = dx[id].ijmp = 0;
                                        dx[id].offset = offset;
                                        offset += sizeof(struct jmp) + sizeof(offset);
                                }
                        }
                        dx[id].jp.n[ij] = −ndely[yy];
                        dx[id].jp.x[ij] = xx;
                        dx[id].score = dely[yy];
                }
                if (xx == len0 && yy < len1) {
                        /* last col
                         */
                        if (endgaps)
                                col1[yy] −= ins0+ins1*(len1−yy);
                        if (col1[yy] > smax) {
                                smax = col1[yy];
                                dmax = id;
                        }
                }
        }
        if (endgaps && xx < len0)
                col1[yy−1] −= ins0+ins1*(len0−xx);
        if (col1[yy−1] > smax) {
                smax = col1[yy−1];
                dmax = id;
        }
        tmp = col0; col0 = col1; col1 = tmp;
    }
    (void) free((char *)ndely);
    (void) free((char *)dely);
    (void) free((char *)col0);
    (void) free((char *)col1); }
/*
 *
 * print( ) -- only routine visible outside this module
 *
 * static:
 * getmat( ) -- trace back best path, count matches: print( )
 * pr_align( ) -- print alignment of described in array p[ ]: print( )
 * dumpblock( ) -- dump a block of lines with numbers, stars: pr_align( )
 * nums( ) -- put out a number line: dumpblock( )
 * putline( ) -- put out a line (name, [num], seq, [num]): dumpblock( )
 * stars( ) - -put a line of stars: dumpblock( )
 * stripname( ) -- strip any path and prefix from a seqname
 */
#include "nw.h"
#define SPC         3
#define P_LINE      256     /* maximum output line */
#define P_SPC       3       /* space between name or num and seq */
extern      _day[26][26];
int         olen;           /* set output line length */
FILE        *fx;            /* output file */
print( )                                                                print
```

TABLE 1-continued

```
{
        int        lx, ly, firstgap, lastgap;        /* overlap */
        if ((fx = fopen(ofile, "w")) == 0) {
                fprintf(stderr, "%s: can't write %s\n", prog, ofile);
                cleanup(1);
        }
        fprintf(fx, "<first sequence: %s (length = %d)\n", namex[0], len0);
        fprintf(fx, "<second sequence: %s (length = %d)\n", namex[1], len1);
        olen = 60;
        lx = len0;
        ly = len1;
        firstgap = lastgap = 0;
        if (dmax < len1 − 1) {          /* leading gap in x */
                pp[0].spc = firstgap = len1 − dmax − 1;
                ly −= pp[0].spc;
        }
        else if (dmax > len1 − 1) {      /* leading gap in y */
                pp[1].spc = firstgap = dmax − (len1 − 1);
                lx −= pp[1].spc;
        }
        if (dmax0 < len0 − 1) {          /* trailing gap in x */
                lastgap = len0 − dmax0 −1;
                lx −= lastgap;
        }
        else if (dmax0 > len0 − 1) {     /* trailing gap in y */
                lastgap = dmax0 − (len0 − 1);
                ly −= lastgap;
        }
        getmat(lx, ly, firstgap, lastgap);
        pr_align( );
}
/*
 * trace back the best path, count matches
 */
static
getmat(lx, ly, firstgap, lastgap)                                       getmat
        int        lx, ly;                        /* "core" (minus endgaps) */
        int        firstgap, lastgap;             /* leading trailing overlap */
{
        int                nm, i0, i1, siz0, siz1;
        char               outx[32];
        double             pct;
        register           n0, n1;
        register char      *p0, *p1;
        /* get total matches, score
         */
        i0 = i1 = siz0 = siz1 = 0;
        p0 = seqx[0] + pp[1].spc;
        p1 = seqx[1] + pp[0].spc;
        n0 = pp[1].spc + 1;
        n1 = pp[0].spc + 1;
        nm = 0;
        while ( *p0 && *p1 ) {
                if (siz0) {
                        p1++;
                        n1++;
                        siz0−−;
                }
                else if (siz1) {
                        p0++;
                        n0++;
                        siz1−−;
                }
                else {
                        if (xbm[*p0−'A']&xbm[*p1−'A'])
                                nm++;
                        if (n0++ == pp[0].x[i0])
                                siz0 = pp[0].n[i0++];
                        if (n1++ == pp[1].x[i1])
                                siz1 = pp[1].n[i1++];
                        p0++;
                        p1++;
                }
        }
        /* pct homology:
         * if penalizing endgaps, base is the shorter seq
         * else, knock off overhangs and take shorter core
         */
        if (endgaps)
```

TABLE 1-continued

```
			lx = (len0 < len1)? len0 : len1;
		else
			lx = (lx < ly)? lx : ly;
		pct = 100.*(double)nm/(double)lx;
		fprintf(fx, "\n");
		fprintf(fx, "<%d match%s in an overlap of %d: %.2f percent similarity\n",
			nm, (nm == 1)? "" : "es", lx, pct);
		fprintf(fx, "<gaps in first sequence: %d", gapx);                                   ...getmat
		if (gapx) {
			(void) sprintf(outx, " (%d %s%s)",
				ngapx, (dna)? "base":"residue", (ngapx == 1)? "":"s");
			fprintf(fx, "%s", outx);
		fprintf(fx, ", gaps in second sequence: %d", gapy);
		if (gapy) {
			(void) sprintf(outx, " (%d %s%s)",
				ngapy, (dna)? "base":"residue", (ngapy == 1)? "":"s");
			fprintf(fx, "%s", outx);
		}
		if (dna)
			fprintf(fx,
			"\n<score: %d (match = %d, mismatch = %d, gap penalty = %d + %d per base)\n",
			smax, DMAT, DMIS, DINS0, DINS1);
		else
			fprintf(fx,
			"\n<score: %d (Dayhoff PAM 250 matrix, gap penalty = %d + %d per residue)\n",
			smax, PINS0, PINS1);
		if (endgaps)
			fprintf(fx,
			"<endgaps penalized. left endgap: %d %s%s, right endgap: %d %s%s\n",
			firstgap, (dna)? "base" : "residue", (firstgap == 1)? "" : "s",
			lastgap, (dna)? "base" : "residue", (lastgap == 1)? "" : "s");
		else
			fprintf(fx, "<endgaps not penalized\n");
}
static		nm;			/* matches in core -- for checking */
static		lmax;			/* lengths of stripped file names */
static		ij[2];			/* jmp index for a path */
static		nc[2];			/* number at start of current line */
static		ni[2];			/* current elem number -- for gapping */
static		siz[2];
static char	*ps[2];			/* ptr to current element */
static char	*po[2];			/* ptr to next output char slot */
static char	out[2][P_LINE];		/* output line */
static char	star[P_LINE];		/* set by stars( ) */
/*
 * print alignment of described in struct path pp[ ]
 */
static
pr_align( )                                                                                  pr_align
{
		int		nn;		/* char count */
		int		more;
		register	i;
		for (i = 0, lmax = 0; i < 2; i++) {
			nn = stripname(namex[i]);
			if (nn > lmax)
				lmax = nn;
			nc[i] = 1;
			ni[i] = 1;
			siz[i] = ij[i] = 0;
			ps[i] = seqx[i];
			po[i] = out[i];				}
		for (nn = nm = 0, more = 1; more; ) {                                               ...pr_align
			for (i = more = 0; i < 2; i++) {
				/*
				 * do we have more of this sequence?
				 */
				if (!*ps[i])
					continue;
				more++;
				if (pp[i].spc) {	/* leading space */
					*po[i]++ = ' ';
					pp[i].spc--;
				}
				else if (siz[i]) {	/* in a gap */
					*po[i]++ = '-';
					siz[i]--;
				}
				else {			/* we're putting a seq element
```

TABLE 1-continued

```
                                        */
                                *po[i] = *ps[i];
                                if (islower(*ps[i]))
                                *ps[i] = toupper(*ps[i]);
                                po[i]++;
                                ps[i]++;
                                /*
                                 * are we at next gap for this seq?
                                 */
                                if (ni[i] == pp[i].x[ij[i]]) {
                                        /*
                                         * we need to merge all gaps
                                         * at this location
                                         */
                                        siz[i] = pp[i].n[ij[i]++];
                                        while (ni[i] == pp[i].x[ij[i]])
                                                siz[i] += pp[i].n[ij[i]++];
                                }
                                ni[i]++;
                        }
                }
                if (++nn == olen || !more && nn) {
                        dumpblock( );
                        for (i = 0; i < 2; i++)
                                po[i] = out[i];
                        nn = 0;
                }
        }
}
/*
 * dump a block of lines, including numbers, stars: pr__align( )
 */
static
dumpblock( )                                                                    dumpblock
{
        register i;
        for (i = 0; i < 2; i++)
                *po[i]-- = '\0';
                                                                                . . .dumpblock
        (void) putc('\n', fx);
        for (i = 0; i < 2; i++) {
                if (*out[i] && (*out[i] != ' ' || *(po[i]) != ' ')) {
                        if (i == 0)
                                nums(i);
                        if (i == 0 && *out[1])
                                stars( );
                        putline(i);
                        if (i == 0 && *out[1])
                                fprintf(fx, star);
                        if (i == 1)
                                nums(i);
                }
        }
}
/*
 * put out a number line: dumpblock( )
 */
static
nums(ix)                                                                        nums
        int             ix;             /* index in out[ ] holding seq line */
{
        char                    nline[P__LINE];
        register                i, j;
        register char           *pn, *px, *py;
        for (pn = nline, i = 0; i < lmax+P__SPC; i++, pn++)
                *pn = ' ';
        for (i = nc[ix], py = out[ix]; *py; py++, pn++) {
                if (*py == ' ' || *py == '-')
                        *pn = ' ';
                else {
                        if (i%10 == 0 || (i == 1 && nc[ix] != 1)) {
                                j = (i < 0)? -i : i;
                                for (px = pn; j; j /= 10, px--)
                                        *px = j%10 + '0';
                                if (i < 0)
                                        *px = '-';
                        }
                        else
                                *pn = ' ';
```

TABLE 1-continued

```
                    i++;
                }
            }
            *pn = '\0';
            nc[ix] = i;
            for (pn = nline; *pn; pn++)
                (void) putc(*pn, fx);
            (void) putc('\n', fx);
}
/*
 * put out a line (name, [num], seq, [num]): dumpblock( )
 */
static
putline(ix)                                                              putline
            int     ix;             {
                                                                         . . .putline
            int             i;
            register char   *px;
            for (px = namex[ix], i = 0; *px && *px != ':'; px++, i++)
                (void) putc(*px, fx);
            for (; i < lmax+P_SPC; i++)
                (void) putc(' ', fx);
            /* these count from 1:
             * ni[ ] is current element (from 1)
             * nc[ ] is number at start of current line
             */
            for (px = out[ix]; *px; px++)
                (void) putc(*px&0x7F, fx);
            (void) putc('\n', fx);
}
/*
 * put a line of stars (seqs always in out[0], out[1]): dumpblock( )
 */
static
stars( )                                                                 stars
{
            int             i;
            register char   *p0, *p1, cx, *px;
            if (!*out[0] || (*out[0] == ' ' && *(po[0]) == ' ') ||
              !*out[1] || (*out[1] == ' ' && *(po[1]) == ' '))
                return;
            px = star;
            for (i = lmax+P_SPC; i; i−−)
                *px++ = ' ';
            for (p0 = out[0], p1 = out[1]; *p0 && *p1; p0++, p1++) {
                if (isalpha(*p0) && isalpha(*p1)) {
                    if (xbm[*p0−'A']&xbm[*p1−'A']) {
                        cx = '*';
                        nm++;
                    }
                    else if (!dna && _day[*p0−'A'][*p1−'A'] > 0)
                        cx = '.';
                    else
                        cx = ' ';
                }
                else
                    cx = ' ';
                *px++ = cx;
            }
            *px++ = '\n';
            *px = '\0';
}
/*
 * strip path or prefix from pn, return len: pr_align( )
 */
static
stripname(pn)                                                            stripname
            char    *pn;    /* file name (may be path) */
{
            register char   *px, *py;
            py = 0;
            for (px = pn; *px; px++)
                if (*px == '/')
                    py = px + 1;
            if (py)
                (void) strcpy(pn, py);
            return(strlen(pn));
}
/*
```

TABLE 1-continued

```
 * cleanup( ) -- cleanup any tmp file
 * getseq( ) -- read in seq, set dna, len, maxlen
 * g_calloc( ) -- calloc( ) with error checkin
 * readjmps( ) -- get the good jmps, from tmp file if necessary
 * writejmps( ) -- write a filled array of jmps to a tmp file: nw( )
 */
#include "nw.h"
#include <sys/file.h>
char    *jname = "/tmp/homgXXXXXX";        /* tmp file for jmps */
FILE    *fj;
int     cleanup( );                        /* cleanup tmp file */
long    lseek( );
/*
 * remove any tmp file if we blow
 */
cleanup(i)                                                          cleanup
        int     i;
{
        if (fj)
                (void) unlink(jname);
        exit(i);
}
/*
 * read, return ptr to seq, set dna, len, maxlen
 * skip lines starting with ';', '<', or '>'
 * seq in upper or lower case
 */
char    *
getseq(file, len)                                                   getseq
        char    *file;  /* file name */
        int     *len;   /* seq len */
{
        char            line[1024], *pseq;
        register char   *px, *py;
        int             natgc, tlen;
        FILE            *fp;
        if ((fp = fopen(file,"r")) == 0) {
                fprintf(stderr,"%s: can't read %s\n", prog, file);
                exit(1);
        }
        tlen = natgc = 0;
        while (fgets(line, 1024, fp)) {
                if (*line == ';' || *line == '<' || *line == '>')
                        continue;
                for (px = line; *px != '\n'; px++)
                        if (isupper(*px) || islower(*px))
                                tlen++;
        }
        if ((pseq = malloc((unsigned)(tlen+6))) == 0) {
                fprintf(stderr,"%s: malloc( ) failed to get %d bytes for %s\n", prog, tlen+6, file);
                exit(1);
        }
        pseq[0] = pseq[1] = pseq[2] = pseq[3] = '\0';
                                                                    ...getseq
        py = pseq + 4;
        *len = tlen;
        rewind(fp);
        while (fgets(line, 1024, fp)) {
                if (*line == ';' || *line == '<' || *line == '>')
                        continue;
                for (px = line; *px != '\n'; px++) {
                        if (isupper(*px))
                                *py++ = *px;
                        else if (islower(*px))
                                *py++ = toupper(*px);
                        if (index("ATGCU",*(py-1)))
                                natgc++;
                }
        }
        *py++ = '\0';
        *py = '\0';
        (void) fclose(fp);
        dna = natgc > (tlen/3);
        return(pseq+4);
}
char    *
g_calloc(msg, nx, sz)                                               g_calloc
        char    *msg;           /* program, calling routine */
        int     nx, sz;         /* number and size of elements */
```

TABLE 1-continued

```
{
        char            *px, *calloc( );
        if ((px = calloc((unsigned)nx, (unsigned)sz)) == 0) {
                if (*msg) {
                        fprintf(stderr, "%s: g_calloc( ) failed %s (n=%d, sz=%d)\n", prog, msg, nx, sz);
                        exit(1);
                }
        }
        return(px);
}
/*
 * get final jmps from dx[ ] or tmp file, set pp[ ], reset dmax: main( )
 */
readjmps( )                                                                     readjmps
{
        int             fd = -1;
        int             siz, i0, i1;
        register i, j, xx;
        if (fj) {
                (void) fclose(fj);
                if ((fd = open(jname, O_RDONLY, 0)) < 0) {
                        fprintf(stderr, "%s: can't open( ) %s\n", prog, jname);
                        cleanup(1);
                }
        }
        for (i = i0 = i1 = 0, dmax0 = dmax, xx = len0; ; i++) {
                while (1) {
                        for (j = dx[dmax].ijmp; j >= 0 && dx[dmax].jp.x[j] >= xx; j--)
                                ;
                                                                                ...readjmps
                        if (j < 0 && dx[dmax].offset && fj) {
                                (void) lseek(fd, dx[dmax].offset, 0);
                                (void) read(fd, (char *)&dx[dmax].jp, sizeof(struct jmp));
                                (void) read(fd, (char *)&dx[dmax].offset, sizeof(dx[dmax].offset));
                                dx[dmax].ijmp = MAXJMP-1;
                        }
                        else
                                break;
                }
                if (i >= JMPS) {
                        fprintf(stderr, "%s: too many gaps in alignment\n", prog);
                        cleanup(1);
                }
                if (j >= 0) {
                        siz = dx[dmax].jp.n[j];
                        xx = dx[dmax].jp.x[j];
                        dmax += siz;
                        if (siz < 0) {          /* gap in second seq */
                                pp[1].n[i1] = -siz;
                                xx += siz;
                                /* id = xx - yy + len1 - 1
                                 */
                                pp[1].x[i1] = xx - dmax + len1 - 1;
                                gapy++;
                                ngapy -= siz;
/* ignore MAXGAP when doing endgaps */
                                siz = (-siz < MAXGAP || endgaps)? -siz : MAXGAP;
                                i1++;
                        }
                        else if (siz > 0) { /* gap in first seq */
                                pp[0].n[i0] = siz;
                                pp[0].x[i0] = xx;
                                gapx++;
                                ngapx += siz;
/* ignore MAXGAP when doing endgaps */
                                siz = (siz < MAXGAP || endgaps)? siz : MAXGAP;
                                i0++;
                        }
                }
                else
                        break;
        }
        /* reverse the order of jmps
         */
        for (j = 0, i0--; j < i0; j++, i0--) {
                i = pp[0].n[j]; pp[0].n[j] = pp[0].n[i0]; pp[0].n[i0] = i;
                i = pp[0].x[j]; pp[0].x[j] = pp[0].x[i0]; pp[0].x[i0] = i;
        }
        for (j = 0, i1--; j < i1; j++, i1--) {
```

TABLE 1-continued

```
                    i = pp[1].n[j]; pp[1].n[j] = pp[1].n[i1]; pp[1].n[i1] = i;
                    i = pp[1].x[j]; pp[1].x[j] = pp[1].x[i1]; pp[1].x[i1] = i;
          }
          if (fd >= 0)
                    (void) close(fd);
          if (fj) {
                    (void) unlink(jname);
                    fj = 0;
                    offset = 0;
          }                                       }
/*
 * write a filled jmp struct offset of the prev one (if any): nw( )
 */
writejmps(ix)                                                                                writejmps
          int       ix;
{
          char      *mktemp( );
          if (!fj) {
                    if (mktemp(jname) < 0) {
                              fprintf(stderr, "%s: can't mktemp( ) %s\n", prog, jname);
                              cleanup(1);
                    }
                    if ((fj = fopen(jname, "w")) == 0) {
                              fprintf(stderr, "%s: can't write %s\n", prog, jname);
                              exit(1);
                    }
          }
          (void) fwrite((char *)&dx[ix].jp, sizeof(struct jmp), 1, fj);
          (void) fwrite((char *)&dx[ix].offset, sizeof(dx[ix].offset), 1, fj);
}
```

TABLE 2

| | | |
|---|---|---|
| PRO | XXXXXXXXXXXXXXX | (Length = 15 amino acids) |
| Comparison Protein | XXXXXYYYYYYY | (Length = 12 amino acids) |

% amino acid sequence identity = (the number of identically matching amino acid residues between the two polypeptide sequences as determined by ALIGN-2) divided by (the total number of amino acid residues of the PRO polypeptide) = 5 divided by 15 = 33.3%

TABLE 3

| | | |
|---|---|---|
| PRO | XXXXXXXXXX | (Length = 10 amino acids) |
| Comparison Protein | XXXXXYYYYYYZZYZ | (Length = 15 amino acids) |

% amino acid sequence identity = (the number of identically matching amino acid residues between the two polypeptide sequences as determined by ALIGN-2) divided by (the total number of amino acid residues of the PRO polypeptide) = 5 divided by 10 = 50%

TABLE 4

| | | |
|---|---|---|
| PRO-DNA | NNNNNNNNNNNNNN | (Length = 14 nucleotides) |
| Comparison DNA | NNNNNNLLLLLLLLLL | (Length = 16 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 6 divided by 14 = 42.9%

TABLE 5

| | | |
|---|---|---|
| PRO-DNA | NNNNNNNNNNNN | (Length = 12 nucleotides) |
| Comparison DNA | NNNNLLLVV | (Length = 9 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 4 divided by 12 = 33.3%

II. Compositions and Methods of the Invention

A. Full-Length PRO Polypeptides

The present invention provides newly identified and isolated nucleotide sequences encoding polypeptides referred to in the present application as PRO polypeptides. In particular, cDNAs encoding various PRO polypeptides have been identified and isolated, as disclosed in further detail in the Examples below. It is noted that proteins produced in separate expression rounds may be given different PRO numbers but the UNQ number is unique for any given DNA and the encoded protein, and will not be changed. However, for sake of simplicity, in the present specification the protein encoded by the full length native nucleic acid molecules disclosed herein as well as all further native homologues and variants included in the foregoing definition of PRO, will be referred to as "PRO/number", regardless of their origin or mode of preparation.

As disclosed in the Examples below, various cDNA clones have been deposited with the ATCC®. The actual nucleotide sequences of those clones can readily be determined by the skilled artisan by sequencing of the deposited clone using routine methods in the art. The predicted amino acid sequence can be determined from the nucleotide sequence using routine skill. For the PRO polypeptides and encoding nucleic acids described herein, Applicants have identified what is believed to be the reading frame best identifiable with the sequence information available at the time.

B. PRO Polypeptide Variants

In addition to the full-length native sequence PRO polypeptides described herein, it is contemplated that PRO variants can be prepared. PRO variants can be prepared by introducing appropriate nucleotide changes into the PRO DNA, and/or by synthesis of the desired PRO polypeptide. Those skilled in the art will appreciate that amino acid changes may alter post-translational processes of the PRO, such as changing the number or position of glycosylation sites or altering the membrane anchoring characteristics.

Variations in the native full-length sequence PRO or in various domains of the PRO described herein, can be made, for example, using any of the techniques and guidelines for conservative and non-conservative mutations set forth, for instance, in U.S. Pat. No. 5,364,934. Variations may be a substitution, deletion or insertion of one or more codons encoding the PRO that results in a change in the amino acid sequence of the PRO as compared with the native sequence PRO. Optionally the variation is by substitution of at least one amino acid with any other amino acid in one or more of the domains of the PRO. Guidance in determining which amino acid residue may be inserted, substituted or deleted without adversely affecting the desired activity may be found by comparing the sequence of the PRO with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

PRO polypeptide fragments are provided herein. Such fragments may be truncated at the N-terminus or C-terminus, or may lack internal residues, for example, when compared with a full length native protein. Certain fragments lack amino acid residues that are not essential for a desired biological activity of the PRO polypeptide.

PRO fragments may be prepared by any of a number of conventional techniques. Desired peptide fragments may be chemically synthesized. An alternative approach involves generating PRO fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, PRO polypeptide fragments share at least one biological and/or immunological activity with the native PRO polypeptide disclosed herein.

In particular embodiments, conservative substitutions of interest are shown in Table 6 under the heading of preferred substitutions. If such substitutions result in a change in biological activity, then more substantial changes, denominated exemplary substitutions in Table 6, or as further described below in reference to amino acid classes, are introduced and the products screened.

TABLE 6

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |

TABLE 6-continued

| Original Residue | Exemplary Substitutions | Preferred Substitutions |
|---|---|---|
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the PRO polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;

(2) neutral hydrophilic: cys, ser, thr;

(3) acidic: asp, glu;

(4) basic: asn, gln, his, lys, arg;

(5) residues that influence chain orientation: gly, pro; and (6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.,* 13:4331 (1986); Zoller et al., *Nucl. Acids Res.,* 10:6487 (1987)], cassette mutagenesis [Wells et al., *Gene,* 34:315 (1985)], restriction selection mutagenesis [Wells et al., *Philos. Trans. R. Soc. London SerA,* 317:415 (1986)] or other known techniques can be performed on the cloned DNA to produce the PRO variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science,* 244: 1081-1085 (1989)]. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.,* 150:1 (1976)]. If alanine substitution does not yield adequate amounts of variant, an isoteric amino acid can be used.

C. Modifications of PRO

Covalent modifications of PRO are included within the scope of this invention. One type of covalent modification includes reacting targeted amino acid residues of a PRO polypeptide with an organic derivatizing agent that is capable of reacting with selected side chains or the N- or C-terminal residues of the PRO. Derivatization with bifunctional agents is useful, for instance, for crosslinking PRO to a water-insoluble support matrix or surface for use in the method for purifying anti-PRO antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification of the PRO polypeptide included within the scope of this invention comprises altering the native glycosylation pattern of the polypeptide. "Altering the native glycosylation pattern" is intended for purposes herein to mean deleting one or more carbohydrate moieties found in native sequence PRO (either by removing the underlying glycosylation site or by deleting the glycosylation by chemical and/or enzymatic means), and/or adding one or more glycosylation sites that are not present in the native sequence PRO. In addition, the phrase includes qualitative changes in the glycosylation of the native proteins, involving a change in the nature and proportions of the various carbohydrate moieties present.

Addition of glycosylation sites to the PRO polypeptide may be accomplished by altering the amino acid sequence. The alteration may be made, for example, by the addition of, or substitution by, one or more serine or threonine residues to the native sequence PRO (for O-linked glycosylation sites). The PRO amino acid sequence may optionally be altered through changes at the DNA level, particularly by mutating the DNA encoding the PRO polypeptide at preselected bases such that codons are generated that will translate into the desired amino acids.

Another means of increasing the number of carbohydrate moieties on the PRO polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259-306 (1981).

Removal of carbohydrate moieties present on the PRO polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of PRO comprises linking the PRO polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The PRO of the present invention may also be modified in a way to form a chimeric molecule comprising PRO fused to another, heterologous polypeptide or amino acid sequence.

In one embodiment, such a chimeric molecule comprises a fusion of the PRO with a tag polypeptide which provides an epitope to which an anti-tag antibody can selectively bind. The epitope tag is generally placed at the amino- or carboxyl-terminus of the PRO. The presence of such epitope-tagged forms of the PRO can be detected using an antibody against the tag polypeptide. Also, provision of the epitope tag enables the PRO to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an α-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

In an alternative embodiment, the chimeric molecule may comprise a fusion of the PRO with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a PRO polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

D. Preparation of PRO

The description below relates primarily to production of PRO by culturing cells transformed or transfected with a vector containing PRO nucleic acid. It is, of course, contemplated that alternative methods, which are well known in the art, may be employed to prepare PRO. For instance, the PRO sequence, or portions thereof, may be produced by direct peptide synthesis using solid-phase techniques [see, e.g., Stewart et al., *Solid-Phase Pentide Synthesis*, W.H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the PRO may be chemically synthesized separately and combined using chemical or enzymatic methods to produce the full-length PRO.

1. Isolation of DNA Encoding PRO

DNA encoding PRO may be obtained from a cDNA library prepared from tissue believed to possess the PRO mRNA and to express it at a detectable level. Accordingly, human PRO DNA can be conveniently obtained from a cDNA library prepared from human tissue, such as described in the Examples. The PRO-encoding gene may also be obtained from a genomic library or by known synthetic procedures (e.g., automated nucleic acid synthesis).

Libraries can be screened with probes (such as antibodies to the PRO or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding PRO is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}P$-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GENBANK® (US Department of Health and Human Services, Bethesda, Md.) or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for PRO production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene,* 23:315 (1983) and WO 89/05859 published 29 Jun. 1989. For mammalian cells without such cell walls, the calcium phosphate precipitation method of Graham and van der Eb, *Virology,* 52:456-457 (1978) can be employed. General aspects of mammalian cell host system transfections have been described in U.S. Pat. No. 4,399,216. Transformations into yeast are typically carried out according to the method of Van Solingen et al., *J. Bact.,* 130:946 (1977) and Hsiao et al., *Proc. Natl. Acad. Sci.* (USA), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology,* 185:527-537 (1990) and Mansour et al., *Nature,* 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC® 31,446); *E. coli* X1776 (ATCC® 31,537); *E. coli* strain W3110 (ATCC® 27,325) and K5 772 (ATCC® 53,635). Other suitable prokaryotic host cells include Enterobacteriaceae such as *Escherichia*, e.g., *E. coli, Enterobacter, Envinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC® 55,244), which has the complete genotype tonA ptr3 phoA E15 (argF-lac)169 degP ompT $kan^r$; *E. coli* W3110 strain 37D6, which has the complete genotype tonA ptr3 phoA E15 (argF-lac)169 degP ompT rbs7 ilvG $kan^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for PRO-encoding vectors. *Saccharomyces cerevisiae* is a commonly used lower eukaryotic host microorganism. Others include *Schizosaccharomyces pombe* (Beach and Nurse, *Nature,* 290: 140 [1981]; EP 139,383 published 2 May 1985); *Kluyveromyces* hosts (U.S. Pat. No. 4,943,529; Fleer et al., *Bio/Technology,* 9:968-975 (1991)) such as, e.g., *K. lactis* (MW98-8C, CBS683, CBS4574; Louvencourt et al., *J. Bacteriol.,* 154(2):737-742 [1983]), *K. fragilis* (ATCC® 12,424), *K. bulgaricus* (ATCC® 16,045), *K. wickeramii* (ATCC® 24,178), *K. waltii* (ATCC® 56,500), *K. drosophilarum* (ATCC® 36,906; Van den Berg et al., *Bio/Technology,* 8:135 (1990)), *K. thermotolerans*, and *K. marxianus; yarrowia* (EP 402,226); *Pichia pastoris* (EP 183,070; Sreekrishna et al., *J. Basic Microbiol.,* 28:265-278 [1988]); *Candida; Trichoderma reesia* (EP 244,234); *Neurospora crassa* (Case et al., *Proc. Natl. Acad. Sci. USA,* 76:5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.,* 112: 284-289 [1983]; Tilburn et al., *Gene,* 26:205-221 [1983]; Yelton et al., *Proc. Natl. Acad. Sci. USA,* 81: 1470-1474 [1984]) and *A. niger* (Kelly and Hynes, *EMBO J.,* 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, *The Biochemistry of Methylotrophs,* 269 (1982).

Suitable host cells for the expression of glycosylated PRO are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC® CRL 1651); human embryonic kidney line (293 or 293 cells subcloned for growth in suspension culture, Graham et al., *J. Gen Virol.,* 36:59 (1977)); Chinese hamster ovary cells/−DHFR (CHO, Urlaub and Chasin, *Proc. Natl. Acad. Sci. USA,* 77:4216 (1980)); mouse sertoli cells (TM4, Mather, *Biol. Reprod.,* 23:243-251 (1980)); human lung cells (W138, ATCC® CCL 75); human liver cells (Hep G2, HB 8065); and mouse mammary tumor (MMT 060562, ATCC® CCL51). The selection of the appropriate host cell is deemed to be within the skill in the art.

3. Selection and Use of a Replicable Vector

The nucleic acid (e.g., cDNA or genomic DNA) encoding PRO may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The PRO may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the PRO-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the PRO-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA,* 77:4216 (1980). A suitable selection gene for use in yeast is the trp1 gene present in the yeast plasmid YRp7 [Stinchcomb et al., *Nature,* 282:39 (1979); Kingsman et al., *Gene,* 7:141 (1979); Tschemper et al., *Gene,* 10:157 (1980)]. The trp1 gene provides a selection marker for a mutant strain of yeast lacking the ability to grow in tryptophan, for example, ATCC® No. 44076 or PEP4-1 [Jones, *Genetics,* 85:12 (1977)].

Expression and cloning vectors usually contain a promoter operably linked to the PRO-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature,* 275:615 (1978); Goeddel et al., *Nature,* 281:544 (1979)], alkaline phosphatase, a tryptophan (trp) promoter system [Goeddel, *Nucleic Acids Res.,* 8:4057 (1980); EP 36,776], and hybrid promoters such as the tac promoter [deBoer et al., *Proc. Natl. Acad. Sci. USA,* 80:21-25 (1983)]. Promoters for use in bacterial systems also will contain a Shine-Dalgarno (S.D.) sequence operably linked to the DNA encoding PRO.

Examples of suitable promoting sequences for use with yeast hosts include the promoters for 3-phosphoglycerate kinase [Hitzeman et al., *J. Biol. Chem.,* 255:2073 (1980)] or other glycolytic enzymes [Hess et al., *J. Adv. Enzyme Reg.,* 7:149 (1968); Holland, *Biochemistry,* 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

PRO transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the PRO by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the PRO coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding PRO.

Still other methods, vectors, and host cells suitable for adaptation to the synthesis of PRO in recombinant vertebrate cell culture are described in Gething et al., *Nature,* 293:620-625 (1981); Mantei et al., *Nature,* 281:40-46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA,* 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence PRO polypeptide or against a synthetic peptide based on the DNA sequences provided herein or against exogenous sequence fused to PRO DNA and encoding a specific antibody epitope.

5. Purification of Polypeptide

Forms of PRO may be recovered from culture medium or from host cell lysates. If membrane-bound, it can be released from the membrane using a suitable detergent solution (e.g. Triton-X 100) or by enzymatic cleavage. Cells employed in expression of PRO can be disrupted by various physical or chemical means, such as freeze-thaw cycling, sonication, mechanical disruption, or cell lysing agents.

It may be desired to purify PRO from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, SEPHADEX® G-75 (Amersham Biosciences AB Corp., Uppsala, Sweden); PROTEIN A-SEPHAROSE™ (Pharmacia Biotech AB, Uppsala, Sweden) columns to remove contaminants such as IgG; and metal chelating columns to bind epitope-tagged forms of the PRO. Various methods of protein purification may be employed and such methods are known in the art and described for example in Deutscher, *Methods in Enzymology,* 182 (1990); Scopes, *Protein Purification: Principles and Practice*, Springer-Verlag, New York (1982). The purification step(s) selected will depend, for example, on the nature of the production process used and the particular PRO produced.

E. Uses for PRO

Nucleotide sequences (or their complement) encoding PRO have various applications in the art of molecular biology, including uses as hybridization probes, in chromosome and gene mapping and in the generation of anti-sense RNA and DNA. PRO nucleic acid will also be useful for the preparation of PRO polypeptides by the recombinant techniques described herein.

The full-length native sequence PRO gene, or portions thereof, may be used as hybridization probes for a cDNA library to isolate the full-length PRO cDNA or to isolate still other cDNAs (for instance, those encoding naturally-occurring variants of PRO or PRO from other species) which have a desired sequence identity to the native PRO sequence disclosed herein. Optionally, the length of the probes will be about 20 to about 50 bases. The hybridization probes may be derived from at least partially novel regions of the full length native nucleotide sequence wherein those regions may be determined without undue experimentation or from genomic sequences including promoters, enhancer elements and introns of native sequence PRO. By way of example, a screening method will comprise isolating the coding region of the PRO gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the PRO gene of the present invention can be used to screen libraries of human cDNA, genomic DNA or mRNA to determine which members of such libraries the probe hybridizes to. Hybridization techniques are described in further detail in the Examples below.

Any EST sequences disclosed in the present application may similarly be employed as probes, using the methods disclosed herein.

Other useful fragments of the PRO nucleic acids include antisense or sense oligonucleotides comprising a singe-stranded nucleic acid sequence (either RNA or DNA) capable of binding to target PRO mRNA (sense) or PRO DNA (antisense) sequences. Antisense or sense oligonucleotides, according to the present invention, comprise a fragment of the coding region of PRO DNA. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to block expression of PRO proteins. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Antisense or sense RNA or DNA molecules are generally at least about 5 bases in length, about 10 bases in length, about 15 bases in length, about 20 bases in length, about 25 bases in length, about 30 bases in length, about 35 bases in length, about 40 bases in length, about 45 bases in length, about 50 bases in length, about 55 bases in length, about 60 bases in length, about 65 bases in length, about 70 bases in length, about 75 bases in length, about 80 bases in length, about 85 bases in length, about 90 bases in length, about 95 bases in length, about 100 bases in length, or more.

The probes may also be employed in PCR techniques to generate a pool of sequences for identification of closely related PRO coding sequences.

Nucleotide sequences encoding a PRO can also be used to construct hybridization probes for mapping the gene which encodes that PRO and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for PRO encode a protein which binds to another protein (example, where the PRO is a receptor), the PRO can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor PRO can be used to isolate correlative ligand(s). Screening assays can be designed to find lead compounds that mimic the biological activity of a native PRO or a receptor for PRO. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode PRO or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding PRO can be used to clone genomic DNA encoding PRO in accordance with established techniques and the genomic sequences used to generate transgenic animals that contain cells which express DNA encoding PRO. Methods for generating transgenic animals, particularly animals such as mice or rats, have become conventional in the art and are described, for example, in U.S. Pat. Nos. 4,736,866 and 4,870,009. Typically, particular cells would be targeted for PRO transgene incorporation with tissue-specific enhancers. Transgenic animals that include a copy of a transgene encoding PRO introduced into the germ line of the animal at an embryonic stage can be used to examine the effect of increased expression of DNA encoding PRO. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of PRO can be used to construct a PRO "knock out" animal which has a defective or altered gene encoding PRO as a result of homologous recombination between the endogenous gene encoding PRO and altered genomic DNA encoding PRO introduced into an embryonic stem cell of the animal. For example, cDNA encoding PRO can be used to clone genomic DNA encoding PRO in accordance with established techniques. A portion of the genomic DNA encoding PRO can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell,* 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell,* 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the PRO polypeptide.

Nucleic acid encoding the PRO polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83:4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429-4432 (1987); and Wagner et al., *Proc. Natl. Acad. Sci. USA* 87, 3410-3414 (1990). For review of gene marking and gene therapy protocols see Anderson et al., *Science* 256, 808-813 (1992).

The PRO polypeptides described herein may also be employed as molecular weight markers for protein electrophoresis purposes and the isolated nucleic acid sequences may be used for recombinantly expressing those markers.

The nucleic acid molecules encoding the PRO polypeptides or fragments thereof described herein are useful for chromosome identification. In this regard, there exists an ongoing need to identify new chromosome markers, since relatively few chromosome marking reagents, based upon actual sequence data are presently available. Each PRO nucleic acid molecule of the present invention can be used as a chromosome marker.

The PRO polypeptides and nucleic acid molecules of the present invention may also be used diagnostically for tissue typing, wherein the PRO polypeptides of the present invention may be differentially expressed in one tissue as compared to another, preferably in a diseased tissue as compared to a normal tissue of the same tissue type. PRO nucleic acid molecules will find use for generating probes for PCR, Northern analysis, Southern analysis and Western analysis.

The PRO polypeptides described herein may also be employed as therapeutic agents. The PRO polypeptides of the present invention can be formulated according to known methods to prepare pharmaceutically useful compositions, whereby the PRO product hereof is combined in admixture with a pharmaceutically acceptable carrier vehicle. Therapeutic formulations are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN®, PLURONICS® or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

When in vivo administration of a PRO polypeptide or agonist or antagonist thereof is employed, normal dosage amounts may vary from about 10 ng/kg to up to 100 mg/kg of mammal body weight or more per day, preferably about 1 μg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

Where sustained-release administration of a PRO polypeptide is desired in a formulation with release characteristics suitable for the treatment of any disease or disorder requiring administration of the PRO polypeptide, microencapsulation of the PRO polypeptide is contemplated. Microencapsulation of recombinant proteins for sustained release has been successfully performed with human growth hormone (rhGH), interferon-(rhIFN−), interleukin-2, and MN rgp120. Johnson et al., *Nat. Med.,* 2:795-799 (1996); Yasuda, *Biomed. Ther.,* 27:1221-1223 (1993); Hora et al., *Bio/Technology,* 8:755-758 (1990); Cleland, "Design and Production of Single Immunization Vaccines Using Polylactide Polyglycolide Microsphere Systems," in *Vaccine Design: The Subunit and Adjuvant Approach*, Powell and Newman, eds, (Plenum Press: New York, 1995), pp. 439-462; WO 97/03692, WO 96/40072, WO 96/07399; and U.S. Pat. No. 5,654,010.

The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), *Biodegradable Polymers as Drug Delivery Systems* (Marcel Dekker: New York, 1990), pp. 1-41.

This invention encompasses methods of screening compounds to identify those that mimic the PRO polypeptide (agonists) or prevent the effect of the PRO polypeptide (antagonists). Screening assays for antagonist drug candidates are designed to identify compounds that bind or complex with the PRO polypeptides encoded by the genes identified herein, or otherwise interfere with the interaction of the encoded polypeptides with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a PRO polypeptide encoded by a nucleic acid identified herein under conditions and for a time sufficient to allow these two components to interact.

In binding assays, the interaction is binding and the complex formed can be isolated or detected in the reaction mixture. In a particular embodiment, the PRO polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the PRO polypeptide and drying. Alternatively, an immobilized antibody, e.g., a monoclonal antibody, specific for the PRO polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular PRO polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature* (*London*), 340:245-246 (1989); Chien et al., *Proc. Natl. Acad. Sci. USA,* 88:9578-9582 (1991)) as disclosed by Chevray and Nathans, *Proc. Natl. Acad. Sci. USA,* 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech, Palo Alto, Calif. This system can also be extended to map protein domains involved in specific protein interactions as well as to pinpoint amino acid residues that are crucial for these interactions.

Compounds that interfere with the interaction of a gene encoding a PRO polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the PRO polypeptide may be added to a cell along with the compound to be screened for a particular activity and the ability of the compound to inhibit the activity of interest in the presence of the PRO polypeptide indicates that the compound is an antagonist to the PRO polypeptide. Alternatively, antagonists may be detected by combining the PRO polypeptide and a potential antagonist with membrane-bound PRO polypeptide receptors or recombinant receptors under appropriate conditions for a competitive inhibition assay. The PRO polypeptide can be labeled, such as by radioactivity, such that the number of PRO polypeptide molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immun.,* 1(2): Chapter 5 (1991). Preferably, expression cloning is employed wherein polyadenylated RNA is prepared from a cell responsive to the PRO polypeptide and a cDNA library created from this RNA is divided into pools and used to transfect COS cells or other cells that are not responsive to the PRO polypeptide. Transfected cells that are grown on glass slides are exposed to labeled PRO polypeptide. The PRO polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, labeled PRO polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

In another assay for antagonists, mammalian cells or a membrane preparation expressing the receptor would be incubated with labeled PRO polypeptide in the presence of the candidate compound. The ability of the compound to enhance or block this interaction could then be measured.

More specific examples of potential antagonists include an oligonucleotide that binds to the fusions of immunoglobulin with PRO polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the PRO polypeptide that recognizes the receptor but imparts no effect, thereby competitively inhibiting the action of the PRO polypeptide.

Another potential PRO polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature PRO polypeptides herein, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.,* 6:3073 (1979); Cooney et al., *Science,* 241: 456 (1988); Dervan et al., *Science,* 251:1360 (1991)), thereby preventing transcription and the production of the PRO polypeptide. The antisense RNA oligonucleotide hybridizes to the mRNA in vivo and blocks translation of the mRNA molecule into the PRO polypeptide (antisense—Okano, *Neurochem.,* 56:560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the PRO polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the PRO polypeptide, thereby blocking the normal biological activity of the PRO polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology,* 4:469-471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

Diagnostic and therapeutic uses of the herein disclosed molecules may also be based upon the positive functional assay hits disclosed and described below.

F. Anti-PRO Antibodies

The present invention further provides anti-PRO antibodies. Exemplary antibodies include polyclonal, monoclonal, humanized, bispecific, and heteroconjugate antibodies.

1. Polyclonal Antibodies

The anti-PRO antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the PRO polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-PRO antibodies may, alternatively, be monoclonal antibodies. Monoclonal antibodies may be prepared using hybridoma methods, such as those described by Kohler and Milstein, *Nature,* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the PRO polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.,* 133:3001 (1984); Brodeur et al., *Monoclonal Antibody Production Techniques and Applications*, Marcel Dekker, Inc., New York, (1987) pp. 51-63].

The culture medium in which the hybridoma cells are cultured can then be assayed for the presence of monoclonal antibodies directed against PRO. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.,* 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Human and Humanized Antibodies

The anti-PRO antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature,* 321:522-525 (1986); Riechmann et al., *Nature,* 332:323-329 (1988); and Presta, *Curr. On. Struct. Biol.,* 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature,* 321:522-525 (1986); Riechmann et al., *Nature,* 332:323-327 (1988); Verhoeyen et al., *Science,* 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.,* 227:381 (1991); Marks et al., *J. Mol. Biol.,* 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.,* 147(1):86-95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779-783 (1992); Lonberg et al., *Nature* 368 856-859 (1994); Morrison, *Nature* 368, 812-13 (1994); Fishwild et al., *Nature Biotechnology* 14, 845-51 (1996); Neuberger, *Nature Biotechnology* 14, 826 (1996); Lonberg and Huszar, *Intern. Rev. Immunol.* 13 65-93 (1995).

The antibodies may also be affinity matured using known selection and/or mutagenesis methods as described above. Preferred affinity matured antibodies have an affinity which is five times, more preferably 10 times, even more preferably 20 or 30 times greater than the starting antibody (generally murine, humanized or human) from which the matured antibody is prepared.

4. Bispecific Antibodies

Bispecific antibodies are monoclonal, preferably human or humanized, antibodies that have binding specificities for at least two different antigens. In the present case, one of the binding specificities is for the PRO, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature,* 305:537-539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.,* 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology,* 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. $F(ab')_2$ bispecific antibodies). Techniques for generating bispecific antibodies from antibody fragments have been described in the literature. For example, bispecific antibodies can be prepared can be prepared using chemical linkage. Brennan et al., *Science* 229:81 (1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175:217-225 (1992) describe the production of a fully humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various technique for making and isolating bispecific antibody fragments directly from recombinant cell culture have also been described. For example, bispecific antibodies have been produced using leucine zippers. Kostelny et al., *J. Immunol.* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., *J. Immunol.* 152:5368 (1994).

Antibodies with more than two valencies are contemplated. For example, trispecific antibodies can be prepared. Tutt et al., *J. Immunol.* 147:60 (1991).

Exemplary bispecific antibodies may bind to two different epitopes on a given PRO polypeptide herein. Alternatively, an anti-PRO polypeptide arm may be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular PRO polypeptide. Bispecific antibodies may also be used to localize cytotoxic agents to cells which express a particular PRO polypeptide. These antibodies possess a PRO-binding arm and an arm which binds a cytotoxic agent or a radionuclide chelator, such as EOTUBE, DPTA, DOTA, or TETA. Another bispecific antibody of interest binds the PRO polypeptide and further binds tissue factor (TF).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

6. Effector Function Engineering

It may be desirable to modify the antibody of the invention with respect to effector function, so as to enhance, e.g., the effectiveness of the antibody in treating cancer. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.,* 176: 1191-1195 (1992) and Shopes, *J. Immunol.,* 148: 2918-2922 (1992). Homodimeric antibodies with enhanced anti-tumor activity may also be prepared using heterobifunctional cross-linkers as described in Wolff et al. *Cancer Research,* 53: 2560-2565 (1993). Alternatively, an antibody can be engineered that has dual Fc regions and may thereby have enhanced complement lysis and ADCC capabilities. See Stevenson et al., *Anti-Cancer Drug Design,* 3: 219-230 (1989).

7. Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as his (p-azidobenzoyl) hexanediamine), bis-diazonium derivatives (such as bis-(p-diazoniumbenzoyl)-ethylenediamine), diisocyanates (such as tolyene 2,6-diisocyanate), and his-active fluorine compounds (such as 1,5-difluoro-2,4-dinitrobenzene). For example, a ricin immunotoxin can be prepared as described in Vitetta et al., *Science,* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

8. Immunolinosomes

The antibodies disclosed herein may also be formulated as immunoliposomes. Liposomes containing the antibody are prepared by methods known in the art, such as described in Epstein et al., *Proc. Natl. Acad. Sci. USA,* 82: 3688 (1985); Hwang et al., *Proc. Natl. Acad. Sci. USA,* 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.,* 257: 286-288 (1982) via a disulfide-interchange reaction. A chemotherapeutic agent (such as Doxorubicin) is optionally contained within the liposome. See Gabizon et al., *J. National Cancer Inst.,* 81(19): 1484 (1989).

9. Pharmaceutical Compositions of Antibodies

Antibodies specifically binding a PRO polypeptide identified herein, as well as other molecules identified by the screening assays disclosed hereinbefore, can be administered for the treatment of various disorders in the form of pharmaceutical compositions.

If the PRO polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA,* 90: 7889-7893 (1993). The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's *Pharmaceutical Sciences*, supra.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and $\gamma$ ethyl-L-glutamate, non-degradable ethylene-vinyl acetate, degradable lactic acid-glycolic acid copolymers such as the LUPRON DEPOT® (TAP Pharmaceuticals, Inc., North Chicago, Ill.) (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

G. Uses for Anti-Pro Antibodies

The anti-PRO antibodies of the invention have various utilities. For example, anti-PRO antibodies may be used in diagnostic assays for PRO, e.g., detecting its expression (and in some cases, differential expression) in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147-158]. The antibodies used in the diagnostic assays can be labeled with a detectable moiety. The detectable moiety should be capable of producing, either directly or indirectly, a detectable signal. For example, the detectable moiety may be a radioisotope, such as $^{3}H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature,* 144:945 (1962); David et al., *Biochemistry,* 13: 1014 (1974); Pain et al., *J. Immunol. Meth.,* 40:219 (1981); and Nygren, *J. Histochem. and Cytochem.,* 30:407 (1982).

Anti-PRO antibodies also are useful for the affinity purification of PRO from recombinant cell culture or natural sources. In this process, the antibodies against PRO are immobilized on a suitable support, such a Sephadex resin or filter paper, using methods well known in the art. The immobilized antibody then is contacted with a sample containing the PRO to be purified, and thereafter the support is washed with a suitable solvent that will remove substantially all the material in the sample except the PRO, which is bound to the immobilized antibody. Finally, the support is washed with another suitable solvent that will release the PRO from the antibody.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC® accession numbers is the American Type Culture Collection, Manassas, Va.

Example 1

Extracellular Domain Homology Screening to Identify Novel Polypeptides and cDNA Encoding Therefor The extracellular domain (ECD) sequences (including the secretion signal sequence, if any) from about 950 known secreted proteins from the Swiss-Prot public database were used to search EST databases. The EST databases included public databases (e.g., Dayhoff, GENBANK® (US Department of Health and Human Services, Bethesda, Md.), and proprietary databases (e.g. LIFESEQ®, Incyte Pharmaceuticals, Palo Alto, Calif.). The search was performed using the computer program BLAST or BLAST-2 (Altschul et al., *Methods in Enzymology,* 266:460-480 (1996)) as a comparison of the ECD protein sequences to a 6 frame translation of the EST sequences. Those comparisons with a BLAST score of 70 (or in some cases 90) or greater that did not encode known proteins were clustered and assembled into consensus DNA sequences with the program "phrap" (Phil Green, University of Washington, Seattle, Wash.).

Using this extracellular domain homology screen, consensus DNA sequences were assembled relative to the other identified EST sequences using phrap. In addition, the consensus DNA sequences obtained were often (but not always) extended using repeated cycles of BLAST or BLAST-2 and phrap to extend the consensus sequence as far as possible using the sources of EST sequences discussed above.

Based upon the consensus sequences obtained as described above, oligonucleotides were then synthesized and used to identify by PCR a cDNA library that contained the sequence of interest and for use as probes to isolate a clone of the full-length coding sequence for a PRO polypeptide. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., *Current Protocols in Molecular Biology*, with the PCR primer pair. A positive library was then used to isolate clones encoding the gene of interest using the probe oligonucleotide and one of the primer pairs.

The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science,* 253: 1278-1280 (1991)) in the unique XhoI and NotI sites.

Example 2

Isolation of cDNA Clones by Amylase Screening

1. Preparation of Oligo dT Primed cDNA Library mRNA was isolated from a human tissue of interest using reagents and protocols from Invitrogen, San Diego, Calif. (FastTrack 2™). This RNA was used to generate an oligo dT primed cDNA library in the vector pRK5D using reagents and protocols from Life Technologies, Gaithersburg, Md. (SuperScript™ Plasmid System). In this procedure, the double stranded cDNA was sized to greater than 1000 bp and the SalI/NotI linkered cDNA was cloned into XhoI/NotI cleaved vector. pRK5D is a cloning vector that has an sp6 transcription initiation site followed by an SfiI restriction enzyme site preceding the XhoI/NotI cDNA cloning sites.

2. Preparation of Random Primed cDNA Library

A secondary cDNA library was generated in order to preferentially represent the 5' ends of the primary cDNA clones. Sp6 RNA was generated from the primary library (described above), and this RNA was used to generate a random primed cDNA library in the vector pSST-AMY.0 using reagents and protocols from Life Technologies (Super Script Plasmid System, referenced above). In this procedure the double stranded cDNA was sized to 500-1000 bp, linkered with blunt to NotI adaptors, cleaved with SfiI, and cloned into SfiI/NotI cleaved vector. pSST-AMY.0 is a cloning vector that has a yeast alcohol dehydrogenase promoter preceding the cDNA cloning sites and the mouse amylase sequence (the mature sequence without the secretion signal) followed by the yeast alcohol dehydrogenase terminator, after the cloning sites. Thus, cDNAs cloned into this vector that are fused in frame with amylase sequence will lead to the secretion of amylase from appropriately transfected yeast colonies.

3. Transformation and Detection

DNA from the library described in paragraph 2 above was chilled on ice to which was added electrocompetent DH10B bacteria (Life Technologies, 20 ml). The bacteria and vector mixture was then electroporated as recommended by the manufacturer. Subsequently, SOC media (Life Technologies, 1 ml) was added and the mixture was incubated at 37° C. for 30 minutes. The transformants were then plated onto 20 standard 150 mm LB plates containing ampicillin and incubated for 16 hours (37° C.). Positive colonies were scraped off the plates and the DNA was isolated from the bacterial pellet using standard protocols, e.g. CsCl-gradient. The purified DNA was then carried on to the yeast protocols below.

The yeast methods were divided into three categories: (1) Transformation of yeast with the plasmid/cDNA combined vector; (2) Detection and isolation of yeast clones secreting amylase; and (3) PCR amplification of the insert directly from the yeast colony and purification of the DNA for sequencing and further analysis.

The yeast strain used was HD56-5A (ATCC-90785). This strain has the following genotype: MAT alpha, ura3-52, leu2-3, leu2-112, his3-11, his3-15, $MAL^+$, $SUC^+$, $GAL^+$. Preferably, yeast mutants can be employed that have deficient post-translational pathways. Such mutants may have translocation deficient alleles in sec71, sec72, sec62, with truncated sec71 being most preferred. Alternatively, antagonists (including antisense nucleotides and/or ligands) which interfere with the normal operation of these genes, other proteins implicated in this post translation pathway (e.g., SEC61p, SEC72p, SEC62p, SEC63p, TDJ1p or SSA1p-4p) or the complex formation of these proteins may also be preferably employed in combination with the amylase-expressing yeast.

Transformation was performed based on the protocol outlined by Gietz et al., *Nucl. Acid. Res.,* 20: 1425 (1992). Transformed cells were then inoculated from agar into YEPD complex media broth (100 ml) and grown overnight at 30° C. The YEPD broth was prepared as described in Kaiser et al., *Methods in Yeast Genetics*, Cold Spring Harbor Press, Cold Spring Harbor, N.Y., p. 207 (1994). The overnight culture was then diluted to about $2\times10^6$ cells/ml (approx. $OD_{600}$=0.1) into fresh YEPD broth (500 ml) and regrown to $1\times10^7$ cells/ml (approx. $OD_{600}$=0.4-0.5).

The cells were then harvested and prepared for transformation by transfer into GS3 rotor bottles in a Sorval GS3 rotor at 5,000 rpm for 5 minutes, the supernatant discarded, and then resuspended into sterile water, and centrifuged again in 50 ml falcon tubes at 3,500 rpm in a Beckman GS-6KR centrifuge. The supernatant was discarded and the cells were subsequently washed with LiAc/TE (10 ml, 10 mM Tris-HCl, 1 mM EDTA pH 7.5, 100 mM $Li_2OOCCH_3$), and resuspended into LiAc/TE (2.5 ml).

Transformation took place by mixing the prepared cells (100 μl) with freshly denatured single stranded salmon testes DNA (Lofstrand Labs, Gaithersburg, Md.) and transforming DNA (1 μg, vol. <10 μl) in microfuge tubes. The mixture was mixed briefly by vortexing, then 40% PEG/TE (600 μl, 40% polyethylene glycol-4000, 10 mM Tris-HCl, 1 mM EDTA, 100 mM $Li_2OOCCH_3$, pH 7.5) was added. This mixture was gently mixed and incubated at 30° C. while agitating for 30 minutes. The cells were then heat shocked at 42° C. for 15 minutes, and the reaction vessel centrifuged in a microfuge at 12,000 rpm for 5-10 seconds, decanted and resuspended into TE (500 μl, 10 mM Tris-HCl, 1 mM EDTA pH 7.5) followed by recentrifugation. The cells were then diluted into TE (1 ml) and aliquots (200 μl) were spread onto the selective media previously prepared in 150 mm growth plates (VWR).

Alternatively, instead of multiple small reactions, the transformation was performed using a single, large scale reaction, wherein reagent amounts were scaled up accordingly.

The selective media used was a synthetic complete dextrose agar lacking uracil (SCD-Ura) prepared as described in Kaiser et al., *Methods in Yeast Genetics*, Cold Spring Harbor Press, Cold Spring Harbor, N.Y., p. 208-210 (1994). Transformants were grown at 30° C. for 2-3 days.

The detection of colonies secreting amylase was performed by including red starch in the selective growth media. Starch was coupled to the red dye (Reactive Red-120, Sigma) as per the procedure described by Biely et al., *Anal. Biochem.,* 172: 176-179 (1988). The coupled starch was incorporated into the SCD-Ura agar plates at a final concentration of 0.15% (w/v), and was buffered with potassium phosphate to a pH of 7.0 (50-100 mM final concentration).

The positive colonies were picked and streaked across fresh selective media (onto 150 mm plates) in order to obtain well isolated and identifiable single colonies. Well isolated single colonies positive for amylase secretion were detected by direct incorporation of red starch into buffered SCD-Ura agar. Positive colonies were determined by their ability to break down starch resulting in a clear halo around the positive colony visualized directly.

4. Isolation of DNA by PCR Amplification

When a positive colony was isolated, a portion of it was picked by a toothpick and diluted into sterile water (30 μl) in a 96 well plate. At this time, the positive colonies were either frozen and stored for subsequent analysis or immediately amplified. An aliquot of cells (5 μl) was used as a template for the PCR reaction in a 25 μl volume containing: 0.5 μl KLENTAQ® (Clontech, Palo Alto, Calif.); 4.0 μl 10 mM dNTP's (Perkin Elmer-Cetus); 2.5 μl KLENTAQ® buffer (Clontech); 0.25 μl forward oligo 1; 0.25 μl reverse oligo 2; 12.5 μl distilled water. The sequence of the forward oligonucleotide 1 was:

(SEQ ID NO: 245)
5'-TGTAAAACGACGGCCAGTTAAATAGACCTGCAATTATTAATCT-3'

The sequence of reverse oligonucleotide 2 was:

(SEQ ID NO: 246)
5'-CAGGAAACAGCTATGACCACCTGCACACCTGCAAATCCATT-3'

PCR was then performed as follows:

| | | | | |
|---|---|---|---|---|
| a. | | Denature | 92° C., | 5 minutes |
| b. | 3 cycles of: | Denature | 92° C., | 30 seconds |
| | | Anneal | 59° C., | 30 seconds |
| | | Extend | 72° C., | 60 seconds |
| c. | 3 cycles of: | Denature | 92° C., | 30 seconds |
| | | Anneal | 57° C., | 30 seconds |
| | | Extend | 72° C., | 60 seconds |
| d. | 25 cycles of: | Denature | 92° C., | 30 seconds |
| | | Anneal | 55° C., | 30 seconds |
| | | Extend | 72° C., | 60 seconds |
| e. | Hold | | 4° C. | |

The underlined regions of the oligonucleotides annealed to the ADH promoter region and the amylase region, respectively, and amplified a 307 bp region from vector pSST-AMY.0 when no insert was present. Typically, the first 18 nucleotides of the 5' end of these oligonucleotides contained annealing sites for the sequencing primers. Thus, the total product of the PCR reaction from an empty vector was 343 bp. However, signal sequence-fused cDNA resulted in considerably longer nucleotide sequences.

Following the PCR, an aliquot of the reaction (5 μl) was examined by agarose gel electrophoresis in a 1% agarose gel using a Tris-Borate-EDTA (TBE) buffering system as described by Sambrook et al., supra. Clones resulting in a single strong PCR product larger than 400 bp were further analyzed by DNA sequencing after purification with a 96 QIAQUICK® PCR clean-up column (Qiagen Inc., Chatsworth, Calif.).

Example 3

Isolation of cDNA Clones Using Signal Algorithm Analysis

Various polypeptide-encoding nucleic acid sequences were identified by applying a proprietary signal sequence finding algorithm developed by Genentech, Inc. (South San Francisco, Calif.) upon ESTs as well as clustered and assembled EST fragments from public (e.g., GENBANK® (US Department of Health and Human Services, Bethesda, Md.) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals. Use of this algorithm resulted in the identification of numerous polypeptide-encoding nucleic acid sequences.

Example 4

Isolation of cDNA clones Encoding Human PRO Polypeptides

Using the techniques described in Examples 1 to 3 above, numerous full-length cDNA clones were identified as encoding PRO polypeptides as disclosed herein. These cDNAs were then deposited under the terms of the Budapest Treaty with the American Type Culture Collection, 10801 University Blvd., Manassas, Va. 20110-2209, USA (ATCC®) as shown in Table 7 below.

TABLE 7

| Material | ATCC Dep. No. | Deposit Date |
|---|---|---|
| DNA94849-2960 | PTA-2306 | Jul. 25, 2000 |
| DNA96883-2745 | PTA-544 | Aug. 17, 1999 |
| DNA96894-2675 | PTA-260 | Jun. 22, 1999 |
| DNA100272-2969 | PTA-2299 | Jul. 25, 2000 |
| DNA108696-2966 | PTA-2315 | Aug. 1, 2000 |
| DNA117935-2801 | PTA-1088 | Dec. 22, 1999 |
| DNA119474-2803 | PTA-1097 | Dec. 22, 1999 |
| DNA119498-2965 | PTA-2298 | Jul. 25, 2000 |
| DNA119502-2789 | PTA-1082 | Dec. 22, 1999 |
| DNA119516-2797 | PTA-1083 | Dec. 22, 1999 |
| DNA119530-2968 | PTA-2396 | Aug. 8, 2000 |
| DNA121772-2741 | PTA-1030 | Dec. 7, 1999 |
| DNA125148-2782 | PTA-955 | Nov. 16, 1999 |
| DNA125150-2793 | PTA-1085 | Dec. 22, 1999 |
| DNA125151-2784 | PTA-1029 | Dec. 7, 1999 |
| DNA125181-2804 | PTA-1096 | Dec. 22, 1999 |
| DNA125192-2794 | PTA-1086 | Dec. 22, 1999 |
| DNA125196-2792 | PTA-1091 | Dec. 22, 1999 |
| DNA125200-2810 | PTA-1186 | Jan. 11, 2000 |
| DNA125214-2814 | PTA-1270 | Feb. 2, 2000 |
| DNA125219-2799 | PTA-1084 | Dec. 22, 1999 |
| DNA128309-2825 | PTA-1340 | Feb. 8, 2000 |
| DNA129535-2796 | PTA-1087 | Dec. 22, 1999 |
| DNA129549-2798 | PTA-1099 | Dec. 22, 1999 |
| DNA129580-2863 | PTA-1584 | Mar. 28, 2000 |
| DNA129794-2967 | PTA-2305 | Jul. 25, 2000 |
| DNA131590-2962 | PTA-2297 | Jul. 25, 2000 |
| DNA135173-2811 | PTA-1184 | Jan. 11, 2000 |
| DNA138039-2828 | PTA-1343 | Feb. 8, 2000 |
| DNA139540-2807 | PTA-1187 | Jan. 11, 2000 |
| DNA139602-2859 | PTA-1588 | Mar. 28, 2000 |
| DNA139632-2880 | PTA-1629 | Apr. 4, 2000 |
| DNA139686-2823 | PTA-1264 | Feb. 2, 2000 |
| DNA142392-2800 | PTA-1092 | Dec. 22, 1999 |
| DNA143076-2787 | PTA-1028 | Dec. 7, 1999 |
| DNA143294-2818 | PTA-1182 | Jan. 11, 2000 |
| DNA143514-2817 | PTA-1266 | Feb. 2, 2000 |
| DNA144841-2816 | PTA-1188 | Jan. 11, 2000 |
| DNA148380-2827 | PTA-1181 | Jan. 11, 2000 |
| DNA149995-2871 | PTA-1971 | May 31, 2000 |
| DNA167678-2963 | PTA-2302 | Jul. 25, 2000 |
| DNA168028-2956 | PTA-2304 | Jul. 25, 2000 |
| DNA173894-2947 | PTA-2108 | Jun. 20, 2000 |
| DNA176775-2957 | PTA-2303 | Jul. 25, 2000 |
| DNA177313-2982 | PTA-2251 | Jul. 19, 2000 |
| DNA57700-1408 | 203583 | Jan. 12, 1999 |
| DNA62872-1509 | 203100 | Aug. 4, 1998 |
| DNA62876-1517 | 203095 | Aug. 4, 1998 |
| DNA66660-1585 | 203279 | Sep. 22, 1998 |
| DNA34434-1139 | 209252 | Sep. 16, 1997 |

TABLE 7-continued

| Material | ATCC Dep. No. | Deposit Date |
|---|---|---|
| DNA44804-1248 | 209527 | Dec. 10, 1997 |
| DNA52758-1399 | 209773 | Apr. 14, 1998 |
| DNA59849-1504 | 209986 | Jun. 16, 1998 |
| DNA65410-1569 | 203231 | Sep. 15, 1998 |
| DNA71290-1630 | 203275 | Sep. 22, 1998 |
| DNA33100-1159 | 209377 | Oct. 16, 1997 |
| DNA64896-1539 | 203238 | Sep. 9, 1998 |
| DNA84920-2614 | 203966 | Apr. 27, 1999 |
| DNA23330-1390 | 209775 | Apr. 14, 1998 |
| DNA32286-1191 | 209385 | Oct. 16, 1997 |
| DNA35673-1201 | 209418 | Oct. 28, 1997 |
| DNA43316-1237 | 209487 | Nov. 21, 1997 |
| DNA44184-1319 | 209704 | Mar. 26, 1998 |
| DNA45419-1252 | 209616 | Feb. 5, 1998 |
| DNA48314-1320 | 209702 | Mar. 26, 1998 |
| DNA50921-1458 | 209859 | May 12, 1998 |
| DNA53987 | 209858 | May 12, 1998 |
| DNA56047-1456 | 209948 | Jun. 9, 1998 |
| DNA56405-1357 | 209849 | May 6, 1998 |
| DNA56531-1648 | 203286 | Sep. 29, 1998 |
| DNA56865-1491 | 203022 | Jun. 23, 1998 |
| DNA57694-1341 | 203017 | Jun. 23, 1998 |
| DNA57708-1411 | 203021 | Jun. 23, 1998 |
| DNA57836-1338 | 203025 | Jun. 23, 1998 |
| DNA57841-1522 | 203458 | Nov. 3, 1998 |
| DNA58847-1383 | 209879 | May 20, 1998 |
| DNA59212-1627 | 203245 | Sep. 9, 1998 |
| DNA59588-1571 | 203106 | Aug. 11, 1998 |
| DNA59622-1334 | 209984 | Jun. 16, 1998 |
| DNA59847-2510 | 203576 | Jan. 12, 1999 |
| DNA60615-1483 | 209980 | Jun. 16, 1998 |
| DNA60621-1516 | 203091 | Aug. 4, 1998 |
| DNA62814-1521 | 203093 | Aug. 4, 1998 |
| DNA64883-1526 | 203253 | Sep. 9, 1998 |
| DNA64889-1541 | 203250 | Sep. 9, 1998 |
| DNA64897-1628 | 203216 | Sep. 15, 1998 |
| DNA64903-1553 | 203223 | Sep. 15, 1998 |
| DNA64907-1163-1 | 203242 | Sep. 9, 1998 |
| DNA64950-1590 | 203224 | Sep. 15, 1998 |
| DNA64952-1568 | 203222 | Sep. 15, 1998 |
| DNA65402-1540 | 203252 | Sep. 9, 1998 |
| DNA65405-1547 | 203476 | Nov. 17, 1998 |
| DNA66663-1598 | 203268 | Sep. 22, 1998 |
| DNA66667 | 203267 | Sep. 22, 1998 |
| DNA66675-1587 | 203282 | Sep. 22, 1998 |
| DNA67300-1605 | 203163 | Aug. 25, 1998 |
| DNA68872-1620 | 203160 | Aug. 25, 1998 |
| DNA71269-1621 | 203284 | Sep. 22, 1998 |
| DNA73736-1657 | 203466 | Nov. 17, 1998 |
| DNA73739-1645 | 203270 | Sep. 22, 1998 |
| DNA76400-2528 | 203573 | Jan. 12, 1999 |
| DNA76532-1702 | 203473 | Nov. 17, 1998 |
| DNA76541-1675 | 203409 | Oct. 27, 1998 |
| DNA79862-2522 | 203550 | Dec. 22, 1998 |
| DNA81754-2532 | 203542 | Dec. 15, 1998 |
| DNA81761-2583 | 203862 | Mar. 23, 1999 |
| DNA83500-2506 | 203391 | Oct. 29, 1998 |
| DNA84210-2576 | 203818 | Mar. 2, 1999 |
| DNA86571-2551 | 203660 | Feb. 9, 1999 |
| DNA92218-2554 | 203834 | Mar. 9, 1999 |
| DNA92223-2567 | 203851 | Mar. 16, 1999 |
| DNA92265-2669 | PTA-256 | Jun. 22, 1999 |
| DNA92274-2617 | 203971 | Apr. 27, 1999 |
| DNA108760-2740 | PTA-548 | Aug. 17, 1999 |
| DNA108792-2753 | PTA-617 | Aug. 31, 1999 |
| DNA111750-2706 | PTA-489 | Aug. 3, 1999 |
| DNA119514-2772 | PTA-946 | Nov. 9, 1999 |
| DNA125185-2806 | PTA-1031 | Dec. 7, 1999 |

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit and for at least five (5) years after the most recent request for the furnishing of a sample of the deposit received by the depository. The deposits will be made available by ATCC® under the terms of the Budapest Treaty, and subject to an agreement between Genentech, Inc. and ATCC®, which assures that all restrictions imposed by the depositor on the availability to the public of the deposited material will be irrevocably removed upon the granting of the pertinent U.S. patent, assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

Example 5

Isolation of cDNA clones Encoding Human PRO6004, PRO5723, PRO3444, and PRO9940

DNA molecules encoding the PRO840, PRO1338, PRO6004, PRO5723, PRO3444, and PRO9940 polypeptides shown in the accompanying figures were obtained through GenBank.

Example 6

Use of Pro as a Hybridization Probe

The following method describes use of a nucleotide sequence encoding PRO as a hybridization probe.

DNA comprising the coding sequence of full-length or mature PRO as disclosed herein is employed as a probe to screen for homologous DNAs (such as those encoding naturally-occurring variants of PRO) in human tissue cDNA libraries or human tissue genomic libraries.

Hybridization and washing of filters containing either library DNAs is performed under the following high stringency conditions. Hybridization of radiolabeled PRO-derived probe to the filters is performed in a solution of 50% formamide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence PRO can then be identified using standard techniques known in the art.

Example 7

Expression of PRO in *E. coli*

This example illustrates preparation of an unglycosylated form of PRO by recombinant expression in *E. coli.*

The DNA sequence encoding PRO is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., *Gene,* 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the PRO coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized PRO protein can then be purified using a metal chelating column under conditions that allow tight binding of the protein.

PRO may be expressed in *E. coli* in a poly-His tagged form, using the following procedure. The DNA encoding PRO is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an *E. coli* host based on strain 52 (W3110 fuhA(tonA) lon galE rpoHts(htpRts) clpP(lacIq). Transformants are first grown in LB containing 50 mg/ml carbenicillin at 30° C. with shaking until an O.D.600 of 3-5 is reached. Cultures are then diluted 50-100 fold into CRAP media (prepared by mixing 3.57 g $(NH_4)_2SO_4$, 0.71 g sodium citrate.2H2O, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20-30 hours at 30° C. with shaking. Samples are removed to verify expression by SDS-PAGE analysis, and the bulk culture is centrifuged to pellet the cells. Cell pellets are frozen until purification and refolding.

*E. coli* paste from 0.5 to 1 L fermentations (6-10 g pellets) is resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution is stirred overnight at 4° C. This step results in a denatured protein with all cysteine residues blocked by sulfitolization. The solution is centrifuged at 40,000 rpm in a Beckman Ultracentifuge for 30 min. The supernatant is diluted with 3-5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C.

Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12-36 hours. The refolding reaction is quenched by the addition of TFA to a final concentration of 0.4% (pH of approximately 3). Before further purification of the protein, the solution is filtered through a 0.22 micron filter and acetonitrile is added to 2-10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded PRO polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 SUPERFINE™ (Pharmacia) resins equilibrated in the formulation buffer and sterile filtered.

Many of the PRO polypeptides disclosed herein were successfully expressed as described above.

Example 8

Expression of PRO in Mammalian Cells

This example illustrates preparation of a potentially glycosylated form of PRO by recombinant expression in mammalian cells.

The vector, pRK5 (see EP 307,247, published Mar. 15, 1989), is employed as the expression vector. Optionally, the PRO DNA is ligated into pRK5 with selected restriction enzymes to allow insertion of the PRO DNA using ligation methods such as described in Sambrook et al., supra. The resulting vector is called pRK5-PRO.

In one embodiment, the selected host cells may be 293 cells. Human 293 cells (ATCC® CCL 1573) are grown to confluence in tissue culture plates in medium such as DMEM supplemented with fetal calf serum and optionally, nutrient components and/or antibiotics. About 10 μg pRK5-PRO DNA is mixed with about 1 μg DNA encoding the VA RNA gene [Thimmappaya et al., *Cell,* 31:543 (1982)] and dissolved in 500 μl of 1 mM Tris-HCl, 0.1 mM EDTA, 0.227 M $CaCl_2$. To this mixture is added, dropwise, 500 μl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of PRO polypeptide. The cultures containing transfected cells may undergo further incubation (in serum free medium) and the medium is tested in selected bioassays.

In an alternative technique, PRO may be introduced into 293 cells transiently using the dextran sulfate method described by Somparyrac et al., *Proc. Natl. Acad. Sci.,* 12:7575 (1981). 293 cells are grown to maximal density in a spinner flask and 700 μg pRK5-PRO DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed PRO can then be concentrated and purified by any selected method, such as dialysis and/or column chromatography.

In another embodiment, PRO can be expressed in CHO cells. The pRK5-PRO can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of PRO polypeptide, the culture medium may be replaced with serum free medium. Preferably, the cultures are incubated for about 6 days, and then the conditioned medium is harvested. The medium containing the expressed PRO can then be concentrated and purified by any selected method.

Epitope-tagged PRO may also be expressed in host CHO cells. The PRO may be subcloned out of the pRK5 vector. The subclone insert can undergo PCR to fuse in frame with a selected epitope tag such as a poly-his tag into a Baculovirus expression vector. The poly-his tagged PRO insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged PRO can then be concentrated and purified by any selected method, such as by $Ni^{2+}$-chelate affinity chromatography.

PRO may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., *Nucl. Acids Res.* 24:9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available SUPERFECT® (Qiagen), DOSPER™ (Roche Applied Science, Indianapolis, Ind.) or FUGENE® (Boehringer Mannheim) transfection reagents. The cells are grown as described in Lucas et al., supra. Approximately $3\times10^7$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 μm filtered PS20 with 5% 0.2 μm diafiltered fetal bovine serum). The cells are then aliquoted into a 100 mL spinner containing 90 mL of selective media. After 1-2 days, the cells are transferred into a 250 mL spinner filled with 150 mL selective growth medium and incubated at 37° C. After another 2-3 days, 250 mL, 500 mL and 2000 mL spinners are seeded with $3\times10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3 L production spinner is seeded at $1.2\times10^6$ cells/mL. On day 0, the cell number pH ie determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 μm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 μL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Many of the PRO polypeptides disclosed herein were successfully expressed as described above.

Example 9

Expression of PRO in Yeast

The following method describes recombinant expression of PRO in yeast.

First, yeast expression vectors are constructed for intracellular production or secretion of PRO from the ADH2/GAPDH promoter. DNA encoding PRO and the promoter is inserted into suitable restriction enzyme sites in the selected plasmid to direct intracellular expression of PRO. For secretion, DNA encoding PRO can be cloned into the selected plasmid, together with DNA encoding the ADH2/GAPDH promoter, a native PRO signal peptide or other mammalian signal peptide, or, for example, a yeast alpha-factor or invertase secretory signal/leader sequence, and linker sequences (if needed) for expression of PRO.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant PRO can subsequently be isolated and purified by removing the yeast cells from the fermentation medium by centrifugation and then concentrating the medium using selected cartridge filters. The concentrate containing PRO may further be purified using selected column chromatography resins.

Many of the PRO polypeptides disclosed herein were successfully expressed as described above.

Example 10

Expression of PRO in Baculovirus-Infected Insect Cells

The following method describes recombinant expression of PRO in Baculovirus-infected insect cells.

The sequence coding for PRO is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding PRO or the desired portion of the coding sequence of PRO such as the sequence encoding the extracellular domain of a transmembrane protein or the sequence encoding the mature protein if the protein is extracellular is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BACULOGOLD™ virus DNA (Pharmingen Corp., San Diego, Calif.) into *Spodoptera frugiperda* ("Sf9") cells (ATCC® CRL 1711) using lipofectin (commercially available from GIBCO-BRL). After 4-5 days of incubation at 28° C., the released viruses are harvested and used for further amplifications. Viral infection and protein expression are performed as described by O'Reilley et al., *Baculovirus expression vectors: A Laboratory Manual*, Oxford: Oxford University Press (1994).

Expressed poly-his tagged PRO can then be purified, for example, by $Ni^{2+}$-chelate affinity chromatography as follows. Extracts are prepared from recombinant virus-infected Sf9 cells as described by Rupert et al., *Nature,* 362: 175-179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 μm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged PRO are pooled and dialyzed against loading buffer.

Alternatively, purification of the IgG tagged (or Fc tagged) PRO can be performed using known chromatography techniques, including for instance, Protein A or protein G column chromatography.

Many of the PRO polypeptides disclosed herein were successfully expressed as described above.

Example 11

Preparation of Antibodies that Bind Pro

This example illustrates preparation of monoclonal antibodies which can specifically bind PRO.

Techniques for producing the monoclonal antibodies are known in the art and are described, for instance, in Goding, supra. Immunogens that may be employed include purified PRO, fusion proteins containing PRO, and cells expressing recombinant PRO on the cell surface. Selection of the immunogen can be made by the skilled artisan without undue experimentation.

Mice, such as Balb/c, are immunized with the PRO immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-PRO antibodies.

After a suitable antibody titer has been detected, the animals "positive" for antibodies can be injected with a final intravenous injection of PRO. Three to four days later, the mice are sacrificed and the spleen cells are harvested. The spleen cells are then fused (using 35% polyethylene glycol) to a selected murine myeloma cell line such as P3X63AgU.1, available from ATCC®, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against PRO. Determination of "positive" hybridoma cells secreting the desired monoclonal antibodies against PRO is within the skill in the art.

The positive hybridoma cells can be injected intraperitoneally into syngeneic Balb/c mice to produce ascites containing the anti-PRO monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 12

Purification of PRO Polypeptides Using Specific Antibodies

Native or recombinant PRO polypeptides may be purified by a variety of standard techniques in the art of protein purification. For example, pro-PRO polypeptide, mature PRO polypeptide, or pre-PRO polypeptide is purified by immunoaffinity chromatography using antibodies specific for the PRO polypeptide of interest. In general, an immunoaffinity column is constructed by covalently coupling the anti-PRO polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of PRO polypeptide by preparing a fraction from cells containing PRO polypeptide in a soluble form. This preparation is derived by solubilization of the whole cell or of a subcellular fraction obtained via differential centrifugation by the addition of detergent or by other methods well known in the art. Alternatively, soluble PRO polypeptide containing a signal sequence may be secreted in useful quantity into the medium in which the cells are grown.

A soluble PRO polypeptide-containing preparation is passed over the immunoaffinity column, and the column is washed under conditions that allow the preferential absorbance of PRO polypeptide (e.g., high ionic strength buffers in the presence of detergent). Then, the column is eluted under conditions that disrupt antibody/PRO polypeptide binding (e.g., a low pH buffer such as approximately pH 2-3, or a high concentration of a chaotrope such as urea or thiocyanate ion), and PRO polypeptide is collected.

Example 13

Drug Screening

This invention is particularly useful for screening compounds by using PRO polypeptides or binding fragment thereof in any of a variety of drug screening techniques. The PRO polypeptide or fragment employed in such a test may either be free in solution, affixed to a solid support, borne on a cell surface, or located intracellularly. One method of drug screening utilizes eukaryotic or prokaryotic host cells which are stably transformed with recombinant nucleic acids expressing the PRO polypeptide or fragment. Drugs are screened against such transformed cells in competitive binding assays. Such cells, either in viable or fixed form, can be used for standard binding assays. One may measure, for example, the formation of complexes between PRO polypeptide or a fragment and the agent being tested. Alternatively, one can examine the diminution in complex formation between the PRO polypeptide and its target cell or target receptors caused by the agent being tested.

Thus, the present invention provides methods of screening for drugs or any other agents which can affect a PRO polypeptide-associated disease or disorder. These methods comprise contacting such an agent with an PRO polypeptide or fragment thereof and assaying (I) for the presence of a complex between the agent and the PRO polypeptide or fragment, or (ii) for the presence of a complex between the PRO polypeptide or fragment and the cell, by methods well known in the art. In such competitive binding assays, the PRO polypeptide or fragment is typically labeled. After suitable incubation, free PRO polypeptide or fragment is separated from that present in bound form, and the amount of free or uncomplexed label is a measure of the ability of the particular agent to bind to PRO polypeptide or to interfere with the PRO polypeptide/cell complex.

Another technique for drug screening provides high throughput screening for compounds having suitable binding affinity to a polypeptide and is described in detail in WO 84/03564, published on Sep. 13, 1984. Briefly stated, large numbers of different small peptide test compounds are synthesized on a solid substrate, such as plastic pins or some other surface. As applied to a PRO polypeptide, the peptide test compounds are reacted with PRO polypeptide and washed. Bound PRO polypeptide is detected by methods well known in the art. Purified PRO polypeptide can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding PRO polypeptide specifically compete with a test compound for binding to PRO polypeptide or fragments thereof. In this manner, the antibodies can be used to detect the presence of any peptide which shares one or more antigenic determinants with PRO polypeptide.

Example 14

Rational Drug Design

The goal of rational drug design is to produce structural analogs of biologically active polypeptide of interest (i.e., a PRO polypeptide) or of small molecules with which they interact, e.g., agonists, antagonists, or inhibitors. Any of these examples can be used to fashion drugs which are more active or stable forms of the PRO polypeptide or which enhance or interfere with the function of the PRO polypeptide in vivo (cf., Hodgson, *Bio/Technology,* 2: 19-21 (1991)).

In one approach, the three-dimensional structure of the PRO polypeptide, or of an PRO polypeptide-inhibitor complex, is determined by x-ray crystallography, by computer modeling or, most typically, by a combination of the two approaches. Both the shape and charges of the PRO polypeptide must be ascertained to elucidate the structure and to determine active site(s) of the molecule. Less often, useful information regarding the structure of the PRO polypeptide may be gained by modeling based on the structure of homologous proteins. In both cases, relevant structural information is used to design analogous PRO polypeptide-like molecules or to identify efficient inhibitors. Useful examples of rational drug design may include molecules which have improved activity or stability as shown by Braxton and Wells, *Biochemistry,* 31:7796-7801 (1992) or which act as inhibitors, agonists, or antagonists of native peptides as shown by Athauda et al., *J. Biochem.,* 113:742-746 (1993).

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amounts of the PRO polypeptide may be made available to perform such analytical studies as X-ray crystallography. In addition, knowledge of the PRO polypeptide amino acid sequence provided herein will provide guidance to those employing computer modeling techniques in place of or in addition to x-ray crystallography.

Example 15

Pericyte c-Fos Induction (Assay 93)

This assay shows that certain polypeptides of the invention act to induce the expression of c-fos in pericyte cells and, therefore, are useful not only as diagnostic markers for particular types of pericyte-associated tumors but also for giving rise to antagonists which would be expected to be useful for the therapeutic treatment of pericyte-associated tumors. Induction of c-fos expression in pericytes is also indicative of the induction of angiogenesis and, as such, PRO polypeptides capable of inducing the expression of c-fos would be expected to be useful for the treatment of conditions where induced angiogenesis would be beneficial including, for example, wound healing, and the like. Specifically, on day 1, pericytes are received from VEC Technologies and all but 5 ml of media is removed from flask. On day 2, the pericytes are trypsinized, washed, spun and then plated onto 96 well plates. On day 7, the media is removed and the pericytes are treated with 100 μl of PRO polypeptide test samples and controls (positive control=DME+5% serum+/−PDGF at 500 ng/ml; negative control=protein 32). Replicates are averaged and SD/CV are determined. Fold increase over Protein 32 (buffer control) value indicated by chemiluminescence units (RLU) luminometer reading verses frequency is plotted on a histogram. Two-fold above Protein 32 value is considered positive for the assay. ASY Matrix: Growth media=low glucose DMEM=20% FBS+1× pen strep+1× fungizone. Assay Media=low glucose DMEM+5% FBS.

The following polypeptides tested positive in this assay: PRO982, PRO1160, PRO1187, and PRO1329.

Example 16

Chondrocyte Re-Differentiation Assay (Assay 110)

This assay shows that certain polypeptides of the invention act to induce redifferentiation of chondrocytes, therefore, are expected to be useful for the treatment of various bone and/or cartilage disorders such as, for example, sports injuries and arthritis. The assay is performed as follows. Porcine chondrocytes are isolated by overnight collagenase digestion of articulary cartilage of metacarpophalangeal joints of 4-6 month old female pigs. The isolated cells are then seeded at 25,000 cells/cm$^2$ in Ham F-12 containing 10% FBS and 4 μg/ml gentamycin. The culture media is changed every third day and the cells are then seeded in 96 well plates at 5,000 cells/well in 100 μl of the same media without serum and 100 μl of the test PRO polypeptide, 5 nM staurosporin (positive control) or medium alone (negative control) is added to give a final volume of 200 μl/well. After 5 days of incubation at 37° C., a picture of each well is taken and the differentiation state of the chondrocytes is determined. A positive result in the assay occurs when the redifferentiation of the chondrocytes is determined to be more similar to the positive control than the negative control.

The following polypeptide tested positive in this assay: PRO357.

Example 17

Identification of Pro Polypeptides that Stimulate TNF-α Release in Human Blood (Assay 128)

This assay shows that certain PRO polypeptides of the present invention act to stimulate the release of TNF-α in human blood. PRO polypeptides testing positive in this assay are useful for, among other things, research purposes where stimulation of the release of TNF-α would be desired and for the therapeutic treatment of conditions wherein enhanced TNF-α release would be beneficial. Specifically, 200 μl of human blood supplemented with 50 mM Hepes buffer (pH 7.2) is aliquoted per well in a 96 well test plate. To each well is then added 300 μl of either the test PRO polypeptide in 50 mM Hepes buffer (at various concentrations) or 50 mM Hepes buffer alone (negative control) and the plates are incubated at 37° C. for 6 hours. The samples are then centrifuged and 50 μl of plasma is collected from each well and tested for the presence of TNF-α by ELISA assay. A positive in the assay is a higher amount of TNF-α in the PRO polypeptide treated samples as compared to the negative control samples.

The following PRO polypeptides tested positive in this assay: PRO231, PRO357, PRO725, PRO1155, PRO1306, and PRO1419.

Example 18

Promotion of Chondrocyte Redifferentiation (Assay 129)

This assay is designed to determine whether PRO polypeptides of the present invention show the ability to induce the proliferation and/or redifferentiation of chondrocytes in culture. PRO polypeptides testing positive in this assay would be expected to be useful for the therapeutic treatment of various bone and/or cartilage disorders such as, for example, sports injuries and arthritis.

Porcine chondrocytes are isolated by overnight collagenase digestion of articular cartilage of the metacarpophalangeal joint of 4-6 month old female pigs. The isolated cells are then seeded at 25,000 cells/cm$^2$ in Ham F-12 containing 10% FBS and 4 μg/ml gentamycin. The culture media is changed every third day. On day 12, the cells are seeded in 96 well plates at 5,000 cells/well in 100 μl of the same media without serum and 100 μl of either serum-free medium (negative control), staurosporin (final concentration of 5 nM; positive control) or the test PRO polypeptide are added to give a final volume of 200 μl/well. After 5 days at 37° C., 22 μl of media containing 100 μg/ml Hoechst 33342 and 50 μg/ml 5-CFDA is added to each well and incubated for an additional 10 minutes at 37° C. A picture of the green fluorescence is taken for each well and the differentiation state of the chondrocytes is calculated by morphometric analysis. A positive result in the assay is obtained when the >50% of the PRO polypeptide treated cells are differentiated (compared to the background obtained by the negative control).

The following PRO polypeptides tested positive in this assay: PRO229, PRO1272, and PRO4405.

Example 19

Normal Human Dermal Fibroblast Proliferation (Assay 141)

This assay is designed to determine whether PRO polypeptides of the present invention show the ability to induce proliferation of human dermal fibroblast cells in culture and, therefore, function as useful growth factors.

On day 0, human dermal fibroblast cells (from cell lines, maximum of 12-14 passages) were plated in 96-well plates at 1000 cells/well per 100 microliter and incubated overnight in complete media [fibroblast growth media (FGM, Clonetics), plus supplements: insulin, human epithelial growth factor (hEGF), gentamicin (GA-1000), and fetal bovine serum (FBS, Clonetics)]. On day 1, complete media was replaced by basal media [FGM plus 1% FBS] and addition of PRO polypeptides at 1%, 0.1% and 0.01%. On day 7, an assessment of cell proliferation was performed by Alamar Blue assay followed by Crystal Violet. Results are expressed as % of the cell growth observed with control buffer.

The following PRO polypeptides stimulated normal human dermal fibroblast proliferation in this assay: PRO982, PRO357, PRO725, PRO1306, PRO1419, PRO214, PRO247, PRO337, PRO526, PRO363, PRO531, PRO1083, PRO840, PRO1080, PRO1478, PRO1134, PRO826, PRO1005, PRO809, PRO1071, PRO1411, PRO1309, PRO1025, PRO1181, PRO1126, PRO1186, PRO1192, PRO1244, PRO1274, PRO1412, PRO1286, PRO1330, PRO1347, PRO1305, PRO1273, PRO1279, PRO1340, PRO1338, PRO1343, PRO1376, PRO1387, PRO1409, PRO1474, PRO1917, PRO1760, PRO1567, PRO1887, PRO1928, PRO4341, PRO1801, PRO4333, PRO3543, PRO3444, PRO4322, PRO9940, PRO6079, PRO9836 and PRO10096.

The following PRO polypeptides inhibited normal human dermal fibroblast proliferation in this assay: PRO181, PRO229, PRO788, PRO1194, PRO1272, PRO1488, PRO4302, PRO4408, PRO5723, PRO5725, PRO7154, and PRO7425.

Example 20

Microarray Analysis to Detect Overexpression of PRO Polypeptides in Cancerous Tumors Nucleic acid microarrays, often containing thousands of gene sequences, are useful for identifying differentially expressed genes in diseased tissues as compared to their normal counterparts. Using nucleic acid microarrays, test and control mRNA samples from test and control tissue samples are reverse transcribed and labeled to generate cDNA probes. The cDNA probes are then hybridized to an array of nucleic acids immobilized on a solid support. The array is configured such that the sequence and position of each member of the array is known. For example, a selection of genes known to be expressed in certain disease states may be arrayed on a solid support. Hybridization of a labeled probe with a particular array member indicates that the sample from which the probe was derived expresses that gene. If the hybridization signal of a probe from a test (disease tissue) sample is greater than hybridization signal of a probe from a control (normal tissue) sample, the gene or genes overexpressed in the disease tissue are identified. The implication of this result is that an overexpressed protein in a diseased tissue is useful not only as a diagnostic marker for the presence of the disease condition, but also as a therapeutic target for treatment of the disease condition.

The methodology of hybridization of nucleic acids and microarray technology is well known in the art. In the present example, the specific preparation of nucleic acids for hybridization and probes, slides, and hybridization conditions are all detailed in U.S. Provisional Patent Application Ser. No. 60/193,767, filed on Mar. 31, 2000 and which is herein incorporated by reference.

In the present example, cancerous tumors derived from various human tissues were studied for PRO polypeptide-encoding gene expression relative to non-cancerous human tissue in an attempt to identify those PRO polypeptides which are overexpressed in cancerous tumors. Cancerous human tumor tissue from any of a variety of different human tumors was obtained and compared to a “universal” epithelial control sample which was prepared by pooling non-cancerous human tissues of epithelial origin, including liver, kidney, and lung. mRNA isolated from the pooled tissues represents a mixture of expressed gene products from these different tissues. Microarray hybridization experiments using the pooled control samples generated a linear plot in a 2-color analysis. The slope of the line generated in a 2-color analysis was then used to normalize the ratios of (test: control detection) within each experiment. The normalized ratios from various experiments were then compared and used to identify clustering of gene expression. Thus, the pooled “universal control” sample not only allowed effective relative gene expression determinations in a simple 2-sample comparison, it also allowed multi-sample comparisons across several experiments.

In the present experiments, nucleic acid probes derived from the herein described PRO polypeptide-encoding nucleic acid sequences were used in the creation of the microarray and RNA from a panel of nine different tumor tissues (listed below) were used for the hybridization thereto. A value based upon the normalized ratio:experimental ratio was designated as a “cutoff ratio”. Only values that were above this cutoff ratio were determined to be significant. Table 8 below shows the results of these experiments, demonstrating that various PRO polypeptides of the present invention are significantly overexpressed in various human tumor tissues, as compared to a non-cancerous human tissue control or other human tumor tissues. As described above, these data demonstrate that the PRO polypeptides of the present invention are useful not only as diagnostic markers for the presence of one or more cancerous tumors, but also serve as therapeutic targets for the treatment of those tumors.

TABLE 8

| Molecule | is overexpressed in: | as compared to normal control: |
|---|---|---|
| PRO6004 | colon tumor | universal normal control |
| PRO4981 | colon tumor | universal normal control |
| PRO4981 | lung tumor | universal normal control |
| PRO7174 | colon tumor | universal normal control |
| PRO5778 | lung tumor | universal normal control |
| PRO5778 | breast tumor | universal normal control |
| PRO5778 | liver tumor | universal normal control |
| PRO4332 | colon tumor | universal normal control |
| PRO9799 | colon tumor | universal normal control |
| PRO9909 | colon tumor | universal normal control |
| PRO9917 | colon tumor | universal normal control |
| PRO9917 | lung tumor | universal normal control |
| PRO9917 | breast tumor | universal normal control |
| PRO9771 | colon tumor | universal normal control |
| PRO9877 | colon tumor | universal normal control |
| PRO9903 | colon tumor | universal normal control |
| PRO9830 | colon tumor | universal normal control |
| PRO7155 | colon tumor | universal normal control |
| PRO7155 | lung tumor | universal normal control |
| PRO7155 | prostate tumor | universal normal control |
| PRO9862 | colon tumor | universal normal control |
| PRO9882 | colon tumor | universal normal control |
| PRO9864 | colon tumor | universal normal control |
| PRO10013 | colon tumor | universal normal control |
| PRO9885 | colon tumor | universal normal control |
| PRO9879 | colon tumor | universal normal control |
| PRO10111 | colon tumor | universal normal control |
| PRO10111 | rectal tumor | universal normal control |
| PRO9925 | breast tumor | universal normal control |
| PRO9925 | rectal tumor | universal normal control |
| PRO9925 | colon tumor | universal normal control |
| PRO9925 | lung tumor | universal normal control |
| PRO9905 | colon tumor | universal normal control |
| PRO10276 | colon tumor | universal normal control |
| PRO9898 | colon tumor | universal normal control |
| PRO9904 | colon tumor | universal normal control |
| PRO19632 | colon tumor | universal normal control |
| PRO19672 | colon tumor | universal normal control |
| PRO9783 | colon tumor | universal normal control |
| PRO9783 | lung tumor | universal normal control |
| PRO9783 | breast tumor | universal normal control |
| PRO9783 | prostate tumor | universal normal control |
| PRO9783 | rectal tumor | universal normal control |
| PRO10112 | colon tumor | universal normal control |
| PRO10284 | colon tumor | universal normal control |
| PRO10100 | colon tumor | universal normal control |
| PRO19628 | colon tumor | universal normal control |
| PRO19684 | colon tumor | universal normal control |
| PRO10274 | colon tumor | universal normal control |
| PRO9907 | colon tumor | universal normal control |
| PRO9873 | colon tumor | universal normal control |
| PRO10201 | colon tumor | universal normal control |
| PRO10200 | colon tumor | universal normal control |
| PRO10196 | colon tumor | universal normal control |
| PRO10282 | lung tumor | universal normal control |
| PRO10282 | breast tumor | universal normal control |
| PRO10282 | colon tumor | universal normal control |
| PRO10282 | rectal tumor | universal normal control |
| PRO19650 | colon tumor | universal normal control |
| PRO21184 | lung tumor | universal normal control |
| PRO21184 | breast tumor | universal normal control |
| PRO21184 | colon tumor | universal normal control |
| PRO21201 | breast tumor | universal normal control |
| PRO21201 | colon tumor | universal normal control |
| PRO21175 | breast tumor | universal normal control |

TABLE 8-continued

| Molecule | is overexpressed in: | as compared to normal control: |
|---|---|---|
| PRO21175 | colon tumor | universal normal control |
| PRO21175 | lung tumor | universal normal control |
| PRO21340 | colon tumor | universal normal control |
| PRO21340 | prostate tumor | universal normal control |
| PRO21384 | colon tumor | universal normal control |
| PRO21384 | lung tumor | universal normal control |
| PRO21384 | breast tumor | universal normal control |

Example 21

Tumor Versus Normal Differential Tissue Expression Distribution

Oligonucleotide probes were constructed from some of the PRO polypeptide-encoding nucleotide sequences shown in the accompanying figures for use in quantitative PCR amplification reactions. The oligonucleotide probes were chosen so as to give an approximately 200-600 base pair amplified fragment from the 3' end of its associated template in a standard PCR reaction. The oligonucleotide probes were employed in standard quantitative PCR amplification reactions with cDNA libraries isolated from different human tumor and normal human tissue samples and analyzed by agarose gel electrophoresis so as to obtain a quantitative determination of the level of expression of the PRO polypeptide-encoding nucleic acid in the various tumor and normal tissues tested. β-actin was used as a control to assure that equivalent amounts of nucleic acid was used in each reaction. Identification of the differential expression of the PRO polypeptide-encoding nucleic acid in one or more tumor tissues as compared to one or more normal tissues of the same tissue type renders the molecule useful diagnostically for the determination of the presence or absence of tumor in a subject suspected of possessing a tumor as well as therapeutically as a target for the treatment of a tumor in a subject possessing such a tumor. These assays provided the following results.

(1) the DNA94849-2960 molecule is significantly expressed in the following tissues: cartilage, testis, colon tumor, heart, placenta, bone marrow, adrenal gland, prostate, spleen aortic endothelial cells and uterus, and not significantly expressed in the following tissues: HUVEC.

(2) the DNA 100272-2969 molecule is significantly expressed in cartilage, testis, human umbilical vein endothelial cells (HUVEC), colon tumor, heart, placenta, bone marrow, adrenal gland, prostate, spleen and aortic endothelial cells; and not significantly expressed in uterus. Among a panel of normal and tumor cells examined, the DNA100272-2969 was found to be expressed in normal esophagus, esophageal tumor, normal stomach, stomach tumor, normal kidney, kidney tumor, normal lung, lung tumor, normal rectum, rectal tumor, normal liver and liver tumor.

(3) the DNA108696-2966 molecule is highly expressed in prostate and also expressed in testis, bone marrow and spleen. The DNA108696-2966 molecule is expressed in normal stomach, but not expressed in stomach tumor. The DNA108696-2966 molecule is not expressed in normal kidney, kidney tumor, normal lung, or lung tumor. The DNA108696-2966 molecule is highly expressed in normal rectum, lower expression in rectal tumor. The DNA108696-2966 molecule is not expressed in normal liver or liver tumor. The DNA108696-2966 molecule is not expressed in normal esophagus, esophagial tumor, cartilage, HUVEC, colon tumor, heart, placenta, adrenal gland, aortic endothelial cells and uterus.

(4) the DNA119498-2965 molecule is significantly expressed in the following tissues: highly expressed in aortic endothelial cells, and also significantly expressed in cartilage, testis, HUVEC, colon tumor, heart, placenta, bone marrow, adrenal gland, prostate and spleen. It is not significantly expressed in uterus.

(5) the DNA119530-2968 molecule is expressed in the following tissues: normal esophagus and not expressed in the following tissues: esophageal tumors, stomach tumors, normal stomach, normal kidney, kidney tumor, normal lung, lung tumor, normal rectum, rectal tumors, normal liver or liver tumors.

(6) the DNA129794-2967 molecule is significantly expressed in testis and adrenal gland; and not significantly expressed in cartilage, human umbilical vein endothelial cells (HUVEC), colon tumor, heart, placenta, bone marrow, prostate, spleen, aortic endothelial cells and uterus.

(7) the DNA131590-2962 molecule is significantly expressed in the following tissues: bone marrow, adrenal gland, prostate, spleen, uterus, cartilage, testis, colon tumor, heart, and placenta, and not significantly expressed in the following tissues: HUVEC, and aortic endothelial cells.

(8) the DNA149995-2871 molecule is highly expressed in testis, and adrenal gland; expressed in cartilage, human umbilical vein endothelial cells (HUVEC), colon tumor, heart, prostate and uterus; weakly expressed in bone marrow, spleen and aortic endothelial cells; and not significantly expressed in placenta.

(9) the DNA 167678-2963 molecule is significantly expressed in the following tissues: normal esophagus, esophagial tumor, highly expressed in normal stomach, stomach tumor, highly expressed in normal kidney, kidney tumor, expressed in lung, lung tumor, normal rectum, rectal tumor, weakly expressed in normal liver, and not significantly expressed in liver tumor.

(10) the DNA168028-2956 molecule is highly expressed in bone marrow; expressed in testis, human umbilical vein endothelial cells (HUVEC), colon tumor, heart, placenta, adrenal gland, prostate, spleen, aortic endothelial cells and uterus; and is weakly expressed in cartilage. Among a panel of normal and tumor samples examined, the DNA168028-2956 was found to be expressed in stomach tumor, normal kidney, kidney tumor, lung tumor, normal rectum and rectal tumor; and not expressed in normal esophagus, esophageal tumor, normal stomach, normal lung, normal liver and liver tumor.

(11) the DNA176775-2957 molecule is highly expressed in testis; expressed in cartilage and prostate; weakly expressed in adrenal gland, spleen and uterus; and not significantly expressed in human umbilical vein endothelial cells (HUVEC), colon tumor, heart, placenta, bone marrow and aortic endothelial cells.

(12) the DNA177313-2982 molecule is significantly expressed in prostate and aortic endothelial cells; and not significantly expressed in cartilage, testis, human umbilical vein endothelial cells (HUVEC), colon tumor, heart, placenta, bone marrow, adrenal gland, spleen and uterus. Among a panel of normal and tumor cells, the DNA177313-2982 molecule was found to be expressed in esophageal tumor but not in normal esophagus, normal stomach, stomach tumor, normal kidney, kidney tumor, normal lung, lung tumor, normal rectum, rectal tumor, normal liver and liver tumor.

What is claimed is:

1. A method for detecting the presence of a lung tumor, colon tumor, or breast tumor in a mammal, said method comprising contacting a test sample of tissue cells obtained from the mammal with an antibody that specifically binds to (a) the polypeptide of SEQ ID NO:16 or (b) the polypeptide of SEQ ID NO:16, lacking its associated signal peptide; and detecting significant overexpression of the polypeptide in the test sample compared to a control sample, wherein significant overexpression of the polypeptide is indicative of the presence of a lung tumor, colon tumor, or breast tumor in the mammal.

2. The method of claim 1, wherein the antibody is labeled with a detectable moiety.

* * * * *